(12) United States Patent
Raymond et al.

(10) Patent No.: US 11,319,594 B2
(45) Date of Patent: May 3, 2022

(54) METHODS FOR THE DETECTION OF GENOMIC COPY CHANGES IN DNA SAMPLES

(71) Applicant: Resolution Bioscience, Inc., Bellevue, WA (US)

(72) Inventors: Christopher Raymond, Bellevue, WA (US); Lee Lim, Bellevue, WA (US); Jennifer Hernandez, Bellevue, WA (US)

(73) Assignee: Resolution Bioscience, Inc., Kirkland, WA (US)

( * ) Notice: Subject to any disclaimer, the term of this patent is extended or adjusted under 35 U.S.C. 154(b) by 0 days.

(21) Appl. No.: 15/685,834

(22) Filed: Aug. 24, 2017

(65) Prior Publication Data

US 2018/0163272 A1   Jun. 14, 2018

Related U.S. Application Data

(60) Provisional application No. 62/379,593, filed on Aug. 25, 2016, provisional application No. 62/481,538, filed on Apr. 4, 2017.

(51) Int. Cl.

| | | |
|---|---|---|
| *C12Q 1/6886* | (2018.01) | |
| *G16B 20/00* | (2019.01) | |
| *G16B 30/00* | (2019.01) | |
| *C12Q 1/68* | (2018.01) | |
| *C12Q 1/6809* | (2018.01) | |
| *G16B 30/10* | (2019.01) | |
| *G16B 20/40* | (2019.01) | |
| *G16B 20/10* | (2019.01) | |
| *G16B 25/10* | (2019.01) | |
| *G16B 20/20* | (2019.01) | |
| *C12Q 1/6806* | (2018.01) | |
| *C12Q 1/686* | (2018.01) | |
| *C12Q 1/6869* | (2018.01) | |
| *C12Q 1/6851* | (2018.01) | |
| *C40B 40/08* | (2006.01) | |

(52) U.S. Cl.
CPC ........... *C12Q 1/6886* (2013.01); *C12Q 1/68* (2013.01); *C12Q 1/686* (2013.01); *C12Q 1/6806* (2013.01); *C12Q 1/6809* (2013.01); *C12Q 1/6869* (2013.01); *G16B 20/00* (2019.02); *G16B 20/10* (2019.02); *G16B 20/20* (2019.02); *G16B 20/40* (2019.02); *G16B 25/10* (2019.02); *G16B 30/00* (2019.02); *G16B 30/10* (2019.02); *C12Q 1/6851* (2013.01); *C12Q 2525/191* (2013.01); *C12Q 2545/114* (2013.01); *C12Q 2563/159* (2013.01); *C12Q 2563/179* (2013.01); *C12Q 2600/156* (2013.01); *C40B 40/08* (2013.01); *G01N 2570/00* (2013.01); *G01N 2800/7028* (2013.01)

(58) Field of Classification Search
CPC ...... C12Q 1/6886; C12Q 1/68; C12Q 1/6806; C12Q 1/6809; C12Q 1/686; C12Q 1/6869; C12Q 1/6851; C12Q 2525/191; C12Q 2545/114; C12Q 2563/159; C12Q 2563/179; C12Q 2600/156; G16B 20/00; G16B 30/00; C40B 40/80; G01N 2570/00; G01N 2800/7028
See application file for complete search history.

(56) References Cited

U.S. PATENT DOCUMENTS

| | | |
|---|---|---|
| 5,591,582 A | 1/1997 | Bos et al. |
| 6,025,139 A | 2/2000 | Yager et al. |
| 6,480,791 B1 | 11/2002 | Strathmann |
| 6,812,341 B1 | 11/2004 | Conrad |
| 7,393,665 B2 | 7/2008 | Brenner |
| 8,148,068 B2 | 4/2012 | Brenner |
| 8,168,385 B2 | 5/2012 | Brenner |
| 8,318,433 B2 | 11/2012 | Brenner |
| 8,383,338 B2 | 2/2013 | Kitzman et al. |
| 8,470,996 B2 | 6/2013 | Brenner |
| 8,476,018 B2 | 7/2013 | Brenner |
| 8,828,688 B2 | 9/2014 | Namsaraev |
| 8,835,358 B2 | 9/2014 | Fodor et al. |
| 8,865,410 B2 | 10/2014 | Shendure et al. |
| 9,018,365 B2 | 4/2015 | Brenner |
| 9,085,798 B2 | 7/2015 | Chee |
| 9,121,069 B2 | 9/2015 | Lo et al. |
| 9,290,808 B2 | 3/2016 | Fodor et al. |

(Continued)

FOREIGN PATENT DOCUMENTS

| | | |
|---|---|---|
| CN | 101932729 A | 12/2010 |
| CN | 102439177 A | 5/2012 |

(Continued)

OTHER PUBLICATIONS

Rittie et al. ("Enzymes used in molecular biology: a useful guide" J. Cell Commun. Signal. (2008) 2:25-45).*

(Continued)

*Primary Examiner* — Robert H Havlin
(74) *Attorney, Agent, or Firm* — Cooley LLP

(57) ABSTRACT

The present invention includes compositions and methods useful for the detection of a mutational change, SNP, translocation, inversion, deletion, change in copy number, or other genetic variation within a sample of cellular genomic DNA or cell-free DNA (cfDNA). In some embodiments, the compositions and methods of the present invention provide an extremely high level of resolution that is particularly useful in detecting copy number variations in a small fraction of the total cfDNA from a biological sample (e.g., blood).

56 Claims, 108 Drawing Sheets

Specification includes a Sequence Listing.

(56) References Cited

U.S. PATENT DOCUMENTS

| | | |
|---|---|---|
| 9,290,809 B2 | 3/2016 | Fodor et al. |
| 9,315,857 B2 | 4/2016 | Fu et al. |
| 9,340,830 B2 | 5/2016 | Lipson et al. |
| 9,410,954 B2 | 8/2016 | Boshoff et al. |
| 9,546,399 B2 | 1/2017 | Amorese et al. |
| 9,598,731 B2 | 3/2017 | Talasaz |
| 9,702,002 B2 | 7/2017 | Boutell |
| 9,708,659 B2 | 7/2017 | Fodor et al. |
| 9,783,847 B2 | 10/2017 | Chee |
| 9,792,403 B2 | 10/2017 | Sun et al. |
| 9,816,137 B2 | 11/2017 | Fodor et al. |
| 9,834,822 B2 | 12/2017 | Talasaz |
| 9,840,743 B2 | 12/2017 | Talasaz |
| 9,850,523 B1 | 12/2017 | Chudova et al. |
| 9,902,992 B2 | 2/2018 | Talasaz et al. |
| 9,907,798 B2 | 3/2018 | Boshoff et al. |
| 9,920,366 B2 | 3/2018 | Eltoukhy et al. |
| 9,932,576 B2 | 4/2018 | Raymond et al. |
| 9,965,585 B2 | 5/2018 | Lo et al. |
| 10,000,800 B2 | 6/2018 | Chee |
| 10,047,394 B2 | 8/2018 | Fodor et al. |
| 10,059,991 B2 | 8/2018 | Fodor et al. |
| 10,095,831 B2 | 10/2018 | Duenwald et al. |
| 10,119,165 B2 | 11/2018 | Chee |
| 10,202,646 B2 | 2/2019 | Fodor et al. |
| 10,227,587 B2 | 3/2019 | Zhang et al. |
| 10,240,209 B2 | 3/2019 | Lo et al. |
| 10,266,883 B2 | 4/2019 | Chee |
| 10,266,889 B2 | 4/2019 | Behlke et al. |
| 10,287,630 B2 | 5/2019 | Xie et al. |
| 10,297,342 B2 | 5/2019 | Lo et al. |
| 10,378,064 B1 | 8/2019 | Schutz et al. |
| 10,388,403 B2 | 8/2019 | Rava et al. |
| 10,392,661 B2 | 8/2019 | Fodor et al. |
| 10,453,556 B2 | 10/2019 | Lo et al. |
| 10,494,678 B2 | 12/2019 | Talasaz |
| 10,501,793 B2 | 12/2019 | Chee |
| 10,501,810 B2 | 12/2019 | Talasaz |
| 10,538,759 B2 | 1/2020 | Stuelpnagel et al. |
| 10,577,601 B2 | 3/2020 | Shendure et al. |
| 10,597,653 B2 | 3/2020 | Sabot et al. |
| 10,597,708 B2 | 3/2020 | Zimmermann et al. |
| 10,597,709 B2 | 3/2020 | Zimmermann et al. |
| 10,619,203 B2 | 4/2020 | Fodor et al. |
| 10,619,214 B2 | 4/2020 | Lo et al. |
| 10,689,699 B2 | 6/2020 | Salk et al. |
| 10,704,085 B2 | 7/2020 | Talasaz et al. |
| 10,704,086 B2 | 7/2020 | Talasaz et al. |
| 10,741,270 B2 | 8/2020 | Lo et al. |
| 10,752,951 B2 | 8/2020 | Salk et al. |
| 10,793,916 B2 | 10/2020 | Talasaz |
| 10,801,063 B2 | 10/2020 | Eltoukhy et al. |
| 10,847,249 B2 | 11/2020 | Sun et al. |
| 10,876,152 B2 | 12/2020 | Talasaz et al. |
| 10,883,139 B2 | 1/2021 | Eltoukhy et al. |
| 10,889,858 B2 | 1/2021 | Talasaz et al. |
| 10,894,974 B2 | 1/2021 | Talasaz et al. |
| 10,907,149 B2 | 2/2021 | Raymond et al. |
| 2003/0148310 A1 | 8/2003 | Sorge |
| 2004/0058328 A1 | 3/2004 | Chan et al. |
| 2005/0032057 A1 | 2/2005 | Shoemaker |
| 2007/0037139 A1 | 2/2007 | Tomono et al. |
| 2007/0128624 A1 | 6/2007 | Gormley et al. |
| 2007/0172873 A1 | 7/2007 | Brenner et al. |
| 2008/0038782 A1 | 2/2008 | Borns |
| 2009/0117573 A1 | 5/2009 | Fu et al. |
| 2009/0143243 A1 | 6/2009 | Gunning et al. |
| 2009/0191563 A1 | 7/2009 | Steemers et al. |
| 2009/0264305 A1 | 10/2009 | Brandon et al. |
| 2010/0093550 A1 | 4/2010 | Stuelpnagel et al. |
| 2010/0273219 A1 | 10/2010 | May et al. |
| 2011/0014657 A1 | 1/2011 | Rigatti et al. |
| 2011/0160078 A1 | 6/2011 | Fodor et al. |
| 2011/0294689 A1 | 12/2011 | Namsaraev |
| 2011/0313145 A1 | 12/2011 | Sharon et al. |
| 2012/0157322 A1 | 6/2012 | Myllykangas et al. |
| 2013/0288915 A1 | 10/2013 | Seligmann et al. |
| 2014/0100792 A1 | 4/2014 | Deciu et al. |
| 2014/0242581 A1 | 8/2014 | Johnson |
| 2014/0274731 A1 | 9/2014 | Raymond et al. |
| 2014/0274740 A1 | 9/2014 | Srinivasan et al. |
| 2015/0046180 A1 | 2/2015 | Futscher De Deus et al. |
| 2015/0072344 A1 | 3/2015 | Wiley |
| 2015/0111757 A1 | 4/2015 | Boyden et al. |
| 2015/0159222 A1 | 6/2015 | Gaulis et al. |
| 2015/0275289 A1 | 10/2015 | Otwinowski et al. |
| 2015/0376700 A1 | 12/2015 | Schnall-levin et al. |
| 2016/0053253 A1 | 2/2016 | Salathia et al. |
| 2016/0053301 A1 | 2/2016 | Raymond et al. |
| 2017/0088887 A1* | 3/2017 | Makarov .............. C12Q 1/6806 |
| 2017/0096706 A1 | 4/2017 | Behlke et al. |
| 2017/0242960 A1 | 8/2017 | Rabinowitz et al. |
| 2017/0283869 A1 | 10/2017 | Fang et al. |
| 2017/0355984 A1 | 12/2017 | Evans et al. |
| 2017/0356053 A1 | 12/2017 | Otto et al. |
| 2018/0142234 A1 | 5/2018 | Raymond et al. |
| 2018/0179578 A1 | 6/2018 | Raymond et al. |
| 2018/0245072 A1 | 8/2018 | Raymond et al. |
| 2018/0300449 A1 | 10/2018 | Kermani et al. |
| 2018/0300456 A1 | 10/2018 | Eltoukhy et al. |
| 2018/0363066 A1 | 12/2018 | Chalmers et al. |
| 2019/0032118 A1 | 1/2019 | Lipson et al. |
| 2019/0136301 A1 | 5/2019 | Lipson et al. |
| 2019/0233897 A1 | 8/2019 | Cronin et al. |
| 2020/0048703 A1 | 2/2020 | Chee |
| 2020/0299775 A1 | 9/2020 | Hawryluk et al. |
| 2021/0198658 A1 | 7/2021 | Raymond et al. |

FOREIGN PATENT DOCUMENTS

| | | |
|---|---|---|
| CN | 103103624 A | 5/2013 |
| CN | 103668471 A | 3/2014 |
| EP | 3192869 A1 | 7/2017 |
| EP | 3202915 A1 | 8/2017 |
| EP | 3363904 A2 | 8/2018 |
| EP | 3421613 A1 | 1/2019 |
| EP | 3470533 A1 | 4/2019 |
| EP | 3502273 A1 | 6/2019 |
| EP | 3551769 A2 | 10/2019 |
| EP | 3567120 A1 | 11/2019 |
| JP | 2013-536679 A | 9/2013 |
| JP | 2014-512817 A | 5/2014 |
| JP | 2020-516281 A | 6/2020 |
| WO | WO 1999/011819 A1 | 3/1999 |
| WO | WO 2004/053127 A1 | 6/2004 |
| WO | WO 2009/076238 A2 | 6/2009 |
| WO | WO 2009/091798 A1 | 7/2009 |
| WO | WO 2010/129937 A2 | 11/2010 |
| WO | WO 2011/156529 A2 | 12/2011 |
| WO | WO 2012/028746 A1 | 3/2012 |
| WO | WO 2012/040387 A1 | 3/2012 |
| WO | WO 2012/129363 A2 | 9/2012 |
| WO | WO 2012/142213 A2 | 10/2012 |
| WO | WO 2012/142334 A2 | 10/2012 |
| WO | WO 2012/148477 A1 | 11/2012 |
| WO | WO 2014/052487 A1 | 4/2014 |
| WO | WO 2014/055790 A2 | 4/2014 |
| WO | WO 2014/071295 A1 | 5/2014 |
| WO | WO 2014/093330 A1 | 6/2014 |
| WO | WO 2014/093825 A1 | 6/2014 |
| WO | WO 2014/122288 A1 | 8/2014 |
| WO | WO 2015/134552 A1 | 9/2014 |
| WO | WO 2015/117040 A1 | 8/2015 |
| WO | WO 2015/134552 A1 | 9/2015 |
| WO | WO 2016/022833 A1 | 2/2016 |
| WO | WO 2016/028316 A1 | 2/2016 |
| WO | WO 2016/037389 A1 | 3/2016 |
| WO | WO 2016/040901 A1 | 3/2016 |
| WO | WO 2016/094853 A1 | 6/2016 |
| WO | WO 2016/109452 A1 | 7/2016 |
| WO | WO 2017/083562 A1 | 5/2017 |
| WO | WO 2018/039463 A1 | 3/2018 |
| WO | WO 2018/064629 A1 | 4/2018 |

(56) References Cited

FOREIGN PATENT DOCUMENTS

| WO | WO 2018/094183 A1 | 5/2018 |
|---|---|---|
| WO | WO 2018/104908 A2 | 6/2018 |
| WO | WO 2020/106906 A1 | 5/2020 |

OTHER PUBLICATIONS

Atamaniuk et al., "Cell-free plasma DNA: a marker for apoptosis during hemodialysis." Clinical Chemistry (2006); 52.3: 523-526.
Blake, R. D., and Delcourt, S.G. "Thermodynamic effects of formamide on DNA stability." Nucleic Acids Research (1996); 24.11:2095-2103.
Chan et al. "Cancer genome scanning in plasma: detection of tumor-associated copy number aberrations, singlenucleotide variants, and tu moral heterogeneity by massively parallel sequencing." Clinical Chemistry (2013); 59(1): 211-224.
Extended European Search Report in Application No. EP 13862440. 8, dated Oct. 11, 2016, 19 pages.
Hoeijmakers et al., "Linear amplification for deep sequencing." Nature Protocols (2011); 6.7:1026-1036.
KAPA Biosystems "KAPA Library Quantification Kits Technical Data Sheet" (2011); 6 pages, www.kapabiosystems.com.
Leary et al. "Detection of chromosomal alterations in the circulation of cancer patients with whole-genome sequencing." Science Translational Medicine (2012); 4(162):162ra154.
Lin et al., "Exon array profiling detects EML4-ALK fusion in breast, colorectal, and non-small cell lung cancers." Molecular Cancer Research (2009); 7.9:1466-1476.
Mano, H., "Non-solid oncogenes in solid tumors: EML4-ALK fusion genes in lung cancer." Cancer Science (2008); 99.12:2349-2355.
McKernan et al., "Sequence and structural variation in a human genome uncovered by short-read, massively parallel ligation sequencing using two-base encoding." Genome Research (2009); 19.9: 1527-1541.
Melchior, W.B. and Hippel, P.H. "Alteration of the relative stability of dA• dT and dG• dC base pairs in DNA." Proceedings of the National Academy of Sciences USA (1973); 70.2: 298-302.
Meyer et al., "Targeted high-throughput sequencing of tagged nucleic acid samples." Nucleic Acids Research (2007); 35.15: e97, 5 pages.
Meyer et al., "From micrograms to picograms: quantitative PCR reduces the material demands of high-throughput sequencing" Nucleic Acids Research (2008); 36(1 ):e5.
Partial Supplementary European Search Report in European Application No. 13862440.8 dated Jul. 4, 2016, 11 pages.
PCT/US2013/074102, International Preliminary Report on Patentability dated Jun. 16, 2015.
PCT/US2014/052317, International Preliminary Report on Patentability dated Feb. 28, 2017, 8 pages.
PCT/US2013/074102, International Search Report and Written Opinion dated Feb. 28, 2014.
PCT/US2014/052317, International Search Report and Written Opinion dated Jan. 13, 2015, 13 pages.
PCT/US2016/061395, International Search Report and Written Opinion dated Feb. 7, 2017, 14 pages.
PCT/US2017/048434, International Search Report and Written Opinion dated Dec. 26, 2017, 15 pages.
Samorodnitsky, et al., "Comparison of Custom Capture for Targeted Next-Generation DNA Sequencing." The Journal of Molecular Diagnostics (2015); 17(1): 64-75.
Shevelev and Hübscher, "The 3' 5' exonucleases", *Nat Rev Mol Cell Biol.*, 3(5): 364-376 (2002).
Shiroguchi, et al., "Digital RNA sequencing minimizes sequence-dependent bias and amplification noise with optimized single-molecule barcodes." PNAS (2012); 109(4): 1347-1352, Supporting Information, 14 pages.
Stellwagen, Earle, et al. "Monovalent cation size and DNA conformational stability." Biochemistry (2011); 50.15: 3084-3094.

Taton, T. Andrew, et al. "Scanometric DNA array detection with nanoparticle probes." Science (2000); 289.5485: 1757-1760.
Vogelstein et al., "Cancer genome landscapes." Science (2013); 339.6127: 1546-1558.
Yegnasubramanian et al., "Preparation of Fragment Libraries for Next-Generation Sequencing on the Applied Biosystems SOLiD Platform." Methods in Enzymology (2013); 529: 185-200.
Horn, Susanne, "Target Enrichment via DNA Hybridization Capture" in Ancient DNA: Methods and Protocols, Methods in Molecular Biology (2012); 840: 177-188. Epub Dec. 8, 2011.
PCT/US2017/048434, International Preliminary Reporton Patentability dated Feb. 26, 2019, 10 pages.
Cheng, et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology". J Mol Diagn. (May 2015); 17(3): 251-264. Epub Mar. 20, 2015.
Extended European Search Report in Application No. EP 17844424. 6, dated Mar. 27, 2020, 8 pages.
Miura, et al., "Highly efficient single-stranded DNA ligation technique improves low-input whole-genome bisulfite sequencing by post-bisulfite adaptor tagging." Nucleic Acids Research 47.15 (2019): e85-e85.
[Author Unknown] "SureSelectXT Target Enrichment System for Illumina Paired-End Multiplexed Sequencing Library". Protocol, Version C3, Sep. 2019, Agilent Technologies, ©Agilent Technologies, Inc. 2010-2019, 100 pages.
Wisegeek, "How many species of bacteria are there?" WiseGeek. com, accessed Jan. 21, 2014, 2 pages. (Year: 2014).
Wikipedia, "List of sequenced bacterial genomes" Wikipedia.com, accessed Jan. 24, 2014, 57 pages. (Year: 2014).
Begley, Sharon, "Psst, The Human Genome Was Never Completely Sequenced. Some Scientists Say It Should Be", STAT News, Jun. 20, 2017 (Year: 2017), downloaded Sep. 3, 2018 from https://www.statnews.com/2017 /06/20/human-genome-not-fully-sequenced/, 8 pages.
Extended European Search Report in Application No. EP 16865029. 9, dated Apr. 29, 2019, 11 pages.
Extended European Search Report in Application No. EP 19153893. 3, dated Sep. 17, 2019, 9 pages.
Extended European Search Report in Application No. EP 21152311. 3, dated Sep. 7, 2021, 14 pages.
Fakruddin, et al., "Nucleic acid amplification: Alternative methods of polymerase chain reaction". Journal of Pharmacy and Bioallied Sciences (Oct. 2013-Dec.); 5(4): 245-252.
Forster, et al., "A human gut bacterial genome and culture collection for improved metagenomic analyses". Nat Biotechnol. (Feb. 2019); 37(2): 186-192. Epub Feb. 4, 2019.
Jacobs, et al., "The thermal stability of oligonucleotide duplexes is sequence independent in tetraalkylammonium salt solutions: application to identifying recombinant DNA clones". Nucleic Acids Res. (May 25, 1988); 16(10): 4637-4650.
PCT/US2016/061395, International Preliminary Report on Patentability dated May 15, 2018, 10 pages.
Piovesan, et al., "On the length, weight and GC content of the human genome". BMC Res Notes (Feb. 27, 2019); 12:106, 7 pages.
Shevelev and Hübscher, "The 3' 5' exonucleases", Nat Rev Mol Cell Biol. (May 2002); 3(5): 364-376.
Oxford Dictionary of Biochemistry and Molecular Biology, Definition of "base composition," general eds Attwood, et al. Revised Edition (2000), 3 pages.
Beltran, et al., "Circulating tumor DNA profile recognizes transformation to castration-resistant neuroendocrine prostate cancer". J Clin Invest (Apr. 1, 2020); 130(4): 1653-1668.
Zhou, et al., "Systematic evaluation of library preparation methods and sequencing platforms for high-throughput whole genome bisulfite sequencing." Scientific Reports (2019); 9:10383,16 pages.
PCT/US2021/049448, International Search Report and Written Opinion dated Dec. 28, 2021, 12 pages.
[Author Unknown] "TruSeq™ RNA and DNA Library Preparation Kits v2". Data Sheet: Illumina® Sequencing, ©2011,2014 Illumina, Inc., Pub. No. 770-2009-039 Current as ☐ of Nov. 17, 2014, 4 pages.

(56) References Cited

OTHER PUBLICATIONS

Hess, et al., "Library preparation for next generation sequencing: A review of automation strategies". Biotechnol Adv. (Jul.-Aug. 2020); 41: 107537, 14 pages. Epub ☐ Mar. 19, 2020.

Hong and Shin, "Bisulfite-Converted DNA Quantity Evaluation: A Multiplex Quantitative Real-Time PCR System for Evaluation of Bisulfite Conversion". Front ☐ Genet. (Feb. 25, 2021); 12: 618955. eCollection 2021.

Ma, et al., "Pan-cancer genome and transcriptome analyses of 1,699 paediatric -leukaemias and solid tumours". Nature (2018); 55: 371-376. Epub Feb. 28, 2018.

Malone, et al., "Molecular profiling for precision cancer therapies". Genome Med. -(Jan. 14, 2020); 12(1): 8, 19 pages.

Mamanova, et al., "Target-enrichment strategies for next-generation sequencing". Nature Methods. (Feb. 2010); 7(2): 111-118.

Manier, et al., "Whole-exome sequencing of cell-free DNA and circulating tumor cells -in multiple myeloma". Nat Commun. (Apr. 2, 20187); 9(1): 1691, 11 pages.

Wang, et al., "Enzymatic approaches for profiling cytosine methylation and -hydroxymethylation". Mol Metab. (Mar. 2022); 57: 101314. Epub Aug. 8, 2021.

Wang, et al., "Low-pass genome sequencing versus chromosomal microarray analysis: implementation in prenatal diagnosis". Genet Med. (Mar. 2020); 22(3): 500- ☐ 510. Epub Aug. 26, 2019.

\* cited by examiner 249 tags → 1 anchor sequence

FIG. 8A
| Sample | Input |
|---|---|
| Sample 1 | Female gDNA + 8% BRCA2 delete |
| Sample 2 | Female gDNA + 4% BRCA2 delete |
| Sample 3 | Female gDNA + 2% BRCA2 delete |
| Sample 4 | Pure Female gDNA |
| Sample 5 | Female gDNA + 8% ATM delete |
| Sample 6 | Female gDNA + 4% ATM delete |
| Sample 7 | Female gDNA + 2% ATM delete |
| Sample 8 | Pure Female gDNA |
FIG. 8B
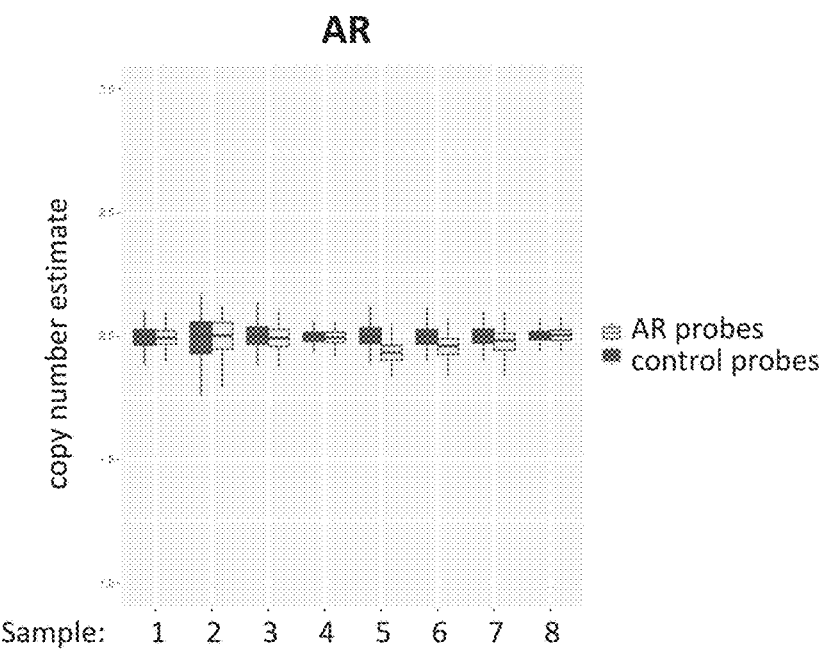
FIG. 8C
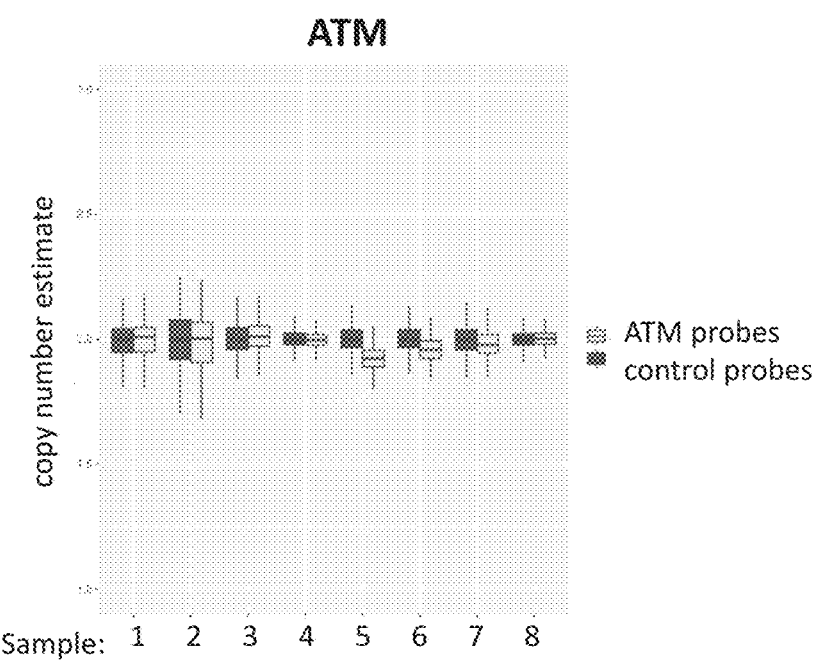

| Sample | Input |
|---|---|
| Sample 1 | Female gDNA + 8% BRCA2 delete |
| Sample 2 | Female gDNA + 4% BRCA2 delete |
| Sample 3 | Female gDNA + 2% BRCA2 delete |
| Sample 4 | Pure Female gDNA |
| Sample 5 | Female gDNA + 8% ATM delete |
| Sample 6 | Female gDNA + 4% ATM delete |
| Sample 7 | Female gDNA + 2% ATM delete |
| Sample 8 | Pure Female gDNA |

| Sample | Input |
|---|---|
| Sample 1 | F_cfDNA + 10% M_cfDNA |
| Sample 2 | F_cfDNA + 5% M_cfDNA |
| Sample 3 | Pure F_cfDNA |
| Sample 4 | Pure F_cfDNA |
| Sample 5 | F_cfDNA + 10% ATM |
| Sample 6 | F_cfDNA + 5% ATM |
| Sample 7 | F_cfDNA + 10% BRCA2 |
| Sample 8 | F_cfDNA + 5% BRCA2 |

Measured ΔATM SNP frequency:          5.5   2.5
Measured ΔBRCA2 SNP frequency:                      7.2   2.6

Distribution of targeted sequencing reads

Unique  Duplicate  Off target  Unalignable

FIG. 12A

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CACGAGCTTANNNACGTATGCCA | 9 | TGCAGGACCAGAGAATTCGAATA CACCCTGTCGNNNACGTATGCCA | 249 | TGCAGGACCAGAGAATTCGAATA CAACGTCAACNNNACGTATGCCA | 489 |
| TGCAGGACCAGAGAATTCGAATA CATTGCTCACNNNACGTATGCCA | 10 | TGCAGGACCAGAGAATTCGAATA CATATCAATGNNNACGTATGCCA | 250 | TGCAGGACCAGAGAATTCGAATA CAGTGTCTAGNNNACGTATGCCA | 490 |
| TGCAGGACCAGAGAATTCGAATA CATAATACACNNNACGTATGCCA | 11 | TGCAGGACCAGAGAATTCGAATA CACTGCAGATNNNACGTATGCCA | 251 | TGCAGGACCAGAGAATTCGAATA CAGCGGCCAGTNNNACGTATGCCA | 491 |
| TGCAGGACCAGAGAATTCGAATA CATCAGCATGNNNACGTATGCCA | 12 | TGCAGGACCAGAGAATTCGAATA CAATCGGATCNNNACGTATGCCA | 252 | TGCAGGACCAGAGAATTCGAATA CAGCTCTGAANNNACGTATGCCA | 492 |
| TGCAGGACCAGAGAATTCGAATA CAACTGTAGCNNNACGTATGCCA | 13 | TGCAGGACCAGAGAATTCGAATA CACTGTTCCANNNACGTATGCCA | 253 | TGCAGGACCAGAGAATTCGAATA CAAGACTTGCNNNACGTATGCCA | 493 |
| TGCAGGACCAGAGAATTCGAATA CAATTATGCANNNACGTATGCCA | 14 | TGCAGGACCAGAGAATTCGAATA CATCACATTTNNNACGTATGCCA | 254 | TGCAGGACCAGAGAATTCGAATA CAGATGGTCTNNNACGTATGCCA | 494 |
| TGCAGGACCAGAGAATTCGAATA CATGACCTTCNNNACGTATGCCA | 15 | TGCAGGACCAGAGAATTCGAATA CAGCGTGGCTNNNACGTATGCCA | 255 | TGCAGGACCAGAGAATTCGAATA CATTGTGAATNNNACGTATGCCA | 495 |
| TGCAGGACCAGAGAATTCGAATA CAAAAATCCTNNNACGTATGCCA | 16 | TGCAGGACCAGAGAATTCGAATA CACGGAGTAANNNACGTATGCCA | 256 | TGCAGGACCAGAGAATTCGAATA CACAGCGCGTNNNACGTATGCCA | 496 |
| TGCAGGACCAGAGAATTCGAATA CAGGTTCCGGNNNACGTATGCCA | 17 | TGCAGGACCAGAGAATTCGAATA CAGTGTCCGGNNNACGTATGCCA | 257 | TGCAGGACCAGAGAATTCGAATA CATGCCAAGTNNNACGTATGCCA | 497 |
| TGCAGGACCAGAGAATTCGAATA CAACGTGCATNNNACGTATGCCA | 18 | TGCAGGACCAGAGAATTCGAATA CATATTGTAGNNNACGTATGCCA | 258 | TGCAGGACCAGAGAATTCGAATA CACGTCGTTTNNNACGTATGCCA | 498 |
| TGCAGGACCAGAGAATTCGAATA CACGCCCCATNNNACGTATGCCA | 19 | TGCAGGACCAGAGAATTCGAATA CATAGTATTGNNNACGTATGCCA | 259 | TGCAGGACCAGAGAATTCGAATA CACCAACGGCNNNACGTATGCCA | 499 |
| TGCAGGACCAGAGAATTCGAATA CAGTAAGCCTNNNACGTATGCCA | 20 | TGCAGGACCAGAGAATTCGAATA CAAGCGCTTANNNACGTATGCCA | 260 | TGCAGGACCAGAGAATTCGAATA CACAGTTATANNNACGTATGCCA | 500 |
| TGCAGGACCAGAGAATTCGAATA CAAGTAATAGNNNACGTATGCCA | 21 | TGCAGGACCAGAGAATTCGAATA CATGCAGGTTNNNACGTATGCCA | 261 | TGCAGGACCAGAGAATTCGAATA CACGAAGGCGNNNACGTATGCCA | 501 |
| TGCAGGACCAGAGAATTCGAATA CAAAGTCCANNNACGTATGCCA | 22 | TGCAGGACCAGAGAATTCGAATA CACCTCCGGTNNNACGTATGCCA | 262 | TGCAGGACCAGAGAATTCGAATA CAATGGCTACNNNACGTATGCCA | 502 |
| TGCAGGACCAGAGAATTCGAATA CAAGTGCATCNNNACGTATGCCA | 23 | TGCAGGACCAGAGAATTCGAATA CAAGACGGATNNNACGTATGCCA | 263 | TGCAGGACCAGAGAATTCGAATA CATCGCATGANNNACGTATGCCA | 503 |
| TGCAGGACCAGAGAATTCGAATA CAGACATATTNNNACGTATGCCA | 24 | TGCAGGACCAGAGAATTCGAATA CATCTGTCTGNNNACGTATGCCA | 264 | TGCAGGACCAGAGAATTCGAATA CAATATCCTTNNNACGTATGCCA | 504 |
| TGCAGGACCAGAGAATTCGAATA CAGTCCACAANNNACGTATGCCA | 25 | TGCAGGACCAGAGAATTCGAATA CATTCACCGTNNNACGTATGCCA | 265 | TGCAGGACCAGAGAATTCGAATA CATGAAGCAGNNNACGTATGCCA | 505 |
| TGCAGGACCAGAGAATTCGAATA CATCTCAGAGNNNACGTATGCCA | 26 | TGCAGGACCAGAGAATTCGAATA CACGTAAGGNNNNACGTATGCCA | 266 | TGCAGGACCAGAGAATTCGAATA CAGACCACCGNNNACGTATGCCA | 506 |
| TGCAGGACCAGAGAATTCGAATA CAAAAACGTANNNACGTATGCCA | 27 | TGCAGGACCAGAGAATTCGAATA CAAGAAAGAANNNACGTATGCCA | 267 | TGCAGGACCAGAGAATTCGAATA CAAGATTAGANNNACGTATGCCA | 507 |
| TGCAGGACCAGAGAATTCGAATA CACTACCAAGNNNACGTATGCCA | 28 | TGCAGGACCAGAGAATTCGAATA CAAGTAGTTTNNNACGTATGCCA | 268 | TGCAGGACCAGAGAATTCGAATA CAAGATCTATNNNACGTATGCCA | 508 |
| TGCAGGACCAGAGAATTCGAATA CACCCTGACTTNNNACGTATGCCA | 29 | TGCAGGACCAGAGAATTCGAATA CAGGTACCTANNNACGTATGCCA | 269 | TGCAGGACCAGAGAATTCGAATA CAACGTACACNNNACGTATGCCA | 509 |
| TGCAGGACCAGAGAATTCGAATA CACTCCTATGNNNACGTATGCCA | 30 | TGCAGGACCAGAGAATTCGAATA CAGAAGCACANNNACGTATGCCA | 270 | TGCAGGACCAGAGAATTCGAATA CACGGTTACANNNACGTATGCCA | 510 |
| TGCAGGACCAGAGAATTCGAATA CAATCATGATNNNACGTATGCCA | 31 | TGCAGGACCAGAGAATTCGAATA CACTAATAACNNNACGTATGCCA | 271 | TGCAGGACCAGAGAATTCGAATA CAAAACCTATNNNACGTATGCCA | 511 |
| TGCAGGACCAGAGAATTCGAATA CATGACGGTTNNNACGTATGCCA | 32 | TGCAGGACCAGAGAATTCGAATA CAACGGACAANNNACGTATGCCA | 272 | TGCAGGACCAGAGAATTCGAATA CACTGATTTTNNNACGTATGCCA | 512 |
| TGCAGGACCAGAGAATTCGAATA CAGTCGGCGTNNNACGTATGCCA | 33 | TGCAGGACCAGAGAATTCGAATA CAATCCAGTGNNNACGTATGCCA | 273 | TGCAGGACCAGAGAATTCGAATA CATGAATATCNNNACGTATGCCA | 513 |
| TGCAGGACCAGAGAATTCGAATA CAGTTACCCTNNNACGTATGCCA | 34 | TGCAGGACCAGAGAATTCGAATA CAGGACAACANNNACGTATGCCA | 274 | TGCAGGACCAGAGAATTCGAATA CAACTGCGCGNNNACGTATGCCA | 514 |
| TGCAGGACCAGAGAATTCGAATA CACTTAACGGNNNACGTATGCCA | 35 | TGCAGGACCAGAGAATTCGAATA CAGAAAGTTANNNACGTATGCCA | 275 | TGCAGGACCAGAGAATTCGAATA CAGAACGACANNNACGTATGCCA | 515 |
| TGCAGGACCAGAGAATTCGAATA CACGCTCCTGNNNACGTATGCCA | 36 | TGCAGGACCAGAGAATTCGAATA CAAACACAGGNNNACGTATGCCA | 276 | TGCAGGACCAGAGAATTCGAATA CATATATTGGNNNACGTATGCCA | 516 |
| TGCAGGACCAGAGAATTCGAATA CATCTCGGTTNNNACGTATGCCA | 37 | TGCAGGACCAGAGAATTCGAATA CACCAGAATCNNNACGTATGCCA | 277 | TGCAGGACCAGAGAATTCGAATA CATAGATGCCNNNACGTATGCCA | 517 |
| TGCAGGACCAGAGAATTCGAATA CAGCTCGAGCNNNACGTATGCCA | 38 | TGCAGGACCAGAGAATTCGAATA CATTCACCACNNNACGTATGCCA | 278 | TGCAGGACCAGAGAATTCGAATA CAGCAAGTAGNNNACGTATGCCA | 518 |
| TGCAGGACCAGAGAATTCGAATA CACGCTTCGCNNNACGTATGCCA | 39 | TGCAGGACCAGAGAATTCGAATA CATGGAGANNNNACGTATGCCA | 279 | TGCAGGACCAGAGAATTCGAATA CAAACGACCTNNNACGTATGCCA | 519 |
| TGCAGGACCAGAGAATTCGAATA CAATCCAGACNNNACGTATGCCA | 40 | TGCAGGACCAGAGAATTCGAATA CACGATGTCANNNACGTATGCCA | 280 | TGCAGGACCAGAGAATTCGAATA CAGTACAGTCNNNACGTATGCCA | 520 |
| TGCAGGACCAGAGAATTCGAATA CATAGCACTGNNNACGTATGCCA | 41 | TGCAGGACCAGAGAATTCGAATA CACGGCAGGANNNACGTATGCCA | 281 | TGCAGGACCAGAGAATTCGAATA CATATGCGGTNNNACGTATGCCA | 521 |

FIG. 12B

| Pool-1 | SEQ ID NO: | Pool-2 | SEQ ID NO: | Pool-3 | SEQ ID NO: |
|---|---|---|---|---|---|
| TGCAGGACCAGAGAATTCGAATACACTGGCTTTNNNACGTATGCCA | 42 | TGCAGGACCAGAGAATTCGAATACAAGAACCAGNNNACGTATGCCA | 282 | TGCAGGACCAGAGAATTCGAATACAATAATAGGNNNACGTATGCCA | 522 |
| TGCAGGACCAGAGAATTCGAATACAGCAAATGGNNNACGTATGCCA | 43 | TGCAGGACCAGAGAATTCGAATACAGATTTTGANNNACGTATGCCA | 283 | TGCAGGACCAGAGAATTCGAATACAGTTACTAANNNACGTATGCCA | 523 |
| TGCAGGACCAGAGAATTCGAATACAGGATGACANNNACGTATGCCA | 44 | TGCAGGACCAGAGAATTCGAATACAAACACGTCNNNACGTATGCCA | 284 | TGCAGGACCAGAGAATTCGAATACACCCTTGTANNNACGTATGCCA | 524 |
| TGCAGGACCAGAGAATTCGAATACAGCCCCACTNNNACGTATGCCA | 45 | TGCAGGACCAGAGAATTCGAATACAACCTCTACNNNACGTATGCCA | 285 | TGCAGGACCAGAGAATTCGAATACAACATTTCTNNNACGTATGCCA | 525 |
| TGCAGGACCAGAGAATTCGAATACACTAGCCGGNNNACGTATGCCA | 46 | TGCAGGACCAGAGAATTCGAATACAGGCGTTTANNNACGTATGCCA | 286 | TGCAGGACCAGAGAATTCGAATACACCGACTTTNNNACGTATGCCA | 526 |
| TGCAGGACCAGAGAATTCGAATACACCCTCCTCNNNACGTATGCCA | 47 | TGCAGGACCAGAGAATTCGAATACACCCGAAGCNNNACGTATGCCA | 287 | TGCAGGACCAGAGAATTCGAATACATATGAACTNNNACGTATGCCA | 527 |
| TGCAGGACCAGAGAATTCGAATACATGTAGTGCNNNACGTATGCCA | 48 | TGCAGGACCAGAGAATTCGAATACATACCTACCNNNACGTATGCCA | 288 | TGCAGGACCAGAGAATTCGAATACATTCTTTTCNNNACGTATGCCA | 528 |
| TGCAGGACCAGAGAATTCGAATACAGAATGTGGNNNACGTATGCCA | 49 | TGCAGGACCAGAGAATTCGAATACATTTACGCCNNNACGTATGCCA | 289 | TGCAGGACCAGAGAATTCGAATACAATAGGTTTNNNACGTATGCCA | 529 |
| TGCAGGACCAGAGAATTCGAATACAAATGATCTNNNACGTATGCCA | 50 | TGCAGGACCAGAGAATTCGAATACAAGGTATGGNNNACGTATGCCA | 290 | TGCAGGACCAGAGAATTCGAATACACGACGTTANNNACGTATGCCA | 530 |
| TGCAGGACCAGAGAATTCGAATACACACTAACGNNNACGTATGCCA | 51 | TGCAGGACCAGAGAATTCGAATACAACTACAATNNNACGTATGCCA | 291 | TGCAGGACCAGAGAATTCGAATACAAGCATAGGNNNACGTATGCCA | 531 |
| TGCAGGACCAGAGAATTCGAATACACGTCGGACNNNACGTATGCCA | 52 | TGCAGGACCAGAGAATTCGAATACACTCCTCAANNNACGTATGCCA | 292 | TGCAGGACCAGAGAATTCGAATACACTGCATCTNNNACGTATGCCA | 532 |
| TGCAGGACCAGAGAATTCGAATACAGCAACTTGNNNACGTATGCCA | 53 | TGCAGGACCAGAGAATTCGAATACAGATACAAANNNACGTATGCCA | 293 | TGCAGGACCAGAGAATTCGAATACACGACGCCANNNACGTATGCCA | 533 |
| TGCAGGACCAGAGAATTCGAATACACGGTGGAGNNNACGTATGCCA | 54 | TGCAGGACCAGAGAATTCGAATACACCAACACANNNACGTATGCCA | 294 | TGCAGGACCAGAGAATTCGAATACAAACGCCCGNNNACGTATGCCA | 534 |
| TGCAGGACCAGAGAATTCGAATACAGTAACCGTNNNACGTATGCCA | 55 | TGCAGGACCAGAGAATTCGAATACAACCCATTCNNNACGTATGCCA | 295 | TGCAGGACCAGAGAATTCGAATACACTCTCGATNNNACGTATGCCA | 535 |
| TGCAGGACCAGAGAATTCGAATACATAGTTTTCNNNACGTATGCCA | 56 | TGCAGGACCAGAGAATTCGAATACATCTAAGCGNNNACGTATGCCA | 296 | TGCAGGACCAGAGAATTCGAATACACCCTGACCNNNACGTATGCCA | 536 |
| TGCAGGACCAGAGAATTCGAATACACTGTCGTTNNNACGTATGCCA | 57 | TGCAGGACCAGAGAATTCGAATACACTTAAGGCNNNACGTATGCCA | 297 | TGCAGGACCAGAGAATTCGAATACAGTTGTAATNNNACGTATGCCA | 537 |
| TGCAGGACCAGAGAATTCGAATACATTCGAGGTNNNACGTATGCCA | 58 | TGCAGGACCAGAGAATTCGAATACACGAATCCANNNACGTATGCCA | 298 | TGCAGGACCAGAGAATTCGAATACAAAAAGACTNNNACGTATGCCA | 538 |
| TGCAGGACCAGAGAATTCGAATACACCTCCACGNNNACGTATGCCA | 59 | TGCAGGACCAGAGAATTCGAATACACAACTAATNNNACGTATGCCA | 299 | TGCAGGACCAGAGAATTCGAATACATCCTAGCTNNNACGTATGCCA | 539 |
| TGCAGGACCAGAGAATTCGAATACAGAGACTAGNNNACGTATGCCA | 60 | TGCAGGACCAGAGAATTCGAATACATCACACCTNNNACGTATGCCA | 300 | TGCAGGACCAGAGAATTCGAATACAACCAAAGGNNNACGTATGCCA | 540 |
| TGCAGGACCAGAGAATTCGAATACATGAACTATNNNACGTATGCCA | 61 | TGCAGGACCAGAGAATTCGAATACAGACCGTCGNNNACGTATGCCA | 301 | TGCAGGACCAGAGAATTCGAATACAACGAGTTCNNNACGTATGCCA | 541 |
| TGCAGGACCAGAGAATTCGAATACAGTTGATTANNNACGTATGCCA | 62 | TGCAGGACCAGAGAATTCGAATACACTTTAAGANNNACGTATGCCA | 302 | TGCAGGACCAGAGAATTCGAATACACTATGGTGNNNACGTATGCCA | 542 |
| TGCAGGACCAGAGAATTCGAATACATCCACTCANNNACGTATGCCA | 63 | TGCAGGACCAGAGAATTCGAATACATGTGATTANNNACGTATGCCA | 303 | TGCAGGACCAGAGAATTCGAATACACCACCGTCNNNACGTATGCCA | 543 |
| TGCAGGACCAGAGAATTCGAATACAGTGACTGTNNNACGTATGCCA | 64 | TGCAGGACCAGAGAATTCGAATACAACCCAATGNNNACGTATGCCA | 304 | TGCAGGACCAGAGAATTCGAATACAGAATCGCTNNNACGTATGCCA | 544 |
| TGCAGGACCAGAGAATTCGAATACATTACGGCANNNACGTATGCCA | 65 | TGCAGGACCAGAGAATTCGAATACAACGTGTACNNNACGTATGCCA | 305 | TGCAGGACCAGAGAATTCGAATACAAGTGTTATNNNACGTATGCCA | 545 |
| TGCAGGACCAGAGAATTCGAATACACACCTCCGNNNACGTATGCCA | 66 | TGCAGGACCAGAGAATTCGAATACAATGAAATGNNNACGTATGCCA | 306 | TGCAGGACCAGAGAATTCGAATACAACGCGTCGNNNACGTATGCCA | 546 |
| TGCAGGACCAGAGAATTCGAATACAAAGAAGAANNNACGTATGCCA | 67 | TGCAGGACCAGAGAATTCGAATACATCCTCGTANNNACGTATGCCA | 307 | TGCAGGACCAGAGAATTCGAATACACTCGTGTTNNNACGTATGCCA | 547 |
| TGCAGGACCAGAGAATTCGAATACAGAACCTGTNNNACGTATGCCA | 68 | TGCAGGACCAGAGAATTCGAATACAGTAACAGGNNNACGTATGCCA | 308 | TGCAGGACCAGAGAATTCGAATACATTGTAGATNNNACGTATGCCA | 548 |
| TGCAGGACCAGAGAATTCGAATACAGAATAACANNNCTAGCGTTAC | 69 | TGCAGGACCAGAGAATTCGAATACAACTCGGTANNNCTAGCGTTAC | 309 | TGCAGGACCAGAGAATTCGAATACAGCCGCAGTNNNCTAGCGTTAC | 549 |
| TGCAGGACCAGAGAATTCGAATACAGCCTCGTCNNNCTAGCGTTAC | 70 | TGCAGGACCAGAGAATTCGAATACAACGCTTAGNNNCTAGCGTTAC | 310 | TGCAGGACCAGAGAATTCGAATACAAGTGACGANNNCTAGCGTTAC | 550 |
| TGCAGGACCAGAGAATTCGAATACACCCGCACTNNNCTAGCGTTAC | 71 | TGCAGGACCAGAGAATTCGAATACATCAAGCTGNNNCTAGCGTTAC | 311 | TGCAGGACCAGAGAATTCGAATACAATACCTCCNNNCTAGCGTTAC | 551 |
| TGCAGGACCAGAGAATTCGAATACACCACGATANNNCTAGCGTTAC | 72 | TGCAGGACCAGAGAATTCGAATACATAGCTAATNNNCTAGCGTTAC | 312 | TGCAGGACCAGAGAATTCGAATACACTTTTTGANNNCTAGCGTTAC | 552 |
| TGCAGGACCAGAGAATTCGAATACACGGTACATNNNCTAGCGTTAC | 73 | TGCAGGACCAGAGAATTCGAATACACGGCATTANNNCTAGCGTTAC | 313 | TGCAGGACCAGAGAATTCGAATACAATATCATGNNNCTAGCGTTAC | 553 |
| TGCAGGACCAGAGAATTCGAATACACCATATCCNNNCTAGCGTTAC | 74 | TGCAGGACCAGAGAATTCGAATACAAATGATGANNNCTAGCGTTAC | 314 | TGCAGGACCAGAGAATTCGAATACATACATATGNNNCTAGCGTTAC | 554 |

FIG. 12C

| Pool-1 | SEQ ID NO: | Pool-2 | SEQ ID NO: | Pool-3 | SEQ ID NO: |
|---|---|---|---|---|---|
| TGCAGGACCAGAGAATTCGAATACACATACGGTNNNCTAGCGTTAC | 75 | TGCAGGACCAGAGAATTCGAATACATCGCGATANNNCTAGCGTTAC | 315 | TGCAGGACCAGAGAATTCGAATACAACTTTTGTNNNCTAGCGTTAC | 555 |
| TGCAGGACCAGAGAATTCGAATACAAATAGCTTNNNCTAGCGTTAC | 76 | TGCAGGACCAGAGAATTCGAATACACACAGGTTNNNCTAGCGTTAC | 316 | TGCAGGACCAGAGAATTCGAATACATAATGTACNNNCTAGCGTTAC | 556 |
| TGCAGGACCAGAGAATTCGAATACACCAGGTATNNNCTAGCGTTAC | 77 | TGCAGGACCAGAGAATTCGAATACAACGGTGCCNNNCTAGCGTTAC | 317 | TGCAGGACCAGAGAATTCGAATACAAACGACAGNNNCTAGCGTTAC | 557 |
| TGCAGGACCAGAGAATTCGAATACACAACCTGANNNCTAGCGTTAC | 78 | TGCAGGACCAGAGAATTCGAATACAGTTACAGCNNNCTAGCGTTAC | 318 | TGCAGGACCAGAGAATTCGAATACAGCTCCTATNNNCTAGCGTTAC | 558 |
| TGCAGGACCAGAGAATTCGAATACATGATGGTCNNNCTAGCGTTAC | 79 | TGCAGGACCAGAGAATTCGAATACATGCGATGTNNNCTAGCGTTAC | 319 | TGCAGGACCAGAGAATTCGAATACACCGAAACTNNNCTAGCGTTAC | 559 |
| TGCAGGACCAGAGAATTCGAATACAGGAGCCGANNNCTAGCGTTAC | 80 | TGCAGGACCAGAGAATTCGAATACAATGGTGCTNNNCTAGCGTTAC | 320 | TGCAGGACCAGAGAATTCGAATACAGCTAGGAANNNCTAGCGTTAC | 560 |
| TGCAGGACCAGAGAATTCGAATACAATGCGGCCNNNCTAGCGTTAC | 81 | TGCAGGACCAGAGAATTCGAATACAACCCCAGGNNNCTAGCGTTAC | 321 | TGCAGGACCAGAGAATTCGAATACAGCTTCCGCNNNCTAGCGTTAC | 561 |
| TGCAGGACCAGAGAATTCGAATACATGCTGTAGNNNCTAGCGTTAC | 82 | TGCAGGACCAGAGAATTCGAATACAGCAGACGGNNNCTAGCGTTAC | 322 | TGCAGGACCAGAGAATTCGAATACAACAGCATCNNNCTAGCGTTAC | 562 |
| TGCAGGACCAGAGAATTCGAATACAGCATTGACNNNCTAGCGTTAC | 83 | TGCAGGACCAGAGAATTCGAATACACTGGCAGCNNNCTAGCGTTAC | 323 | TGCAGGACCAGAGAATTCGAATACAACGAGAGTNNNCTAGCGTTAC | 563 |
| TGCAGGACCAGAGAATTCGAATACATTTGTACTNNNCTAGCGTTAC | 84 | TGCAGGACCAGAGAATTCGAATACAAGAGAGTCNNNCTAGCGTTAC | 324 | TGCAGGACCAGAGAATTCGAATACAATCATATGNNNCTAGCGTTAC | 564 |
| TGCAGGACCAGAGAATTCGAATACACATATGGCNNNCTAGCGTTAC | 85 | TGCAGGACCAGAGAATTCGAATACACGTTTTATNNNCTAGCGTTAC | 325 | TGCAGGACCAGAGAATTCGAATACATGAGATTTNNNCTAGCGTTAC | 565 |
| TGCAGGACCAGAGAATTCGAATACAGCATGAAGNNNCTAGCGTTAC | 86 | TGCAGGACCAGAGAATTCGAATACAAGAGGTCANNNCTAGCGTTAC | 326 | TGCAGGACCAGAGAATTCGAATACAGCCGGCCGNNNCTAGCGTTAC | 566 |
| TGCAGGACCAGAGAATTCGAATACACAGGAAACNNNCTAGCGTTAC | 87 | TGCAGGACCAGAGAATTCGAATACATTCTCTCCNNNCTAGCGTTAC | 327 | TGCAGGACCAGAGAATTCGAATACAAGGCGCAGNNNCTAGCGTTAC | 567 |
| TGCAGGACCAGAGAATTCGAATACACCTAAGACNNNCTAGCGTTAC | 88 | TGCAGGACCAGAGAATTCGAATACACGTGTCTTNNNCTAGCGTTAC | 328 | TGCAGGACCAGAGAATTCGAATACAGTACACACNNNCTAGCGTTAC | 568 |
| TGCAGGACCAGAGAATTCGAATACAACCTAGGTNNNCTAGCGTTAC | 89 | TGCAGGACCAGAGAATTCGAATACACTCGCAANNNCTAGCGTTAC | 329 | TGCAGGACCAGAGAATTCGAATACAAGATTTCANNNCTAGCGTTAC | 569 |
| TGCAGGACCAGAGAATTCGAATACACCATTGTCNNNCTAGCGTTAC | 90 | TGCAGGACCAGAGAATTCGAATACATCTTATGTNNNCTAGCGTTAC | 330 | TGCAGGACCAGAGAATTCGAATACATGCATCTCNNNCTAGCGTTAC | 570 |
| TGCAGGACCAGAGAATTCGAATACATCGGTTTCNNNCTAGCGTTAC | 91 | TGCAGGACCAGAGAATTCGAATACATCGGCACGNNNCTAGCGTTAC | 331 | TGCAGGACCAGAGAATTCGAATACACTCAGAGTNNNCTAGCGTTAC | 571 |
| TGCAGGACCAGAGAATTCGAATACACACCTGTTNNNCTAGCGTTAC | 92 | TGCAGGACCAGAGAATTCGAATACACGTTTCTGNNNCTAGCGTTAC | 332 | TGCAGGACCAGAGAATTCGAATACAACTCTGTCNNNCTAGCGTTAC | 572 |
| TGCAGGACCAGAGAATTCGAATACAAGAGAGAGNNNCTAGCGTTAC | 93 | TGCAGGACCAGAGAATTCGAATACAATGTGAGGNNNCTAGCGTTAC | 333 | TGCAGGACCAGAGAATTCGAATACATTATCCGCNNNCTAGCGTTAC | 573 |
| TGCAGGACCAGAGAATTCGAATACAATGCCCGNNNCTAGCGTTAC | 94 | TGCAGGACCAGAGAATTCGAATACAAGAAACATNNNCTAGCGTTAC | 334 | TGCAGGACCAGAGAATTCGAATACAGCCCTTGCNNNCTAGCGTTAC | 574 |
| TGCAGGACCAGAGAATTCGAATACATAGCGTGTNNNCTAGCGTTAC | 95 | TGCAGGACCAGAGAATTCGAATACAGAGAGAAGNNNCTAGCGTTAC | 335 | TGCAGGACCAGAGAATTCGAATACAAACTTCTTNNNCTAGCGTTAC | 575 |
| TGCAGGACCAGAGAATTCGAATACAGAAGACACNNNCTAGCGTTAC | 96 | TGCAGGACCAGAGAATTCGAATACACTTCAGGANNNCTAGCGTTAC | 336 | TGCAGGACCAGAGAATTCGAATACATTGTAGGCNNNCTAGCGTTAC | 576 |
| TGCAGGACCAGAGAATTCGAATACATCATTTGTNNNCTAGCGTTAC | 97 | TGCAGGACCAGAGAATTCGAATACATCCCTCGGNNNCTAGCGTTAC | 337 | TGCAGGACCAGAGAATTCGAATACATGACCCAANNNCTAGCGTTAC | 577 |
| TGCAGGACCAGAGAATTCGAATACATCGAACACNNNCTAGCGTTAC | 98 | TGCAGGACCAGAGAATTCGAATACACCTTCCTTNNNCTAGCGTTAC | 338 | TGCAGGACCAGAGAATTCGAATACACCTCTGTANNNCTAGCGTTAC | 578 |
| TGCAGGACCAGAGAATTCGAATACAAGCTTACGNNNCTAGCGTTAC | 99 | TGCAGGACCAGAGAATTCGAATACATAGTTATGNNNCTAGCGTTAC | 339 | TGCAGGACCAGAGAATTCGAATACAAGCCACTANNNCTAGCGTTAC | 579 |
| TGCAGGACCAGAGAATTCGAATACACTCGGTTTNNNCTAGCGTTAC | 100 | TGCAGGACCAGAGAATTCGAATACAGCATAGAGNNNCTAGCGTTAC | 340 | TGCAGGACCAGAGAATTCGAATACATGTATGATNNNCTAGCGTTAC | 580 |
| TGCAGGACCAGAGAATTCGAATACAAATCGTTANNNCTAGCGTTAC | 101 | TGCAGGACCAGAGAATTCGAATACATAGCTCCTNNNCTAGCGTTAC | 341 | TGCAGGACCAGAGAATTCGAATACACAGGTCGCNNNCTAGCGTTAC | 581 |
| TGCAGGACCAGAGAATTCGAATACATAACAGTTNNNCTAGCGTTAC | 102 | TGCAGGACCAGAGAATTCGAATACAACCACGTANNNCTAGCGTTAC | 342 | TGCAGGACCAGAGAATTCGAATACATTTTTTTNNNCTAGCGTTAC | 582 |
| TGCAGGACCAGAGAATTCGAATACAATCCTGTCNNNCTAGCGTTAC | 103 | TGCAGGACCAGAGAATTCGAATACACATCGTCTNNNCTAGCGTTAC | 343 | TGCAGGACCAGAGAATTCGAATACATTTGCGGANNNCTAGCGTTAC | 583 |
| TGCAGGACCAGAGAATTCGAATACAGTAATGTTNNNCTAGCGTTAC | 104 | TGCAGGACCAGAGAATTCGAATACAAGAGATTANNNCTAGCGTTAC | 344 | TGCAGGACCAGAGAATTCGAATACAAGCCTGTANNNCTAGCGTTAC | 584 |
| TGCAGGACCAGAGAATTCGAATACATTGCGCGGNNNCTAGCGTTAC | 105 | TGCAGGACCAGAGAATTCGAATACAATCAAAGANNNCTAGCGTTAC | 345 | TGCAGGACCAGAGAATTCGAATACAGCGGCACTNNNCTAGCGTTAC | 585 |
| TGCAGGACCAGAGAATTCGAATACAGTCAGGAANNNCTAGCGTTAC | 106 | TGCAGGACCAGAGAATTCGAATACAGGAGTACANNNCTAGCGTTAC | 346 | TGCAGGACCAGAGAATTCGAATACATGTTGAGCNNNCTAGCGTTAC | 586 |
| TGCAGGACCAGAGAATTCGAATACAGTTAAAAGNNNCTAGCGTTAC | 107 | TGCAGGACCAGAGAATTCGAATACAATAGCAGGNNNCTAGCGTTAC | 347 | TGCAGGACCAGAGAATTCGAATACAAAAAGTTGNNNCTAGCGTTAC | 587 |

FIG. 12D

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CATGTCATAANNNCTAGCGTTAC | 108 | TGCAGGACCAGAGAATTCGAATA CATCTAATTCNNNCTAGCGTTAC | 348 | TGCAGGACCAGAGAATTCGAATA CACGGTGCCANNNCTAGCGTTAC | 588 |
| TGCAGGACCAGAGAATTCGAATA CAACTTGAATNNNCTAGCGTTAC | 109 | TGCAGGACCAGAGAATTCGAATA CAGTTCCCGCNNNCTAGCGTTAC | 349 | TGCAGGACCAGAGAATTCGAATA CACAGCGGTCNNNCTAGCGTTAC | 589 |
| TGCAGGACCAGAGAATTCGAATA CATGTGGCATNNNCTAGCGTTAC | 110 | TGCAGGACCAGAGAATTCGAATA CATAGATTGNNNCTAGCGTTAC | 350 | TGCAGGACCAGAGAATTCGAATA CAAGCTAACCNNNCTAGCGTTAC | 590 |
| TGCAGGACCAGAGAATTCGAATA CATCTACACCNNNCTAGCGTTAC | 111 | TGCAGGACCAGAGAATTCGAATA CACGGCAGAGNNNCTAGCGTTAC | 351 | TGCAGGACCAGAGAATTCGAATA CAACGGCGTCNNNCTAGCGTTAC | 591 |
| TGCAGGACCAGAGAATTCGAATA CATCATGCCTNNNCTAGCGTTAC | 112 | TGCAGGACCAGAGAATTCGAATA CACCTCGTGCNNNCTAGCGTTAC | 352 | TGCAGGACCAGAGAATTCGAATA CATAGTTCAANNNCTAGCGTTAC | 592 |
| TGCAGGACCAGAGAATTCGAATA CATCTAGCCTNNNCTAGCGTTAC | 113 | TGCAGGACCAGAGAATTCGAATA CACCCTTGATNNNCTAGCGTTAC | 353 | TGCAGGACCAGAGAATTCGAATA CAATGTAGCCNNNCTAGCGTTAC | 593 |
| TGCAGGACCAGAGAATTCGAATA CAATAAAGCANNNCTAGCGTTAC | 114 | TGCAGGACCAGAGAATTCGAATA CACGTCACGNNNCTAGCGTTAC | 354 | TGCAGGACCAGAGAATTCGAATA CAAGAAGCACNNNCTAGCGTTAC | 594 |
| TGCAGGACCAGAGAATTCGAATA CATGCATAATNNNCTAGCGTTAC | 115 | TGCAGGACCAGAGAATTCGAATA CAGTTTGGCANNNCTAGCGTTAC | 355 | TGCAGGACCAGAGAATTCGAATA CAGAAGCGCGNNNCTAGCGTTAC | 595 |
| TGCAGGACCAGAGAATTCGAATA CACATGACGTNNNCTAGCGTTAC | 116 | TGCAGGACCAGAGAATTCGAATA CATGCTCTGTNNNCTAGCGTTAC | 356 | TGCAGGACCAGAGAATTCGAATA CACGGTATACNNNCTAGCGTTAC | 596 |
| TGCAGGACCAGAGAATTCGAATA CACTTATCATNNNCTAGCGTTAC | 117 | TGCAGGACCAGAGAATTCGAATA CATCAGGTATANNNCTAGCGTTAC | 357 | TGCAGGACCAGAGAATTCGAATA CATAACATACNNNCTAGCGTTAC | 597 |
| TGCAGGACCAGAGAATTCGAATA CACGGCCTGANNNCTAGCGTTAC | 118 | TGCAGGACCAGAGAATTCGAATA CACCCAAGTANNNCTAGCGTTAC | 358 | TGCAGGACCAGAGAATTCGAATA CACTGCTATCNNNCTAGCGTTAC | 598 |
| TGCAGGACCAGAGAATTCGAATA CACGTCAATGNNNCTAGCGTTAC | 119 | TGCAGGACCAGAGAATTCGAATA CAAAGCTAAANNNCTAGCGTTAC | 359 | TGCAGGACCAGAGAATTCGAATA CACGGCAACCNNNCTAGCGTTAC | 599 |
| TGCAGGACCAGAGAATTCGAATA CACTTATACTNNNCTAGCGTTAC | 120 | TGCAGGACCAGAGAATTCGAATA CAAGATCCACNNNCTAGCGTTAC | 360 | TGCAGGACCAGAGAATTCGAATA CACAAAAACANNNCTAGCGTTAC | 600 |
| TGCAGGACCAGAGAATTCGAATA CAGGAGGTATNNNCTAGCGTTAC | 121 | TGCAGGACCAGAGAATTCGAATA CAGCATCGGCNNNCTAGCGTTAC | 361 | TGCAGGACCAGAGAATTCGAATA CACGTTAGCANNNCTAGCGTTAC | 601 |
| TGCAGGACCAGAGAATTCGAATA CAATTGTTCTNNNCTAGCGTTAC | 122 | TGCAGGACCAGAGAATTCGAATA CACTCTGGAANNNCTAGCGTTAC | 362 | TGCAGGACCAGAGAATTCGAATA CACCCTAATCNNNCTAGCGTTAC | 602 |
| TGCAGGACCAGAGAATTCGAATA CAAACTCCAGNNNCTAGCGTTAC | 123 | TGCAGGACCAGAGAATTCGAATA CAAGCTCTGACNNNCTAGCGTTAC | 363 | TGCAGGACCAGAGAATTCGAATA CATGTGGCCGNNNCTAGCGTTAC | 603 |
| TGCAGGACCAGAGAATTCGAATA CACGAGGTCCNNNCTAGCGTTAC | 124 | TGCAGGACCAGAGAATTCGAATA CAGAGGCCGANNNCTAGCGTTAC | 364 | TGCAGGACCAGAGAATTCGAATA CATCTAGAGCNNNCTAGCGTTAC | 604 |
| TGCAGGACCAGAGAATTCGAATA CACGCGACCANNNCTAGCGTTAC | 125 | TGCAGGACCAGAGAATTCGAATA CATGGTGGAANNNCTAGCGTTAC | 365 | TGCAGGACCAGAGAATTCGAATA CATACGCATGNNNCTAGCGTTAC | 605 |
| TGCAGGACCAGAGAATTCGAATA CATGCCGCCTNNNCTAGCGTTAC | 126 | TGCAGGACCAGAGAATTCGAATA CACGGTGTTANNNCTAGCGTTAC | 366 | TGCAGGACCAGAGAATTCGAATA CATTGCCCGNNNCTAGCGTTAC | 606 |
| TGCAGGACCAGAGAATTCGAATA CAGTTACGACNNNCTAGCGTTAC | 127 | TGCAGGACCAGAGAATTCGAATA CATCCGCGANNNCTAGCGTTAC | 367 | TGCAGGACCAGAGAATTCGAATA CATGGTTCCTNNNCTAGCGTTAC | 607 |
| TGCAGGACCAGAGAATTCGAATA CATTATCATCNNNCTAGCGTTAC | 128 | TGCAGGACCAGAGAATTCGAATA CAGCTGTGTANNNCTAGCGTTAC | 368 | TGCAGGACCAGAGAATTCGAATA CAAACGGTGANNNCTAGCGTTAC | 608 |
| TGCAGGACCAGAGAATTCGAATA CACCTTCTCTNNNGATCGACATG | 129 | TGCAGGACCAGAGAATTCGAATA CAACGTGCGCNNNGATCGACATG | 369 | TGCAGGACCAGAGAATTCGAATA CAGGCTATACNNNGATCGACATG | 609 |
| TGCAGGACCAGAGAATTCGAATA CAAACAGGTGNNNGATCGACATG | 130 | TGCAGGACCAGAGAATTCGAATA CAATCAGCCANNNGATCGACATG | 370 | TGCAGGACCAGAGAATTCGAATA CAATTGGTTANNNGATCGACATG | 610 |
| TGCAGGACCAGAGAATTCGAATA CAACTTGTCCNNNGATCGACATG | 131 | TGCAGGACCAGAGAATTCGAATA CAGATACTTANNNGATCGACATG | 371 | TGCAGGACCAGAGAATTCGAATA CACAGGATGANNNGATCGACATG | 611 |
| TGCAGGACCAGAGAATTCGAATA CATTGGTAATNNNGATCGACATG | 132 | TGCAGGACCAGAGAATTCGAATA CAATTCGCCNNNGATCGACATG | 372 | TGCAGGACCAGAGAATTCGAATA CACGTTATCCNNNGATCGACATG | 612 |
| TGCAGGACCAGAGAATTCGAATA CAGGACTCGCNNNGATCGACATG | 133 | TGCAGGACCAGAGAATTCGAATA CACTTAAAGTNNNGATCGACATG | 373 | TGCAGGACCAGAGAATTCGAATA CAGTTCAATANNNGATCGACATG | 613 |
| TGCAGGACCAGAGAATTCGAATA CATGCGTCAANNNGATCGACATG | 134 | TGCAGGACCAGAGAATTCGAATA CATATGCCCTNNNGATCGACATG | 374 | TGCAGGACCAGAGAATTCGAATA CACAAAATCTNNNGATCGACATG | 614 |
| TGCAGGACCAGAGAATTCGAATA CACAGAATAANNNGATCGACATG | 135 | TGCAGGACCAGAGAATTCGAATA CAACTTGGCANNNGATCGACATG | 375 | TGCAGGACCAGAGAATTCGAATA CACTGCAAACNNNGATCGACATG | 615 |
| TGCAGGACCAGAGAATTCGAATA CATCCCAGGCNNNGATCGACATG | 136 | TGCAGGACCAGAGAATTCGAATA CAAGGACCANNNGATCGACATG | 376 | TGCAGGACCAGAGAATTCGAATA CAGGTGCCCANNNGATCGACATG | 616 |
| TGCAGGACCAGAGAATTCGAATA CAATTCTTGNNNGATCGACATG | 137 | TGCAGGACCAGAGAATTCGAATA CATGAGCGAANNNGATCGACATG | 377 | TGCAGGACCAGAGAATTCGAATA CACGATAACCNNNGATCGACATG | 617 |
| TGCAGGACCAGAGAATTCGAATA CAACTTGTAANNNGATCGACATG | 138 | TGCAGGACCAGAGAATTCGAATA CATGCTGTGANNNGATCGACATG | 378 | TGCAGGACCAGAGAATTCGAATA CATTATGACANNNGATCGACATG | 618 |
| TGCAGGACCAGAGAATTCGAATA CACACGGTGCNNNGATCGACATG | 139 | TGCAGGACCAGAGAATTCGAATA CAGGTTCGTANNNGATCGACATG | 379 | TGCAGGACCAGAGAATTCGAATA CAACCTTCACNNNGATCGACATG | 619 |
| TGCAGGACCAGAGAATTCGAATA CAAACTCGGTNNNGATCGACATG | 140 | TGCAGGACCAGAGAATTCGAATA CAACAAACAANNNGATCGACATG | 380 | TGCAGGACCAGAGAATTCGAATA CATCTTCTCCNNNGATCGACATG | 620 |

FIG. 12E

| Pool-1 | SEQ ID NO: | Pool-2 | SEQ ID NO: | Pool-3 | SEQ ID NO: |
|---|---|---|---|---|---|
| TGCAGGACCAGAGAATTCGAATACAGCCTATTCNNNGATCGACATG | 141 | TGCAGGACCAGAGAATTCGAATACAAGCTAGAGNNNGATCGACATG | 381 | TGCAGGACCAGAGAATTCGAATACACCCCAGCTNNNGATCGACATG | 621 |
| TGCAGGACCAGAGAATTCGAATACACCGCTAAANNNGATCGACATG | 142 | TGCAGGACCAGAGAATTCGAATACATTAAATATNNNGATCGACATG | 382 | TGCAGGACCAGAGAATTCGAATACACTAGTGTGNNNGATCGACATG | 622 |
| TGCAGGACCAGAGAATTCGAATACAGTGAGATGNNNGATCGACATG | 143 | TGCAGGACCAGAGAATTCGAATACAAGGAGTCANNNGATCGACATG | 383 | TGCAGGACCAGAGAATTCGAATACAGTTCTAAANNNGATCGACATG | 623 |
| TGCAGGACCAGAGAATTCGAATACATCTCTCAGNNNGATCGACATG | 144 | TGCAGGACCAGAGAATTCGAATACACGCACAGCNNNGATCGACATG | 384 | TGCAGGACCAGAGAATTCGAATACAGCGTTTTCNNNGATCGACATG | 624 |
| TGCAGGACCAGAGAATTCGAATACATCTCTAGCNNNGATCGACATG | 145 | TGCAGGACCAGAGAATTCGAATACAGCGGACAGNNNGATCGACATG | 385 | TGCAGGACCAGAGAATTCGAATACAGTCTGCCCNNNGATCGACATG | 625 |
| TGCAGGACCAGAGAATTCGAATACACAAGCGCCNNNGATCGACATG | 146 | TGCAGGACCAGAGAATTCGAATACACGCTCGTCNNNGATCGACATG | 386 | TGCAGGACCAGAGAATTCGAATACAACAGAAATNNNGATCGACATG | 626 |
| TGCAGGACCAGAGAATTCGAATACAGGCAGTAANNNGATCGACATG | 147 | TGCAGGACCAGAGAATTCGAATACATCTGATGGNNNGATCGACATG | 387 | TGCAGGACCAGAGAATTCGAATACATTGCTATTNNNGATCGACATG | 627 |
| TGCAGGACCAGAGAATTCGAATACATTGGCTGANNNGATCGACATG | 148 | TGCAGGACCAGAGAATTCGAATACAGGCTAGAANNNGATCGACATG | 388 | TGCAGGACCAGAGAATTCGAATACACCCTGTGCNNNGATCGACATG | 628 |
| TGCAGGACCAGAGAATTCGAATACAACAGCGAANNNGATCGACATG | 149 | TGCAGGACCAGAGAATTCGAATACAATGAGGCANNNGATCGACATG | 389 | TGCAGGACCAGAGAATTCGAATACAGCAGTCCGNNNGATCGACATG | 629 |
| TGCAGGACCAGAGAATTCGAATACAAAGTTTCANNNGATCGACATG | 150 | TGCAGGACCAGAGAATTCGAATACACACCCGTCNNNGATCGACATG | 390 | TGCAGGACCAGAGAATTCGAATACAGTAACCCANNNGATCGACATG | 630 |
| TGCAGGACCAGAGAATTCGAATACACGCTCTATNNNGATCGACATG | 151 | TGCAGGACCAGAGAATTCGAATACATCATCGGANNNGATCGACATG | 391 | TGCAGGACCAGAGAATTCGAATACAACATTGTANNNGATCGACATG | 631 |
| TGCAGGACCAGAGAATTCGAATACATAGGAGTGNNNGATCGACATG | 152 | TGCAGGACCAGAGAATTCGAATACAGGCAAGCGNNNGATCGACATG | 392 | TGCAGGACCAGAGAATTCGAATACAAAACCGTCNNNGATCGACATG | 632 |
| TGCAGGACCAGAGAATTCGAATACATCAGCACANNNGATCGACATG | 153 | TGCAGGACCAGAGAATTCGAATACACAGTCGATNNNGATCGACATG | 393 | TGCAGGACCAGAGAATTCGAATACAATTCTGCCNNNGATCGACATG | 633 |
| TGCAGGACCAGAGAATTCGAATACACGAACTACNNNGATCGACATG | 154 | TGCAGGACCAGAGAATTCGAATACATGCTACTCNNNGATCGACATG | 394 | TGCAGGACCAGAGAATTCGAATACATCTAGGCANNNGATCGACATG | 634 |
| TGCAGGACCAGAGAATTCGAATACATACTAAACNNNGATCGACATG | 155 | TGCAGGACCAGAGAATTCGAATACATCCATACANNNGATCGACATG | 395 | TGCAGGACCAGAGAATTCGAATACAGGTCTACANNNGATCGACATG | 635 |
| TGCAGGACCAGAGAATTCGAATACAGGTACAAGNNNGATCGACATG | 156 | TGCAGGACCAGAGAATTCGAATACAACCGCGACNNNGATCGACATG | 396 | TGCAGGACCAGAGAATTCGAATACAGGTGAGCGNNNGATCGACATG | 636 |
| TGCAGGACCAGAGAATTCGAATACAACAGGCTTNNNGATCGACATG | 157 | TGCAGGACCAGAGAATTCGAATACAGGCAAAGTNNNGATCGACATG | 397 | TGCAGGACCAGAGAATTCGAATACATGTCTTTANNNGATCGACATG | 637 |
| TGCAGGACCAGAGAATTCGAATACAGAAACCCTNNNGATCGACATG | 158 | TGCAGGACCAGAGAATTCGAATACAGGATCCCGNNNGATCGACATG | 398 | TGCAGGACCAGAGAATTCGAATACATGGCTTGANNNGATCGACATG | 638 |
| TGCAGGACCAGAGAATTCGAATACATCCGCATTNNNGATCGACATG | 159 | TGCAGGACCAGAGAATTCGAATACACCTCTCTTNNNGATCGACATG | 399 | TGCAGGACCAGAGAATTCGAATACAATTACGCGNNNGATCGACATG | 639 |
| TGCAGGACCAGAGAATTCGAATACACAATCTGGNNNGATCGACATG | 160 | TGCAGGACCAGAGAATTCGAATACATCGTCGCCNNNGATCGACATG | 400 | TGCAGGACCAGAGAATTCGAATACATGGCTCTTNNNGATCGACATG | 640 |
| TGCAGGACCAGAGAATTCGAATACAACCTTACCNNNGATCGACATG | 161 | TGCAGGACCAGAGAATTCGAATACACCTATGTCNNNGATCGACATG | 401 | TGCAGGACCAGAGAATTCGAATACACACTCACTNNNGATCGACATG | 641 |
| TGCAGGACCAGAGAATTCGAATACAGCGGTCTGNNNGATCGACATG | 162 | TGCAGGACCAGAGAATTCGAATACAGGATGCTTNNNGATCGACATG | 402 | TGCAGGACCAGAGAATTCGAATACACTGCAGGCNNNGATCGACATG | 642 |
| TGCAGGACCAGAGAATTCGAATACAAATCACGCNNNGATCGACATG | 163 | TGCAGGACCAGAGAATTCGAATACAATTGAGAANNNGATCGACATG | 403 | TGCAGGACCAGAGAATTCGAATACACCCAATCTNNNGATCGACATG | 643 |
| TGCAGGACCAGAGAATTCGAATACAAATAGTAGNNNGATCGACATG | 164 | TGCAGGACCAGAGAATTCGAATACAGTGTTGTGNNNGATCGACATG | 404 | TGCAGGACCAGAGAATTCGAATACAACGTAACCNNNGATCGACATG | 644 |
| TGCAGGACCAGAGAATTCGAATACAGGCATCTANNNGATCGACATG | 165 | TGCAGGACCAGAGAATTCGAATACAAAGCAATAGNNNGATCGACATG | 405 | TGCAGGACCAGAGAATTCGAATACAACCGTCCCNNNGATCGACATG | 645 |
| TGCAGGACCAGAGAATTCGAATACAACCGCCTGNNNGATCGACATG | 166 | TGCAGGACCAGAGAATTCGAATACATTAGCGCANNNGATCGACATG | 406 | TGCAGGACCAGAGAATTCGAATACATTCGCGAANNNGATCGACATG | 646 |
| TGCAGGACCAGAGAATTCGAATACAGACCCGGTNNNGATCGACATG | 167 | TGCAGGACCAGAGAATTCGAATACAAACGGATGNNNGATCGACATG | 407 | TGCAGGACCAGAGAATTCGAATACACGCACAATNNNGATCGACATG | 647 |
| TGCAGGACCAGAGAATTCGAATACACGGTAAAGNNNGATCGACATG | 168 | TGCAGGACCAGAGAATTCGAATACAGCATGGAANNNGATCGACATG | 408 | TGCAGGACCAGAGAATTCGAATACACAATCTCCNNNGATCGACATG | 648 |
| TGCAGGACCAGAGAATTCGAATACAAGGATGCANNNGATCGACATG | 169 | TGCAGGACCAGAGAATTCGAATACATCTCTATANNNGATCGACATG | 409 | TGCAGGACCAGAGAATTCGAATACATCAGAGTCNNNGATCGACATG | 649 |
| TGCAGGACCAGAGAATTCGAATACATTCTGGAGNNNGATCGACATG | 170 | TGCAGGACCAGAGAATTCGAATACACTGCGCCTNNNGATCGACATG | 410 | TGCAGGACCAGAGAATTCGAATACAAATCGTGCNNNGATCGACATG | 650 |
| TGCAGGACCAGAGAATTCGAATACAGCTCAAACNNNGATCGACATG | 171 | TGCAGGACCAGAGAATTCGAATACAGATTCGCANNNGATCGACATG | 411 | TGCAGGACCAGAGAATTCGAATACACTAGCATGNNNGATCGACATG | 651 |
| TGCAGGACCAGAGAATTCGAATACATAAGTTACNNNGATCGACATG | 172 | TGCAGGACCAGAGAATTCGAATACAATCTATCTNNNGATCGACATG | 412 | TGCAGGACCAGAGAATTCGAATACAGATTAACTNNNGATCGACATG | 652 |
| TGCAGGACCAGAGAATTCGAATACACAACCCTTNNNGATCGACATG | 173 | TGCAGGACCAGAGAATTCGAATACAGTCACCCCNNNGATCGACATG | 413 | TGCAGGACCAGAGAATTCGAATACAGGCTACGCNNNGATCGACATG | 653 |

FIG. 12F

| Pool-1 | SEQ ID NO: | Pool-2 | SEQ ID NO: | Pool-3 | SEQ ID NO: |
|---|---|---|---|---|---|
| TGCAGGACCAGAGAATTCGAATACACCTTCCGGNNNGATCGACATG | 174 | TGCAGGACCAGAGAATTCGAATACACGTTGTGANNNGATCGACATG | 414 | TGCAGGACCAGAGAATTCGAATACAATACGAGGNNNGATCGACATG | 654 |
| TGCAGGACCAGAGAATTCGAATACAGTGAGAGTNNNGATCGACATG | 175 | TGCAGGACCAGAGAATTCGAATACAGCTCTGCCNNNGATCGACATG | 415 | TGCAGGACCAGAGAATTCGAATACAAAATGTCTNNNGATCGACATG | 655 |
| TGCAGGACCAGAGAATTCGAATACAGCGTCCAGNNNGATCGACATG | 176 | TGCAGGACCAGAGAATTCGAATACACATCGATGNNNGATCGACATG | 416 | TGCAGGACCAGAGAATTCGAATACAGCCCATCGNNNGATCGACATG | 656 |
| TGCAGGACCAGAGAATTCGAATACATTTATTCGNNNGATCGACATG | 177 | TGCAGGACCAGAGAATTCGAATACAAGTCGCCGNNNGATCGACATG | 417 | TGCAGGACCAGAGAATTCGAATACACTCCCGTGNNNGATCGACATG | 657 |
| TGCAGGACCAGAGAATTCGAATACAGTAATAAGNNNGATCGACATG | 178 | TGCAGGACCAGAGAATTCGAATACAGATAGCGANNNGATCGACATG | 418 | TGCAGGACCAGAGAATTCGAATACAGATAAGGCNNNGATCGACATG | 658 |
| TGCAGGACCAGAGAATTCGAATACATACAAGCCNNNGATCGACATG | 179 | TGCAGGACCAGAGAATTCGAATACATCTTTGGCNNNGATCGACATG | 419 | TGCAGGACCAGAGAATTCGAATACAGCACATCANNNGATCGACATG | 659 |
| TGCAGGACCAGAGAATTCGAATACAAAGCCGAANNNGATCGACATG | 180 | TGCAGGACCAGAGAATTCGAATACATCTCATCGNNNGATCGACATG | 420 | TGCAGGACCAGAGAATTCGAATACATCCTATGCNNNGATCGACATG | 660 |
| TGCAGGACCAGAGAATTCGAATACAATACTTTCNNNGATCGACATG | 181 | TGCAGGACCAGAGAATTCGAATACATGAGCGCCNNNGATCGACATG | 421 | TGCAGGACCAGAGAATTCGAATACACGCATCCNNNGATCGACATG | 661 |
| TGCAGGACCAGAGAATTCGAATACACTGGATCANNNGATCGACATG | 182 | TGCAGGACCAGAGAATTCGAATACAAGTCTCGANNNGATCGACATG | 422 | TGCAGGACCAGAGAATTCGAATACAACCGGTCGNNNGATCGACATG | 662 |
| TGCAGGACCAGAGAATTCGAATACAAACGCCTANNNGATCGACATG | 183 | TGCAGGACCAGAGAATTCGAATACAAAGGTATANNNGATCGACATG | 423 | TGCAGGACCAGAGAATTCGAATACACACGATGTNNNGATCGACATG | 663 |
| TGCAGGACCAGAGAATTCGAATACAGTCGAGAANNNGATCGACATG | 184 | TGCAGGACCAGAGAATTCGAATACAGGTGTCGCNNNGATCGACATG | 424 | TGCAGGACCAGAGAATTCGAATACAAACTCGCANNNGATCGACATG | 664 |
| TGCAGGACCAGAGAATTCGAATACATAATTCTCNNNGATCGACATG | 185 | TGCAGGACCAGAGAATTCGAATACATCACATCCNNNGATCGACATG | 425 | TGCAGGACCAGAGAATTCGAATACACCCCTTCCNNNGATCGACATG | 665 |
| TGCAGGACCAGAGAATTCGAATACATAACCCTCNNNGATCGACATG | 186 | TGCAGGACCAGAGAATTCGAATACAGCATACACNNNGATCGACATG | 426 | TGCAGGACCAGAGAATTCGAATACATCTTCGTGNNNGATCGACATG | 666 |
| TGCAGGACCAGAGAATTCGAATACAGCGCTTGGNNNGATCGACATG | 187 | TGCAGGACCAGAGAATTCGAATACATCCAACAGNNNGATCGACATG | 427 | TGCAGGACCAGAGAATTCGAATACATATTTAAANNNGATCGACATG | 667 |
| TGCAGGACCAGAGAATTCGAATACACGGACACCNNNGATCGACATG | 188 | TGCAGGACCAGAGAATTCGAATACATCTGCCTANNNGATCGACATG | 428 | TGCAGGACCAGAGAATTCGAATACATTAATGCANNNGATCGACATG | 668 |
| TGCAGGACCAGAGAATTCGAATACATGGAAGTGNNNTGCATCAGGT | 189 | TGCAGGACCAGAGAATTCGAATACACACACCGGNNNTGCATCAGGT | 429 | TGCAGGACCAGAGAATTCGAATACACTTTGGTCNNNTGCATCAGGT | 669 |
| TGCAGGACCAGAGAATTCGAATACAAAGTCTATNNNTGCATCAGGT | 190 | TGCAGGACCAGAGAATTCGAATACAGACCTCCCNNNTGCATCAGGT | 430 | TGCAGGACCAGAGAATTCGAATACATACGAAGGNNNTGCATCAGGT | 670 |
| TGCAGGACCAGAGAATTCGAATACAATGATAGNNNTGCATCAGGT | 191 | TGCAGGACCAGAGAATTCGAATACATGGCAATCNNNTGCATCAGGT | 431 | TGCAGGACCAGAGAATTCGAATACAAGTCACTGNNNTGCATCAGGT | 671 |
| TGCAGGACCAGAGAATTCGAATACATTCTCCTCNNNTGCATCAGGT | 192 | TGCAGGACCAGAGAATTCGAATACATCTCCGGCNNNTGCATCAGGT | 432 | TGCAGGACCAGAGAATTCGAATACAGTTTATCTNNNTGCATCAGGT | 672 |
| TGCAGGACCAGAGAATTCGAATACACCAGCCCTNNNTGCATCAGGT | 193 | TGCAGGACCAGAGAATTCGAATACACCAGCGTGNNNTGCATCAGGT | 433 | TGCAGGACCAGAGAATTCGAATACATTTCGAAANNNTGCATCAGGT | 673 |
| TGCAGGACCAGAGAATTCGAATACAAACAAAACNNNTGCATCAGGT | 194 | TGCAGGACCAGAGAATTCGAATACAAAATATAANNNTGCATCAGGT | 434 | TGCAGGACCAGAGAATTCGAATACACAGATCACNNNTGCATCAGGT | 674 |
| TGCAGGACCAGAGAATTCGAATACACGCTCACCNNNTGCATCAGGT | 195 | TGCAGGACCAGAGAATTCGAATACAGCAATTTANNNTGCATCAGGT | 435 | TGCAGGACCAGAGAATTCGAATACATTGGAAGGNNNTGCATCAGGT | 675 |
| TGCAGGACCAGAGAATTCGAATACATGGTGATCNNNTGCATCAGGT | 196 | TGCAGGACCAGAGAATTCGAATACAACTCAGTGNNNTGCATCAGGT | 436 | TGCAGGACCAGAGAATTCGAATACAGTGCGGCTNNNTGCATCAGGT | 676 |
| TGCAGGACCAGAGAATTCGAATACAGTTGCTAGNNNTGCATCAGGT | 197 | TGCAGGACCAGAGAATTCGAATACAAGAGGCATNNNTGCATCAGGT | 437 | TGCAGGACCAGAGAATTCGAATACATGAAGGCANNNTGCATCAGGT | 677 |
| TGCAGGACCAGAGAATTCGAATACATCACCCTANNNTGCATCAGGT | 198 | TGCAGGACCAGAGAATTCGAATACATAGGCTTGNNNTGCATCAGGT | 438 | TGCAGGACCAGAGAATTCGAATACAAAAAGTACNNNTGCATCAGGT | 678 |
| TGCAGGACCAGAGAATTCGAATACAGACTCTGANNNTGCATCAGGT | 199 | TGCAGGACCAGAGAATTCGAATACACACACAGTNNNTGCATCAGGT | 439 | TGCAGGACCAGAGAATTCGAATACAGATGGAACNNNTGCATCAGGT | 679 |
| TGCAGGACCAGAGAATTCGAATACACGTATGACNNNTGCATCAGGT | 200 | TGCAGGACCAGAGAATTCGAATACATGATAGAANNNTGCATCAGGT | 440 | TGCAGGACCAGAGAATTCGAATACAGCCCTCGAGNNNTGCATCAGGT | 680 |
| TGCAGGACCAGAGAATTCGAATACATGCACCGNNNTGCATCAGGT | 201 | TGCAGGACCAGAGAATTCGAATACAGACACANNNTGCATCAGGT | 441 | TGCAGGACCAGAGAATTCGAATACAAAATAAATNNNTGCATCAGGT | 681 |
| TGCAGGACCAGAGAATTCGAATACAACTGATGCNNNTGCATCAGGT | 202 | TGCAGGACCAGAGAATTCGAATACACTGCCTCGNNNTGCATCAGGT | 442 | TGCAGGACCAGAGAATTCGAATACATTCCCCCNNNTGCATCAGGT | 682 |
| TGCAGGACCAGAGAATTCGAATACATACGTTCCNNNTGCATCAGGT | 203 | TGCAGGACCAGAGAATTCGAATACAGTTCCCANNNTGCATCAGGT | 443 | TGCAGGACCAGAGAATTCGAATACATTCTTCTTNNNTGCATCAGGT | 683 |
| TGCAGGACCAGAGAATTCGAATACACGGCCGCGNNNTGCATCAGGT | 204 | TGCAGGACCAGAGAATTCGAATACATTCAATAGNNNTGCATCAGGT | 444 | TGCAGGACCAGAGAATTCGAATACATTGTGGCANNNTGCATCAGGT | 684 |
| TGCAGGACCAGAGAATTCGAATACAATCTTTGTNNNTGCATCAGGT | 205 | TGCAGGACCAGAGAATTCGAATACATAGCCATGNNNTGCATCAGGT | 445 | TGCAGGACCAGAGAATTCGAATACATCCCATGTNNNTGCATCAGGT | 685 |
| TGCAGGACCAGAGAATTCGAATACATTGTACTTNNNTGCATCAGGT | 206 | TGCAGGACCAGAGAATTCGAATACAGTTGTTAANNNTGCATCAGGT | 446 | TGCAGGACCAGAGAATTCGAATACAGTGTTGACNNNTGCATCAGGT | 686 |

FIG. 12G

| Pool-1 | SEQ ID NO: | Pool-2 | SEQ ID NO: | Pool-3 | SEQ ID NO: |
|---|---|---|---|---|---|
| TGCAGGACCAGAGAATTCGAATACATGTTAATGNNNTGCATCAGGT | 207 | TGCAGGACCAGAGAATTCGAATACACTTGCACTNNNTGCATCAGGT | 447 | TGCAGGACCAGAGAATTCGAATACATCGCCTATNNNTGCATCAGGT | 687 |
| TGCAGGACCAGAGAATTCGAATACAAACATTGTNNNTGCATCAGGT | 208 | TGCAGGACCAGAGAATTCGAATACATTAGAGCCNNNTGCATCAGGT | 448 | TGCAGGACCAGAGAATTCGAATACACGCTGACGNNNTGCATCAGGT | 688 |
| TGCAGGACCAGAGAATTCGAATACACGCCCGAANNNTGCATCAGGT | 209 | TGCAGGACCAGAGAATTCGAATACAGCCCCTACNNNTGCATCAGGT | 449 | TGCAGGACCAGAGAATTCGAATACATGGTGGTTNNNTGCATCAGGT | 689 |
| TGCAGGACCAGAGAATTCGAATACACAGCGCACNNNTGCATCAGGT | 210 | TGCAGGACCAGAGAATTCGAATACAAATGGACGNNNTGCATCAGGT | 450 | TGCAGGACCAGAGAATTCGAATACACTATCTTANNNTGCATCAGGT | 690 |
| TGCAGGACCAGAGAATTCGAATACACGAGTATCNNNTGCATCAGGT | 211 | TGCAGGACCAGAGAATTCGAATACAAGACCTGTNNNTGCATCAGGT | 451 | TGCAGGACCAGAGAATTCGAATACAATAACCTANNNTGCATCAGGT | 691 |
| TGCAGGACCAGAGAATTCGAATACAATGGTGGANNNTGCATCAGGT | 212 | TGCAGGACCAGAGAATTCGAATACACTTACATTNNNTGCATCAGGT | 452 | TGCAGGACCAGAGAATTCGAATACAAGAGTGTGNNNTGCATCAGGT | 692 |
| TGCAGGACCAGAGAATTCGAATACATCACACTCNNNTGCATCAGGT | 213 | TGCAGGACCAGAGAATTCGAATACATAAGAAACNNNTGCATCAGGT | 453 | TGCAGGACCAGAGAATTCGAATACAAATGGCGANNNTGCATCAGGT | 693 |
| TGCAGGACCAGAGAATTCGAATACAGAAACGACNNNTGCATCAGGT | 214 | TGCAGGACCAGAGAATTCGAATACAGATTCTTTNNNTGCATCAGGT | 454 | TGCAGGACCAGAGAATTCGAATACAGTCTCTTGNNNTGCATCAGGT | 694 |
| TGCAGGACCAGAGAATTCGAATACAGAGTTTTANNNTGCATCAGGT | 215 | TGCAGGACCAGAGAATTCGAATACATCTAGGTGNNNTGCATCAGGT | 455 | TGCAGGACCAGAGAATTCGAATACATGCCCCANNNTGCATCAGGT | 695 |
| TGCAGGACCAGAGAATTCGAATACAGGCCTTTTNNNTGCATCAGGT | 216 | TGCAGGACCAGAGAATTCGAATACAGTGTCTTCNNNTGCATCAGGT | 456 | TGCAGGACCAGAGAATTCGAATACACGAGCTCGNNNTGCATCAGGT | 696 |
| TGCAGGACCAGAGAATTCGAATACACAACTCTCNNNTGCATCAGGT | 217 | TGCAGGACCAGAGAATTCGAATACATAAACTTGNNNTGCATCAGGT | 457 | TGCAGGACCAGAGAATTCGAATACAACTGAACCNNNTGCATCAGGT | 697 |
| TGCAGGACCAGAGAATTCGAATACATGTACTGGNNNTGCATCAGGT | 218 | TGCAGGACCAGAGAATTCGAATACAGACATCCANNNTGCATCAGGT | 458 | TGCAGGACCAGAGAATTCGAATACACTCGTATCNNNTGCATCAGGT | 698 |
| TGCAGGACCAGAGAATTCGAATACATTTGGCTCNNNTGCATCAGGT | 219 | TGCAGGACCAGAGAATTCGAATACATAAGTCCGNNNTGCATCAGGT | 459 | TGCAGGACCAGAGAATTCGAATACACACTTCCANNNTGCATCAGGT | 699 |
| TGCAGGACCAGAGAATTCGAATACAGAAGTATANNNTGCATCAGGT | 220 | TGCAGGACCAGAGAATTCGAATACAAGGCGCGANNNTGCATCAGGT | 460 | TGCAGGACCAGAGAATTCGAATACAGATCCTGANNNTGCATCAGGT | 700 |
| TGCAGGACCAGAGAATTCGAATACAGAATCACCNNNTGCATCAGGT | 221 | TGCAGGACCAGAGAATTCGAATACAGAGCTCTANNNTGCATCAGGT | 461 | TGCAGGACCAGAGAATTCGAATACAAGAAGTATNNNTGCATCAGGT | 701 |
| TGCAGGACCAGAGAATTCGAATACACTTACCGTNNNTGCATCAGGT | 222 | TGCAGGACCAGAGAATTCGAATACATCATAATGNNNTGCATCAGGT | 462 | TGCAGGACCAGAGAATTCGAATACAAACCCACANNNTGCATCAGGT | 702 |
| TGCAGGACCAGAGAATTCGAATACATCTTTACANNNTGCATCAGGT | 223 | TGCAGGACCAGAGAATTCGAATACAGGATGGTANNNTGCATCAGGT | 463 | TGCAGGACCAGAGAATTCGAATACATGCCGAATNNNTGCATCAGGT | 703 |
| TGCAGGACCAGAGAATTCGAATACACGAAGTGANNNTGCATCAGGT | 224 | TGCAGGACCAGAGAATTCGAATACATAGCCTTCNNNTGCATCAGGT | 464 | TGCAGGACCAGAGAATTCGAATACAATCAGAGGNNNTGCATCAGGT | 704 |
| TGCAGGACCAGAGAATTCGAATACACTTGTGGANNNTGCATCAGGT | 225 | TGCAGGACCAGAGAATTCGAATACAATCCCGCNNNTGCATCAGGT | 465 | TGCAGGACCAGAGAATTCGAATACAGTCATATANNNTGCATCAGGT | 705 |
| TGCAGGACCAGAGAATTCGAATACAGTTCTCTGNNNTGCATCAGGT | 226 | TGCAGGACCAGAGAATTCGAATACAGATTGCTGNNNTGCATCAGGT | 466 | TGCAGGACCAGAGAATTCGAATACAACCCACCNNNTGCATCAGGT | 706 |
| TGCAGGACCAGAGAATTCGAATACACCTTCAACNNNTGCATCAGGT | 227 | TGCAGGACCAGAGAATTCGAATACAGTGATGAGNNNTGCATCAGGT | 467 | TGCAGGACCAGAGAATTCGAATACACCCACAGGNNNTGCATCAGGT | 707 |
| TGCAGGACCAGAGAATTCGAATACAAAATGCTTNNNTGCATCAGGT | 228 | TGCAGGACCAGAGAATTCGAATACACGGAACGNNNTGCATCAGGT | 468 | TGCAGGACCAGAGAATTCGAATACATGCTGAACNNNTGCATCAGGT | 708 |
| TGCAGGACCAGAGAATTCGAATACAATCGCGATNNNTGCATCAGGT | 229 | TGCAGGACCAGAGAATTCGAATACAGCTCTTTGNNNTGCATCAGGT | 469 | TGCAGGACCAGAGAATTCGAATACAGCAGCATTNNNTGCATCAGGT | 709 |
| TGCAGGACCAGAGAATTCGAATACAGGCTCGTGNNNTGCATCAGGT | 230 | TGCAGGACCAGAGAATTCGAATACAGTAATCGCNNNTGCATCAGGT | 470 | TGCAGGACCAGAGAATTCGAATACAGGCGATGGNNNTGCATCAGGT | 710 |
| TGCAGGACCAGAGAATTCGAATACAGACCCTAANNNTGCATCAGGT | 231 | TGCAGGACCAGAGAATTCGAATACACTTGTTATNNNTGCATCAGGT | 471 | TGCAGGACCAGAGAATTCGAATACATTCGATGGNNNTGCATCAGGT | 711 |
| TGCAGGACCAGAGAATTCGAATACACAAATTTGNNNTGCATCAGGT | 232 | TGCAGGACCAGAGAATTCGAATACACACACANNNTGCATCAGGT | 472 | TGCAGGACCAGAGAATTCGAATACATGGACGCGNNNTGCATCAGGT | 712 |
| TGCAGGACCAGAGAATTCGAATACATTTTTTCCNNNTGCATCAGGT | 233 | TGCAGGACCAGAGAATTCGAATACATAAATAANNNTGCATCAGGT | 473 | TGCAGGACCAGAGAATTCGAATACAGTATTACANNNTGCATCAGGT | 713 |
| TGCAGGACCAGAGAATTCGAATACATTTAACGANNNTGCATCAGGT | 234 | TGCAGGACCAGAGAATTCGAATACAAACGCATCNNNTGCATCAGGT | 474 | TGCAGGACCAGAGAATTCGAATACACGACAATCNNNTGCATCAGGT | 714 |
| TGCAGGACCAGAGAATTCGAATACAGTGGTCTANNNTGCATCAGGT | 235 | TGCAGGACCAGAGAATTCGAATACACATATGATNNNTGCATCAGGT | 475 | TGCAGGACCAGAGAATTCGAATACAGTGGCCACNNNTGCATCAGGT | 715 |
| TGCAGGACCAGAGAATTCGAATACATTCTAATCNNNTGCATCAGGT | 236 | TGCAGGACCAGAGAATTCGAATACAGCGTCATANNNTGCATCAGGT | 476 | TGCAGGACCAGAGAATTCGAATACATACGCGCGNNNTGCATCAGGT | 716 |
| TGCAGGACCAGAGAATTCGAATACAATTGATTGNNNTGCATCAGGT | 237 | TGCAGGACCAGAGAATTCGAATACATAAGCCTANNNTGCATCAGGT | 477 | TGCAGGACCAGAGAATTCGAATACACGAAGACANNNTGCATCAGGT | 717 |
| TGCAGGACCAGAGAATTCGAATACATGCATAGCNNNTGCATCAGGT | 238 | TGCAGGACCAGAGAATTCGAATACATAGCAGAGNNNTGCATCAGGT | 478 | TGCAGGACCAGAGAATTCGAATACACCAATGACNNNTGCATCAGGT | 718 |
| TGCAGGACCAGAGAATTCGAATACAGACAGATGNNNTGCATCAGGT | 239 | TGCAGGACCAGAGAATTCGAATACACTTGGAACNNNTGCATCAGGT | 479 | TGCAGGACCAGAGAATTCGAATACAAGCCTTCTNNNTGCATCAGGT | 719 |

FIG. 12H

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CATGCTCTACNNNTGCATCAGGT | 240 | TGCAGGACCAGAGAATTCGAATA CAACCGAGAANNNTGCATCAGGT | 480 | TGCAGGACCAGAGAATTCGAATA CATATCACCCNNNTGCATCAGGT | 720 |
| TGCAGGACCAGAGAATTCGAATA CATGCGATACNNNTGCATCAGGT | 241 | TGCAGGACCAGAGAATTCGAATA CACTATCTATNNNTGCATCAGGT | 481 | TGCAGGACCAGAGAATTCGAATA CACCTTATGCNNNTGCATCAGGT | 721 |
| TGCAGGACCAGAGAATTCGAATA CAACACTGCANNNTGCATCAGGT | 242 | TGCAGGACCAGAGAATTCGAATA CACAATTTAGNNNTGCATCAGGT | 482 | TGCAGGACCAGAGAATTCGAATA CATTAATGACNNNTGCATCAGGT | 722 |
| TGCAGGACCAGAGAATTCGAATA CAGTCACTCTNNNTGCATCAGGT | 243 | TGCAGGACCAGAGAATTCGAATA CACTAAACGCNNNTGCATCAGGT | 483 | TGCAGGACCAGAGAATTCGAATA CACTACCTTGNNNTGCATCAGGT | 723 |
| TGCAGGACCAGAGAATTCGAATA CATTGTATTCNNNTGCATCAGGT | 244 | TGCAGGACCAGAGAATTCGAATA CATAGTAGAANNNTGCATCAGGT | 484 | TGCAGGACCAGAGAATTCGAATA CAAGGATCTCNNNTGCATCAGGT | 724 |
| TGCAGGACCAGAGAATTCGAATA CAAACCTAGCNNNTGCATCAGGT | 245 | TGCAGGACCAGAGAATTCGAATA CAGCAAAGTGNNNTGCATCAGGT | 485 | TGCAGGACCAGAGAATTCGAATA CAAAGATCAANNNTGCATCAGGT | 725 |
| TGCAGGACCAGAGAATTCGAATA CAGCCGGATCNNNTGCATCAGGT | 246 | TGCAGGACCAGAGAATTCGAATA CACAAGTTATNNNTGCATCAGGT | 486 | TGCAGGACCAGAGAATTCGAATA CAGAATGAGCNNNTGCATCAGGT | 726 |
| TGCAGGACCAGAGAATTCGAATA CAAGGATCCTNNNTGCATCAGGT | 247 | TGCAGGACCAGAGAATTCGAATA CACAACTGACNNNTGCATCAGGT | 487 | TGCAGGACCAGAGAATTCGAATA CAACTAGATTNNNTGCATCAGGT | 727 |
| TGCAGGACCAGAGAATTCGAATA CATACTGGACNNNTGCATCAGGT | 248 | TGCAGGACCAGAGAATTCGAATA CATTCGTCGTNNNTGCATCAGGT | 488 | TGCAGGACCAGAGAATTCGAATA CATTTTCCGGNNNTGCATCAGGT | 728 |

FIG. 13A

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATATGCGCANNNACGTATGCCA | 729 | TGCAGGACCAGAGAATTCGAATA CAGCGATTACNNNACGTATGCCA | 969 | TGCAGGACCAGAGAATTCGAATA CACAATGACCNNNACGTATGCCA | 1209 |
| TGCAGGACCAGAGAATTCGAATA CAGTTCACCTNNNACGTATGCCA | 730 | TGCAGGACCAGAGAATTCGAATA CATGGTCCTCNNNACGTATGCCA | 970 | TGCAGGACCAGAGAATTCGAATA CAGCTACGTANNNACGTATGCCA | 1210 |
| TGCAGGACCAGAGAATTCGAATA CATCCTACACNNNACGTATGCCA | 731 | TGCAGGACCAGAGAATTCGAATA CAGTTATAACNNNACGTATGCCA | 971 | TGCAGGACCAGAGAATTCGAATA CAGCCAGCACNNNACGTATGCCA | 1211 |
| TGCAGGACCAGAGAATTCGAATA CACTACTCTGNNNACGTATGCCA | 732 | TGCAGGACCAGAGAATTCGAATA CGTATCTTCANNNACGTATGCCA | 972 | TGCAGGACCAGAGAATTCGAATA CACGATCCGGNNNACGTATGCCA | 1212 |
| TGCAGGACCAGAGAATTCGAATA CACCTTCCCCNNNACGTATGCCA | 733 | TGCAGGACCAGAGAATTCGAATA CAACGTTCGANNNACGTATGCCA | 973 | TGCAGGACCAGAGAATTCGAATA CATTGGACACNNNACGTATGCCA | 1213 |
| TGCAGGACCAGAGAATTCGAATA CAGAAGATCGNNNACGTATGCCA | 734 | TGCAGGACCAGAGAATTCGAATA CAACTCGTGANNNACGTATGCCA | 974 | TGCAGGACCAGAGAATTCGAATA CAACAATGCCNNNACGTATGCCA | 1214 |
| TGCAGGACCAGAGAATTCGAATA CACTCCGCTGNNNACGTATGCCA | 735 | TGCAGGACCAGAGAATTCGAATA CAGGACTACTNNNACGTATGCCA | 975 | TGCAGGACCAGAGAATTCGAATA CACCTTTATANNNACGTATGCCA | 1215 |
| TGCAGGACCAGAGAATTCGAATA CATATGTCCCNNNACGTATGCCA | 736 | TGCAGGACCAGAGAATTCGAATA CATCTGTACCNNNACGTATGCCA | 976 | TGCAGGACCAGAGAATTCGAATA CAGTGGCTGCNNNACGTATGCCA | 1216 |
| TGCAGGACCAGAGAATTCGAATA CATATTTGCTNNNACGTATGCCA | 737 | TGCAGGACCAGAGAATTCGAATA CACCCTAACTNNNACGTATGCCA | 977 | TGCAGGACCAGAGAATTCGAATA CAATCTCCGTNNNACGTATGCCA | 1217 |
| TGCAGGACCAGAGAATTCGAATA CAGTCCAGGCNNNACGTATGCCA | 738 | TGCAGGACCAGAGAATTCGAATA CATTGGAGAGNNNACGTATGCCA | 978 | TGCAGGACCAGAGAATTCGAATA CAATGGCCATNNNACGTATGCCA | 1218 |
| TGCAGGACCAGAGAATTCGAATA CAAAGATGGCNNNACGTATGCCA | 739 | TGCAGGACCAGAGAATTCGAATA CAGAATCAAANNNACGTATGCCA | 979 | TGCAGGACCAGAGAATTCGAATA CATTTGATAGNNNACGTATGCCA | 1219 |
| TGCAGGACCAGAGAATTCGAATA CAGTCCCGAGNNNACGTATGCCA | 740 | TGCAGGACCAGAGAATTCGAATA CAGTTTCGTCNNNACGTATGCCA | 980 | TGCAGGACCAGAGAATTCGAATA CAGTCCCGGANNNACGTATGCCA | 1220 |
| TGCAGGACCAGAGAATTCGAATA CAAGGTTTCGNNNACGTATGCCA | 741 | TGCAGGACCAGAGAATTCGAATA CACTACACAGNNNACGTATGCCA | 981 | TGCAGGACCAGAGAATTCGAATA CAGGGTTCAANNNACGTATGCCA | 1221 |
| TGCAGGACCAGAGAATTCGAATA CATGCAAAGGNNNACGTATGCCA | 742 | TGCAGGACCAGAGAATTCGAATA CAAGTCAGTCNNNACGTATGCCA | 982 | TGCAGGACCAGAGAATTCGAATA CACCTTTTTTNNNACGTATGCCA | 1222 |
| TGCAGGACCAGAGAATTCGAATA CAAGGTGTAGNNNACGTATGCCA | 743 | TGCAGGACCAGAGAATTCGAATA CACAACGAGANNNACGTATGCCA | 983 | TGCAGGACCAGAGAATTCGAATA CAACGCCCGANNNACGTATGCCA | 1223 |
| TGCAGGACCAGAGAATTCGAATA CACACGAGTTNNNACGTATGCCA | 744 | TGCAGGACCAGAGAATTCGAATA CATAGGCTCANNNACGTATGCCA | 984 | TGCAGGACCAGAGAATTCGAATA CACCCCTAGCNNNACGTATGCCA | 1224 |
| TGCAGGACCAGAGAATTCGAATA CACACCGCCTNNNACGTATGCCA | 745 | TGCAGGACCAGAGAATTCGAATA CAGGCCCATGNNNACGTATGCCA | 985 | TGCAGGACCAGAGAATTCGAATA CACGGAGGCANNNACGTATGCCA | 1225 |
| TGCAGGACCAGAGAATTCGAATA CAAAGCTACCNNNACGTATGCCA | 746 | TGCAGGACCAGAGAATTCGAATA CAGGCCAGTCCNNNACGTATGCCA | 986 | TGCAGGACCAGAGAATTCGAATA CACTATGAATNNNACGTATGCCA | 1226 |
| TGCAGGACCAGAGAATTCGAATA CAGAACCGAANNNACGTATGCCA | 747 | TGCAGGACCAGAGAATTCGAATA CATCGATTGGNNNACGTATGCCA | 987 | TGCAGGACCAGAGAATTCGAATA CAGACCGCGTNNNACGTATGCCA | 1227 |
| TGCAGGACCAGAGAATTCGAATA CAAGTACTGCNNNACGTATGCCA | 748 | TGCAGGACCAGAGAATTCGAATA CATGGACAGGNNNACGTATGCCA | 988 | TGCAGGACCAGAGAATTCGAATA CATACTAGTANNNACGTATGCCA | 1228 |
| TGCAGGACCAGAGAATTCGAATA CAAACAATTCNNNACGTATGCCA | 749 | TGCAGGACCAGAGAATTCGAATA CAACTAAGTTNNNACGTATGCCA | 989 | TGCAGGACCAGAGAATTCGAATA CAACCAGTGTNNNACGTATGCCA | 1229 |
| TGCAGGACCAGAGAATTCGAATA CAGTATTAACNNNACGTATGCCA | 750 | TGCAGGACCAGAGAATTCGAATA CAATGTTCGGNNNACGTATGCCA | 990 | TGCAGGACCAGAGAATTCGAATA CAGATGCCTANNNACGTATGCCA | 1230 |
| TGCAGGACCAGAGAATTCGAATA CATGATTATGNNNACGTATGCCA | 751 | TGCAGGACCAGAGAATTCGAATA CAAGCCCAATNNNACGTATGCCA | 991 | TGCAGGACCAGAGAATTCGAATA CACCATATTTNNNACGTATGCCA | 1231 |
| TGCAGGACCAGAGAATTCGAATA CAGCAAACCTNNNACGTATGCCA | 752 | TGCAGGACCAGAGAATTCGAATA CAGTGAGTTCNNNACGTATGCCA | 992 | TGCAGGACCAGAGAATTCGAATA CAAAACCACCNNNACGTATGCCA | 1232 |
| TGCAGGACCAGAGAATTCGAATA CAGAATCTTANNNACGTATGCCA | 753 | TGCAGGACCAGAGAATTCGAATA CAGTGCTAACNNNACGTATGCCA | 993 | TGCAGGACCAGAGAATTCGAATA CAGCACGAAANNNACGTATGCCA | 1233 |
| TGCAGGACCAGAGAATTCGAATA CAGAGGACGCNNNACGTATGCCA | 754 | TGCAGGACCAGAGAATTCGAATA CAGCCACCGANNNACGTATGCCA | 994 | TGCAGGACCAGAGAATTCGAATA CAACGACAGANNNACGTATGCCA | 1234 |
| TGCAGGACCAGAGAATTCGAATA CAAGCCAAAGNNNACGTATGCCA | 755 | TGCAGGACCAGAGAATTCGAATA CAAGTCCGATNNNACGTATGCCA | 995 | TGCAGGACCAGAGAATTCGAATA CAATACCATANNNACGTATGCCA | 1235 |
| TGCAGGACCAGAGAATTCGAATA CAGGACGCTCNNNACGTATGCCA | 756 | TGCAGGACCAGAGAATTCGAATA CAGTTAAATCNNNACGTATGCCA | 996 | TGCAGGACCAGAGAATTCGAATA CACCAGTTCCNNNACGTATGCCA | 1236 |
| TGCAGGACCAGAGAATTCGAATA CAGCTGCCCTNNNACGTATGCCA | 757 | TGCAGGACCAGAGAATTCGAATA CAACTGACTGNNNACGTATGCCA | 997 | TGCAGGACCAGAGAATTCGAATA CATTGCTGGANNNACGTATGCCA | 1237 |
| TGCAGGACCAGAGAATTCGAATA CACCCTTTTCNNNACGTATGCCA | 758 | TGCAGGACCAGAGAATTCGAATA CACTTCATGCNNNACGTATGCCA | 998 | TGCAGGACCAGAGAATTCGAATA CAGCCCATTNNNACGTATGCCA | 1238 |
| TGCAGGACCAGAGAATTCGAATA CATCGCAGTANNNACGTATGCCA | 759 | TGCAGGACCAGAGAATTCGAATA CAACCAGATNNNACGTATGCCA | 999 | TGCAGGACCAGAGAATTCGAATA CAAACAGTANNNACGTATGCCA | 1239 |
| TGCAGGACCAGAGAATTCGAATA CAATCGCATGNNNACGTATGCCA | 760 | TGCAGGACCAGAGAATTCGAATA CAGCCGTCCANNNACGTATGCCA | 1000 | TGCAGGACCAGAGAATTCGAATA CACTGTTCTGNNNACGTATGCCA | 1240 |

FIG. 13B

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CAAGATGGCANNNACGTATGCCA | 761 | TGCAGGACCAGAGAATTCGAATA CAAACAACCCNNNACGTATGCCA | 1001 | TGCAGGACCAGAGAATTCGAATA CATGCAATAANNNACGTATGCCA | 1241 |
| TGCAGGACCAGAGAATTCGAATA CATCATCGCTNNNACGTATGCCA | 762 | TGCAGGACCAGAGAATTCGAATA CAGGTCTTAGNNNACGTATGCCA | 1002 | TGCAGGACCAGAGAATTCGAATA CATTCCCTTCNNNACGTATGCCA | 1242 |
| TGCAGGACCAGAGAATTCGAATA CACGTGTTCTNNNACGTATGCCA | 763 | TGCAGGACCAGAGAATTCGAATA CAGCCCGGATNNNACGTATGCCA | 1003 | TGCAGGACCAGAGAATTCGAATA CACACGCAATNNNACGTATGCCA | 1243 |
| TGCAGGACCAGAGAATTCGAATA CAGGTTATTANNNACGTATGCCA | 764 | TGCAGGACCAGAGAATTCGAATA CAATCCCGAANNNACGTATGCCA | 1004 | TGCAGGACCAGAGAATTCGAATA CAGCTTATCCNNNACGTATGCCA | 1244 |
| TGCAGGACCAGAGAATTCGAATA CAAGAGTTAANNNACGTATGCCA | 765 | TGCAGGACCAGAGAATTCGAATA CATTTACTCANNNACGTATGCCA | 1005 | TGCAGGACCAGAGAATTCGAATA CAGGCATAGANNNACGTATGCCA | 1245 |
| TGCAGGACCAGAGAATTCGAATA CATGAAATTCNNNACGTATGCCA | 766 | TGCAGGACCAGAGAATTCGAATA CATCCACCGCNNNACGTATGCCA | 1006 | TGCAGGACCAGAGAATTCGAATA CAAGCGCCGTNNNACGTATGCCA | 1246 |
| TGCAGGACCAGAGAATTCGAATA CACTTACCTGNNNACGTATGCCA | 767 | TGCAGGACCAGAGAATTCGAATA CACCAGATTGNNNACGTATGCCA | 1007 | TGCAGGACCAGAGAATTCGAATA CACAAATTCANNNACGTATGCCA | 1247 |
| TGCAGGACCAGAGAATTCGAATA CAAACTCGTGNNNACGTATGCCA | 768 | TGCAGGACCAGAGAATTCGAATA CACATGGTCANNNACGTATGCCA | 1008 | TGCAGGACCAGAGAATTCGAATA CATAATGCATNNNACGTATGCCA | 1248 |
| TGCAGGACCAGAGAATTCGAATA CAGGACACGGNNNACGTATGCCA | 769 | TGCAGGACCAGAGAATTCGAATA CACCATTCGNNNACGTATGCCA | 1009 | TGCAGGACCAGAGAATTCGAATA CAACTCGTCTNNNACGTATGCCA | 1249 |
| TGCAGGACCAGAGAATTCGAATA CATCTCGCGCNNNACGTATGCCA | 770 | TGCAGGACCAGAGAATTCGAATA CATGTCGCGGNNNACGTATGCCA | 1010 | TGCAGGACCAGAGAATTCGAATA CAAATTTGTGNNNACGTATGCCA | 1250 |
| TGCAGGACCAGAGAATTCGAATA CACTTCCAGTNNNACGTATGCCA | 771 | TGCAGGACCAGAGAATTCGAATA CAAACAATAGNNNACGTATGCCA | 1011 | TGCAGGACCAGAGAATTCGAATA CATGGAGGTNNNACGTATGCCA | 1251 |
| TGCAGGACCAGAGAATTCGAATA CAATAGTTACNNNACGTATGCCA | 772 | TGCAGGACCAGAGAATTCGAATA CATTCGACGANNNACGTATGCCA | 1012 | TGCAGGACCAGAGAATTCGAATA CAGCCATACANNNACGTATGCCA | 1252 |
| TGCAGGACCAGAGAATTCGAATA CACGACTTGANNNACGTATGCCA | 773 | TGCAGGACCAGAGAATTCGAATA CACCTTGAGANNNACGTATGCCA | 1013 | TGCAGGACCAGAGAATTCGAATA CAGTCCTTCANNNACGTATGCCA | 1253 |
| TGCAGGACCAGAGAATTCGAATA CATGCTTTATNNNACGTATGCCA | 774 | TGCAGGACCAGAGAATTCGAATA CAACGCTCTTNNNACGTATGCCA | 1014 | TGCAGGACCAGAGAATTCGAATA CAGTGCGGAGNNNACGTATGCCA | 1254 |
| TGCAGGACCAGAGAATTCGAATA CAGCCACTTTNNNACGTATGCCA | 775 | TGCAGGACCAGAGAATTCGAATA CACACGAAGANNNACGTATGCCA | 1015 | TGCAGGACCAGAGAATTCGAATA CATTTAGACANNNACGTATGCCA | 1255 |
| TGCAGGACCAGAGAATTCGAATA CATATCGGACNNNACGTATGCCA | 776 | TGCAGGACCAGAGAATTCGAATA CAGGCCACACNNNACGTATGCCA | 1016 | TGCAGGACCAGAGAATTCGAATA CACACCCGCTNNNACGTATGCCA | 1256 |
| TGCAGGACCAGAGAATTCGAATA CAATTCCATTNNNACGTATGCCA | 777 | TGCAGGACCAGAGAATTCGAATA CATCTGTGAGNNNACGTATGCCA | 1017 | TGCAGGACCAGAGAATTCGAATA CAATTCTAGANNNACGTATGCCA | 1257 |
| TGCAGGACCAGAGAATTCGAATA CAAATGCTGCNNNACGTATGCCA | 778 | TGCAGGACCAGAGAATTCGAATA CAAAAGCCAGNNNACGTATGCCA | 1018 | TGCAGGACCAGAGAATTCGAATA CACGGACGAGNNNACGTATGCCA | 1258 |
| TGCAGGACCAGAGAATTCGAATA CAACGCGATTNNNACGTATGCCA | 779 | TGCAGGACCAGAGAATTCGAATA CACCAGTTGANNNACGTATGCCA | 1019 | TGCAGGACCAGAGAATTCGAATA CACGACCCANNNACGTATGCCA | 1259 |
| TGCAGGACCAGAGAATTCGAATA CATAGCTAGCNNNACGTATGCCA | 780 | TGCAGGACCAGAGAATTCGAATA CACTTGTAGGNNNACGTATGCCA | 1020 | TGCAGGACCAGAGAATTCGAATA CACATATAGTNNNACGTATGCCA | 1260 |
| TGCAGGACCAGAGAATTCGAATA CAGCAACGTTNNNACGTATGCCA | 781 | TGCAGGACCAGAGAATTCGAATA CAATATGCATNNNACGTATGCCA | 1021 | TGCAGGACCAGAGAATTCGAATA CATGTGATATNNNACGTATGCCA | 1261 |
| TGCAGGACCAGAGAATTCGAATA CACGTCCTATNNNACGTATGCCA | 782 | TGCAGGACCAGAGAATTCGAATA CACCAGGCGTNNNACGTATGCCA | 1022 | TGCAGGACCAGAGAATTCGAATA CAATCCTAAANNNACGTATGCCA | 1262 |
| TGCAGGACCAGAGAATTCGAATA CAGCCACACGNNNACGTATGCCA | 783 | TGCAGGACCAGAGAATTCGAATA CAATGTTTAGNNNACGTATGCCA | 1023 | TGCAGGACCAGAGAATTCGAATA CATGATGAGGNNNACGTATGCCA | 1263 |
| TGCAGGACCAGAGAATTCGAATA CAGGCTTCCCNNNACGTATGCCA | 784 | TGCAGGACCAGAGAATTCGAATA CACTGTCCGCNNNACGTATGCCA | 1024 | TGCAGGACCAGAGAATTCGAATA CAGCTCGACGNNNACGTATGCCA | 1264 |
| TGCAGGACCAGAGAATTCGAATA CAGTTGACACNNNACGTATGCCA | 785 | TGCAGGACCAGAGAATTCGAATA CATTTTACCANNNACGTATGCCA | 1025 | TGCAGGACCAGAGAATTCGAATA CATTAGCTAANNNACGTATGCCA | 1265 |
| TGCAGGACCAGAGAATTCGAATA CAGCATCTTCNNNACGTATGCCA | 786 | TGCAGGACCAGAGAATTCGAATA CATGCCCTGCNNNACGTATGCCA | 1026 | TGCAGGACCAGAGAATTCGAATA CATGCTTTANNNACGTATGCCA | 1266 |
| TGCAGGACCAGAGAATTCGAATA CAACAATTGTNNNACGTATGCCA | 787 | TGCAGGACCAGAGAATTCGAATA CACCTTTGACNNNACGTATGCCA | 1027 | TGCAGGACCAGAGAATTCGAATA CAATCACAGCNNNACGTATGCCA | 1267 |
| TGCAGGACCAGAGAATTCGAATA CAGATCCCCNNNACGTATGCCA | 788 | TGCAGGACCAGAGAATTCGAATA CAATTATTTTNNNACGTATGCCA | 1028 | TGCAGGACCAGAGAATTCGAATA CAAATCTCGGNNNACGTATGCCA | 1268 |
| TGCAGGACCAGAGAATTCGAATA CAGCCCAGTGNNNCTAGCGTTAC | 789 | TGCAGGACCAGAGAATTCGAATA CAGTGTGGAANNNCTAGCGTTAC | 1029 | TGCAGGACCAGAGAATTCGAATA CAACACTGGTNNNCTAGCGTTAC | 1269 |
| TGCAGGACCAGAGAATTCGAATA CAGCGGTGCTNNNCTAGCGTTAC | 790 | TGCAGGACCAGAGAATTCGAATA CAACTCGTAGNNNCTAGCGTTAC | 1030 | TGCAGGACCAGAGAATTCGAATA CATTTGTTTGNNNCTAGCGTTAC | 1270 |
| TGCAGGACCAGAGAATTCGAATA CATACGTGCANNNCTAGCGTTAC | 791 | TGCAGGACCAGAGAATTCGAATA CATCGCGTCCNNNCTAGCGTTAC | 1031 | TGCAGGACCAGAGAATTCGAATA CACGACACGGNNNCTAGCGTTAC | 1271 |
| TGCAGGACCAGAGAATTCGAATA CACACCCACCNNNCTAGCGTTAC | 792 | TGCAGGACCAGAGAATTCGAATA CAGCCTAATGNNNCTAGCGTTAC | 1032 | TGCAGGACCAGAGAATTCGAATA CACGCGAGAGNNNCTAGCGTTAC | 1272 |

FIG. 13C

| Pool-4 | SEQ ID NO: | Pool-5 | SEQ ID NO: | Pool-6 | SEQ ID NO: |
|---|---|---|---|---|---|
| TGCAGGACCAGAGAATTCGAATACACACAGAAGNNNCTAGCGTTAC | 793 | TGCAGGACCAGAGAATTCGAATACAGCGTGTTANNNCTAGCGTTAC | 1033 | TGCAGGACCAGAGAATTCGAATACATAAGTAGANNNCTAGCGTTAC | 1273 |
| TGCAGGACCAGAGAATTCGAATACACGCTAACANNNCTAGCGTTAC | 794 | TGCAGGACCAGAGAATTCGAATACACGAGAAACNNNCTAGCGTTAC | 1034 | TGCAGGACCAGAGAATTCGAATACAAAGACGTGNNNCTAGCGTTAC | 1274 |
| TGCAGGACCAGAGAATTCGAATACAGACCTATGNNNCTAGCGTTAC | 795 | TGCAGGACCAGAGAATTCGAATACAATGCTCAGNNNCTAGCGTTAC | 1035 | TGCAGGACCAGAGAATTCGAATACACGGAACANNNCTAGCGTTAC | 1275 |
| TGCAGGACCAGAGAATTCGAATACAAAAAGGAANNNCTAGCGTTAC | 796 | TGCAGGACCAGAGAATTCGAATACAGTCAGCTANNNCTAGCGTTAC | 1036 | TGCAGGACCAGAGAATTCGAATACACTGTCGAANNNCTAGCGTTAC | 1276 |
| TGCAGGACCAGAGAATTCGAATACAACAGAGGTNNNCTAGCGTTAC | 797 | TGCAGGACCAGAGAATTCGAATACAGGTAGCGNNNCTAGCGTTAC | 1037 | TGCAGGACCAGAGAATTCGAATACAAGCCTACANNNCTAGCGTTAC | 1277 |
| TGCAGGACCAGAGAATTCGAATACACGTAGCATNNNCTAGCGTTAC | 798 | TGCAGGACCAGAGAATTCGAATACACCTGGTCCNNNCTAGCGTTAC | 1038 | TGCAGGACCAGAGAATTCGAATACACCAATTCGNNNCTAGCGTTAC | 1278 |
| TGCAGGACCAGAGAATTCGAATACATCCCCAGCNNNCTAGCGTTAC | 799 | TGCAGGACCAGAGAATTCGAATACACAGCACCGNNNCTAGCGTTAC | 1039 | TGCAGGACCAGAGAATTCGAATACAGAGTCTACNNNCTAGCGTTAC | 1279 |
| TGCAGGACCAGAGAATTCGAATACAGTACCTGNNNCTAGCGTTAC | 800 | TGCAGGACCAGAGAATTCGAATACACATTGTGGNNNCTAGCGTTAC | 1040 | TGCAGGACCAGAGAATTCGAATACAAATGTTACNNNCTAGCGTTAC | 1280 |
| TGCAGGACCAGAGAATTCGAATACAAGAGAGGANNNCTAGCGTTAC | 801 | TGCAGGACCAGAGAATTCGAATACAAGGAACTGNNNCTAGCGTTAC | 1041 | TGCAGGACCAGAGAATTCGAATACAAGTGGCAANNNCTAGCGTTAC | 1281 |
| TGCAGGACCAGAGAATTCGAATACAGTAACTCGNNNCTAGCGTTAC | 802 | TGCAGGACCAGAGAATTCGAATACAGTTATTAGNNNCTAGCGTTAC | 1042 | TGCAGGACCAGAGAATTCGAATACAGGTTAACCNNNCTAGCGTTAC | 1282 |
| TGCAGGACCAGAGAATTCGAATACAGGTACATCNNNCTAGCGTTAC | 803 | TGCAGGACCAGAGAATTCGAATACAAATCTTCTNNNCTAGCGTTAC | 1043 | TGCAGGACCAGAGAATTCGAATACATTGTGGTGNNNCTAGCGTTAC | 1283 |
| TGCAGGACCAGAGAATTCGAATACAGTTAACCGNNNCTAGCGTTAC | 804 | TGCAGGACCAGAGAATTCGAATACAGACAATCCNNNCTAGCGTTAC | 1044 | TGCAGGACCAGAGAATTCGAATACAAAATGGCGNNNCTAGCGTTAC | 1284 |
| TGCAGGACCAGAGAATTCGAATACAAACGAGTGNNNCTAGCGTTAC | 805 | TGCAGGACCAGAGAATTCGAATACAATCTAGATNNNCTAGCGTTAC | 1045 | TGCAGGACCAGAGAATTCGAATACACTGTAGGTNNNCTAGCGTTAC | 1285 |
| TGCAGGACCAGAGAATTCGAATACATCTCACTGNNNCTAGCGTTAC | 806 | TGCAGGACCAGAGAATTCGAATACAGCGACGTCNNNCTAGCGTTAC | 1046 | TGCAGGACCAGAGAATTCGAATACACTAAGCGTNNNCTAGCGTTAC | 1286 |
| TGCAGGACCAGAGAATTCGAATACATACGAGCTNNNCTAGCGTTAC | 807 | TGCAGGACCAGAGAATTCGAATACACACCCCGTNNNCTAGCGTTAC | 1047 | TGCAGGACCAGAGAATTCGAATACAGTTTATGANNNCTAGCGTTAC | 1287 |
| TGCAGGACCAGAGAATTCGAATACACAGATACCNNNCTAGCGTTAC | 808 | TGCAGGACCAGAGAATTCGAATACACGCCTCGTNNNCTAGCGTTAC | 1048 | TGCAGGACCAGAGAATTCGAATACAACGACTGTNNNCTAGCGTTAC | 1288 |
| TGCAGGACCAGAGAATTCGAATACATACATTCNNNCTAGCGTTAC | 809 | TGCAGGACCAGAGAATTCGAATACACTGACACANNNCTAGCGTTAC | 1049 | TGCAGGACCAGAGAATTCGAATACACCTAGTAGNNNCTAGCGTTAC | 1289 |
| TGCAGGACCAGAGAATTCGAATACAGTGTAAGGNNNCTAGCGTTAC | 810 | TGCAGGACCAGAGAATTCGAATACATGCTTTGCNNNCTAGCGTTAC | 1050 | TGCAGGACCAGAGAATTCGAATACAGGTTCTGANNNCTAGCGTTAC | 1290 |
| TGCAGGACCAGAGAATTCGAATACAGGTTGAAGNNNCTAGCGTTAC | 811 | TGCAGGACCAGAGAATTCGAATACAACTGTCTCNNNCTAGCGTTAC | 1051 | TGCAGGACCAGAGAATTCGAATACATACATCCCNNNCTAGCGTTAC | 1291 |
| TGCAGGACCAGAGAATTCGAATACACGTCCCTGNNNCTAGCGTTAC | 812 | TGCAGGACCAGAGAATTCGAATACATATTGTCTNNNCTAGCGTTAC | 1052 | TGCAGGACCAGAGAATTCGAATACACTCGGAATNNNCTAGCGTTAC | 1292 |
| TGCAGGACCAGAGAATTCGAATACAAATCCCTCNNNCTAGCGTTAC | 813 | TGCAGGACCAGAGAATTCGAATACAATTTGACANNNCTAGCGTTAC | 1053 | TGCAGGACCAGAGAATTCGAATACATCAGTTGGNNNCTAGCGTTAC | 1293 |
| TGCAGGACCAGAGAATTCGAATACATGCCCACNNNCTAGCGTTAC | 814 | TGCAGGACCAGAGAATTCGAATACACGCACACGNNNCTAGCGTTAC | 1054 | TGCAGGACCAGAGAATTCGAATACAAGTGCCTANNNCTAGCGTTAC | 1294 |
| TGCAGGACCAGAGAATTCGAATACAGTATTATGNNNCTAGCGTTAC | 815 | TGCAGGACCAGAGAATTCGAATACACCCGGAACNNNCTAGCGTTAC | 1055 | TGCAGGACCAGAGAATTCGAATACAGTATGTATNNNCTAGCGTTAC | 1295 |
| TGCAGGACCAGAGAATTCGAATACATTGATTGANNNCTAGCGTTAC | 816 | TGCAGGACCAGAGAATTCGAATACATTAGGCGTNNNCTAGCGTTAC | 1056 | TGCAGGACCAGAGAATTCGAATACAGCAGCAGGNNNCTAGCGTTAC | 1296 |
| TGCAGGACCAGAGAATTCGAATACATGCGACGCNNNCTAGCGTTAC | 817 | TGCAGGACCAGAGAATTCGAATACATCGGAGCCNNNCTAGCGTTAC | 1057 | TGCAGGACCAGAGAATTCGAATACAGCAGGTCCNNNCTAGCGTTAC | 1297 |
| TGCAGGACCAGAGAATTCGAATACAGTGGTTCANNNCTAGCGTTAC | 818 | TGCAGGACCAGAGAATTCGAATACAGTCTACAGNNNCTAGCGTTAC | 1058 | TGCAGGACCAGAGAATTCGAATACATGTAGGCTNNNCTAGCGTTAC | 1298 |
| TGCAGGACCAGAGAATTCGAATACAGCCGGCTANNNCTAGCGTTAC | 819 | TGCAGGACCAGAGAATTCGAATACACCGCGTCTNNNCTAGCGTTAC | 1059 | TGCAGGACCAGAGAATTCGAATACATAACGACCNNNCTAGCGTTAC | 1299 |
| TGCAGGACCAGAGAATTCGAATACACCTTGCGCNNNCTAGCGTTAC | 820 | TGCAGGACCAGAGAATTCGAATACATTAAACTGNNNCTAGCGTTAC | 1060 | TGCAGGACCAGAGAATTCGAATACACGATCGGCNNNCTAGCGTTAC | 1300 |
| TGCAGGACCAGAGAATTCGAATACAGGTAAGTGNNNCTAGCGTTAC | 821 | TGCAGGACCAGAGAATTCGAATACAATAAGAACNNNCTAGCGTTAC | 1061 | TGCAGGACCAGAGAATTCGAATACAGGCCAACGNNNCTAGCGTTAC | 1301 |
| TGCAGGACCAGAGAATTCGAATACAGTGTCCAANNNCTAGCGTTAC | 822 | TGCAGGACCAGAGAATTCGAATACAATCATGCGNNNCTAGCGTTAC | 1062 | TGCAGGACCAGAGAATTCGAATACAGACATAAANNNCTAGCGTTAC | 1302 |
| TGCAGGACCAGAGAATTCGAATACATGCACTGANNNCTAGCGTTAC | 823 | TGCAGGACCAGAGAATTCGAATACACCACTCAGNNNCTAGCGTTAC | 1063 | TGCAGGACCAGAGAATTCGAATACACGCACATANNNCTAGCGTTAC | 1303 |
| TGCAGGACCAGAGAATTCGAATACAGAAACTTTNNNCTAGCGTTAC | 824 | TGCAGGACCAGAGAATTCGAATACACTCGAGTANNNCTAGCGTTAC | 1064 | TGCAGGACCAGAGAATTCGAATACAGCCTAGGCNNNCTAGCGTTAC | 1304 |

FIG. 13D

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATGTGTAGCNNNCTAGCGTTAC | 825 | TGCAGGACCAGAGAATTCGAATA CACTTTGCCANNNCTAGCGTTAC | 1065 | TGCAGGACCAGAGAATTCGAATA CATCCGCAAANNNCTAGCGTTAC | 1305 |
| TGCAGGACCAGAGAATTCGAATA CATCTACCTGNNNCTAGCGTTAC | 826 | TGCAGGACCAGAGAATTCGAATA CAAATTCTGANNNCTAGCGTTAC | 1066 | TGCAGGACCAGAGAATTCGAATA CACTTATAGANNNCTAGCGTTAC | 1306 |
| TGCAGGACCAGAGAATTCGAATA CATCTCTTAANNNCTAGCGTTAC | 827 | TGCAGGACCAGAGAATTCGAATA CAGATCGCATNNNCTAGCGTTAC | 1067 | TGCAGGACCAGAGAATTCGAATA CACGGCGGAANNNCTAGCGTTAC | 1307 |
| TGCAGGACCAGAGAATTCGAATA CAATCGAATTNNNCTAGCGTTAC | 828 | TGCAGGACCAGAGAATTCGAATA CATGTGTTGGNNNCTAGCGTTAC | 1068 | TGCAGGACCAGAGAATTCGAATA CAGTAGCACTNNNCTAGCGTTAC | 1308 |
| TGCAGGACCAGAGAATTCGAATA CATTTTTGGTNNNCTAGCGTTAC | 829 | TGCAGGACCAGAGAATTCGAATA CAGTAACATTNNNCTAGCGTTAC | 1069 | TGCAGGACCAGAGAATTCGAATA CAGCTGTCAANNNCTAGCGTTAC | 1309 |
| TGCAGGACCAGAGAATTCGAATA CATCAGTCCTNNNCTAGCGTTAC | 830 | TGCAGGACCAGAGAATTCGAATA CAACGCATCANNNCTAGCGTTAC | 1070 | TGCAGGACCAGAGAATTCGAATA CAGTGCCAGCNNNCTAGCGTTAC | 1310 |
| TGCAGGACCAGAGAATTCGAATA CAGTGCACATNNNCTAGCGTTAC | 831 | TGCAGGACCAGAGAATTCGAATA CATAGGAAGCNNNCTAGCGTTAC | 1071 | TGCAGGACCAGAGAATTCGAATA CATTCATATCNNNCTAGCGTTAC | 1311 |
| TGCAGGACCAGAGAATTCGAATA CAGTAGAAGCNNNCTAGCGTTAC | 832 | TGCAGGACCAGAGAATTCGAATA CAGCAATGTCNNNCTAGCGTTAC | 1072 | TGCAGGACCAGAGAATTCGAATA CACCCATGCCNNNCTAGCGTTAC | 1312 |
| TGCAGGACCAGAGAATTCGAATA CACAGCATTGNNNCTAGCGTTAC | 833 | TGCAGGACCAGAGAATTCGAATA CAGCCGGCATNNNCTAGCGTTAC | 1073 | TGCAGGACCAGAGAATTCGAATA CATTAGTTGANNNCTAGCGTTAC | 1313 |
| TGCAGGACCAGAGAATTCGAATA CACGCCTAGGNNNCTAGCGTTAC | 834 | TGCAGGACCAGAGAATTCGAATA CACTGAGCGCNNNCTAGCGTTAC | 1074 | TGCAGGACCAGAGAATTCGAATA CAATCAGAAANNNCTAGCGTTAC | 1314 |
| TGCAGGACCAGAGAATTCGAATA CACAGTTTGGNNNCTAGCGTTAC | 835 | TGCAGGACCAGAGAATTCGAATA CACTGCCTACNNNCTAGCGTTAC | 1075 | TGCAGGACCAGAGAATTCGAATA CATTAGAACTNNNCTAGCGTTAC | 1315 |
| TGCAGGACCAGAGAATTCGAATA CATCCCAAGANNNCTAGCGTTAC | 836 | TGCAGGACCAGAGAATTCGAATA CAGTGCGGANNNCTAGCGTTAC | 1076 | TGCAGGACCAGAGAATTCGAATA CAGTGCTATGNNNCTAGCGTTAC | 1316 |
| TGCAGGACCAGAGAATTCGAATA CATTAGGACCNNNCTAGCGTTAC | 837 | TGCAGGACCAGAGAATTCGAATA CAAGGCTACTNNNCTAGCGTTAC | 1077 | TGCAGGACCAGAGAATTCGAATA CATTGGATCGNNNCTAGCGTTAC | 1317 |
| TGCAGGACCAGAGAATTCGAATA CAACAATTTGNNNCTAGCGTTAC | 838 | TGCAGGACCAGAGAATTCGAATA CAACTTTGTTNNNCTAGCGTTAC | 1078 | TGCAGGACCAGAGAATTCGAATA CACAAGAATANNNCTAGCGTTAC | 1318 |
| TGCAGGACCAGAGAATTCGAATA CATGCTCGAANNNCTAGCGTTAC | 839 | TGCAGGACCAGAGAATTCGAATA CAGCCATATGNNNCTAGCGTTAC | 1079 | TGCAGGACCAGAGAATTCGAATA CAAGCACCATNNNCTAGCGTTAC | 1319 |
| TGCAGGACCAGAGAATTCGAATA CAGGCGGTAGNNNCTAGCGTTAC | 840 | TGCAGGACCAGAGAATTCGAATA CAAGCCTGGCNNNCTAGCGTTAC | 1080 | TGCAGGACCAGAGAATTCGAATA CAACTAGACCNNNCTAGCGTTAC | 1320 |
| TGCAGGACCAGAGAATTCGAATA CAAATTAACCNNNCTAGCGTTAC | 841 | TGCAGGACCAGAGAATTCGAATA CAACGTGTGTNNNCTAGCGTTAC | 1081 | TGCAGGACCAGAGAATTCGAATA CAATCATTAGNNNCTAGCGTTAC | 1321 |
| TGCAGGACCAGAGAATTCGAATA CACGACACGNNNCTAGCGTTAC | 842 | TGCAGGACCAGAGAATTCGAATA CATTTTCATGNNNCTAGCGTTAC | 1082 | TGCAGGACCAGAGAATTCGAATA CAAGAACCTCNNNCTAGCGTTAC | 1322 |
| TGCAGGACCAGAGAATTCGAATA CAGTGAGGATNNNCTAGCGTTAC | 843 | TGCAGGACCAGAGAATTCGAATA CAGCTGCGACNNNCTAGCGTTAC | 1083 | TGCAGGACCAGAGAATTCGAATA CAGATTTTCTNNNCTAGCGTTAC | 1323 |
| TGCAGGACCAGAGAATTCGAATA CAAAATTAAANNNCTAGCGTTAC | 844 | TGCAGGACCAGAGAATTCGAATA CACAAAATAGNNNCTAGCGTTAC | 1084 | TGCAGGACCAGAGAATTCGAATA CAAGTACGGANNNCTAGCGTTAC | 1324 |
| TGCAGGACCAGAGAATTCGAATA CACATGCCAANNNCTAGCGTTAC | 845 | TGCAGGACCAGAGAATTCGAATA CACTAACTANNNCTAGCGTTAC | 1085 | TGCAGGACCAGAGAATTCGAATA CACGCCTAAANNNCTAGCGTTAC | 1325 |
| TGCAGGACCAGAGAATTCGAATA CACCATCAGANNNCTAGCGTTAC | 846 | TGCAGGACCAGAGAATTCGAATA CAAAATGATGNNNCTAGCGTTAC | 1086 | TGCAGGACCAGAGAATTCGAATA CAAGTTGGTCNNNCTAGCGTTAC | 1326 |
| TGCAGGACCAGAGAATTCGAATA CAATATAAANNNCTAGCGTTAC | 847 | TGCAGGACCAGAGAATTCGAATA CACTTGCTTGNNNCTAGCGTTAC | 1087 | TGCAGGACCAGAGAATTCGAATA CATGCGCACGNNNCTAGCGTTAC | 1327 |
| TGCAGGACCAGAGAATTCGAATA CAGCCTCCGTNNNCTAGCGTTAC | 848 | TGCAGGACCAGAGAATTCGAATA CAGATAGGCANNNCTAGCGTTAC | 1088 | TGCAGGACCAGAGAATTCGAATA CATTGGTACGNNNCTAGCGTTAC | 1328 |
| TGCAGGACCAGAGAATTCGAATA CATCCAATCCNNNGATCGACATG | 849 | TGCAGGACCAGAGAATTCGAATA CACAGATTATNNNGATCGACATG | 1089 | TGCAGGACCAGAGAATTCGAATA CAATGAGATANNNGATCGACATG | 1329 |
| TGCAGGACCAGAGAATTCGAATA CAAATGCCCNNNGATCGACATG | 850 | TGCAGGACCAGAGAATTCGAATA CAGTTACGGTNNNGATCGACATG | 1090 | TGCAGGACCAGAGAATTCGAATA CAATCGGTACNNNGATCGACATG | 1330 |
| TGCAGGACCAGAGAATTCGAATA CAACTGTCGANNNGATCGACATG | 851 | TGCAGGACCAGAGAATTCGAATA CAACAGTTGCNNNGATCGACATG | 1091 | TGCAGGACCAGAGAATTCGAATA CATGTCGTTCNNNGATCGACATG | 1331 |
| TGCAGGACCAGAGAATTCGAATA CAGCTGTTGANNNGATCGACATG | 852 | TGCAGGACCAGAGAATTCGAATA CAAACTGCACNNNGATCGACATG | 1092 | TGCAGGACCAGAGAATTCGAATA CATGTGTATANNNGATCGACATG | 1332 |
| TGCAGGACCAGAGAATTCGAATA CAGGTAACCTNNNGATCGACATG | 853 | TGCAGGACCAGAGAATTCGAATA CAAGAATATGNNNGATCGACATG | 1093 | TGCAGGACCAGAGAATTCGAATA CAGTGGATCTNNNGATCGACATG | 1333 |
| TGCAGGACCAGAGAATTCGAATA CACTTTTCCNNNGATCGACATG | 854 | TGCAGGACCAGAGAATTCGAATA CATCGTCCTANNNGATCGACATG | 1094 | TGCAGGACCAGAGAATTCGAATA CATCTTCAATNNNGATCGACATG | 1334 |
| TGCAGGACCAGAGAATTCGAATA CAGAGAGCCGNNNGATCGACATG | 855 | TGCAGGACCAGAGAATTCGAATA CACAGAACCNNNGATCGACATG | 1095 | TGCAGGACCAGAGAATTCGAATA CACGCGTGTGNNNGATCGACATG | 1335 |
| TGCAGGACCAGAGAATTCGAATA CACAGACAGANNNGATCGACATG | 856 | TGCAGGACCAGAGAATTCGAATA CACTTGACAGNNNGATCGACATG | 1096 | TGCAGGACCAGAGAATTCGAATA CACTCCTCGGNNNGATCGACATG | 1336 |

FIG. 13E

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATATATGACNNNGATCGACATG | 857 | TGCAGGACCAGAGAATTCGAATA CACTGGTAGTNNNGATCGACATG | 1097 | TGCAGGACCAGAGAATTCGAATA CAGACTAATTNNNGATCGACATG | 1337 |
| TGCAGGACCAGAGAATTCGAATA CAGTCCGACGNNNGATCGACATG | 858 | TGCAGGACCAGAGAATTCGAATA CACGGATCTANNNGATCGACATG | 1098 | TGCAGGACCAGAGAATTCGAATA CACAATAAGANNNGATCGACATG | 1338 |
| TGCAGGACCAGAGAATTCGAATA CAACTGCATGNNNGATCGACATG | 859 | TGCAGGACCAGAGAATTCGAATA CAAAAAAGAGNNNGATCGACATG | 1099 | TGCAGGACCAGAGAATTCGAATA CATTTACCGCNNNGATCGACATG | 1339 |
| TGCAGGACCAGAGAATTCGAATA CATACCTAAANNNGATCGACATG | 860 | TGCAGGACCAGAGAATTCGAATA CAGGAGACATNNNGATCGACATG | 1100 | TGCAGGACCAGAGAATTCGAATA CAGTGTATTANNNGATCGACATG | 1340 |
| TGCAGGACCAGAGAATTCGAATA CAACCAGATCNNNGATCGACATG | 861 | TGCAGGACCAGAGAATTCGAATA CATCGGAGCNNNGATCGACATG | 1101 | TGCAGGACCAGAGAATTCGAATA CAAGATGTAANNNGATCGACATG | 1341 |
| TGCAGGACCAGAGAATTCGAATA CAGGCAAATGNNNGATCGACATG | 862 | TGCAGGACCAGAGAATTCGAATA CATGTTATTCNNNGATCGACATG | 1102 | TGCAGGACCAGAGAATTCGAATA CATTATTCGTNNNGATCGACATG | 1342 |
| TGCAGGACCAGAGAATTCGAATA CAGAACGTCTNNNGATCGACATG | 863 | TGCAGGACCAGAGAATTCGAATA CAGCGAGACGNNNGATCGACATG | 1103 | TGCAGGACCAGAGAATTCGAATA CAAGTCACACNNNGATCGACATG | 1343 |
| TGCAGGACCAGAGAATTCGAATA CACCACCAAANNNGATCGACATG | 864 | TGCAGGACCAGAGAATTCGAATA CATTATCGAANNNGATCGACATG | 1104 | TGCAGGACCAGAGAATTCGAATA CACTGACAACNNNGATCGACATG | 1344 |
| TGCAGGACCAGAGAATTCGAATA CATTTTCCAANNNGATCGACATG | 865 | TGCAGGACCAGAGAATTCGAATA CAGTGCCAATNNNGATCGACATG | 1105 | TGCAGGACCAGAGAATTCGAATA CAACGCGGTNNNGATCGACATG | 1345 |
| TGCAGGACCAGAGAATTCGAATA CAGTTAGTTANNNGATCGACATG | 866 | TGCAGGACCAGAGAATTCGAATA CAGCTAAAANNNGATCGACATG | 1106 | TGCAGGACCAGAGAATTCGAATA CAGGTGACCCNNNGATCGACATG | 1346 |
| TGCAGGACCAGAGAATTCGAATA CATCAGCTCTNNNGATCGACATG | 867 | TGCAGGACCAGAGAATTCGAATA CAATCCAATANNNGATCGACATG | 1107 | TGCAGGACCAGAGAATTCGAATA CACCTTAGCTNNNGATCGACATG | 1347 |
| TGCAGGACCAGAGAATTCGAATA CATGCGGAGGNNNGATCGACATG | 868 | TGCAGGACCAGAGAATTCGAATA CATTCAAGGCNNNGATCGACATG | 1108 | TGCAGGACCAGAGAATTCGAATA CACTCGCTATNNNGATCGACATG | 1348 |
| TGCAGGACCAGAGAATTCGAATA CATCTGCAAGNNNGATCGACATG | 869 | TGCAGGACCAGAGAATTCGAATA CATTATTAAANNNGATCGACATG | 1109 | TGCAGGACCAGAGAATTCGAATA CAAGCCTAGTNNNGATCGACATG | 1349 |
| TGCAGGACCAGAGAATTCGAATA CATCTAACCCNNNGATCGACATG | 870 | TGCAGGACCAGAGAATTCGAATA CAAACTCTAANNNGATCGACATG | 1110 | TGCAGGACCAGAGAATTCGAATA CAGAGAGTTGNNNGATCGACATG | 1350 |
| TGCAGGACCAGAGAATTCGAATA CACGTAGGAANNNGATCGACATG | 871 | TGCAGGACCAGAGAATTCGAATA CAGACTCCAANNNGATCGACATG | 1111 | TGCAGGACCAGAGAATTCGAATA CATAAGAGGCNNNGATCGACATG | 1351 |
| TGCAGGACCAGAGAATTCGAATA CACAAGACTCNNNGATCGACATG | 872 | TGCAGGACCAGAGAATTCGAATA CACAGCCTCNNNGATCGACATG | 1112 | TGCAGGACCAGAGAATTCGAATA CAGTTAATACNNNGATCGACATG | 1352 |
| TGCAGGACCAGAGAATTCGAATA CATTCCGTGTNNNGATCGACATG | 873 | TGCAGGACCAGAGAATTCGAATA CAGAGTCACTNNNGATCGACATG | 1113 | TGCAGGACCAGAGAATTCGAATA CAGGTCCGCANNNGATCGACATG | 1353 |
| TGCAGGACCAGAGAATTCGAATA CAGTGAACGANNNGATCGACATG | 874 | TGCAGGACCAGAGAATTCGAATA CAAGAACTGGNNNGATCGACATG | 1114 | TGCAGGACCAGAGAATTCGAATA CATAAGCATTNNNGATCGACATG | 1354 |
| TGCAGGACCAGAGAATTCGAATA CAGCTAAACCNNNGATCGACATG | 875 | TGCAGGACCAGAGAATTCGAATA CAGCGTATTGNNNGATCGACATG | 1115 | TGCAGGACCAGAGAATTCGAATA CAGTACGCATNNNGATCGACATG | 1355 |
| TGCAGGACCAGAGAATTCGAATA CACAATTTTCNNNGATCGACATG | 876 | TGCAGGACCAGAGAATTCGAATA CACTTAAATGNNNGATCGACATG | 1116 | TGCAGGACCAGAGAATTCGAATA CAAACGAACGNNNGATCGACATG | 1356 |
| TGCAGGACCAGAGAATTCGAATA CATGAGGAACNNNGATCGACATG | 877 | TGCAGGACCAGAGAATTCGAATA CATTAGCCTCNNNGATCGACATG | 1117 | TGCAGGACCAGAGAATTCGAATA CAGTAGGTTCNNNGATCGACATG | 1357 |
| TGCAGGACCAGAGAATTCGAATA CAGTAATCTANNNGATCGACATG | 878 | TGCAGGACCAGAGAATTCGAATA CAACCAGAGANNNGATCGACATG | 1118 | TGCAGGACCAGAGAATTCGAATA CACTTTTTTCNNNGATCGACATG | 1358 |
| TGCAGGACCAGAGAATTCGAATA CATATCTCCGNNNGATCGACATG | 879 | TGCAGGACCAGAGAATTCGAATA CATCAGCCAANNNGATCGACATG | 1119 | TGCAGGACCAGAGAATTCGAATA CAATGACCCANNNGATCGACATG | 1359 |
| TGCAGGACCAGAGAATTCGAATA CAGCTACGGCNNNGATCGACATG | 880 | TGCAGGACCAGAGAATTCGAATA CACCGAATACNNNGATCGACATG | 1120 | TGCAGGACCAGAGAATTCGAATA CAATCAGTTANNNGATCGACATG | 1360 |
| TGCAGGACCAGAGAATTCGAATA CAATATCTGANNNGATCGACATG | 881 | TGCAGGACCAGAGAATTCGAATA CAGCGGCAAGNNNGATCGACATG | 1121 | TGCAGGACCAGAGAATTCGAATA CATAGTAAAGNNNGATCGACATG | 1361 |
| TGCAGGACCAGAGAATTCGAATA CATACTTAGANNNGATCGACATG | 882 | TGCAGGACCAGAGAATTCGAATA CATAAATCGTNNNGATCGACATG | 1122 | TGCAGGACCAGAGAATTCGAATA CACCCGATGNNNGATCGACATG | 1362 |
| TGCAGGACCAGAGAATTCGAATA CATCATTTTGNNNGATCGACATG | 883 | TGCAGGACCAGAGAATTCGAATA CAAGCTTCGNNNGATCGACATG | 1123 | TGCAGGACCAGAGAATTCGAATA CACACAGCATNNNGATCGACATG | 1363 |
| TGCAGGACCAGAGAATTCGAATA CAGCGTGGAGNNNGATCGACATG | 884 | TGCAGGACCAGAGAATTCGAATA CAATGCATATNNNGATCGACATG | 1124 | TGCAGGACCAGAGAATTCGAATA CACAGGTACTNNNGATCGACATG | 1364 |
| TGCAGGACCAGAGAATTCGAATA CATAAGACGGNNNGATCGACATG | 885 | TGCAGGACCAGAGAATTCGAATA CATCTCTCCTNNNGATCGACATG | 1125 | TGCAGGACCAGAGAATTCGAATA CACATAACCGNNNGATCGACATG | 1365 |
| TGCAGGACCAGAGAATTCGAATA CAAGGCCTTANNNGATCGACATG | 886 | TGCAGGACCAGAGAATTCGAATA CATAGTGGTCNNNGATCGACATG | 1126 | TGCAGGACCAGAGAATTCGAATA CAGTACTGGTNNNGATCGACATG | 1366 |
| TGCAGGACCAGAGAATTCGAATA CACATCTCACNNNGATCGACATG | 887 | TGCAGGACCAGAGAATTCGAATA CAGAAACCTCNNNGATCGACATG | 1127 | TGCAGGACCAGAGAATTCGAATA CAGCAAGTCTNNNGATCGACATG | 1367 |
| TGCAGGACCAGAGAATTCGAATA CATGCCGATCANNNGATCGACATG | 888 | TGCAGGACCAGAGAATTCGAATA CATGACTATANNNGATCGACATG | 1128 | TGCAGGACCAGAGAATTCGAATA CACGTGCTCCNNNGATCGACATG | 1368 |

FIG. 13F

| Pool-4 | SEQ ID NO: | Pool-5 | SEQ ID NO: | Pool-6 | SEQ ID NO: |
|---|---|---|---|---|---|
| TGCAGGACCAGAGAATTCGAATACACGGAGGACNNNGATCGACATG | 889 | TGCAGGACCAGAGAATTCGAATACACATGACTGNNNGATCGACATG | 1129 | TGCAGGACCAGAGAATTCGAATACACACTACCTNNNGATCGACATG | 1369 |
| TGCAGGACCAGAGAATTCGAATACAACTAATTGNNNGATCGACATG | 890 | TGCAGGACCAGAGAATTCGAATACACCAAAGTCNNNGATCGACATG | 1130 | TGCAGGACCAGAGAATTCGAATACAGTGTATATNNNGATCGACATG | 1370 |
| TGCAGGACCAGAGAATTCGAATACATGCCTAGANNNGATCGACATG | 891 | TGCAGGACCAGAGAATTCGAATACACGCATTCNNNGATCGACATG | 1131 | TGCAGGACCAGAGAATTCGAATACAATGACGCTNNNGATCGACATG | 1371 |
| TGCAGGACCAGAGAATTCGAATACACTATCCGTNNNGATCGACATG | 892 | TGCAGGACCAGAGAATTCGAATACAACCCGGTGNNNGATCGACATG | 1132 | TGCAGGACCAGAGAATTCGAATACAAGGCACTTNNNGATCGACATG | 1372 |
| TGCAGGACCAGAGAATTCGAATACATGCCAGGCNNNGATCGACATG | 893 | TGCAGGACCAGAGAATTCGAATACACTTGCGTTNNNGATCGACATG | 1133 | TGCAGGACCAGAGAATTCGAATACAGGCAGGCANNNGATCGACATG | 1373 |
| TGCAGGACCAGAGAATTCGAATACAGCGGAGCANNNGATCGACATG | 894 | TGCAGGACCAGAGAATTCGAATACATTATGCAANNNGATCGACATG | 1134 | TGCAGGACCAGAGAATTCGAATACACTATGTTTNNNGATCGACATG | 1374 |
| TGCAGGACCAGAGAATTCGAATACAAGACCCATNNNGATCGACATG | 895 | TGCAGGACCAGAGAATTCGAATACATATTTGAGNNNGATCGACATG | 1135 | TGCAGGACCAGAGAATTCGAATACATAAATATTNNNGATCGACATG | 1375 |
| TGCAGGACCAGAGAATTCGAATACATTGACCTCNNNGATCGACATG | 896 | TGCAGGACCAGAGAATTCGAATACATGTTCGCTNNNGATCGACATG | 1136 | TGCAGGACCAGAGAATTCGAATACAGACACCATNNNGATCGACATG | 1376 |
| TGCAGGACCAGAGAATTCGAATACACTTGCTCANNNGATCGACATG | 897 | TGCAGGACCAGAGAATTCGAATACATAGCATCGNNNGATCGACATG | 1137 | TGCAGGACCAGAGAATTCGAATACATAGATACTNNNGATCGACATG | 1377 |
| TGCAGGACCAGAGAATTCGAATACAATGCTGCANNNGATCGACATG | 898 | TGCAGGACCAGAGAATTCGAATACATTCAGAGCNNNGATCGACATG | 1138 | TGCAGGACCAGAGAATTCGAATACATACCCTGTNNNGATCGACATG | 1378 |
| TGCAGGACCAGAGAATTCGAATACAAACGGACANNNGATCGACATG | 899 | TGCAGGACCAGAGAATTCGAATACAAACGCGAGNNNGATCGACATG | 1139 | TGCAGGACCAGAGAATTCGAATACAGTCGCCGANNNGATCGACATG | 1379 |
| TGCAGGACCAGAGAATTCGAATACAGCGATCATNNNGATCGACATG | 900 | TGCAGGACCAGAGAATTCGAATACATATGCCGTNNNGATCGACATG | 1140 | TGCAGGACCAGAGAATTCGAATACACCTCTTAGNNNGATCGACATG | 1380 |
| TGCAGGACCAGAGAATTCGAATACATGACAGCAGNNNGATCGACATG | 901 | TGCAGGACCAGAGAATTCGAATACAAGCCTATGNNNGATCGACATG | 1141 | TGCAGGACCAGAGAATTCGAATACATAAGATTCNNNGATCGACATG | 1381 |
| TGCAGGACCAGAGAATTCGAATACAGCCACTGGNNNGATCGACATG | 902 | TGCAGGACCAGAGAATTCGAATACACACTCTACNNNGATCGACATG | 1142 | TGCAGGACCAGAGAATTCGAATACACGCGTACGNNNGATCGACATG | 1382 |
| TGCAGGACCAGAGAATTCGAATACAGGTTTGACNNNGATCGACATG | 903 | TGCAGGACCAGAGAATTCGAATACAAAACTGAANNNGATCGACATG | 1143 | TGCAGGACCAGAGAATTCGAATACACTGACCAANNNGATCGACATG | 1383 |
| TGCAGGACCAGAGAATTCGAATACAAACTTGGCNNNGATCGACATG | 904 | TGCAGGACCAGAGAATTCGAATACACTTCCGCGNNNGATCGACATG | 1144 | TGCAGGACCAGAGAATTCGAATACAAAGACCGANNNGATCGACATG | 1384 |
| TGCAGGACCAGAGAATTCGAATACAACCTAATANNNGATCGACATG | 905 | TGCAGGACCAGAGAATTCGAATACAACGTCGGCNNNGATCGACATG | 1145 | TGCAGGACCAGAGAATTCGAATACAAATGATTCNNNGATCGACATG | 1385 |
| TGCAGGACCAGAGAATTCGAATACAGCACAANNNGATCGACATG | 906 | TGCAGGACCAGAGAATTCGAATACAGTACCAANNNGATCGACATG | 1146 | TGCAGGACCAGAGAATTCGAATACACCCCCCANNNGATCGACATG | 1386 |
| TGCAGGACCAGAGAATTCGAATACATGTGTCAGNNNGATCGACATG | 907 | TGCAGGACCAGAGAATTCGAATACAACCGCATANNNGATCGACATG | 1147 | TGCAGGACCAGAGAATTCGAATACAGCCTGAATNNNGATCGACATG | 1387 |
| TGCAGGACCAGAGAATTCGAATACAAGTAACAANNNGATCGACATG | 908 | TGCAGGACCAGAGAATTCGAATACAAACCAGCTNNNGATCGACATG | 1148 | TGCAGGACCAGAGAATTCGAATACATCGGTAGTNNNGATCGACATG | 1388 |
| TGCAGGACCAGAGAATTCGAATACATCTGAGCANNNTGCATCAGGT | 909 | TGCAGGACCAGAGAATTCGAATACAGAGCCAGCNNNTGCATCAGGT | 1149 | TGCAGGACCAGAGAATTCGAATACATGGCTCGGNNNTGCATCAGGT | 1389 |
| TGCAGGACCAGAGAATTCGAATACAAGTGAACNNNTGCATCAGGT | 910 | TGCAGGACCAGAGAATTCGAATACATTTTATTANNNTGCATCAGGT | 1150 | TGCAGGACCAGAGAATTCGAATACACAATCCTCNNNTGCATCAGGT | 1390 |
| TGCAGGACCAGAGAATTCGAATACAGAACTCGTNNNTGCATCAGGT | 911 | TGCAGGACCAGAGAATTCGAATACAGCTAGGTTNNNTGCATCAGGT | 1151 | TGCAGGACCAGAGAATTCGAATACATAGAGACGNNNTGCATCAGGT | 1391 |
| TGCAGGACCAGAGAATTCGAATACAGCAGGCGANNNTGCATCAGGT | 912 | TGCAGGACCAGAGAATTCGAATACATTTGACTTNNNTGCATCAGGT | 1152 | TGCAGGACCAGAGAATTCGAATACAGCGGATGGNNNTGCATCAGGT | 1392 |
| TGCAGGACCAGAGAATTCGAATACAGGCTCTCCNNNTGCATCAGGT | 913 | TGCAGGACCAGAGAATTCGAATACACAAACATTNNNTGCATCAGGT | 1153 | TGCAGGACCAGAGAATTCGAATACACTCACCATNNNTGCATCAGGT | 1393 |
| TGCAGGACCAGAGAATTCGAATACAAATACATCNNNTGCATCAGGT | 914 | TGCAGGACCAGAGAATTCGAATACATTGCAATANNNTGCATCAGGT | 1154 | TGCAGGACCAGAGAATTCGAATACAATGGTAAANNNTGCATCAGGT | 1394 |
| TGCAGGACCAGAGAATTCGAATACAAGGTCAAGNNNTGCATCAGGT | 915 | TGCAGGACCAGAGAATTCGAATACAACAAGGCANNNTGCATCAGGT | 1155 | TGCAGGACCAGAGAATTCGAATACATATCAACANNNTGCATCAGGT | 1395 |
| TGCAGGACCAGAGAATTCGAATACATGAGCCGCNNNTGCATCAGGT | 916 | TGCAGGACCAGAGAATTCGAATACAGGTGCTGCNNNTGCATCAGGT | 1156 | TGCAGGACCAGAGAATTCGAATACAAAAGTCAANNNTGCATCAGGT | 1396 |
| TGCAGGACCAGAGAATTCGAATACATTAGTTTCNNNTGCATCAGGT | 917 | TGCAGGACCAGAGAATTCGAATACAAGGTCGTTNNNTGCATCAGGT | 1157 | TGCAGGACCAGAGAATTCGAATACACAAAGGCANNNTGCATCAGGT | 1397 |
| TGCAGGACCAGAGAATTCGAATACAGTCGTAGTNNNTGCATCAGGT | 918 | TGCAGGACCAGAGAATTCGAATACACAACGGAANNNTGCATCAGGT | 1158 | TGCAGGACCAGAGAATTCGAATACACGATGACTNNNTGCATCAGGT | 1398 |
| TGCAGGACCAGAGAATTCGAATACAAAAGGATTNNNTGCATCAGGT | 919 | TGCAGGACCAGAGAATTCGAATACAGATCCAATNNNTGCATCAGGT | 1159 | TGCAGGACCAGAGAATTCGAATACACGATTGTGNNNTGCATCAGGT | 1399 |
| TGCAGGACCAGAGAATTCGAATACATTTTTAGCNNNTGCATCAGGT | 920 | TGCAGGACCAGAGAATTCGAATACAGGAAGACTNNNTGCATCAGGT | 1160 | TGCAGGACCAGAGAATTCGAATACATTATCTTGNNNTGCATCAGGT | 1400 |

FIG. 13G

| Pool-4 | SEQ ID NO: | Pool-5 | SEQ ID NO: | Pool-6 | SEQ ID NO: |
|---|---|---|---|---|---|
| TGCAGGACCAGAGAATTCGAATACAATAACTCANNNTGCATCAGGT | 921 | TGCAGGACCAGAGAATTCGAATACAGGTAAATANNNTGCATCAGGT | 1161 | TGCAGGACCAGAGAATTCGAATACAGTATTGATNNNTGCATCAGGT | 1401 |
| TGCAGGACCAGAGAATTCGAATACATTTTAACCNNNTGCATCAGGT | 922 | TGCAGGACCAGAGAATTCGAATACAGGTAGAACNNNTGCATCAGGT | 1162 | TGCAGGACCAGAGAATTCGAATACAAGGAGGTTNNNTGCATCAGGT | 1402 |
| TGCAGGACCAGAGAATTCGAATACAGTGCCGACNNNTGCATCAGGT | 923 | TGCAGGACCAGAGAATTCGAATACAATATGAGANNNTGCATCAGGT | 1163 | TGCAGGACCAGAGAATTCGAATACAACTGCCCCNNNTGCATCAGGT | 1403 |
| TGCAGGACCAGAGAATTCGAATACAGAATAGATNNNTGCATCAGGT | 924 | TGCAGGACCAGAGAATTCGAATACATGGAAATANNNTGCATCAGGT | 1164 | TGCAGGACCAGAGAATTCGAATACAAAATCTCANNNTGCATCAGGT | 1404 |
| TGCAGGACCAGAGAATTCGAATACAGCTGAGCCNNNTGCATCAGGT | 925 | TGCAGGACCAGAGAATTCGAATACATAACCAATNNNTGCATCAGGT | 1165 | TGCAGGACCAGAGAATTCGAATACACCATGTGANNNTGCATCAGGT | 1405 |
| TGCAGGACCAGAGAATTCGAATACAACAGGCAANNNTGCATCAGGT | 926 | TGCAGGACCAGAGAATTCGAATACAGTCTGATGNNNTGCATCAGGT | 1166 | TGCAGGACCAGAGAATTCGAATACACCCCTTTTNNNTGCATCAGGT | 1406 |
| TGCAGGACCAGAGAATTCGAATACAGACCGCACNNNTGCATCAGGT | 927 | TGCAGGACCAGAGAATTCGAATACATTTATGAGNNNTGCATCAGGT | 1167 | TGCAGGACCAGAGAATTCGAATACAGCTAGCGCNNNTGCATCAGGT | 1407 |
| TGCAGGACCAGAGAATTCGAATACACTTATTCANNNTGCATCAGGT | 928 | TGCAGGACCAGAGAATTCGAATACAATGATTTGNNNTGCATCAGGT | 1168 | TGCAGGACCAGAGAATTCGAATACAAACACCCNNNTGCATCAGGT | 1408 |
| TGCAGGACCAGAGAATTCGAATACAGTGTGCTANNNTGCATCAGGT | 929 | TGCAGGACCAGAGAATTCGAATACACTCATCGTNNNTGCATCAGGT | 1169 | TGCAGGACCAGAGAATTCGAATACACTGAGATCNNNTGCATCAGGT | 1409 |
| TGCAGGACCAGAGAATTCGAATACAATTTAGTGNNNTGCATCAGGT | 930 | TGCAGGACCAGAGAATTCGAATACACTCCATACNNNTGCATCAGGT | 1170 | TGCAGGACCAGAGAATTCGAATACAAATGCGTCNNNTGCATCAGGT | 1410 |
| TGCAGGACCAGAGAATTCGAATACATCGGAGAANNNTGCATCAGGT | 931 | TGCAGGACCAGAGAATTCGAATACAGCTACATNNNTGCATCAGGT | 1171 | TGCAGGACCAGAGAATTCGAATACAATTGCCAGNNNTGCATCAGGT | 1411 |
| TGCAGGACCAGAGAATTCGAATACACGCCGAACNNNTGCATCAGGT | 932 | TGCAGGACCAGAGAATTCGAATACAAATCATCANNNTGCATCAGGT | 1172 | TGCAGGACCAGAGAATTCGAATACATTAATTCCNNNTGCATCAGGT | 1412 |
| TGCAGGACCAGAGAATTCGAATACAGCTTCGCCNNNTGCATCAGGT | 933 | TGCAGGACCAGAGAATTCGAATACACGTCTCATNNNTGCATCAGGT | 1173 | TGCAGGACCAGAGAATTCGAATACAAGCATATTNNNTGCATCAGGT | 1413 |
| TGCAGGACCAGAGAATTCGAATACAACAATCATNNNTGCATCAGGT | 934 | TGCAGGACCAGAGAATTCGAATACAACTCGTTCNNNTGCATCAGGT | 1174 | TGCAGGACCAGAGAATTCGAATACACCCATTACNNNTGCATCAGGT | 1414 |
| TGCAGGACCAGAGAATTCGAATACATGATCGCANNNTGCATCAGGT | 935 | TGCAGGACCAGAGAATTCGAATACAAGTTCTGGNNNTGCATCAGGT | 1175 | TGCAGGACCAGAGAATTCGAATACACTCGTTTGNNNTGCATCAGGT | 1415 |
| TGCAGGACCAGAGAATTCGAATACACACAGTACNNNTGCATCAGGT | 936 | TGCAGGACCAGAGAATTCGAATACAACTAGTATNNNTGCATCAGGT | 1176 | TGCAGGACCAGAGAATTCGAATACAGGTATCGTNNNTGCATCAGGT | 1416 |
| TGCAGGACCAGAGAATTCGAATACAGTCAAGTCNNNTGCATCAGGT | 937 | TGCAGGACCAGAGAATTCGAATACAATTGCGCANNNTGCATCAGGT | 1177 | TGCAGGACCAGAGAATTCGAATACAGTACCCTTNNNTGCATCAGGT | 1417 |
| TGCAGGACCAGAGAATTCGAATACAGCTCCCACNNNTGCATCAGGT | 938 | TGCAGGACCAGAGAATTCGAATACACGAGCGCTNNNTGCATCAGGT | 1178 | TGCAGGACCAGAGAATTCGAATACACAACTTTTNNNTGCATCAGGT | 1418 |
| TGCAGGACCAGAGAATTCGAATACATTACTTGTNNNTGCATCAGGT | 939 | TGCAGGACCAGAGAATTCGAATACAACGACCATNNNTGCATCAGGT | 1179 | TGCAGGACCAGAGAATTCGAATACAGAACTTGCNNNTGCATCAGGT | 1419 |
| TGCAGGACCAGAGAATTCGAATACATAATGTGTNNNTGCATCAGGT | 940 | TGCAGGACCAGAGAATTCGAATACATAAGTGAANNNTGCATCAGGT | 1180 | TGCAGGACCAGAGAATTCGAATACATATTATGGNNNTGCATCAGGT | 1420 |
| TGCAGGACCAGAGAATTCGAATACATACCATTTNNNTGCATCAGGT | 941 | TGCAGGACCAGAGAATTCGAATACATCTGCCGGNNNTGCATCAGGT | 1181 | TGCAGGACCAGAGAATTCGAATACAGCCCGCGNNNTGCATCAGGT | 1421 |
| TGCAGGACCAGAGAATTCGAATACAGTCCGTAANNNTGCATCAGGT | 942 | TGCAGGACCAGAGAATTCGAATACAAATACTGTNNNTGCATCAGGT | 1182 | TGCAGGACCAGAGAATTCGAATACAGCAAAAGCNNNTGCATCAGGT | 1422 |
| TGCAGGACCAGAGAATTCGAATACAAGCGGTAANNNTGCATCAGGT | 943 | TGCAGGACCAGAGAATTCGAATACATATGTTCTNNNTGCATCAGGT | 1183 | TGCAGGACCAGAGAATTCGAATACAGATACGCTNNNTGCATCAGGT | 1423 |
| TGCAGGACCAGAGAATTCGAATACAGGAAACTGNNNTGCATCAGGT | 944 | TGCAGGACCAGAGAATTCGAATACACCAGCGGTNNNTGCATCAGGT | 1184 | TGCAGGACCAGAGAATTCGAATACACAGTATCGNNNTGCATCAGGT | 1424 |
| TGCAGGACCAGAGAATTCGAATACAGGCCACGTNNNTGCATCAGGT | 945 | TGCAGGACCAGAGAATTCGAATACACGGTTGATNNNTGCATCAGGT | 1185 | TGCAGGACCAGAGAATTCGAATACACTCACTGTNNNTGCATCAGGT | 1425 |
| TGCAGGACCAGAGAATTCGAATACATCATTGAANNNTGCATCAGGT | 946 | TGCAGGACCAGAGAATTCGAATACACGCGTGCANNNTGCATCAGGT | 1186 | TGCAGGACCAGAGAATTCGAATACACCCGTCAGGNNNTGCATCAGGT | 1426 |
| TGCAGGACCAGAGAATTCGAATACAGCGTCAATNNNTGCATCAGGT | 947 | TGCAGGACCAGAGAATTCGAATACAGTCTAAATNNNTGCATCAGGT | 1187 | TGCAGGACCAGAGAATTCGAATACAGCTTCTGTNNNTGCATCAGGT | 1427 |
| TGCAGGACCAGAGAATTCGAATACACGGAAGCGNNNTGCATCAGGT | 948 | TGCAGGACCAGAGAATTCGAATACAGTAATTACNNNTGCATCAGGT | 1188 | TGCAGGACCAGAGAATTCGAATACATTATATTTNNNTGCATCAGGT | 1428 |
| TGCAGGACCAGAGAATTCGAATACAGTTCGAACNNNTGCATCAGGT | 949 | TGCAGGACCAGAGAATTCGAATACATTCCGGTTNNNTGCATCAGGT | 1189 | TGCAGGACCAGAGAATTCGAATACAGGTTTACGNNNTGCATCAGGT | 1429 |
| TGCAGGACCAGAGAATTCGAATACAGGCCCCTTNNNTGCATCAGGT | 950 | TGCAGGACCAGAGAATTCGAATACAGAGCGTGGNNNTGCATCAGGT | 1190 | TGCAGGACCAGAGAATTCGAATACAGGACGATANNNTGCATCAGGT | 1430 |
| TGCAGGACCAGAGAATTCGAATACAATGGCTCANNNTGCATCAGGT | 951 | TGCAGGACCAGAGAATTCGAATACAATTTACTCNNNTGCATCAGGT | 1191 | TGCAGGACCAGAGAATTCGAATACAAGTCAGGANNNTGCATCAGGT | 1431 |
| TGCAGGACCAGAGAATTCGAATACATTGACGGTNNNTGCATCAGGT | 952 | TGCAGGACCAGAGAATTCGAATACACAACACTGNNNTGCATCAGGT | 1192 | TGCAGGACCAGAGAATTCGAATACACTACGAACNNNTGCATCAGGT | 1432 |

FIG. 13H

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATGGACGTTNNNTGCATCAGGT | 953 | TGCAGGACCAGAGAATTCGAATA CACCGCGGCGNNNTGCATCAGGT | 1193 | TGCAGGACCAGAGAATTCGAATA CAAGCCATGTNNNTGCATCAGGT | 1433 |
| TGCAGGACCAGAGAATTCGAATA CATGACAGTCNNNTGCATCAGGT | 954 | TGCAGGACCAGAGAATTCGAATA CACTAAGCTGNNNTGCATCAGGT | 1194 | TGCAGGACCAGAGAATTCGAATA CATTCCACTGNNNTGCATCAGGT | 1434 |
| TGCAGGACCAGAGAATTCGAATA CACTACCTGTNNNTGCATCAGGT | 955 | TGCAGGACCAGAGAATTCGAATA CAATTCAAGTNNNTGCATCAGGT | 1195 | TGCAGGACCAGAGAATTCGAATA CAACCCTGTTNNNTGCATCAGGT | 1435 |
| TGCAGGACCAGAGAATTCGAATA CAAGGTCCCGNNNTGCATCAGGT | 956 | TGCAGGACCAGAGAATTCGAATA CAATTGGCGTNNNTGCATCAGGT | 1196 | TGCAGGACCAGAGAATTCGAATA CACCCTTTCTNNNTGCATCAGGT | 1436 |
| TGCAGGACCAGAGAATTCGAATA CATTCATCTANNNTGCATCAGGT | 957 | TGCAGGACCAGAGAATTCGAATA CATGATTTGANNNTGCATCAGGT | 1197 | TGCAGGACCAGAGAATTCGAATA CAATGTTGATNNNTGCATCAGGT | 1437 |
| TGCAGGACCAGAGAATTCGAATA CAGATAAAGTNNNTGCATCAGGT | 958 | TGCAGGACCAGAGAATTCGAATA CAACTGCCGGNNNTGCATCAGGT | 1198 | TGCAGGACCAGAGAATTCGAATA CACACTGGCGNNNTGCATCAGGT | 1438 |
| TGCAGGACCAGAGAATTCGAATA CACACGGAAANNNTGCATCAGGT | 959 | TGCAGGACCAGAGAATTCGAATA CATTAATCCTNNNTGCATCAGGT | 1199 | TGCAGGACCAGAGAATTCGAATA CATTCGGTAGNNNTGCATCAGGT | 1439 |
| TGCAGGACCAGAGAATTCGAATA CATGTGAGGANNNTGCATCAGGT | 960 | TGCAGGACCAGAGAATTCGAATA CACTACGCTTNNNTGCATCAGGT | 1200 | TGCAGGACCAGAGAATTCGAATA CAACCCTGCCNNNTGCATCAGGT | 1440 |
| TGCAGGACCAGAGAATTCGAATA CACGTGATCANNNTGCATCAGGT | 961 | TGCAGGACCAGAGAATTCGAATA CATAGCTATANNNTGCATCAGGT | 1201 | TGCAGGACCAGAGAATTCGAATA CAGTACCTAGNNNTGCATCAGGT | 1441 |
| TGCAGGACCAGAGAATTCGAATA CATGCGTTGANNNTGCATCAGGT | 962 | TGCAGGACCAGAGAATTCGAATA CATGCACTCTNNNTGCATCAGGT | 1202 | TGCAGGACCAGAGAATTCGAATA CACGATAATTNNNTGCATCAGGT | 1442 |
| TGCAGGACCAGAGAATTCGAATA CATCGCTCCGNNNTGCATCAGGT | 963 | TGCAGGACCAGAGAATTCGAATA CAGTGCTCCCNNNTGCATCAGGT | 1203 | TGCAGGACCAGAGAATTCGAATA CAGCCAACCGNNNTGCATCAGGT | 1443 |
| TGCAGGACCAGAGAATTCGAATA CACCAGTCAANNNTGCATCAGGT | 964 | TGCAGGACCAGAGAATTCGAATA CAGCCACCAGNNNTGCATCAGGT | 1204 | TGCAGGACCAGAGAATTCGAATA CATAACATCANNNTGCATCAGGT | 1444 |
| TGCAGGACCAGAGAATTCGAATA CACACATTCCNNNTGCATCAGGT | 965 | TGCAGGACCAGAGAATTCGAATA CATTATGTGANNNTGCATCAGGT | 1205 | TGCAGGACCAGAGAATTCGAATA CAGCAAGAACNNNTGCATCAGGT | 1445 |
| TGCAGGACCAGAGAATTCGAATA CAGGTATATTNNNTGCATCAGGT | 966 | TGCAGGACCAGAGAATTCGAATA CAATACTCCCNNNTGCATCAGGT | 1206 | TGCAGGACCAGAGAATTCGAATA CAACGTGATCNNNTGCATCAGGT | 1446 |
| TGCAGGACCAGAGAATTCGAATA CATAAGATGANNNTGCATCAGGT | 967 | TGCAGGACCAGAGAATTCGAATA CAACTATGGCNNNTGCATCAGGT | 1207 | TGCAGGACCAGAGAATTCGAATA CACGTTCCTANNNTGCATCAGGT | 1447 |
| TGCAGGACCAGAGAATTCGAATA CATTAAAATTNNNTGCATCAGGT | 968 | TGCAGGACCAGAGAATTCGAATA CAACGGCCTGNNNTGCATCAGGT | 1208 | TGCAGGACCAGAGAATTCGAATA CAATGCCAGTNNNTGCATCAGGT | 1448 |

FIG. 14A

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CACAGGCTCGNNNACGTATGCCA | 1449 | TGCAGGACCAGAGAATTCGAATA CAACTACCAGNNNACGTATGCCA | 1689 | TGCAGGACCAGAGAATTCGAATA CAGAACGCCCNNNACGTATGCCA | 1929 |
| TGCAGGACCAGAGAATTCGAATA CATTGAAGCCNNNACGTATGCCA | 1450 | TGCAGGACCAGAGAATTCGAATA CATTATTGAGNNNACGTATGCCA | 1690 | TGCAGGACCAGAGAATTCGAATA CAACCAATGCNNNACGTATGCCA | 1930 |
| TGCAGGACCAGAGAATTCGAATA CACACAGAGANNNACGTATGCCA | 1451 | TGCAGGACCAGAGAATTCGAATA CAACTGTGTGNNNACGTATGCCA | 1691 | TGCAGGACCAGAGAATTCGAATA CAGACCGATTNNNACGTATGCCA | 1931 |
| TGCAGGACCAGAGAATTCGAATA CAGGACTCCGNNNACGTATGCCA | 1452 | TGCAGGACCAGAGAATTCGAATA CATTGATCGGNNNACGTATGCCA | 1692 | TGCAGGACCAGAGAATTCGAATA CAATGTTATGNNNACGTATGCCA | 1932 |
| TGCAGGACCAGAGAATTCGAATA CATTGGTTAANNNACGTATGCCA | 1453 | TGCAGGACCAGAGAATTCGAATA CATTCTCGGTNNNACGTATGCCA | 1693 | TGCAGGACCAGAGAATTCGAATA CAGGAAGAAGNNNACGTATGCCA | 1933 |
| TGCAGGACCAGAGAATTCGAATA CATACTAACANNNACGTATGCCA | 1454 | TGCAGGACCAGAGAATTCGAATA CACCAGTTAGNNNACGTATGCCA | 1694 | TGCAGGACCAGAGAATTCGAATA CAGTTATACANNNACGTATGCCA | 1934 |
| TGCAGGACCAGAGAATTCGAATA CAGTCCAATGNNNACGTATGCCA | 1455 | TGCAGGACCAGAGAATTCGAATA CAAGAACAATNNNACGTATGCCA | 1695 | TGCAGGACCAGAGAATTCGAATA CACCTCCTAANNNACGTATGCCA | 1935 |
| TGCAGGACCAGAGAATTCGAATA CAAGGCACGGNNNACGTATGCCA | 1456 | TGCAGGACCAGAGAATTCGAATA CATCCGAAGTNNNACGTATGCCA | 1696 | TGCAGGACCAGAGAATTCGAATA CATAAACATCNNNACGTATGCCA | 1936 |
| TGCAGGACCAGAGAATTCGAATA CAATCATGTANNNACGTATGCCA | 1457 | TGCAGGACCAGAGAATTCGAATA CATCGGCTCCNNNACGTATGCCA | 1697 | TGCAGGACCAGAGAATTCGAATA CACGGCGGTTNNNACGTATGCCA | 1937 |
| TGCAGGACCAGAGAATTCGAATA CAAAAAGGTTNNNACGTATGCCA | 1458 | TGCAGGACCAGAGAATTCGAATA CACAGTCCCCNNNACGTATGCCA | 1698 | TGCAGGACCAGAGAATTCGAATA CATTAACAACNNNACGTATGCCA | 1938 |
| TGCAGGACCAGAGAATTCGAATA CAAGGCACCCNNNACGTATGCCA | 1459 | TGCAGGACCAGAGAATTCGAATA CAGTCAACTGNNNACGTATGCCA | 1699 | TGCAGGACCAGAGAATTCGAATA CATGGCCATANNNACGTATGCCA | 1939 |
| TGCAGGACCAGAGAATTCGAATA CATTGAAAGANNNACGTATGCCA | 1460 | TGCAGGACCAGAGAATTCGAATA CAGGCGGCTTNNNACGTATGCCA | 1700 | TGCAGGACCAGAGAATTCGAATA CAGAGTCATGNNNACGTATGCCA | 1940 |
| TGCAGGACCAGAGAATTCGAATA CACTCGACTTNNNACGTATGCCA | 1461 | TGCAGGACCAGAGAATTCGAATA CAATGCGCTANNNACGTATGCCA | 1701 | TGCAGGACCAGAGAATTCGAATA CACTAATGCGNNNACGTATGCCA | 1941 |
| TGCAGGACCAGAGAATTCGAATA CAGCGAATTCNNNACGTATGCCA | 1462 | TGCAGGACCAGAGAATTCGAATA CAGCTCCGANNNACGTATGCCA | 1702 | TGCAGGACCAGAGAATTCGAATA CAAGGTTAAANNNACGTATGCCA | 1942 |
| TGCAGGACCAGAGAATTCGAATA CACCCCCGCGNNNACGTATGCCA | 1463 | TGCAGGACCAGAGAATTCGAATA CATGCTGGCGNNNACGTATGCCA | 1703 | TGCAGGACCAGAGAATTCGAATA CAACAGTACCNNNACGTATGCCA | 1943 |
| TGCAGGACCAGAGAATTCGAATA CAGATAAGCGNNNACGTATGCCA | 1464 | TGCAGGACCAGAGAATTCGAATA CACTAACGTGNNNACGTATGCCA | 1704 | TGCAGGACCAGAGAATTCGAATA CAATGTGATTNNNACGTATGCCA | 1944 |
| TGCAGGACCAGAGAATTCGAATA CAGAACGATGNNNACGTATGCCA | 1465 | TGCAGGACCAGAGAATTCGAATA CAGAATACAANNNACGTATGCCA | 1705 | TGCAGGACCAGAGAATTCGAATA CAGCTGCCGANNNACGTATGCCA | 1945 |
| TGCAGGACCAGAGAATTCGAATA CAAATATTATNNNACGTATGCCA | 1466 | TGCAGGACCAGAGAATTCGAATA CAATGACAAANNNACGTATGCCA | 1706 | TGCAGGACCAGAGAATTCGAATA CACTTTTTAGNNNACGTATGCCA | 1946 |
| TGCAGGACCAGAGAATTCGAATA CATAAGCTATNNNACGTATGCCA | 1467 | TGCAGGACCAGAGAATTCGAATA CAACGGCTCGNNNACGTATGCCA | 1707 | TGCAGGACCAGAGAATTCGAATA CATCCCAAAGNNNACGTATGCCA | 1947 |
| TGCAGGACCAGAGAATTCGAATA CAACTCGGCGNNNACGTATGCCA | 1468 | TGCAGGACCAGAGAATTCGAATA CAACAGATAANNNACGTATGCCA | 1708 | TGCAGGACCAGAGAATTCGAATA CAGACACTACNNNACGTATGCCA | 1948 |
| TGCAGGACCAGAGAATTCGAATA CACGACTGCGNNNACGTATGCCA | 1469 | TGCAGGACCAGAGAATTCGAATA CATGTAGCCANNNACGTATGCCA | 1709 | TGCAGGACCAGAGAATTCGAATA CAATACCGACNNNACGTATGCCA | 1949 |
| TGCAGGACCAGAGAATTCGAATA CATCCGACTTNNNACGTATGCCA | 1470 | TGCAGGACCAGAGAATTCGAATA CACTTCTGCANNNACGTATGCCA | 1710 | TGCAGGACCAGAGAATTCGAATA CAGTTGAAAANNNACGTATGCCA | 1950 |
| TGCAGGACCAGAGAATTCGAATA CAGGAGGAGGNNNACGTATGCCA | 1471 | TGCAGGACCAGAGAATTCGAATA CATTACCTTANNNACGTATGCCA | 1711 | TGCAGGACCAGAGAATTCGAATA CAATTCCTATNNNACGTATGCCA | 1951 |
| TGCAGGACCAGAGAATTCGAATA CACAGGCAGGNNNACGTATGCCA | 1472 | TGCAGGACCAGAGAATTCGAATA CATCAATTCTNNNACGTATGCCA | 1712 | TGCAGGACCAGAGAATTCGAATA CAACGTTCAGNNNACGTATGCCA | 1952 |
| TGCAGGACCAGAGAATTCGAATA CAATCTCATTNNNACGTATGCCA | 1473 | TGCAGGACCAGAGAATTCGAATA CAAGGTTCGTNNNACGTATGCCA | 1713 | TGCAGGACCAGAGAATTCGAATA CAAATACGAANNNACGTATGCCA | 1953 |
| TGCAGGACCAGAGAATTCGAATA CAAGGCGATANNNACGTATGCCA | 1474 | TGCAGGACCAGAGAATTCGAATA CAATTTTAAANNNACGTATGCCA | 1714 | TGCAGGACCAGAGAATTCGAATA CACCAACTGANNNACGTATGCCA | 1954 |
| TGCAGGACCAGAGAATTCGAATA CACCTAGATGNNNACGTATGCCA | 1475 | TGCAGGACCAGAGAATTCGAATA CATTGCAGACNNNACGTATGCCA | 1715 | TGCAGGACCAGAGAATTCGAATA CAATCCGTCTNNNACGTATGCCA | 1955 |
| TGCAGGACCAGAGAATTCGAATA CACCTACCATNNNACGTATGCCA | 1476 | TGCAGGACCAGAGAATTCGAATA CACCCACTGNNNACGTATGCCA | 1716 | TGCAGGACCAGAGAATTCGAATA CACGTCCGCTNNNACGTATGCCA | 1956 |

FIG. 14B

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAAACGTCCANNNACGTATGCCA | 1477 | TGCAGGACCAGAGAATTCGAATA CACTTCCTGANNNACGTATGCCA | 1717 | TGCAGGACCAGAGAATTCGAATA CATATACACANNNACGTATGCCA | 1957 |
| TGCAGGACCAGAGAATTCGAATA CAGCACTTAGNNNACGTATGCCA | 1478 | TGCAGGACCAGAGAATTCGAATA CAAGAACTCCNNNACGTATGCCA | 1718 | TGCAGGACCAGAGAATTCGAATA CACTCTATATNNNACGTATGCCA | 1958 |
| TGCAGGACCAGAGAATTCGAATA CAGATCGGAANNNACGTATGCCA | 1479 | TGCAGGACCAGAGAATTCGAATA CACTGTAAGCNNNACGTATGCCA | 1719 | TGCAGGACCAGAGAATTCGAATA CACTCACAGANNNACGTATGCCA | 1959 |
| TGCAGGACCAGAGAATTCGAATA CACGCCATAANNNACGTATGCCA | 1480 | TGCAGGACCAGAGAATTCGAATA CAAGTCGATCNNNACGTATGCCA | 1720 | TGCAGGACCAGAGAATTCGAATA CAGCCGGTGTNNNACGTATGCCA | 1960 |
| TGCAGGACCAGAGAATTCGAATA CATTAAGTTGNNNACGTATGCCA | 1481 | TGCAGGACCAGAGAATTCGAATA CAGTAATAGANNNACGTATGCCA | 1721 | TGCAGGACCAGAGAATTCGAATA CATACGTCAGNNNACGTATGCCA | 1961 |
| TGCAGGACCAGAGAATTCGAATA CAGCCAGCTGNNNACGTATGCCA | 1482 | TGCAGGACCAGAGAATTCGAATA CACGGAGCTCNNNACGTATGCCA | 1722 | TGCAGGACCAGAGAATTCGAATA CATCTGCTCANNNACGTATGCCA | 1962 |
| TGCAGGACCAGAGAATTCGAATA CAAAACGCCTNNNACGTATGCCA | 1483 | TGCAGGACCAGAGAATTCGAATA CATTGTCTTANNNACGTATGCCA | 1723 | TGCAGGACCAGAGAATTCGAATA CAACGTATATNNNACGTATGCCA | 1963 |
| TGCAGGACCAGAGAATTCGAATA CAGTATTTCTNNNACGTATGCCA | 1484 | TGCAGGACCAGAGAATTCGAATA CATTTCGTANNNACGTATGCCA | 1724 | TGCAGGACCAGAGAATTCGAATA CACGAGCCACNNNACGTATGCCA | 1964 |
| TGCAGGACCAGAGAATTCGAATA CAGGTCTCCCNNNACGTATGCCA | 1485 | TGCAGGACCAGAGAATTCGAATA CAAACGGAACNNNACGTATGCCA | 1725 | TGCAGGACCAGAGAATTCGAATA CATCGCTCTANNNACGTATGCCA | 1965 |
| TGCAGGACCAGAGAATTCGAATA CACAAGTCTGNNNACGTATGCCA | 1486 | TGCAGGACCAGAGAATTCGAATA CAACCACGGCNNNACGTATGCCA | 1726 | TGCAGGACCAGAGAATTCGAATA CACGGAAGATNNNACGTATGCCA | 1966 |
| TGCAGGACCAGAGAATTCGAATA CAGAGCACAANNNACGTATGCCA | 1487 | TGCAGGACCAGAGAATTCGAATA CAGAGTATTTNNNACGTATGCCA | 1727 | TGCAGGACCAGAGAATTCGAATA CATTAGCGGTNNNACGTATGCCA | 1967 |
| TGCAGGACCAGAGAATTCGAATA CATCAAACCGNNNACGTATGCCA | 1488 | TGCAGGACCAGAGAATTCGAATA CACCCGCCTANNNACGTATGCCA | 1728 | TGCAGGACCAGAGAATTCGAATA CATGAGCTCANNNACGTATGCCA | 1968 |
| TGCAGGACCAGAGAATTCGAATA CATTCCGCTANNNACGTATGCCA | 1489 | TGCAGGACCAGAGAATTCGAATA CAAGTATGCCNNNACGTATGCCA | 1729 | TGCAGGACCAGAGAATTCGAATA CATACACGTGNNNACGTATGCCA | 1969 |
| TGCAGGACCAGAGAATTCGAATA CAATTCACGNNNACGTATGCCA | 1490 | TGCAGGACCAGAGAATTCGAATA CATAGCAGCTNNNACGTATGCCA | 1730 | TGCAGGACCAGAGAATTCGAATA CATAGTGTATNNNACGTATGCCA | 1970 |
| TGCAGGACCAGAGAATTCGAATA CAATACCTAANNNACGTATGCCA | 1491 | TGCAGGACCAGAGAATTCGAATA CACGCGTGACNNNACGTATGCCA | 1731 | TGCAGGACCAGAGAATTCGAATA CACATTAGGCNNNACGTATGCCA | 1971 |
| TGCAGGACCAGAGAATTCGAATA CAGGACCGGANNNACGTATGCCA | 1492 | TGCAGGACCAGAGAATTCGAATA CAAAATACGANNNACGTATGCCA | 1732 | TGCAGGACCAGAGAATTCGAATA CAACACCACANNNACGTATGCCA | 1972 |
| TGCAGGACCAGAGAATTCGAATA CATGTCCCGCNNNACGTATGCCA | 1493 | TGCAGGACCAGAGAATTCGAATA CACTAGATATNNNACGTATGCCA | 1733 | TGCAGGACCAGAGAATTCGAATA CAGTGCGTCGNNNACGTATGCCA | 1973 |
| TGCAGGACCAGAGAATTCGAATA CAGCCCCAGANNNACGTATGCCA | 1494 | TGCAGGACCAGAGAATTCGAATA CAATGTTGGCNNNACGTATGCCA | 1734 | TGCAGGACCAGAGAATTCGAATA CATATGTTTCNNNACGTATGCCA | 1974 |
| TGCAGGACCAGAGAATTCGAATA CACAAGCCCGNNNACGTATGCCA | 1495 | TGCAGGACCAGAGAATTCGAATA CACTACGCAANNNACGTATGCCA | 1735 | TGCAGGACCAGAGAATTCGAATA CAGTGGTCGCNNNACGTATGCCA | 1975 |
| TGCAGGACCAGAGAATTCGAATA CAGCCATTGANNNACGTATGCCA | 1496 | TGCAGGACCAGAGAATTCGAATA CATTTCTGTANNNACGTATGCCA | 1736 | TGCAGGACCAGAGAATTCGAATA CACTGGACCGNNNACGTATGCCA | 1976 |
| TGCAGGACCAGAGAATTCGAATA CATGAACACCNNNACGTATGCCA | 1497 | TGCAGGACCAGAGAATTCGAATA CACCTCCCTCNNNACGTATGCCA | 1737 | TGCAGGACCAGAGAATTCGAATA CAGGCGTGTCNNNACGTATGCCA | 1977 |
| TGCAGGACCAGAGAATTCGAATA CAGAATCCGTNNNACGTATGCCA | 1498 | TGCAGGACCAGAGAATTCGAATA CAGACTTGACNNNACGTATGCCA | 1738 | TGCAGGACCAGAGAATTCGAATA CAAGTCTAATNNNACGTATGCCA | 1978 |
| TGCAGGACCAGAGAATTCGAATA CATTAATCGANNNACGTATGCCA | 1499 | TGCAGGACCAGAGAATTCGAATA CAGTCATCGANNNACGTATGCCA | 1739 | TGCAGGACCAGAGAATTCGAATA CACTCATGCTNNNACGTATGCCA | 1979 |
| TGCAGGACCAGAGAATTCGAATA CACGCCACTCNNNACGTATGCCA | 1500 | TGCAGGACCAGAGAATTCGAATA CAATCTAGTANNNACGTATGCCA | 1740 | TGCAGGACCAGAGAATTCGAATA CAAGTTCTCCNNNACGTATGCCA | 1980 |
| TGCAGGACCAGAGAATTCGAATA CACCCTTAGTNNNACGTATGCCA | 1501 | TGCAGGACCAGAGAATTCGAATA CACGAAGATGNNNACGTATGCCA | 1741 | TGCAGGACCAGAGAATTCGAATA CAGTGAAGGTNNNACGTATGCCA | 1981 |
| TGCAGGACCAGAGAATTCGAATA CATTCCTGGNNNACGTATGCCA | 1502 | TGCAGGACCAGAGAATTCGAATA CAATTTGCAANNNACGTATGCCA | 1742 | TGCAGGACCAGAGAATTCGAATA CAGTTTTAAGNNNACGTATGCCA | 1982 |
| TGCAGGACCAGAGAATTCGAATA CATTCAACGNNNACGTATGCCA | 1503 | TGCAGGACCAGAGAATTCGAATA CAGACCGGCTNNNACGTATGCCA | 1743 | TGCAGGACCAGAGAATTCGAATA CAAAAGCAATNNNACGTATGCCA | 1983 |
| TGCAGGACCAGAGAATTCGAATA CATTGAGGAGNNNACGTATGCCA | 1504 | TGCAGGACCAGAGAATTCGAATA CACTTGTCACNNNACGTATGCCA | 1744 | TGCAGGACCAGAGAATTCGAATA CATGAAGCGANNNACGTATGCCA | 1984 |
| TGCAGGACCAGAGAATTCGAATA CATTCACGGCTNNNACGTATGCCA | 1505 | TGCAGGACCAGAGAATTCGAATA CACTCGTAAGNNNACGTATGCCA | 1745 | TGCAGGACCAGAGAATTCGAATA CAGTAGTGCTNNNACGTATGCCA | 1985 |

FIG. 14C

| Pool-7 | SEQ ID NO: | Pool-8 | SEQ ID NO: | Pool-9 | SEQ ID NO: |
|---|---|---|---|---|---|
| TGCAGGACCAGAGAATTCGAATACATCGCGGTGNNNACGTATGCCA | 1506 | TGCAGGACCAGAGAATTCGAATACAGCCTTACTNNNACGTATGCCA | 1746 | TGCAGGACCAGAGAATTCGAATACAACTATGTANNNACGTATGCCA | 1986 |
| TGCAGGACCAGAGAATTCGAATACAAATTCCGGNNNACGTATGCCA | 1507 | TGCAGGACCAGAGAATTCGAATACAGCATGTGTNNNACGTATGCCA | 1747 | TGCAGGACCAGAGAATTCGAATACAGAAGTTCCNNNACGTATGCCA | 1987 |
| TGCAGGACCAGAGAATTCGAATACACGTCATGANNNACGTATGCCA | 1508 | TGCAGGACCAGAGAATTCGAATACACTACTGTCNNNACGTATGCCA | 1748 | TGCAGGACCAGAGAATTCGAATACACGGTGCTGNNNACGTATGCCA | 1988 |
| TGCAGGACCAGAGAATTCGAATACACGTTTATTNNNCTAGCGTTAC | 1509 | TGCAGGACCAGAGAATTCGAATACAATCTAACANNNCTAGCGTTAC | 1749 | TGCAGGACCAGAGAATTCGAATACATGCAAATTNNNCTAGCGTTAC | 1989 |
| TGCAGGACCAGAGAATTCGAATACACTGCACGGNNNCTAGCGTTAC | 1510 | TGCAGGACCAGAGAATTCGAATACAACGATTGGNNNCTAGCGTTAC | 1750 | TGCAGGACCAGAGAATTCGAATACAACTTGTGGNNNCTAGCGTTAC | 1990 |
| TGCAGGACCAGAGAATTCGAATACAACCTTGTCNNNCTAGCGTTAC | 1511 | TGCAGGACCAGAGAATTCGAATACAAAACCTTANNNCTAGCGTTAC | 1751 | TGCAGGACCAGAGAATTCGAATACATCGCTGCCNNNCTAGCGTTAC | 1991 |
| TGCAGGACCAGAGAATTCGAATACATCCACCCGNNNCTAGCGTTAC | 1512 | TGCAGGACCAGAGAATTCGAATACACGTAAAAANNNCTAGCGTTAC | 1752 | TGCAGGACCAGAGAATTCGAATACATCCCTTCTNNNCTAGCGTTAC | 1992 |
| TGCAGGACCAGAGAATTCGAATACAAAGGCCGGNNNCTAGCGTTAC | 1513 | TGCAGGACCAGAGAATTCGAATACATCTGAGACNNNCTAGCGTTAC | 1753 | TGCAGGACCAGAGAATTCGAATACACGGTACTANNNCTAGCGTTAC | 1993 |
| TGCAGGACCAGAGAATTCGAATACAGGCAATAGNNNCTAGCGTTAC | 1514 | TGCAGGACCAGAGAATTCGAATACATGGCGATTNNNCTAGCGTTAC | 1754 | TGCAGGACCAGAGAATTCGAATACAAGATATCNNNCTAGCGTTAC | 1994 |
| TGCAGGACCAGAGAATTCGAATACACGGTAGCGNNNCTAGCGTTAC | 1515 | TGCAGGACCAGAGAATTCGAATACACATCTTGCNNNCTAGCGTTAC | 1755 | TGCAGGACCAGAGAATTCGAATACACTCAAGTGNNNCTAGCGTTAC | 1995 |
| TGCAGGACCAGAGAATTCGAATACATGTTCTATNNNCTAGCGTTAC | 1516 | TGCAGGACCAGAGAATTCGAATACATCTTTCGGNNNCTAGCGTTAC | 1756 | TGCAGGACCAGAGAATTCGAATACAACCTCCTANNNCTAGCGTTAC | 1996 |
| TGCAGGACCAGAGAATTCGAATACATTAATATANNNCTAGCGTTAC | 1517 | TGCAGGACCAGAGAATTCGAATACAGCGAACANNNCTAGCGTTAC | 1757 | TGCAGGACCAGAGAATTCGAATACAAGCAATTNNNCTAGCGTTAC | 1997 |
| TGCAGGACCAGAGAATTCGAATACAATATGGTTNNNCTAGCGTTAC | 1518 | TGCAGGACCAGAGAATTCGAATACAGAGTAGACNNNCTAGCGTTAC | 1758 | TGCAGGACCAGAGAATTCGAATACAGCCCCGAANNNCTAGCGTTAC | 1998 |
| TGCAGGACCAGAGAATTCGAATACAGCTGGTTANNNCTAGCGTTAC | 1519 | TGCAGGACCAGAGAATTCGAATACACTCATGGANNNCTAGCGTTAC | 1759 | TGCAGGACCAGAGAATTCGAATACACCAAATCGNNNCTAGCGTTAC | 1999 |
| TGCAGGACCAGAGAATTCGAATACAAGACTGAGNNNCTAGCGTTAC | 1520 | TGCAGGACCAGAGAATTCGAATACATTCCCGGCNNNCTAGCGTTAC | 1760 | TGCAGGACCAGAGAATTCGAATACAGATCGGTTNNNCTAGCGTTAC | 2000 |
| TGCAGGACCAGAGAATTCGAATACAGACTTGCANNNCTAGCGTTAC | 1521 | TGCAGGACCAGAGAATTCGAATACATGGCCTAANNNCTAGCGTTAC | 1761 | TGCAGGACCAGAGAATTCGAATACAACCCCTGCNNNCTAGCGTTAC | 2001 |
| TGCAGGACCAGAGAATTCGAATACAGTCTATCCNNNCTAGCGTTAC | 1522 | TGCAGGACCAGAGAATTCGAATACAAGCGCAAANNNCTAGCGTTAC | 1762 | TGCAGGACCAGAGAATTCGAATACAACCCACTNNNCTAGCGTTAC | 2002 |
| TGCAGGACCAGAGAATTCGAATACAAGCTATCGNNNCTAGCGTTAC | 1523 | TGCAGGACCAGAGAATTCGAATACAATAGAAACNNNCTAGCGTTAC | 1763 | TGCAGGACCAGAGAATTCGAATACAAGACCTTGNNNCTAGCGTTAC | 2003 |
| TGCAGGACCAGAGAATTCGAATACAGGCGAACGNNNCTAGCGTTAC | 1524 | TGCAGGACCAGAGAATTCGAATACATCGGCTGGNNNCTAGCGTTAC | 1764 | TGCAGGACCAGAGAATTCGAATACACCTTGATCNNNCTAGCGTTAC | 2004 |
| TGCAGGACCAGAGAATTCGAATACAACGAATGGNNNCTAGCGTTAC | 1525 | TGCAGGACCAGAGAATTCGAATACAGTGCTCGGNNNCTAGCGTTAC | 1765 | TGCAGGACCAGAGAATTCGAATACAAAGTATTCNNNCTAGCGTTAC | 2005 |
| TGCAGGACCAGAGAATTCGAATACATCATGCTCNNNCTAGCGTTAC | 1526 | TGCAGGACCAGAGAATTCGAATACAAATGCCACNNNCTAGCGTTAC | 1766 | TGCAGGACCAGAGAATTCGAATACACATCCAAGNNNCTAGCGTTAC | 2006 |
| TGCAGGACCAGAGAATTCGAATACATTGCTTATNNNCTAGCGTTAC | 1527 | TGCAGGACCAGAGAATTCGAATACAATCACGTGNNNCTAGCGTTAC | 1767 | TGCAGGACCAGAGAATTCGAATACACACAAGTCNNNCTAGCGTTAC | 2007 |
| TGCAGGACCAGAGAATTCGAATACAAAGCCAGANNNCTAGCGTTAC | 1528 | TGCAGGACCAGAGAATTCGAATACATCACGACANNNCTAGCGTTAC | 1768 | TGCAGGACCAGAGAATTCGAATACATAAAATGNNNCTAGCGTTAC | 2008 |
| TGCAGGACCAGAGAATTCGAATACAGCAGCTCGNNNCTAGCGTTAC | 1529 | TGCAGGACCAGAGAATTCGAATACATGTTACGNNNCTAGCGTTAC | 1769 | TGCAGGACCAGAGAATTCGAATACAATCTACAANNNCTAGCGTTAC | 2009 |
| TGCAGGACCAGAGAATTCGAATACACCGAGTCGNNNCTAGCGTTAC | 1530 | TGCAGGACCAGAGAATTCGAATACATTACCGCTNNNCTAGCGTTAC | 1770 | TGCAGGACCAGAGAATTCGAATACAGCGAGAATNNNCTAGCGTTAC | 2010 |
| TGCAGGACCAGAGAATTCGAATACAAACAGACGNNNCTAGCGTTAC | 1531 | TGCAGGACCAGAGAATTCGAATACACCCTTTAGNNNCTAGCGTTAC | 1771 | TGCAGGACCAGAGAATTCGAATACAGTAGCCATNNNCTAGCGTTAC | 2011 |
| TGCAGGACCAGAGAATTCGAATACACCCAAACANNNCTAGCGTTAC | 1532 | TGCAGGACCAGAGAATTCGAATACAGTCTTGAGNNNCTAGCGTTAC | 1772 | TGCAGGACCAGAGAATTCGAATACAAAGGCAGTNNNCTAGCGTTAC | 2012 |
| TGCAGGACCAGAGAATTCGAATACAAAGGCGATNNNCTAGCGTTAC | 1533 | TGCAGGACCAGAGAATTCGAATACACTTTGACCNNNCTAGCGTTAC | 1773 | TGCAGGACCAGAGAATTCGAATACAGTAGACTCNNNCTAGCGTTAC | 2013 |
| TGCAGGACCAGAGAATTCGAATACACCTTAAAANNNCTAGCGTTAC | 1534 | TGCAGGACCAGAGAATTCGAATACACTTCTCAGNNNCTAGCGTTAC | 1774 | TGCAGGACCAGAGAATTCGAATACAGGTATGCTNNNCTAGCGTTAC | 2014 |

FIG. 14D

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CACATACCTCNNNCTAGCGTTAC | 1535 | TGCAGGACCAGAGAATTCGAATA CATGTTGCAGNNNCTAGCGTTAC | 1775 | TGCAGGACCAGAGAATTCGAATA CAGGTTTTAANNNCTAGCGTTAC | 2015 |
| TGCAGGACCAGAGAATTCGAATA CAGCCAATCANNNCTAGCGTTAC | 1536 | TGCAGGACCAGAGAATTCGAATA CAAACCCAACNNNCTAGCGTTAC | 1776 | TGCAGGACCAGAGAATTCGAATA CAACAGAAGCNNNCTAGCGTTAC | 2016 |
| TGCAGGACCAGAGAATTCGAATA CACTTAGGCANNNCTAGCGTTAC | 1537 | TGCAGGACCAGAGAATTCGAATA CATAAGCACCNNNCTAGCGTTAC | 1777 | TGCAGGACCAGAGAATTCGAATA CACAGCACGCNNNCTAGCGTTAC | 2017 |
| TGCAGGACCAGAGAATTCGAATA CACGCACCAGNNNCTAGCGTTAC | 1538 | TGCAGGACCAGAGAATTCGAATA CAGATGTAAANNNCTAGCGTTAC | 1778 | TGCAGGACCAGAGAATTCGAATA CAACCGTAACNNNCTAGCGTTAC | 2018 |
| TGCAGGACCAGAGAATTCGAATA CATTCCCGTANNNCTAGCGTTAC | 1539 | TGCAGGACCAGAGAATTCGAATA CAGTTATGCGNNNCTAGCGTTAC | 1779 | TGCAGGACCAGAGAATTCGAATA CAGGAAGCCGNNNCTAGCGTTAC | 2019 |
| TGCAGGACCAGAGAATTCGAATA CATTCAGAATNNNCTAGCGTTAC | 1540 | TGCAGGACCAGAGAATTCGAATA CAGCGCGGAANNNCTAGCGTTAC | 1780 | TGCAGGACCAGAGAATTCGAATA CAGAGGATCANNNCTAGCGTTAC | 2020 |
| TGCAGGACCAGAGAATTCGAATA CAGGCATTACNNNCTAGCGTTAC | 1541 | TGCAGGACCAGAGAATTCGAATA CAAGATTTGTNNNCTAGCGTTAC | 1781 | TGCAGGACCAGAGAATTCGAATA CACGGTTCGGNNNCTAGCGTTAC | 2021 |
| TGCAGGACCAGAGAATTCGAATA CAAACCAAABNNNCTAGCGTTAC | 1542 | TGCAGGACCAGAGAATTCGAATA CACACAGCTANNNCTAGCGTTAC | 1782 | TGCAGGACCAGAGAATTCGAATA CAATCCACAGNNNCTAGCGTTAC | 2022 |
| TGCAGGACCAGAGAATTCGAATA CAACGCTGTANNNCTAGCGTTAC | 1543 | TGCAGGACCAGAGAATTCGAATA CAACGCAGGNNNNCTAGCGTTAC | 1783 | TGCAGGACCAGAGAATTCGAATA CAGAGACCCCNNNCTAGCGTTAC | 2023 |
| TGCAGGACCAGAGAATTCGAATA CAACGATCTGNNNCTAGCGTTAC | 1544 | TGCAGGACCAGAGAATTCGAATA CATACGAAGNNNNCTAGCGTTAC | 1784 | TGCAGGACCAGAGAATTCGAATA CACTCCGGAGNNNCTAGCGTTAC | 2024 |
| TGCAGGACCAGAGAATTCGAATA CAGCATGAGANNNCTAGCGTTAC | 1545 | TGCAGGACCAGAGAATTCGAATA CACTCGATGANNNCTAGCGTTAC | 1785 | TGCAGGACCAGAGAATTCGAATA CATGCCTCGNNNNCTAGCGTTAC | 2025 |
| TGCAGGACCAGAGAATTCGAATA CAGTAAGTCCNNNCTAGCGTTAC | 1546 | TGCAGGACCAGAGAATTCGAATA CATCCCCCTNNNNCTAGCGTTAC | 1786 | TGCAGGACCAGAGAATTCGAATA CATCATTCCGNNNCTAGCGTTAC | 2026 |
| TGCAGGACCAGAGAATTCGAATA CAAAGCGAGTNNNCTAGCGTTAC | 1547 | TGCAGGACCAGAGAATTCGAATA CACCATCTACNNNCTAGCGTTAC | 1787 | TGCAGGACCAGAGAATTCGAATA CAGAACTACCNNNCTAGCGTTAC | 2027 |
| TGCAGGACCAGAGAATTCGAATA CAAGATCTGNNNNCTAGCGTTAC | 1548 | TGCAGGACCAGAGAATTCGAATA CAAAGCAGGTNNNCTAGCGTTAC | 1788 | TGCAGGACCAGAGAATTCGAATA CATAATTTTTNNNCTAGCGTTAC | 2028 |
| TGCAGGACCAGAGAATTCGAATA CACCCGTCACNNNCTAGCGTTAC | 1549 | TGCAGGACCAGAGAATTCGAATA CAAAGTCAAANNNCTAGCGTTAC | 1789 | TGCAGGACCAGAGAATTCGAATA CAGATTGTGCNNNCTAGCGTTAC | 2029 |
| TGCAGGACCAGAGAATTCGAATA CATCCTCGCGNNNCTAGCGTTAC | 1550 | TGCAGGACCAGAGAATTCGAATA CAATTCGACNNNNCTAGCGTTAC | 1790 | TGCAGGACCAGAGAATTCGAATA CATGGCGCACNNNCTAGCGTTAC | 2030 |
| TGCAGGACCAGAGAATTCGAATA CACATGTCGANNNCTAGCGTTAC | 1551 | TGCAGGACCAGAGAATTCGAATA CAACCAGCCGNNNCTAGCGTTAC | 1791 | TGCAGGACCAGAGAATTCGAATA CAAAATCAGNNNNCTAGCGTTAC | 2031 |
| TGCAGGACCAGAGAATTCGAATA CAAACGGTTCNNNCTAGCGTTAC | 1552 | TGCAGGACCAGAGAATTCGAATA CATAGTCGGTNNNCTAGCGTTAC | 1792 | TGCAGGACCAGAGAATTCGAATA CAAGGCTATCNNNCTAGCGTTAC | 2032 |
| TGCAGGACCAGAGAATTCGAATA CACCCCAATTNNNCTAGCGTTAC | 1553 | TGCAGGACCAGAGAATTCGAATA CATGCGCATANNNCTAGCGTTAC | 1793 | TGCAGGACCAGAGAATTCGAATA CATCTTGTGCNNNCTAGCGTTAC | 2033 |
| TGCAGGACCAGAGAATTCGAATA CAACCGTTCTNNNCTAGCGTTAC | 1554 | TGCAGGACCAGAGAATTCGAATA CATAGAACCNNNNCTAGCGTTAC | 1794 | TGCAGGACCAGAGAATTCGAATA CACCATTCANNNNCTAGCGTTAC | 2034 |
| TGCAGGACCAGAGAATTCGAATA CAACTCTAAANNNCTAGCGTTAC | 1555 | TGCAGGACCAGAGAATTCGAATA CAGGTTTGTNNNNCTAGCGTTAC | 1795 | TGCAGGACCAGAGAATTCGAATA CATAGATTACNNNCTAGCGTTAC | 2035 |
| TGCAGGACCAGAGAATTCGAATA CAATGAGCTCNNNCTAGCGTTAC | 1556 | TGCAGGACCAGAGAATTCGAATA CAAAGTTTGTNNNCTAGCGTTAC | 1796 | TGCAGGACCAGAGAATTCGAATA CAGTTTGCTCNNNCTAGCGTTAC | 2036 |
| TGCAGGACCAGAGAATTCGAATA CATCTAAGGCNNNCTAGCGTTAC | 1557 | TGCAGGACCAGAGAATTCGAATA CATTAGCGACNNNCTAGCGTTAC | 1797 | TGCAGGACCAGAGAATTCGAATA CATCTTCGGTNNNCTAGCGTTAC | 2037 |
| TGCAGGACCAGAGAATTCGAATA CACAATAGCCNNNCTAGCGTTAC | 1558 | TGCAGGACCAGAGAATTCGAATA CAGATATATCNNNCTAGCGTTAC | 1798 | TGCAGGACCAGAGAATTCGAATA CAAGTAGTCCNNNCTAGCGTTAC | 2038 |
| TGCAGGACCAGAGAATTCGAATA CATCTTGCGTNNNCTAGCGTTAC | 1559 | TGCAGGACCAGAGAATTCGAATA CAAACTGTGCNNNCTAGCGTTAC | 1799 | TGCAGGACCAGAGAATTCGAATA CACGGTGTATNNNCTAGCGTTAC | 2039 |
| TGCAGGACCAGAGAATTCGAATA CACAAGAGCANNNCTAGCGTTAC | 1560 | TGCAGGACCAGAGAATTCGAATA CACGAATGGANNNCTAGCGTTAC | 1800 | TGCAGGACCAGAGAATTCGAATA CACTGTTTGCNNNCTAGCGTTAC | 2040 |
| TGCAGGACCAGAGAATTCGAATA CAGCTTGGATNNNCTAGCGTTAC | 1561 | TGCAGGACCAGAGAATTCGAATA CACTTCGTTGNNNCTAGCGTTAC | 1801 | TGCAGGACCAGAGAATTCGAATA CAAACGTGCNNNNCTAGCGTTAC | 2041 |
| TGCAGGACCAGAGAATTCGAATA CACTAAATACNNNCTAGCGTTAC | 1562 | TGCAGGACCAGAGAATTCGAATA CATCGTGGTANNNCTAGCGTTAC | 1802 | TGCAGGACCAGAGAATTCGAATA CAATAAATGNNNNCTAGCGTTAC | 2042 |
| TGCAGGACCAGAGAATTCGAATA CACCTAAAATNNNCTAGCGTTAC | 1563 | TGCAGGACCAGAGAATTCGAATA CAGCAAAATANNNCTAGCGTTAC | 1803 | TGCAGGACCAGAGAATTCGAATA CAACGCGTGCNNNCTAGCGTTAC | 2043 |

FIG. 14E

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGAACCTCANNNCTAGCGTTAC | 1564 | TGCAGGACCAGAGAATTCGAATA CAAGACTAAANNNCTAGCGTTAC | 1804 | TGCAGGACCAGAGAATTCGAATA CACGTTGGTANNNCTAGCGTTAC | 2044 |
| TGCAGGACCAGAGAATTCGAATA CAGAGGCCTCNNNCTAGCGTTAC | 1565 | TGCAGGACCAGAGAATTCGAATA CATGGGAGTTNNNCTAGCGTTAC | 1805 | TGCAGGACCAGAGAATTCGAATA CAAGGCGTAANNNCTAGCGTTAC | 2045 |
| TGCAGGACCAGAGAATTCGAATA CAAGGTGATGNNNCTAGCGTTAC | 1566 | TGCAGGACCAGAGAATTCGAATA CAGTTCTGAGNNNCTAGCGTTAC | 1806 | TGCAGGACCAGAGAATTCGAATA CATGCCTATCNNNCTAGCGTTAC | 2046 |
| TGCAGGACCAGAGAATTCGAATA CAACGCGTTANNNCTAGCGTTAC | 1567 | TGCAGGACCAGAGAATTCGAATA CATCGGCGTGNNNCTAGCGTTAC | 1807 | TGCAGGACCAGAGAATTCGAATA CAAAAGCTCCNNNCTAGCGTTAC | 2047 |
| TGCAGGACCAGAGAATTCGAATA CAGGTGGCTCNNNCTAGCGTTAC | 1568 | TGCAGGACCAGAGAATTCGAATA CAGATCCGGCNNNCTAGCGTTAC | 1808 | TGCAGGACCAGAGAATTCGAATA CAAGGACGATNNNCTAGCGTTAC | 2048 |
| TGCAGGACCAGAGAATTCGAATA CAGAGATCAGNNNGATCGACATG | 1569 | TGCAGGACCAGAGAATTCGAATA CAGTGTATGCNNNGATCGACATG | 1809 | TGCAGGACCAGAGAATTCGAATA CACTTGAAGCNNNGATCGACATG | 2049 |
| TGCAGGACCAGAGAATTCGAATA CATACGTGTGNNNGATCGACATG | 1570 | TGCAGGACCAGAGAATTCGAATA CAAGTATTTGNNNGATCGACATG | 1810 | TGCAGGACCAGAGAATTCGAATA CATGCCCTCGNNNGATCGACATG | 2050 |
| TGCAGGACCAGAGAATTCGAATA CAAGTTATCANNNGATCGACATG | 1571 | TGCAGGACCAGAGAATTCGAATA CAAGTAAAACNNNGATCGACATG | 1811 | TGCAGGACCAGAGAATTCGAATA CAAGCGAAACNNNGATCGACATG | 2051 |
| TGCAGGACCAGAGAATTCGAATA CACAGTGATCNNNGATCGACATG | 1572 | TGCAGGACCAGAGAATTCGAATA CAAGCCACCGNNNGATCGACATG | 1812 | TGCAGGACCAGAGAATTCGAATA CATAGAGTGGNNNGATCGACATG | 2052 |
| TGCAGGACCAGAGAATTCGAATA CATACGCGGCNNNGATCGACATG | 1573 | TGCAGGACCAGAGAATTCGAATA CAAAGTGTCCNNNGATCGACATG | 1813 | TGCAGGACCAGAGAATTCGAATA CAAGCAGCAANNNGATCGACATG | 2053 |
| TGCAGGACCAGAGAATTCGAATA CAGTGTGTANNNGATCGACATG | 1574 | TGCAGGACCAGAGAATTCGAATA CACTATTTGTNNNGATCGACATG | 1814 | TGCAGGACCAGAGAATTCGAATA CACCTATTATNNNGATCGACATG | 2054 |
| TGCAGGACCAGAGAATTCGAATA CAGTGTTTAANNNGATCGACATG | 1575 | TGCAGGACCAGAGAATTCGAATA CAGTGTATCGNNNGATCGACATG | 1815 | TGCAGGACCAGAGAATTCGAATA CAGCGACGAGNNNGATCGACATG | 2055 |
| TGCAGGACCAGAGAATTCGAATA CAGCTCTACTNNNGATCGACATG | 1576 | TGCAGGACCAGAGAATTCGAATA CAATAGTATCNNNGATCGACATG | 1816 | TGCAGGACCAGAGAATTCGAATA CAACGATTTANNNGATCGACATG | 2056 |
| TGCAGGACCAGAGAATTCGAATA CATTGTGCTCNNNGATCGACATG | 1577 | TGCAGGACCAGAGAATTCGAATA CACCGCTGAGNNNGATCGACATG | 1817 | TGCAGGACCAGAGAATTCGAATA CAAATTGTTGNNNGATCGACATG | 2057 |
| TGCAGGACCAGAGAATTCGAATA CATATAAGCTNNNGATCGACATG | 1578 | TGCAGGACCAGAGAATTCGAATA CATTATTTANNNGATCGACATG | 1818 | TGCAGGACCAGAGAATTCGAATA CACATTAAGTNNNGATCGACATG | 2058 |
| TGCAGGACCAGAGAATTCGAATA CAAGAACGACNNNGATCGACATG | 1579 | TGCAGGACCAGAGAATTCGAATA CAACAAGACGNNNGATCGACATG | 1819 | TGCAGGACCAGAGAATTCGAATA CAGACGGAGCNNNGATCGACATG | 2059 |
| TGCAGGACCAGAGAATTCGAATA CATACGATATNNNGATCGACATG | 1580 | TGCAGGACCAGAGAATTCGAATA CATAAGTATCNNNGATCGACATG | 1820 | TGCAGGACCAGAGAATTCGAATA CACCGATAGTNNNGATCGACATG | 2060 |
| TGCAGGACCAGAGAATTCGAATA CATAAACCTANNNGATCGACATG | 1581 | TGCAGGACCAGAGAATTCGAATA CAGGCACACCNNNGATCGACATG | 1821 | TGCAGGACCAGAGAATTCGAATA CAAGTATTGTNNNGATCGACATG | 2061 |
| TGCAGGACCAGAGAATTCGAATA CATAACGTTANNNGATCGACATG | 1582 | TGCAGGACCAGAGAATTCGAATA CAGTACCTCANNNGATCGACATG | 1822 | TGCAGGACCAGAGAATTCGAATA CATTTCGGCTNNNGATCGACATG | 2062 |
| TGCAGGACCAGAGAATTCGAATA CAGCACGTGCNNNGATCGACATG | 1583 | TGCAGGACCAGAGAATTCGAATA CACTGTGATGNNNGATCGACATG | 1823 | TGCAGGACCAGAGAATTCGAATA CAGTAGACAGNNNGATCGACATG | 2063 |
| TGCAGGACCAGAGAATTCGAATA CACCCTCGACNNNGATCGACATG | 1584 | TGCAGGACCAGAGAATTCGAATA CAACAAGGACNNNGATCGACATG | 1824 | TGCAGGACCAGAGAATTCGAATA CAACGAAGTGNNNGATCGACATG | 2064 |
| TGCAGGACCAGAGAATTCGAATA CATTGCATCCNNNGATCGACATG | 1585 | TGCAGGACCAGAGAATTCGAATA CAAGAGGCTANNNGATCGACATG | 1825 | TGCAGGACCAGAGAATTCGAATA CACGTCTTTGNNNGATCGACATG | 2065 |
| TGCAGGACCAGAGAATTCGAATA CATCAACTGGNNNGATCGACATG | 1586 | TGCAGGACCAGAGAATTCGAATA CAATTGAGTTNNNGATCGACATG | 1826 | TGCAGGACCAGAGAATTCGAATA CAACACAGGANNNGATCGACATG | 2066 |
| TGCAGGACCAGAGAATTCGAATA CAATTGCCCTNNNGATCGACATG | 1587 | TGCAGGACCAGAGAATTCGAATA CACGTTCTCANNNGATCGACATG | 1827 | TGCAGGACCAGAGAATTCGAATA CAGGTCACTANNNGATCGACATG | 2067 |
| TGCAGGACCAGAGAATTCGAATA CATACATGTANNNGATCGACATG | 1588 | TGCAGGACCAGAGAATTCGAATA CAGGTAGCTTNNNGATCGACATG | 1828 | TGCAGGACCAGAGAATTCGAATA CAGAACGAACNNNGATCGACATG | 2068 |
| TGCAGGACCAGAGAATTCGAATA CAGACTTGGTNNNGATCGACATG | 1589 | TGCAGGACCAGAGAATTCGAATA CATCCTTGTGNNNGATCGACATG | 1829 | TGCAGGACCAGAGAATTCGAATA CACCTAACTCNNNGATCGACATG | 2069 |
| TGCAGGACCAGAGAATTCGAATA CAGTCCCATTNNNGATCGACATG | 1590 | TGCAGGACCAGAGAATTCGAATA CAGCCGACACNNNGATCGACATG | 1830 | TGCAGGACCAGAGAATTCGAATA CAAAGACTTTNNNGATCGACATG | 2070 |
| TGCAGGACCAGAGAATTCGAATA CAAGATGGTGNNNGATCGACATG | 1591 | TGCAGGACCAGAGAATTCGAATA CAACTAGAGGNNNGATCGACATG | 1831 | TGCAGGACCAGAGAATTCGAATA CAGGACATCTNNNGATCGACATG | 2071 |
| TGCAGGACCAGAGAATTCGAATA CAGACACAGANNNGATCGACATG | 1592 | TGCAGGACCAGAGAATTCGAATA CAACAGTCGTNNNGATCGACATG | 1832 | TGCAGGACCAGAGAATTCGAATA CAGGCGTAAANNNGATCGACATG | 2072 |

FIG. 14F

| Pool-7 | SEQ ID NO: | Pool-8 | SEQ ID NO: | Pool-9 | SEQ ID NO: |
|---|---|---|---|---|---|
| TGCAGGACCAGAGAATTCGAATACACGCGTTTTNNNGATCGACATG | 1593 | TGCAGGACCAGAGAATTCGAATACACGAGGCGANNNGATCGACATG | 1833 | TGCAGGACCAGAGAATTCGAATACAGTACCAGTNNNGATCGACATG | 2073 |
| TGCAGGACCAGAGAATTCGAATACACCCAGAGCNNNGATCGACATG | 1594 | TGCAGGACCAGAGAATTCGAATACAACCGAAAGNNNGATCGACATG | 1834 | TGCAGGACCAGAGAATTCGAATACAGAATTACNNNGATCGACATG | 2074 |
| TGCAGGACCAGAGAATTCGAATACACGCAGCTGNNNGATCGACATG | 1595 | TGCAGGACCAGAGAATTCGAATACAGTTTGAGCNNNGATCGACATG | 1835 | TGCAGGACCAGAGAATTCGAATACAAACACCCANNNGATCGACATG | 2075 |
| TGCAGGACCAGAGAATTCGAATACACTTTGGCTNNNGATCGACATG | 1596 | TGCAGGACCAGAGAATTCGAATACAGTATGCGTNNNGATCGACATG | 1836 | TGCAGGACCAGAGAATTCGAATACAAGTTATTGNNNGATCGACATG | 2076 |
| TGCAGGACCAGAGAATTCGAATACAGTTGATCGNNNGATCGACATG | 1597 | TGCAGGACCAGAGAATTCGAATACAATGTAACTNNNGATCGACATG | 1837 | TGCAGGACCAGAGAATTCGAATACACTTCTTTTNNNGATCGACATG | 2077 |
| TGCAGGACCAGAGAATTCGAATACAGTGAAGTGNNNGATCGACATG | 1598 | TGCAGGACCAGAGAATTCGAATACAAGACGTAGNNNGATCGACATG | 1838 | TGCAGGACCAGAGAATTCGAATACAGAGCTCCGNNNGATCGACATG | 2078 |
| TGCAGGACCAGAGAATTCGAATACACACGTTGANNNGATCGACATG | 1599 | TGCAGGACCAGAGAATTCGAATACATTGGCGCGNNNGATCGACATG | 1839 | TGCAGGACCAGAGAATTCGAATACAGAACCCCGNNNGATCGACATG | 2079 |
| TGCAGGACCAGAGAATTCGAATACACAATCCAGNNNGATCGACATG | 1600 | TGCAGGACCAGAGAATTCGAATACAGGACTCATNNNGATCGACATG | 1840 | TGCAGGACCAGAGAATTCGAATACAATTGTGATNNNGATCGACATG | 2080 |
| TGCAGGACCAGAGAATTCGAATACAGCGCAGAGNNNGATCGACATG | 1601 | TGCAGGACCAGAGAATTCGAATACAGTCCGGTGNNNGATCGACATG | 1841 | TGCAGGACCAGAGAATTCGAATACAAGTTCTTTNNNGATCGACATG | 2081 |
| TGCAGGACCAGAGAATTCGAATACACTCTGATCNNNGATCGACATG | 1602 | TGCAGGACCAGAGAATTCGAATACAGCAAGCCCNNNGATCGACATG | 1842 | TGCAGGACCAGAGAATTCGAATACAGCACGGTCNNNGATCGACATG | 2082 |
| TGCAGGACCAGAGAATTCGAATACATATGCCAGNNNGATCGACATG | 1603 | TGCAGGACCAGAGAATTCGAATACAAGCATGGANNNGATCGACATG | 1843 | TGCAGGACCAGAGAATTCGAATACAGTATCCCTNNNGATCGACATG | 2083 |
| TGCAGGACCAGAGAATTCGAATACAGTTGGTCANNNGATCGACATG | 1604 | TGCAGGACCAGAGAATTCGAATACAAGCAGCCCNNNGATCGACATG | 1844 | TGCAGGACCAGAGAATTCGAATACAGCAAGTGANNNGATCGACATG | 2084 |
| TGCAGGACCAGAGAATTCGAATACACCTCTCGGNNNGATCGACATG | 1605 | TGCAGGACCAGAGAATTCGAATACAATCTCTATNNNGATCGACATG | 1845 | TGCAGGACCAGAGAATTCGAATACATAAGATAGNNNGATCGACATG | 2085 |
| TGCAGGACCAGAGAATTCGAATACATGGTACACNNNGATCGACATG | 1606 | TGCAGGACCAGAGAATTCGAATACATAATGCCGNNNGATCGACATG | 1846 | TGCAGGACCAGAGAATTCGAATACAGCAATCTGNNNGATCGACATG | 2086 |
| TGCAGGACCAGAGAATTCGAATACACCTCGGCTNNNGATCGACATG | 1607 | TGCAGGACCAGAGAATTCGAATACACAGGCGGANNNGATCGACATG | 1847 | TGCAGGACCAGAGAATTCGAATACACTGCCAGGNNNGATCGACATG | 2087 |
| TGCAGGACCAGAGAATTCGAATACAGCGACGGANNNGATCGACATG | 1608 | TGCAGGACCAGAGAATTCGAATACAGCGAATGANNNGATCGACATG | 1848 | TGCAGGACCAGAGAATTCGAATACAGGTTTATANNNGATCGACATG | 2088 |
| TGCAGGACCAGAGAATTCGAATACACCCTGATTNNNGATCGACATG | 1609 | TGCAGGACCAGAGAATTCGAATACAAGCGTACTNNNGATCGACATG | 1849 | TGCAGGACCAGAGAATTCGAATACAAACTTGCGNNNGATCGACATG | 2089 |
| TGCAGGACCAGAGAATTCGAATACAATTCTCTANNNGATCGACATG | 1610 | TGCAGGACCAGAGAATTCGAATACACCCAGGCANNNGATCGACATG | 1850 | TGCAGGACCAGAGAATTCGAATACACCAACGCGNNNGATCGACATG | 2090 |
| TGCAGGACCAGAGAATTCGAATACACTGTCAAGGNNNGATCGACATG | 1611 | TGCAGGACCAGAGAATTCGAATACAGGGCCTGTGNNNGATCGACATG | 1851 | TGCAGGACCAGAGAATTCGAATACATGGAAGACNNNGATCGACATG | 2091 |
| TGCAGGACCAGAGAATTCGAATACAATTACCGGNNNGATCGACATG | 1612 | TGCAGGACCAGAGAATTCGAATACACCTAGGCGNNNGATCGACATG | 1852 | TGCAGGACCAGAGAATTCGAATACAATTGAAGANNNGATCGACATG | 2092 |
| TGCAGGACCAGAGAATTCGAATACATAATATCGNNNGATCGACATG | 1613 | TGCAGGACCAGAGAATTCGAATACACCGTTTTGNNNGATCGACATG | 1853 | TGCAGGACCAGAGAATTCGAATACATTTTCACANNNGATCGACATG | 2093 |
| TGCAGGACCAGAGAATTCGAATACAATAGACTTNNNGATCGACATG | 1614 | TGCAGGACCAGAGAATTCGAATACAGACGCACCNNNGATCGACATG | 1854 | TGCAGGACCAGAGAATTCGAATACAACGAACTCNNNGATCGACATG | 2094 |
| TGCAGGACCAGAGAATTCGAATACACCTGATAGNNNGATCGACATG | 1615 | TGCAGGACCAGAGAATTCGAATACAACTTATGANNNGATCGACATG | 1855 | TGCAGGACCAGAGAATTCGAATACAAGGCCGTCNNNGATCGACATG | 2095 |
| TGCAGGACCAGAGAATTCGAATACAGCCGCACANNNGATCGACATG | 1616 | TGCAGGACCAGAGAATTCGAATACAAGATCACANNNGATCGACATG | 1856 | TGCAGGACCAGAGAATTCGAATACATTGGAGCTNNNGATCGACATG | 2096 |
| TGCAGGACCAGAGAATTCGAATACACGAATATTNNNGATCGACATG | 1617 | TGCAGGACCAGAGAATTCGAATACATACTTCCGNNNGATCGACATG | 1857 | TGCAGGACCAGAGAATTCGAATACAACAGACAGNNNGATCGACATG | 2097 |
| TGCAGGACCAGAGAATTCGAATACAGTCAATCGNNNGATCGACATG | 1618 | TGCAGGACCAGAGAATTCGAATACACGTTAGACNNNGATCGACATG | 1858 | TGCAGGACCAGAGAATTCGAATACAATCGTCAGNNNGATCGACATG | 2098 |
| TGCAGGACCAGAGAATTCGAATACATCAGCCCCNNNGATCGACATG | 1619 | TGCAGGACCAGAGAATTCGAATACAGGAGTTAGNNNGATCGACATG | 1859 | TGCAGGACCAGAGAATTCGAATACATTATGTCTNNNGATCGACATG | 2099 |
| TGCAGGACCAGAGAATTCGAATACAGGAGTTCTNNNGATCGACATG | 1620 | TGCAGGACCAGAGAATTCGAATACAGACCTCTTNNNGATCGACATG | 1860 | TGCAGGACCAGAGAATTCGAATACAGTCACGATNNNGATCGACATG | 2100 |
| TGCAGGACCAGAGAATTCGAATACAGTGAATCCNNNGATCGACATG | 1621 | TGCAGGACCAGAGAATTCGAATACAGCCCGCAANNNGATCGACATG | 1861 | TGCAGGACCAGAGAATTCGAATACACATTCTGCNNNGATCGACATG | 2101 |

FIG. 14G

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAACGATTATNNNGATCGACATG | 1622 | TGCAGGACCAGAGAATTCGAATA CAGAACCCATNNNGATCGACATG | 1862 | TGCAGGACCAGAGAATTCGAATA CAGAAAAACTNNNGATCGACATG | 2102 |
| TGCAGGACCAGAGAATTCGAATA CACAATCCGANNNGATCGACATG | 1623 | TGCAGGACCAGAGAATTCGAATA CACCACTGCCNNNGATCGACATG | 1863 | TGCAGGACCAGAGAATTCGAATA CATCGTCGTTNNNGATCGACATG | 2103 |
| TGCAGGACCAGAGAATTCGAATA CAGGCAATGANNNGATCGACATG | 1624 | TGCAGGACCAGAGAATTCGAATA CACTAATTCNNNGATCGACATG | 1864 | TGCAGGACCAGAGAATTCGAATA CAATTGTGGCNNNGATCGACATG | 2104 |
| TGCAGGACCAGAGAATTCGAATA CACTGTCAGANNNGATCGACATG | 1625 | TGCAGGACCAGAGAATTCGAATA CACGGTCCAGNNNGATCGACATG | 1865 | TGCAGGACCAGAGAATTCGAATA CAACTGGACTNNNGATCGACATG | 2105 |
| TGCAGGACCAGAGAATTCGAATA CACAGACCTANNNGATCGACATG | 1626 | TGCAGGACCAGAGAATTCGAATA CATTTCGCACNNNGATCGACATG | 1866 | TGCAGGACCAGAGAATTCGAATA CACGTTGTTCNNNGATCGACATG | 2106 |
| TGCAGGACCAGAGAATTCGAATA CAGATCATCGNNNGATCGACATG | 1627 | TGCAGGACCAGAGAATTCGAATA CAGGATAAGCNNNGATCGACATG | 1867 | TGCAGGACCAGAGAATTCGAATA CACAAGACCTNNNGATCGACATG | 2107 |
| TGCAGGACCAGAGAATTCGAATA CAGAACGAGTNNNGATCGACATG | 1628 | TGCAGGACCAGAGAATTCGAATA CACTCGCAGGNNNGATCGACATG | 1868 | TGCAGGACCAGAGAATTCGAATA CATACCCCGNNNGATCGACATG | 2108 |
| TGCAGGACCAGAGAATTCGAATA CATCCGTGATNNNTGCATCAGGT | 1629 | TGCAGGACCAGAGAATTCGAATA CAACTGAAAANNNTGCATCAGGT | 1869 | TGCAGGACCAGAGAATTCGAATA CACCTACCGCNNNTGCATCAGGT | 2109 |
| TGCAGGACCAGAGAATTCGAATA CAATTGCAATNNNTGCATCAGGT | 1630 | TGCAGGACCAGAGAATTCGAATA CAAGTCTTTTNNNTGCATCAGGT | 1870 | TGCAGGACCAGAGAATTCGAATA CAAGACAGTGNNNTGCATCAGGT | 2110 |
| TGCAGGACCAGAGAATTCGAATA CATTAACGATNNNTGCATCAGGT | 1631 | TGCAGGACCAGAGAATTCGAATA CAGGTGTTACNNNTGCATCAGGT | 1871 | TGCAGGACCAGAGAATTCGAATA CAGTCCTATCNNNTGCATCAGGT | 2111 |
| TGCAGGACCAGAGAATTCGAATA CATGTACGTGNNNTGCATCAGGT | 1632 | TGCAGGACCAGAGAATTCGAATA CATATCCGCTNNNTGCATCAGGT | 1872 | TGCAGGACCAGAGAATTCGAATA CACGCGCTCTNNNTGCATCAGGT | 2112 |
| TGCAGGACCAGAGAATTCGAATA CAGCGTGTGCNNNTGCATCAGGT | 1633 | TGCAGGACCAGAGAATTCGAATA CAGCGTGAGGNNNTGCATCAGGT | 1873 | TGCAGGACCAGAGAATTCGAATA CATTGATTCTNNNTGCATCAGGT | 2113 |
| TGCAGGACCAGAGAATTCGAATA CACCATATAANNNTGCATCAGGT | 1634 | TGCAGGACCAGAGAATTCGAATA CAGCCGTTCCNNNTGCATCAGGT | 1874 | TGCAGGACCAGAGAATTCGAATA CAATAATGTCNNNTGCATCAGGT | 2114 |
| TGCAGGACCAGAGAATTCGAATA CAAAATTGAGNNNTGCATCAGGT | 1635 | TGCAGGACCAGAGAATTCGAATA CATTACCCCANNNTGCATCAGGT | 1875 | TGCAGGACCAGAGAATTCGAATA CAGAGTTAAANNNTGCATCAGGT | 2115 |
| TGCAGGACCAGAGAATTCGAATA CAGTATCACGNNNTGCATCAGGT | 1636 | TGCAGGACCAGAGAATTCGAATA CAGACCCCTCNNNTGCATCAGGT | 1876 | TGCAGGACCAGAGAATTCGAATA CACGACACATNNNTGCATCAGGT | 2116 |
| TGCAGGACCAGAGAATTCGAATA CACCTTAGGANNNTGCATCAGGT | 1637 | TGCAGGACCAGAGAATTCGAATA CATATGGAGGNNNTGCATCAGGT | 1877 | TGCAGGACCAGAGAATTCGAATA CATTGGCCGNNNTGCATCAGGT | 2117 |
| TGCAGGACCAGAGAATTCGAATA CATAAAAAGCNNNTGCATCAGGT | 1638 | TGCAGGACCAGAGAATTCGAATA CAGACGGTCCNNNTGCATCAGGT | 1878 | TGCAGGACCAGAGAATTCGAATA CAGAACTTTANNNTGCATCAGGT | 2118 |
| TGCAGGACCAGAGAATTCGAATA CATGCATCCTNNNTGCATCAGGT | 1639 | TGCAGGACCAGAGAATTCGAATA CACTACGACANNNTGCATCAGGT | 1879 | TGCAGGACCAGAGAATTCGAATA CACCAAAACCNNNTGCATCAGGT | 2119 |
| TGCAGGACCAGAGAATTCGAATA CACAGCCTGGNNNTGCATCAGGT | 1640 | TGCAGGACCAGAGAATTCGAATA CATGACTACGNNNTGCATCAGGT | 1880 | TGCAGGACCAGAGAATTCGAATA CAATACCAGCNNNTGCATCAGGT | 2120 |
| TGCAGGACCAGAGAATTCGAATA CACACACTAGNNNTGCATCAGGT | 1641 | TGCAGGACCAGAGAATTCGAATA CAGGACGTTNNNTGCATCAGGT | 1881 | TGCAGGACCAGAGAATTCGAATA CAAGTAGAATNNNTGCATCAGGT | 2121 |
| TGCAGGACCAGAGAATTCGAATA CACGTATCCTNNNTGCATCAGGT | 1642 | TGCAGGACCAGAGAATTCGAATA CAAAGCCTCANNNTGCATCAGGT | 1882 | TGCAGGACCAGAGAATTCGAATA CAGTACTACGNNNTGCATCAGGT | 2122 |
| TGCAGGACCAGAGAATTCGAATA CATGGCTTAGNNNTGCATCAGGT | 1643 | TGCAGGACCAGAGAATTCGAATA CACTTTAAAGNNNTGCATCAGGT | 1883 | TGCAGGACCAGAGAATTCGAATA CATTCATGAANNNTGCATCAGGT | 2123 |
| TGCAGGACCAGAGAATTCGAATA CACTGTCATCNNNTGCATCAGGT | 1644 | TGCAGGACCAGAGAATTCGAATA CATTTGATTCNNNTGCATCAGGT | 1884 | TGCAGGACCAGAGAATTCGAATA CACCTAAGGTNNNTGCATCAGGT | 2124 |
| TGCAGGACCAGAGAATTCGAATA CATCCAGAACNNNTGCATCAGGT | 1645 | TGCAGGACCAGAGAATTCGAATA CACTGTATTTNNNTGCATCAGGT | 1885 | TGCAGGACCAGAGAATTCGAATA CAACAAAGGCNNNTGCATCAGGT | 2125 |
| TGCAGGACCAGAGAATTCGAATA CACGAGTACTNNNTGCATCAGGT | 1646 | TGCAGGACCAGAGAATTCGAATA CATTAATTGGNNNTGCATCAGGT | 1886 | TGCAGGACCAGAGAATTCGAATA CAGAGGCAGCNNNTGCATCAGGT | 2126 |
| TGCAGGACCAGAGAATTCGAATA CAGATCGAGANNNTGCATCAGGT | 1647 | TGCAGGACCAGAGAATTCGAATA CACAGAGTTCNNNTGCATCAGGT | 1887 | TGCAGGACCAGAGAATTCGAATA CACTACTCGTNNNTGCATCAGGT | 2127 |
| TGCAGGACCAGAGAATTCGAATA CAAGAATAACNNNTGCATCAGGT | 1648 | TGCAGGACCAGAGAATTCGAATA CAGCATCTAGNNNTGCATCAGGT | 1888 | TGCAGGACCAGAGAATTCGAATA CAGGTAGTGANNNTGCATCAGGT | 2128 |
| TGCAGGACCAGAGAATTCGAATA CAGCGCACCANNNTGCATCAGGT | 1649 | TGCAGGACCAGAGAATTCGAATA CATTGTCTATNNNTGCATCAGGT | 1889 | TGCAGGACCAGAGAATTCGAATA CACCACCACCNNNTGCATCAGGT | 2129 |
| TGCAGGACCAGAGAATTCGAATA CACAGCAACTNNNTGCATCAGGT | 1650 | TGCAGGACCAGAGAATTCGAATA CACATCCTGTNNNTGCATCAGGT | 1890 | TGCAGGACCAGAGAATTCGAATA CATGTGTGACNNNTGCATCAGGT | 2130 |

FIG. 14H

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGTGCCATANNNTGCATCAGGT | 1651 | TGCAGGACCAGAGAATTCGAATA CACATTCAAANNNTGCATCAGGT | 1891 | TGCAGGACCAGAGAATTCGAATA CACACCCTGCNNNTGCATCAGGT | 2131 |
| TGCAGGACCAGAGAATTCGAATA CAATCTATTNNNTGCATCAGGT | 1652 | TGCAGGACCAGAGAATTCGAATA CAAAAGCCTCNNNTGCATCAGGT | 1892 | TGCAGGACCAGAGAATTCGAATA CATCGCCATTNNNTGCATCAGGT | 2132 |
| TGCAGGACCAGAGAATTCGAATA CAAGTATGTTNNNTGCATCAGGT | 1653 | TGCAGGACCAGAGAATTCGAATA CATGATCAATNNNTGCATCAGGT | 1893 | TGCAGGACCAGAGAATTCGAATA CAACTTCGCTNNNTGCATCAGGT | 2133 |
| TGCAGGACCAGAGAATTCGAATA CAGGTTCTTCNNNTGCATCAGGT | 1654 | TGCAGGACCAGAGAATTCGAATA CAATATGATCNNNTGCATCAGGT | 1894 | TGCAGGACCAGAGAATTCGAATA CATTGCTTTANNNTGCATCAGGT | 2134 |
| TGCAGGACCAGAGAATTCGAATA CATAGTGGCTNNNTGCATCAGGT | 1655 | TGCAGGACCAGAGAATTCGAATA CAGGACCGAGNNNTGCATCAGGT | 1895 | TGCAGGACCAGAGAATTCGAATA CAGCACGAGGNNNTGCATCAGGT | 2135 |
| TGCAGGACCAGAGAATTCGAATA CACCAACTTCNNNTGCATCAGGT | 1656 | TGCAGGACCAGAGAATTCGAATA CACCCCTAATNNNTGCATCAGGT | 1896 | TGCAGGACCAGAGAATTCGAATA CACGAATGTCNNNTGCATCAGGT | 2136 |
| TGCAGGACCAGAGAATTCGAATA CAAGTTCAATNNNTGCATCAGGT | 1657 | TGCAGGACCAGAGAATTCGAATA CACTCAAAGCNNNTGCATCAGGT | 1897 | TGCAGGACCAGAGAATTCGAATA CATGGCTAGTNNNTGCATCAGGT | 2137 |
| TGCAGGACCAGAGAATTCGAATA CATTGTTCGCNNNTGCATCAGGT | 1658 | TGCAGGACCAGAGAATTCGAATA CACTTCGTACNNNTGCATCAGGT | 1898 | TGCAGGACCAGAGAATTCGAATA CAGTGTTATANNNTGCATCAGGT | 2138 |
| TGCAGGACCAGAGAATTCGAATA CAGTCATGCANNNTGCATCAGGT | 1659 | TGCAGGACCAGAGAATTCGAATA CAATTGGCCANNNTGCATCAGGT | 1899 | TGCAGGACCAGAGAATTCGAATA CATTCCTTCCNNNTGCATCAGGT | 2139 |
| TGCAGGACCAGAGAATTCGAATA CACTGTAATANNNTGCATCAGGT | 1660 | TGCAGGACCAGAGAATTCGAATA CACGAAGGTANNNTGCATCAGGT | 1900 | TGCAGGACCAGAGAATTCGAATA CATCAACTAANNNTGCATCAGGT | 2140 |
| TGCAGGACCAGAGAATTCGAATA CATTCGGCCCNNNTGCATCAGGT | 1661 | TGCAGGACCAGAGAATTCGAATA CAGGCCTTGGNNNTGCATCAGGT | 1901 | TGCAGGACCAGAGAATTCGAATA CATTTACAAGNNNTGCATCAGGT | 2141 |
| TGCAGGACCAGAGAATTCGAATA CATCTCTCTCNNNTGCATCAGGT | 1662 | TGCAGGACCAGAGAATTCGAATA CAACAATATCNNNTGCATCAGGT | 1902 | TGCAGGACCAGAGAATTCGAATA CATCCTGCCGNNNTGCATCAGGT | 2142 |
| TGCAGGACCAGAGAATTCGAATA CACTTCGCGCNNNTGCATCAGGT | 1663 | TGCAGGACCAGAGAATTCGAATA CATCACAACGNNNTGCATCAGGT | 1903 | TGCAGGACCAGAGAATTCGAATA CATCGGCTAANNNTGCATCAGGT | 2143 |
| TGCAGGACCAGAGAATTCGAATA CAACAGATTTNNNTGCATCAGGT | 1664 | TGCAGGACCAGAGAATTCGAATA CAACTGTACGNNNTGCATCAGGT | 1904 | TGCAGGACCAGAGAATTCGAATA CAAGGAGCATNNNTGCATCAGGT | 2144 |
| TGCAGGACCAGAGAATTCGAATA CACAGACAAGNNNTGCATCAGGT | 1665 | TGCAGGACCAGAGAATTCGAATA CATCTCAATTNNNTGCATCAGGT | 1905 | TGCAGGACCAGAGAATTCGAATA CAGGAATACGNNNTGCATCAGGT | 2145 |
| TGCAGGACCAGAGAATTCGAATA CACAGCTACANNNTGCATCAGGT | 1666 | TGCAGGACCAGAGAATTCGAATA CAAGGCTCTANNNTGCATCAGGT | 1906 | TGCAGGACCAGAGAATTCGAATA CATGAGACGANNNTGCATCAGGT | 2146 |
| TGCAGGACCAGAGAATTCGAATA CAGACCGAGGNNNTGCATCAGGT | 1667 | TGCAGGACCAGAGAATTCGAATA CACCTTACCANNNTGCATCAGGT | 1907 | TGCAGGACCAGAGAATTCGAATA CACCACCAGGNNNTGCATCAGGT | 2147 |
| TGCAGGACCAGAGAATTCGAATA CACCTATAAANNNTGCATCAGGT | 1668 | TGCAGGACCAGAGAATTCGAATA CAGATTCCTCNNNTGCATCAGGT | 1908 | TGCAGGACCAGAGAATTCGAATA CAAGCTCATGNNNTGCATCAGGT | 2148 |
| TGCAGGACCAGAGAATTCGAATA CACCTAACCTNNNTGCATCAGGT | 1669 | TGCAGGACCAGAGAATTCGAATA CATGCCTGTTNNNTGCATCAGGT | 1909 | TGCAGGACCAGAGAATTCGAATA CATATACCGGNNNTGCATCAGGT | 2149 |
| TGCAGGACCAGAGAATTCGAATA CATTTAGCGGNNNTGCATCAGGT | 1670 | TGCAGGACCAGAGAATTCGAATA CATCACCAAGNNNTGCATCAGGT | 1910 | TGCAGGACCAGAGAATTCGAATA CAGATGCCATNNNTGCATCAGGT | 2150 |
| TGCAGGACCAGAGAATTCGAATA CATAAACCATNNNTGCATCAGGT | 1671 | TGCAGGACCAGAGAATTCGAATA CACTTCCGGCNNNTGCATCAGGT | 1911 | TGCAGGACCAGAGAATTCGAATA CATTGAGCTGNNNTGCATCAGGT | 2151 |
| TGCAGGACCAGAGAATTCGAATA CAGCTAACTGNNNTGCATCAGGT | 1672 | TGCAGGACCAGAGAATTCGAATA CAAAACGCAGNNNTGCATCAGGT | 1912 | TGCAGGACCAGAGAATTCGAATA CATAAATGGANNNTGCATCAGGT | 2152 |
| TGCAGGACCAGAGAATTCGAATA CAGTACAGAGNNNTGCATCAGGT | 1673 | TGCAGGACCAGAGAATTCGAATA CACGCATTCNNNTGCATCAGGT | 1913 | TGCAGGACCAGAGAATTCGAATA CAACATGAAANNNTGCATCAGGT | 2153 |
| TGCAGGACCAGAGAATTCGAATA CACCGGACCAGATNNNTGCATCAGGT | 1674 | TGCAGGACCAGAGAATTCGAATA CACCCTATTNNNTGCATCAGGT | 1914 | TGCAGGACCAGAGAATTCGAATA CACTCGGAGCNNNTGCATCAGGT | 2154 |
| TGCAGGACCAGAGAATTCGAATA CACCTCTAGTNNNTGCATCAGGT | 1675 | TGCAGGACCAGAGAATTCGAATA CATCATCATTNNNTGCATCAGGT | 1915 | TGCAGGACCAGAGAATTCGAATA CAGTTTCCTGNNNTGCATCAGGT | 2155 |
| TGCAGGACCAGAGAATTCGAATA CAGCCCCTGTNNNTGCATCAGGT | 1676 | TGCAGGACCAGAGAATTCGAATA CAAATTCAGTNNNTGCATCAGGT | 1916 | TGCAGGACCAGAGAATTCGAATA CACAACATGCNNNTGCATCAGGT | 2156 |
| TGCAGGACCAGAGAATTCGAATA CACGGACTGCNNNTGCATCAGGT | 1677 | TGCAGGACCAGAGAATTCGAATA CAATTCTCGCNNNTGCATCAGGT | 1917 | TGCAGGACCAGAGAATTCGAATA CATGGTGCCCNNNTGCATCAGGT | 2157 |
| TGCAGGACCAGAGAATTCGAATA CACCCTCTGGNNNTGCATCAGGT | 1678 | TGCAGGACCAGAGAATTCGAATA CAATAGAGTANNNTGCATCAGGT | 1918 | TGCAGGACCAGAGAATTCGAATA CATACGGAGANNNTGCATCAGGT | 2158 |
| TGCAGGACCAGAGAATTCGAATA CAACCAAGTCNNNTGCATCAGGT | 1679 | TGCAGGACCAGAGAATTCGAATA CAGAGCGGACNNNTGCATCAGGT | 1919 | TGCAGGACCAGAGAATTCGAATA CAGGCGTGGANNNTGCATCAGGT | 2159 |

FIG. 14I

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGCGTGGTCNNNTGCATCAGGT | 1680 | TGCAGGACCAGAGAATTCGAATA CAACTTTTACNNNTGCATCAGGT | 1920 | TGCAGGACCAGAGAATTCGAATA CATCTAACGGNNNTGCATCAGGT | 2160 |
| TGCAGGACCAGAGAATTCGAATA CACCGACGCANNNTGCATCAGGT | 1681 | TGCAGGACCAGAGAATTCGAATA CAAGTCAAAANNNTGCATCAGGT | 1921 | TGCAGGACCAGAGAATTCGAATA CATATAGCATNNNTGCATCAGGT | 2161 |
| TGCAGGACCAGAGAATTCGAATA CATTACCGGANNNTGCATCAGGT | 1682 | TGCAGGACCAGAGAATTCGAATA CATCTAGACGNNNTGCATCAGGT | 1922 | TGCAGGACCAGAGAATTCGAATA CACGCTCCGTNNNTGCATCAGGT | 2162 |
| TGCAGGACCAGAGAATTCGAATA CATCTTTGCGNNNTGCATCAGGT | 1683 | TGCAGGACCAGAGAATTCGAATA CACAAATGTTNNNTGCATCAGGT | 1923 | TGCAGGACCAGAGAATTCGAATA CAATACATGTNNNTGCATCAGGT | 2163 |
| TGCAGGACCAGAGAATTCGAATA CACACAATTANNNTGCATCAGGT | 1684 | TGCAGGACCAGAGAATTCGAATA CATGGCTTTCNNNTGCATCAGGT | 1924 | TGCAGGACCAGAGAATTCGAATA CAGGCTCGCANNNTGCATCAGGT | 2164 |
| TGCAGGACCAGAGAATTCGAATA CACCTACATCNNNTGCATCAGGT | 1685 | TGCAGGACCAGAGAATTCGAATA CAAGGCTGTTNNNTGCATCAGGT | 1925 | TGCAGGACCAGAGAATTCGAATA CAGTTTAGTANNNTGCATCAGGT | 2165 |
| TGCAGGACCAGAGAATTCGAATA CAATTACTGANNNTGCATCAGGT | 1686 | TGCAGGACCAGAGAATTCGAATA CAAACTATTGNNNTGCATCAGGT | 1926 | TGCAGGACCAGAGAATTCGAATA CACTGAAATTNNNTGCATCAGGT | 2166 |
| TGCAGGACCAGAGAATTCGAATA CATTTTTCGANNNTGCATCAGGT | 1687 | TGCAGGACCAGAGAATTCGAATA CAATGTATTGNNNTGCATCAGGT | 1927 | TGCAGGACCAGAGAATTCGAATA CAAACACCTGNNNTGCATCAGGT | 2167 |
| TGCAGGACCAGAGAATTCGAATA CAAGGTGCTTNNNTGCATCAGGT | 1688 | TGCAGGACCAGAGAATTCGAATA CACGTCGGCANNNTGCATCAGGT | 1928 | TGCAGGACCAGAGAATTCGAATA CAGGAAAACCNNNTGCATCAGGT | 2168 |

FIG. 15A

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAGCTTCTCANNNACGTATGCCA | 2169 | TGCAGGACCAGAGAATTCGAATACAATACGTATNNNACGTATGCCA | 2409 | TGCAGGACCAGAGAATTCGAATACATTGAGAAANNNACGTATGCCA | 2649 |
| TGCAGGACCAGAGAATTCGAATACAATGCTACGNNNACGTATGCCA | 2170 | TGCAGGACCAGAGAATTCGAATACAAACTAGCCNNNACGTATGCCA | 2410 | TGCAGGACCAGAGAATTCGAATACAAATATCCANNNACGTATGCCA | 2650 |
| TGCAGGACCAGAGAATTCGAATACATACTCTCGNNNACGTATGCCA | 2171 | TGCAGGACCAGAGAATTCGAATACACGGATTACNNNACGTATGCCA | 2411 | TGCAGGACCAGAGAATTCGAATACAATGGACCTNNNACGTATGCCA | 2651 |
| TGCAGGACCAGAGAATTCGAATACACGGTCGCANNNACGTATGCCA | 2172 | TGCAGGACCAGAGAATTCGAATACAGGACGCCTNNNACGTATGCCA | 2412 | TGCAGGACCAGAGAATTCGAATACAGGCATACTNNNACGTATGCCA | 2652 |
| TGCAGGACCAGAGAATTCGAATACAACGGTTACNNNACGTATGCCA | 2173 | TGCAGGACCAGAGAATTCGAATACACGTTAAATNNNACGTATGCCA | 2413 | TGCAGGACCAGAGAATTCGAATACACTAAAAAGNNNACGTATGCCA | 2653 |
| TGCAGGACCAGAGAATTCGAATACATAGCACACNNNACGTATGCCA | 2174 | TGCAGGACCAGAGAATTCGAATACACGCTAGTTNNNACGTATGCCA | 2414 | TGCAGGACCAGAGAATTCGAATACAATACATACNNNACGTATGCCA | 2654 |
| TGCAGGACCAGAGAATTCGAATACACGTCTCTANNNACGTATGCCA | 2175 | TGCAGGACCAGAGAATTCGAATACATCAGAAGGNNNACGTATGCCA | 2415 | TGCAGGACCAGAGAATTCGAATACATATGGCANNNACGTATGCCA | 2655 |
| TGCAGGACCAGAGAATTCGAATACAGCTCCGCTNNNACGTATGCCA | 2176 | TGCAGGACCAGAGAATTCGAATACAACCAACTGNNNACGTATGCCA | 2416 | TGCAGGACCAGAGAATTCGAATACAATGATGCCNNNACGTATGCCA | 2656 |
| TGCAGGACCAGAGAATTCGAATACAGTGGCACNNNACGTATGCCA | 2177 | TGCAGGACCAGAGAATTCGAATACATCGACAACNNNACGTATGCCA | 2417 | TGCAGGACCAGAGAATTCGAATACAAGGTAGGTNNNACGTATGCCA | 2657 |
| TGCAGGACCAGAGAATTCGAATACAGCACTATGNNNACGTATGCCA | 2178 | TGCAGGACCAGAGAATTCGAATACAGTCGTACANNNACGTATGCCA | 2418 | TGCAGGACCAGAGAATTCGAATACATCCCTAGTNNNACGTATGCCA | 2658 |
| TGCAGGACCAGAGAATTCGAATACAATAACGANNNACGTATGCCA | 2179 | TGCAGGACCAGAGAATTCGAATACAGCCAGAGGNNNACGTATGCCA | 2419 | TGCAGGACCAGAGAATTCGAATACAGTATTTGANNNACGTATGCCA | 2659 |
| TGCAGGACCAGAGAATTCGAATACAGGTATAGGNNNACGTATGCCA | 2180 | TGCAGGACCAGAGAATTCGAATACACATAGTATNNNACGTATGCCA | 2420 | TGCAGGACCAGAGAATTCGAATACAAGTGAATANNNACGTATGCCA | 2660 |
| TGCAGGACCAGAGAATTCGAATACAGAACCCTNNNACGTATGCCA | 2181 | TGCAGGACCAGAGAATTCGAATACATAAATGTCNNNACGTATGCCA | 2421 | TGCAGGACCAGAGAATTCGAATACAAATCGCACNNNACGTATGCCA | 2661 |
| TGCAGGACCAGAGAATTCGAATACAGCCGCGTANNNACGTATGCCA | 2182 | TGCAGGACCAGAGAATTCGAATACAGCGTCGGTNNNACGTATGCCA | 2422 | TGCAGGACCAGAGAATTCGAATACAGTCCCCANNNACGTATGCCA | 2662 |
| TGCAGGACCAGAGAATTCGAATACATTCCCTGANNNACGTATGCCA | 2183 | TGCAGGACCAGAGAATTCGAATACATTTGAACANNNACGTATGCCA | 2423 | TGCAGGACCAGAGAATTCGAATACAGCCCACTCNNNACGTATGCCA | 2663 |
| TGCAGGACCAGAGAATTCGAATACAATGGCATNNNACGTATGCCA | 2184 | TGCAGGACCAGAGAATTCGAATACATAACTATGNNNACGTATGCCA | 2424 | TGCAGGACCAGAGAATTCGAATACAGAGATATANNNACGTATGCCA | 2664 |
| TGCAGGACCAGAGAATTCGAATACAAAGGATCGNNNACGTATGCCA | 2185 | TGCAGGACCAGAGAATTCGAATACATCAGATGCNNNACGTATGCCA | 2425 | TGCAGGACCAGAGAATTCGAATACAGCACTACANNNACGTATGCCA | 2665 |
| TGCAGGACCAGAGAATTCGAATACAGTGCATCANNNACGTATGCCA | 2186 | TGCAGGACCAGAGAATTCGAATACACTCAACAGNNNACGTATGCCA | 2426 | TGCAGGACCAGAGAATTCGAATACAACTTTGCCNNNACGTATGCCA | 2666 |
| TGCAGGACCAGAGAATTCGAATACAGTCGTCTTNNNACGTATGCCA | 2187 | TGCAGGACCAGAGAATTCGAATACAATAAAGTCNNNACGTATGCCA | 2427 | TGCAGGACCAGAGAATTCGAATACACTGAGGCCNNNACGTATGCCA | 2667 |
| TGCAGGACCAGAGAATTCGAATACACTTGAGGTNNNACGTATGCCA | 2188 | TGCAGGACCAGAGAATTCGAATACAAGAGCAGTNNNACGTATGCCA | 2428 | TGCAGGACCAGAGAATTCGAATACAAAGTAGGCNNNACGTATGCCA | 2668 |
| TGCAGGACCAGAGAATTCGAATACATACATCAANNNACGTATGCCA | 2189 | TGCAGGACCAGAGAATTCGAATACATATGTCTTNNNACGTATGCCA | 2429 | TGCAGGACCAGAGAATTCGAATACAGCTTCTACNNNACGTATGCCA | 2669 |
| TGCAGGACCAGAGAATTCGAATACACCGAACCGNNNACGTATGCCA | 2190 | TGCAGGACCAGAGAATTCGAATACAGCAGAGATNNNACGTATGCCA | 2430 | TGCAGGACCAGAGAATTCGAATACATGGAGGATNNNACGTATGCCA | 2670 |
| TGCAGGACCAGAGAATTCGAATACACCCACACNNNACGTATGCCA | 2191 | TGCAGGACCAGAGAATTCGAATACATCTCACCANNNACGTATGCCA | 2431 | TGCAGGACCAGAGAATTCGAATACAGCTAACCANNNACGTATGCCA | 2671 |
| TGCAGGACCAGAGAATTCGAATACAACGTAAAANNNACGTATGCCA | 2192 | TGCAGGACCAGAGAATTCGAATACACCCCTTGGNNNACGTATGCCA | 2432 | TGCAGGACCAGAGAATTCGAATACAACCCTTACNNNACGTATGCCA | 2672 |
| TGCAGGACCAGAGAATTCGAATACAGTAGAGTGNNNACGTATGCCA | 2193 | TGCAGGACCAGAGAATTCGAATACACAGTGGCCNNNACGTATGCCA | 2433 | TGCAGGACCAGAGAATTCGAATACAGTCTTCTGNNNACGTATGCCA | 2673 |
| TGCAGGACCAGAGAATTCGAATACACCACATAGNNNACGTATGCCA | 2194 | TGCAGGACCAGAGAATTCGAATACACTGATGCANNNACGTATGCCA | 2434 | TGCAGGACCAGAGAATTCGAATACACGGAGCCTNNNACGTATGCCA | 2674 |
| TGCAGGACCAGAGAATTCGAATACATCTGTGCTNNNACGTATGCCA | 2195 | TGCAGGACCAGAGAATTCGAATACATGGTACCTNNNACGTATGCCA | 2435 | TGCAGGACCAGAGAATTCGAATACACCTGATGANNNACGTATGCCA | 2675 |
| TGCAGGACCAGAGAATTCGAATACATAGTACATNNNACGTATGCCA | 2196 | TGCAGGACCAGAGAATTCGAATACAGTACGGCCNNNACGTATGCCA | 2436 | TGCAGGACCAGAGAATTCGAATACATCGATACGNNNACGTATGCCA | 2676 |
| TGCAGGACCAGAGAATTCGAATACACCGGACACNNNACGTATGCCA | 2197 | TGCAGGACCAGAGAATTCGAATACACCATGCGGNNNACGTATGCCA | 2437 | TGCAGGACCAGAGAATTCGAATACAAGAATGTNNNACGTATGCCA | 2677 |
| TGCAGGACCAGAGAATTCGAATACAGTAAGCTCNNNACGTATGCCA | 2198 | TGCAGGACCAGAGAATTCGAATACACAAGTAGGNNNACGTATGCCA | 2438 | TGCAGGACCAGAGAATTCGAATACATGCGCTCCNNNACGTATGCCA | 2678 |
| TGCAGGACCAGAGAATTCGAATACAACTTGGTGNNNACGTATGCCA | 2199 | TGCAGGACCAGAGAATTCGAATACACATCAAATNNNACGTATGCCA | 2439 | TGCAGGACCAGAGAATTCGAATACAAAGTCATTNNNACGTATGCCA | 2679 |
| TGCAGGACCAGAGAATTCGAATACACGACCTGGNNNACGTATGCCA | 2200 | TGCAGGACCAGAGAATTCGAATACAGACTCGGTTNNNACGTATGCCA | 2440 | TGCAGGACCAGAGAATTCGAATACATGTAATGTNNNACGTATGCCA | 2680 |

FIG. 15B

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAT GAGGATGNNNACGTATGCCA | 2201 | TGCAGGACCAGAGAATTCGAATACAG CAAATTTNNNACGTATGCCA | 2441 | TGCAGGACCAGAGAATTCGAATACAA TCTACCCNNNACGTATGCCA | 2681 |
| TGCAGGACCAGAGAATTCGAATACAC TCGTGCCNNNACGTATGCCA | 2202 | TGCAGGACCAGAGAATTCGAATACAT TAGTGTANNNACGTATGCCA | 2442 | TGCAGGACCAGAGAATTCGAATACAT GCCACAANNNACGTATGCCA | 2682 |
| TGCAGGACCAGAGAATTCGAATACAT TGCTCGTNNNACGTATGCCA | 2203 | TGCAGGACCAGAGAATTCGAATACAG ATGAAATNNNACGTATGCCA | 2443 | TGCAGGACCAGAGAATTCGAATACAG AGTGTTCNNNACGTATGCCA | 2683 |
| TGCAGGACCAGAGAATTCGAATACAA CACTGACNNNACGTATGCCA | 2204 | TGCAGGACCAGAGAATTCGAATACAT TGCCGAANNNACGTATGCCA | 2444 | TGCAGGACCAGAGAATTCGAATACAA ACAGCCTNNNACGTATGCCA | 2684 |
| TGCAGGACCAGAGAATTCGAATACAG TTGGTACNNNACGTATGCCA | 2205 | TGCAGGACCAGAGAATTCGAATACAT CCTCCTTNNNACGTATGCCA | 2445 | TGCAGGACCAGAGAATTCGAATACAG GACGACGNNNACGTATGCCA | 2685 |
| TGCAGGACCAGAGAATTCGAATACAT TCAGTCCNNNACGTATGCCA | 2206 | TGCAGGACCAGAGAATTCGAATACAC CCCATTANNNACGTATGCCA | 2446 | TGCAGGACCAGAGAATTCGAATACAA TTCCGGANNNACGTATGCCA | 2686 |
| TGCAGGACCAGAGAATTCGAATACAG TAACAAANNNACGTATGCCA | 2207 | TGCAGGACCAGAGAATTCGAATACAG TTTGTTTNNNACGTATGCCA | 2447 | TGCAGGACCAGAGAATTCGAATACAG GTCTCAANNNACGTATGCCA | 2687 |
| TGCAGGACCAGAGAATTCGAATACAC AACTGGTNNNACGTATGCCA | 2208 | TGCAGGACCAGAGAATTCGAATACAT ATCCCGTNNNACGTATGCCA | 2448 | TGCAGGACCAGAGAATTCGAATACAC ACCATGANNNACGTATGCCA | 2688 |
| TGCAGGACCAGAGAATTCGAATACAT GGATACCNNNACGTATGCCA | 2209 | TGCAGGACCAGAGAATTCGAATACAT TCGGTGANNNACGTATGCCA | 2449 | TGCAGGACCAGAGAATTCGAATACAC AAACGGANNNACGTATGCCA | 2689 |
| TGCAGGACCAGAGAATTCGAATACAA TGCACCANNNACGTATGCCA | 2210 | TGCAGGACCAGAGAATTCGAATACAC GTAAGGANNNACGTATGCCA | 2450 | TGCAGGACCAGAGAATTCGAATACAA GAGCGTANNNACGTATGCCA | 2690 |
| TGCAGGACCAGAGAATTCGAATACAA CTCCTTGNNNACGTATGCCA | 2211 | TGCAGGACCAGAGAATTCGAATACAC TTTCTTTNNNACGTATGCCA | 2451 | TGCAGGACCAGAGAATTCGAATACAC CCCTGACNNNACGTATGCCA | 2691 |
| TGCAGGACCAGAGAATTCGAATACAA ATAGTTCNNNACGTATGCCA | 2212 | TGCAGGACCAGAGAATTCGAATACAG ACTTTTTNNNACGTATGCCA | 2452 | TGCAGGACCAGAGAATTCGAATACAC CAAGTTGNNNACGTATGCCA | 2692 |
| TGCAGGACCAGAGAATTCGAATACAT GAGAGCANNNACGTATGCCA | 2213 | TGCAGGACCAGAGAATTCGAATACAG GTTAAGGNNNACGTATGCCA | 2453 | TGCAGGACCAGAGAATTCGAATACAT GTGTAATNNNACGTATGCCA | 2693 |
| TGCAGGACCAGAGAATTCGAATACAT CACCCCGNNNACGTATGCCA | 2214 | TGCAGGACCAGAGAATTCGAATACAA TCACGGTNNNACGTATGCCA | 2454 | TGCAGGACCAGAGAATTCGAATACAA TTTGTGANNNACGTATGCCA | 2694 |
| TGCAGGACCAGAGAATTCGAATACAT AATGGAANNNACGTATGCCA | 2215 | TGCAGGACCAGAGAATTCGAATACAC ATTTAGANNNACGTATGCCA | 2455 | TGCAGGACCAGAGAATTCGAATACAG TAGCGTTNNNACGTATGCCA | 2695 |
| TGCAGGACCAGAGAATTCGAATACAT CCAAATANNNACGTATGCCA | 2216 | TGCAGGACCAGAGAATTCGAATACAC ACGCGCANNNACGTATGCCA | 2456 | TGCAGGACCAGAGAATTCGAATACAC ACGTGATNNNACGTATGCCA | 2696 |
| TGCAGGACCAGAGAATTCGAATACAG AGGCTCCNNNACGTATGCCA | 2217 | TGCAGGACCAGAGAATTCGAATACAG TGAATCGNNNACGTATGCCA | 2457 | TGCAGGACCAGAGAATTCGAATACAA ACAGCGANNNACGTATGCCA | 2697 |
| TGCAGGACCAGAGAATTCGAATACAT CCGCGTCNNNACGTATGCCA | 2218 | TGCAGGACCAGAGAATTCGAATACAT TGTGTAANNNACGTATGCCA | 2458 | TGCAGGACCAGAGAATTCGAATACAA AATGCGGNNNACGTATGCCA | 2698 |
| TGCAGGACCAGAGAATTCGAATACAG CATTGCANNNACGTATGCCA | 2219 | TGCAGGACCAGAGAATTCGAATACAC CGCGTGANNNACGTATGCCA | 2459 | TGCAGGACCAGAGAATTCGAATACAT ACCAAGCNNNACGTATGCCA | 2699 |
| TGCAGGACCAGAGAATTCGAATACAC CCCTTAANNNACGTATGCCA | 2220 | TGCAGGACCAGAGAATTCGAATACAA ACCAAGGNNNACGTATGCCA | 2460 | TGCAGGACCAGAGAATTCGAATACAC GACCCTCNNNACGTATGCCA | 2700 |
| TGCAGGACCAGAGAATTCGAATACAG ACCGCCANNNACGTATGCCA | 2221 | TGCAGGACCAGAGAATTCGAATACAT CGTTTGCNNNACGTATGCCA | 2461 | TGCAGGACCAGAGAATTCGAATACAA CACCCCTNNNACGTATGCCA | 2701 |
| TGCAGGACCAGAGAATTCGAATACAG ATCTGACNNNACGTATGCCA | 2222 | TGCAGGACCAGAGAATTCGAATACAC TATTCGCNNNACGTATGCCA | 2462 | TGCAGGACCAGAGAATTCGAATACAC TGTCGCCNNNACGTATGCCA | 2702 |
| TGCAGGACCAGAGAATTCGAATACAG CATGTTGNNNACGTATGCCA | 2223 | TGCAGGACCAGAGAATTCGAATACAA ACAGATANNNACGTATGCCA | 2463 | TGCAGGACCAGAGAATTCGAATACAA GCCGCCANNNACGTATGCCA | 2703 |
| TGCAGGACCAGAGAATTCGAATACAT AGCACGTNNNACGTATGCCA | 2224 | TGCAGGACCAGAGAATTCGAATACAC TATTATCNNNACGTATGCCA | 2464 | TGCAGGACCAGAGAATTCGAATACAT GTACAATNNNACGTATGCCA | 2704 |
| TGCAGGACCAGAGAATTCGAATACAG GTCCAATNNNACGTATGCCA | 2225 | TGCAGGACCAGAGAATTCGAATACAT CCCAATCNNNACGTATGCCA | 2465 | TGCAGGACCAGAGAATTCGAATACAG ATCTACGNNNACGTATGCCA | 2705 |
| TGCAGGACCAGAGAATTCGAATACAA CCCTCTANNNACGTATGCCA | 2226 | TGCAGGACCAGAGAATTCGAATACAC TAAAGTTNNNACGTATGCCA | 2466 | TGCAGGACCAGAGAATTCGAATACAC CAGTCTTNNNACGTATGCCA | 2706 |
| TGCAGGACCAGAGAATTCGAATACAT TACGACGNNNACGTATGCCA | 2227 | TGCAGGACCAGAGAATTCGAATACAA GCTAATTNNNACGTATGCCA | 2467 | TGCAGGACCAGAGAATTCGAATACAG CTGCAATNNNACGTATGCCA | 2707 |
| TGCAGGACCAGAGAATTCGAATACAC ATATCGGNNNACGTATGCCA | 2228 | TGCAGGACCAGAGAATTCGAATACAT TGTTATCNNNACGTATGCCA | 2468 | TGCAGGACCAGAGAATTCGAATACAG AAGAGTCNNNACGTATGCCA | 2708 |
| TGCAGGACCAGAGAATTCGAATACAG CGATATCNNNCTAGCGTTAC | 2229 | TGCAGGACCAGAGAATTCGAATACAA AGTACGCNNNCTAGCGTTAC | 2469 | TGCAGGACCAGAGAATTCGAATACAA CAACTCGNNNCTAGCGTTAC | 2709 |
| TGCAGGACCAGAGAATTCGAATACAT ACGAGGANNNCTAGCGTTAC | 2230 | TGCAGGACCAGAGAATTCGAATACAC AGGCTATNNNCTAGCGTTAC | 2470 | TGCAGGACCAGAGAATTCGAATACAT GCGCAATNNNCTAGCGTTAC | 2710 |
| TGCAGGACCAGAGAATTCGAATACAT CTTACATNNNCTAGCGTTAC | 2231 | TGCAGGACCAGAGAATTCGAATACAC ATTAGTANNNCTAGCGTTAC | 2471 | TGCAGGACCAGAGAATTCGAATACAT AAGAACANNNCTAGCGTTAC | 2711 |
| TGCAGGACCAGAGAATTCGAATACAG CGTCTCCNNNCTAGCGTTAC | 2232 | TGCAGGACCAGAGAATTCGAATACAC CTCTAACNNNCTAGCGTTAC | 2472 | TGCAGGACCAGAGAATTCGAATACAC GCTTGCCNNNCTAGCGTTAC | 2712 |

FIG. 15C

| Pool-10 | SEQ ID NO: | Pool-11 | SEQ ID NO: | Pool-12 | SEQ ID NO: |
|---|---|---|---|---|---|
| TGCAGGACCAGAGAATTCGAATACATAATCCGGNNNCTAGCGTTAC | 2233 | TGCAGGACCAGAGAATTCGAATACATAGTGTCGNNNCTAGCGTTAC | 2473 | TGCAGGACCAGAGAATTCGAATACATTACACGGNNNCTAGCGTTAC | 2713 |
| TGCAGGACCAGAGAATTCGAATACACAGCATACNNNCTAGCGTTAC | 2234 | TGCAGGACCAGAGAATTCGAATACACGCAGAGGNNNCTAGCGTTAC | 2474 | TGCAGGACCAGAGAATTCGAATACACTCCACCGNNNCTAGCGTTAC | 2714 |
| TGCAGGACCAGAGAATTCGAATACAGTTCTCCANNNCTAGCGTTAC | 2235 | TGCAGGACCAGAGAATTCGAATACAGCGGTTCGNNNCTAGCGTTAC | 2475 | TGCAGGACCAGAGAATTCGAATACACGACCCAGNNNCTAGCGTTAC | 2715 |
| TGCAGGACCAGAGAATTCGAATACAAGTTCCTCNNNCTAGCGTTAC | 2236 | TGCAGGACCAGAGAATTCGAATACACCAGAGTTNNNCTAGCGTTAC | 2476 | TGCAGGACCAGAGAATTCGAATACACGGTCAGNNNCTAGCGTTAC | 2716 |
| TGCAGGACCAGAGAATTCGAATACAAAATCGAANNNCTAGCGTTAC | 2237 | TGCAGGACCAGAGAATTCGAATACATGATGAAANNNCTAGCGTTAC | 2477 | TGCAGGACCAGAGAATTCGAATACACACTATCCNNNCTAGCGTTAC | 2717 |
| TGCAGGACCAGAGAATTCGAATACAAGATTATCNNNCTAGCGTTAC | 2238 | TGCAGGACCAGAGAATTCGAATACACGTGAATGNNNCTAGCGTTAC | 2478 | TGCAGGACCAGAGAATTCGAATACACTAGTCTCNNNCTAGCGTTAC | 2718 |
| TGCAGGACCAGAGAATTCGAATACAGTTTCACCNNNCTAGCGTTAC | 2239 | TGCAGGACCAGAGAATTCGAATACACTATGTGCNNNCTAGCGTTAC | 2479 | TGCAGGACCAGAGAATTCGAATACATACCTTCGNNNCTAGCGTTAC | 2719 |
| TGCAGGACCAGAGAATTCGAATACAATTACATGNNNCTAGCGTTAC | 2240 | TGCAGGACCAGAGAATTCGAATACAAATACTACNNNCTAGCGTTAC | 2480 | TGCAGGACCAGAGAATTCGAATACAAACCAGAGNNNCTAGCGTTAC | 2720 |
| TGCAGGACCAGAGAATTCGAATACAACCATCCTNNNCTAGCGTTAC | 2241 | TGCAGGACCAGAGAATTCGAATACATTCGGATGNNNCTAGCGTTAC | 2481 | TGCAGGACCAGAGAATTCGAATACATGACTCGANNNCTAGCGTTAC | 2721 |
| TGCAGGACCAGAGAATTCGAATACACAGACTACNNNCTAGCGTTAC | 2242 | TGCAGGACCAGAGAATTCGAATACATACATTAGNNNCTAGCGTTAC | 2482 | TGCAGGACCAGAGAATTCGAATACAACCCAGATNNNCTAGCGTTAC | 2722 |
| TGCAGGACCAGAGAATTCGAATACACATTGGTGNNNCTAGCGTTAC | 2243 | TGCAGGACCAGAGAATTCGAATACATGGCCCGANNNCTAGCGTTAC | 2483 | TGCAGGACCAGAGAATTCGAATACATGCGCTTTNNNCTAGCGTTAC | 2723 |
| TGCAGGACCAGAGAATTCGAATACAGAGACCTTNNNCTAGCGTTAC | 2244 | TGCAGGACCAGAGAATTCGAATACAGTTGAGTCNNNCTAGCGTTAC | 2484 | TGCAGGACCAGAGAATTCGAATACAGGAGGACCNNNCTAGCGTTAC | 2724 |
| TGCAGGACCAGAGAATTCGAATACATCAGGCCGNNNCTAGCGTTAC | 2245 | TGCAGGACCAGAGAATTCGAATACAGTTAGCACNNNCTAGCGTTAC | 2485 | TGCAGGACCAGAGAATTCGAATACATCGTCCATNNNCTAGCGTTAC | 2725 |
| TGCAGGACCAGAGAATTCGAATACACAACACACNNNCTAGCGTTAC | 2246 | TGCAGGACCAGAGAATTCGAATACAAGTTCCCTNNNCTAGCGTTAC | 2486 | TGCAGGACCAGAGAATTCGAATACACGACCTCCNNNCTAGCGTTAC | 2726 |
| TGCAGGACCAGAGAATTCGAATACACGACGTCGNNNCTAGCGTTAC | 2247 | TGCAGGACCAGAGAATTCGAATACACATGGAGANNNCTAGCGTTAC | 2487 | TGCAGGACCAGAGAATTCGAATACAAGATTCCGNNNCTAGCGTTAC | 2727 |
| TGCAGGACCAGAGAATTCGAATACATAGACTATNNNCTAGCGTTAC | 2248 | TGCAGGACCAGAGAATTCGAATACAAATCGTCGNNNCTAGCGTTAC | 2488 | TGCAGGACCAGAGAATTCGAATACAACTCGAACNNNCTAGCGTTAC | 2728 |
| TGCAGGACCAGAGAATTCGAATACACCGAGAAANNNCTAGCGTTAC | 2249 | TGCAGGACCAGAGAATTCGAATACAACTCGCAANNNCTAGCGTTAC | 2489 | TGCAGGACCAGAGAATTCGAATACAAGACGATGNNNCTAGCGTTAC | 2729 |
| TGCAGGACCAGAGAATTCGAATACATTCCATATNNNCTAGCGTTAC | 2250 | TGCAGGACCAGAGAATTCGAATACATCAGCCTTNNNCTAGCGTTAC | 2490 | TGCAGGACCAGAGAATTCGAATACAGAACTTATNNNCTAGCGTTAC | 2730 |
| TGCAGGACCAGAGAATTCGAATACAGCCATGATNNNCTAGCGTTAC | 2251 | TGCAGGACCAGAGAATTCGAATACATTGCCTCANNNCTAGCGTTAC | 2491 | TGCAGGACCAGAGAATTCGAATACAACCAGCGCNNNCTAGCGTTAC | 2731 |
| TGCAGGACCAGAGAATTCGAATACAGGCGACGANNNCTAGCGTTAC | 2252 | TGCAGGACCAGAGAATTCGAATACAGGACCCACNNNCTAGCGTTAC | 2492 | TGCAGGACCAGAGAATTCGAATACATACCTCTGNNNCTAGCGTTAC | 2732 |
| TGCAGGACCAGAGAATTCGAATACACCCAGTAANNNCTAGCGTTAC | 2253 | TGCAGGACCAGAGAATTCGAATACATTCTCCAGNNNCTAGCGTTAC | 2493 | TGCAGGACCAGAGAATTCGAATACACGGAGCGANNNCTAGCGTTAC | 2733 |
| TGCAGGACCAGAGAATTCGAATACACTCAAACGNNNCTAGCGTTAC | 2254 | TGCAGGACCAGAGAATTCGAATACAGTCCTCGCNNNCTAGCGTTAC | 2494 | TGCAGGACCAGAGAATTCGAATACAACCCGAAANNNCTAGCGTTAC | 2734 |
| TGCAGGACCAGAGAATTCGAATACACAGATCTGNNNCTAGCGTTAC | 2255 | TGCAGGACCAGAGAATTCGAATACAAATAGTCTNNNCTAGCGTTAC | 2495 | TGCAGGACCAGAGAATTCGAATACAGGATCGCCNNNCTAGCGTTAC | 2735 |
| TGCAGGACCAGAGAATTCGAATACAAGAAAATCNNNCTAGCGTTAC | 2256 | TGCAGGACCAGAGAATTCGAATACAGCTGGATTNNNCTAGCGTTAC | 2496 | TGCAGGACCAGAGAATTCGAATACAATCAGCACNNNCTAGCGTTAC | 2736 |
| TGCAGGACCAGAGAATTCGAATACAATCTTTCANNNCTAGCGTTAC | 2257 | TGCAGGACCAGAGAATTCGAATACATTCGTCACNNNCTAGCGTTAC | 2497 | TGCAGGACCAGAGAATTCGAATACAAACTCTCCNNNCTAGCGTTAC | 2737 |
| TGCAGGACCAGAGAATTCGAATACACCCATCTANNNCTAGCGTTAC | 2258 | TGCAGGACCAGAGAATTCGAATACAATTATGACNNNCTAGCGTTAC | 2498 | TGCAGGACCAGAGAATTCGAATACATATGAGTTNNNCTAGCGTTAC | 2738 |
| TGCAGGACCAGAGAATTCGAATACACTAAGGTCNNNCTAGCGTTAC | 2259 | TGCAGGACCAGAGAATTCGAATACATTTTAGAGNNNCTAGCGTTAC | 2499 | TGCAGGACCAGAGAATTCGAATACAAGGCGTCCNNNCTAGCGTTAC | 2739 |
| TGCAGGACCAGAGAATTCGAATACACACCGACGNNNCTAGCGTTAC | 2260 | TGCAGGACCAGAGAATTCGAATACAGATATACTNNNCTAGCGTTAC | 2500 | TGCAGGACCAGAGAATTCGAATACAAGAATTAGNNNCTAGCGTTAC | 2740 |
| TGCAGGACCAGAGAATTCGAATACAGTTTAGATNNNCTAGCGTTAC | 2261 | TGCAGGACCAGAGAATTCGAATACAGCTACCCGNNNCTAGCGTTAC | 2501 | TGCAGGACCAGAGAATTCGAATACAAATTTAGTNNNCTAGCGTTAC | 2741 |
| TGCAGGACCAGAGAATTCGAATACATCCCCTCCNNNCTAGCGTTAC | 2262 | TGCAGGACCAGAGAATTCGAATACAAACCTTTTNNNCTAGCGTTAC | 2502 | TGCAGGACCAGAGAATTCGAATACATATTTCTGNNNCTAGCGTTAC | 2742 |
| TGCAGGACCAGAGAATTCGAATACATTAATCAGNNNCTAGCGTTAC | 2263 | TGCAGGACCAGAGAATTCGAATACAATGTGTATNNNCTAGCGTTAC | 2503 | TGCAGGACCAGAGAATTCGAATACAGCTGTACANNNCTAGCGTTAC | 2743 |
| TGCAGGACCAGAGAATTCGAATACACATTCGAGNNNCTAGCGTTAC | 2264 | TGCAGGACCAGAGAATTCGAATACATCCCACGCNNNCTAGCGTTAC | 2504 | TGCAGGACCAGAGAATTCGAATACAGCTTACGANNNCTAGCGTTAC | 2744 |

FIG. 15D

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAAACCGTGTNNNCTAGCGTTAC | 2265 | TGCAGGACCAGAGAATTCGAATACACGCCTCTGNNNCTAGCGTTAC | 2505 | TGCAGGACCAGAGAATTCGAATACACCCACGGANNNCTAGCGTTAC | 2745 |
| TGCAGGACCAGAGAATTCGAATACACCCAATTCNNNCTAGCGTTAC | 2266 | TGCAGGACCAGAGAATTCGAATACACTATAACANNNCTAGCGTTAC | 2506 | TGCAGGACCAGAGAATTCGAATACATGGATCTGNNNCTAGCGTTAC | 2746 |
| TGCAGGACCAGAGAATTCGAATACATTGGTGGTNNNCTAGCGTTAC | 2267 | TGCAGGACCAGAGAATTCGAATACAGACTGACTNNNCTAGCGTTAC | 2507 | TGCAGGACCAGAGAATTCGAATACATCCACGAANNNCTAGCGTTAC | 2747 |
| TGCAGGACCAGAGAATTCGAATACATGCTTAGGNNNCTAGCGTTAC | 2268 | TGCAGGACCAGAGAATTCGAATACACTGGCCAGNNNCTAGCGTTAC | 2508 | TGCAGGACCAGAGAATTCGAATACATCAAGACCNNNCTAGCGTTAC | 2748 |
| TGCAGGACCAGAGAATTCGAATACAACACCCCCNNNCTAGCGTTAC | 2269 | TGCAGGACCAGAGAATTCGAATACAAAGCGAGNNNCTAGCGTTAC | 2509 | TGCAGGACCAGAGAATTCGAATACAGGCAGACGNNNCTAGCGTTAC | 2749 |
| TGCAGGACCAGAGAATTCGAATACACCATTGAGNNNCTAGCGTTAC | 2270 | TGCAGGACCAGAGAATTCGAATACACGCTTTTGNNNCTAGCGTTAC | 2510 | TGCAGGACCAGAGAATTCGAATACATTTTTACGNNNCTAGCGTTAC | 2750 |
| TGCAGGACCAGAGAATTCGAATACAACTTAAACNNNCTAGCGTTAC | 2271 | TGCAGGACCAGAGAATTCGAATACATTTCCCTCNNNCTAGCGTTAC | 2511 | TGCAGGACCAGAGAATTCGAATACAGCGTTTGANNNCTAGCGTTAC | 2751 |
| TGCAGGACCAGAGAATTCGAATACATATAGTACNNNCTAGCGTTAC | 2272 | TGCAGGACCAGAGAATTCGAATACACTTACTCGNNNCTAGCGTTAC | 2512 | TGCAGGACCAGAGAATTCGAATACAAGGTACTNNNCTAGCGTTAC | 2752 |
| TGCAGGACCAGAGAATTCGAATACACAGTGTACNNNCTAGCGTTAC | 2273 | TGCAGGACCAGAGAATTCGAATACAATCGAGTCNNNCTAGCGTTAC | 2513 | TGCAGGACCAGAGAATTCGAATACATTCTGTTANNNCTAGCGTTAC | 2753 |
| TGCAGGACCAGAGAATTCGAATACAGCGTCTTTNNNCTAGCGTTAC | 2274 | TGCAGGACCAGAGAATTCGAATACATTGTACGGNNNCTAGCGTTAC | 2514 | TGCAGGACCAGAGAATTCGAATACACCGATGTANNNCTAGCGTTAC | 2754 |
| TGCAGGACCAGAGAATTCGAATACATGACTCAGNNNCTAGCGTTAC | 2275 | TGCAGGACCAGAGAATTCGAATACACACCATTCNNNCTAGCGTTAC | 2515 | TGCAGGACCAGAGAATTCGAATACAGTCGGTTANNNCTAGCGTTAC | 2755 |
| TGCAGGACCAGAGAATTCGAATACAACTTAGTANNNCTAGCGTTAC | 2276 | TGCAGGACCAGAGAATTCGAATACACCCTCTTTNNNCTAGCGTTAC | 2516 | TGCAGGACCAGAGAATTCGAATACACGAACCCGNNNCTAGCGTTAC | 2756 |
| TGCAGGACCAGAGAATTCGAATACAAAACATGANNNCTAGCGTTAC | 2277 | TGCAGGACCAGAGAATTCGAATACATGCATTAANNNCTAGCGTTAC | 2517 | TGCAGGACCAGAGAATTCGAATACATTCGACTCNNNCTAGCGTTAC | 2757 |
| TGCAGGACCAGAGAATTCGAATACAGTTAGGCTNNNCTAGCGTTAC | 2278 | TGCAGGACCAGAGAATTCGAATACACGTAGCGCNNNCTAGCGTTAC | 2518 | TGCAGGACCAGAGAATTCGAATACATTCAGCCTNNNCTAGCGTTAC | 2758 |
| TGCAGGACCAGAGAATTCGAATACATCCGCAGGNNNCTAGCGTTAC | 2279 | TGCAGGACCAGAGAATTCGAATACAGTCTCCTANNNCTAGCGTTAC | 2519 | TGCAGGACCAGAGAATTCGAATACACACTTGAGNNNCTAGCGTTAC | 2759 |
| TGCAGGACCAGAGAATTCGAATACAAGTACATTNNNCTAGCGTTAC | 2280 | TGCAGGACCAGAGAATTCGAATACATGCGCCGANNNCTAGCGTTAC | 2520 | TGCAGGACCAGAGAATTCGAATACATCACGCGGNNNCTAGCGTTAC | 2760 |
| TGCAGGACCAGAGAATTCGAATACAGGTCGTATNNNCTAGCGTTAC | 2281 | TGCAGGACCAGAGAATTCGAATACACAATGATTNNNCTAGCGTTAC | 2521 | TGCAGGACCAGAGAATTCGAATACACACTGTAGNNNCTAGCGTTAC | 2761 |
| TGCAGGACCAGAGAATTCGAATACAAGACGACANNNCTAGCGTTAC | 2282 | TGCAGGACCAGAGAATTCGAATACAAGCGAGGCNNNCTAGCGTTAC | 2522 | TGCAGGACCAGAGAATTCGAATACAACCAAGCTNNNCTAGCGTTAC | 2762 |
| TGCAGGACCAGAGAATTCGAATACAAAGTTCTANNNCTAGCGTTAC | 2283 | TGCAGGACCAGAGAATTCGAATACATTGAATACNNNCTAGCGTTAC | 2523 | TGCAGGACCAGAGAATTCGAATACAACTGCAACNNNCTAGCGTTAC | 2763 |
| TGCAGGACCAGAGAATTCGAATACAACCGAACTNNNCTAGCGTTAC | 2284 | TGCAGGACCAGAGAATTCGAATACAACCGCCAGNNNCTAGCGTTAC | 2524 | TGCAGGACCAGAGAATTCGAATACATAACGGTCNNNCTAGCGTTAC | 2764 |
| TGCAGGACCAGAGAATTCGAATACAGGCAATTCNNNCTAGCGTTAC | 2285 | TGCAGGACCAGAGAATTCGAATACAGGCGACAGNNNCTAGCGTTAC | 2525 | TGCAGGACCAGAGAATTCGAATACAAGTTTGTANNNCTAGCGTTAC | 2765 |
| TGCAGGACCAGAGAATTCGAATACAGTCACACANNNCTAGCGTTAC | 2286 | TGCAGGACCAGAGAATTCGAATACATATCCAANNNCTAGCGTTAC | 2526 | TGCAGGACCAGAGAATTCGAATACACACGTTTCNNNCTAGCGTTAC | 2766 |
| TGCAGGACCAGAGAATTCGAATACACGGAAATGNNNCTAGCGTTAC | 2287 | TGCAGGACCAGAGAATTCGAATACAATGTTGTANNNCTAGCGTTAC | 2527 | TGCAGGACCAGAGAATTCGAATACATTAAAACCNNNCTAGCGTTAC | 2767 |
| TGCAGGACCAGAGAATTCGAATACACTGTCTACNNNCTAGCGTTAC | 2288 | TGCAGGACCAGAGAATTCGAATACAGATTGTTANNNCTAGCGTTAC | 2528 | TGCAGGACCAGAGAATTCGAATACATTCGTAGGNNNCTAGCGTTAC | 2768 |
| TGCAGGACCAGAGAATTCGAATACAGAGCCAGGNNNGATCGACATG | 2289 | TGCAGGACCAGAGAATTCGAATACAGTCCACGGNNNGATCGACATG | 2529 | TGCAGGACCAGAGAATTCGAATACATGCGTAGTNNNGATCGACATG | 2769 |
| TGCAGGACCAGAGAATTCGAATACACACTCCTANNNGATCGACATG | 2290 | TGCAGGACCAGAGAATTCGAATACATGACTGACNNNGATCGACATG | 2530 | TGCAGGACCAGAGAATTCGAATACAGCTTTGNNNGATCGACATG | 2770 |
| TGCAGGACCAGAGAATTCGAATACACTTTCCCTNNNGATCGACATG | 2291 | TGCAGGACCAGAGAATTCGAATACATGATTTAGNNNGATCGACATG | 2531 | TGCAGGACCAGAGAATTCGAATACAGTAAATAGNNNGATCGACATG | 2771 |
| TGCAGGACCAGAGAATTCGAATACACTGAGCTANNNGATCGACATG | 2292 | TGCAGGACCAGAGAATTCGAATACAACATACTANNNGATCGACATG | 2532 | TGCAGGACCAGAGAATTCGAATACACGCTGTCCNNNGATCGACATG | 2772 |
| TGCAGGACCAGAGAATTCGAATACAGTCTGACANNNGATCGACATG | 2293 | TGCAGGACCAGAGAATTCGAATACAAGCATCANNNGATCGACATG | 2533 | TGCAGGACCAGAGAATTCGAATACACTTAGAGCNNNGATCGACATG | 2773 |
| TGCAGGACCAGAGAATTCGAATACACTGACGCGNNNGATCGACATG | 2294 | TGCAGGACCAGAGAATTCGAATACAACGGCAAANNNGATCGACATG | 2534 | TGCAGGACCAGAGAATTCGAATACAGGACATAGNNNGATCGACATG | 2774 |
| TGCAGGACCAGAGAATTCGAATACAGTGATGGANNNGATCGACATG | 2295 | TGCAGGACCAGAGAATTCGAATACACTTTGCTGNNNGATCGACATG | 2535 | TGCAGGACCAGAGAATTCGAATACATCTACAGGNNNGATCGACATG | 2775 |
| TGCAGGACCAGAGAATTCGAATACAGAATTCTANNNGATCGACATG | 2296 | TGCAGGACCAGAGAATTCGAATACATTAACTAGNNNGATCGACATG | 2536 | TGCAGGACCAGAGAATTCGAATACACAAACTCGNNNGATCGACATG | 2776 |

FIG. 15E

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAC GTGCATANNNGATCGACATG | 2297 | TGCAGGACCAGAGAATTCGAATACAC GTACTGANNNGATCGACATG | 2537 | TGCAGGACCAGAGAATTCGAATACAG CTATTCCNNNGATCGACATG | 2777 |
| TGCAGGACCAGAGAATTCGAATACAT GGCGTGCNNNGATCGACATG | 2298 | TGCAGGACCAGAGAATTCGAATACAT AGTATCANNNGATCGACATG | 2538 | TGCAGGACCAGAGAATTCGAATACAG TCCAGTANNNGATCGACATG | 2778 |
| TGCAGGACCAGAGAATTCGAATACAC CAGTGCGNNNGATCGACATG | 2299 | TGCAGGACCAGAGAATTCGAATACAC CTGACAANNNGATCGACATG | 2539 | TGCAGGACCAGAGAATTCGAATACAG GCGAGACNNNGATCGACATG | 2779 |
| TGCAGGACCAGAGAATTCGAATACAT GCCCCTGNNNGATCGACATG | 2300 | TGCAGGACCAGAGAATTCGAATACAC GTGGCCANNNGATCGACATG | 2540 | TGCAGGACCAGAGAATTCGAATACAT TTCATACNNNGATCGACATG | 2780 |
| TGCAGGACCAGAGAATTCGAATACAT CCGTCGCNNNGATCGACATG | 2301 | TGCAGGACCAGAGAATTCGAATACAG CGTATACNNNGATCGACATG | 2541 | TGCAGGACCAGAGAATTCGAATACAC AGCTGTANNNGATCGACATG | 2781 |
| TGCAGGACCAGAGAATTCGAATACAC TCCTCCGNNNGATCGACATG | 2302 | TGCAGGACCAGAGAATTCGAATACAG CGCTGCANNNGATCGACATG | 2542 | TGCAGGACCAGAGAATTCGAATACAA CTGCTCTNNNGATCGACATG | 2782 |
| TGCAGGACCAGAGAATTCGAATACAG CTCCATTNNNGATCGACATG | 2303 | TGCAGGACCAGAGAATTCGAATACAA CCGTTAGNNNGATCGACATG | 2543 | TGCAGGACCAGAGAATTCGAATACAA AAGTTCTNNNGATCGACATG | 2783 |
| TGCAGGACCAGAGAATTCGAATACAG ACTCCTTNNNGATCGACATG | 2304 | TGCAGGACCAGAGAATTCGAATACAT GTACTTTNNNGATCGACATG | 2544 | TGCAGGACCAGAGAATTCGAATACAG AATCGAGNNNGATCGACATG | 2784 |
| TGCAGGACCAGAGAATTCGAATACAT GTAACTANNNGATCGACATG | 2305 | TGCAGGACCAGAGAATTCGAATACAC ATTATGANNNGATCGACATG | 2545 | TGCAGGACCAGAGAATTCGAATACAC TCCCGCANNNGATCGACATG | 2785 |
| TGCAGGACCAGAGAATTCGAATACAA GAGTCTCNNNGATCGACATG | 2306 | TGCAGGACCAGAGAATTCGAATACAC AGACCCGNNNGATCGACATG | 2546 | TGCAGGACCAGAGAATTCGAATACAG AAAACTANNNGATCGACATG | 2786 |
| TGCAGGACCAGAGAATTCGAATACAC TTTCTAANNNGATCGACATG | 2307 | TGCAGGACCAGAGAATTCGAATACAT AGCACCANNNGATCGACATG | 2547 | TGCAGGACCAGAGAATTCGAATACAA CCCTAAGNNNGATCGACATG | 2787 |
| TGCAGGACCAGAGAATTCGAATACAC GAGACCCNNNGATCGACATG | 2308 | TGCAGGACCAGAGAATTCGAATACAT GGAGTGANNNGATCGACATG | 2548 | TGCAGGACCAGAGAATTCGAATACAG GTCATACNNNGATCGACATG | 2788 |
| TGCAGGACCAGAGAATTCGAATACAT TTTAGTCNNNGATCGACATG | 2309 | TGCAGGACCAGAGAATTCGAATACAG GACGTGNNNGATCGACATG | 2549 | TGCAGGACCAGAGAATTCGAATACAT GGTTGTGNNNGATCGACATG | 2789 |
| TGCAGGACCAGAGAATTCGAATACAA TGTGCTGNNNGATCGACATG | 2310 | TGCAGGACCAGAGAATTCGAATACAC CTTACACNNNGATCGACATG | 2550 | TGCAGGACCAGAGAATTCGAATACAA AGTTCCGNNNGATCGACATG | 2790 |
| TGCAGGACCAGAGAATTCGAATACAC CCAGGTGNNNGATCGACATG | 2311 | TGCAGGACCAGAGAATTCGAATACAT GGCAGCCNNNGATCGACATG | 2551 | TGCAGGACCAGAGAATTCGAATACAA TCAATGTNNNGATCGACATG | 2791 |
| TGCAGGACCAGAGAATTCGAATACAG AACCAAGNNNGATCGACATG | 2312 | TGCAGGACCAGAGAATTCGAATACAC CTTACTGNNNGATCGACATG | 2552 | TGCAGGACCAGAGAATTCGAATACAC ATTGATANNNGATCGACATG | 2792 |
| TGCAGGACCAGAGAATTCGAATACAC CTGAGGCNNNGATCGACATG | 2313 | TGCAGGACCAGAGAATTCGAATACAT TACTCTANNNGATCGACATG | 2553 | TGCAGGACCAGAGAATTCGAATACAG GAGGAAANNNGATCGACATG | 2793 |
| TGCAGGACCAGAGAATTCGAATACAA TAAGCGGNNNGATCGACATG | 2314 | TGCAGGACCAGAGAATTCGAATACAC CGCCTACNNNGATCGACATG | 2554 | TGCAGGACCAGAGAATTCGAATACAC ATTTTACNNNGATCGACATG | 2794 |
| TGCAGGACCAGAGAATTCGAATACAT TTGTCATNNNGATCGACATG | 2315 | TGCAGGACCAGAGAATTCGAATACAC CTTAGAGNNNGATCGACATG | 2555 | TGCAGGACCAGAGAATTCGAATACAG AACTTCGNNNGATCGACATG | 2795 |
| TGCAGGACCAGAGAATTCGAATACAA GCGTTTGNNNGATCGACATG | 2316 | TGCAGGACCAGAGAATTCGAATACAT TCTATGTNNNGATCGACATG | 2556 | TGCAGGACCAGAGAATTCGAATACAC GTCACCCNNNGATCGACATG | 2796 |
| TGCAGGACCAGAGAATTCGAATACAG CTATTTNNNGATCGACATG | 2317 | TGCAGGACCAGAGAATTCGAATACAT TTTACACNNNGATCGACATG | 2557 | TGCAGGACCAGAGAATTCGAATACAA CGTTAATNNNGATCGACATG | 2797 |
| TGCAGGACCAGAGAATTCGAATACAT GACACCANNNGATCGACATG | 2318 | TGCAGGACCAGAGAATTCGAATACAT TGTTTTGNNNGATCGACATG | 2558 | TGCAGGACCAGAGAATTCGAATACAG GTGTGTTNNNGATCGACATG | 2798 |
| TGCAGGACCAGAGAATTCGAATACAC GCTCAAANNNGATCGACATG | 2319 | TGCAGGACCAGAGAATTCGAATACAC AAAGACGNNNGATCGACATG | 2559 | TGCAGGACCAGAGAATTCGAATACAG AAATAGTNNNGATCGACATG | 2799 |
| TGCAGGACCAGAGAATTCGAATACAG CGCATTANNNGATCGACATG | 2320 | TGCAGGACCAGAGAATTCGAATACAA CCTCCGCNNNGATCGACATG | 2560 | TGCAGGACCAGAGAATTCGAATACAG TCTATTTNNNGATCGACATG | 2800 |
| TGCAGGACCAGAGAATTCGAATACAT CTAAATGNNNGATCGACATG | 2321 | TGCAGGACCAGAGAATTCGAATACAG TTAACATNNNGATCGACATG | 2561 | TGCAGGACCAGAGAATTCGAATACAT AGTAGCCNNNGATCGACATG | 2801 |
| TGCAGGACCAGAGAATTCGAATACAA GCACTACNNNGATCGACATG | 2322 | TGCAGGACCAGAGAATTCGAATACAC GATGCGCNNNGATCGACATG | 2562 | TGCAGGACCAGAGAATTCGAATACAG TACAAAANNNGATCGACATG | 2802 |
| TGCAGGACCAGAGAATTCGAATACAC ATTCAGNNNGATCGACATG | 2323 | TGCAGGACCAGAGAATTCGAATACAC CTCGAAANNNGATCGACATG | 2563 | TGCAGGACCAGAGAATTCGAATACAA GAGTACGNNNGATCGACATG | 2803 |
| TGCAGGACCAGAGAATTCGAATACAC TGCTCCGNNNGATCGACATG | 2324 | TGCAGGACCAGAGAATTCGAATACAA TGTCGACNNNGATCGACATG | 2564 | TGCAGGACCAGAGAATTCGAATACAT AGACTTANNNGATCGACATG | 2804 |
| TGCAGGACCAGAGAATTCGAATACAG CACGATTNNNGATCGACATG | 2325 | TGCAGGACCAGAGAATTCGAATACAT AACAGCCNNNGATCGACATG | 2565 | TGCAGGACCAGAGAATTCGAATACAG GAGCAAANNNGATCGACATG | 2805 |
| TGCAGGACCAGAGAATTCGAATACAA TGTCATANNNGATCGACATG | 2326 | TGCAGGACCAGAGAATTCGAATACAG CGCAGTCNNNGATCGACATG | 2566 | TGCAGGACCAGAGAATTCGAATACAA GCGTCGCNNNGATCGACATG | 2806 |
| TGCAGGACCAGAGAATTCGAATACAA CAGGACANNNGATCGACATG | 2327 | TGCAGGACCAGAGAATTCGAATACAA TCATAACNNNGATCGACATG | 2567 | TGCAGGACCAGAGAATTCGAATACAG CTGGTCGNNNGATCGACATG | 2807 |
| TGCAGGACCAGAGAATTCGAATACAC CGTAAGTNNNGATCGACATG | 2328 | TGCAGGACCAGAGAATTCGAATACAA AGGTCTCNNNGATCGACATG | 2568 | TGCAGGACCAGAGAATTCGAATACAA GTCCACANNNGATCGACATG | 2808 |

FIG. 15F

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAAAAGAATCNNNGATCGACATG | 2329 | TGCAGGACCAGAGAATTCGAATACAGAAATACANNNGATCGACATG | 2569 | TGCAGGACCAGAGAATTCGAATACATCCCTTAGNNNGATCGACATG | 2809 |
| TGCAGGACCAGAGAATTCGAATACACAAGCCTANNNGATCGACATG | 2330 | TGCAGGACCAGAGAATTCGAATACAACGTACTGNNNGATCGACATG | 2570 | TGCAGGACCAGAGAATTCGAATACACCGGATGCNNNGATCGACATG | 2810 |
| TGCAGGACCAGAGAATTCGAATACACTAACTAANNNGATCGACATG | 2331 | TGCAGGACCAGAGAATTCGAATACAATTAAGTCNNNGATCGACATG | 2571 | TGCAGGACCAGAGAATTCGAATACATCTATATCNNNGATCGACATG | 2811 |
| TGCAGGACCAGAGAATTCGAATACACGCGTAATNNNGATCGACATG | 2332 | TGCAGGACCAGAGAATTCGAATACACGTGAAAGNNNGATCGACATG | 2572 | TGCAGGACCAGAGAATTCGAATACAAGACCCTANNNGATCGACATG | 2812 |
| TGCAGGACCAGAGAATTCGAATACAGACGTCTTNNNGATCGACATG | 2333 | TGCAGGACCAGAGAATTCGAATACAGGTTAATNNNGATCGACATG | 2573 | TGCAGGACCAGAGAATTCGAATACAGGCTGGTCNNNGATCGACATG | 2813 |
| TGCAGGACCAGAGAATTCGAATACAAGCCCGTNNNGATCGACATG | 2334 | TGCAGGACCAGAGAATTCGAATACAGGACAGGTNNNGATCGACATG | 2574 | TGCAGGACCAGAGAATTCGAATACAGACGATGANNNGATCGACATG | 2814 |
| TGCAGGACCAGAGAATTCGAATACAGCTCAACANNNGATCGACATG | 2335 | TGCAGGACCAGAGAATTCGAATACACCCAGTGNNNGATCGACATG | 2575 | TGCAGGACCAGAGAATTCGAATACAGCCCATAANNNGATCGACATG | 2815 |
| TGCAGGACCAGAGAATTCGAATACAATCAGGAGNNNGATCGACATG | 2336 | TGCAGGACCAGAGAATTCGAATACATCCAAGGTNNNGATCGACATG | 2576 | TGCAGGACCAGAGAATTCGAATACAACTTTCATNNNGATCGACATG | 2816 |
| TGCAGGACCAGAGAATTCGAATACACCCCAGAGNNNGATCGACATG | 2337 | TGCAGGACCAGAGAATTCGAATACATGAGTATTNNNGATCGACATG | 2577 | TGCAGGACCAGAGAATTCGAATACATCGACTTCNNNGATCGACATG | 2817 |
| TGCAGGACCAGAGAATTCGAATACAGAGGTGGCNNNGATCGACATG | 2338 | TGCAGGACCAGAGAATTCGAATACATGTACGGTNNNGATCGACATG | 2578 | TGCAGGACCAGAGAATTCGAATACACGCTACTTNNNGATCGACATG | 2818 |
| TGCAGGACCAGAGAATTCGAATACACCCAAGCCNNNGATCGACATG | 2339 | TGCAGGACCAGAGAATTCGAATACACGCGTCAGNNNGATCGACATG | 2579 | TGCAGGACCAGAGAATTCGAATACACGAAAACGNNNGATCGACATG | 2819 |
| TGCAGGACCAGAGAATTCGAATACACTGGTGGCNNNGATCGACATG | 2340 | TGCAGGACCAGAGAATTCGAATACACGGATGTNNNGATCGACATG | 2580 | TGCAGGACCAGAGAATTCGAATACATTATGCGNNNGATCGACATG | 2820 |
| TGCAGGACCAGAGAATTCGAATACACGTATGTNNNGATCGACATG | 2341 | TGCAGGACCAGAGAATTCGAATACACACAAGGTNNNGATCGACATG | 2581 | TGCAGGACCAGAGAATTCGAATACAGCTATTANNNGATCGACATG | 2821 |
| TGCAGGACCAGAGAATTCGAATACATGCGTTTCNNNGATCGACATG | 2342 | TGCAGGACCAGAGAATTCGAATACAATTAAAAANNNGATCGACATG | 2582 | TGCAGGACCAGAGAATTCGAATACAGGCCCGCGNNNGATCGACATG | 2822 |
| TGCAGGACCAGAGAATTCGAATACATAAATTTANNNGATCGACATG | 2343 | TGCAGGACCAGAGAATTCGAATACAACGACCCGNNNGATCGACATG | 2583 | TGCAGGACCAGAGAATTCGAATACAGACGCTGCNNNGATCGACATG | 2823 |
| TGCAGGACCAGAGAATTCGAATACATCGGACATNNNGATCGACATG | 2344 | TGCAGGACCAGAGAATTCGAATACATCAAACTANNNGATCGACATG | 2584 | TGCAGGACCAGAGAATTCGAATACAGCGAGCCCNNNGATCGACATG | 2824 |
| TGCAGGACCAGAGAATTCGAATACATAAACACTNNNGATCGACATG | 2345 | TGCAGGACCAGAGAATTCGAATACACACGCCGANNNGATCGACATG | 2585 | TGCAGGACCAGAGAATTCGAATACATTCATCGCNNNGATCGACATG | 2825 |
| TGCAGGACCAGAGAATTCGAATACATTAGGCCANNNGATCGACATG | 2346 | TGCAGGACCAGAGAATTCGAATACACGATCAGTNNNGATCGACATG | 2586 | TGCAGGACCAGAGAATTCGAATACACATAAAAGNNNGATCGACATG | 2826 |
| TGCAGGACCAGAGAATTCGAATACAAGCCCTCCNNNGATCGACATG | 2347 | TGCAGGACCAGAGAATTCGAATACACACTTTGCNNNGATCGACATG | 2587 | TGCAGGACCAGAGAATTCGAATACACTCGCGCTNNNGATCGACATG | 2827 |
| TGCAGGACCAGAGAATTCGAATACACGGAAAACNNNGATCGACATG | 2348 | TGCAGGACCAGAGAATTCGAATACATCCTGATCNNNGATCGACATG | 2588 | TGCAGGACCAGAGAATTCGAATACAGACATGTCNNNGATCGACATG | 2828 |
| TGCAGGACCAGAGAATTCGAATACAGGCCGGTTNNNTGCATCAGGT | 2349 | TGCAGGACCAGAGAATTCGAATACAGAACTCCANNNTGCATCAGGT | 2589 | TGCAGGACCAGAGAATTCGAATACACTCACCGCNNNTGCATCAGGT | 2829 |
| TGCAGGACCAGAGAATTCGAATACATAGGCTACNNNTGCATCAGGT | 2350 | TGCAGGACCAGAGAATTCGAATACAGGTCAATCNNNTGCATCAGGT | 2590 | TGCAGGACCAGAGAATTCGAATACACACGTCTTNNNTGCATCAGGT | 2830 |
| TGCAGGACCAGAGAATTCGAATACACCACTTGTNNNTGCATCAGGT | 2351 | TGCAGGACCAGAGAATTCGAATACATATGCAGCNNNTGCATCAGGT | 2591 | TGCAGGACCAGAGAATTCGAATACAACTGCGTANNNTGCATCAGGT | 2831 |
| TGCAGGACCAGAGAATTCGAATACAGATAGAGCNNNTGCATCAGGT | 2352 | TGCAGGACCAGAGAATTCGAATACAGCACCTCCNNNTGCATCAGGT | 2592 | TGCAGGACCAGAGAATTCGAATACATAAATTATNNNTGCATCAGGT | 2832 |
| TGCAGGACCAGAGAATTCGAATACAAGTCCAGTNNNTGCATCAGGT | 2353 | TGCAGGACCAGAGAATTCGAATACATCAAGTGCNNNTGCATCAGGT | 2593 | TGCAGGACCAGAGAATTCGAATACATAGTCTAANNNTGCATCAGGT | 2833 |
| TGCAGGACCAGAGAATTCGAATACAGTCATCAGNNNTGCATCAGGT | 2354 | TGCAGGACCAGAGAATTCGAATACATTGCCGTTNNNTGCATCAGGT | 2594 | TGCAGGACCAGAGAATTCGAATACACAAACTATNNNTGCATCAGGT | 2834 |
| TGCAGGACCAGAGAATTCGAATACATTTCGGAGNNNTGCATCAGGT | 2355 | TGCAGGACCAGAGAATTCGAATACAGTGGAGTANNNTGCATCAGGT | 2595 | TGCAGGACCAGAGAATTCGAATACATCACTGTCNNNTGCATCAGGT | 2835 |
| TGCAGGACCAGAGAATTCGAATACACTCAGGATNNNTGCATCAGGT | 2356 | TGCAGGACCAGAGAATTCGAATACAGCCTCACCNNNTGCATCAGGT | 2596 | TGCAGGACCAGAGAATTCGAATACAACAAATGNNNTGCATCAGGT | 2836 |
| TGCAGGACCAGAGAATTCGAATACACCTATCCANNNTGCATCAGGT | 2357 | TGCAGGACCAGAGAATTCGAATACACACACCANNNTGCATCAGGT | 2597 | TGCAGGACCAGAGAATTCGAATACATTTTCTTCNNNTGCATCAGGT | 2837 |
| TGCAGGACCAGAGAATTCGAATACAAATGCTGNNNTGCATCAGGT | 2358 | TGCAGGACCAGAGAATTCGAATACAACCCCATTNNNTGCATCAGGT | 2598 | TGCAGGACCAGAGAATTCGAATACACTTCAGTCNNNTGCATCAGGT | 2838 |
| TGCAGGACCAGAGAATTCGAATACAGGTGAAANNNTGCATCAGGT | 2359 | TGCAGGACCAGAGAATTCGAATACAATAGTCTANNNTGCATCAGGT | 2599 | TGCAGGACCAGAGAATTCGAATACAGGTCTGTNNNTGCATCAGGT | 2839 |
| TGCAGGACCAGAGAATTCGAATACAGTTGCAACNNNTGCATCAGGT | 2360 | TGCAGGACCAGAGAATTCGAATACAGAATGTCCNNNTGCATCAGGT | 2600 | TGCAGGACCAGAGAATTCGAATACAGCAAACAGNNNTGCATCAGGT | 2840 |

FIG. 15G

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAGAGAGCTANNNTGCATCAGGT | 2361 | TGCAGGACCAGAGAATTCGAATACACTAGATCGNNNTGCATCAGGT | 2601 | TGCAGGACCAGAGAATTCGAATACACCGAGAGGNNNTGCATCAGGT | 2841 |
| TGCAGGACCAGAGAATTCGAATACAGCCTAACANNNTGCATCAGGT | 2362 | TGCAGGACCAGAGAATTCGAATACACGCAACCCNNNTGCATCAGGT | 2602 | TGCAGGACCAGAGAATTCGAATACAATATTGCANNNTGCATCAGGT | 2842 |
| TGCAGGACCAGAGAATTCGAATACACTGAGACTNNNTGCATCAGGT | 2363 | TGCAGGACCAGAGAATTCGAATACAGGAGAGAANNNTGCATCAGGT | 2603 | TGCAGGACCAGAGAATTCGAATACATCTCTGGTNNNTGCATCAGGT | 2843 |
| TGCAGGACCAGAGAATTCGAATACAACGTTGCANNNTGCATCAGGT | 2364 | TGCAGGACCAGAGAATTCGAATACAGTTGTCCTNNNTGCATCAGGT | 2604 | TGCAGGACCAGAGAATTCGAATACAATTGGAGGNNNTGCATCAGGT | 2844 |
| TGCAGGACCAGAGAATTCGAATACAGGAAGCTANNNTGCATCAGGT | 2365 | TGCAGGACCAGAGAATTCGAATACATGGCATACNNNTGCATCAGGT | 2605 | TGCAGGACCAGAGAATTCGAATACACATCATTTNNNTGCATCAGGT | 2845 |
| TGCAGGACCAGAGAATTCGAATACACCCTGTATNNNTGCATCAGGT | 2366 | TGCAGGACCAGAGAATTCGAATACAGAGGCAATNNNTGCATCAGGT | 2606 | TGCAGGACCAGAGAATTCGAATACAGAGGTGATNNNTGCATCAGGT | 2846 |
| TGCAGGACCAGAGAATTCGAATACATAGCCTCTNNNTGCATCAGGT | 2367 | TGCAGGACCAGAGAATTCGAATACATCTCACGTNNNTGCATCAGGT | 2607 | TGCAGGACCAGAGAATTCGAATACACCCCGTCANNNTGCATCAGGT | 2847 |
| TGCAGGACCAGAGAATTCGAATACAAGGTACCTNNNTGCATCAGGT | 2368 | TGCAGGACCAGAGAATTCGAATACACTGCGGCANNNTGCATCAGGT | 2608 | TGCAGGACCAGAGAATTCGAATACAGACAGGTANNNTGCATCAGGT | 2848 |
| TGCAGGACCAGAGAATTCGAATACATGTTATCTNNNTGCATCAGGT | 2369 | TGCAGGACCAGAGAATTCGAATACACTTAATGANNNTGCATCAGGT | 2609 | TGCAGGACCAGAGAATTCGAATACAGCCTTAGANNNTGCATCAGGT | 2849 |
| TGCAGGACCAGAGAATTCGAATACAGACTTACGNNNTGCATCAGGT | 2370 | TGCAGGACCAGAGAATTCGAATACAAACTCACGNNNTGCATCAGGT | 2610 | TGCAGGACCAGAGAATTCGAATACACCTTCTAGNNNTGCATCAGGT | 2850 |
| TGCAGGACCAGAGAATTCGAATACAACTTCCACNNNTGCATCAGGT | 2371 | TGCAGGACCAGAGAATTCGAATACAAGCAGTGANNNTGCATCAGGT | 2611 | TGCAGGACCAGAGAATTCGAATACAAGGCTTGTNNNTGCATCAGGT | 2851 |
| TGCAGGACCAGAGAATTCGAATACACCTTCTGANNNTGCATCAGGT | 2372 | TGCAGGACCAGAGAATTCGAATACATAATACTGNNNTGCATCAGGT | 2612 | TGCAGGACCAGAGAATTCGAATACATGGAGTTCNNNTGCATCAGGT | 2852 |
| TGCAGGACCAGAGAATTCGAATACACGACACTANNNTGCATCAGGT | 2373 | TGCAGGACCAGAGAATTCGAATACAAAGTCCCNNNTGCATCAGGT | 2613 | TGCAGGACCAGAGAATTCGAATACACCACCGAGNNNTGCATCAGGT | 2853 |
| TGCAGGACCAGAGAATTCGAATACACTGTGAGTNNNTGCATCAGGT | 2374 | TGCAGGACCAGAGAATTCGAATACAGCTGGAANNNTGCATCAGGT | 2614 | TGCAGGACCAGAGAATTCGAATACAGGAATGCANNNTGCATCAGGT | 2854 |
| TGCAGGACCAGAGAATTCGAATACAAGAGACACNNNTGCATCAGGT | 2375 | TGCAGGACCAGAGAATTCGAATACAAAGAGGAGNNNTGCATCAGGT | 2615 | TGCAGGACCAGAGAATTCGAATACAACATTACANNNTGCATCAGGT | 2855 |
| TGCAGGACCAGAGAATTCGAATACATAATTGTGNNNTGCATCAGGT | 2376 | TGCAGGACCAGAGAATTCGAATACAGTGGAAGTNNNTGCATCAGGT | 2616 | TGCAGGACCAGAGAATTCGAATACAAGTCTCTNNNTGCATCAGGT | 2856 |
| TGCAGGACCAGAGAATTCGAATACAGTAATTGNNNTGCATCAGGT | 2377 | TGCAGGACCAGAGAATTCGAATACACGGGACTNNNTGCATCAGGT | 2617 | TGCAGGACCAGAGAATTCGAATACATAGTGCCANNNTGCATCAGGT | 2857 |
| TGCAGGACCAGAGAATTCGAATACACATACTATNNNTGCATCAGGT | 2378 | TGCAGGACCAGAGAATTCGAATACATACTTGTNNNTGCATCAGGT | 2618 | TGCAGGACCAGAGAATTCGAATACAGCAATGCTNNNTGCATCAGGT | 2858 |
| TGCAGGACCAGAGAATTCGAATACAAGTGGATNNNTGCATCAGGT | 2379 | TGCAGGACCAGAGAATTCGAATACAABCTGACCNNNTGCATCAGGT | 2619 | TGCAGGACCAGAGAATTCGAATACAGTTGAATNNNTGCATCAGGT | 2859 |
| TGCAGGACCAGAGAATTCGAATACATTATAGACNNNTGCATCAGGT | 2380 | TGCAGGACCAGAGAATTCGAATACATGCTGGTANNNTGCATCAGGT | 2620 | TGCAGGACCAGAGAATTCGAATACACCACTTCANNNTGCATCAGGT | 2860 |
| TGCAGGACCAGAGAATTCGAATACAGAGTTTCGNNNTGCATCAGGT | 2381 | TGCAGGACCAGAGAATTCGAATACAATATTTTNNNTGCATCAGGT | 2621 | TGCAGGACCAGAGAATTCGAATACATCCATTCGNNNTGCATCAGGT | 2861 |
| TGCAGGACCAGAGAATTCGAATACACAGAGATGNNNTGCATCAGGT | 2382 | TGCAGGACCAGAGAATTCGAATACATCCCCATANNNTGCATCAGGT | 2622 | TGCAGGACCAGAGAATTCGAATACACACTCTCANNNTGCATCAGGT | 2862 |
| TGCAGGACCAGAGAATTCGAATACAGACTCAACNNNTGCATCAGGT | 2383 | TGCAGGACCAGAGAATTCGAATACACAAGTTGCNNNTGCATCAGGT | 2623 | TGCAGGACCAGAGAATTCGAATACAGACCTGATNNNTGCATCAGGT | 2863 |
| TGCAGGACCAGAGAATTCGAATACATTCGCTGTNNNTGCATCAGGT | 2384 | TGCAGGACCAGAGAATTCGAATACATGAACCGTNNNTGCATCAGGT | 2624 | TGCAGGACCAGAGAATTCGAATACAAGAGCTCNNNTGCATCAGGT | 2864 |
| TGCAGGACCAGAGAATTCGAATACACGTCCGAGNNNTGCATCAGGT | 2385 | TGCAGGACCAGAGAATTCGAATACACGCATTGANNNTGCATCAGGT | 2625 | TGCAGGACCAGAGAATTCGAATACACTGGATTGNNNTGCATCAGGT | 2865 |
| TGCAGGACCAGAGAATTCGAATACAGCATGCATNNNTGCATCAGGT | 2386 | TGCAGGACCAGAGAATTCGAATACAGGCGTTGNNNTGCATCAGGT | 2626 | TGCAGGACCAGAGAATTCGAATACATGCTATCGNNNTGCATCAGGT | 2866 |
| TGCAGGACCAGAGAATTCGAATACAAAGTGCCNNNTGCATCAGGT | 2387 | TGCAGGACCAGAGAATTCGAATACACCCGCCCGNNNTGCATCAGGT | 2627 | TGCAGGACCAGAGAATTCGAATACAGACGTTGTNNNTGCATCAGGT | 2867 |
| TGCAGGACCAGAGAATTCGAATACAGAAAGCACNNNTGCATCAGGT | 2388 | TGCAGGACCAGAGAATTCGAATACACAAGCTACNNNTGCATCAGGT | 2628 | TGCAGGACCAGAGAATTCGAATACAATTCATCTNNNTGCATCAGGT | 2868 |
| TGCAGGACCAGAGAATTCGAATACAGGCTGCTGNNNTGCATCAGGT | 2389 | TGCAGGACCAGAGAATTCGAATACACGGTTCANNNTGCATCAGGT | 2629 | TGCAGGACCAGAGAATTCGAATACACGATTCAGNNNTGCATCAGGT | 2869 |
| TGCAGGACCAGAGAATTCGAATACAGCGGAAGCNNNTGCATCAGGT | 2390 | TGCAGGACCAGAGAATTCGAATACACAACGTTGNNNTGCATCAGGT | 2630 | TGCAGGACCAGAGAATTCGAATACATGGTGCATNNNTGCATCAGGT | 2870 |
| TGCAGGACCAGAGAATTCGAATACATCACATANNNTGCATCAGGT | 2391 | TGCAGGACCAGAGAATTCGAATACAGTACTAGCNNNTGCATCAGGT | 2631 | TGCAGGACCAGAGAATTCGAATACATGTGTTTTNNNTGCATCAGGT | 2871 |
| TGCAGGACCAGAGAATTCGAATACAACTCTCTGNNNTGCATCAGGT | 2392 | TGCAGGACCAGAGAATTCGAATACATGAGTGTCNNNTGCATCAGGT | 2632 | TGCAGGACCAGAGAATTCGAATACATGGCATCANNNTGCATCAGGT | 2872 |

FIG. 15H

| Pool-10 | SEQ ID NO: | Pool-11 | SEQ ID NO: | Pool-12 | SEQ ID NO: |
|---|---|---|---|---|---|
| TGCAGGACCAGAGAATTCGAATACACGCCCCGNNNTGCATCAGGT | 2393 | TGCAGGACCAGAGAATTCGAATACACAAACAGGNNNTGCATCAGGT | 2633 | TGCAGGACCAGAGAATTCGAATACATAAGCTGCNNNTGCATCAGGT | 2873 |
| TGCAGGACCAGAGAATTCGAATACATTTAATCCNNNTGCATCAGGT | 2394 | TGCAGGACCAGAGAATTCGAATACAGCATGCTANNNTGCATCAGGT | 2634 | TGCAGGACCAGAGAATTCGAATACAACGGACTTNNNTGCATCAGGT | 2874 |
| TGCAGGACCAGAGAATTCGAATACACCGTCGGANNNTGCATCAGGT | 2395 | TGCAGGACCAGAGAATTCGAATACAGATTCACGNNNTGCATCAGGT | 2635 | TGCAGGACCAGAGAATTCGAATACATGAATTACNNNTGCATCAGGT | 2875 |
| TGCAGGACCAGAGAATTCGAATACATGAGAAATNNNTGCATCAGGT | 2396 | TGCAGGACCAGAGAATTCGAATACAGTAGATCCNNNTGCATCAGGT | 2636 | TGCAGGACCAGAGAATTCGAATACAAACAGAGCNNNTGCATCAGGT | 2876 |
| TGCAGGACCAGAGAATTCGAATACACGTTATAANNNTGCATCAGGT | 2397 | TGCAGGACCAGAGAATTCGAATACAGGCCAACGNNNTGCATCAGGT | 2637 | TGCAGGACCAGAGAATTCGAATACACATGTTCCNNNTGCATCAGGT | 2877 |
| TGCAGGACCAGAGAATTCGAATACATCTAAAACNNNTGCATCAGGT | 2398 | TGCAGGACCAGAGAATTCGAATACAGAGCATAGNNNTGCATCAGGT | 2638 | TGCAGGACCAGAGAATTCGAATACATCGTCTACNNNTGCATCAGGT | 2878 |
| TGCAGGACCAGAGAATTCGAATACAACACTCGANNNTGCATCAGGT | 2399 | TGCAGGACCAGAGAATTCGAATACAGGTGTCATNNNTGCATCAGGT | 2639 | TGCAGGACCAGAGAATTCGAATACATAGAGACNNNTGCATCAGGT | 2879 |
| TGCAGGACCAGAGAATTCGAATACAGCATCGTANNNTGCATCAGGT | 2400 | TGCAGGACCAGAGAATTCGAATACATCTTCGACNNNTGCATCAGGT | 2640 | TGCAGGACCAGAGAATTCGAATACATATAGTGTNNNTGCATCAGGT | 2880 |
| TGCAGGACCAGAGAATTCGAATACAGTAAGACGNNNTGCATCAGGT | 2401 | TGCAGGACCAGAGAATTCGAATACAGATCAGCTNNNTGCATCAGGT | 2641 | TGCAGGACCAGAGAATTCGAATACAGGAGAGTTNNNTGCATCAGGT | 2881 |
| TGCAGGACCAGAGAATTCGAATACAAAAGCCCTNNNTGCATCAGGT | 2402 | TGCAGGACCAGAGAATTCGAATACATCGACCTTNNNTGCATCAGGT | 2642 | TGCAGGACCAGAGAATTCGAATACATACATTCTNNNTGCATCAGGT | 2882 |
| TGCAGGACCAGAGAATTCGAATACACCATGGTANNNTGCATCAGGT | 2403 | TGCAGGACCAGAGAATTCGAATACAAGCCCACGNNNTGCATCAGGT | 2643 | TGCAGGACCAGAGAATTCGAATACACACAATGCNNNTGCATCAGGT | 2883 |
| TGCAGGACCAGAGAATTCGAATACACGAAATAANNNTGCATCAGGT | 2404 | TGCAGGACCAGAGAATTCGAATACAGAGATCTCNNNTGCATCAGGT | 2644 | TGCAGGACCAGAGAATTCGAATACAGATATTACNNNTGCATCAGGT | 2884 |
| TGCAGGACCAGAGAATTCGAATACAGATCAAAANNNTGCATCAGGT | 2405 | TGCAGGACCAGAGAATTCGAATACATCTTTAACNNNTGCATCAGGT | 2645 | TGCAGGACCAGAGAATTCGAATACACGGCTTTTNNNTGCATCAGGT | 2885 |
| TGCAGGACCAGAGAATTCGAATACAAGTGCCGCNNNTGCATCAGGT | 2406 | TGCAGGACCAGAGAATTCGAATACATCCCTAACNNNTGCATCAGGT | 2646 | TGCAGGACCAGAGAATTCGAATACAGCTGCTGGNNNTGCATCAGGT | 2886 |
| TGCAGGACCAGAGAATTCGAATACACCCTGGCTNNNTGCATCAGGT | 2407 | TGCAGGACCAGAGAATTCGAATACAACTCGACANNNTGCATCAGGT | 2647 | TGCAGGACCAGAGAATTCGAATACAAAGGCGCGNNNTGCATCAGGT | 2887 |
| TGCAGGACCAGAGAATTCGAATACACAAGTTCGNNNTGCATCAGGT | 2408 | TGCAGGACCAGAGAATTCGAATACATGAGAGACNNNTGCATCAGGT | 2648 | TGCAGGACCAGAGAATTCGAATACAACGGTGAANNNTGCATCAGGT | 2888 |

FIG. 16A

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAC CACGGACNNNACGTATGCCA | 2889 | TGCAGGACCAGAGAATTCGAATACAC ATGCGTANNNACGTATGCCA | 3129 | TGCAGGACCAGAGAATTCGAATACAG TGTGATCNNNACGTATGCCA | 3369 |
| TGCAGGACCAGAGAATTCGAATACAA ATCCTCCNNNACGTATGCCA | 2890 | TGCAGGACCAGAGAATTCGAATACAT CGTGCGGNNNACGTATGCCA | 3130 | TGCAGGACCAGAGAATTCGAATACAA AAGCGCANNNACGTATGCCA | 3370 |
| TGCAGGACCAGAGAATTCGAATACAG TGGCCGTNNNACGTATGCCA | 2891 | TGCAGGACCAGAGAATTCGAATACAG TAGTGGANNNACGTATGCCA | 3131 | TGCAGGACCAGAGAATTCGAATACAT CGTGGATNNNACGTATGCCA | 3371 |
| TGCAGGACCAGAGAATTCGAATACAA GAGTAGCNNNACGTATGCCA | 2892 | TGCAGGACCAGAGAATTCGAATACAA TTGTTGGNNNACGTATGCCA | 3132 | TGCAGGACCAGAGAATTCGAATACAT CACCGAANNNACGTATGCCA | 3372 |
| TGCAGGACCAGAGAATTCGAATACAT CCTGCGCNNNACGTATGCCA | 2893 | TGCAGGACCAGAGAATTCGAATACAA GAGCTTCNNNACGTATGCCA | 3133 | TGCAGGACCAGAGAATTCGAATACAG CCGTTGGNNNACGTATGCCA | 3373 |
| TGCAGGACCAGAGAATTCGAATACAT TCTCGTGNNNACGTATGCCA | 2894 | TGCAGGACCAGAGAATTCGAATACAG TACTGTGNNNACGTATGCCA | 3134 | TGCAGGACCAGAGAATTCGAATACAA CACGGTNNNACGTATGCCA | 3374 |
| TGCAGGACCAGAGAATTCGAATACAT GGTATGCNNNACGTATGCCA | 2895 | TGCAGGACCAGAGAATTCGAATACAA GCAACCTNNNACGTATGCCA | 3135 | TGCAGGACCAGAGAATTCGAATACAG CTCACGGNNNACGTATGCCA | 3375 |
| TGCAGGACCAGAGAATTCGAATACAA TCACTCCNNNACGTATGCCA | 2896 | TGCAGGACCAGAGAATTCGAATACAG CCCTGCTNNNACGTATGCCA | 3136 | TGCAGGACCAGAGAATTCGAATACAC AATCGCANNNACGTATGCCA | 3376 |
| TGCAGGACCAGAGAATTCGAATACAA ACAAGGCNNNACGTATGCCA | 2897 | TGCAGGACCAGAGAATTCGAATACAC TCTCGCGNNNACGTATGCCA | 3137 | TGCAGGACCAGAGAATTCGAATACAT AATATATNNNACGTATGCCA | 3377 |
| TGCAGGACCAGAGAATTCGAATACAC CGTCTTANNNACGTATGCCA | 2898 | TGCAGGACCAGAGAATTCGAATACAC TACTTGCNNNACGTATGCCA | 3138 | TGCAGGACCAGAGAATTCGAATACAC ATTACCCNNNACGTATGCCA | 3378 |
| TGCAGGACCAGAGAATTCGAATACAA AAAATTANNNACGTATGCCA | 2899 | TGCAGGACCAGAGAATTCGAATACAA TAATGAGNNNACGTATGCCA | 3139 | TGCAGGACCAGAGAATTCGAATACAG ACTACTGNNNACGTATGCCA | 3379 |
| TGCAGGACCAGAGAATTCGAATACAA CACAGAGNNNACGTATGCCA | 2900 | TGCAGGACCAGAGAATTCGAATACAC CGTAGTANNNACGTATGCCA | 3140 | TGCAGGACCAGAGAATTCGAATACAG TGCCGCNNNACGTATGCCA | 3380 |
| TGCAGGACCAGAGAATTCGAATACAA GTGCGCTNNNACGTATGCCA | 2901 | TGCAGGACCAGAGAATTCGAATACAC GCAACAGNNNACGTATGCCA | 3141 | TGCAGGACCAGAGAATTCGAATACAG GCTATTGNNNACGTATGCCA | 3381 |
| TGCAGGACCAGAGAATTCGAATACAC GTGACGCNNNACGTATGCCA | 2902 | TGCAGGACCAGAGAATTCGAATACAC TGTGTCTNNNACGTATGCCA | 3142 | TGCAGGACCAGAGAATTCGAATACAG GTGGTGGNNNACGTATGCCA | 3382 |
| TGCAGGACCAGAGAATTCGAATACAG ACCCCCTNNNACGTATGCCA | 2903 | TGCAGGACCAGAGAATTCGAATACAT CCAAACGNNNACGTATGCCA | 3143 | TGCAGGACCAGAGAATTCGAATACAT GCGTACANNNACGTATGCCA | 3383 |
| TGCAGGACCAGAGAATTCGAATACAA CATTTGANNNACGTATGCCA | 2904 | TGCAGGACCAGAGAATTCGAATACAT GTCAAGCNNNACGTATGCCA | 3144 | TGCAGGACCAGAGAATTCGAATACAA TTCTTCANNNACGTATGCCA | 3384 |
| TGCAGGACCAGAGAATTCGAATACAG GTGGCAGNNNACGTATGCCA | 2905 | TGCAGGACCAGAGAATTCGAATACAA GTGTCACNNNACGTATGCCA | 3145 | TGCAGGACCAGAGAATTCGAATACAT CTGGTCTNNNACGTATGCCA | 3385 |
| TGCAGGACCAGAGAATTCGAATACAG AGGCCAGNNNACGTATGCCA | 2906 | TGCAGGACCAGAGAATTCGAATACAC CTCAAGANNNACGTATGCCA | 3146 | TGCAGGACCAGAGAATTCGAATACAG CGAGCCTNNNACGTATGCCA | 3386 |
| TGCAGGACCAGAGAATTCGAATACAA CTCGAGTNNNACGTATGCCA | 2907 | TGCAGGACCAGAGAATTCGAATACAG TGAAAGCNNNACGTATGCCA | 3147 | TGCAGGACCAGAGAATTCGAATACAA GCCGTGCNNNACGTATGCCA | 3387 |
| TGCAGGACCAGAGAATTCGAATACAA CAAAAGGNNNACGTATGCCA | 2908 | TGCAGGACCAGAGAATTCGAATACAT TGCGCCNNNACGTATGCCA | 3148 | TGCAGGACCAGAGAATTCGAATACAG ATAACCCNNNACGTATGCCA | 3388 |
| TGCAGGACCAGAGAATTCGAATACAA AGCAACGNNNACGTATGCCA | 2909 | TGCAGGACCAGAGAATTCGAATACAG TATTGCGNNNACGTATGCCA | 3149 | TGCAGGACCAGAGAATTCGAATACAC GGAACCCNNNACGTATGCCA | 3389 |
| TGCAGGACCAGAGAATTCGAATACAG GCTTTGTNNNACGTATGCCA | 2910 | TGCAGGACCAGAGAATTCGAATACAA CAAATAGNNNACGTATGCCA | 3150 | TGCAGGACCAGAGAATTCGAATACAG TCCAGCGNNNACGTATGCCA | 3390 |
| TGCAGGACCAGAGAATTCGAATACAT GGATGCTNNNACGTATGCCA | 2911 | TGCAGGACCAGAGAATTCGAATACAC TACGCGGNNNACGTATGCCA | 3151 | TGCAGGACCAGAGAATTCGAATACAC GTGAGCCNNNACGTATGCCA | 3391 |
| TGCAGGACCAGAGAATTCGAATACAT CAATGGCNNNACGTATGCCA | 2912 | TGCAGGACCAGAGAATTCGAATACAT GTATACANNNACGTATGCCA | 3152 | TGCAGGACCAGAGAATTCGAATACAT CGGCCAGNNNACGTATGCCA | 3392 |
| TGCAGGACCAGAGAATTCGAATACAA ACTACTANNNACGTATGCCA | 2913 | TGCAGGACCAGAGAATTCGAATACAA GACCTACNNNACGTATGCCA | 3153 | TGCAGGACCAGAGAATTCGAATACAC CGGCAAGNNNACGTATGCCA | 3393 |
| TGCAGGACCAGAGAATTCGAATACAT TGCGATGNNNACGTATGCCA | 2914 | TGCAGGACCAGAGAATTCGAATACAT TCCCATGNNNACGTATGCCA | 3154 | TGCAGGACCAGAGAATTCGAATACAG GCTGTTANNNACGTATGCCA | 3394 |
| TGCAGGACCAGAGAATTCGAATACAG AGATACGNNNACGTATGCCA | 2915 | TGCAGGACCAGAGAATTCGAATACAT AGCCCTNNNACGTATGCCA | 3155 | TGCAGGACCAGAGAATTCGAATACAT GAAAATGNNNACGTATGCCA | 3395 |
| TGCAGGACCAGAGAATTCGAATACAT CCTTTTTNNNACGTATGCCA | 2916 | TGCAGGACCAGAGAATTCGAATACAG GTTCACNNNACGTATGCCA | 3156 | TGCAGGACCAGAGAATTCGAATACAC TTCTATANNNACGTATGCCA | 3396 |
| TGCAGGACCAGAGAATTCGAATACAG TTAGCGTNNNACGTATGCCA | 2917 | TGCAGGACCAGAGAATTCGAATACAG ACGTTGNNNACGTATGCCA | 3157 | TGCAGGACCAGAGAATTCGAATACAT CCCCGCANNNACGTATGCCA | 3397 |
| TGCAGGACCAGAGAATTCGAATACAG CGGCGCCNNNACGTATGCCA | 2918 | TGCAGGACCAGAGAATTCGAATACAT GTTGATANNNACGTATGCCA | 3158 | TGCAGGACCAGAGAATTCGAATACAT GTCTACCNNNACGTATGCCA | 3398 |
| TGCAGGACCAGAGAATTCGAATACAA TGCTCTCNNNACGTATGCCA | 2919 | TGCAGGACCAGAGAATTCGAATACAA GTATTACNNNACGTATGCCA | 3159 | TGCAGGACCAGAGAATTCGAATACAT GTAGTTANNNACGTATGCCA | 3399 |
| TGCAGGACCAGAGAATTCGAATACAT TATCTACNNNACGTATGCCA | 2920 | TGCAGGACCAGAGAATTCGAATACAG AGAACACNNNACGTATGCCA | 3160 | TGCAGGACCAGAGAATTCGAATACAT GGTTTANNNACGTATGCCA | 3400 |
| TGCAGGACCAGAGAATTCGAATACAT TCTATTGNNNACGTATGCCA | 2921 | TGCAGGACCAGAGAATTCGAATACAC CTAAATANNNACGTATGCCA | 3161 | TGCAGGACCAGAGAATTCGAATACAG AGACGGCNNNACGTATGCCA | 3401 |

FIG. 16B

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAC CAGTACANNNACGTATGCCA | 2922 | TGCAGGACCAGAGAATTCGAATACAA TTTCACTNNNACGTATGCCA | 3162 | TGCAGGACCAGAGAATTCGAATACAC GTCGAGCNNNACGTATGCCA | 3402 |
| TGCAGGACCAGAGAATTCGAATACAA CAGAATANNNACGTATGCCA | 2923 | TGCAGGACCAGAGAATTCGAATACAG TCAACGTNNNACGTATGCCA | 3163 | TGCAGGACCAGAGAATTCGAATACAC AACAGTCNNNACGTATGCCA | 3403 |
| TGCAGGACCAGAGAATTCGAATACAG TATATACNNNACGTATGCCA | 2924 | TGCAGGACCAGAGAATTCGAATACAG CGTGCTGNNNACGTATGCCA | 3164 | TGCAGGACCAGAGAATTCGAATACAT GTTGCGANNNACGTATGCCA | 3404 |
| TGCAGGACCAGAGAATTCGAATACAT ATTAACGNNNACGTATGCCA | 2925 | TGCAGGACCAGAGAATTCGAATACAA AACCCACNNNACGTATGCCA | 3165 | TGCAGGACCAGAGAATTCGAATACAC GTATTTTNNNACGTATGCCA | 3405 |
| TGCAGGACCAGAGAATTCGAATACAG GTTAGAGNNNACGTATGCCA | 2926 | TGCAGGACCAGAGAATTCGAATACAC CCCTGTGNNNACGTATGCCA | 3166 | TGCAGGACCAGAGAATTCGAATACAG TACGTCANNNACGTATGCCA | 3406 |
| TGCAGGACCAGAGAATTCGAATACAC TAGGATCNNNACGTATGCCA | 2927 | TGCAGGACCAGAGAATTCGAATACAC GTAGCCTNNNACGTATGCCA | 3167 | TGCAGGACCAGAGAATTCGAATACAC CTAGCGGNNNACGTATGCCA | 3407 |
| TGCAGGACCAGAGAATTCGAATACAG ACTAGGANNNACGTATGCCA | 2928 | TGCAGGACCAGAGAATTCGAATACAA TCCATGGNNNACGTATGCCA | 3168 | TGCAGGACCAGAGAATTCGAATACAA GAGCCGGNNNACGTATGCCA | 3408 |
| TGCAGGACCAGAGAATTCGAATACAA CTTATCTNNNACGTATGCCA | 2929 | TGCAGGACCAGAGAATTCGAATACAC GCATCTTNNNACGTATGCCA | 3169 | TGCAGGACCAGAGAATTCGAATACAG GCGCCCGNNNACGTATGCCA | 3409 |
| TGCAGGACCAGAGAATTCGAATACAG ACGTCCGNNNACGTATGCCA | 2930 | TGCAGGACCAGAGAATTCGAATACAA GAATCCCNNNACGTATGCCA | 3170 | TGCAGGACCAGAGAATTCGAATACAC AGCATGTNNNACGTATGCCA | 3410 |
| TGCAGGACCAGAGAATTCGAATACAA TGGAAATNNNACGTATGCCA | 2931 | TGCAGGACCAGAGAATTCGAATACAC CTTGTGTNNNACGTATGCCA | 3171 | TGCAGGACCAGAGAATTCGAATACAA GCTTAATNNNACGTATGCCA | 3411 |
| TGCAGGACCAGAGAATTCGAATACAT GTTCAGGNNNACGTATGCCA | 2932 | TGCAGGACCAGAGAATTCGAATACAG AAACCAGNNNACGTATGCCA | 3172 | TGCAGGACCAGAGAATTCGAATACAC TCACCCGNNNACGTATGCCA | 3412 |
| TGCAGGACCAGAGAATTCGAATACAT GCAATCGNNNACGTATGCCA | 2933 | TGCAGGACCAGAGAATTCGAATACAG GATATCTNNNACGTATGCCA | 3173 | TGCAGGACCAGAGAATTCGAATACAT CGGAGCGNNNACGTATGCCA | 3413 |
| TGCAGGACCAGAGAATTCGAATACAT TATGGATNNNACGTATGCCA | 2934 | TGCAGGACCAGAGAATTCGAATACAA GGCCGAGNNNACGTATGCCA | 3174 | TGCAGGACCAGAGAATTCGAATACAC ACTGCCTNNNACGTATGCCA | 3414 |
| TGCAGGACCAGAGAATTCGAATACAA CATCGTGNNNACGTATGCCA | 2935 | TGCAGGACCAGAGAATTCGAATACAC ACTGTTCNNNACGTATGCCA | 3175 | TGCAGGACCAGAGAATTCGAATACAG CCTCCTGNNNACGTATGCCA | 3415 |
| TGCAGGACCAGAGAATTCGAATACAA AAGTAGTNNNACGTATGCCA | 2936 | TGCAGGACCAGAGAATTCGAATACAG TGGAGGCNNNACGTATGCCA | 3176 | TGCAGGACCAGAGAATTCGAATACAT AGTTAACNNNACGTATGCCA | 3416 |
| TGCAGGACCAGAGAATTCGAATACAT AATAACCNNNACGTATGCCA | 2937 | TGCAGGACCAGAGAATTCGAATACAA GTATCGCNNNACGTATGCCA | 3177 | TGCAGGACCAGAGAATTCGAATACAG GACTTCANNNACGTATGCCA | 3417 |
| TGCAGGACCAGAGAATTCGAATACAA TTCTCATNNNACGTATGCCA | 2938 | TGCAGGACCAGAGAATTCGAATACAT CGAGATCNNNACGTATGCCA | 3178 | TGCAGGACCAGAGAATTCGAATACAG CCGCATGNNNACGTATGCCA | 3418 |
| TGCAGGACCAGAGAATTCGAATACAA CATCCCTNNNACGTATGCCA | 2939 | TGCAGGACCAGAGAATTCGAATACAC GGTAGTTNNNACGTATGCCA | 3179 | TGCAGGACCAGAGAATTCGAATACAT GGAGTAGNNNACGTATGCCA | 3419 |
| TGCAGGACCAGAGAATTCGAATACAT GAAAGTANNNACGTATGCCA | 2940 | TGCAGGACCAGAGAATTCGAATACAC CGTATCTNNNACGTATGCCA | 3180 | TGCAGGACCAGAGAATTCGAATACAC TGTTATTNNNACGTATGCCA | 3420 |
| TGCAGGACCAGAGAATTCGAATACAG ACATTATNNNACGTATGCCA | 2941 | TGCAGGACCAGAGAATTCGAATACAA ACGCACTNNNACGTATGCCA | 3181 | TGCAGGACCAGAGAATTCGAATACAA AGAGCACNNNACGTATGCCA | 3421 |
| TGCAGGACCAGAGAATTCGAATACAG GATACGANNNACGTATGCCA | 2942 | TGCAGGACCAGAGAATTCGAATACAC CGATTGANNNACGTATGCCA | 3182 | TGCAGGACCAGAGAATTCGAATACAC GTCGAATNNNACGTATGCCA | 3422 |
| TGCAGGACCAGAGAATTCGAATACAG TACATATNNNACGTATGCCA | 2943 | TGCAGGACCAGAGAATTCGAATACAG CTCTAAGNNNACGTATGCCA | 3183 | TGCAGGACCAGAGAATTCGAATACAC TCGTGAANNNACGTATGCCA | 3423 |
| TGCAGGACCAGAGAATTCGAATACAT CATAGCGNNNACGTATGCCA | 2944 | TGCAGGACCAGAGAATTCGAATACAG GTGAGTANNNACGTATGCCA | 3184 | TGCAGGACCAGAGAATTCGAATACAG ATGGCAANNNACGTATGCCA | 3424 |
| TGCAGGACCAGAGAATTCGAATACAC TTGAACGNNNACGTATGCCA | 2945 | TGCAGGACCAGAGAATTCGAATACAG CCTATGANNNACGTATGCCA | 3185 | TGCAGGACCAGAGAATTCGAATACAT AGGTGGANNNACGTATGCCA | 3425 |
| TGCAGGACCAGAGAATTCGAATACAC TTCCCANNNNACGTATGCCA | 2946 | TGCAGGACCAGAGAATTCGAATACAA CGGAGCGNNNACGTATGCCA | 3186 | TGCAGGACCAGAGAATTCGAATACAG ATGACTCNNNACGTATGCCA | 3426 |
| TGCAGGACCAGAGAATTCGAATACAA GAGCCCCNNNACGTATGCCA | 2947 | TGCAGGACCAGAGAATTCGAATACAC TGTGACANNNACGTATGCCA | 3187 | TGCAGGACCAGAGAATTCGAATACAG CTCTGTTNNNACGTATGCCA | 3427 |
| TGCAGGACCAGAGAATTCGAATACAA TAATCACNNNACGTATGCCA | 2948 | TGCAGGACCAGAGAATTCGAATACAC GTCCGTCNNNACGTATGCCA | 3188 | TGCAGGACCAGAGAATTCGAATACAA CGCAACTNNNACGTATGCCA | 3428 |
| TGCAGGACCAGAGAATTCGAATACAG ACGACAANNNCTAGCGTTAC | 2949 | TGCAGGACCAGAGAATTCGAATACAA TCGTGACNNNCTAGCGTTAC | 3189 | TGCAGGACCAGAGAATTCGAATACAC GAATGCTNNNCTAGCGTTAC | 3429 |
| TGCAGGACCAGAGAATTCGAATACAC GAATTATNNNCTAGCGTTAC | 2950 | TGCAGGACCAGAGAATTCGAATACAC CATGTCTNNNCTAGCGTTAC | 3190 | TGCAGGACCAGAGAATTCGAATACAA GCCAATCNNNCTAGCGTTAC | 3430 |
| TGCAGGACCAGAGAATTCGAATACAC GCGCTGANNNCTAGCGTTAC | 2951 | TGCAGGACCAGAGAATTCGAATACAC CTTTTGGNNNCTAGCGTTAC | 3191 | TGCAGGACCAGAGAATTCGAATACAG CAGTTTGNNNCTAGCGTTAC | 3431 |
| TGCAGGACCAGAGAATTCGAATACAT CAATTAGNNNCTAGCGTTAC | 2952 | TGCAGGACCAGAGAATTCGAATACAC GCGTCGANNNCTAGCGTTAC | 3192 | TGCAGGACCAGAGAATTCGAATACAC GCAATGTNNNCTAGCGTTAC | 3432 |
| TGCAGGACCAGAGAATTCGAATACAA TGAGCAGNNNCTAGCGTTAC | 2953 | TGCAGGACCAGAGAATTCGAATACAG CCCCCATNNNCTAGCGTTAC | 3193 | TGCAGGACCAGAGAATTCGAATACAT GCAGTGTNNNCTAGCGTTAC | 3433 |
| TGCAGGACCAGAGAATTCGAATACAT GACTTAANNNCTAGCGTTAC | 2954 | TGCAGGACCAGAGAATTCGAATACAG TCTTTCGNNNCTAGCGTTAC | 3194 | TGCAGGACCAGAGAATTCGAATACAA GTCCATGNNNCTAGCGTTAC | 3434 |

FIG. 16C

| Pool-13 | SEQ ID NO: | Pool-14 | SEQ ID NO: | Pool-15 | SEQ ID NO: |
|---|---|---|---|---|---|
| TGCAGGACCAGAGAATTCGAATACATGAGAATANNNCTAGCGTTAC | 2955 | TGCAGGACCAGAGAATTCGAATACAAPCCACGANNNCTAGCGTTAC | 3195 | TGCAGGACCAGAGAATTCGAATACACTATTCATNNNCTAGCGTTAC | 3435 |
| TGCAGGACCAGAGAATTCGAATACACTTTTTCTNNNCTAGCGTTAC | 2956 | TGCAGGACCAGAGAATTCGAATACATATGCATANNNCTAGCGTTAC | 3196 | TGCAGGACCAGAGAATTCGAATACAGTCGTTCTNNNCTAGCGTTAC | 3436 |
| TGCAGGACCAGAGAATTCGAATACAGTCGCAATNNNCTAGCGTTAC | 2957 | TGCAGGACCAGAGAATTCGAATACAGAGAAATTNNNCTAGCGTTAC | 3197 | TGCAGGACCAGAGAATTCGAATACACGTTGTAGNNNCTAGCGTTAC | 3437 |
| TGCAGGACCAGAGAATTCGAATACAATCCATCCNNNCTAGCGTTAC | 2958 | TGCAGGACCAGAGAATTCGAATACACCTCAATCNNNCTAGCGTTAC | 3198 | TGCAGGACCAGAGAATTCGAATACAGACAGCGGNNNCTAGCGTTAC | 3438 |
| TGCAGGACCAGAGAATTCGAATACAAGATATGANNNCTAGCGTTAC | 2959 | TGCAGGACCAGAGAATTCGAATACACAAAACAANNNCTAGCGTTAC | 3199 | TGCAGGACCAGAGAATTCGAATACATACACCCTNNNCTAGCGTTAC | 3439 |
| TGCAGGACCAGAGAATTCGAATACATAGCTACGNNNCTAGCGTTAC | 2960 | TGCAGGACCAGAGAATTCGAATACAGTGATGTCNNNCTAGCGTTAC | 3200 | TGCAGGACCAGAGAATTCGAATACACGTTAAGCNNNCTAGCGTTAC | 3440 |
| TGCAGGACCAGAGAATTCGAATACATTACAGGCNNNCTAGCGTTAC | 2961 | TGCAGGACCAGAGAATTCGAATACATGCCGTAANNNCTAGCGTTAC | 3201 | TGCAGGACCAGAGAATTCGAATACAATCGCCTTNNNCTAGCGTTAC | 3441 |
| TGCAGGACCAGAGAATTCGAATACATACTACACNNNCTAGCGTTAC | 2962 | TGCAGGACCAGAGAATTCGAATACAGGCTCTAGNNNCTAGCGTTAC | 3202 | TGCAGGACCAGAGAATTCGAATACAGCTATGCANNNCTAGCGTTAC | 3442 |
| TGCAGGACCAGAGAATTCGAATACAATTTTAGGNNNCTAGCGTTAC | 2963 | TGCAGGACCAGAGAATTCGAATACAGGCGTGCTNNNCTAGCGTTAC | 3203 | TGCAGGACCAGAGAATTCGAATACAACGCACGCNNNCTAGCGTTAC | 3443 |
| TGCAGGACCAGAGAATTCGAATACATTTTCAGTNNNCTAGCGTTAC | 2964 | TGCAGGACCAGAGAATTCGAATACAGACGTCATNNNCTAGCGTTAC | 3204 | TGCAGGACCAGAGAATTCGAATACACGTCACAANNNCTAGCGTTAC | 3444 |
| TGCAGGACCAGAGAATTCGAATACAGCAGAACANNNCTAGCGTTAC | 2965 | TGCAGGACCAGAGAATTCGAATACATGTATTAGNNNCTAGCGTTAC | 3205 | TGCAGGACCAGAGAATTCGAATACACGCGATCGNNNCTAGCGTTAC | 3445 |
| TGCAGGACCAGAGAATTCGAATACACGAGTAGANNNCTAGCGTTAC | 2966 | TGCAGGACCAGAGAATTCGAATACAATGATTACNNNCTAGCGTTAC | 3206 | TGCAGGACCAGAGAATTCGAATACAGTTAGACCNNNCTAGCGTTAC | 3446 |
| TGCAGGACCAGAGAATTCGAATACAGTCGGAGNNNCTAGCGTTAC | 2967 | TGCAGGACCAGAGAATTCGAATACAACTCCGAANNNCTAGCGTTAC | 3207 | TGCAGGACCAGAGAATTCGAATACATCGCGAGCNNNCTAGCGTTAC | 3447 |
| TGCAGGACCAGAGAATTCGAATACAATGTACTANNNCTAGCGTTAC | 2968 | TGCAGGACCAGAGAATTCGAATACATTCTTCCCNNNCTAGCGTTAC | 3208 | TGCAGGACCAGAGAATTCGAATACATGTAAACTNNNCTAGCGTTAC | 3448 |
| TGCAGGACCAGAGAATTCGAATACATACTCCGTNNNCTAGCGTTAC | 2969 | TGCAGGACCAGAGAATTCGAATACATCTCCTAGNNNCTAGCGTTAC | 3209 | TGCAGGACCAGAGAATTCGAATACATGCCATAGNNNCTAGCGTTAC | 3449 |
| TGCAGGACCAGAGAATTCGAATACACBCATTGNNNNCTAGCGTTAC | 2970 | TGCAGGACCAGAGAATTCGAATACAGACTTATANNNCTAGCGTTAC | 3210 | TGCAGGACCAGAGAATTCGAATACATAATTACGNNNCTAGCGTTAC | 3450 |
| TGCAGGACCAGAGAATTCGAATACATTAGCAATNNNCTAGCGTTAC | 2971 | TGCAGGACCAGAGAATTCGAATACACGAGTGAANNNCTAGCGTTAC | 3211 | TGCAGGACCAGAGAATTCGAATACACCCCGCCNNNNCTAGCGTTAC | 3451 |
| TGCAGGACCAGAGAATTCGAATACATCCAACGANNNCTAGCGTTAC | 2972 | TGCAGGACCAGAGAATTCGAATACATATAAATTNNNCTAGCGTTAC | 3212 | TGCAGGACCAGAGAATTCGAATACACAATATCANNNCTAGCGTTAC | 3452 |
| TGCAGGACCAGAGAATTCGAATACATTGATCCCNNNCTAGCGTTAC | 2973 | TGCAGGACCAGAGAATTCGAATACAGCCGTGAGNNNCTAGCGTTAC | 3213 | TGCAGGACCAGAGAATTCGAATACAATTAAGGANNNCTAGCGTTAC | 3453 |
| TGCAGGACCAGAGAATTCGAATACATATTAATANNNCTAGCGTTAC | 2974 | TGCAGGACCAGAGAATTCGAATACAAGTCCCTTNNNCTAGCGTTAC | 3214 | TGCAGGACCAGAGAATTCGAATACAATATACACNNNCTAGCGTTAC | 3454 |
| TGCAGGACCAGAGAATTCGAATACATAAGTTTGNNNCTAGCGTTAC | 2975 | TGCAGGACCAGAGAATTCGAATACAAGACTTANNNNCTAGCGTTAC | 3215 | TGCAGGACCAGAGAATTCGAATACATATTGACANNNCTAGCGTTAC | 3455 |
| TGCAGGACCAGAGAATTCGAATACAGGCCGCGCNNNCTAGCGTTAC | 2976 | TGCAGGACCAGAGAATTCGAATACATGGCACTANNNCTAGCGTTAC | 3216 | TGCAGGACCAGAGAATTCGAATACAACGAAAATNNNCTAGCGTTAC | 3456 |
| TGCAGGACCAGAGAATTCGAATACATCACACGANNNCTAGCGTTAC | 2977 | TGCAGGACCAGAGAATTCGAATACAATTCCTATNNNCTAGCGTTAC | 3217 | TGCAGGACCAGAGAATTCGAATACAGTAGGACANNNCTAGCGTTAC | 3457 |
| TGCAGGACCAGAGAATTCGAATACAGAGTCGTTNNNCTAGCGTTAC | 2978 | TGCAGGACCAGAGAATTCGAATACATGATATANNNNCTAGCGTTAC | 3218 | TGCAGGACCAGAGAATTCGAATACACCCCAGTNNNNCTAGCGTTAC | 3458 |
| TGCAGGACCAGAGAATTCGAATACAAGAGCCTTNNNCTAGCGTTAC | 2979 | TGCAGGACCAGAGAATTCGAATACACAAGCACTNNNCTAGCGTTAC | 3219 | TGCAGGACCAGAGAATTCGAATACACCTACGTTNNNCTAGCGTTAC | 3459 |
| TGCAGGACCAGAGAATTCGAATACACCTTGCTANNNCTAGCGTTAC | 2980 | TGCAGGACCAGAGAATTCGAATACAGCGCATGCNNNCTAGCGTTAC | 3220 | TGCAGGACCAGAGAATTCGAATACATGGTGAGANNNCTAGCGTTAC | 3460 |
| TGCAGGACCAGAGAATTCGAATACAATCATAGTNNNCTAGCGTTAC | 2981 | TGCAGGACCAGAGAATTCGAATACATCCTCAATNNNCTAGCGTTAC | 3221 | TGCAGGACCAGAGAATTCGAATACATTAGCACANNNCTAGCGTTAC | 3461 |
| TGCAGGACCAGAGAATTCGAATACATAGCAATNNNNCTAGCGTTAC | 2982 | TGCAGGACCAGAGAATTCGAATACATCGCACCNNNNCTAGCGTTAC | 3222 | TGCAGGACCAGAGAATTCGAATACATCATGTAANNNCTAGCGTTAC | 3462 |
| TGCAGGACCAGAGAATTCGAATACACAATTGTANNNCTAGCGTTAC | 2983 | TGCAGGACCAGAGAATTCGAATACATGACGGACNNNCTAGCGTTAC | 3223 | TGCAGGACCAGAGAATTCGAATACAGGACGAATNNNCTAGCGTTAC | 3463 |
| TGCAGGACCAGAGAATTCGAATACATTCGGCAANNNCTAGCGTTAC | 2984 | TGCAGGACCAGAGAATTCGAATACACGAACAGANNNCTAGCGTTAC | 3224 | TGCAGGACCAGAGAATTCGAATACAGGATGGCGNNNCTAGCGTTAC | 3464 |
| TGCAGGACCAGAGAATTCGAATACACCTAGTCTNNNCTAGCGTTAC | 2985 | TGCAGGACCAGAGAATTCGAATACATATCTCGCNNNCTAGCGTTAC | 3225 | TGCAGGACCAGAGAATTCGAATACATCCCAGTTNNNCTAGCGTTAC | 3465 |
| TGCAGGACCAGAGAATTCGAATACACTAGGCTANNNCTAGCGTTAC | 2986 | TGCAGGACCAGAGAATTCGAATACATGCATCAGNNNCTAGCGTTAC | 3226 | TGCAGGACCAGAGAATTCGAATACACGAGACAANNNCTAGCGTTAC | 3466 |
| TGCAGGACCAGAGAATTCGAATACAAATCAATCNNNCTAGCGTTAC | 2987 | TGCAGGACCAGAGAATTCGAATACACCTAAAGCNNNCTAGCGTTAC | 3227 | TGCAGGACCAGAGAATTCGAATACACAATACCGNNNCTAGCGTTAC | 3467 |

FIG. 16D

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAGCCCTCGTNNNCTAGCGTTAC | 2988 | TGCAGGACCAGAGAATTCGAATACATTTGACAANNNCTAGCGTTAC | 3228 | TGCAGGACCAGAGAATTCGAATACATTTATGTCNNNCTAGCGTTAC | 3468 |
| TGCAGGACCAGAGAATTCGAATACAAGGTTGAGNNNCTAGCGTTAC | 2989 | TGCAGGACCAGAGAATTCGAATACACCCGCCATNNNCTAGCGTTAC | 3229 | TGCAGGACCAGAGAATTCGAATACATGGTAACCNNNCTAGCGTTAC | 3469 |
| TGCAGGACCAGAGAATTCGAATACACAGCCAGCNNNCTAGCGTTAC | 2990 | TGCAGGACCAGAGAATTCGAATACATTGCATAANNNCTAGCGTTAC | 3230 | TGCAGGACCAGAGAATTCGAATACAAGCCCATANNNCTAGCGTTAC | 3470 |
| TGCAGGACCAGAGAATTCGAATACAACTAATGTNNNCTAGCGTTAC | 2991 | TGCAGGACCAGAGAATTCGAATACAACAGAGCANNNCTAGCGTTAC | 3231 | TGCAGGACCAGAGAATTCGAATACAATCCTCCANNNCTAGCGTTAC | 3471 |
| TGCAGGACCAGAGAATTCGAATACAGGTAAGACNNNCTAGCGTTAC | 2992 | TGCAGGACCAGAGAATTCGAATACAGGTACGTTNNNCTAGCGTTAC | 3232 | TGCAGGACCAGAGAATTCGAATACATTTTTGACNNNCTAGCGTTAC | 3472 |
| TGCAGGACCAGAGAATTCGAATACACTCGCGAGNNNCTAGCGTTAC | 2993 | TGCAGGACCAGAGAATTCGAATACAATGCACTNNNCTAGCGTTAC | 3233 | TGCAGGACCAGAGAATTCGAATACAATAGCCTGNNNCTAGCGTTAC | 3473 |
| TGCAGGACCAGAGAATTCGAATACACTGCCGCTNNNCTAGCGTTAC | 2994 | TGCAGGACCAGAGAATTCGAATACAATCTAAACNNNCTAGCGTTAC | 3234 | TGCAGGACCAGAGAATTCGAATACAGGAGTCTNNNCTAGCGTTAC | 3474 |
| TGCAGGACCAGAGAATTCGAATACAACTGCGGCNNNCTAGCGTTAC | 2995 | TGCAGGACCAGAGAATTCGAATACAACGAGAACNNNCTAGCGTTAC | 3235 | TGCAGGACCAGAGAATTCGAATACAACCCCACCNNNCTAGCGTTAC | 3475 |
| TGCAGGACCAGAGAATTCGAATACACCTCTACANNNCTAGCGTTAC | 2996 | TGCAGGACCAGAGAATTCGAATACACCGCAAGCNNNCTAGCGTTAC | 3236 | TGCAGGACCAGAGAATTCGAATACACGCGGCATNNNCTAGCGTTAC | 3476 |
| TGCAGGACCAGAGAATTCGAATACATGGCCACGNNNCTAGCGTTAC | 2997 | TGCAGGACCAGAGAATTCGAATACAACGACAAGNNNCTAGCGTTAC | 3237 | TGCAGGACCAGAGAATTCGAATACATCCAGACANNNCTAGCGTTAC | 3477 |
| TGCAGGACCAGAGAATTCGAATACAACGCAATCNNNCTAGCGTTAC | 2998 | TGCAGGACCAGAGAATTCGAATACACGCCGATGNNNCTAGCGTTAC | 3238 | TGCAGGACCAGAGAATTCGAATACAAAATGCAANNNCTAGCGTTAC | 3478 |
| TGCAGGACCAGAGAATTCGAATACAGGTTTGCANNNCTAGCGTTAC | 2999 | TGCAGGACCAGAGAATTCGAATACAAATCGACGNNNCTAGCGTTAC | 3239 | TGCAGGACCAGAGAATTCGAATACAAATTCGCGNNNCTAGCGTTAC | 3479 |
| TGCAGGACCAGAGAATTCGAATACAGGTTAGGANNNCTAGCGTTAC | 3000 | TGCAGGACCAGAGAATTCGAATACAATTAATGCNNNCTAGCGTTAC | 3240 | TGCAGGACCAGAGAATTCGAATACAGTGTCCTTNNNCTAGCGTTAC | 3480 |
| TGCAGGACCAGAGAATTCGAATACATCCTCGGCNNNCTAGCGTTAC | 3001 | TGCAGGACCAGAGAATTCGAATACAGCGCTTCNNNCTAGCGTTAC | 3241 | TGCAGGACCAGAGAATTCGAATACACATGTAATNNNCTAGCGTTAC | 3481 |
| TGCAGGACCAGAGAATTCGAATACAAACACGGNNNCTAGCGTTAC | 3002 | TGCAGGACCAGAGAATTCGAATACATACAATTGNNNCTAGCGTTAC | 3242 | TGCAGGACCAGAGAATTCGAATACAACGCATACNNNCTAGCGTTAC | 3482 |
| TGCAGGACCAGAGAATTCGAATACAGAAAATCANNNCTAGCGTTAC | 3003 | TGCAGGACCAGAGAATTCGAATACAGTGGAACANNNCTAGCGTTAC | 3243 | TGCAGGACCAGAGAATTCGAATACAAGCCCCCNNNCTAGCGTTAC | 3483 |
| TGCAGGACCAGAGAATTCGAATACACGTATCTCNNNCTAGCGTTAC | 3004 | TGCAGGACCAGAGAATTCGAATACACTCTGTGTNNNCTAGCGTTAC | 3244 | TGCAGGACCAGAGAATTCGAATACACTCCCCAGNNNCTAGCGTTAC | 3484 |
| TGCAGGACCAGAGAATTCGAATACACGGCCACANNNCTAGCGTTAC | 3005 | TGCAGGACCAGAGAATTCGAATACATGCAGTACNNNCTAGCGTTAC | 3245 | TGCAGGACCAGAGAATTCGAATACATCTACTTANNNCTAGCGTTAC | 3485 |
| TGCAGGACCAGAGAATTCGAATACATCATTCATNNNCTAGCGTTAC | 3006 | TGCAGGACCAGAGAATTCGAATACAGACAACTCNNNCTAGCGTTAC | 3246 | TGCAGGACCAGAGAATTCGAATACATACCGGTANNNCTAGCGTTAC | 3486 |
| TGCAGGACCAGAGAATTCGAATACAATAGATGANNNCTAGCGTTAC | 3007 | TGCAGGACCAGAGAATTCGAATACACGAGAGGCNNNCTAGCGTTAC | 3247 | TGCAGGACCAGAGAATTCGAATACAAACCTATANNNCTAGCGTTAC | 3487 |
| TGCAGGACCAGAGAATTCGAATACAGCACTGCGNNNCTAGCGTTAC | 3008 | TGCAGGACCAGAGAATTCGAATACACTAAATGTNNNCTAGCGTTAC | 3248 | TGCAGGACCAGAGAATTCGAATACAGCGACTGCNNNCTAGCGTTAC | 3488 |
| TGCAGGACCAGAGAATTCGAATACACCTCCCTANNNGATCGACATG | 3009 | TGCAGGACCAGAGAATTCGAATACAGGCTCACGNNNGATCGACATG | 3249 | TGCAGGACCAGAGAATTCGAATACACGAGTCTANNNGATCGACATG | 3489 |
| TGCAGGACCAGAGAATTCGAATACAACAAAACANNNGATCGACATG | 3010 | TGCAGGACCAGAGAATTCGAATACAACGTTTCCNNNGATCGACATG | 3250 | TGCAGGACCAGAGAATTCGAATACATATGAAAGNNNGATCGACATG | 3490 |
| TGCAGGACCAGAGAATTCGAATACATATGTACANNNGATCGACATG | 3011 | TGCAGGACCAGAGAATTCGAATACATGCCAGTANNNGATCGACATG | 3251 | TGCAGGACCAGAGAATTCGAATACAACTGGCCGNNNGATCGACATG | 3491 |
| TGCAGGACCAGAGAATTCGAATACATCGGTCTTNNNGATCGACATG | 3012 | TGCAGGACCAGAGAATTCGAATACAGTAAGTGGNNNGATCGACATG | 3252 | TGCAGGACCAGAGAATTCGAATACACAACCATGNNNGATCGACATG | 3492 |
| TGCAGGACCAGAGAATTCGAATACATCCATATTNNNGATCGACATG | 3013 | TGCAGGACCAGAGAATTCGAATACACACCTACTNNNGATCGACATG | 3253 | TGCAGGACCAGAGAATTCGAATACAAAGGTAGCNNNGATCGACATG | 3493 |
| TGCAGGACCAGAGAATTCGAATACAATGACTCGNNNGATCGACATG | 3014 | TGCAGGACCAGAGAATTCGAATACAGATTTGATNNNGATCGACATG | 3254 | TGCAGGACCAGAGAATTCGAATACATTCTCAGCNNNGATCGACATG | 3494 |
| TGCAGGACCAGAGAATTCGAATACATAATCTCTNNNGATCGACATG | 3015 | TGCAGGACCAGAGAATTCGAATACAACTACATNNNGATCGACATG | 3255 | TGCAGGACCAGAGAATTCGAATACATTCAGGTGNNNGATCGACATG | 3495 |
| TGCAGGACCAGAGAATTCGAATACAGAATACTTNNNGATCGACATG | 3016 | TGCAGGACCAGAGAATTCGAATACAGCCTTGAANNNGATCGACATG | 3256 | TGCAGGACCAGAGAATTCGAATACACCAATCCTNNNGATCGACATG | 3496 |
| TGCAGGACCAGAGAATTCGAATACACCACTAGANNNGATCGACATG | 3017 | TGCAGGACCAGAGAATTCGAATACATAATATTANNNGATCGACATG | 3257 | TGCAGGACCAGAGAATTCGAATACAGACAGTTCNNNGATCGACATG | 3497 |
| TGCAGGACCAGAGAATTCGAATACATTTGGACCNNNGATCGACATG | 3018 | TGCAGGACCAGAGAATTCGAATACAGGTTTAATNNNGATCGACATG | 3258 | TGCAGGACCAGAGAATTCGAATACAATCTTTACNNNGATCGACATG | 3498 |
| TGCAGGACCAGAGAATTCGAATACAGAAGTCCTNNNGATCGACATG | 3019 | TGCAGGACCAGAGAATTCGAATACACCCACCGTNNNGATCGACATG | 3259 | TGCAGGACCAGAGAATTCGAATACAGCAATATTNNNGATCGACATG | 3499 |
| TGCAGGACCAGAGAATTCGAATACACCTATGCTNNNGATCGACATG | 3020 | TGCAGGACCAGAGAATTCGAATACACTACTTCGNNNGATCGACATG | 3260 | TGCAGGACCAGAGAATTCGAATACAGTCTCCATNNNGATCGACATG | 3500 |

FIG. 16E

| Pool-13 | SEQ ID NO: | Pool-14 | SEQ ID NO: | Pool-15 | SEQ ID NO: |
|---|---|---|---|---|---|
| TGCAGGACCAGAGAATTCGAATACATCGATGTGNNNGATCGACATG | 3021 | TGCAGGACCAGAGAATTCGAATACAATGCGTCANNNGATCGACATG | 3261 | TGCAGGACCAGAGAATTCGAATACACAACAATTNNNGATCGACATG | 3501 |
| TGCAGGACCAGAGAATTCGAATACATGTACACGNNNGATCGACATG | 3022 | TGCAGGACCAGAGAATTCGAATACAAACATGTTNNNGATCGACATG | 3262 | TGCAGGACCAGAGAATTCGAATACATCGTAGACNNNGATCGACATG | 3502 |
| TGCAGGACCAGAGAATTCGAATACATCTTTAGTNNNGATCGACATG | 3023 | TGCAGGACCAGAGAATTCGAATACACCTGTTTGNNNGATCGACATG | 3263 | TGCAGGACCAGAGAATTCGAATACAGTAGATAANNNGATCGACATG | 3503 |
| TGCAGGACCAGAGAATTCGAATACACGTAGGCCNNNGATCGACATG | 3024 | TGCAGGACCAGAGAATTCGAATACAAACAAGCTNNNGATCGACATG | 3264 | TGCAGGACCAGAGAATTCGAATACAACATATACNNNGATCGACATG | 3504 |
| TGCAGGACCAGAGAATTCGAATACAACCTTTATNNNGATCGACATG | 3025 | TGCAGGACCAGAGAATTCGAATACAGATAAGATNNNGATCGACATG | 3265 | TGCAGGACCAGAGAATTCGAATACACACGACGCNNNGATCGACATG | 3505 |
| TGCAGGACCAGAGAATTCGAATACACGTCTATCNNNGATCGACATG | 3026 | TGCAGGACCAGAGAATTCGAATACACGACCTCANNNGATCGACATG | 3266 | TGCAGGACCAGAGAATTCGAATACACACAAAAANNNGATCGACATG | 3506 |
| TGCAGGACCAGAGAATTCGAATACAGTAGAAATNNNGATCGACATG | 3027 | TGCAGGACCAGAGAATTCGAATACACTCCAAGANNNGATCGACATG | 3267 | TGCAGGACCAGAGAATTCGAATACACGTACCGGNNNGATCGACATG | 3507 |
| TGCAGGACCAGAGAATTCGAATACACGTACCAANNNGATCGACATG | 3028 | TGCAGGACCAGAGAATTCGAATACAGGTATTCGNNNGATCGACATG | 3268 | TGCAGGACCAGAGAATTCGAATACACCACAATGNNNGATCGACATG | 3508 |
| TGCAGGACCAGAGAATTCGAATACACACCACCCNNNGATCGACATG | 3029 | TGCAGGACCAGAGAATTCGAATACAACTCGGATNNNGATCGACATG | 3269 | TGCAGGACCAGAGAATTCGAATACACGCTCTGCNNNGATCGACATG | 3509 |
| TGCAGGACCAGAGAATTCGAATACATGCGGCGTNNNGATCGACATG | 3030 | TGCAGGACCAGAGAATTCGAATACATATATGGANNNGATCGACATG | 3270 | TGCAGGACCAGAGAATTCGAATACAGTCAAGCTNNNGATCGACATG | 3510 |
| TGCAGGACCAGAGAATTCGAATACAGCCCCCCGNNNGATCGACATG | 3031 | TGCAGGACCAGAGAATTCGAATACAATCCACTCNNNGATCGACATG | 3271 | TGCAGGACCAGAGAATTCGAATACAACTCTTCGNNNGATCGACATG | 3511 |
| TGCAGGACCAGAGAATTCGAATACATAGTAAGANNNGATCGACATG | 3032 | TGCAGGACCAGAGAATTCGAATACAGAACTGGANNNGATCGACATG | 3272 | TGCAGGACCAGAGAATTCGAATACAAACACGANNNGATCGACATG | 3512 |
| TGCAGGACCAGAGAATTCGAATACATCTGAATANNNGATCGACATG | 3033 | TGCAGGACCAGAGAATTCGAATACAGATCAGAGNNNGATCGACATG | 3273 | TGCAGGACCAGAGAATTCGAATACAACCGCGCANNNGATCGACATG | 3513 |
| TGCAGGACCAGAGAATTCGAATACACTAATACANNNGATCGACATG | 3034 | TGCAGGACCAGAGAATTCGAATACATTGAACTANNNGATCGACATG | 3274 | TGCAGGACCAGAGAATTCGAATACACACCTTGTNNNGATCGACATG | 3514 |
| TGCAGGACCAGAGAATTCGAATACAATGTCACGNNNGATCGACATG | 3035 | TGCAGGACCAGAGAATTCGAATACAGCCAGCANNNGATCGACATG | 3275 | TGCAGGACCAGAGAATTCGAATACATTATGCGGNNNGATCGACATG | 3515 |
| TGCAGGACCAGAGAATTCGAATACAAACAGAATNNNGATCGACATG | 3036 | TGCAGGACCAGAGAATTCGAATACATTTACTGTNNNGATCGACATG | 3276 | TGCAGGACCAGAGAATTCGAATACAGACTCTTCNNNGATCGACATG | 3516 |
| TGCAGGACCAGAGAATTCGAATACAGCCCAGGTNNNGATCGACATG | 3037 | TGCAGGACCAGAGAATTCGAATACATGTCAGGTNNNGATCGACATG | 3277 | TGCAGGACCAGAGAATTCGAATACAGAGTCTTGNNNGATCGACATG | 3517 |
| TGCAGGACCAGAGAATTCGAATACAGCTCATGANNNGATCGACATG | 3038 | TGCAGGACCAGAGAATTCGAATACACAGCGTTANNNGATCGACATG | 3278 | TGCAGGACCAGAGAATTCGAATACATAGAATCTNNNGATCGACATG | 3518 |
| TGCAGGACCAGAGAATTCGAATACACCCGTCGANNNGATCGACATG | 3039 | TGCAGGACCAGAGAATTCGAATACATGTGATCGNNNGATCGACATG | 3279 | TGCAGGACCAGAGAATTCGAATACACGACCAGCNNNGATCGACATG | 3519 |
| TGCAGGACCAGAGAATTCGAATACACAATTCCNNNGATCGACATG | 3040 | TGCAGGACCAGAGAATTCGAATACAGCTCGTAANNNGATCGACATG | 3280 | TGCAGGACCAGAGAATTCGAATACATGGATTCGNNNGATCGACATG | 3520 |
| TGCAGGACCAGAGAATTCGAATACACCAGGCCANNNGATCGACATG | 3041 | TGCAGGACCAGAGAATTCGAATACAATTCTACTNNNGATCGACATG | 3281 | TGCAGGACCAGAGAATTCGAATACACGACTAGTNNNGATCGACATG | 3521 |
| TGCAGGACCAGAGAATTCGAATACACCTGCGGANNNGATCGACATG | 3042 | TGCAGGACCAGAGAATTCGAATACAGATCAGTCNNNGATCGACATG | 3282 | TGCAGGACCAGAGAATTCGAATACACCCAAAACNNNGATCGACATG | 3522 |
| TGCAGGACCAGAGAATTCGAATACAGCTAAAGGNNNGATCGACATG | 3043 | TGCAGGACCAGAGAATTCGAATACAGGATTATTNNNGATCGACATG | 3283 | TGCAGGACCAGAGAATTCGAATACATGACCCCCNNNGATCGACATG | 3523 |
| TGCAGGACCAGAGAATTCGAATACATTTAAGGTNNNGATCGACATG | 3044 | TGCAGGACCAGAGAATTCGAATACACCATTCGTNNNGATCGACATG | 3284 | TGCAGGACCAGAGAATTCGAATACAGCATTAGCNNNGATCGACATG | 3524 |
| TGCAGGACCAGAGAATTCGAATACAAACGTAANNNGATCGACATG | 3045 | TGCAGGACCAGAGAATTCGAATACAGTACATGCNNNGATCGACATG | 3285 | TGCAGGACCAGAGAATTCGAATACAGCCAGATTNNNGATCGACATG | 3525 |
| TGCAGGACCAGAGAATTCGAATACAAATTTGGTNNNGATCGACATG | 3046 | TGCAGGACCAGAGAATTCGAATACACGTCCAGNNNGATCGACATG | 3286 | TGCAGGACCAGAGAATTCGAATACAACAACTATNNNGATCGACATG | 3526 |
| TGCAGGACCAGAGAATTCGAATACAACGTTAGCNNNGATCGACATG | 3047 | TGCAGGACCAGAGAATTCGAATACATATTTGTCNNNGATCGACATG | 3287 | TGCAGGACCAGAGAATTCGAATACAGTAGGTCNNNGATCGACATG | 3527 |
| TGCAGGACCAGAGAATTCGAATACAAGTTTTGNNNGATCGACATG | 3048 | TGCAGGACCAGAGAATTCGAATACAACAGTCCANNNGATCGACATG | 3288 | TGCAGGACCAGAGAATTCGAATACAAATAAGGTNNNGATCGACATG | 3528 |
| TGCAGGACCAGAGAATTCGAATACAAGCGTTCANNNGATCGACATG | 3049 | TGCAGGACCAGAGAATTCGAATACAGCGATTGTNNNGATCGACATG | 3289 | TGCAGGACCAGAGAATTCGAATACAAAGAGAAANNNGATCGACATG | 3529 |
| TGCAGGACCAGAGAATTCGAATACAGGACTTGTNNNGATCGACATG | 3050 | TGCAGGACCAGAGAATTCGAATACACCTGGAATNNNGATCGACATG | 3290 | TGCAGGACCAGAGAATTCGAATACATTTTGTGTNNNGATCGACATG | 3530 |
| TGCAGGACCAGAGAATTCGAATACACGTCAGATNNNGATCGACATG | 3051 | TGCAGGACCAGAGAATTCGAATACAAGGAGCAANNNGATCGACATG | 3291 | TGCAGGACCAGAGAATTCGAATACAAGGCGTTTNNNGATCGACATG | 3531 |
| TGCAGGACCAGAGAATTCGAATACACCAGAAGANNNGATCGACATG | 3052 | TGCAGGACCAGAGAATTCGAATACAACACCAACNNNGATCGACATG | 3292 | TGCAGGACCAGAGAATTCGAATACAAAAAGCTANNNGATCGACATG | 3532 |
| TGCAGGACCAGAGAATTCGAATACAGCGATCTANNNGATCGACATG | 3053 | TGCAGGACCAGAGAATTCGAATACATTTAGTCTNNNGATCGACATG | 3293 | TGCAGGACCAGAGAATTCGAATACAACCGGATTNNNGATCGACATG | 3533 |

FIG. 16F

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAATCACCGANNNGATCGACATG | 3054 | TGCAGGACCAGAGAATTCGAATACATGTAGCTGNNNGATCGACATG | 3294 | TGCAGGACCAGAGAATTCGAATACACTCAAATANNNGATCGACATG | 3534 |
| TGCAGGACCAGAGAATTCGAATACAACACTAATNNNGATCGACATG | 3055 | TGCAGGACCAGAGAATTCGAATACAGGCTTACANNNGATCGACATG | 3295 | TGCAGGACCAGAGAATTCGAATACACGAGAACANNNGATCGACATG | 3535 |
| TGCAGGACCAGAGAATTCGAATACAATATGAAGNNNGATCGACATG | 3056 | TGCAGGACCAGAGAATTCGAATACAGGACCAGCNNNGATCGACATG | 3296 | TGCAGGACCAGAGAATTCGAATACACCCAGGACNNNGATCGACATG | 3536 |
| TGCAGGACCAGAGAATTCGAATACAAGTAAGCGNNNGATCGACATG | 3057 | TGCAGGACCAGAGAATTCGAATACACCCAAAAGNNNGATCGACATG | 3297 | TGCAGGACCAGAGAATTCGAATACACCAGCTCCNNNGATCGACATG | 3537 |
| TGCAGGACCAGAGAATTCGAATACAGACGCTATNNNGATCGACATG | 3058 | TGCAGGACCAGAGAATTCGAATACACGAGGTANNNGATCGACATG | 3298 | TGCAGGACCAGAGAATTCGAATACATATACATGNNNGATCGACATG | 3538 |
| TGCAGGACCAGAGAATTCGAATACATGACATCGNNNGATCGACATG | 3059 | TGCAGGACCAGAGAATTCGAATACACAGTCATGNNNGATCGACATG | 3299 | TGCAGGACCAGAGAATTCGAATACATATAGTTGNNNGATCGACATG | 3539 |
| TGCAGGACCAGAGAATTCGAATACAGCAGAAACNNNGATCGACATG | 3060 | TGCAGGACCAGAGAATTCGAATACATGACCACANNNGATCGACATG | 3300 | TGCAGGACCAGAGAATTCGAATACACATAGTTANNNGATCGACATG | 3540 |
| TGCAGGACCAGAGAATTCGAATACATTTTGCANNNGATCGACATG | 3061 | TGCAGGACCAGAGAATTCGAATACATGAACACANNNGATCGACATG | 3301 | TGCAGGACCAGAGAATTCGAATACATTCATTACNNNGATCGACATG | 3541 |
| TGCAGGACCAGAGAATTCGAATACACTACCCGCNNNGATCGACATG | 3062 | TGCAGGACCAGAGAATTCGAATACATAGTAATCNNNGATCGACATG | 3302 | TGCAGGACCAGAGAATTCGAATACATGCTACCTNNNGATCGACATG | 3542 |
| TGCAGGACCAGAGAATTCGAATACAATAATGCTNNNGATCGACATG | 3063 | TGCAGGACCAGAGAATTCGAATACACCGACGGTNNNGATCGACATG | 3303 | TGCAGGACCAGAGAATTCGAATACAGTAGCTTGNNNGATCGACATG | 3543 |
| TGCAGGACCAGAGAATTCGAATACAAAGCAGTGNNNGATCGACATG | 3064 | TGCAGGACCAGAGAATTCGAATACATTGCCTTGNNNGATCGACATG | 3304 | TGCAGGACCAGAGAATTCGAATACACCGGATANNNGATCGACATG | 3544 |
| TGCAGGACCAGAGAATTCGAATACAACACGTCANNNGATCGACATG | 3065 | TGCAGGACCAGAGAATTCGAATACAGAGCGCANNNGATCGACATG | 3305 | TGCAGGACCAGAGAATTCGAATACACAGCCGCANNNGATCGACATG | 3545 |
| TGCAGGACCAGAGAATTCGAATACAGTAATACTNNNGATCGACATG | 3066 | TGCAGGACCAGAGAATTCGAATACAGGCCTGCANNNGATCGACATG | 3306 | TGCAGGACCAGAGAATTCGAATACAGATCCTCTNNNGATCGACATG | 3546 |
| TGCAGGACCAGAGAATTCGAATACAAACAAACANNNGATCGACATG | 3067 | TGCAGGACCAGAGAATTCGAATACATCCGTCAAGNNNGATCGACATG | 3307 | TGCAGGACCAGAGAATTCGAATACAAGTACCCANNNGATCGACATG | 3547 |
| TGCAGGACCAGAGAATTCGAATACATACATGGCNNNGATCGACATG | 3068 | TGCAGGACCAGAGAATTCGAATACAGGACGGCANNNGATCGACATG | 3308 | TGCAGGACCAGAGAATTCGAATACAACGGAGTANNNGATCGACATG | 3548 |
| TGCAGGACCAGAGAATTCGAATACACGTGTCAANNNTGCATCAGGT | 3069 | TGCAGGACCAGAGAATTCGAATACAGCATGCCGNNNTGCATCAGGT | 3309 | TGCAGGACCAGAGAATTCGAATACAGTAAAAGTNNNTGCATCAGGT | 3549 |
| TGCAGGACCAGAGAATTCGAATACACTTTAACTNNNTGCATCAGGT | 3070 | TGCAGGACCAGAGAATTCGAATACACGTCTAAGNNNTGCATCAGGT | 3310 | TGCAGGACCAGAGAATTCGAATACATAGGTGTCNNNTGCATCAGGT | 3550 |
| TGCAGGACCAGAGAATTCGAATACAGTAAGGTGNNNTGCATCAGGT | 3071 | TGCAGGACCAGAGAATTCGAATACAGCGTGATTNNNTGCATCAGGT | 3311 | TGCAGGACCAGAGAATTCGAATACATAGACCGTNNNTGCATCAGGT | 3551 |
| TGCAGGACCAGAGAATTCGAATACAGAATAGCGNNNTGCATCAGGT | 3072 | TGCAGGACCAGAGAATTCGAATACATTAGTCCCNNNTGCATCAGGT | 3312 | TGCAGGACCAGAGAATTCGAATACAGCTCGTTTNNNTGCATCAGGT | 3552 |
| TGCAGGACCAGAGAATTCGAATACATAATTAATNNNTGCATCAGGT | 3073 | TGCAGGACCAGAGAATTCGAATACATGGCATTGNNNTGCATCAGGT | 3313 | TGCAGGACCAGAGAATTCGAATACAAAATCTGNNNTGCATCAGGT | 3553 |
| TGCAGGACCAGAGAATTCGAATACACTCTTGTGNNNTGCATCAGGT | 3074 | TGCAGGACCAGAGAATTCGAATACAGACCGTGGNNNTGCATCAGGT | 3314 | TGCAGGACCAGAGAATTCGAATACAGACCAACTNNNTGCATCAGGT | 3554 |
| TGCAGGACCAGAGAATTCGAATACATGCGCGTGNNNTGCATCAGGT | 3075 | TGCAGGACCAGAGAATTCGAATACAGCGCTTTTNNNTGCATCAGGT | 3315 | TGCAGGACCAGAGAATTCGAATACATCACCTACNNNTGCATCAGGT | 3555 |
| TGCAGGACCAGAGAATTCGAATACAGACGAAACNNNTGCATCAGGT | 3076 | TGCAGGACCAGAGAATTCGAATACACGTGGACCNNNTGCATCAGGT | 3316 | TGCAGGACCAGAGAATTCGAATACAGTTAATTGNNNTGCATCAGGT | 3556 |
| TGCAGGACCAGAGAATTCGAATACACGTTTAGGNNNTGCATCAGGT | 3077 | TGCAGGACCAGAGAATTCGAATACAATGTCTTTNNNTGCATCAGGT | 3317 | TGCAGGACCAGAGAATTCGAATACAGCAATTATNNNTGCATCAGGT | 3557 |
| TGCAGGACCAGAGAATTCGAATACAGTAGCCTANNNTGCATCAGGT | 3078 | TGCAGGACCAGAGAATTCGAATACATGAAAGCGNNNTGCATCAGGT | 3318 | TGCAGGACCAGAGAATTCGAATACAAACGAGACNNNTGCATCAGGT | 3558 |
| TGCAGGACCAGAGAATTCGAATACAATTCCCTGNNNTGCATCAGGT | 3079 | TGCAGGACCAGAGAATTCGAATACACCGTGCGANNNTGCATCAGGT | 3319 | TGCAGGACCAGAGAATTCGAATACAATCGGCATNNNTGCATCAGGT | 3559 |
| TGCAGGACCAGAGAATTCGAATACAACGAAATNNNTGCATCAGGT | 3080 | TGCAGGACCAGAGAATTCGAATACATACAACATNNNTGCATCAGGT | 3320 | TGCAGGACCAGAGAATTCGAATACACACACGGNNNTGCATCAGGT | 3560 |
| TGCAGGACCAGAGAATTCGAATACAACCCCCCNNNTGCATCAGGT | 3081 | TGCAGGACCAGAGAATTCGAATACAATTACTCTNNNTGCATCAGGT | 3321 | TGCAGGACCAGAGAATTCGAATACAGCCAGGANNNTGCATCAGGT | 3561 |
| TGCAGGACCAGAGAATTCGAATACATATGATANNNTGCATCAGGT | 3082 | TGCAGGACCAGAGAATTCGAATACAATTCCCTANNNTGCATCAGGT | 3322 | TGCAGGACCAGAGAATTCGAATACAGAGGAGTTNNNTGCATCAGGT | 3562 |
| TGCAGGACCAGAGAATTCGAATACATACATGATNNNTGCATCAGGT | 3083 | TGCAGGACCAGAGAATTCGAATACACACACGGCNNNTGCATCAGGT | 3323 | TGCAGGACCAGAGAATTCGAATACACCACCGCTNNNTGCATCAGGT | 3563 |
| TGCAGGACCAGAGAATTCGAATACATGTACATANNNTGCATCAGGT | 3084 | TGCAGGACCAGAGAATTCGAATACATAGAATTCNNNTGCATCAGGT | 3324 | TGCAGGACCAGAGAATTCGAATACACGATGAGNNNTGCATCAGGT | 3564 |
| TGCAGGACCAGAGAATTCGAATACATACGAAAANNNTGCATCAGGT | 3085 | TGCAGGACCAGAGAATTCGAATACACTTGAAGGNNNTGCATCAGGT | 3325 | TGCAGGACCAGAGAATTCGAATACATTAGCATANNNTGCATCAGGT | 3565 |
| TGCAGGACCAGAGAATTCGAATACACATAACATNNNTGCATCAGGT | 3086 | TGCAGGACCAGAGAATTCGAATACACTTAACTTNNNTGCATCAGGT | 3326 | TGCAGGACCAGAGAATTCGAATACAAGTCCCAANNNTGCATCAGGT | 3566 |

FIG. 16G

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAGGAGAATCNNNTGCATCAGGT | 3087 | TGCAGGACCAGAGAATTCGAATACAACTTACCCNNNTGCATCAGGT | 3327 | TGCAGGACCAGAGAATTCGAATACAAGCCTCTTNNNTGCATCAGGT | 3567 |
| TGCAGGACCAGAGAATTCGAATACATCTTGTCGNNNTGCATCAGGT | 3088 | TGCAGGACCAGAGAATTCGAATACAGAGTTCGTNNNTGCATCAGGT | 3328 | TGCAGGACCAGAGAATTCGAATACATCACCATCNNNTGCATCAGGT | 3568 |
| TGCAGGACCAGAGAATTCGAATACATAAGCGCTNNNTGCATCAGGT | 3089 | TGCAGGACCAGAGAATTCGAATACATTTCCAATNNNTGCATCAGGT | 3329 | TGCAGGACCAGAGAATTCGAATACACTCATCACNNNTGCATCAGGT | 3569 |
| TGCAGGACCAGAGAATTCGAATACATTCTAGAANNNTGCATCAGGT | 3090 | TGCAGGACCAGAGAATTCGAATACAATAAGTTCNNNTGCATCAGGT | 3330 | TGCAGGACCAGAGAATTCGAATACAACGGCGAGNNNTGCATCAGGT | 3570 |
| TGCAGGACCAGAGAATTCGAATACATTGCTTGCNNNTGCATCAGGT | 3091 | TGCAGGACCAGAGAATTCGAATACAAATGTACTNNNTGCATCAGGT | 3331 | TGCAGGACCAGAGAATTCGAATACACTCGGACGNNNTGCATCAGGT | 3571 |
| TGCAGGACCAGAGAATTCGAATACACAGCGTATNNNTGCATCAGGT | 3092 | TGCAGGACCAGAGAATTCGAATACATCCAAGCNNNTGCATCAGGT | 3332 | TGCAGGACCAGAGAATTCGAATACATACGGCATNNNTGCATCAGGT | 3572 |
| TGCAGGACCAGAGAATTCGAATACAAAGGAGCTNNNTGCATCAGGT | 3093 | TGCAGGACCAGAGAATTCGAATACATCGACCAANNNTGCATCAGGT | 3333 | TGCAGGACCAGAGAATTCGAATACATTTAGTAGNNNTGCATCAGGT | 3573 |
| TGCAGGACCAGAGAATTCGAATACACATGCCTTNNNTGCATCAGGT | 3094 | TGCAGGACCAGAGAATTCGAATACACTCGATAGNNNTGCATCAGGT | 3334 | TGCAGGACCAGAGAATTCGAATACAAGGAAGAGNNNTGCATCAGGT | 3574 |
| TGCAGGACCAGAGAATTCGAATACACGCGGTGTNNNTGCATCAGGT | 3095 | TGCAGGACCAGAGAATTCGAATACAACTTCCCANNNTGCATCAGGT | 3335 | TGCAGGACCAGAGAATTCGAATACACCGCGCAANNNTGCATCAGGT | 3575 |
| TGCAGGACCAGAGAATTCGAATACACTGAAAGGNNNTGCATCAGGT | 3096 | TGCAGGACCAGAGAATTCGAATACATTAGATTGNNNTGCATCAGGT | 3336 | TGCAGGACCAGAGAATTCGAATACAGTCGTGGCNNNTGCATCAGGT | 3576 |
| TGCAGGACCAGAGAATTCGAATACAAGTTACGCNNNTGCATCAGGT | 3097 | TGCAGGACCAGAGAATTCGAATACACATTGCCANNNTGCATCAGGT | 3337 | TGCAGGACCAGAGAATTCGAATACAATACACTANNNTGCATCAGGT | 3577 |
| TGCAGGACCAGAGAATTCGAATACAGCTAAGCTNNNTGCATCAGGT | 3098 | TGCAGGACCAGAGAATTCGAATACACAGCACATNNNTGCATCAGGT | 3338 | TGCAGGACCAGAGAATTCGAATACACCACGCCTNNNTGCATCAGGT | 3578 |
| TGCAGGACCAGAGAATTCGAATACATCGCAGTANNNTGCATCAGGT | 3099 | TGCAGGACCAGAGAATTCGAATACACCCGGCAANNNTGCATCAGGT | 3339 | TGCAGGACCAGAGAATTCGAATACACGAAGTGGNNNTGCATCAGGT | 3579 |
| TGCAGGACCAGAGAATTCGAATACACAGATCGTNNNTGCATCAGGT | 3100 | TGCAGGACCAGAGAATTCGAATACAACAGATGGNNNTGCATCAGGT | 3340 | TGCAGGACCAGAGAATTCGAATACAGAGTTGTCNNNTGCATCAGGT | 3580 |
| TGCAGGACCAGAGAATTCGAATACACGAAAATNNNTGCATCAGGT | 3101 | TGCAGGACCAGAGAATTCGAATACATGCGTATGNNNTGCATCAGGT | 3341 | TGCAGGACCAGAGAATTCGAATACACCCGGCTTNNNTGCATCAGGT | 3581 |
| TGCAGGACCAGAGAATTCGAATACAGCCAGACCNNNTGCATCAGGT | 3102 | TGCAGGACCAGAGAATTCGAATACAACAGGAGTNNNTGCATCAGGT | 3342 | TGCAGGACCAGAGAATTCGAATACACAGATAGGNNNTGCATCAGGT | 3582 |
| TGCAGGACCAGAGAATTCGAATACAGCTGCACGNNNTGCATCAGGT | 3103 | TGCAGGACCAGAGAATTCGAATACACATCCATCNNNTGCATCAGGT | 3343 | TGCAGGACCAGAGAATTCGAATACAAAGTCCGTNNNTGCATCAGGT | 3583 |
| TGCAGGACCAGAGAATTCGAATACACTGGAACTNNNTGCATCAGGT | 3104 | TGCAGGACCAGAGAATTCGAATACACTACGCCCNNNTGCATCAGGT | 3344 | TGCAGGACCAGAGAATTCGAATACAAATCAGAANNNTGCATCAGGT | 3584 |
| TGCAGGACCAGAGAATTCGAATACAATAGCAAANNNTGCATCAGGT | 3105 | TGCAGGACCAGAGAATTCGAATACAGACCTACANNNTGCATCAGGT | 3345 | TGCAGGACCAGAGAATTCGAATACACACTCAGANNNTGCATCAGGT | 3585 |
| TGCAGGACCAGAGAATTCGAATACAGAGCTATNNNTGCATCAGGT | 3106 | TGCAGGACCAGAGAATTCGAATACATCCCACCGNNNTGCATCAGGT | 3346 | TGCAGGACCAGAGAATTCGAATACATTATTCCANNNTGCATCAGGT | 3586 |
| TGCAGGACCAGAGAATTCGAATACAAGGTATCCNNNTGCATCAGGT | 3107 | TGCAGGACCAGAGAATTCGAATACACATTCGCTNNNTGCATCAGGT | 3347 | TGCAGGACCAGAGAATTCGAATACAAAGTAACANNNTGCATCAGGT | 3587 |
| TGCAGGACCAGAGAATTCGAATACATTGGAGTCNNNTGCATCAGGT | 3108 | TGCAGGACCAGAGAATTCGAATACAGATCTGGTNNNTGCATCAGGT | 3348 | TGCAGGACCAGAGAATTCGAATACATTGTGCCTNNNTGCATCAGGT | 3588 |
| TGCAGGACCAGAGAATTCGAATACACGGCTTCCNNNTGCATCAGGT | 3109 | TGCAGGACCAGAGAATTCGAATACATATCGTTNNNTGCATCAGGT | 3349 | TGCAGGACCAGAGAATTCGAATACAAAGAGTCGNNNTGCATCAGGT | 3589 |
| TGCAGGACCAGAGAATTCGAATACATCAGGTTCNNNTGCATCAGGT | 3110 | TGCAGGACCAGAGAATTCGAATACAGGATTCTGNNNTGCATCAGGT | 3350 | TGCAGGACCAGAGAATTCGAATACAAGCTGTTGNNNTGCATCAGGT | 3590 |
| TGCAGGACCAGAGAATTCGAATACACGGCGCGCNNNTGCATCAGGT | 3111 | TGCAGGACCAGAGAATTCGAATACACCGCATCCNNNTGCATCAGGT | 3351 | TGCAGGACCAGAGAATTCGAATACAATATTGACNNNTGCATCAGGT | 3591 |
| TGCAGGACCAGAGAATTCGAATACAATGTGTCCNNNTGCATCAGGT | 3112 | TGCAGGACCAGAGAATTCGAATACAGACTAAAANNNTGCATCAGGT | 3352 | TGCAGGACCAGAGAATTCGAATACAAAATATTTNNNTGCATCAGGT | 3592 |
| TGCAGGACCAGAGAATTCGAATACACTTTGGAGNNNTGCATCAGGT | 3113 | TGCAGGACCAGAGAATTCGAATACAGTGGATGTNNNTGCATCAGGT | 3353 | TGCAGGACCAGAGAATTCGAATACACTCAAGACNNNTGCATCAGGT | 3593 |
| TGCAGGACCAGAGAATTCGAATACACGCCCACTNNNTGCATCAGGT | 3114 | TGCAGGACCAGAGAATTCGAATACACCGTTTACNNNTGCATCAGGT | 3354 | TGCAGGACCAGAGAATTCGAATACAAGACGAACNNNTGCATCAGGT | 3594 |
| TGCAGGACCAGAGAATTCGAATACAAACACTGCNNNTGCATCAGGT | 3115 | TGCAGGACCAGAGAATTCGAATACAAATTATCGNNNTGCATCAGGT | 3355 | TGCAGGACCAGAGAATTCGAATACAAGGCAGGCNNNTGCATCAGGT | 3595 |
| TGCAGGACCAGAGAATTCGAATACAGCGCCGTANNNTGCATCAGGT | 3116 | TGCAGGACCAGAGAATTCGAATACACACTCGAANNNTGCATCAGGT | 3356 | TGCAGGACCAGAGAATTCGAATACAACTTATAGNNNTGCATCAGGT | 3596 |
| TGCAGGACCAGAGAATTCGAATACAGTAGCATCNNNTGCATCAGGT | 3117 | TGCAGGACCAGAGAATTCGAATACAGAACGTTCNNNTGCATCAGGT | 3357 | TGCAGGACCAGAGAATTCGAATACACTACTAAANNNTGCATCAGGT | 3597 |
| TGCAGGACCAGAGAATTCGAATACATGCAGCATNNNTGCATCAGGT | 3118 | TGCAGGACCAGAGAATTCGAATACAACCCGCAGNNNTGCATCAGGT | 3358 | TGCAGGACCAGAGAATTCGAATACATTTAGAGTNNNTGCATCAGGT | 3598 |
| TGCAGGACCAGAGAATTCGAATACATGCAGACTNNNTGCATCAGGT | 3119 | TGCAGGACCAGAGAATTCGAATACAGTCTCTGTNNNTGCATCAGGT | 3359 | TGCAGGACCAGAGAATTCGAATACACTGCTTCANNNTGCATCAGGT | 3599 |

FIG. 16H

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAAAGATGCGNNNTGCATCAGGT | 3120 | TGCAGGACCAGAGAATTCGAATACAATTGATCANNNTGCATCAGGT | 3360 | TGCAGGACCAGAGAATTCGAATACAAGGTTCTGNNNTGCATCAGGT | 3600 |
| TGCAGGACCAGAGAATTCGAATACAAACATATCNNNTGCATCAGGT | 3121 | TGCAGGACCAGAGAATTCGAATACAAAGTTTACNNNTGCATCAGGT | 3361 | TGCAGGACCAGAGAATTCGAATACAAGTAGGTGNNNTGCATCAGGT | 3601 |
| TGCAGGACCAGAGAATTCGAATACATGGAACGANNNTGCATCAGGT | 3122 | TGCAGGACCAGAGAATTCGAATACATGTTGTAANNNTGCATCAGGT | 3362 | TGCAGGACCAGAGAATTCGAATACACCCGATAANNNTGCATCAGGT | 3602 |
| TGCAGGACCAGAGAATTCGAATACATGCTCTTGNNNTGCATCAGGT | 3123 | TGCAGGACCAGAGAATTCGAATACACTCTCAACNNNTGCATCAGGT | 3363 | TGCAGGACCAGAGAATTCGAATACACAGAGTGANNNTGCATCAGGT | 3603 |
| TGCAGGACCAGAGAATTCGAATACAACTCCTGTNNNTGCATCAGGT | 3124 | TGCAGGACCAGAGAATTCGAATACAAACGGCCCNNNTGCATCAGGT | 3364 | TGCAGGACCAGAGAATTCGAATACAGTTCGCTTNNNTGCATCAGGT | 3604 |
| TGCAGGACCAGAGAATTCGAATACAAAACGTGGNNNTGCATCAGGT | 3125 | TGCAGGACCAGAGAATTCGAATACAAATGGTAANNNTGCATCAGGT | 3365 | TGCAGGACCAGAGAATTCGAATACAGTTATCAANNNTGCATCAGGT | 3605 |
| TGCAGGACCAGAGAATTCGAATACATGTCCCTANNNTGCATCAGGT | 3126 | TGCAGGACCAGAGAATTCGAATACATACAACCGNNNTGCATCAGGT | 3366 | TGCAGGACCAGAGAATTCGAATACAAGATGCTCNNNTGCATCAGGT | 3606 |
| TGCAGGACCAGAGAATTCGAATACAAATCGCTGNNNTGCATCAGGT | 3127 | TGCAGGACCAGAGAATTCGAATACAATACGGTCNNNTGCATCAGGT | 3367 | TGCAGGACCAGAGAATTCGAATACAAACGTAAANNNTGCATCAGGT | 3607 |
| TGCAGGACCAGAGAATTCGAATACAGAAGCATGNNNTGCATCAGGT | 3128 | TGCAGGACCAGAGAATTCGAATACATGCGCTGGNNNTGCATCAGGT | 3368 | TGCAGGACCAGAGAATTCGAATACAGCATTTCCNNNTGCATCAGGT | 3608 |

FIG. 17A

| Pool-16 | SEQ ID NO: | Pool-17 | SEQ ID NO: | Pool-18 | SEQ ID NO: |
|---|---|---|---|---|---|
| TGCAGGACCAGAGAATTCGAATACATGATTCAANNNACGTATGCCA | 3609 | TGCAGGACCAGAGAATTCGAATACAATTTCCCGNNNACGTATGCCA | 3849 | TGCAGGACCAGAGAATTCGAATACAACGAGACANNNACGTATGCCA | 4089 |
| TGCAGGACCAGAGAATTCGAATACAACAAGTAANNNACGTATGCCA | 3610 | TGCAGGACCAGAGAATTCGAATACAATCCCAGANNNACGTATGCCA | 3850 | TGCAGGACCAGAGAATTCGAATACACGCTAATGNNNACGTATGCCA | 4090 |
| TGCAGGACCAGAGAATTCGAATACAATGACCGTNNNACGTATGCCA | 3611 | TGCAGGACCAGAGAATTCGAATACACGGAGACGNNNACGTATGCCA | 3851 | TGCAGGACCAGAGAATTCGAATACATACGTCGANNNACGTATGCCA | 4091 |
| TGCAGGACCAGAGAATTCGAATACAATCTCGTNNNACGTATGCCA | 3612 | TGCAGGACCAGAGAATTCGAATACACGATACGTNNNACGTATGCCA | 3852 | TGCAGGACCAGAGAATTCGAATACAATTCGTGNNNACGTATGCCA | 4092 |
| TGCAGGACCAGAGAATTCGAATACAGGCAACAANNNACGTATGCCA | 3613 | TGCAGGACCAGAGAATTCGAATACATCCTGCTANNNACGTATGCCA | 3853 | TGCAGGACCAGAGAATTCGAATACAATAGAGGTNNNACGTATGCCA | 4093 |
| TGCAGGACCAGAGAATTCGAATACAAGGCGCCTNNNACGTATGCCA | 3614 | TGCAGGACCAGAGAATTCGAATACAAATTACACNNNACGTATGCCA | 3854 | TGCAGGACCAGAGAATTCGAATACAGGCGGTTCNNNACGTATGCCA | 4094 |
| TGCAGGACCAGAGAATTCGAATACATGCTTACCNNNACGTATGCCA | 3615 | TGCAGGACCAGAGAATTCGAATACATTTCCGACNNNACGTATGCCA | 3855 | TGCAGGACCAGAGAATTCGAATACAATAGGCTCNNNACGTATGCCA | 4095 |
| TGCAGGACCAGAGAATTCGAATACACGCACGACNNNACGTATGCCA | 3616 | TGCAGGACCAGAGAATTCGAATACACTCCCCTNNNACGTATGCCA | 3856 | TGCAGGACCAGAGAATTCGAATACATCCAATTTNNNACGTATGCCA | 4096 |
| TGCAGGACCAGAGAATTCGAATACAGAGGCTTTNNNACGTATGCCA | 3617 | TGCAGGACCAGAGAATTCGAATACAACAATTCANNNACGTATGCCA | 3857 | TGCAGGACCAGAGAATTCGAATACACTGCCGAGNNNACGTATGCCA | 4097 |
| TGCAGGACCAGAGAATTCGAATACACATTCATTNNNACGTATGCCA | 3618 | TGCAGGACCAGAGAATTCGAATACAAGCAGCGGNNNACGTATGCCA | 3858 | TGCAGGACCAGAGAATTCGAATACACTGTAGTGNNNACGTATGCCA | 4098 |
| TGCAGGACCAGAGAATTCGAATACACBATCATANNNACGTATGCCA | 3619 | TGCAGGACCAGAGAATTCGAATACAATCCGATGNNNACGTATGCCA | 3859 | TGCAGGACCAGAGAATTCGAATACAAACGGTCTNNNACGTATGCCA | 4099 |
| TGCAGGACCAGAGAATTCGAATACACTACGATGNNNACGTATGCCA | 3620 | TGCAGGACCAGAGAATTCGAATACACACGCACANNNACGTATGCCA | 3860 | TGCAGGACCAGAGAATTCGAATACACAGGCGTCNNNACGTATGCCA | 4100 |
| TGCAGGACCAGAGAATTCGAATACAGAGGTACANNNACGTATGCCA | 3621 | TGCAGGACCAGAGAATTCGAATACACCACCATTNNNACGTATGCCA | 3861 | TGCAGGACCAGAGAATTCGAATACACTTGCCTANNNACGTATGCCA | 4101 |
| TGCAGGACCAGAGAATTCGAATACACTCGTCTANNNACGTATGCCA | 3622 | TGCAGGACCAGAGAATTCGAATACAAAAGGTCGNNNACGTATGCCA | 3862 | TGCAGGACCAGAGAATTCGAATACACTTCCGTANNNACGTATGCCA | 4102 |
| TGCAGGACCAGAGAATTCGAATACAAGAAGGAGNNNACGTATGCCA | 3623 | TGCAGGACCAGAGAATTCGAATACAGCAGTGTTNNNACGTATGCCA | 3863 | TGCAGGACCAGAGAATTCGAATACACAGACGTTNNNACGTATGCCA | 4103 |
| TGCAGGACCAGAGAATTCGAATACAGTGACATCNNNACGTATGCCA | 3624 | TGCAGGACCAGAGAATTCGAATACATCGAACTGNNNACGTATGCCA | 3864 | TGCAGGACCAGAGAATTCGAATACAAGGAACGTNNNACGTATGCCA | 4104 |
| TGCAGGACCAGAGAATTCGAATACAGCGGTGANNNACGTATGCCA | 3625 | TGCAGGACCAGAGAATTCGAATACATTCGCTANNNACGTATGCCA | 3865 | TGCAGGACCAGAGAATTCGAATACATTGCGTAGNNNACGTATGCCA | 4105 |
| TGCAGGACCAGAGAATTCGAATACACACAAATTNNNACGTATGCCA | 3626 | TGCAGGACCAGAGAATTCGAATACATATTCATCNNNACGTATGCCA | 3866 | TGCAGGACCAGAGAATTCGAATACAGCCCGATGNNNACGTATGCCA | 4106 |
| TGCAGGACCAGAGAATTCGAATACACCGTGCAGNNNACGTATGCCA | 3627 | TGCAGGACCAGAGAATTCGAATACAAACTACTNNNACGTATGCCA | 3867 | TGCAGGACCAGAGAATTCGAATACAAACGTCTGNNNACGTATGCCA | 4107 |
| TGCAGGACCAGAGAATTCGAATACAAAATTACCNNNACGTATGCCA | 3628 | TGCAGGACCAGAGAATTCGAATACAGCCCGTAGNNNACGTATGCCA | 3868 | TGCAGGACCAGAGAATTCGAATACACTCTACACNNNACGTATGCCA | 4108 |
| TGCAGGACCAGAGAATTCGAATACAGCAGACAANNNACGTATGCCA | 3629 | TGCAGGACCAGAGAATTCGAATACAAGTCGTGNNNACGTATGCCA | 3869 | TGCAGGACCAGAGAATTCGAATACAACGGGTCNNNACGTATGCCA | 4109 |
| TGCAGGACCAGAGAATTCGAATACATTCTAAGANNNACGTATGCCA | 3630 | TGCAGGACCAGAGAATTCGAATACATGACAGCTNNNACGTATGCCA | 3870 | TGCAGGACCAGAGAATTCGAATACACATCCAGANNNACGTATGCCA | 4110 |
| TGCAGGACCAGAGAATTCGAATACACATTGAGCNNNACGTATGCCA | 3631 | TGCAGGACCAGAGAATTCGAATACATCAGCGATNNNACGTATGCCA | 3871 | TGCAGGACCAGAGAATTCGAATACAAAGTCGAGNNNACGTATGCCA | 4111 |
| TGCAGGACCAGAGAATTCGAATACAATGAGAGCNNNACGTATGCCA | 3632 | TGCAGGACCAGAGAATTCGAATACAGAGTAAATNNNACGTATGCCA | 3872 | TGCAGGACCAGAGAATTCGAATACAGGCAGCCTNNNACGTATGCCA | 4112 |
| TGCAGGACCAGAGAATTCGAATACATTTCCCGANNNACGTATGCCA | 3633 | TGCAGGACCAGAGAATTCGAATACAGCTGCCTCNNNACGTATGCCA | 3873 | TGCAGGACCAGAGAATTCGAATACATTATACAGNNNACGTATGCCA | 4113 |
| TGCAGGACCAGAGAATTCGAATACATTGCGAACNNNACGTATGCCA | 3634 | TGCAGGACCAGAGAATTCGAATACACTTGACGANNNACGTATGCCA | 3874 | TGCAGGACCAGAGAATTCGAATACACCCGTCGTNNNACGTATGCCA | 4114 |
| TGCAGGACCAGAGAATTCGAATACATGGAGATGNNNACGTATGCCA | 3635 | TGCAGGACCAGAGAATTCGAATACACCTCTTTCNNNACGTATGCCA | 3875 | TGCAGGACCAGAGAATTCGAATACATAATTTAANNNACGTATGCCA | 4115 |
| TGCAGGACCAGAGAATTCGAATACACCAACCCCNNNACGTATGCCA | 3636 | TGCAGGACCAGAGAATTCGAATACAACACAAGGNNNACGTATGCCA | 3876 | TGCAGGACCAGAGAATTCGAATACATCATCATNNNACGTATGCCA | 4116 |
| TGCAGGACCAGAGAATTCGAATACAGACAATGGNNNACGTATGCCA | 3637 | TGCAGGACCAGAGAATTCGAATACATCTCCAGTNNNACGTATGCCA | 3877 | TGCAGGACCAGAGAATTCGAATACACATGTATANNNACGTATGCCA | 4117 |
| TGCAGGACCAGAGAATTCGAATACACAGAGCCCNNNACGTATGCCA | 3638 | TGCAGGACCAGAGAATTCGAATACATATTGGTANNNACGTATGCCA | 3878 | TGCAGGACCAGAGAATTCGAATACAGTAGTTATNNNACGTATGCCA | 4118 |
| TGCAGGACCAGAGAATTCGAATACAAAGAATANNNACGTATGCCA | 3639 | TGCAGGACCAGAGAATTCGAATACAGCTTCATCNNNACGTATGCCA | 3879 | TGCAGGACCAGAGAATTCGAATACATGTATCGGNNNACGTATGCCA | 4119 |
| TGCAGGACCAGAGAATTCGAATACAAGGTAAATNNNACGTATGCCA | 3640 | TGCAGGACCAGAGAATTCGAATACATTCGTTANNNACGTATGCCA | 3880 | TGCAGGACCAGAGAATTCGAATACAAGACGGTGNNNACGTATGCCA | 4120 |

FIG. 17B

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAG CCCCAAGNNNACGTATGCCA | 3641 | TGCAGGACCAGAGAATTCGAATACAT ACGTGACNNNACGTATGCCA | 3881 | TGCAGGACCAGAGAATTCGAATACAG CACAAGANNNACGTATGCCA | 4121 |
| TGCAGGACCAGAGAATTCGAATACAC TGCTTGTNNNACGTATGCCA | 3642 | TGCAGGACCAGAGAATTCGAATACAT GTTGGTGNNNACGTATGCCA | 3882 | TGCAGGACCAGAGAATTCGAATACAA ACCCGGCNNNACGTATGCCA | 4122 |
| TGCAGGACCAGAGAATTCGAATACAA CACGGCCNNNACGTATGCCA | 3643 | TGCAGGACCAGAGAATTCGAATACAT ATCACAGNNNACGTATGCCA | 3883 | TGCAGGACCAGAGAATTCGAATACAT GTGGCTANNNACGTATGCCA | 4123 |
| TGCAGGACCAGAGAATTCGAATACAA CGACCTANNNACGTATGCCA | 3644 | TGCAGGACCAGAGAATTCGAATACAA ACGGCGGNNNACGTATGCCA | 3884 | TGCAGGACCAGAGAATTCGAATACAG TAGCTCANNNACGTATGCCA | 4124 |
| TGCAGGACCAGAGAATTCGAATACAA TTAGAAGNNNACGTATGCCA | 3645 | TGCAGGACCAGAGAATTCGAATACAA ATGTGAANNNACGTATGCCA | 3885 | TGCAGGACCAGAGAATTCGAATACAG GCTGGCTNNNACGTATGCCA | 4125 |
| TGCAGGACCAGAGAATTCGAATACAG CCGTACGNNNACGTATGCCA | 3646 | TGCAGGACCAGAGAATTCGAATACAG TAGCCGCNNNACGTATGCCA | 3886 | TGCAGGACCAGAGAATTCGAATACAT ACAGCTGNNNACGTATGCCA | 4126 |
| TGCAGGACCAGAGAATTCGAATACAC AGAAAGCNNNACGTATGCCA | 3647 | TGCAGGACCAGAGAATTCGAATACAT GTGAATTNNNACGTATGCCA | 3887 | TGCAGGACCAGAGAATTCGAATACAC TTGTGTCNNNACGTATGCCA | 4127 |
| TGCAGGACCAGAGAATTCGAATACAC CACCTTANNNACGTATGCCA | 3648 | TGCAGGACCAGAGAATTCGAATACAC GGTAAGANNNACGTATGCCA | 3888 | TGCAGGACCAGAGAATTCGAATACAA GCATCGTNNNACGTATGCCA | 4128 |
| TGCAGGACCAGAGAATTCGAATACAA AGGATTANNNACGTATGCCA | 3649 | TGCAGGACCAGAGAATTCGAATACAT CTGGTGANNNACGTATGCCA | 3889 | TGCAGGACCAGAGAATTCGAATACAA ATAAAGCNNNACGTATGCCA | 4129 |
| TGCAGGACCAGAGAATTCGAATACAA GCAAATANNNACGTATGCCA | 3650 | TGCAGGACCAGAGAATTCGAATACAG TCCGTTTNNNACGTATGCCA | 3890 | TGCAGGACCAGAGAATTCGAATACAC TATCGGANNNACGTATGCCA | 4130 |
| TGCAGGACCAGAGAATTCGAATACAC ACTTCGTNNNACGTATGCCA | 3651 | TGCAGGACCAGAGAATTCGAATACAC CGTCGAGNNNACGTATGCCA | 3891 | TGCAGGACCAGAGAATTCGAATACAC CGCCCGCNNNACGTATGCCA | 4131 |
| TGCAGGACCAGAGAATTCGAATACAA TTCGTCCNNNACGTATGCCA | 3652 | TGCAGGACCAGAGAATTCGAATACAT CGATCCTNNNACGTATGCCA | 3892 | TGCAGGACCAGAGAATTCGAATACAT CGTTTCGNNNACGTATGCCA | 4132 |
| TGCAGGACCAGAGAATTCGAATACAT TCTTGGCNNNACGTATGCCA | 3653 | TGCAGGACCAGAGAATTCGAATACAT TTGCGTCNNNACGTATGCCA | 3893 | TGCAGGACCAGAGAATTCGAATACAC CTAGCAANNNACGTATGCCA | 4133 |
| TGCAGGACCAGAGAATTCGAATACAT TGGCTCTNNNACGTATGCCA | 3654 | TGCAGGACCAGAGAATTCGAATACAC TCGGCTCNNNACGTATGCCA | 3894 | TGCAGGACCAGAGAATTCGAATACAT GAACATNNNACGTATGCCA | 4134 |
| TGCAGGACCAGAGAATTCGAATACAG GAGACTANNNACGTATGCCA | 3655 | TGCAGGACCAGAGAATTCGAATACAG CCACGCCNNNACGTATGCCA | 3895 | TGCAGGACCAGAGAATTCGAATACAT GTAACATNNNACGTATGCCA | 4135 |
| TGCAGGACCAGAGAATTCGAATACAA ATACTTGNNNACGTATGCCA | 3656 | TGCAGGACCAGAGAATTCGAATACAA CGTGCCGNNNACGTATGCCA | 3896 | TGCAGGACCAGAGAATTCGAATACAG TCGGAAANNNACGTATGCCA | 4136 |
| TGCAGGACCAGAGAATTCGAATACAG CTGTTAGNNNACGTATGCCA | 3657 | TGCAGGACCAGAGAATTCGAATACAT GTGGTACNNNACGTATGCCA | 3897 | TGCAGGACCAGAGAATTCGAATACAG TTGGCCGNNNACGTATGCCA | 4137 |
| TGCAGGACCAGAGAATTCGAATACAA CAACCTGNNNACGTATGCCA | 3658 | TGCAGGACCAGAGAATTCGAATACAA GCCGAAANNNACGTATGCCA | 3898 | TGCAGGACCAGAGAATTCGAATACAG CGATAGANNNACGTATGCCA | 4138 |
| TGCAGGACCAGAGAATTCGAATACAT CGTGCCCNNNACGTATGCCA | 3659 | TGCAGGACCAGAGAATTCGAATACAC TCCTAACNNNACGTATGCCA | 3899 | TGCAGGACCAGAGAATTCGAATACAT TAACGTANNNACGTATGCCA | 4139 |
| TGCAGGACCAGAGAATTCGAATACAG ACTCTCTNNNACGTATGCCA | 3660 | TGCAGGACCAGAGAATTCGAATACAG AAGGCGCNNNACGTATGCCA | 3900 | TGCAGGACCAGAGAATTCGAATACAC CTTATATNNNACGTATGCCA | 4140 |
| TGCAGGACCAGAGAATTCGAATACAT ATAACACNNNACGTATGCCA | 3661 | TGCAGGACCAGAGAATTCGAATACAC GTTCACTNNNACGTATGCCA | 3901 | TGCAGGACCAGAGAATTCGAATACAA AACAGATNNNACGTATGCCA | 4141 |
| TGCAGGACCAGAGAATTCGAATACAT GAGCCTANNNACGTATGCCA | 3662 | TGCAGGACCAGAGAATTCGAATACAG AGATGTGNNNACGTATGCCA | 3902 | TGCAGGACCAGAGAATTCGAATACAT ACCCATCNNNACGTATGCCA | 4142 |
| TGCAGGACCAGAGAATTCGAATACAC AGACGAANNNACGTATGCCA | 3663 | TGCAGGACCAGAGAATTCGAATACAG CTCACTTNNNACGTATGCCA | 3903 | TGCAGGACCAGAGAATTCGAATACAA AAAGAGANNNACGTATGCCA | 4143 |
| TGCAGGACCAGAGAATTCGAATACAC GGAATGANNNACGTATGCCA | 3664 | TGCAGGACCAGAGAATTCGAATACAC GAAGCTTNNNACGTATGCCA | 3904 | TGCAGGACCAGAGAATTCGAATACAC GTTCGAANNNACGTATGCCA | 4144 |
| TGCAGGACCAGAGAATTCGAATACAG GTGATGANNNACGTATGCCA | 3665 | TGCAGGACCAGAGAATTCGAATACAT ACTCGAGNNNACGTATGCCA | 3905 | TGCAGGACCAGAGAATTCGAATACAA TGGATCCNNNACGTATGCCA | 4145 |
| TGCAGGACCAGAGAATTCGAATACAC ACCTCTANNNACGTATGCCA | 3666 | TGCAGGACCAGAGAATTCGAATACAT TCTTGTANNNACGTATGCCA | 3906 | TGCAGGACCAGAGAATTCGAATACAG CTCGATANNNACGTATGCCA | 4146 |
| TGCAGGACCAGAGAATTCGAATACAA CTGGTACNNNACGTATGCCA | 3667 | TGCAGGACCAGAGAATTCGAATACAG AAGAAGGNNNACGTATGCCA | 3907 | TGCAGGACCAGAGAATTCGAATACAT GTAACCGNNNACGTATGCCA | 4147 |
| TGCAGGACCAGAGAATTCGAATACAG CAAATCCNNNACGTATGCCA | 3668 | TGCAGGACCAGAGAATTCGAATACAA GCCACGCNNNACGTATGCCA | 3908 | TGCAGGACCAGAGAATTCGAATACAA TCTACTTNNNACGTATGCCA | 4148 |
| TGCAGGACCAGAGAATTCGAATACAA ATATAAANNNCTAGCGTTAC | 3669 | TGCAGGACCAGAGAATTCGAATACAA TATACCGNNNCTAGCGTTAC | 3909 | TGCAGGACCAGAGAATTCGAATACAG ATCGTACNNNCTAGCGTTAC | 4149 |
| TGCAGGACCAGAGAATTCGAATACAT GGTTATANNNCTAGCGTTAC | 3670 | TGCAGGACCAGAGAATTCGAATACAA GATCTTANNNCTAGCGTTAC | 3910 | TGCAGGACCAGAGAATTCGAATACAT GAACGTCNNNCTAGCGTTAC | 4150 |
| TGCAGGACCAGAGAATTCGAATACAA CCCGCTCNNNCTAGCGTTAC | 3671 | TGCAGGACCAGAGAATTCGAATACAA CAACCCANNNCTAGCGTTAC | 3911 | TGCAGGACCAGAGAATTCGAATACAA CCAACTCNNNCTAGCGTTAC | 4151 |
| TGCAGGACCAGAGAATTCGAATACAT GCGAAAGNNNCTAGCGTTAC | 3672 | TGCAGGACCAGAGAATTCGAATACAT GCTAACGNNNCTAGCGTTAC | 3912 | TGCAGGACCAGAGAATTCGAATACAG CGGAGGTNNNCTAGCGTTAC | 4152 |
| TGCAGGACCAGAGAATTCGAATACAC GTCTGCCNNNCTAGCGTTAC | 3673 | TGCAGGACCAGAGAATTCGAATACAT GTAGTCGNNNCTAGCGTTAC | 3913 | TGCAGGACCAGAGAATTCGAATACAT GCCCATTNNNCTAGCGTTAC | 4153 |

FIG. 17C

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAAGTTGTATNNNCTAGCGTTAC | 3674 | TGCAGGACCAGAGAATTCGAATACAATCGTCGTNNNCTAGCGTTAC | 3914 | TGCAGGACCAGAGAATTCGAATACAACGATCACNNNCTAGCGTTAC | 4154 |
| TGCAGGACCAGAGAATTCGAATACAGGCTACTANNNCTAGCGTTAC | 3675 | TGCAGGACCAGAGAATTCGAATACAAGTAGGACNNNCTAGCGTTAC | 3915 | TGCAGGACCAGAGAATTCGAATACATAAGGTAANNNCTAGCGTTAC | 4155 |
| TGCAGGACCAGAGAATTCGAATACAACATCATANNNCTAGCGTTAC | 3676 | TGCAGGACCAGAGAATTCGAATACAAAAAAAAANNNCTAGCGTTAC | 3916 | TGCAGGACCAGAGAATTCGAATACAACCTACGANNNCTAGCGTTAC | 4156 |
| TGCAGGACCAGAGAATTCGAATACAATTCCAGGNNNCTAGCGTTAC | 3677 | TGCAGGACCAGAGAATTCGAATACAAGTTCATANNNCTAGCGTTAC | 3917 | TGCAGGACCAGAGAATTCGAATACACACACCAANNNCTAGCGTTAC | 4157 |
| TGCAGGACCAGAGAATTCGAATACATTTTGTTGNNNCTAGCGTTAC | 3678 | TGCAGGACCAGAGAATTCGAATACAGAAGGTCANNNCTAGCGTTAC | 3918 | TGCAGGACCAGAGAATTCGAATACATGGTCGGCNNNCTAGCGTTAC | 4158 |
| TGCAGGACCAGAGAATTCGAATACAAGTGGACANNNCTAGCGTTAC | 3679 | TGCAGGACCAGAGAATTCGAATACATGAATGCCNNNCTAGCGTTAC | 3919 | TGCAGGACCAGAGAATTCGAATACATTATCTGTNNNCTAGCGTTAC | 4159 |
| TGCAGGACCAGAGAATTCGAATACAGAGAGGTTNNNCTAGCGTTAC | 3680 | TGCAGGACCAGAGAATTCGAATACAACACCCGGNNNCTAGCGTTAC | 3920 | TGCAGGACCAGAGAATTCGAATACATCGACCGNNNCTAGCGTTAC | 4160 |
| TGCAGGACCAGAGAATTCGAATACACTTCCCGGNNNCTAGCGTTAC | 3681 | TGCAGGACCAGAGAATTCGAATACACTAACGCANNNCTAGCGTTAC | 3921 | TGCAGGACCAGAGAATTCGAATACATACCGATGNNNCTAGCGTTAC | 4161 |
| TGCAGGACCAGAGAATTCGAATACAACCTCCATNNNCTAGCGTTAC | 3682 | TGCAGGACCAGAGAATTCGAATACAACCCCTATNNNCTAGCGTTAC | 3922 | TGCAGGACCAGAGAATTCGAATACAGAACGGATNNNCTAGCGTTAC | 4162 |
| TGCAGGACCAGAGAATTCGAATACACAAGAGGTNNNCTAGCGTTAC | 3683 | TGCAGGACCAGAGAATTCGAATACAAGATAGATNNNCTAGCGTTAC | 3923 | TGCAGGACCAGAGAATTCGAATACATTGTTCTANNNCTAGCGTTAC | 4163 |
| TGCAGGACCAGAGAATTCGAATACAGAAAGTCGNNNCTAGCGTTAC | 3684 | TGCAGGACCAGAGAATTCGAATACAGGAGTGATNNNCTAGCGTTAC | 3924 | TGCAGGACCAGAGAATTCGAATACAGGTCGTCGNNNCTAGCGTTAC | 4164 |
| TGCAGGACCAGAGAATTCGAATACACGCGAAAANNNCTAGCGTTAC | 3685 | TGCAGGACCAGAGAATTCGAATACAATAGAGGCNNNCTAGCGTTAC | 3925 | TGCAGGACCAGAGAATTCGAATACAATGCTTCCNNNCTAGCGTTAC | 4165 |
| TGCAGGACCAGAGAATTCGAATACACCTGGCAGNNNCTAGCGTTAC | 3686 | TGCAGGACCAGAGAATTCGAATACACCCCGCGCNNNCTAGCGTTAC | 3926 | TGCAGGACCAGAGAATTCGAATACATCAGGACTNNNCTAGCGTTAC | 4166 |
| TGCAGGACCAGAGAATTCGAATACAAGCAGATGNNNCTAGCGTTAC | 3687 | TGCAGGACCAGAGAATTCGAATACACCATACTCNNNCTAGCGTTAC | 3927 | TGCAGGACCAGAGAATTCGAATACAAAGACATANNNCTAGCGTTAC | 4167 |
| TGCAGGACCAGAGAATTCGAATACAAGAGGCCGNNNCTAGCGTTAC | 3688 | TGCAGGACCAGAGAATTCGAATACATGATTCCNNNCTAGCGTTAC | 3928 | TGCAGGACCAGAGAATTCGAATACACCATCGTTNNNCTAGCGTTAC | 4168 |
| TGCAGGACCAGAGAATTCGAATACACGTGCGTGNNNCTAGCGTTAC | 3689 | TGCAGGACCAGAGAATTCGAATACAAGAACGGTNNNCTAGCGTTAC | 3929 | TGCAGGACCAGAGAATTCGAATACATAACACGNNNCTAGCGTTAC | 4169 |
| TGCAGGACCAGAGAATTCGAATACATGGTAGGANNNCTAGCGTTAC | 3690 | TGCAGGACCAGAGAATTCGAATACAGCTTCAAGNNNCTAGCGTTAC | 3930 | TGCAGGACCAGAGAATTCGAATACACCTCCTCCNNNCTAGCGTTAC | 4170 |
| TGCAGGACCAGAGAATTCGAATACACGCGCCAANNNCTAGCGTTAC | 3691 | TGCAGGACCAGAGAATTCGAATACAAAATATCCNNNCTAGCGTTAC | 3931 | TGCAGGACCAGAGAATTCGAATACATCGGACTANNNCTAGCGTTAC | 4171 |
| TGCAGGACCAGAGAATTCGAATACATGAGCACTNNNCTAGCGTTAC | 3692 | TGCAGGACCAGAGAATTCGAATACACGTCCCANNNCTAGCGTTAC | 3932 | TGCAGGACCAGAGAATTCGAATACAGGCAAACANNNCTAGCGTTAC | 4172 |
| TGCAGGACCAGAGAATTCGAATACATCATCGTNNNCTAGCGTTAC | 3693 | TGCAGGACCAGAGAATTCGAATACAACTAATCANNNCTAGCGTTAC | 3933 | TGCAGGACCAGAGAATTCGAATACAGGAAACACNNNCTAGCGTTAC | 4173 |
| TGCAGGACCAGAGAATTCGAATACAAGCCAAGANNNCTAGCGTTAC | 3694 | TGCAGGACCAGAGAATTCGAATACATGACGCGNNNCTAGCGTTAC | 3934 | TGCAGGACCAGAGAATTCGAATACATACACTCCNNNCTAGCGTTAC | 4174 |
| TGCAGGACCAGAGAATTCGAATACACGAGGACGNNNCTAGCGTTAC | 3695 | TGCAGGACCAGAGAATTCGAATACAGCCGTGCCANNNCTAGCGTTAC | 3935 | TGCAGGACCAGAGAATTCGAATACACGGACCTGNNNCTAGCGTTAC | 4175 |
| TGCAGGACCAGAGAATTCGAATACATGTGACTGNNNCTAGCGTTAC | 3696 | TGCAGGACCAGAGAATTCGAATACAAAATTGANNNCTAGCGTTAC | 3936 | TGCAGGACCAGAGAATTCGAATACAATCCTGAGNNNCTAGCGTTAC | 4176 |
| TGCAGGACCAGAGAATTCGAATACACCTTGAGNNNCTAGCGTTAC | 3697 | TGCAGGACCAGAGAATTCGAATACATGTTCACCNNNCTAGCGTTAC | 3937 | TGCAGGACCAGAGAATTCGAATACACCCGTCTGNNNCTAGCGTTAC | 4177 |
| TGCAGGACCAGAGAATTCGAATACAGTTAAGTTNNNCTAGCGTTAC | 3698 | TGCAGGACCAGAGAATTCGAATACAATCCGCAANNNCTAGCGTTAC | 3938 | TGCAGGACCAGAGAATTCGAATACAGGCTCAATNNNCTAGCGTTAC | 4178 |
| TGCAGGACCAGAGAATTCGAATACAACCCAGGCNNNCTAGCGTTAC | 3699 | TGCAGGACCAGAGAATTCGAATACATCAGATTANNNCTAGCGTTAC | 3939 | TGCAGGACCAGAGAATTCGAATACAGTGCTTGANNNCTAGCGTTAC | 4179 |
| TGCAGGACCAGAGAATTCGAATACACCGATGATNNNCTAGCGTTAC | 3700 | TGCAGGACCAGAGAATTCGAATACACGCTAAGTNNNCTAGCGTTAC | 3940 | TGCAGGACCAGAGAATTCGAATACAATTAACTGNNNCTAGCGTTAC | 4180 |
| TGCAGGACCAGAGAATTCGAATACAGATCTCGANNNCTAGCGTTAC | 3701 | TGCAGGACCAGAGAATTCGAATACACACACCCTNNNCTAGCGTTAC | 3941 | TGCAGGACCAGAGAATTCGAATACATCCAGATGNNNCTAGCGTTAC | 4181 |
| TGCAGGACCAGAGAATTCGAATACAGAGATGTNNNCTAGCGTTAC | 3702 | TGCAGGACCAGAGAATTCGAATACAAGCCTGTNNNCTAGCGTTAC | 3942 | TGCAGGACCAGAGAATTCGAATACACCGCGCGGNNNCTAGCGTTAC | 4182 |
| TGCAGGACCAGAGAATTCGAATACATAGGTAAANNNCTAGCGTTAC | 3703 | TGCAGGACCAGAGAATTCGAATACAGGTCCAGCNNNCTAGCGTTAC | 3943 | TGCAGGACCAGAGAATTCGAATACACCATAAGCNNNCTAGCGTTAC | 4183 |
| TGCAGGACCAGAGAATTCGAATACAACTCAGCANNNCTAGCGTTAC | 3704 | TGCAGGACCAGAGAATTCGAATACATGTCGCTTNNNCTAGCGTTAC | 3944 | TGCAGGACCAGAGAATTCGAATACAGGTTGGTTNNNCTAGCGTTAC | 4184 |
| TGCAGGACCAGAGAATTCGAATACAAGATAGGCNNNCTAGCGTTAC | 3705 | TGCAGGACCAGAGAATTCGAATACAGAAATTTCNNNCTAGCGTTAC | 3945 | TGCAGGACCAGAGAATTCGAATACAGGCAGATANNNCTAGCGTTAC | 4185 |
| TGCAGGACCAGAGAATTCGAATACACGAATTGCNNNCTAGCGTTAC | 3706 | TGCAGGACCAGAGAATTCGAATACATACGGTGTNNNCTAGCGTTAC | 3946 | TGCAGGACCAGAGAATTCGAATACAATGCAACCNNNCTAGCGTTAC | 4186 |

FIG. 17D

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAT ACCAGGTNNNCTAGCGTTAC | 3707 | TGCAGGACCAGAGAATTCGAATACAC CGACCAGNNNCTAGCGTTAC | 3947 | TGCAGGACCAGAGAATTCGAATACAG CGCGCCGNNNCTAGCGTTAC | 4187 |
| TGCAGGACCAGAGAATTCGAATACAT ATACTCTNNNCTAGCGTTAC | 3708 | TGCAGGACCAGAGAATTCGAATACAT GATAAAGNNNCTAGCGTTAC | 3948 | TGCAGGACCAGAGAATTCGAATACAC AAAGTGGNNNCTAGCGTTAC | 4188 |
| TGCAGGACCAGAGAATTCGAATACAA GCTTCTCNNNCTAGCGTTAC | 3709 | TGCAGGACCAGAGAATTCGAATACAT ATGGCTGNNNCTAGCGTTAC | 3949 | TGCAGGACCAGAGAATTCGAATACAT AAAAGCANNNCTAGCGTTAC | 4189 |
| TGCAGGACCAGAGAATTCGAATACAA CCTGAGTNNNCTAGCGTTAC | 3710 | TGCAGGACCAGAGAATTCGAATACAC CCCTCCTNNNCTAGCGTTAC | 3950 | TGCAGGACCAGAGAATTCGAATACAA TCTGTGGNNNCTAGCGTTAC | 4190 |
| TGCAGGACCAGAGAATTCGAATACAC ATAGATTNNNCTAGCGTTAC | 3711 | TGCAGGACCAGAGAATTCGAATACAT CTTACCGNNNCTAGCGTTAC | 3951 | TGCAGGACCAGAGAATTCGAATACAA GTATATANNNCTAGCGTTAC | 4191 |
| TGCAGGACCAGAGAATTCGAATACAA GCGGAATNNNCTAGCGTTAC | 3712 | TGCAGGACCAGAGAATTCGAATACAG CAATCGTNNNCTAGCGTTAC | 3952 | TGCAGGACCAGAGAATTCGAATACAG GTATTGNNNCTAGCGTTAC | 4192 |
| TGCAGGACCAGAGAATTCGAATACAG GCATGCCNNNCTAGCGTTAC | 3713 | TGCAGGACCAGAGAATTCGAATACAC TAGCGCGNNNCTAGCGTTAC | 3953 | TGCAGGACCAGAGAATTCGAATACAT ACAAACTNNNCTAGCGTTAC | 4193 |
| TGCAGGACCAGAGAATTCGAATACAA ATATCCGNNNCTAGCGTTAC | 3714 | TGCAGGACCAGAGAATTCGAATACAT ACTCTGCNNNCTAGCGTTAC | 3954 | TGCAGGACCAGAGAATTCGAATACAC TCTTAATNNNCTAGCGTTAC | 4194 |
| TGCAGGACCAGAGAATTCGAATACAG CTCAGCGNNNCTAGCGTTAC | 3715 | TGCAGGACCAGAGAATTCGAATACAA TGGCAGANNNCTAGCGTTAC | 3955 | TGCAGGACCAGAGAATTCGAATACAG GTCTGATNNNCTAGCGTTAC | 4195 |
| TGCAGGACCAGAGAATTCGAATACAC TTCAAGGNNNCTAGCGTTAC | 3716 | TGCAGGACCAGAGAATTCGAATACAC GAGGTTTNNNCTAGCGTTAC | 3956 | TGCAGGACCAGAGAATTCGAATACAT CAGGAAGNNNCTAGCGTTAC | 4196 |
| TGCAGGACCAGAGAATTCGAATACAT CAGTAATNNNCTAGCGTTAC | 3717 | TGCAGGACCAGAGAATTCGAATACAC CAGCTAANNNCTAGCGTTAC | 3957 | TGCAGGACCAGAGAATTCGAATACAC ACGCTTTNNNCTAGCGTTAC | 4197 |
| TGCAGGACCAGAGAATTCGAATACAC CGGCCAANNNCTAGCGTTAC | 3718 | TGCAGGACCAGAGAATTCGAATACAT GTGCCGGNNNCTAGCGTTAC | 3958 | TGCAGGACCAGAGAATTCGAATACAG GCGGCAANNNCTAGCGTTAC | 4198 |
| TGCAGGACCAGAGAATTCGAATACAA TGATCATNNNCTAGCGTTAC | 3719 | TGCAGGACCAGAGAATTCGAATACAT GCCGTTTNNNCTAGCGTTAC | 3959 | TGCAGGACCAGAGAATTCGAATACAG AAGTTGGNNNCTAGCGTTAC | 4199 |
| TGCAGGACCAGAGAATTCGAATACAG GCGCGTTNNNCTAGCGTTAC | 3720 | TGCAGGACCAGAGAATTCGAATACAC TCCGTGCNNNCTAGCGTTAC | 3960 | TGCAGGACCAGAGAATTCGAATACAG CAGGTGGNNNCTAGCGTTAC | 4200 |
| TGCAGGACCAGAGAATTCGAATACAC GTCCGCGNNNCTAGCGTTAC | 3721 | TGCAGGACCAGAGAATTCGAATACAC CACAATCNNNCTAGCGTTAC | 3961 | TGCAGGACCAGAGAATTCGAATACAT GTAATCANNNCTAGCGTTAC | 4201 |
| TGCAGGACCAGAGAATTCGAATACAC ACTGGTANNNCTAGCGTTAC | 3722 | TGCAGGACCAGAGAATTCGAATACAC ATCGTGANNNCTAGCGTTAC | 3962 | TGCAGGACCAGAGAATTCGAATACAG TCAACCANNNCTAGCGTTAC | 4202 |
| TGCAGGACCAGAGAATTCGAATACAC TAAGACCNNNCTAGCGTTAC | 3723 | TGCAGGACCAGAGAATTCGAATACAC AAGGTTCNNNCTAGCGTTAC | 3963 | TGCAGGACCAGAGAATTCGAATACAG AGCAACANNNCTAGCGTTAC | 4203 |
| TGCAGGACCAGAGAATTCGAATACAA CGCTACANNNCTAGCGTTAC | 3724 | TGCAGGACCAGAGAATTCGAATACAG AAAGGTCNNNCTAGCGTTAC | 3964 | TGCAGGACCAGAGAATTCGAATACAA CCGTCGGNNNCTAGCGTTAC | 4204 |
| TGCAGGACCAGAGAATTCGAATACAA CCAAAAANNNCTAGCGTTAC | 3725 | TGCAGGACCAGAGAATTCGAATACAA GAAGGTCNNNCTAGCGTTAC | 3965 | TGCAGGACCAGAGAATTCGAATACAT AGGCGCCNNNCTAGCGTTAC | 4205 |
| TGCAGGACCAGAGAATTCGAATACAC GAGTGCCNNNCTAGCGTTAC | 3726 | TGCAGGACCAGAGAATTCGAATACAC CATGCTTNNNCTAGCGTTAC | 3966 | TGCAGGACCAGAGAATTCGAATACAG AAGCAGTNNNCTAGCGTTAC | 4206 |
| TGCAGGACCAGAGAATTCGAATACAA ACCGAANNNCTAGCGTTAC | 3727 | TGCAGGACCAGAGAATTCGAATACAT TCAACTNNNCTAGCGTTAC | 3967 | TGCAGGACCAGAGAATTCGAATACAT TGGTATANNNCTAGCGTTAC | 4207 |
| TGCAGGACCAGAGAATTCGAATACAC AAAGCATNNNCTAGCGTTAC | 3728 | TGCAGGACCAGAGAATTCGAATACAT CTGGCAANNNCTAGCGTTAC | 3968 | TGCAGGACCAGAGAATTCGAATACAG AAGTGTGNNNCTAGCGTTAC | 4208 |
| TGCAGGACCAGAGAATTCGAATACAC CCCCGGNNNGATCGACATG | 3729 | TGCAGGACCAGAGAATTCGAATACAG TTTACAANNNGATCGACATG | 3969 | TGCAGGACCAGAGAATTCGAATACAC TGCTTTGNNNGATCGACATG | 4209 |
| TGCAGGACCAGAGAATTCGAATACAT TGGTTGGNNNGATCGACATG | 3730 | TGCAGGACCAGAGAATTCGAATACAA CCCACANNNGATCGACATG | 3970 | TGCAGGACCAGAGAATTCGAATACAG TTCCGCCNNNGATCGACATG | 4210 |
| TGCAGGACCAGAGAATTCGAATACAT CCACGTTNNNGATCGACATG | 3731 | TGCAGGACCAGAGAATTCGAATACAG GCTCATANNNGATCGACATG | 3971 | TGCAGGACCAGAGAATTCGAATACAC GACTATGNNNGATCGACATG | 4211 |
| TGCAGGACCAGAGAATTCGAATACAA TGAAGTANNNGATCGACATG | 3732 | TGCAGGACCAGAGAATTCGAATACAA GCATTGCNNNGATCGACATG | 3972 | TGCAGGACCAGAGAATTCGAATACAC TGTAGCANNNGATCGACATG | 4212 |
| TGCAGGACCAGAGAATTCGAATACAA CAATAAGNNNGATCGACATG | 3733 | TGCAGGACCAGAGAATTCGAATACAA ACCCGATNNNGATCGACATG | 3973 | TGCAGGACCAGAGAATTCGAATACAC GCGGTCANNNGATCGACATG | 4213 |
| TGCAGGACCAGAGAATTCGAATACAC ATGTTTNNNGATCGACATG | 3734 | TGCAGGACCAGAGAATTCGAATACAT GACCAACNNNGATCGACATG | 3974 | TGCAGGACCAGAGAATTCGAATACAT CCATGAGNNNGATCGACATG | 4214 |
| TGCAGGACCAGAGAATTCGAATACAT CCGGTCCNNNGATCGACATG | 3735 | TGCAGGACCAGAGAATTCGAATACAT CCGAGGANNNGATCGACATG | 3975 | TGCAGGACCAGAGAATTCGAATACAC GCTCCCTNNNGATCGACATG | 4215 |
| TGCAGGACCAGAGAATTCGAATACAG TTACGTGNNNGATCGACATG | 3736 | TGCAGGACCAGAGAATTCGAATACAA ATATGGANNNGATCGACATG | 3976 | TGCAGGACCAGAGAATTCGAATACAA GCCTAACNNNGATCGACATG | 4216 |
| TGCAGGACCAGAGAATTCGAATACAG GTCCTGGNNNGATCGACATG | 3737 | TGCAGGACCAGAGAATTCGAATACAT TTCGGTCNNNGATCGACATG | 3977 | TGCAGGACCAGAGAATTCGAATACAC GAGGAATNNNGATCGACATG | 4217 |
| TGCAGGACCAGAGAATTCGAATACAC TGTACAGNNNGATCGACATG | 3738 | TGCAGGACCAGAGAATTCGAATACAT TAGGTTANNNGATCGACATG | 3978 | TGCAGGACCAGAGAATTCGAATACAC CCGAGCANNNGATCGACATG | 4218 |
| TGCAGGACCAGAGAATTCGAATACAG ATAAGTTNNNGATCGACATG | 3739 | TGCAGGACCAGAGAATTCGAATACAA ACGCGTTNNNGATCGACATG | 3979 | TGCAGGACCAGAGAATTCGAATACAT ACAATACNNNGATCGACATG | 4219 |

FIG. 17E

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAAAATCCTANNNGATCGACATG | 3740 | TGCAGGACCAGAGAATTCGAATACAAGGTAAGCNNNGATCGACATG | 3980 | TGCAGGACCAGAGAATTCGAATACATAACATGTNNNGATCGACATG | 4220 |
| TGCAGGACCAGAGAATTCGAATACACATCATGGNNNGATCGACATG | 3741 | TGCAGGACCAGAGAATTCGAATACAAATTGACTNNNGATCGACATG | 3981 | TGCAGGACCAGAGAATTCGAATACAGTTGCGGCNNNGATCGACATG | 4221 |
| TGCAGGACCAGAGAATTCGAATACATTCACTGCNNNGATCGACATG | 3742 | TGCAGGACCAGAGAATTCGAATACAAACTGTANNNGATCGACATG | 3982 | TGCAGGACCAGAGAATTCGAATACATTCTGCAGNNNGATCGACATG | 4222 |
| TGCAGGACCAGAGAATTCGAATACATTGCCGCCNNNGATCGACATG | 3743 | TGCAGGACCAGAGAATTCGAATACATTCTCTGGNNNGATCGACATG | 3983 | TGCAGGACCAGAGAATTCGAATACAGGTTAGTCNNNGATCGACATG | 4223 |
| TGCAGGACCAGAGAATTCGAATACATGTCCTGTNNNGATCGACATG | 3744 | TGCAGGACCAGAGAATTCGAATACAAGAAGAAANNNGATCGACATG | 3984 | TGCAGGACCAGAGAATTCGAATACACTTAAGATNNNGATCGACATG | 4224 |
| TGCAGGACCAGAGAATTCGAATACAGGCGGTCTNNNGATCGACATG | 3745 | TGCAGGACCAGAGAATTCGAATACAAAATGAACNNNGATCGACATG | 3985 | TGCAGGACCAGAGAATTCGAATACACTCCTACANNNGATCGACATG | 4225 |
| TGCAGGACCAGAGAATTCGAATACAACCCACGGNNNGATCGACATG | 3746 | TGCAGGACCAGAGAATTCGAATACAAACACACCNNNGATCGACATG | 3986 | TGCAGGACCAGAGAATTCGAATACAGCTCAGTANNNGATCGACATG | 4226 |
| TGCAGGACCAGAGAATTCGAATACATCCTTTAANNNGATCGACATG | 3747 | TGCAGGACCAGAGAATTCGAATACATAAATGCTNNNGATCGACATG | 3987 | TGCAGGACCAGAGAATTCGAATACAGGTACTACNNNGATCGACATG | 4227 |
| TGCAGGACCAGAGAATTCGAATACATTACAAGTNNNGATCGACATG | 3748 | TGCAGGACCAGAGAATTCGAATACAACCCGTTANNNGATCGACATG | 3988 | TGCAGGACCAGAGAATTCGAATACATAGTATGTNNNGATCGACATG | 4228 |
| TGCAGGACCAGAGAATTCGAATACATCGAGGAANNNGATCGACATG | 3749 | TGCAGGACCAGAGAATTCGAATACACCGGCGTANNNGATCGACATG | 3989 | TGCAGGACCAGAGAATTCGAATACAAAGCATCCNNNGATCGACATG | 4229 |
| TGCAGGACCAGAGAATTCGAATACAGACACTCANNNGATCGACATG | 3750 | TGCAGGACCAGAGAATTCGAATACACGTAGACTNNNGATCGACATG | 3990 | TGCAGGACCAGAGAATTCGAATACAACTAAAAGNNNGATCGACATG | 4230 |
| TGCAGGACCAGAGAATTCGAATACAACTCTAGGNNNGATCGACATG | 3751 | TGCAGGACCAGAGAATTCGAATACAGGAAGTCANNNGATCGACATG | 3991 | TGCAGGACCAGAGAATTCGAATACAACTTTAAGNNNGATCGACATG | 4231 |
| TGCAGGACCAGAGAATTCGAATACATCTTACTNNNGATCGACATG | 3752 | TGCAGGACCAGAGAATTCGAATACAAGAATTGANNNGATCGACATG | 3992 | TGCAGGACCAGAGAATTCGAATACAACGAATAANNNGATCGACATG | 4232 |
| TGCAGGACCAGAGAATTCGAATACAAAGAGAANNNGATCGACATG | 3753 | TGCAGGACCAGAGAATTCGAATACAACCCCTTANNNGATCGACATG | 3993 | TGCAGGACCAGAGAATTCGAATACATAGCGTCANNNGATCGACATG | 4233 |
| TGCAGGACCAGAGAATTCGAATACAACAGCAGANNNGATCGACATG | 3754 | TGCAGGACCAGAGAATTCGAATACATACAGACCNNNGATCGACATG | 3994 | TGCAGGACCAGAGAATTCGAATACAATCATCCCNNNGATCGACATG | 4234 |
| TGCAGGACCAGAGAATTCGAATACATGAGTACCNNNGATCGACATG | 3755 | TGCAGGACCAGAGAATTCGAATACAATTAGACTNNNGATCGACATG | 3995 | TGCAGGACCAGAGAATTCGAATACAAAACAACNNNGATCGACATG | 4235 |
| TGCAGGACCAGAGAATTCGAATACAGACTGTCANNNGATCGACATG | 3756 | TGCAGGACCAGAGAATTCGAATACAAACTAGACNNNGATCGACATG | 3996 | TGCAGGACCAGAGAATTCGAATACACTATCAGGNNNGATCGACATG | 4236 |
| TGCAGGACCAGAGAATTCGAATACATCGAGGCCNNNGATCGACATG | 3757 | TGCAGGACCAGAGAATTCGAATACAGCCCTAAANNNGATCGACATG | 3997 | TGCAGGACCAGAGAATTCGAATACATACTGTCCNNNGATCGACATG | 4237 |
| TGCAGGACCAGAGAATTCGAATACAGTCCATANNNGATCGACATG | 3758 | TGCAGGACCAGAGAATTCGAATACAAGAGTGGTNNNGATCGACATG | 3998 | TGCAGGACCAGAGAATTCGAATACAAGGACACANNNGATCGACATG | 4238 |
| TGCAGGACCAGAGAATTCGAATACAGACTGTTGNNNGATCGACATG | 3759 | TGCAGGACCAGAGAATTCGAATACAATCTGAATNNNGATCGACATG | 3999 | TGCAGGACCAGAGAATTCGAATACACTGACGTNNNGATCGACATG | 4239 |
| TGCAGGACCAGAGAATTCGAATACAACACACTGNNNGATCGACATG | 3760 | TGCAGGACCAGAGAATTCGAATACAAGCATCACNNNGATCGACATG | 4000 | TGCAGGACCAGAGAATTCGAATACACTTGTACCNNNGATCGACATG | 4240 |
| TGCAGGACCAGAGAATTCGAATACAAGGTGACANNNGATCGACATG | 3761 | TGCAGGACCAGAGAATTCGAATACAAATTGGAANNNGATCGACATG | 4001 | TGCAGGACCAGAGAATTCGAATACAGGATGCGGNNNGATCGACATG | 4241 |
| TGCAGGACCAGAGAATTCGAATACAAACAATGNNNGATCGACATG | 3762 | TGCAGGACCAGAGAATTCGAATACACTAGCCCCNNNGATCGACATG | 4002 | TGCAGGACCAGAGAATTCGAATACACTGATTGGNNNGATCGACATG | 4242 |
| TGCAGGACCAGAGAATTCGAATACAGATTTGTANNNGATCGACATG | 3763 | TGCAGGACCAGAGAATTCGAATACATCTTGCTGNNNGATCGACATG | 4003 | TGCAGGACCAGAGAATTCGAATACAGCAACTCANNNGATCGACATG | 4243 |
| TGCAGGACCAGAGAATTCGAATACACCCCCGATNNNGATCGACATG | 3764 | TGCAGGACCAGAGAATTCGAATACACCGTCCTGNNNGATCGACATG | 4004 | TGCAGGACCAGAGAATTCGAATACATACCTCACNNNGATCGACATG | 4244 |
| TGCAGGACCAGAGAATTCGAATACAAGGAGCGCNNNGATCGACATG | 3765 | TGCAGGACCAGAGAATTCGAATACACCTAACGANNNGATCGACATG | 4005 | TGCAGGACCAGAGAATTCGAATACATGCACCCCNNNGATCGACATG | 4245 |
| TGCAGGACCAGAGAATTCGAATACACCCTGGAGNNNGATCGACATG | 3766 | TGCAGGACCAGAGAATTCGAATACAAAAATAGCNNNGATCGACATG | 4006 | TGCAGGACCAGAGAATTCGAATACAGTTCCTACNNNGATCGACATG | 4246 |
| TGCAGGACCAGAGAATTCGAATACACGCACTCCNNNGATCGACATG | 3767 | TGCAGGACCAGAGAATTCGAATACAAAGCACTCNNNGATCGACATG | 4007 | TGCAGGACCAGAGAATTCGAATACATACTGTTTNNNGATCGACATG | 4247 |
| TGCAGGACCAGAGAATTCGAATACAGAAGTCAGNNNGATCGACATG | 3768 | TGCAGGACCAGAGAATTCGAATACAGTTCAACGNNNGATCGACATG | 4008 | TGCAGGACCAGAGAATTCGAATACACTTCATATNNNGATCGACATG | 4248 |
| TGCAGGACCAGAGAATTCGAATACAGGCGTCGTNNNGATCGACATG | 3769 | TGCAGGACCAGAGAATTCGAATACACGTCTGTTNNNGATCGACATG | 4009 | TGCAGGACCAGAGAATTCGAATACATCTGCTGTNNNGATCGACATG | 4249 |
| TGCAGGACCAGAGAATTCGAATACACATTGTCNNNGATCGACATG | 3770 | TGCAGGACCAGAGAATTCGAATACAGCACGGCTNNNGATCGACATG | 4010 | TGCAGGACCAGAGAATTCGAATACATGGTATTANNNGATCGACATG | 4250 |
| TGCAGGACCAGAGAATTCGAATACATAGTAACTNNNGATCGACATG | 3771 | TGCAGGACCAGAGAATTCGAATACAACCCAAACNNNGATCGACATG | 4011 | TGCAGGACCAGAGAATTCGAATACAAGAATGTANNNGATCGACATG | 4251 |
| TGCAGGACCAGAGAATTCGAATACATAGATGTTNNNGATCGACATG | 3772 | TGCAGGACCAGAGAATTCGAATACACATAAACTNNNGATCGACATG | 4012 | TGCAGGACCAGAGAATTCGAATACAGGCGAGCANNNGATCGACATG | 4252 |

FIG. 17F

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAAATGAGCGNNNGATCGACATG | 3773 | TGCAGGACCAGAGAATTCGAATACATCCGTAAGCNNNGATCGACATG | 4013 | TGCAGGACCAGAGAATTCGAATACAGCCACAATNNNGATCGACATG | 4253 |
| TGCAGGACCAGAGAATTCGAATACAACTTGCGANNNGATCGACATG | 3774 | TGCAGGACCAGAGAATTCGAATACAGAGCTTGTNNNGATCGACATG | 4014 | TGCAGGACCAGAGAATTCGAATACATATTCTCANNNGATCGACATG | 4254 |
| TGCAGGACCAGAGAATTCGAATACAGGCGTACCNNNGATCGACATG | 3775 | TGCAGGACCAGAGAATTCGAATACATTTTTGTTNNNGATCGACATG | 4015 | TGCAGGACCAGAGAATTCGAATACAAAGACCTCNNNGATCGACATG | 4255 |
| TGCAGGACCAGAGAATTCGAATACAGGTCACATNNNGATCGACATG | 3776 | TGCAGGACCAGAGAATTCGAATACATGAGTAGGNNNGATCGACATG | 4016 | TGCAGGACCAGAGAATTCGAATACACACATAATNNNGATCGACATG | 4256 |
| TGCAGGACCAGAGAATTCGAATACACACTTAAANNNGATCGACATG | 3777 | TGCAGGACCAGAGAATTCGAATACATGAGTCTGNNNGATCGACATG | 4017 | TGCAGGACCAGAGAATTCGAATACAACCCTGAANNNGATCGACATG | 4257 |
| TGCAGGACCAGAGAATTCGAATACATTTACCTANNNGATCGACATG | 3778 | TGCAGGACCAGAGAATTCGAATACAAGAAGCTGNNNGATCGACATG | 4018 | TGCAGGACCAGAGAATTCGAATACAGTAGACCTNNNGATCGACATG | 4258 |
| TGCAGGACCAGAGAATTCGAATACAAGTTTGGCNNNGATCGACATG | 3779 | TGCAGGACCAGAGAATTCGAATACATAGAAGCGNNNGATCGACATG | 4019 | TGCAGGACCAGAGAATTCGAATACACCCTACCGNNNGATCGACATG | 4259 |
| TGCAGGACCAGAGAATTCGAATACAGAGACATGNNNGATCGACATG | 3780 | TGCAGGACCAGAGAATTCGAATACAGCTTATGNNNGATCGACATG | 4020 | TGCAGGACCAGAGAATTCGAATACATATCCCACNNNGATCGACATG | 4260 |
| TGCAGGACCAGAGAATTCGAATACAGAGGCATANNNGATCGACATG | 3781 | TGCAGGACCAGAGAATTCGAATACAGGCATATCNNNGATCGACATG | 4021 | TGCAGGACCAGAGAATTCGAATACAAGTCATTANNNGATCGACATG | 4261 |
| TGCAGGACCAGAGAATTCGAATACACCTGCTCGNNNGATCGACATG | 3782 | TGCAGGACCAGAGAATTCGAATACATCCGCTTANNNGATCGACATG | 4022 | TGCAGGACCAGAGAATTCGAATACAGGAACAACNNNGATCGACATG | 4262 |
| TGCAGGACCAGAGAATTCGAATACATTGCTAGGNNNGATCGACATG | 3783 | TGCAGGACCAGAGAATTCGAATACATTTATAGGNNNGATCGACATG | 4023 | TGCAGGACCAGAGAATTCGAATACAATCTCTGCNNNGATCGACATG | 4263 |
| TGCAGGACCAGAGAATTCGAATACATCCCGACNNNGATCGACATG | 3784 | TGCAGGACCAGAGAATTCGAATACAATGCTTAANNNGATCGACATG | 4024 | TGCAGGACCAGAGAATTCGAATACACTGTACCTNNNGATCGACATG | 4264 |
| TGCAGGACCAGAGAATTCGAATACACACGAATCNNNGATCGACATG | 3785 | TGCAGGACCAGAGAATTCGAATACATGACGTACNNNGATCGACATG | 4025 | TGCAGGACCAGAGAATTCGAATACAGATCCAGTNNNGATCGACATG | 4265 |
| TGCAGGACCAGAGAATTCGAATACAGCGTCGCANNNGATCGACATG | 3786 | TGCAGGACCAGAGAATTCGAATACAAGAGAAANNNGATCGACATG | 4026 | TGCAGGACCAGAGAATTCGAATACATAAGTTCANNNGATCGACATG | 4266 |
| TGCAGGACCAGAGAATTCGAATACAAATCCAATNNNGATCGACATG | 3787 | TGCAGGACCAGAGAATTCGAATACATGTCTCGTNNNGATCGACATG | 4027 | TGCAGGACCAGAGAATTCGAATACACCGTTAGANNNGATCGACATG | 4267 |
| TGCAGGACCAGAGAATTCGAATACACGCGAACCNNNGATCGACATG | 3788 | TGCAGGACCAGAGAATTCGAATACACGTTATGGNNNGATCGACATG | 4028 | TGCAGGACCAGAGAATTCGAATACAAAGAGACCNNNGATCGACATG | 4268 |
| TGCAGGACCAGAGAATTCGAATACATATGATCANNNTGCATCAGGT | 3789 | TGCAGGACCAGAGAATTCGAATACATATTGAGTNNNTGCATCAGGT | 4029 | TGCAGGACCAGAGAATTCGAATACACGCCCTACNNNTGCATCAGGT | 4269 |
| TGCAGGACCAGAGAATTCGAATACATTGGCACANNNTGCATCAGGT | 3790 | TGCAGGACCAGAGAATTCGAATACAAATAGAGTNNNTGCATCAGGT | 4030 | TGCAGGACCAGAGAATTCGAATACAGACGGCCTNNNTGCATCAGGT | 4270 |
| TGCAGGACCAGAGAATTCGAATACACTACACCTNNNTGCATCAGGT | 3791 | TGCAGGACCAGAGAATTCGAATACACAGACATCNNNTGCATCAGGT | 4031 | TGCAGGACCAGAGAATTCGAATACACGCGGAGANNNTGCATCAGGT | 4271 |
| TGCAGGACCAGAGAATTCGAATACATTAGAGTTNNNTGCATCAGGT | 3792 | TGCAGGACCAGAGAATTCGAATACAGAAGCCAANNNTGCATCAGGT | 4032 | TGCAGGACCAGAGAATTCGAATACAGCGATAAGNNNTGCATCAGGT | 4272 |
| TGCAGGACCAGAGAATTCGAATACAGGTGTTGTNNNTGCATCAGGT | 3793 | TGCAGGACCAGAGAATTCGAATACACAGTCCANNNTGCATCAGGT | 4033 | TGCAGGACCAGAGAATTCGAATACAACGCTAGTNNNTGCATCAGGT | 4273 |
| TGCAGGACCAGAGAATTCGAATACACCAGACGCNNNTGCATCAGGT | 3794 | TGCAGGACCAGAGAATTCGAATACATTCCGACTNNNTGCATCAGGT | 4034 | TGCAGGACCAGAGAATTCGAATACATTTGAATGNNNTGCATCAGGT | 4274 |
| TGCAGGACCAGAGAATTCGAATACATGTTGGCANNNTGCATCAGGT | 3795 | TGCAGGACCAGAGAATTCGAATACAACAGTATTNNNTGCATCAGGT | 4035 | TGCAGGACCAGAGAATTCGAATACATATTAAATNNNTGCATCAGGT | 4275 |
| TGCAGGACCAGAGAATTCGAATACATCTTCCTCNNNTGCATCAGGT | 3796 | TGCAGGACCAGAGAATTCGAATACAGAGAATATNNNTGCATCAGGT | 4036 | TGCAGGACCAGAGAATTCGAATACACGTGTTGANNNTGCATCAGGT | 4276 |
| TGCAGGACCAGAGAATTCGAATACACAAGATAANNNTGCATCAGGT | 3797 | TGCAGGACCAGAGAATTCGAATACAAGTAAGGCNNNTGCATCAGGT | 4037 | TGCAGGACCAGAGAATTCGAATACAAAGCTTATNNNTGCATCAGGT | 4277 |
| TGCAGGACCAGAGAATTCGAATACATACTAGCGNNNTGCATCAGGT | 3798 | TGCAGGACCAGAGAATTCGAATACAAGCGTATCNNNTGCATCAGGT | 4038 | TGCAGGACCAGAGAATTCGAATACACCCCGACTNNNTGCATCAGGT | 4278 |
| TGCAGGACCAGAGAATTCGAATACAGACACAAGNNNTGCATCAGGT | 3799 | TGCAGGACCAGAGAATTCGAATACATACGGTTGNNNTGCATCAGGT | 4039 | TGCAGGACCAGAGAATTCGAATACAGTCGTCAANNNTGCATCAGGT | 4279 |
| TGCAGGACCAGAGAATTCGAATACAGTTACCTCNNNTGCATCAGGT | 3800 | TGCAGGACCAGAGAATTCGAATACAAACGAAGGNNNTGCATCAGGT | 4040 | TGCAGGACCAGAGAATTCGAATACATACATCCGNNNTGCATCAGGT | 4280 |
| TGCAGGACCAGAGAATTCGAATACATCTACCACNNNTGCATCAGGT | 3801 | TGCAGGACCAGAGAATTCGAATACACATTGGACNNNTGCATCAGGT | 4041 | TGCAGGACCAGAGAATTCGAATACAGACTTTCNNNTGCATCAGGT | 4281 |
| TGCAGGACCAGAGAATTCGAATACATAGTCGTGNNNTGCATCAGGT | 3802 | TGCAGGACCAGAGAATTCGAATACATAAGGCTCNNNTGCATCAGGT | 4042 | TGCAGGACCAGAGAATTCGAATACATGCCCTATNNNTGCATCAGGT | 4282 |
| TGCAGGACCAGAGAATTCGAATACAAATGCAGGNNNTGCATCAGGT | 3803 | TGCAGGACCAGAGAATTCGAATACACGAAGCGGNNNTGCATCAGGT | 4043 | TGCAGGACCAGAGAATTCGAATACATGACGGAANNNTGCATCAGGT | 4283 |
| TGCAGGACCAGAGAATTCGAATACACATGGACTNNNTGCATCAGGT | 3804 | TGCAGGACCAGAGAATTCGAATACAGACGATTCNNNTGCATCAGGT | 4044 | TGCAGGACCAGAGAATTCGAATACAGCTGCCAGNNNTGCATCAGGT | 4284 |
| TGCAGGACCAGAGAATTCGAATACATTGCGAGTNNNTGCATCAGGT | 3805 | TGCAGGACCAGAGAATTCGAATACAGTCGATACNNNTGCATCAGGT | 4045 | TGCAGGACCAGAGAATTCGAATACATCATATAGNNNTGCATCAGGT | 4285 |

FIG. 17G

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAT TGCAAGCNNNTGCATCAGGT | 3806 | TGCAGGACCAGAGAATTCGAATACAC ATCAATANNNTGCATCAGGT | 4046 | TGCAGGACCAGAGAATTCGAATACAT GTGCGATNNNTGCATCAGGT | 4286 |
| TGCAGGACCAGAGAATTCGAATACAC CTCGGAGNNNTGCATCAGGT | 3807 | TGCAGGACCAGAGAATTCGAATACAC ACACATGNNNTGCATCAGGT | 4047 | TGCAGGACCAGAGAATTCGAATACAC ACGATCANNNTGCATCAGGT | 4287 |
| TGCAGGACCAGAGAATTCGAATACAT AACATTGNNNTGCATCAGGT | 3808 | TGCAGGACCAGAGAATTCGAATACAC CAGCGAGNNNTGCATCAGGT | 4048 | TGCAGGACCAGAGAATTCGAATACAG ACTGCCGNNNTGCATCAGGT | 4288 |
| TGCAGGACCAGAGAATTCGAATACAG AGGTTAGNNNTGCATCAGGT | 3809 | TGCAGGACCAGAGAATTCGAATACAT ACGGCTANNNTGCATCAGGT | 4049 | TGCAGGACCAGAGAATTCGAATACAC TGGTCATNNNTGCATCAGGT | 4289 |
| TGCAGGACCAGAGAATTCGAATACAA GAAACTANNNTGCATCAGGT | 3810 | TGCAGGACCAGAGAATTCGAATACAC AGCAGAANNNTGCATCAGGT | 4050 | TGCAGGACCAGAGAATTCGAATACAT GTGAGCTNNNTGCATCAGGT | 4290 |
| TGCAGGACCAGAGAATTCGAATACAT CCACCTANNNTGCATCAGGT | 3811 | TGCAGGACCAGAGAATTCGAATACAA AGATTAGNNNTGCATCAGGT | 4051 | TGCAGGACCAGAGAATTCGAATACAA ACCGTCANNNTGCATCAGGT | 4291 |
| TGCAGGACCAGAGAATTCGAATACAT CCTTCCTNNNTGCATCAGGT | 3812 | TGCAGGACCAGAGAATTCGAATACAC CAAAGACNNNTGCATCAGGT | 4052 | TGCAGGACCAGAGAATTCGAATACAA TTACAGTNNNTGCATCAGGT | 4292 |
| TGCAGGACCAGAGAATTCGAATACAA ACTCCGANNNTGCATCAGGT | 3813 | TGCAGGACCAGAGAATTCGAATACAA TAAACAGNNNTGCATCAGGT | 4053 | TGCAGGACCAGAGAATTCGAATACAG CAATAAANNNTGCATCAGGT | 4293 |
| TGCAGGACCAGAGAATTCGAATACAA ATTAGCTNNNTGCATCAGGT | 3814 | TGCAGGACCAGAGAATTCGAATACAT TCCAAAANNNTGCATCAGGT | 4054 | TGCAGGACCAGAGAATTCGAATACAA GCTTAGCNNNTGCATCAGGT | 4294 |
| TGCAGGACCAGAGAATTCGAATACAA TAGTAAGNNNTGCATCAGGT | 3815 | TGCAGGACCAGAGAATTCGAATACAT GGTATCGNNNTGCATCAGGT | 4055 | TGCAGGACCAGAGAATTCGAATACAT CATTGCCNNNTGCATCAGGT | 4295 |
| TGCAGGACCAGAGAATTCGAATACAG TTTTACTNNNTGCATCAGGT | 3816 | TGCAGGACCAGAGAATTCGAATACAA ACACTTANNNTGCATCAGGT | 4056 | TGCAGGACCAGAGAATTCGAATACAC ACTATAANNNTGCATCAGGT | 4296 |
| TGCAGGACCAGAGAATTCGAATACAC GCAATTGNNNTGCATCAGGT | 3817 | TGCAGGACCAGAGAATTCGAATACAA CCGTGGCNNNTGCATCAGGT | 4057 | TGCAGGACCAGAGAATTCGAATACAC TGCGTCCNNNTGCATCAGGT | 4297 |
| TGCAGGACCAGAGAATTCGAATACAC GAGGCGTNNNTGCATCAGGT | 3818 | TGCAGGACCAGAGAATTCGAATACAA GTCTAGCNNNTGCATCAGGT | 4058 | TGCAGGACCAGAGAATTCGAATACAC GATGACANNNTGCATCAGGT | 4298 |
| TGCAGGACCAGAGAATTCGAATACAG TAACTGCNNNTGCATCAGGT | 3819 | TGCAGGACCAGAGAATTCGAATACAA GACTCCANNNTGCATCAGGT | 4059 | TGCAGGACCAGAGAATTCGAATACAT AGAAGGCNNNTGCATCAGGT | 4299 |
| TGCAGGACCAGAGAATTCGAATACAT GTCAACGNNNTGCATCAGGT | 3820 | TGCAGGACCAGAGAATTCGAATACAC CAGGATTNNNTGCATCAGGT | 4060 | TGCAGGACCAGAGAATTCGAATACAA TACACCGNNNTGCATCAGGT | 4300 |
| TGCAGGACCAGAGAATTCGAATACAC GATTTTTNNNTGCATCAGGT | 3821 | TGCAGGACCAGAGAATTCGAATACAA GAATGATNNNTGCATCAGGT | 4061 | TGCAGGACCAGAGAATTCGAATACAT CCAGCAANNNTGCATCAGGT | 4301 |
| TGCAGGACCAGAGAATTCGAATACAC CGTATTCNNNTGCATCAGGT | 3822 | TGCAGGACCAGAGAATTCGAATACAA CGACATCNNNTGCATCAGGT | 4062 | TGCAGGACCAGAGAATTCGAATACAG TGTTCCTNNNTGCATCAGGT | 4302 |
| TGCAGGACCAGAGAATTCGAATACAG CCGCGATNNNTGCATCAGGT | 3823 | TGCAGGACCAGAGAATTCGAATACAG TAAAAACNNNTGCATCAGGT | 4063 | TGCAGGACCAGAGAATTCGAATACAG AAACGTGNNNTGCATCAGGT | 4303 |
| TGCAGGACCAGAGAATTCGAATACAG GCCCTAGNNNTGCATCAGGT | 3824 | TGCAGGACCAGAGAATTCGAATACAA TTAACACNNNTGCATCAGGT | 4064 | TGCAGGACCAGAGAATTCGAATACAC CCTCTAANNNTGCATCAGGT | 4304 |
| TGCAGGACCAGAGAATTCGAATACAA ACAGGCANNNTGCATCAGGT | 3825 | TGCAGGACCAGAGAATTCGAATACAA CAAATTCNNNTGCATCAGGT | 4065 | TGCAGGACCAGAGAATTCGAATACAA CCGAGCCNNNTGCATCAGGT | 4305 |
| TGCAGGACCAGAGAATTCGAATACAA CCTATGGNNNTGCATCAGGT | 3826 | TGCAGGACCAGAGAATTCGAATACAC GTCCATTNNNTGCATCAGGT | 4066 | TGCAGGACCAGAGAATTCGAATACAG CGCCCTTNNNTGCATCAGGT | 4306 |
| TGCAGGACCAGAGAATTCGAATACAT GTGTCGANNNTGCATCAGGT | 3827 | TGCAGGACCAGAGAATTCGAATACAA GAAATCANNNTGCATCAGGT | 4067 | TGCAGGACCAGAGAATTCGAATACAA AATAGACNNNTGCATCAGGT | 4307 |
| TGCAGGACCAGAGAATTCGAATACAG TGGATTCNNNTGCATCAGGT | 3828 | TGCAGGACCAGAGAATTCGAATACAA AATCACTNNNTGCATCAGGT | 4068 | TGCAGGACCAGAGAATTCGAATACAT GACACTGNNNTGCATCAGGT | 4308 |
| TGCAGGACCAGAGAATTCGAATACAT CGGACCGNNNTGCATCAGGT | 3829 | TGCAGGACCAGAGAATTCGAATACAC TCCACGCNNNTGCATCAGGT | 4069 | TGCAGGACCAGAGAATTCGAATACAG GCGCGAGNNNTGCATCAGGT | 4309 |
| TGCAGGACCAGAGAATTCGAATACAA AACATAGNNNTGCATCAGGT | 3830 | TGCAGGACCAGAGAATTCGAATACAG AATAATGNNNTGCATCAGGT | 4070 | TGCAGGACCAGAGAATTCGAATACAG CAGAAGTNNNTGCATCAGGT | 4310 |
| TGCAGGACCAGAGAATTCGAATACAA GAAGCGTNNNTGCATCAGGT | 3831 | TGCAGGACCAGAGAATTCGAATACAT GTGACCANNNTGCATCAGGT | 4071 | TGCAGGACCAGAGAATTCGAATACAG GCTGATTNNNTGCATCAGGT | 4311 |
| TGCAGGACCAGAGAATTCGAATACAC CCTCACGNNNTGCATCAGGT | 3832 | TGCAGGACCAGAGAATTCGAATACAT CGATTAANNNTGCATCAGGT | 4072 | TGCAGGACCAGAGAATTCGAATACAG TAGAATANNNTGCATCAGGT | 4312 |
| TGCAGGACCAGAGAATTCGAATACAA ACTGTCGNNNTGCATCAGGT | 3833 | TGCAGGACCAGAGAATTCGAATACAC GCCAAATNNNTGCATCAGGT | 4073 | TGCAGGACCAGAGAATTCGAATACAC CATCGAANNNTGCATCAGGT | 4313 |
| TGCAGGACCAGAGAATTCGAATACAT CTTGGAGNNNTGCATCAGGT | 3834 | TGCAGGACCAGAGAATTCGAATACAC TTGTAAANNNTGCATCAGGT | 4074 | TGCAGGACCAGAGAATTCGAATACAT TGCCTACNNNTGCATCAGGT | 4314 |
| TGCAGGACCAGAGAATTCGAATACAG TGAAATANNNTGCATCAGGT | 3835 | TGCAGGACCAGAGAATTCGAATACAA ATTAGAGNNNTGCATCAGGT | 4075 | TGCAGGACCAGAGAATTCGAATACAA CTCCCATNNNTGCATCAGGT | 4315 |
| TGCAGGACCAGAGAATTCGAATACAT GCTTCTGNNNTGCATCAGGT | 3836 | TGCAGGACCAGAGAATTCGAATACAT AGCTTGGNNNTGCATCAGGT | 4076 | TGCAGGACCAGAGAATTCGAATACAA TTTCCACNNNTGCATCAGGT | 4316 |
| TGCAGGACCAGAGAATTCGAATACAT GACTTCCNNNTGCATCAGGT | 3837 | TGCAGGACCAGAGAATTCGAATACAA TAGGAGCNNNTGCATCAGGT | 4077 | TGCAGGACCAGAGAATTCGAATACAG ATATTGTNNNTGCATCAGGT | 4317 |
| TGCAGGACCAGAGAATTCGAATACAC CCGGATGNNNTGCATCAGGT | 3838 | TGCAGGACCAGAGAATTCGAATACAT TATACTCNNNTGCATCAGGT | 4078 | TGCAGGACCAGAGAATTCGAATACAA CTGAGGANNNTGCATCAGGT | 4318 |

FIG. 17H

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAGAGGACATNNNTGCATCAGGT | 3839 | TGCAGGACCAGAGAATTCGAATACATTGTTGCCNNNTGCATCAGGT | 4079 | TGCAGGACCAGAGAATTCGAATACAGTAGTCTGNNNTGCATCAGGT | 4319 |
| TGCAGGACCAGAGAATTCGAATACACAGGTATCNNNTGCATCAGGT | 3840 | TGCAGGACCAGAGAATTCGAATACATTCCGAGANNNTGCATCAGGT | 4080 | TGCAGGACCAGAGAATTCGAATACATGTAAATCNNNTGCATCAGGT | 4320 |
| TGCAGGACCAGAGAATTCGAATACAGTAGTATTNNNTGCATCAGGT | 3841 | TGCAGGACCAGAGAATTCGAATACAATCCCATCNNNTGCATCAGGT | 4081 | TGCAGGACCAGAGAATTCGAATACAGCATATGCNNNTGCATCAGGT | 4321 |
| TGCAGGACCAGAGAATTCGAATACAAAGGAGGANNNTGCATCAGGT | 3842 | TGCAGGACCAGAGAATTCGAATACATTTGCCACNNNTGCATCAGGT | 4082 | TGCAGGACCAGAGAATTCGAATACAATTCGTAANNNTGCATCAGGT | 4322 |
| TGCAGGACCAGAGAATTCGAATACAAAGAGCCANNNTGCATCAGGT | 3843 | TGCAGGACCAGAGAATTCGAATACAGTGAGCGGNNNTGCATCAGGT | 4083 | TGCAGGACCAGAGAATTCGAATACAAATCCACGNNNTGCATCAGGT | 4323 |
| TGCAGGACCAGAGAATTCGAATACAGTCTCTCANNNTGCATCAGGT | 3844 | TGCAGGACCAGAGAATTCGAATACATCGCATCTNNNTGCATCAGGT | 4084 | TGCAGGACCAGAGAATTCGAATACAGCGCCGCGNNNTGCATCAGGT | 4324 |
| TGCAGGACCAGAGAATTCGAATACAACGGTGTTNNNTGCATCAGGT | 3845 | TGCAGGACCAGAGAATTCGAATACATCTGCAGNNNTGCATCAGGT | 4085 | TGCAGGACCAGAGAATTCGAATACAGGCTCTGACNNNTGCATCAGGT | 4325 |
| TGCAGGACCAGAGAATTCGAATACACGTACGATNNNTGCATCAGGT | 3846 | TGCAGGACCAGAGAATTCGAATACAGCCCAAGCNNNTGCATCAGGT | 4086 | TGCAGGACCAGAGAATTCGAATACAACCCCGAGNNNTGCATCAGGT | 4326 |
| TGCAGGACCAGAGAATTCGAATACAGAGGTGTANNNTGCATCAGGT | 3847 | TGCAGGACCAGAGAATTCGAATACATTTCTCGGNNNTGCATCAGGT | 4087 | TGCAGGACCAGAGAATTCGAATACAAGTCACCANNNTGCATCAGGT | 4327 |
| TGCAGGACCAGAGAATTCGAATACACACCACAANNNTGCATCAGGT | 3848 | TGCAGGACCAGAGAATTCGAATACAGGCCTACGNNNTGCATCAGGT | 4088 | TGCAGGACCAGAGAATTCGAATACAAAAATTCNNNTGCATCAGGT | 4328 |

FIG. 18A

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGCCCTCTGNNNACGTATGCCA | 4329 | TGCAGGACCAGAGAATTCGAATA CATGTTGTCCNNNACGTATGCCA | 4569 | TGCAGGACCAGAGAATTCGAATA CATGAAACAANNNACGTATGCCA | 4809 |
| TGCAGGACCAGAGAATTCGAATA CAGCAAAGGTNNNACGTATGCCA | 4330 | TGCAGGACCAGAGAATTCGAATA CATAACCAGCNNNACGTATGCCA | 4570 | TGCAGGACCAGAGAATTCGAATA CACCCGTTGCNNNACGTATGCCA | 4810 |
| TGCAGGACCAGAGAATTCGAATA CATTTCTATGNNNACGTATGCCA | 4331 | TGCAGGACCAGAGAATTCGAATA CATGCCGCGANNNACGTATGCCA | 4571 | TGCAGGACCAGAGAATTCGAATA CAGCATTGGTNNNACGTATGCCA | 4811 |
| TGCAGGACCAGAGAATTCGAATA CACGTGCAATNNNACGTATGCCA | 4332 | TGCAGGACCAGAGAATTCGAATA CAATCGTCTCNNNACGTATGCCA | 4572 | TGCAGGACCAGAGAATTCGAATA CATAGGCCATNNNACGTATGCCA | 4812 |
| TGCAGGACCAGAGAATTCGAATA CAGTTTAGGCNNNACGTATGCCA | 4333 | TGCAGGACCAGAGAATTCGAATA CATCCGCACCNNNACGTATGCCA | 4573 | TGCAGGACCAGAGAATTCGAATA CAACTCCTCANNNACGTATGCCA | 4813 |
| TGCAGGACCAGAGAATTCGAATA CAAAAATGACNNNACGTATGCCA | 4334 | TGCAGGACCAGAGAATTCGAATA CATTACTGAANNNACGTATGCCA | 4574 | TGCAGGACCAGAGAATTCGAATA CACTAGGCGCNNNACGTATGCCA | 4814 |
| TGCAGGACCAGAGAATTCGAATA CACTACTAGGNNNACGTATGCCA | 4335 | TGCAGGACCAGAGAATTCGAATA CAAGGTCCGCNNNACGTATGCCA | 4575 | TGCAGGACCAGAGAATTCGAATA CAAGTTTAGTNNNACGTATGCCA | 4815 |
| TGCAGGACCAGAGAATTCGAATA CACACCCAGGNNNACGTATGCCA | 4336 | TGCAGGACCAGAGAATTCGAATA CAGTGCCCTCNNNACGTATGCCA | 4576 | TGCAGGACCAGAGAATTCGAATA CATTGATACANNNACGTATGCCA | 4816 |
| TGCAGGACCAGAGAATTCGAATA CAGCCGCCTTNNNACGTATGCCA | 4337 | TGCAGGACCAGAGAATTCGAATA CAGCGTAGCCNNNACGTATGCCA | 4577 | TGCAGGACCAGAGAATTCGAATA CAACAATTACNNNACGTATGCCA | 4817 |
| TGCAGGACCAGAGAATTCGAATA CACAACGTCANNNACGTATGCCA | 4338 | TGCAGGACCAGAGAATTCGAATA CATAGCCAACNNNACGTATGCCA | 4578 | TGCAGGACCAGAGAATTCGAATA CAATACCGGTNNNACGTATGCCA | 4818 |
| TGCAGGACCAGAGAATTCGAATA CATCTCAAGGNNNACGTATGCCA | 4339 | TGCAGGACCAGAGAATTCGAATA CAATATACCANNNACGTATGCCA | 4579 | TGCAGGACCAGAGAATTCGAATA CATGAAGCCTNNNACGTATGCCA | 4819 |
| TGCAGGACCAGAGAATTCGAATA CATCATAAACNNNACGTATGCCA | 4340 | TGCAGGACCAGAGAATTCGAATA CATAAAATCCNNNACGTATGCCA | 4580 | TGCAGGACCAGAGAATTCGAATA CATTACCTGCNNNACGTATGCCA | 4820 |
| TGCAGGACCAGAGAATTCGAATA CATCCTCCCCNNNACGTATGCCA | 4341 | TGCAGGACCAGAGAATTCGAATA CAGATGGTGANNNACGTATGCCA | 4581 | TGCAGGACCAGAGAATTCGAATA CATATCAGATNNNACGTATGCCA | 4821 |
| TGCAGGACCAGAGAATTCGAATA CAAGTAACCCNNNACGTATGCCA | 4342 | TGCAGGACCAGAGAATTCGAATA CAGAACGTAGNNNACGTATGCCA | 4582 | TGCAGGACCAGAGAATTCGAATA CAGAAGAATTNNNACGTATGCCA | 4822 |
| TGCAGGACCAGAGAATTCGAATA CAGTGACAAGNNNACGTATGCCA | 4343 | TGCAGGACCAGAGAATTCGAATA CAATATTAATNNNACGTATGCCA | 4583 | TGCAGGACCAGAGAATTCGAATA CAGATCACGTNNNACGTATGCCA | 4823 |
| TGCAGGACCAGAGAATTCGAATA CAGCAATACCNNNACGTATGCCA | 4344 | TGCAGGACCAGAGAATTCGAATA CATACTGAATNNNACGTATGCCA | 4584 | TGCAGGACCAGAGAATTCGAATA CAAGGTAGACNNNACGTATGCCA | 4824 |
| TGCAGGACCAGAGAATTCGAATA CAAATACGTTNNNACGTATGCCA | 4345 | TGCAGGACCAGAGAATTCGAATA CAGTCCGAGCNNNACGTATGCCA | 4585 | TGCAGGACCAGAGAATTCGAATA CATTGACCGANNNACGTATGCCA | 4825 |
| TGCAGGACCAGAGAATTCGAATA CACCATGTAGNNNACGTATGCCA | 4346 | TGCAGGACCAGAGAATTCGAATA CACCTGGTAANNNACGTATGCCA | 4586 | TGCAGGACCAGAGAATTCGAATA CACCACTGTTNNNACGTATGCCA | 4826 |
| TGCAGGACCAGAGAATTCGAATA CACCCAACGGNNNACGTATGCCA | 4347 | TGCAGGACCAGAGAATTCGAATA CACCCTAGAANNNACGTATGCCA | 4587 | TGCAGGACCAGAGAATTCGAATA CAGTCAGAAGNNNACGTATGCCA | 4827 |
| TGCAGGACCAGAGAATTCGAATA CAGCGCGTTGCNNNACGTATGCCA | 4348 | TGCAGGACCAGAGAATTCGAATA CATTAAAGTCNNNACGTATGCCA | 4588 | TGCAGGACCAGAGAATTCGAATA CACCGACCTCNNNACGTATGCCA | 4828 |
| TGCAGGACCAGAGAATTCGAATA CAGTGATCTGNNNACGTATGCCA | 4349 | TGCAGGACCAGAGAATTCGAATA CAACCTGTGCNNNACGTATGCCA | 4589 | TGCAGGACCAGAGAATTCGAATA CAATTAGTGTNNNACGTATGCCA | 4829 |
| TGCAGGACCAGAGAATTCGAATA CATAAGCCGTNNNACGTATGCCA | 4350 | TGCAGGACCAGAGAATTCGAATA CAGCTATCCTNNNACGTATGCCA | 4590 | TGCAGGACCAGAGAATTCGAATA CAGCATACCANNNACGTATGCCA | 4830 |
| TGCAGGACCAGAGAATTCGAATA CATGTTTGTTNNNACGTATGCCA | 4351 | TGCAGGACCAGAGAATTCGAATA CAAGCGTTGTNNNACGTATGCCA | 4591 | TGCAGGACCAGAGAATTCGAATA CAAGTTTTCTNNNACGTATGCCA | 4831 |
| TGCAGGACCAGAGAATTCGAATA CAACGAGCGGNNNACGTATGCCA | 4352 | TGCAGGACCAGAGAATTCGAATA CACTTCGCTANNNACGTATGCCA | 4592 | TGCAGGACCAGAGAATTCGAATA CATTCGCGTTNNNACGTATGCCA | 4832 |
| TGCAGGACCAGAGAATTCGAATA CATAGATCGCNNNACGTATGCCA | 4353 | TGCAGGACCAGAGAATTCGAATA CACATTTTGTNNNACGTATGCCA | 4593 | TGCAGGACCAGAGAATTCGAATA CATGGAGCCCNNNACGTATGCCA | 4833 |
| TGCAGGACCAGAGAATTCGAATA CATGATACGCNNNACGTATGCCA | 4354 | TGCAGGACCAGAGAATTCGAATA CAAACTTCGGNNNACGTATGCCA | 4594 | TGCAGGACCAGAGAATTCGAATA CACGTGGCACNNNACGTATGCCA | 4834 |
| TGCAGGACCAGAGAATTCGAATA CATAGTTACANNNACGTATGCCA | 4355 | TGCAGGACCAGAGAATTCGAATA CATACCGTGANNNACGTATGCCA | 4595 | TGCAGGACCAGAGAATTCGAATA CATCTTACTANNNACGTATGCCA | 4835 |
| TGCAGGACCAGAGAATTCGAATA CACTTGGTGANNNACGTATGCCA | 4356 | TGCAGGACCAGAGAATTCGAATA CAAGCTTTTTNNNACGTATGCCA | 4596 | TGCAGGACCAGAGAATTCGAATA CAATCCGGTANNNACGTATGCCA | 4836 |
| TGCAGGACCAGAGAATTCGAATA CATTAATCTCNNNACGTATGCCA | 4357 | TGCAGGACCAGAGAATTCGAATA CATGTTCTCGNNNACGTATGCCA | 4597 | TGCAGGACCAGAGAATTCGAATA CAGACACCTANNNACGTATGCCA | 4837 |
| TGCAGGACCAGAGAATTCGAATA CATTAGACCTNNNACGTATGCCA | 4358 | TGCAGGACCAGAGAATTCGAATA CAAATCGCGTNNNACGTATGCCA | 4598 | TGCAGGACCAGAGAATTCGAATA CATCCGTCTANNNACGTATGCCA | 4838 |
| TGCAGGACCAGAGAATTCGAATA CAACACCAGTNNNACGTATGCCA | 4359 | TGCAGGACCAGAGAATTCGAATA CATGAACCACNNNACGTATGCCA | 4599 | TGCAGGACCAGAGAATTCGAATA CAAGATTACTNNNACGTATGCCA | 4839 |
| TGCAGGACCAGAGAATTCGAATA CAACCAGGAANNNACGTATGCCA | 4360 | TGCAGGACCAGAGAATTCGAATA CAATTTCATNNNACGTATGCCA | 4600 | TGCAGGACCAGAGAATTCGAATA CAAGATTGAANNNACGTATGCCA | 4840 |
| TGCAGGACCAGAGAATTCGAATA CAATGCATGCNNNACGTATGCCA | 4361 | TGCAGGACCAGAGAATTCGAATA CACAGTCACANNNACGTATGCCA | 4601 | TGCAGGACCAGAGAATTCGAATA CATTTAAAGCNNNACGTATGCCA | 4841 |

FIG. 18B

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CATACACATANNNACGTATGCCA | 4362 | TGCAGGACCAGAGAATTCGAATA CACCCATAGANNNACGTATGCCA | 4602 | TGCAGGACCAGAGAATTCGAATA CAGAATTGCCNNNACGTATGCCA | 4842 |
| TGCAGGACCAGAGAATTCGAATA CATCGTTCAANNNACGTATGCCA | 4363 | TGCAGGACCAGAGAATTCGAATA CACAGAATGCNNNACGTATGCCA | 4603 | TGCAGGACCAGAGAATTCGAATA CATTACGTCNNNACGTATGCCA | 4843 |
| TGCAGGACCAGAGAATTCGAATA CACTATCAAANNNACGTATGCCA | 4364 | TGCAGGACCAGAGAATTCGAATA CAGTATGAANNNACGTATGCCA | 4604 | TGCAGGACCAGAGAATTCGAATA CAATGAGGACNNNACGTATGCCA | 4844 |
| TGCAGGACCAGAGAATTCGAATA CATTACCAAANNNACGTATGCCA | 4365 | TGCAGGACCAGAGAATTCGAATA CAGTTTAAGTNNNACGTATGCCA | 4605 | TGCAGGACCAGAGAATTCGAATA CAATTGTTAGNNNACGTATGCCA | 4845 |
| TGCAGGACCAGAGAATTCGAATA CACCGGCGATNNNACGTATGCCA | 4366 | TGCAGGACCAGAGAATTCGAATA CAGCGTTATGNNNACGTATGCCA | 4606 | TGCAGGACCAGAGAATTCGAATA CAGCTTGTAGNNNACGTATGCCA | 4846 |
| TGCAGGACCAGAGAATTCGAATA CAGTTGTATANNNACGTATGCCA | 4367 | TGCAGGACCAGAGAATTCGAATA CATCCGTTACNNNACGTATGCCA | 4607 | TGCAGGACCAGAGAATTCGAATA CATTGTTCGNNNACGTATGCCA | 4847 |
| TGCAGGACCAGAGAATTCGAATA CAATACGGCTNNNACGTATGCCA | 4368 | TGCAGGACCAGAGAATTCGAATA CACGAAACCTNNNACGTATGCCA | 4608 | TGCAGGACCAGAGAATTCGAATA CAAAAGGCTNNNACGTATGCCA | 4848 |
| TGCAGGACCAGAGAATTCGAATA CATGGCAACTNNNACGTATGCCA | 4369 | TGCAGGACCAGAGAATTCGAATA CACGGCCATGNNNACGTATGCCA | 4609 | TGCAGGACCAGAGAATTCGAATA CACTTACGAGNNNACGTATGCCA | 4849 |
| TGCAGGACCAGAGAATTCGAATA CAGATTTCAANNNACGTATGCCA | 4370 | TGCAGGACCAGAGAATTCGAATA CACGAAAAGCNNNACGTATGCCA | 4610 | TGCAGGACCAGAGAATTCGAATA CAATCTATAGNNNACGTATGCCA | 4850 |
| TGCAGGACCAGAGAATTCGAATA CAGTATCTTTNNNACGTATGCCA | 4371 | TGCAGGACCAGAGAATTCGAATA CAAGGTTGTCNNNACGTATGCCA | 4611 | TGCAGGACCAGAGAATTCGAATA CAGGTACACTNNNACGTATGCCA | 4851 |
| TGCAGGACCAGAGAATTCGAATA CAGCAACAGANNNACGTATGCCA | 4372 | TGCAGGACCAGAGAATTCGAATA CAACGAAGGTNNNACGTATGCCA | 4612 | TGCAGGACCAGAGAATTCGAATA CACCGCCTCANNNACGTATGCCA | 4852 |
| TGCAGGACCAGAGAATTCGAATA CAGCGTTCAANNNACGTATGCCA | 4373 | TGCAGGACCAGAGAATTCGAATA CATCCCCCGANNNACGTATGCCA | 4613 | TGCAGGACCAGAGAATTCGAATA CACAGGACGGNNNACGTATGCCA | 4853 |
| TGCAGGACCAGAGAATTCGAATA CAGTATTCGNNNACGTATGCCA | 4374 | TGCAGGACCAGAGAATTCGAATA CAAGCGATCTNNNACGTATGCCA | 4614 | TGCAGGACCAGAGAATTCGAATA CAATCATGGCNNNACGTATGCCA | 4854 |
| TGCAGGACCAGAGAATTCGAATA CATCCTATATNNNACGTATGCCA | 4375 | TGCAGGACCAGAGAATTCGAATA CACTATAATGNNNACGTATGCCA | 4615 | TGCAGGACCAGAGAATTCGAATA CATATAGGTNNNACGTATGCCA | 4855 |
| TGCAGGACCAGAGAATTCGAATA CAAGTCGTACNNNACGTATGCCA | 4376 | TGCAGGACCAGAGAATTCGAATA CATTCGTCTGNNNACGTATGCCA | 4616 | TGCAGGACCAGAGAATTCGAATA CAGATTTAACNNNACGTATGCCA | 4856 |
| TGCAGGACCAGAGAATTCGAATA CACCTAGACANNNACGTATGCCA | 4377 | TGCAGGACCAGAGAATTCGAATA CAGCGCCTTNNNACGTATGCCA | 4617 | TGCAGGACCAGAGAATTCGAATA CAATGGAACGNNNACGTATGCCA | 4857 |
| TGCAGGACCAGAGAATTCGAATA CAATTGGTCGNNNACGTATGCCA | 4378 | TGCAGGACCAGAGAATTCGAATA CACGCAATCANNNACGTATGCCA | 4618 | TGCAGGACCAGAGAATTCGAATA CAGCTTTCACNNNACGTATGCCA | 4858 |
| TGCAGGACCAGAGAATTCGAATA CAGGTCACGCNNNACGTATGCCA | 4379 | TGCAGGACCAGAGAATTCGAATA CAGTGGGTCGNNNACGTATGCCA | 4619 | TGCAGGACCAGAGAATTCGAATA CAGTCCGTGGNNNACGTATGCCA | 4859 |
| TGCAGGACCAGAGAATTCGAATA CACACCAAACNNNACGTATGCCA | 4380 | TGCAGGACCAGAGAATTCGAATA CATAGCAGGANNNACGTATGCCA | 4620 | TGCAGGACCAGAGAATTCGAATA CATACTCCCANNNACGTATGCCA | 4860 |
| TGCAGGACCAGAGAATTCGAATA CAGAATTCATNNNACGTATGCCA | 4381 | TGCAGGACCAGAGAATTCGAATA CAGATGGAGTNNNACGTATGCCA | 4621 | TGCAGGACCAGAGAATTCGAATA CAGCCCGTCTNNNACGTATGCCA | 4861 |
| TGCAGGACCAGAGAATTCGAATA CATTCGCACTNNNACGTATGCCA | 4382 | TGCAGGACCAGAGAATTCGAATA CAAACGCTNNNACGTATGCCA | 4622 | TGCAGGACCAGAGAATTCGAATA CAGTCACTGNNNACGTATGCCA | 4862 |
| TGCAGGACCAGAGAATTCGAATA CACCGTTAAGNNNACGTATGCCA | 4383 | TGCAGGACCAGAGAATTCGAATA CAAGCGGCCTNNNACGTATGCCA | 4623 | TGCAGGACCAGAGAATTCGAATA CAAGCCGAGGNNNACGTATGCCA | 4863 |
| TGCAGGACCAGAGAATTCGAATA CACGCCTGCTNNNACGTATGCCA | 4384 | TGCAGGACCAGAGAATTCGAATA CACGTTTGCTNNNACGTATGCCA | 4624 | TGCAGGACCAGAGAATTCGAATA CAGCTATATANNNACGTATGCCA | 4864 |
| TGCAGGACCAGAGAATTCGAATA CAAAAACAGTNNNACGTATGCCA | 4385 | TGCAGGACCAGAGAATTCGAATA CACCTGCATTNNNACGTATGCCA | 4625 | TGCAGGACCAGAGAATTCGAATA CATCTCTCGANNNACGTATGCCA | 4865 |
| TGCAGGACCAGAGAATTCGAATA CAGAGATTTNNNACGTATGCCA | 4386 | TGCAGGACCAGAGAATTCGAATA CAATTGAATCNNNACGTATGCCA | 4626 | TGCAGGACCAGAGAATTCGAATA CAACAATAGANNNACGTATGCCA | 4866 |
| TGCAGGACCAGAGAATTCGAATA CAACCAGTTGNNNACGTATGCCA | 4387 | TGCAGGACCAGAGAATTCGAATA CATCCGTGCCNNNACGTATGCCA | 4627 | TGCAGGACCAGAGAATTCGAATA CAGAGAGCATNNNACGTATGCCA | 4867 |
| TGCAGGACCAGAGAATTCGAATA CAAGTTCGCANNNACGTATGCCA | 4388 | TGCAGGACCAGAGAATTCGAATA CATCTCAGGANNNACGTATGCCA | 4628 | TGCAGGACCAGAGAATTCGAATA CACGATATGCNNNACGTATGCCA | 4868 |
| TGCAGGACCAGAGAATTCGAATA CAGATGACCTNNNCTAGCGTTAC | 4389 | TGCAGGACCAGAGAATTCGAATA CAAAGCCGTTNNNCTAGCGTTAC | 4629 | TGCAGGACCAGAGAATTCGAATA CACTTCCTCTNNNCTAGCGTTAC | 4869 |
| TGCAGGACCAGAGAATTCGAATA CACACGTATGNNNCTAGCGTTAC | 4390 | TGCAGGACCAGAGAATTCGAATA CACACCCTCGNNNCTAGCGTTAC | 4630 | TGCAGGACCAGAGAATTCGAATA CAAACAGTTTNNNCTAGCGTTAC | 4870 |
| TGCAGGACCAGAGAATTCGAATA CATGTCGGCGNNNCTAGCGTTAC | 4391 | TGCAGGACCAGAGAATTCGAATA CAGCTAGTTGNNNCTAGCGTTAC | 4631 | TGCAGGACCAGAGAATTCGAATA CATGTGGACTNNNCTAGCGTTAC | 4871 |
| TGCAGGACCAGAGAATTCGAATA CAGACCAAAGNNNCTAGCGTTAC | 4392 | TGCAGGACCAGAGAATTCGAATA CACCGTTACTNNNCTAGCGTTAC | 4632 | TGCAGGACCAGAGAATTCGAATA CACCTCCGCACNNNCTAGCGTTAC | 4872 |
| TGCAGGACCAGAGAATTCGAATA CACTGCTACTNNNCTAGCGTTAC | 4393 | TGCAGGACCAGAGAATTCGAATA CATAGCTCGNNNCTAGCGTTAC | 4633 | TGCAGGACCAGAGAATTCGAATA CACGGTTTCNNNCTAGCGTTAC | 4873 |
| TGCAGGACCAGAGAATTCGAATA CACTCCAACTNNNCTAGCGTTAC | 4394 | TGCAGGACCAGAGAATTCGAATA CAGGTAAACGNNNCTAGCGTTAC | 4634 | TGCAGGACCAGAGAATTCGAATA CAACGTCGATNNNCTAGCGTTAC | 4874 |

FIG. 18C

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CACAATCCCTNNNCTAGCGTTAC | 4395 | TGCAGGACCAGAGAATTCGAATA CAGAACCAGANNNCTAGCGTTAC | 4635 | TGCAGGACCAGAGAATTCGAATA CATTGGCTTCNNNCTAGCGTTAC | 4875 |
| TGCAGGACCAGAGAATTCGAATA CATCGTGCAANNNCTAGCGTTAC | 4396 | TGCAGGACCAGAGAATTCGAATA CAGGACTGTTNNNCTAGCGTTAC | 4636 | TGCAGGACCAGAGAATTCGAATA CAATGGACGANNNCTAGCGTTAC | 4876 |
| TGCAGGACCAGAGAATTCGAATA CAAAGCCATCNNNCTAGCGTTAC | 4397 | TGCAGGACCAGAGAATTCGAATA CAATCGTGTGNNNCTAGCGTTAC | 4637 | TGCAGGACCAGAGAATTCGAATA CATGCAAGAGNNNCTAGCGTTAC | 4877 |
| TGCAGGACCAGAGAATTCGAATA CAATGAACTTNNNCTAGCGTTAC | 4398 | TGCAGGACCAGAGAATTCGAATA CAGTCACGGCNNNCTAGCGTTAC | 4638 | TGCAGGACCAGAGAATTCGAATA CAGAAATATGNNNCTAGCGTTAC | 4878 |
| TGCAGGACCAGAGAATTCGAATA CATGGCCGGTNNNCTAGCGTTAC | 4399 | TGCAGGACCAGAGAATTCGAATA CATCTCGTACNNNCTAGCGTTAC | 4639 | TGCAGGACCAGAGAATTCGAATA CAACACATATNNNCTAGCGTTAC | 4879 |
| TGCAGGACCAGAGAATTCGAATA CATGCCACGGNNNCTAGCGTTAC | 4400 | TGCAGGACCAGAGAATTCGAATA CAAGTCGCGCNNNCTAGCGTTAC | 4640 | TGCAGGACCAGAGAATTCGAATA CAGTACGACTNNNCTAGCGTTAC | 4880 |
| TGCAGGACCAGAGAATTCGAATA CAGTCTTCGTNNNCTAGCGTTAC | 4401 | TGCAGGACCAGAGAATTCGAATA CACATAGTCGNNNCTAGCGTTAC | 4641 | TGCAGGACCAGAGAATTCGAATA CACGCCGCGGNNNCTAGCGTTAC | 4881 |
| TGCAGGACCAGAGAATTCGAATA CAAACGTAGGNNNCTAGCGTTAC | 4402 | TGCAGGACCAGAGAATTCGAATA CACATGTACGNNNCTAGCGTTAC | 4642 | TGCAGGACCAGAGAATTCGAATA CATAGTGCACNNNCTAGCGTTAC | 4882 |
| TGCAGGACCAGAGAATTCGAATA CAATGGAGCANNNCTAGCGTTAC | 4403 | TGCAGGACCAGAGAATTCGAATA CAGGGTATCANNNCTAGCGTTAC | 4643 | TGCAGGACCAGAGAATTCGAATA CATCAATGCGNNNCTAGCGTTAC | 4883 |
| TGCAGGACCAGAGAATTCGAATA CATGGGGCNNNCTAGCGTTAC | 4404 | TGCAGGACCAGAGAATTCGAATA CACAATTCTTNNNCTAGCGTTAC | 4644 | TGCAGGACCAGAGAATTCGAATA CAATGTAAGANNNCTAGCGTTAC | 4884 |
| TGCAGGACCAGAGAATTCGAATA CACTTAGGACNNNCTAGCGTTAC | 4405 | TGCAGGACCAGAGAATTCGAATA CAACTCTATTNNNCTAGCGTTAC | 4645 | TGCAGGACCAGAGAATTCGAATA CATATGTTAGNNNCTAGCGTTAC | 4885 |
| TGCAGGACCAGAGAATTCGAATA CAGACAGAGTNNNCTAGCGTTAC | 4406 | TGCAGGACCAGAGAATTCGAATA CATCATCCGCNNNCTAGCGTTAC | 4646 | TGCAGGACCAGAGAATTCGAATA CATCAAATCANNNCTAGCGTTAC | 4886 |
| TGCAGGACCAGAGAATTCGAATA CAAAGTCGTCNNNCTAGCGTTAC | 4407 | TGCAGGACCAGAGAATTCGAATA CAGGCTTGGCNNNCTAGCGTTAC | 4647 | TGCAGGACCAGAGAATTCGAATA CACACTTAGCNNNCTAGCGTTAC | 4887 |
| TGCAGGACCAGAGAATTCGAATA CATACAAAAGNNNCTAGCGTTAC | 4408 | TGCAGGACCAGAGAATTCGAATA CAGTTCCTTGNNNCTAGCGTTAC | 4648 | TGCAGGACCAGAGAATTCGAATA CATAGGATAANNNCTAGCGTTAC | 4888 |
| TGCAGGACCAGAGAATTCGAATA CATCTCCTGANNNCTAGCGTTAC | 4409 | TGCAGGACCAGAGAATTCGAATA CAATGAGAATNNNCTAGCGTTAC | 4649 | TGCAGGACCAGAGAATTCGAATA CAATCCCGTTNNNCTAGCGTTAC | 4889 |
| TGCAGGACCAGAGAATTCGAATA CAAGCTGGTTNNNCTAGCGTTAC | 4410 | TGCAGGACCAGAGAATTCGAATA CACTGTATCCNNNCTAGCGTTAC | 4650 | TGCAGGACCAGAGAATTCGAATA CAACAATCCGNNNCTAGCGTTAC | 4890 |
| TGCAGGACCAGAGAATTCGAATA CAAATCAAGANNNCTAGCGTTAC | 4411 | TGCAGGACCAGAGAATTCGAATA CATACGCCCCNNNCTAGCGTTAC | 4651 | TGCAGGACCAGAGAATTCGAATA CACTATTAAGNNNCTAGCGTTAC | 4891 |
| TGCAGGACCAGAGAATTCGAATA CAACCACAACNNNCTAGCGTTAC | 4412 | TGCAGGACCAGAGAATTCGAATA CATGGCCGACNNNCTAGCGTTAC | 4652 | TGCAGGACCAGAGAATTCGAATA CAGCGTATGTNNNCTAGCGTTAC | 4892 |
| TGCAGGACCAGAGAATTCGAATA CAGCTATAATNNNCTAGCGTTAC | 4413 | TGCAGGACCAGAGAATTCGAATA CACCGCTGCTNNNCTAGCGTTAC | 4653 | TGCAGGACCAGAGAATTCGAATA CAATTGGTATNNNCTAGCGTTAC | 4893 |
| TGCAGGACCAGAGAATTCGAATA CAGGACCGCTNNNCTAGCGTTAC | 4414 | TGCAGGACCAGAGAATTCGAATA CAGGTAGCCCNNNCTAGCGTTAC | 4654 | TGCAGGACCAGAGAATTCGAATA CATTTCTGCGNNNCTAGCGTTAC | 4894 |
| TGCAGGACCAGAGAATTCGAATA CAGTCCCTATNNNCTAGCGTTAC | 4415 | TGCAGGACCAGAGAATTCGAATA CATGACGTTCNNNCTAGCGTTAC | 4655 | TGCAGGACCAGAGAATTCGAATA CAGAATCCCANNNCTAGCGTTAC | 4895 |
| TGCAGGACCAGAGAATTCGAATA CATTGCTGAGNNNCTAGCGTTAC | 4416 | TGCAGGACCAGAGAATTCGAATA CACCCACTATNNNCTAGCGTTAC | 4656 | TGCAGGACCAGAGAATTCGAATA CACTTTCACGNNNCTAGCGTTAC | 4896 |
| TGCAGGACCAGAGAATTCGAATA CATTGGCCTTNNNCTAGCGTTAC | 4417 | TGCAGGACCAGAGAATTCGAATA CAAAGTGTAANNNCTAGCGTTAC | 4657 | TGCAGGACCAGAGAATTCGAATA CACGGATCATNNNCTAGCGTTAC | 4897 |
| TGCAGGACCAGAGAATTCGAATA CAATCATTTCNNNCTAGCGTTAC | 4418 | TGCAGGACCAGAGAATTCGAATA CAGGAGTATGNNNCTAGCGTTAC | 4658 | TGCAGGACCAGAGAATTCGAATA CAACAGTGCTNNNCTAGCGTTAC | 4898 |
| TGCAGGACCAGAGAATTCGAATA CAGATGTATTNNNCTAGCGTTAC | 4419 | TGCAGGACCAGAGAATTCGAATA CAAGTGATAANNNCTAGCGTTAC | 4659 | TGCAGGACCAGAGAATTCGAATA CACTTAGTCCNNNCTAGCGTTAC | 4899 |
| TGCAGGACCAGAGAATTCGAATA CAGATCATATNNNCTAGCGTTAC | 4420 | TGCAGGACCAGAGAATTCGAATA CATAATTCGANNNCTAGCGTTAC | 4660 | TGCAGGACCAGAGAATTCGAATA CAAGTGCCGGNNNCTAGCGTTAC | 4900 |
| TGCAGGACCAGAGAATTCGAATA CACCCCGCTANNNCTAGCGTTAC | 4421 | TGCAGGACCAGAGAATTCGAATA CAAGCTTTGGNNNCTAGCGTTAC | 4661 | TGCAGGACCAGAGAATTCGAATA CATGAAATCTNNNCTAGCGTTAC | 4901 |
| TGCAGGACCAGAGAATTCGAATA CAAAAATCGANNNCTAGCGTTAC | 4422 | TGCAGGACCAGAGAATTCGAATA CAACATGTCGNNNCTAGCGTTAC | 4662 | TGCAGGACCAGAGAATTCGAATA CATCAGTTAANNNCTAGCGTTAC | 4902 |
| TGCAGGACCAGAGAATTCGAATA CAATGTACATNNNCTAGCGTTAC | 4423 | TGCAGGACCAGAGAATTCGAATA CATCAGCGCGNNNCTAGCGTTAC | 4663 | TGCAGGACCAGAGAATTCGAATA CAAACCCTGANNNCTAGCGTTAC | 4903 |
| TGCAGGACCAGAGAATTCGAATA CAGCCATCTTNNNCTAGCGTTAC | 4424 | TGCAGGACCAGAGAATTCGAATA CAGGCCGTANNNCTAGCGTTAC | 4664 | TGCAGGACCAGAGAATTCGAATA CATCATGATANNNCTAGCGTTAC | 4904 |
| TGCAGGACCAGAGAATTCGAATA CAAATGCTCGNNNCTAGCGTTAC | 4425 | TGCAGGACCAGAGAATTCGAATA CACCATTCACNNNCTAGCGTTAC | 4665 | TGCAGGACCAGAGAATTCGAATA CAAAGCCTTGNNNCTAGCGTTAC | 4905 |
| TGCAGGACCAGAGAATTCGAATA CACACGTCGGNNNCTAGCGTTAC | 4426 | TGCAGGACCAGAGAATTCGAATA CATTCCCCTNNNCTAGCGTTAC | 4666 | TGCAGGACCAGAGAATTCGAATA CAAGCATACCNNNCTAGCGTTAC | 4906 |
| TGCAGGACCAGAGAATTCGAATA CACTATGCGANNNCTAGCGTTAC | 4427 | TGCAGGACCAGAGAATTCGAATA CAACCCTCCGNNNCTAGCGTTAC | 4667 | TGCAGGACCAGAGAATTCGAATA CAGGCATTGNNNCTAGCGTTAC | 4907 |

FIG. 18D

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGTCTGGTANNNCTAGCGTTAC | 4428 | TGCAGGACCAGAGAATTCGAATA CACAGCTTACNNNCTAGCGTTAC | 4668 | TGCAGGACCAGAGAATTCGAATA CAGCGAGTCCNNNCTAGCGTTAC | 4908 |
| TGCAGGACCAGAGAATTCGAATA CAGTCAGTGTNNNCTAGCGTTAC | 4429 | TGCAGGACCAGAGAATTCGAATA CAGGAGTTGANNNCTAGCGTTAC | 4669 | TGCAGGACCAGAGAATTCGAATA CATTTTGAGANNNCTAGCGTTAC | 4909 |
| TGCAGGACCAGAGAATTCGAATA CACTCCAGTTNNNCTAGCGTTAC | 4430 | TGCAGGACCAGAGAATTCGAATA CAGACAAGACNNNCTAGCGTTAC | 4670 | TGCAGGACCAGAGAATTCGAATA CAATCCTTATNNNCTAGCGTTAC | 4910 |
| TGCAGGACCAGAGAATTCGAATA CAGATGAAGCNNNCTAGCGTTAC | 4431 | TGCAGGACCAGAGAATTCGAATA CAGTCTACGANNNCTAGCGTTAC | 4671 | TGCAGGACCAGAGAATTCGAATA CATCGAAAAANNNCTAGCGTTAC | 4911 |
| TGCAGGACCAGAGAATTCGAATA CAAAACCATTNNNCTAGCGTTAC | 4432 | TGCAGGACCAGAGAATTCGAATA CATCGCTCATNNNCTAGCGTTAC | 4672 | TGCAGGACCAGAGAATTCGAATA CAGCTCCGTCNNNCTAGCGTTAC | 4912 |
| TGCAGGACCAGAGAATTCGAATA CACCTGCGCTNNNCTAGCGTTAC | 4433 | TGCAGGACCAGAGAATTCGAATA CACCAAGCCGNNNCTAGCGTTAC | 4673 | TGCAGGACCAGAGAATTCGAATA CACCAGTTTCNNNCTAGCGTTAC | 4913 |
| TGCAGGACCAGAGAATTCGAATA CACACCCGAGNNNCTAGCGTTAC | 4434 | TGCAGGACCAGAGAATTCGAATA CACCCTCGGTNNNCTAGCGTTAC | 4674 | TGCAGGACCAGAGAATTCGAATA CACTTGGCTTNNNCTAGCGTTAC | 4914 |
| TGCAGGACCAGAGAATTCGAATA CATACTACAANNNCTAGCGTTAC | 4435 | TGCAGGACCAGAGAATTCGAATA CAAACTAGTTNNNCTAGCGTTAC | 4675 | TGCAGGACCAGAGAATTCGAATA CACCGCCATCNNNCTAGCGTTAC | 4915 |
| TGCAGGACCAGAGAATTCGAATA CATAACCGACNNNCTAGCGTTAC | 4436 | TGCAGGACCAGAGAATTCGAATA CAGAGTGAGTNNNCTAGCGTTAC | 4676 | TGCAGGACCAGAGAATTCGAATA CAGATCGATCNNNCTAGCGTTAC | 4916 |
| TGCAGGACCAGAGAATTCGAATA CATCTATAGANNNCTAGCGTTAC | 4437 | TGCAGGACCAGAGAATTCGAATA CACAATACTANNNCTAGCGTTAC | 4677 | TGCAGGACCAGAGAATTCGAATA CAACSCGGCTNNNCTAGCGTTAC | 4917 |
| TGCAGGACCAGAGAATTCGAATA CAGGTGAGGCNNNCTAGCGTTAC | 4438 | TGCAGGACCAGAGAATTCGAATA CACCTTTGGTNNNCTAGCGTTAC | 4678 | TGCAGGACCAGAGAATTCGAATA CATCTCGAGANNNCTAGCGTTAC | 4918 |
| TGCAGGACCAGAGAATTCGAATA CACATACTCCNNNCTAGCGTTAC | 4439 | TGCAGGACCAGAGAATTCGAATA CATTCACACCNNNCTAGCGTTAC | 4679 | TGCAGGACCAGAGAATTCGAATA CAATTGGCACNNNCTAGCGTTAC | 4919 |
| TGCAGGACCAGAGAATTCGAATA CATAAGAGTANNNCTAGCGTTAC | 4440 | TGCAGGACCAGAGAATTCGAATA CAGTTATCCCNNNCTAGCGTTAC | 4680 | TGCAGGACCAGAGAATTCGAATA CACGCCGAGTNNNCTAGCGTTAC | 4920 |
| TGCAGGACCAGAGAATTCGAATA CAGTGTGAGANNNCTAGCGTTAC | 4441 | TGCAGGACCAGAGAATTCGAATA CAAAACTTGTNNNCTAGCGTTAC | 4681 | TGCAGGACCAGAGAATTCGAATA CACTTCAGCTNNNCTAGCGTTAC | 4921 |
| TGCAGGACCAGAGAATTCGAATA CATTCCCGATNNNCTAGCGTTAC | 4442 | TGCAGGACCAGAGAATTCGAATA CACAACCCAANNNCTAGCGTTAC | 4682 | TGCAGGACCAGAGAATTCGAATA CAAAATAAGCNNNCTAGCGTTAC | 4922 |
| TGCAGGACCAGAGAATTCGAATA CAAGTACGAGNNNCTAGCGTTAC | 4443 | TGCAGGACCAGAGAATTCGAATA CAGTTCACGANNNCTAGCGTTAC | 4683 | TGCAGGACCAGAGAATTCGAATA CAGCCTAAGTNNNCTAGCGTTAC | 4923 |
| TGCAGGACCAGAGAATTCGAATA CAGGTGAACANNNCTAGCGTTAC | 4444 | TGCAGGACCAGAGAATTCGAATA CACGTCTACTNNNCTAGCGTTAC | 4684 | TGCAGGACCAGAGAATTCGAATA CAGATGTTCGNNNCTAGCGTTAC | 4924 |
| TGCAGGACCAGAGAATTCGAATA CACACTAGCANNNCTAGCGTTAC | 4445 | TGCAGGACCAGAGAATTCGAATA CATCAACAGCNNNCTAGCGTTAC | 4685 | TGCAGGACCAGAGAATTCGAATA CAAACGAGGTNNNCTAGCGTTAC | 4925 |
| TGCAGGACCAGAGAATTCGAATA CAAGCAGAACNNNCTAGCGTTAC | 4446 | TGCAGGACCAGAGAATTCGAATA CATTGAGTCGNNNCTAGCGTTAC | 4686 | TGCAGGACCAGAGAATTCGAATA CAATAGACAANNNCTAGCGTTAC | 4926 |
| TGCAGGACCAGAGAATTCGAATA CATTTTAAAANNNCTAGCGTTAC | 4447 | TGCAGGACCAGAGAATTCGAATA CAGCATCTGANNNCTAGCGTTAC | 4687 | TGCAGGACCAGAGAATTCGAATA CATATTTGGANNNCTAGCGTTAC | 4927 |
| TGCAGGACCAGAGAATTCGAATA CACTTCGAGANNNCTAGCGTTAC | 4448 | TGCAGGACCAGAGAATTCGAATA CATGCATGTTNNNCTAGCGTTAC | 4688 | TGCAGGACCAGAGAATTCGAATA CATCCGTTGTNNNCTAGCGTTAC | 4928 |
| TGCAGGACCAGAGAATTCGAATA CATGCAATGCNNNGATCGACATG | 4449 | TGCAGGACCAGAGAATTCGAATA CAGATCTCTCNNNGATCGACATG | 4689 | TGCAGGACCAGAGAATTCGAATA CATCCTCGATNNNGATCGACATG | 4929 |
| TGCAGGACCAGAGAATTCGAATA CAGACCGCCANNNGATCGACATG | 4450 | TGCAGGACCAGAGAATTCGAATA CAGAGCGCGANNNGATCGACATG | 4690 | TGCAGGACCAGAGAATTCGAATA CATTTGGAGNNNNGATCGACATG | 4930 |
| TGCAGGACCAGAGAATTCGAATA CAGTTTTTCANNNGATCGACATG | 4451 | TGCAGGACCAGAGAATTCGAATA CACTCTCTAGNNNGATCGACATG | 4691 | TGCAGGACCAGAGAATTCGAATA CACTTCCACANNNGATCGACATG | 4931 |
| TGCAGGACCAGAGAATTCGAATA CAGTTTTATCNNNGATCGACATG | 4452 | TGCAGGACCAGAGAATTCGAATA CACGTGGCGTNNNGATCGACATG | 4692 | TGCAGGACCAGAGAATTCGAATA CAAATTTGCANNNGATCGACATG | 4932 |
| TGCAGGACCAGAGAATTCGAATA CAACACCGGCNNNGATCGACATG | 4453 | TGCAGGACCAGAGAATTCGAATA CAAGCTAGTCNNNGATCGACATG | 4693 | TGCAGGACCAGAGAATTCGAATA CAAATCTGATNNNGATCGACATG | 4933 |
| TGCAGGACCAGAGAATTCGAATA CACGCTTTACNNNGATCGACATG | 4454 | TGCAGGACCAGAGAATTCGAATA CAGCTATGTNNNNGATCGACATG | 4694 | TGCAGGACCAGAGAATTCGAATA CATCCACTTGNNNGATCGACATG | 4934 |
| TGCAGGACCAGAGAATTCGAATA CAGTAAATGANNNGATCGACATG | 4455 | TGCAGGACCAGAGAATTCGAATA CATCTGCTTGNNNGATCGACATG | 4695 | TGCAGGACCAGAGAATTCGAATA CATGGTTAGCNNNGATCGACATG | 4935 |
| TGCAGGACCAGAGAATTCGAATA CATTTGAAGTNNNGATCGACATG | 4456 | TGCAGGACCAGAGAATTCGAATA CAGTACGCTANNNGATCGACATG | 4696 | TGCAGGACCAGAGAATTCGAATA CACTGTAACGNNNGATCGACATG | 4936 |
| TGCAGGACCAGAGAATTCGAATA CACACCACTTNNNGATCGACATG | 4457 | TGCAGGACCAGAGAATTCGAATA CAGACCCGTGNNNGATCGACATG | 4697 | TGCAGGACCAGAGAATTCGAATA CATATTAGTGNNNGATCGACATG | 4937 |
| TGCAGGACCAGAGAATTCGAATA CATGTAAGAANNNGATCGACATG | 4458 | TGCAGGACCAGAGAATTCGAATA CAGTCATGACNNNGATCGACATG | 4698 | TGCAGGACCAGAGAATTCGAATA CATGCACATGNNNGATCGACATG | 4938 |
| TGCAGGACCAGAGAATTCGAATA CACGCTGAATNNNGATCGACATG | 4459 | TGCAGGACCAGAGAATTCGAATA CACGCTAGAANNNGATCGACATG | 4699 | TGCAGGACCAGAGAATTCGAATA CAACCTTGCANNNGATCGACATG | 4939 |
| TGCAGGACCAGAGAATTCGAATA CACTTATTGTNNNGATCGACATG | 4460 | TGCAGGACCAGAGAATTCGAATA CAGTAATGAANNNGATCGACATG | 4700 | TGCAGGACCAGAGAATTCGAATA CAGCGTGCACNNNGATCGACATG | 4940 |

FIG. 18E

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CACGTGAGAANNNGATCGACATG | 4461 | TGCAGGACCAGAGAATTCGAATA CATCGTATTTNNNGATCGACATG | 4701 | TGCAGGACCAGAGAATTCGAATA CACGGCCTTTANNNGATCGACATG | 4941 |
| TGCAGGACCAGAGAATTCGAATA CAACCGGCTGNNNGATCGACATG | 4462 | TGCAGGACCAGAGAATTCGAATA CACACGTACANNNGATCGACATG | 4702 | TGCAGGACCAGAGAATTCGAATA CATTGTAAACNNNGATCGACATG | 4942 |
| TGCAGGACCAGAGAATTCGAATA CACAAAATTCNNNGATCGACATG | 4463 | TGCAGGACCAGAGAATTCGAATA CATGACTAATNNNGATCGACATG | 4703 | TGCAGGACCAGAGAATTCGAATA CAAACGCAAGNNNGATCGACATG | 4943 |
| TGCAGGACCAGAGAATTCGAATA CAACTAAAGANNNGATCGACATG | 4464 | TGCAGGACCAGAGAATTCGAATA CACTACCGCCNNNGATCGACATG | 4704 | TGCAGGACCAGAGAATTCGAATA CAGTAATCATNNNGATCGACATG | 4944 |
| TGCAGGACCAGAGAATTCGAATA CATAGTCTCCNNNGATCGACATG | 4465 | TGCAGGACCAGAGAATTCGAATA CAGGCACTTANNNGATCGACATG | 4705 | TGCAGGACCAGAGAATTCGAATA CAGTCTGCTTNNNGATCGACATG | 4945 |
| TGCAGGACCAGAGAATTCGAATA CACTAACATANNNGATCGACATG | 4466 | TGCAGGACCAGAGAATTCGAATA CATCCTTAGCNNNGATCGACATG | 4706 | TGCAGGACCAGAGAATTCGAATA CAGATGGTTCNNNGATCGACATG | 4946 |
| TGCAGGACCAGAGAATTCGAATA CATGCACGCGNNNGATCGACATG | 4467 | TGCAGGACCAGAGAATTCGAATA CAGCTATAGCNNNGATCGACATG | 4707 | TGCAGGACCAGAGAATTCGAATA CACTTGGCAANNNGATCGACATG | 4947 |
| TGCAGGACCAGAGAATTCGAATA CAACTGGAAGNNNGATCGACATG | 4468 | TGCAGGACCAGAGAATTCGAATA CAAATGAACANNNGATCGACATG | 4708 | TGCAGGACCAGAGAATTCGAATA CATACCGAACNNNGATCGACATG | 4948 |
| TGCAGGACCAGAGAATTCGAATA CAGCAATCCANNNGATCGACATG | 4469 | TGCAGGACCAGAGAATTCGAATA CAGTAGTAANNNNGATCGACATG | 4709 | TGCAGGACCAGAGAATTCGAATA CAGTGAGTGANNNGATCGACATG | 4949 |
| TGCAGGACCAGAGAATTCGAATA CAAATCCTAANNNGATCGACATG | 4470 | TGCAGGACCAGAGAATTCGAATA CATAGTTCCGNNNGATCGACATG | 4710 | TGCAGGACCAGAGAATTCGAATA CACAGGTCGANNNGATCGACATG | 4950 |
| TGCAGGACCAGAGAATTCGAATA CAAAGCGGTANNNGATCGACATG | 4471 | TGCAGGACCAGAGAATTCGAATA CAGTTGTGACNNNGATCGACATG | 4711 | TGCAGGACCAGAGAATTCGAATA CAAGGTCAGANNNGATCGACATG | 4951 |
| TGCAGGACCAGAGAATTCGAATA CAGTCAGAGANNNGATCGACATG | 4472 | TGCAGGACCAGAGAATTCGAATA CACGGTAGCNNNNGATCGACATG | 4712 | TGCAGGACCAGAGAATTCGAATA CAGAGCGTTTNNNGATCGACATG | 4952 |
| TGCAGGACCAGAGAATTCGAATA CATCGGATGTNNNGATCGACATG | 4473 | TGCAGGACCAGAGAATTCGAATA CACTATGTGNNNNGATCGACATG | 4713 | TGCAGGACCAGAGAATTCGAATA CAGAAATGGCNNNGATCGACATG | 4953 |
| TGCAGGACCAGAGAATTCGAATA CATCACGCTTNNNGATCGACATG | 4474 | TGCAGGACCAGAGAATTCGAATA CATTGGGTANNNNGATCGACATG | 4714 | TGCAGGACCAGAGAATTCGAATA CAGAGTGTCNNNNGATCGACATG | 4954 |
| TGCAGGACCAGAGAATTCGAATA CATTAGGTGCNNNGATCGACATG | 4475 | TGCAGGACCAGAGAATTCGAATA CAATTATCCTNNNGATCGACATG | 4715 | TGCAGGACCAGAGAATTCGAATA CAAAACATCTNNNGATCGACATG | 4955 |
| TGCAGGACCAGAGAATTCGAATA CATCCGACGGNNNGATCGACATG | 4476 | TGCAGGACCAGAGAATTCGAATA CACTTTGAAANNNGATCGACATG | 4716 | TGCAGGACCAGAGAATTCGAATA CATAAAGCTTNNNGATCGACATG | 4956 |
| TGCAGGACCAGAGAATTCGAATA CAAAAGCAGCNNNGATCGACATG | 4477 | TGCAGGACCAGAGAATTCGAATA CACTAGTACGNNNGATCGACATG | 4717 | TGCAGGACCAGAGAATTCGAATA CATTAGTGCGNNNGATCGACATG | 4957 |
| TGCAGGACCAGAGAATTCGAATA CAGTGCCGGTNNNGATCGACATG | 4478 | TGCAGGACCAGAGAATTCGAATA CATCCCACATNNNGATCGACATG | 4718 | TGCAGGACCAGAGAATTCGAATA CAGTTCGCCNNNNGATCGACATG | 4958 |
| TGCAGGACCAGAGAATTCGAATA CAACGATATTNNNGATCGACATG | 4479 | TGCAGGACCAGAGAATTCGAATA CAGTATCGACNNNGATCGACATG | 4719 | TGCAGGACCAGAGAATTCGAATA CAGTGACCTANNNGATCGACATG | 4959 |
| TGCAGGACCAGAGAATTCGAATA CAACAACAGGNNNGATCGACATG | 4480 | TGCAGGACCAGAGAATTCGAATA CAGGCCTCAGNNNGATCGACATG | 4720 | TGCAGGACCAGAGAATTCGAATA CAGGACAATGNNNGATCGACATG | 4960 |
| TGCAGGACCAGAGAATTCGAATA CACTCCGAAANNNGATCGACATG | 4481 | TGCAGGACCAGAGAATTCGAATA CACGGCTTANNNNGATCGACATG | 4721 | TGCAGGACCAGAGAATTCGAATA CATATAGGAANNNGATCGACATG | 4961 |
| TGCAGGACCAGAGAATTCGAATA CATCAAGCCANNNGATCGACATG | 4482 | TGCAGGACCAGAGAATTCGAATA CACATAGCACNNNGATCGACATG | 4722 | TGCAGGACCAGAGAATTCGAATA CACTAGCGGCNNNGATCGACATG | 4962 |
| TGCAGGACCAGAGAATTCGAATA CACATTAACANNNGATCGACATG | 4483 | TGCAGGACCAGAGAATTCGAATA CACCCACTTTNNNGATCGACATG | 4723 | TGCAGGACCAGAGAATTCGAATA CAGCGTTTAGNNNGATCGACATG | 4963 |
| TGCAGGACCAGAGAATTCGAATA CAAACACGAGNNNGATCGACATG | 4484 | TGCAGGACCAGAGAATTCGAATA CATGTGATGCNNNGATCGACATG | 4724 | TGCAGGACCAGAGAATTCGAATA CAGTATGTCGNNNGATCGACATG | 4964 |
| TGCAGGACCAGAGAATTCGAATA CATCCATCACNNNGATCGACATG | 4485 | TGCAGGACCAGAGAATTCGAATA CAATCGCTAGNNNGATCGACATG | 4725 | TGCAGGACCAGAGAATTCGAATA CACATGTGACNNNGATCGACATG | 4965 |
| TGCAGGACCAGAGAATTCGAATA CAGTCGCACGNNNGATCGACATG | 4486 | TGCAGGACCAGAGAATTCGAATA CAGAATTAGANNNGATCGACATG | 4726 | TGCAGGACCAGAGAATTCGAATA CAATCAAAGNNNNGATCGACATG | 4966 |
| TGCAGGACCAGAGAATTCGAATA CATGGCACGCNNNGATCGACATG | 4487 | TGCAGGACCAGAGAATTCGAATA CAGCGGTCGTNNNGATCGACATG | 4727 | TGCAGGACCAGAGAATTCGAATA CAATAAACTCNNNGATCGACATG | 4967 |
| TGCAGGACCAGAGAATTCGAATA CATTTCAGAANNNGATCGACATG | 4488 | TGCAGGACCAGAGAATTCGAATA CAAATTGCATNNNGATCGACATG | 4728 | TGCAGGACCAGAGAATTCGAATA CACCGGATCGNNNGATCGACATG | 4968 |
| TGCAGGACCAGAGAATTCGAATA CATACGTCTCNNNGATCGACATG | 4489 | TGCAGGACCAGAGAATTCGAATA CATGGAACCTNNNGATCGACATG | 4729 | TGCAGGACCAGAGAATTCGAATA CACCCGCTAGNNNGATCGACATG | 4969 |
| TGCAGGACCAGAGAATTCGAATA CACCGGATCTTNNGATCGACATG | 4490 | TGCAGGACCAGAGAATTCGAATA CAAGCGCATTNNNGATCGACATG | 4730 | TGCAGGACCAGAGAATTCGAATA CACTGTGGTANNNGATCGACATG | 4970 |
| TGCAGGACCAGAGAATTCGAATA CAATTAAGCTNNNGATCGACATG | 4491 | TGCAGGACCAGAGAATTCGAATA CATTCCCTCTNNNGATCGACATG | 4731 | TGCAGGACCAGAGAATTCGAATA CAGAACGTGANNNGATCGACATG | 4971 |
| TGCAGGACCAGAGAATTCGAATA CAAACTTCCCNNNGATCGACATG | 4492 | TGCAGGACCAGAGAATTCGAATA CAATTGTCGGNNNGATCGACATG | 4732 | TGCAGGACCAGAGAATTCGAATA CACGGCTAANNNNGATCGACATG | 4972 |
| TGCAGGACCAGAGAATTCGAATA CAGTCGCTTTNNNGATCGACATG | 4493 | TGCAGGACCAGAGAATTCGAATA CATAATGCGCNNNGATCGACATG | 4733 | TGCAGGACCAGAGAATTCGAATA CAGGCATCATNNNGATCGACATG | 4973 |

FIG. 18F

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGCCAGTATNNNGATCGACATG | 4494 | TGCAGGACCAGAGAATTCGAATA CAACGCCATTGNNNGATCGACATG | 4734 | TGCAGGACCAGAGAATTCGAATA CACCGCAGGTNNNGATCGACATG | 4974 |
| TGCAGGACCAGAGAATTCGAATA CAGAGAAAAANNNGATCGACATG | 4495 | TGCAGGACCAGAGAATTCGAATA CATGTCCGTANNNGATCGACATG | 4735 | TGCAGGACCAGAGAATTCGAATA CATCCTACTGNNNGATCGACATG | 4975 |
| TGCAGGACCAGAGAATTCGAATA CAATAGCCCANNNGATCGACATG | 4496 | TGCAGGACCAGAGAATTCGAATA CATTTTCAACNNNGATCGACATG | 4736 | TGCAGGACCAGAGAATTCGAATA CATCCCGACCNNNGATCGACATG | 4976 |
| TGCAGGACCAGAGAATTCGAATA CACACGTCCCNNNGATCGACATG | 4497 | TGCAGGACCAGAGAATTCGAATA CATAAGTACTNNNGATCGACATG | 4737 | TGCAGGACCAGAGAATTCGAATA CATGTAGGTCNNNGATCGACATG | 4977 |
| TGCAGGACCAGAGAATTCGAATA CAAAGTTATCNNNGATCGACATG | 4498 | TGCAGGACCAGAGAATTCGAATA CAAATTAGTCNNNGATCGACATG | 4738 | TGCAGGACCAGAGAATTCGAATA CACGGCGCTANNNGATCGACATG | 4978 |
| TGCAGGACCAGAGAATTCGAATA CACTTTTCGGNNNGATCGACATG | 4499 | TGCAGGACCAGAGAATTCGAATA CAGGAAATATNNNGATCGACATG | 4739 | TGCAGGACCAGAGAATTCGAATA CACCTATTTANNNGATCGACATG | 4979 |
| TGCAGGACCAGAGAATTCGAATA CACAATCGTGNNNGATCGACATG | 4500 | TGCAGGACCAGAGAATTCGAATA CATTTTTTAANNNGATCGACATG | 4740 | TGCAGGACCAGAGAATTCGAATA CAGAACAAGCNNNGATCGACATG | 4980 |
| TGCAGGACCAGAGAATTCGAATA CAGGACGTAANNNGATCGACATG | 4501 | TGCAGGACCAGAGAATTCGAATA CACACGTAACNNNGATCGACATG | 4741 | TGCAGGACCAGAGAATTCGAATA CATCCATTGNNNGATCGACATG | 4981 |
| TGCAGGACCAGAGAATTCGAATA CACCCGAACGNNNGATCGACATG | 4502 | TGCAGGACCAGAGAATTCGAATA CAGTTTCCGTNNNGATCGACATG | 4742 | TGCAGGACCAGAGAATTCGAATA CATACTGTGGNNNGATCGACATG | 4982 |
| TGCAGGACCAGAGAATTCGAATA CATCCGTATCNNNGATCGACATG | 4503 | TGCAGGACCAGAGAATTCGAATA CAAGTATCTANNNGATCGACATG | 4743 | TGCAGGACCAGAGAATTCGAATA CAGCGCTTANNNGATCGACATG | 4983 |
| TGCAGGACCAGAGAATTCGAATA CATTTCGTTANNNGATCGACATG | 4504 | TGCAGGACCAGAGAATTCGAATA CATCTAGTGNNNGATCGACATG | 4744 | TGCAGGACCAGAGAATTCGAATA CAGCCCTCCCANNNGATCGACATG | 4984 |
| TGCAGGACCAGAGAATTCGAATA CATGCTACAGNNNGATCGACATG | 4505 | TGCAGGACCAGAGAATTCGAATA CAGAGTAGNGATANNNGATCGACATG | 4745 | TGCAGGACCAGAGAATTCGAATA CACACGATANNNGATCGACATG | 4985 |
| TGCAGGACCAGAGAATTCGAATA CAGTTACTTTNNNGATCGACATG | 4506 | TGCAGGACCAGAGAATTCGAATA CAACTCCAGANNNGATCGACATG | 4746 | TGCAGGACCAGAGAATTCGAATA CAGTGTCAACNNNGATCGACATG | 4986 |
| TGCAGGACCAGAGAATTCGAATA CAAATGCCTGNNNGATCGACATG | 4507 | TGCAGGACCAGAGAATTCGAATA CAAAACACAANNNGATCGACATG | 4747 | TGCAGGACCAGAGAATTCGAATA CATACGCCGNNNGATCGACATG | 4987 |
| TGCAGGACCAGAGAATTCGAATA CACCAGGCACNNNGATCGACATG | 4508 | TGCAGGACCAGAGAATTCGAATA CAGCCGCAACNNNGATCGACATG | 4748 | TGCAGGACCAGAGAATTCGAATA CAAATCGACNNNGATCGACATG | 4988 |
| TGCAGGACCAGAGAATTCGAATA CATGGCGACCNNNTGCATCAGGT | 4509 | TGCAGGACCAGAGAATTCGAATA CAGATCTTAANNNTGCATCAGGT | 4749 | TGCAGGACCAGAGAATTCGAATA CAGCCGCCGNNNTGCATCAGGT | 4989 |
| TGCAGGACCAGAGAATTCGAATA CAAAGAGGCTNNNTGCATCAGGT | 4510 | TGCAGGACCAGAGAATTCGAATA CACTAGAGTCNNNTGCATCAGGT | 4750 | TGCAGGACCAGAGAATTCGAATA CACCTGCCGTNNNTGCATCAGGT | 4990 |
| TGCAGGACCAGAGAATTCGAATA CATTACCCACNNNTGCATCAGGT | 4511 | TGCAGGACCAGAGAATTCGAATA CAGCATTCTCNNNTGCATCAGGT | 4751 | TGCAGGACCAGAGAATTCGAATA CACGTTACCTNNNTGCATCAGGT | 4991 |
| TGCAGGACCAGAGAATTCGAATA CATGCGGATTNNNTGCATCAGGT | 4512 | TGCAGGACCAGAGAATTCGAATA CAGCAGCCACNNNTGCATCAGGT | 4752 | TGCAGGACCAGAGAATTCGAATA CACGATTAGCNNNTGCATCAGGT | 4992 |
| TGCAGGACCAGAGAATTCGAATA CACAGGTTGTNNNTGCATCAGGT | 4513 | TGCAGGACCAGAGAATTCGAATA CAAGCTGCGCNNNTGCATCAGGT | 4753 | TGCAGGACCAGAGAATTCGAATA CAAACCTAATNNNTGCATCAGGT | 4993 |
| TGCAGGACCAGAGAATTCGAATA CAAACATAGANNNTGCATCAGGT | 4514 | TGCAGGACCAGAGAATTCGAATA CACCCGCTANNNTGCATCAGGT | 4754 | TGCAGGACCAGAGAATTCGAATA CAATCGGCTANNNTGCATCAGGT | 4994 |
| TGCAGGACCAGAGAATTCGAATA CAGAAATGATNNNTGCATCAGGT | 4515 | TGCAGGACCAGAGAATTCGAATA CACACAAGGCAANNNTGCATCAGGT | 4755 | TGCAGGACCAGAGAATTCGAATA CAGGAACCCNNNTGCATCAGGT | 4995 |
| TGCAGGACCAGAGAATTCGAATA CATGTGCTGANNNTGCATCAGGT | 4516 | TGCAGGACCAGAGAATTCGAATA CAGATGTTATNNNTGCATCAGGT | 4756 | TGCAGGACCAGAGAATTCGAATA CATCCACAGNNNTGCATCAGGT | 4996 |
| TGCAGGACCAGAGAATTCGAATA CAAGGCAGATNNNTGCATCAGGT | 4517 | TGCAGGACCAGAGAATTCGAATA CACGGTATTGNNNTGCATCAGGT | 4757 | TGCAGGACCAGAGAATTCGAATA CACTATTGAANNNTGCATCAGGT | 4997 |
| TGCAGGACCAGAGAATTCGAATA CATAGGTTATNNNTGCATCAGGT | 4518 | TGCAGGACCAGAGAATTCGAATA CAGTATTTAGNNNTGCATCAGGT | 4758 | TGCAGGACCAGAGAATTCGAATA CACGCGATATNNNTGCATCAGGT | 4998 |
| TGCAGGACCAGAGAATTCGAATA CATTTTTGTGNNNTGCATCAGGT | 4519 | TGCAGGACCAGAGAATTCGAATA CAGGATCAGANNNTGCATCAGGT | 4759 | TGCAGGACCAGAGAATTCGAATA CACTTATGTTNNNTGCATCAGGT | 4999 |
| TGCAGGACCAGAGAATTCGAATA CAAAACAAGTNNNTGCATCAGGT | 4520 | TGCAGGACCAGAGAATTCGAATA CAATCGAAAANNNTGCATCAGGT | 4760 | TGCAGGACCAGAGAATTCGAATA CAATTTGGTANNNTGCATCAGGT | 5000 |
| TGCAGGACCAGAGAATTCGAATA CACGTGGTTANNNTGCATCAGGT | 4521 | TGCAGGACCAGAGAATTCGAATA CAGCCATTTCNNNTGCATCAGGT | 4761 | TGCAGGACCAGAGAATTCGAATA CAAGGCAACANNNTGCATCAGGT | 5001 |
| TGCAGGACCAGAGAATTCGAATA CACTTTCGACNNNTGCATCAGGT | 4522 | TGCAGGACCAGAGAATTCGAATA CATCAGACCANNNTGCATCAGGT | 4762 | TGCAGGACCAGAGAATTCGAATA CAGACCTTTCNNNTGCATCAGGT | 5002 |
| TGCAGGACCAGAGAATTCGAATA CATAGACGTCNNNTGCATCAGGT | 4523 | TGCAGGACCAGAGAATTCGAATA CATTTGTTCANNNTGCATCAGGT | 4763 | TGCAGGACCAGAGAATTCGAATA CAGGAACCCANNNTGCATCAGGT | 5003 |
| TGCAGGACCAGAGAATTCGAATA CATCTAGTCNNNTGCATCAGGT | 4524 | TGCAGGACCAGAGAATTCGAATA CAACCCTATCNNNTGCATCAGGT | 4764 | TGCAGGACCAGAGAATTCGAATA CACGTGTAACNNNTGCATCAGGT | 5004 |
| TGCAGGACCAGAGAATTCGAATA CAAACAAGATNNNTGCATCAGGT | 4525 | TGCAGGACCAGAGAATTCGAATA CAAAAGCCGNNNTGCATCAGGT | 4765 | TGCAGGACCAGAGAATTCGAATA CACAGATCCANNNTGCATCAGGT | 5005 |
| TGCAGGACCAGAGAATTCGAATA CATAATGAAGNNNTGCATCAGGT | 4526 | TGCAGGACCAGAGAATTCGAATA CAGAGTGCGGNNNTGCATCAGGT | 4766 | TGCAGGACCAGAGAATTCGAATA CACCAGCACGNNNTGCATCAGGT | 5006 |

FIG. 18G

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CATATTCGCCNNNTGCATCAGGT | 4527 | TGCAGGACCAGAGAATTCGAATA CAATCATACANNNTGCATCAGGT | 4767 | TGCAGGACCAGAGAATTCGAATA CACGAGTCCGNNNTGCATCAGGT | 5007 |
| TGCAGGACCAGAGAATTCGAATA CATTGCACGANNNTGCATCAGGT | 4528 | TGCAGGACCAGAGAATTCGAATA CACAGATGAGNNNTGCATCAGGT | 4768 | TGCAGGACCAGAGAATTCGAATA CAGTCGAATCNNNTGCATCAGGT | 5008 |
| TGCAGGACCAGAGAATTCGAATA CAACTACTAANNNTGCATCAGGT | 4529 | TGCAGGACCAGAGAATTCGAATA CACAGCTTAGNNNTGCATCAGGT | 4769 | TGCAGGACCAGAGAATTCGAATA CATCCATAAANNNTGCATCAGGT | 5009 |
| TGCAGGACCAGAGAATTCGAATA CAACTCATAANNNTGCATCAGGT | 4530 | TGCAGGACCAGAGAATTCGAATA CAACTTCTTANNNTGCATCAGGT | 4770 | TGCAGGACCAGAGAATTCGAATA CAGTCCCACCNNNTGCATCAGGT | 5010 |
| TGCAGGACCAGAGAATTCGAATA CAAGGACTGANNNTGCATCAGGT | 4531 | TGCAGGACCAGAGAATTCGAATA CACAACAGAGNNNTGCATCAGGT | 4771 | TGCAGGACCAGAGAATTCGAATA CATGGTTGACNNNTGCATCAGGT | 5011 |
| TGCAGGACCAGAGAATTCGAATA CACACATCCTNNNTGCATCAGGT | 4532 | TGCAGGACCAGAGAATTCGAATA CACGTAGATCNNNTGCATCAGGT | 4772 | TGCAGGACCAGAGAATTCGAATA CAAGACAACGNNNTGCATCAGGT | 5012 |
| TGCAGGACCAGAGAATTCGAATA CAATAGCGAGNNNTGCATCAGGT | 4533 | TGCAGGACCAGAGAATTCGAATA CACCTCCGANNNTGCATCAGGT | 4773 | TGCAGGACCAGAGAATTCGAATA CAATATTCAGNNNTGCATCAGGT | 5013 |
| TGCAGGACCAGAGAATTCGAATA CAAGGAAGTCNNNTGCATCAGGT | 4534 | TGCAGGACCAGAGAATTCGAATA CAGACTTTGGNNNTGCATCAGGT | 4774 | TGCAGGACCAGAGAATTCGAATA CAGACGAATCNNNTGCATCAGGT | 5014 |
| TGCAGGACCAGAGAATTCGAATA CAGAAGCCTTNNNTGCATCAGGT | 4535 | TGCAGGACCAGAGAATTCGAATA CAGAACATCCNNNTGCATCAGGT | 4775 | TGCAGGACCAGAGAATTCGAATA CAGAGAACCNNNTGCATCAGGT | 5015 |
| TGCAGGACCAGAGAATTCGAATA CACCCCCTTCNNNTGCATCAGGT | 4536 | TGCAGGACCAGAGAATTCGAATA CACACATCANNNTGCATCAGGT | 4776 | TGCAGGACCAGAGAATTCGAATA CAGCAACAAGNNNTGCATCAGGT | 5016 |
| TGCAGGACCAGAGAATTCGAATA CAAGAAACCGNNNTGCATCAGGT | 4537 | TGCAGGACCAGAGAATTCGAATA CACTTCTGACNNNTGCATCAGGT | 4777 | TGCAGGACCAGAGAATTCGAATA CACTAAACCGNNNTGCATCAGGT | 5017 |
| TGCAGGACCAGAGAATTCGAATA CAGACATCTGNNNTGCATCAGGT | 4538 | TGCAGGACCAGAGAATTCGAATA CATCCCGTTANNNTGCATCAGGT | 4778 | TGCAGGACCAGAGAATTCGAATA CAGGAGGTCCNNNTGCATCAGGT | 5018 |
| TGCAGGACCAGAGAATTCGAATA CAACGCCCTCNNNTGCATCAGGT | 4539 | TGCAGGACCAGAGAATTCGAATA CATTTCCATANNNTGCATCAGGT | 4779 | TGCAGGACCAGAGAATTCGAATA CACGCGCGTANNNTGCATCAGGT | 5019 |
| TGCAGGACCAGAGAATTCGAATA CAGTCACCGGNNNTGCATCAGGT | 4540 | TGCAGGACCAGAGAATTCGAATA CACGTGCGACNNNTGCATCAGGT | 4780 | TGCAGGACCAGAGAATTCGAATA CACCGAGTGCNNNTGCATCAGGT | 5020 |
| TGCAGGACCAGAGAATTCGAATA CAAGAGCGATNNNTGCATCAGGT | 4541 | TGCAGGACCAGAGAATTCGAATA CAACGCTGGCNNNTGCATCAGGT | 4781 | TGCAGGACCAGAGAATTCGAATA CAGTTCAAGCNNNTGCATCAGGT | 5021 |
| TGCAGGACCAGAGAATTCGAATA CAATGGCTTGNNNTGCATCAGGT | 4542 | TGCAGGACCAGAGAATTCGAATA CAGAGATTCCNNNTGCATCAGGT | 4782 | TGCAGGACCAGAGAATTCGAATA CACAGCCCGANNNTGCATCAGGT | 5022 |
| TGCAGGACCAGAGAATTCGAATA CACCTGCAAANNNTGCATCAGGT | 4543 | TGCAGGACCAGAGAATTCGAATA CAGAGGACTANNNTGCATCAGGT | 4783 | TGCAGGACCAGAGAATTCGAATA CACCTTGACTNNNTGCATCAGGT | 5023 |
| TGCAGGACCAGAGAATTCGAATA CAGTCGAACTNNNTGCATCAGGT | 4544 | TGCAGGACCAGAGAATTCGAATA CATTGATTAGNNNTGCATCAGGT | 4784 | TGCAGGACCAGAGAATTCGAATA CAGACGCAAANNNTGCATCAGGT | 5024 |
| TGCAGGACCAGAGAATTCGAATA CATGTGGAGNNNTGCATCAGGT | 4545 | TGCAGGACCAGAGAATTCGAATA CACATGCATGNNNTGCATCAGGT | 4785 | TGCAGGACCAGAGAATTCGAATA CATGATCCTCNNNTGCATCAGGT | 5025 |
| TGCAGGACCAGAGAATTCGAATA CAAACGTGCTNNNTGCATCAGGT | 4546 | TGCAGGACCAGAGAATTCGAATA CATTGACCCNNNTGCATCAGGT | 4786 | TGCAGGACCAGAGAATTCGAATA CAAGAAATTGNNNTGCATCAGGT | 5026 |
| TGCAGGACCAGAGAATTCGAATA CAAAGATTGANNNTGCATCAGGT | 4547 | TGCAGGACCAGAGAATTCGAATA CAGGGCACTGNNNTGCATCAGGT | 4787 | TGCAGGACCAGAGAATTCGAATA CAGTCGTGGCNNNTGCATCAGGT | 5027 |
| TGCAGGACCAGAGAATTCGAATA CAACGTTATANNNTGCATCAGGT | 4548 | TGCAGGACCAGAGAATTCGAATA CATTCCTCTCNNNTGCATCAGGT | 4788 | TGCAGGACCAGAGAATTCGAATA CACATGTAGCNNNTGCATCAGGT | 5028 |
| TGCAGGACCAGAGAATTCGAATA CACCGCATAANNNTGCATCAGGT | 4549 | TGCAGGACCAGAGAATTCGAATA CAGCATTCAGNNNTGCATCAGGT | 4789 | TGCAGGACCAGAGAATTCGAATA CATAGCCCCNNNTGCATCAGGT | 5029 |
| TGCAGGACCAGAGAATTCGAATA CACGATTCCNNNTGCATCAGGT | 4550 | TGCAGGACCAGAGAATTCGAATA CAGTAACTTANNNTGCATCAGGT | 4790 | TGCAGGACCAGAGAATTCGAATA CAGTCTTGCTNNNTGCATCAGGT | 5030 |
| TGCAGGACCAGAGAATTCGAATA CAGTAAAACANNNTGCATCAGGT | 4551 | TGCAGGACCAGAGAATTCGAATA CAACTATGATNNNTGCATCAGGT | 4791 | TGCAGGACCAGAGAATTCGAATA CATGTAAGCCNNNTGCATCAGGT | 5031 |
| TGCAGGACCAGAGAATTCGAATA CAGGTGGTCCNNNTGCATCAGGT | 4552 | TGCAGGACCAGAGAATTCGAATA CAACTAAGAANNNTGCATCAGGT | 4792 | TGCAGGACCAGAGAATTCGAATA CAACAGAGACNNNTGCATCAGGT | 5032 |
| TGCAGGACCAGAGAATTCGAATA CAATGTCGTGNNNTGCATCAGGT | 4553 | TGCAGGACCAGAGAATTCGAATA CATAGGTTTANNNTGCATCAGGT | 4793 | TGCAGGACCAGAGAATTCGAATA CAAGTTCAGCNNNTGCATCAGGT | 5033 |
| TGCAGGACCAGAGAATTCGAATA CACGTAATATNNNTGCATCAGGT | 4554 | TGCAGGACCAGAGAATTCGAATA CACCTCGTCGNNNTGCATCAGGT | 4794 | TGCAGGACCAGAGAATTCGAATA CACCTGCTTANNNTGCATCAGGT | 5034 |
| TGCAGGACCAGAGAATTCGAATA CAACTCGCTTNNNTGCATCAGGT | 4555 | TGCAGGACCAGAGAATTCGAATA CAGGCTAGCCNNNTGCATCAGGT | 4795 | TGCAGGACCAGAGAATTCGAATA CAACACCTCNNNTGCATCAGGT | 5035 |
| TGCAGGACCAGAGAATTCGAATA CACCATACGANNNTGCATCAGGT | 4556 | TGCAGGACCAGAGAATTCGAATA CAGGGTTGANNNTGCATCAGGT | 4796 | TGCAGGACCAGAGAATTCGAATA CATATTGAACNNNTGCATCAGGT | 5036 |
| TGCAGGACCAGAGAATTCGAATA CACGGACAAANNNTGCATCAGGT | 4557 | TGCAGGACCAGAGAATTCGAATA CATAAAGCGNNNTGCATCAGGT | 4797 | TGCAGGACCAGAGAATTCGAATA CAGATTGGTCNNNTGCATCAGGT | 5037 |
| TGCAGGACCAGAGAATTCGAATA CACGCTGTTNNNTGCATCAGGT | 4558 | TGCAGGACCAGAGAATTCGAATA CAAATCTTTCNNNTGCATCAGGT | 4798 | TGCAGGACCAGAGAATTCGAATA CAAAAGAAAGNNNTGCATCAGGT | 5038 |
| TGCAGGACCAGAGAATTCGAATA CACTCCCATANNNTGCATCAGGT | 4559 | TGCAGGACCAGAGAATTCGAATA CACCAAGGAANNNTGCATCAGGT | 4799 | TGCAGGACCAGAGAATTCGAATA CATAAAAATANNNTGCATCAGGT | 5039 |

FIG. 18H

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGGCTTGCGNNNTGCATCAGGT | 4560 | TGCAGGACCAGAGAATTCGAATA CAACAAAGTNNNTGCATCAGGT | 4800 | TGCAGGACCAGAGAATTCGAATA CATGTCCAGANNNTGCATCAGGT | 5040 |
| TGCAGGACCAGAGAATTCGAATA CAAAATTTCGNNNTGCATCAGGT | 4561 | TGCAGGACCAGAGAATTCGAATA CAGGCCCGGNNNTGCATCAGGT | 4801 | TGCAGGACCAGAGAATTCGAATA CATTTGAGGCNNNTGCATCAGGT | 5041 |
| TGCAGGACCAGAGAATTCGAATA CATACCTAGGNNNTGCATCAGGT | 4562 | TGCAGGACCAGAGAATTCGAATA CAAACATGCCNNNTGCATCAGGT | 4802 | TGCAGGACCAGAGAATTCGAATA CACCATCCTANNNTGCATCAGGT | 5042 |
| TGCAGGACCAGAGAATTCGAATA CACACGCACGNNNTGCATCAGGT | 4563 | TGCAGGACCAGAGAATTCGAATA CATGGAGTTNNNTGCATCAGGT | 4803 | TGCAGGACCAGAGAATTCGAATA CACTCCAGAANNNTGCATCAGGT | 5043 |
| TGCAGGACCAGAGAATTCGAATA CACATTGCAGNNNTGCATCAGGT | 4564 | TGCAGGACCAGAGAATTCGAATA CATAGCGGAANNNTGCATCAGGT | 4804 | TGCAGGACCAGAGAATTCGAATA CACAGATGGANNNTGCATCAGGT | 5044 |
| TGCAGGACCAGAGAATTCGAATA CAGGCATTAATNNNTGCATCAGGT | 4565 | TGCAGGACCAGAGAATTCGAATA CAGTCTACTCNNNTGCATCAGGT | 4805 | TGCAGGACCAGAGAATTCGAATA CATAATCCCNNNTGCATCAGGT | 5045 |
| TGCAGGACCAGAGAATTCGAATA CAAGACGCCNNNTGCATCAGGT | 4566 | TGCAGGACCAGAGAATTCGAATA CATTTGACCCNNNTGCATCAGGT | 4806 | TGCAGGACCAGAGAATTCGAATA CAAGGCGCTCNNNTGCATCAGGT | 5046 |
| TGCAGGACCAGAGAATTCGAATA CACACACGATNNNTGCATCAGGT | 4567 | TGCAGGACCAGAGAATTCGAATA CAAAGGAGAGNNNTGCATCAGGT | 4807 | TGCAGGACCAGAGAATTCGAATA CAATTGTCAANNNTGCATCAGGT | 5047 |
| TGCAGGACCAGAGAATTCGAATA CATGATTGTANNNTGCATCAGGT | 4568 | TGCAGGACCAGAGAATTCGAATA CATTTCGCCANNNTGCATCAGGT | 4808 | TGCAGGACCAGAGAATTCGAATA CACGCGTTAANNNTGCATCAGGT | 5048 |

FIG. 19A

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CATTGATGCGNNNACGTATGCCA | 5049 | TGCAGGACCAGAGAATTCGAATA CATAACTAACNNNACGTATGCCA | 5289 | TGCAGGACCAGAGAATTCGAATA CAGTTGCGCGNNNACGTATGCCA | 5529 |
| TGCAGGACCAGAGAATTCGAATA CACCCTACGCNNNACGTATGCCA | 5050 | TGCAGGACCAGAGAATTCGAATA CAAAACTCGCNNNACGTATGCCA | 5290 | TGCAGGACCAGAGAATTCGAATA CAGGAACATGNNNACGTATGCCA | 5530 |
| TGCAGGACCAGAGAATTCGAATA CAGCGGCGAANNNACGTATGCCA | 5051 | TGCAGGACCAGAGAATTCGAATA CATGAGTTGCNNNACGTATGCCA | 5291 | TGCAGGACCAGAGAATTCGAATA CACGGTAACTNNNACGTATGCCA | 5531 |
| TGCAGGACCAGAGAATTCGAATA CATAGCCGCGNNNACGTATGCCA | 5052 | TGCAGGACCAGAGAATTCGAATA CAACAACAAANNNACGTATGCCA | 5292 | TGCAGGACCAGAGAATTCGAATA CAATGTGTGCNNNACGTATGCCA | 5532 |
| TGCAGGACCAGAGAATTCGAATA CAGAAGCGATNNNACGTATGCCA | 5053 | TGCAGGACCAGAGAATTCGAATA CAGCCCTACCNNNACGTATGCCA | 5293 | TGCAGGACCAGAGAATTCGAATA CACGGAGTTGNNNACGTATGCCA | 5533 |
| TGCAGGACCAGAGAATTCGAATA CAGACAGTGANNNACGTATGCCA | 5054 | TGCAGGACCAGAGAATTCGAATA CAGTTGAGAGNNNACGTATGCCA | 5294 | TGCAGGACCAGAGAATTCGAATA CATGAACTCGNNNACGTATGCCA | 5534 |
| TGCAGGACCAGAGAATTCGAATA CACTTTATCANNNACGTATGCCA | 5055 | TGCAGGACCAGAGAATTCGAATA CACACTGACTNNNACGTATGCCA | 5295 | TGCAGGACCAGAGAATTCGAATA CAACATCGCANNNACGTATGCCA | 5535 |
| TGCAGGACCAGAGAATTCGAATA CACAGGAAGTNNNACGTATGCCA | 5056 | TGCAGGACCAGAGAATTCGAATA CATGAAGACGNNNACGTATGCCA | 5296 | TGCAGGACCAGAGAATTCGAATA CAGAATTGTTNNNACGTATGCCA | 5536 |
| TGCAGGACCAGAGAATTCGAATA CAGTATTGGCNNNACGTATGCCA | 5057 | TGCAGGACCAGAGAATTCGAATA CACCCTATGTNNNACGTATGCCA | 5297 | TGCAGGACCAGAGAATTCGAATA CAAAACACTTNNNACGTATGCCA | 5537 |
| TGCAGGACCAGAGAATTCGAATA CATCAGCCGGNNNACGTATGCCA | 5058 | TGCAGGACCAGAGAATTCGAATA CATGGTTTGGNNNACGTATGCCA | 5298 | TGCAGGACCAGAGAATTCGAATA CATGTTTGCCNNNACGTATGCCA | 5538 |
| TGCAGGACCAGAGAATTCGAATA CAAGCAGGATNNNACGTATGCCA | 5059 | TGCAGGACCAGAGAATTCGAATA CAGCACTCGCNNNACGTATGCCA | 5299 | TGCAGGACCAGAGAATTCGAATA CACGGCGTGCANNNACGTATGCCA | 5539 |
| TGCAGGACCAGAGAATTCGAATA CAGTTAGTGCNNNACGTATGCCA | 5060 | TGCAGGACCAGAGAATTCGAATA CAAAAGAGTTNNNACGTATGCCA | 5300 | TGCAGGACCAGAGAATTCGAATA CAGTAATGCCNNNACGTATGCCA | 5540 |
| TGCAGGACCAGAGAATTCGAATA CAATTGTAGTNNNACGTATGCCA | 5061 | TGCAGGACCAGAGAATTCGAATA CAGTTCGTGANNNACGTATGCCA | 5301 | TGCAGGACCAGAGAATTCGAATA CAGTTCAGACNNNACGTATGCCA | 5541 |
| TGCAGGACCAGAGAATTCGAATA CAAGCACGTTNNNACGTATGCCA | 5062 | TGCAGGACCAGAGAATTCGAATA CATCCCCACGNNNACGTATGCCA | 5302 | TGCAGGACCAGAGAATTCGAATA CATAATCAGTNNNACGTATGCCA | 5542 |
| TGCAGGACCAGAGAATTCGAATA CACCCCGGTTNNNACGTATGCCA | 5063 | TGCAGGACCAGAGAATTCGAATA CAAAATTCTGNNNACGTATGCCA | 5303 | TGCAGGACCAGAGAATTCGAATA CATTCCCAACNNNACGTATGCCA | 5543 |
| TGCAGGACCAGAGAATTCGAATA CAATATCTCTNNNACGTATGCCA | 5064 | TGCAGGACCAGAGAATTCGAATA CATCCACAGANNNACGTATGCCA | 5304 | TGCAGGACCAGAGAATTCGAATA CACTAGTAGCNNNACGTATGCCA | 5544 |
| TGCAGGACCAGAGAATTCGAATA CAATCTTCATNNNACGTATGCCA | 5065 | TGCAGGACCAGAGAATTCGAATA CAAGAGTTTTNNNACGTATGCCA | 5305 | TGCAGGACCAGAGAATTCGAATA CATTAATACGNNNACGTATGCCA | 5545 |
| TGCAGGACCAGAGAATTCGAATA CAGGTACTCANNNACGTATGCCA | 5066 | TGCAGGACCAGAGAATTCGAATA CATGGAGCGGNNNACGTATGCCA | 5306 | TGCAGGACCAGAGAATTCGAATA CATACAGAGGNNNACGTATGCCA | 5546 |
| TGCAGGACCAGAGAATTCGAATA CACCCACCTATNNNACGTATGCCA | 5067 | TGCAGGACCAGAGAATTCGAATA CACTTTAATCNNNACGTATGCCA | 5307 | TGCAGGACCAGAGAATTCGAATA CACGGACACANNNACGTATGCCA | 5547 |
| TGCAGGACCAGAGAATTCGAATA CAATAATAAANNNACGTATGCCA | 5068 | TGCAGGACCAGAGAATTCGAATA CAACGTCAGTNNNACGTATGCCA | 5308 | TGCAGGACCAGAGAATTCGAATA CATCTCCCANNNACGTATGCCA | 5548 |
| TGCAGGACCAGAGAATTCGAATA CAACATAATCNNNACGTATGCCA | 5069 | TGCAGGACCAGAGAATTCGAATA CATGGAGCTTNNNACGTATGCCA | 5309 | TGCAGGACCAGAGAATTCGAATA CAGTACTCANNNACGTATGCCA | 5549 |
| TGCAGGACCAGAGAATTCGAATA CACGTTCGTANNNACGTATGCCA | 5070 | TGCAGGACCAGAGAATTCGAATA CAGCACACCGNNNACGTATGCCA | 5310 | TGCAGGACCAGAGAATTCGAATA CAGTAGTACCNNNACGTATGCCA | 5550 |
| TGCAGGACCAGAGAATTCGAATA CAGGATCTTGNNNACGTATGCCA | 5071 | TGCAGGACCAGAGAATTCGAATA CATTTGCTGCNNNACGTATGCCA | 5311 | TGCAGGACCAGAGAATTCGAATA CATAACGTCGNNNACGTATGCCA | 5551 |
| TGCAGGACCAGAGAATTCGAATA CAGAGGCGGTNNNACGTATGCCA | 5072 | TGCAGGACCAGAGAATTCGAATA CACAGCGAAANNNACGTATGCCA | 5312 | TGCAGGACCAGAGAATTCGAATA CACGGATAGANNNACGTATGCCA | 5552 |
| TGCAGGACCAGAGAATTCGAATA CACTCAAAATNNNACGTATGCCA | 5073 | TGCAGGACCAGAGAATTCGAATA CAACGATTGCNNNACGTATGCCA | 5313 | TGCAGGACCAGAGAATTCGAATA CAGGAATAGCNNNACGTATGCCA | 5553 |
| TGCAGGACCAGAGAATTCGAATA CACAACTGCANNNACGTATGCCA | 5074 | TGCAGGACCAGAGAATTCGAATA CATAGCGTTGNNNACGTATGCCA | 5314 | TGCAGGACCAGAGAATTCGAATA CAGGAGTCAANNNACGTATGCCA | 5554 |
| TGCAGGACCAGAGAATTCGAATA CACGGTTCCCNNNACGTATGCCA | 5075 | TGCAGGACCAGAGAATTCGAATA CAACGCTGCGNNNACGTATGCCA | 5315 | TGCAGGACCAGAGAATTCGAATA CAATTAGCTANNNACGTATGCCA | 5555 |
| TGCAGGACCAGAGAATTCGAATA CAGTGGTAGANNNACGTATGCCA | 5076 | TGCAGGACCAGAGAATTCGAATA CACTTTATTGNNNACGTATGCCA | 5316 | TGCAGGACCAGAGAATTCGAATA CAAGACATTNNNACGTATGCCA | 5556 |
| TGCAGGACCAGAGAATTCGAATA CATCTGAGTGNNNACGTATGCCA | 5077 | TGCAGGACCAGAGAATTCGAATA CAGCGAAATNNNACGTATGCCA | 5317 | TGCAGGACCAGAGAATTCGAATA CATCTACGCTNNNACGTATGCCA | 5557 |
| TGCAGGACCAGAGAATTCGAATA CACAGCCTTTNNNACGTATGCCA | 5078 | TGCAGGACCAGAGAATTCGAATA CATTTATTGCNNNACGTATGCCA | 5318 | TGCAGGACCAGAGAATTCGAATA CATGCCTTCANNNACGTATGCCA | 5558 |
| TGCAGGACCAGAGAATTCGAATA CAGTGTGTTGNNNACGTATGCCA | 5079 | TGCAGGACCAGAGAATTCGAATA CATCCAGCTGNNNACGTATGCCA | 5319 | TGCAGGACCAGAGAATTCGAATA CAAGATCACCNNNACGTATGCCA | 5559 |
| TGCAGGACCAGAGAATTCGAATA CAATTGTAACNNNACGTATGCCA | 5080 | TGCAGGACCAGAGAATTCGAATA CACCCATGCCNNNACGTATGCCA | 5320 | TGCAGGACCAGAGAATTCGAATA CAATCCTTTANNNACGTATGCCA | 5560 |
| TGCAGGACCAGAGAATTCGAATA CAAAGTTCATNNNACGTATGCCA | 5081 | TGCAGGACCAGAGAATTCGAATA CAATGCTGGTNNNACGTATGCCA | 5321 | TGCAGGACCAGAGAATTCGAATA CAGTAGTTCGNNNACGTATGCCA | 5561 |

FIG. 19B

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAAGTCGCTNNNACGTATGCCA | 5082 | TGCAGGACCAGAGAATTCGAATA CAAATGGCCTNNNACGTATGCCA | 5322 | TGCAGGACCAGAGAATTCGAATA CAGGGCCGGCNNNACGTATGCCA | 5562 |
| TGCAGGACCAGAGAATTCGAATA CAATATCAGTNNNACGTATGCCA | 5083 | TGCAGGACCAGAGAATTCGAATA CAGGTTTAGCNNNACGTATGCCA | 5323 | TGCAGGACCAGAGAATTCGAATA CAAGGCCAGGNNNACGTATGCCA | 5563 |
| TGCAGGACCAGAGAATTCGAATA CATTCTCCGANNNACGTATGCCA | 5084 | TGCAGGACCAGAGAATTCGAATA CATTCCCAGTNNNACGTATGCCA | 5324 | TGCAGGACCAGAGAATTCGAATA CATTGTCAGGNNNACGTATGCCA | 5564 |
| TGCAGGACCAGAGAATTCGAATA CATCTTGAAANNNACGTATGCCA | 5085 | TGCAGGACCAGAGAATTCGAATA CAAGCGATGANNNACGTATGCCA | 5325 | TGCAGGACCAGAGAATTCGAATA CAAAATCTGTNNNACGTATGCCA | 5565 |
| TGCAGGACCAGAGAATTCGAATA CATTACCGAGNNNACGTATGCCA | 5086 | TGCAGGACCAGAGAATTCGAATA CACCGGTCAGNNNACGTATGCCA | 5326 | TGCAGGACCAGAGAATTCGAATA CAATAAAAATNNNACGTATGCCA | 5566 |
| TGCAGGACCAGAGAATTCGAATA CAACTTAGATNNNACGTATGCCA | 5087 | TGCAGGACCAGAGAATTCGAATA CAAGTATACTNNNACGTATGCCA | 5327 | TGCAGGACCAGAGAATTCGAATA CATGTCACAGNNNACGTATGCCA | 5567 |
| TGCAGGACCAGAGAATTCGAATA CACATCGGTANNNACGTATGCCA | 5088 | TGCAGGACCAGAGAATTCGAATA CAGACTGAGANNNACGTATGCCA | 5328 | TGCAGGACCAGAGAATTCGAATA CATCTCATGCNNNACGTATGCCA | 5568 |
| TGCAGGACCAGAGAATTCGAATA CACCAGCGCANNNACGTATGCCA | 5089 | TGCAGGACCAGAGAATTCGAATA CATCACGTTCNNNACGTATGCCA | 5329 | TGCAGGACCAGAGAATTCGAATA CAGAACGCTNNNACGTATGCCA | 5569 |
| TGCAGGACCAGAGAATTCGAATA CATATCGATANNNACGTATGCCA | 5090 | TGCAGGACCAGAGAATTCGAATA CACTCACTACNNNACGTATGCCA | 5330 | TGCAGGACCAGAGAATTCGAATA CATCTCAGCTNNNACGTATGCCA | 5570 |
| TGCAGGACCAGAGAATTCGAATA CAAGACTCTGNNNACGTATGCCA | 5091 | TGCAGGACCAGAGAATTCGAATA CAGAAGGAGANNNACGTATGCCA | 5331 | TGCAGGACCAGAGAATTCGAATA CAGATGCGAANNNACGTATGCCA | 5571 |
| TGCAGGACCAGAGAATTCGAATA CAAGAGCACANNNACGTATGCCA | 5092 | TGCAGGACCAGAGAATTCGAATA CACCCTGCACNNNACGTATGCCA | 5332 | TGCAGGACCAGAGAATTCGAATA CACTCTATCGNNNACGTATGCCA | 5572 |
| TGCAGGACCAGAGAATTCGAATA CATACCGTAGNNNACGTATGCCA | 5093 | TGCAGGACCAGAGAATTCGAATA CAGCAACGAANNNACGTATGCCA | 5333 | TGCAGGACCAGAGAATTCGAATA CAGACGGTAANNNACGTATGCCA | 5573 |
| TGCAGGACCAGAGAATTCGAATA CAGAAGGTGTNNNACGTATGCCA | 5094 | TGCAGGACCAGAGAATTCGAATA CAGCTACCTTNNNACGTATGCCA | 5334 | TGCAGGACCAGAGAATTCGAATA CATATATTTNNNACGTATGCCA | 5574 |
| TGCAGGACCAGAGAATTCGAATA CATTGGACCANNNACGTATGCCA | 5095 | TGCAGGACCAGAGAATTCGAATA CAACACCTTCNNNACGTATGCCA | 5335 | TGCAGGACCAGAGAATTCGAATA CATGCATTCCNNNACGTATGCCA | 5575 |
| TGCAGGACCAGAGAATTCGAATA CAGCAATCACNNNACGTATGCCA | 5096 | TGCAGGACCAGAGAATTCGAATA CACTGTTAAANNNACGTATGCCA | 5336 | TGCAGGACCAGAGAATTCGAATA CATATATCTCNNNACGTATGCCA | 5576 |
| TGCAGGACCAGAGAATTCGAATA CATTGAGCGTNNNACGTATGCCA | 5097 | TGCAGGACCAGAGAATTCGAATA CAATCTCGGANNNACGTATGCCA | 5337 | TGCAGGACCAGAGAATTCGAATA CACCGGCTGANNNACGTATGCCA | 5577 |
| TGCAGGACCAGAGAATTCGAATA CACAAGTGTCNNNACGTATGCCA | 5098 | TGCAGGACCAGAGAATTCGAATA CAATGTTGCGNNNACGTATGCCA | 5338 | TGCAGGACCAGAGAATTCGAATA CAGAATCAGGNNNACGTATGCCA | 5578 |
| TGCAGGACCAGAGAATTCGAATA CAGTCTAATANNNACGTATGCCA | 5099 | TGCAGGACCAGAGAATTCGAATA CAGCACATGTNNNACGTATGCCA | 5339 | TGCAGGACCAGAGAATTCGAATA CATCCTAGAGNNNACGTATGCCA | 5579 |
| TGCAGGACCAGAGAATTCGAATA CAAAGAAATCNNNACGTATGCCA | 5100 | TGCAGGACCAGAGAATTCGAATA CAAATCCGGTNNNACGTATGCCA | 5340 | TGCAGGACCAGAGAATTCGAATA CACCGTGTGGNNNACGTATGCCA | 5580 |
| TGCAGGACCAGAGAATTCGAATA CAGCTAGATCNNNACGTATGCCA | 5101 | TGCAGGACCAGAGAATTCGAATA CACTATTTACNNNACGTATGCCA | 5341 | TGCAGGACCAGAGAATTCGAATA CATAGTTTCTNNNACGTATGCCA | 5581 |
| TGCAGGACCAGAGAATTCGAATA CAGATAAGTANNNACGTATGCCA | 5102 | TGCAGGACCAGAGAATTCGAATA CACGTGCCAGNNNACGTATGCCA | 5342 | TGCAGGACCAGAGAATTCGAATA CAGATAACGANNNACGTATGCCA | 5582 |
| TGCAGGACCAGAGAATTCGAATA CAGGTTCAGTNNNACGTATGCCA | 5103 | TGCAGGACCAGAGAATTCGAATA CACCGGTAGCNNNACGTATGCCA | 5343 | TGCAGGACCAGAGAATTCGAATA CACTCGTACTNNNACGTATGCCA | 5583 |
| TGCAGGACCAGAGAATTCGAATA CAAGCTGACTNNNACGTATGCCA | 5104 | TGCAGGACCAGAGAATTCGAATA CAACATATGTNNNACGTATGCCA | 5344 | TGCAGGACCAGAGAATTCGAATA CAGCACTTTCNNNACGTATGCCA | 5584 |
| TGCAGGACCAGAGAATTCGAATA CATGCGCCAGNNNACGTATGCCA | 5105 | TGCAGGACCAGAGAATTCGAATA CATGGTGGCCNNNACGTATGCCA | 5345 | TGCAGGACCAGAGAATTCGAATA CAGTTCTCGTNNNACGTATGCCA | 5585 |
| TGCAGGACCAGAGAATTCGAATA CATGTCAGTGNNNACGTATGCCA | 5106 | TGCAGGACCAGAGAATTCGAATA CACAACTCAGNNNACGTATGCCA | 5346 | TGCAGGACCAGAGAATTCGAATA CACTTACGTCNNNACGTATGCCA | 5586 |
| TGCAGGACCAGAGAATTCGAATA CAGAATCGTCNNNACGTATGCCA | 5107 | TGCAGGACCAGAGAATTCGAATA CACCAATTTNNNACGTATGCCA | 5347 | TGCAGGACCAGAGAATTCGAATA CACAGAAGACNNNACGTATGCCA | 5587 |
| TGCAGGACCAGAGAATTCGAATA CACCCCATGCNNNACGTATGCCA | 5108 | TGCAGGACCAGAGAATTCGAATA CAAACTGAGGNNNACGTATGCCA | 5348 | TGCAGGACCAGAGAATTCGAATA CATAAGTCTANNNACGTATGCCA | 5588 |
| TGCAGGACCAGAGAATTCGAATA CACATTAGCGNNNCTAGCGTTAC | 5109 | TGCAGGACCAGAGAATTCGAATA CAACCTAGTCNNNCTAGCGTTAC | 5349 | TGCAGGACCAGAGAATTCGAATA CACATACTAANNNCTAGCGTTAC | 5589 |
| TGCAGGACCAGAGAATTCGAATA CAATCCACCTNNNCTAGCGTTAC | 5110 | TGCAGGACCAGAGAATTCGAATA CAGCATGGCCNNNCTAGCGTTAC | 5350 | TGCAGGACCAGAGAATTCGAATA CACCGAATCANNNCTAGCGTTAC | 5590 |
| TGCAGGACCAGAGAATTCGAATA CAACATGCGTNNNCTAGCGTTAC | 5111 | TGCAGGACCAGAGAATTCGAATA CAAGTCAGAANNNCTAGCGTTAC | 5351 | TGCAGGACCAGAGAATTCGAATA CACTATTTGNNNCTAGCGTTAC | 5591 |
| TGCAGGACCAGAGAATTCGAATA CAGCTTTACCNNNCTAGCGTTAC | 5112 | TGCAGGACCAGAGAATTCGAATA CATGAATACTNNNCTAGCGTTAC | 5352 | TGCAGGACCAGAGAATTCGAATA CACCCGACAGNNNCTAGCGTTAC | 5592 |
| TGCAGGACCAGAGAATTCGAATA CAAACCTCCTNNNCTAGCGTTAC | 5113 | TGCAGGACCAGAGAATTCGAATA CAGTATGAGCNNNCTAGCGTTAC | 5353 | TGCAGGACCAGAGAATTCGAATA CAACTTCGAGNNNCTAGCGTTAC | 5593 |
| TGCAGGACCAGAGAATTCGAATA CACTTTATGTNNNCTAGCGTTAC | 5114 | TGCAGGACCAGAGAATTCGAATA CAGACTTGTGNNNCTAGCGTTAC | 5354 | TGCAGGACCAGAGAATTCGAATA CATGATGCTGNNNCTAGCGTTAC | 5594 |

FIG. 19C

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CACTCGCCTGNNNCTAGCGTTAC | 5115 | TGCAGGACCAGAGAATTCGAATA CAAATTAAGGNNNCTAGCGTTAC | 5355 | TGCAGGACCAGAGAATTCGAATA CAGCGCAGGANNNCTAGCGTTAC | 5595 |
| TGCAGGACCAGAGAATTCGAATA CAATGATGTTNNNCTAGCGTTAC | 5116 | TGCAGGACCAGAGAATTCGAATA CACGGTTGTANNNCTAGCGTTAC | 5356 | TGCAGGACCAGAGAATTCGAATA CATTCACAAANNNCTAGCGTTAC | 5596 |
| TGCAGGACCAGAGAATTCGAATA CAGAGTTGGANNNCTAGCGTTAC | 5117 | TGCAGGACCAGAGAATTCGAATA CACCTGTCCGNNNCTAGCGTTAC | 5357 | TGCAGGACCAGAGAATTCGAATA CAATGCACTGNNNCTAGCGTTAC | 5597 |
| TGCAGGACCAGAGAATTCGAATA CAACAACCACNNNCTAGCGTTAC | 5118 | TGCAGGACCAGAGAATTCGAATA CAGTGACGCCNNNCTAGCGTTAC | 5358 | TGCAGGACCAGAGAATTCGAATA CAGTTGCCGGNNNCTAGCGTTAC | 5598 |
| TGCAGGACCAGAGAATTCGAATA CATACCGCAANNNCTAGCGTTAC | 5119 | TGCAGGACCAGAGAATTCGAATA CAGTGTTGCANNNCTAGCGTTAC | 5359 | TGCAGGACCAGAGAATTCGAATA CAATTTTCCANNNCTAGCGTTAC | 5599 |
| TGCAGGACCAGAGAATTCGAATA CAGGTTAAAANNNCTAGCGTTAC | 5120 | TGCAGGACCAGAGAATTCGAATA CACCCGATTTNNNCTAGCGTTAC | 5360 | TGCAGGACCAGAGAATTCGAATA CACCAGCAGCNNNCTAGCGTTAC | 5600 |
| TGCAGGACCAGAGAATTCGAATA CACGGAAAGTNNNCTAGCGTTAC | 5121 | TGCAGGACCAGAGAATTCGAATA CATTTCCGTGNNNCTAGCGTTAC | 5361 | TGCAGGACCAGAGAATTCGAATA CACGGACAGGNNNCTAGCGTTAC | 5601 |
| TGCAGGACCAGAGAATTCGAATA CAGTGGTCGNNNCTAGCGTTAC | 5122 | TGCAGGACCAGAGAATTCGAATA CAAAGGTCCTNNNCTAGCGTTAC | 5362 | TGCAGGACCAGAGAATTCGAATA CATCTGCGTTNNNCTAGCGTTAC | 5602 |
| TGCAGGACCAGAGAATTCGAATA CAGGTGTCCGNNNCTAGCGTTAC | 5123 | TGCAGGACCAGAGAATTCGAATA CAGAGCCAAANNNCTAGCGTTAC | 5363 | TGCAGGACCAGAGAATTCGAATA CATTTGCTATNNNCTAGCGTTAC | 5603 |
| TGCAGGACCAGAGAATTCGAATA CATCGCACTTNNNCTAGCGTTAC | 5124 | TGCAGGACCAGAGAATTCGAATA CACCCTTCAANNNCTAGCGTTAC | 5364 | TGCAGGACCAGAGAATTCGAATA CATTTCCTTTNNNCTAGCGTTAC | 5604 |
| TGCAGGACCAGAGAATTCGAATA CATTCGGTCTNNNCTAGCGTTAC | 5125 | TGCAGGACCAGAGAATTCGAATA CAGCGCGGTTNNNCTAGCGTTAC | 5365 | TGCAGGACCAGAGAATTCGAATA CACGAGACTTNNNCTAGCGTTAC | 5605 |
| TGCAGGACCAGAGAATTCGAATA CAACGAGGATNNNCTAGCGTTAC | 5126 | TGCAGGACCAGAGAATTCGAATA CACTTCTAGCNNNCTAGCGTTAC | 5366 | TGCAGGACCAGAGAATTCGAATA CAAACTAGAANNNCTAGCGTTAC | 5606 |
| TGCAGGACCAGAGAATTCGAATA CAGTAGATGGNNNCTAGCGTTAC | 5127 | TGCAGGACCAGAGAATTCGAATA CAGTGTAAAANNNCTAGCGTTAC | 5367 | TGCAGGACCAGAGAATTCGAATA CACCTCGATTNNNCTAGCGTTAC | 5607 |
| TGCAGGACCAGAGAATTCGAATA CACCACACTTNNNCTAGCGTTAC | 5128 | TGCAGGACCAGAGAATTCGAATA CAACTATGCGNNNCTAGCGTTAC | 5368 | TGCAGGACCAGAGAATTCGAATA CAGTGAAGACNNNCTAGCGTTAC | 5608 |
| TGCAGGACCAGAGAATTCGAATA CAGTTTGCGANNNCTAGCGTTAC | 5129 | TGCAGGACCAGAGAATTCGAATA CACGCCAGACNNNCTAGCGTTAC | 5369 | TGCAGGACCAGAGAATTCGAATA CAACGTTACGNNNCTAGCGTTAC | 5609 |
| TGCAGGACCAGAGAATTCGAATA CAACGGTATCNNNCTAGCGTTAC | 5130 | TGCAGGACCAGAGAATTCGAATA CAATCAGTGCNNNCTAGCGTTAC | 5370 | TGCAGGACCAGAGAATTCGAATA CACGTCCTGCNNNCTAGCGTTAC | 5610 |
| TGCAGGACCAGAGAATTCGAATA CAATGATAGANNNCTAGCGTTAC | 5131 | TGCAGGACCAGAGAATTCGAATA CAGTTCTACCNNNCTAGCGTTAC | 5371 | TGCAGGACCAGAGAATTCGAATA CAACTCCTACNNNCTAGCGTTAC | 5611 |
| TGCAGGACCAGAGAATTCGAATA CACAATAACTNNNCTAGCGTTAC | 5132 | TGCAGGACCAGAGAATTCGAATA CACACCATAGNNNCTAGCGTTAC | 5372 | TGCAGGACCAGAGAATTCGAATA CAGTTAGGTCNNNCTAGCGTTAC | 5612 |
| TGCAGGACCAGAGAATTCGAATA CAGATCCTAGNNNCTAGCGTTAC | 5133 | TGCAGGACCAGAGAATTCGAATA CACAAAGATANNNCTAGCGTTAC | 5373 | TGCAGGACCAGAGAATTCGAATA CACTCATGAGNNNCTAGCGTTAC | 5613 |
| TGCAGGACCAGAGAATTCGAATA CAATTACCCCNNNCTAGCGTTAC | 5134 | TGCAGGACCAGAGAATTCGAATA CACAGGGCTTNNNCTAGCGTTAC | 5374 | TGCAGGACCAGAGAATTCGAATA CATATTTACCNNNCTAGCGTTAC | 5614 |
| TGCAGGACCAGAGAATTCGAATA CACTGTGCGGNNNCTAGCGTTAC | 5135 | TGCAGGACCAGAGAATTCGAATA CAGTCGTTAGNNNCTAGCGTTAC | 5375 | TGCAGGACCAGAGAATTCGAATA CACCCTTCATNNNCTAGCGTTAC | 5615 |
| TGCAGGACCAGAGAATTCGAATA CATATGTGTANNNCTAGCGTTAC | 5136 | TGCAGGACCAGAGAATTCGAATA CAAACGTTCGNNNCTAGCGTTAC | 5376 | TGCAGGACCAGAGAATTCGAATA CAGGACTAGANNNCTAGCGTTAC | 5616 |
| TGCAGGACCAGAGAATTCGAATA CAGCTCCTTANNNCTAGCGTTAC | 5137 | TGCAGGACCAGAGAATTCGAATA CAATGGCTGTNNNCTAGCGTTAC | 5377 | TGCAGGACCAGAGAATTCGAATA CAGTGGCAAANNNCTAGCGTTAC | 5617 |
| TGCAGGACCAGAGAATTCGAATA CAAAAAGCGCNNNCTAGCGTTAC | 5138 | TGCAGGACCAGAGAATTCGAATA CAATTCTATCNNNCTAGCGTTAC | 5378 | TGCAGGACCAGAGAATTCGAATA CAAATAAACGNNNCTAGCGTTAC | 5618 |
| TGCAGGACCAGAGAATTCGAATA CATGGTATATNNNCTAGCGTTAC | 5139 | TGCAGGACCAGAGAATTCGAATA CAGGTAGCAANNNCTAGCGTTAC | 5379 | TGCAGGACCAGAGAATTCGAATA CAGTATACCGNNNCTAGCGTTAC | 5619 |
| TGCAGGACCAGAGAATTCGAATA CACATCACGANNNCTAGCGTTAC | 5140 | TGCAGGACCAGAGAATTCGAATA CATGGTGACTNNNCTAGCGTTAC | 5380 | TGCAGGACCAGAGAATTCGAATA CACCAAATTANNNCTAGCGTTAC | 5620 |
| TGCAGGACCAGAGAATTCGAATA CACTCATTCGNNNCTAGCGTTAC | 5141 | TGCAGGACCAGAGAATTCGAATA CATCCTAATTNNNCTAGCGTTAC | 5381 | TGCAGGACCAGAGAATTCGAATA CATTCTTTAGNNNCTAGCGTTAC | 5621 |
| TGCAGGACCAGAGAATTCGAATA CAGGCGCATCNNNCTAGCGTTAC | 5142 | TGCAGGACCAGAGAATTCGAATA CAGCCGCCTGNNNCTAGCGTTAC | 5382 | TGCAGGACCAGAGAATTCGAATA CATGTTCGTCNNNCTAGCGTTAC | 5622 |
| TGCAGGACCAGAGAATTCGAATA CAAAAGATTGNNNCTAGCGTTAC | 5143 | TGCAGGACCAGAGAATTCGAATA CACCCGCAAGNNNCTAGCGTTAC | 5383 | TGCAGGACCAGAGAATTCGAATA CACCGGCTCTNNNCTAGCGTTAC | 5623 |
| TGCAGGACCAGAGAATTCGAATA CATGAAAGATNNNCTAGCGTTAC | 5144 | TGCAGGACCAGAGAATTCGAATA CATCCCTGGCNNNCTAGCGTTAC | 5384 | TGCAGGACCAGAGAATTCGAATA CACGAGTGTTNNNCTAGCGTTAC | 5624 |
| TGCAGGACCAGAGAATTCGAATA CACAGGCTTANNNCTAGCGTTAC | 5145 | TGCAGGACCAGAGAATTCGAATA CAGATCCCTTNNNCTAGCGTTAC | 5385 | TGCAGGACCAGAGAATTCGAATA CAGGGTATNNNCTAGCGTTAC | 5625 |
| TGCAGGACCAGAGAATTCGAATA CACGAATTCGNNNCTAGCGTTAC | 5146 | TGCAGGACCAGAGAATTCGAATA CATAGATGAANNNCTAGCGTTAC | 5386 | TGCAGGACCAGAGAATTCGAATA CAAAGTCTCGNNNCTAGCGTTAC | 5626 |
| TGCAGGACCAGAGAATTCGAATA CATAACCACGNNNCTAGCGTTAC | 5147 | TGCAGGACCAGAGAATTCGAATA CAAGGCAAGTNNNCTAGCGTTAC | 5387 | TGCAGGACCAGAGAATTCGAATA CAGTAGCAAGNNNCTAGCGTTAC | 5627 |

FIG. 19D

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAGCAGGTANNNCTAGCGTTAC | 5148 | TGCAGGACCAGAGAATTCGAATA CATAATCTGANNNCTAGCGTTAC | 5388 | TGCAGGACCAGAGAATTCGAATA CACGGAGAGCNNNCTAGCGTTAC | 5628 |
| TGCAGGACCAGAGAATTCGAATA CACACAAGGANNNCTAGCGTTAC | 5149 | TGCAGGACCAGAGAATTCGAATA CAGGCCAAAANNNCTAGCGTTAC | 5389 | TGCAGGACCAGAGAATTCGAATA CAGCTTTTGCNNNCTAGCGTTAC | 5629 |
| TGCAGGACCAGAGAATTCGAATA CAACTAGCCAMNNCTAGCGTTAC | 5150 | TGCAGGACCAGAGAATTCGAATA CAAAGCGTCTNNNCTAGCGTTAC | 5390 | TGCAGGACCAGAGAATTCGAATA CATATGTAGTNNNCTAGCGTTAC | 5630 |
| TGCAGGACCAGAGAATTCGAATA CACACGTGGCNNNCTAGCGTTAC | 5151 | TGCAGGACCAGAGAATTCGAATA CACATGGCCNNNCTAGCGTTAC | 5391 | TGCAGGACCAGAGAATTCGAATA CAATCTCTCGNNNCTAGCGTTAC | 5631 |
| TGCAGGACCAGAGAATTCGAATA CACCAGTCGNNNCTAGCGTTAC | 5152 | TGCAGGACCAGAGAATTCGAATA CAGGAAGATCNNNCTAGCGTTAC | 5392 | TGCAGGACCAGAGAATTCGAATA CAGTGTTTCCNNNCTAGCGTTAC | 5632 |
| TGCAGGACCAGAGAATTCGAATA CACACCCCTGNNNCTAGCGTTAC | 5153 | TGCAGGACCAGAGAATTCGAATA CATCAGCTAGNNNCTAGCGTTAC | 5393 | TGCAGGACCAGAGAATTCGAATA CACGTAGTACNNNCTAGCGTTAC | 5633 |
| TGCAGGACCAGAGAATTCGAATA CACAATACATNNNCTAGCGTTAC | 5154 | TGCAGGACCAGAGAATTCGAATA CACTGCTAAGNNNCTAGCGTTAC | 5394 | TGCAGGACCAGAGAATTCGAATA CAGCCGAAATNNNCTAGCGTTAC | 5634 |
| TGCAGGACCAGAGAATTCGAATA CACTGCATAGNNNCTAGCGTTAC | 5155 | TGCAGGACCAGAGAATTCGAATA CACACTTGGANNNCTAGCGTTAC | 5395 | TGCAGGACCAGAGAATTCGAATA CATAATTCAGNNNCTAGCGTTAC | 5635 |
| TGCAGGACCAGAGAATTCGAATA CACTGAAAAANNNCTAGCGTTAC | 5156 | TGCAGGACCAGAGAATTCGAATA CACTCGAATGNNNCTAGCGTTAC | 5396 | TGCAGGACCAGAGAATTCGAATA CACGCGCGGCNNNCTAGCGTTAC | 5636 |
| TGCAGGACCAGAGAATTCGAATA CAGTCCATTCNNNCTAGCGTTAC | 5157 | TGCAGGACCAGAGAATTCGAATA CACGCTTAAGNNNCTAGCGTTAC | 5397 | TGCAGGACCAGAGAATTCGAATA CACGAAGAGTNNNCTAGCGTTAC | 5637 |
| TGCAGGACCAGAGAATTCGAATA CATTAGTGGCNNNCTAGCGTTAC | 5158 | TGCAGGACCAGAGAATTCGAATA CAATATTGTGNNNCTAGCGTTAC | 5398 | TGCAGGACCAGAGAATTCGAATA CAAGCGTGTTNNNCTAGCGTTAC | 5638 |
| TGCAGGACCAGAGAATTCGAATA CAACTGGCATNNNCTAGCGTTAC | 5159 | TGCAGGACCAGAGAATTCGAATA CATTTCACGCNNNCTAGCGTTAC | 5399 | TGCAGGACCAGAGAATTCGAATA CACGAAAGCANNNCTAGCGTTAC | 5639 |
| TGCAGGACCAGAGAATTCGAATA CAATGGTTGCNNNCTAGCGTTAC | 5160 | TGCAGGACCAGAGAATTCGAATA CATTCCATCGNNNCTAGCGTTAC | 5400 | TGCAGGACCAGAGAATTCGAATA CAGTCTACCTNNNCTAGCGTTAC | 5640 |
| TGCAGGACCAGAGAATTCGAATA CATGGCTCCCNNNCTAGCGTTAC | 5161 | TGCAGGACCAGAGAATTCGAATA CAAATGCACNNNCTAGCGTTAC | 5401 | TGCAGGACCAGAGAATTCGAATA CACATGCGGCNNNCTAGCGTTAC | 5641 |
| TGCAGGACCAGAGAATTCGAATA CAGATTTTTCNNNCTAGCGTTAC | 5162 | TGCAGGACCAGAGAATTCGAATA CAATCAGTCGNNNCTAGCGTTAC | 5402 | TGCAGGACCAGAGAATTCGAATA CATGACCGGCNNNCTAGCGTTAC | 5642 |
| TGCAGGACCAGAGAATTCGAATA CAGCCTACAANNNCTAGCGTTAC | 5163 | TGCAGGACCAGAGAATTCGAATA CACTCTGAAGNNNCTAGCGTTAC | 5403 | TGCAGGACCAGAGAATTCGAATA CAACTTTAGANNNCTAGCGTTAC | 5643 |
| TGCAGGACCAGAGAATTCGAATA CAGGATTCACNNNCTAGCGTTAC | 5164 | TGCAGGACCAGAGAATTCGAATA CAAAAGTGATNNNCTAGCGTTAC | 5404 | TGCAGGACCAGAGAATTCGAATA CAAGCTCGCGNNNCTAGCGTTAC | 5644 |
| TGCAGGACCAGAGAATTCGAATA CAATTCGCAGNNNCTAGCGTTAC | 5165 | TGCAGGACCAGAGAATTCGAATA CATCAACCTCNNNCTAGCGTTAC | 5405 | TGCAGGACCAGAGAATTCGAATA CAAGACATCCNNNCTAGCGTTAC | 5645 |
| TGCAGGACCAGAGAATTCGAATA CACGGCTACGNNNCTAGCGTTAC | 5166 | TGCAGGACCAGAGAATTCGAATA CAGCTAATGCNNNCTAGCGTTAC | 5406 | TGCAGGACCAGAGAATTCGAATA CACTCAATGGNNNCTAGCGTTAC | 5646 |
| TGCAGGACCAGAGAATTCGAATA CAATCCTAGGNNNCTAGCGTTAC | 5167 | TGCAGGACCAGAGAATTCGAATA CATATTGGCNNNCTAGCGTTAC | 5407 | TGCAGGACCAGAGAATTCGAATA CATATTCCGCNNNCTAGCGTTAC | 5647 |
| TGCAGGACCAGAGAATTCGAATA CATCGTACCTNNNCTAGCGTTAC | 5168 | TGCAGGACCAGAGAATTCGAATA CATACTATCTNNNCTAGCGTTAC | 5408 | TGCAGGACCAGAGAATTCGAATA CATTCACCTGNNNCTAGCGTTAC | 5648 |
| TGCAGGACCAGAGAATTCGAATA CACATCTAAANNNGATCGACATG | 5169 | TGCAGGACCAGAGAATTCGAATA CAGACTCGGNNNGATCGACATG | 5409 | TGCAGGACCAGAGAATTCGAATA CACTCTGTACNNNGATCGACATG | 5649 |
| TGCAGGACCAGAGAATTCGAATA CAAGTGAACGNNNGATCGACATG | 5170 | TGCAGGACCAGAGAATTCGAATA CAGCTGTATGNNNGATCGACATG | 5410 | TGCAGGACCAGAGAATTCGAATA CATTGATTCNNNGATCGACATG | 5650 |
| TGCAGGACCAGAGAATTCGAATA CACTGAACTGNNNGATCGACATG | 5171 | TGCAGGACCAGAGAATTCGAATA CAAAAATTGCTNNNGATCGACATG | 5411 | TGCAGGACCAGAGAATTCGAATA CAGCACATACNNNGATCGACATG | 5651 |
| TGCAGGACCAGAGAATTCGAATA CAGATACGAGNNNGATCGACATG | 5172 | TGCAGGACCAGAGAATTCGAATA CAACATGTTANNNGATCGACATG | 5412 | TGCAGGACCAGAGAATTCGAATA CAGCTTGTGANNNGATCGACATG | 5652 |
| TGCAGGACCAGAGAATTCGAATA CATTTCCTAANNNGATCGACATG | 5173 | TGCAGGACCAGAGAATTCGAATA CAAGATGGACNNNGATCGACATG | 5413 | TGCAGGACCAGAGAATTCGAATA CATACGGTACNNNGATCGACATG | 5653 |
| TGCAGGACCAGAGAATTCGAATA CATAGTCTTNNNGATCGACATG | 5174 | TGCAGGACCAGAGAATTCGAATA CATGTCTCCANNNGATCGACATG | 5414 | TGCAGGACCAGAGAATTCGAATA CACACGGTCGNNNGATCGACATG | 5654 |
| TGCAGGACCAGAGAATTCGAATA CAAGTTGCCANNNGATCGACATG | 5175 | TGCAGGACCAGAGAATTCGAATA CATTGGCTAGNNNGATCGACATG | 5415 | TGCAGGACCAGAGAATTCGAATA CACCAAGGTTNNNGATCGACATG | 5655 |
| TGCAGGACCAGAGAATTCGAATA CAAGCGACAANNNGATCGACATG | 5176 | TGCAGGACCAGAGAATTCGAATA CATAATTTCCNNNGATCGACATG | 5416 | TGCAGGACCAGAGAATTCGAATA CAGTTCGGCGNNNGATCGACATG | 5656 |
| TGCAGGACCAGAGAATTCGAATA CAGGATAAATNNNGATCGACATG | 5177 | TGCAGGACCAGAGAATTCGAATA CAGTGTTAATNNNGATCGACATG | 5417 | TGCAGGACCAGAGAATTCGAATA CAACGCAGCCNNNGATCGACATG | 5657 |
| TGCAGGACCAGAGAATTCGAATA CATTTGAAACNNNGATCGACATG | 5178 | TGCAGGACCAGAGAATTCGAATA CATGAGCAAGNNNGATCGACATG | 5418 | TGCAGGACCAGAGAATTCGAATA CACCCCGAGANNNGATCGACATG | 5658 |
| TGCAGGACCAGAGAATTCGAATA CAGAGATACNNNGATCGACATG | 5179 | TGCAGGACCAGAGAATTCGAATA CACGGCCCTANNNGATCGACATG | 5419 | TGCAGGACCAGAGAATTCGAATA CACTCCATGTNNNGATCGACATG | 5659 |
| TGCAGGACCAGAGAATTCGAATA CAACTGGATCNNNGATCGACATG | 5180 | TGCAGGACCAGAGAATTCGAATA CAGTCACAGTNNNGATCGACATG | 5420 | TGCAGGACCAGAGAATTCGAATA CATTTGCACCNNNGATCGACATG | 5660 |

FIG. 19E

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAAATGGATNNNGATCGACATG | 5181 | TGCAGGACCAGAGAATTCGAATA CAGTTGGTGTNNNGATCGACATG | 5421 | TGCAGGACCAGAGAATTCGAATA CAATTACAACNNNGATCGACATG | 5661 |
| TGCAGGACCAGAGAATTCGAATA CACGCATGATNNNGATCGACATG | 5182 | TGCAGGACCAGAGAATTCGAATA CACTTATTACNNNGATCGACATG | 5422 | TGCAGGACCAGAGAATTCGAATA CATGCCCACCNNNGATCGACATG | 5662 |
| TGCAGGACCAGAGAATTCGAATA CATACGAATTNNNGATCGACATG | 5183 | TGCAGGACCAGAGAATTCGAATA CACTCGCAAANNNGATCGACATG | 5423 | TGCAGGACCAGAGAATTCGAATA CAGATTGGAGNNNGATCGACATG | 5663 |
| TGCAGGACCAGAGAATTCGAATA CAGGAAAGCTNNNGATCGACATG | 5184 | TGCAGGACCAGAGAATTCGAATA CACTAGGTGTNNNGATCGACATG | 5424 | TGCAGGACCAGAGAATTCGAATA CATCGTACCCNNNGATCGACATG | 5664 |
| TGCAGGACCAGAGAATTCGAATA CACCAACAACNNNGATCGACATG | 5185 | TGCAGGACCAGAGAATTCGAATA CACAACATATNNNGATCGACATG | 5425 | TGCAGGACCAGAGAATTCGAATA CAGGTGGATANNNGATCGACATG | 5665 |
| TGCAGGACCAGAGAATTCGAATA CAACGCGACCNNNGATCGACATG | 5186 | TGCAGGACCAGAGAATTCGAATA CAACCGATACNNNGATCGACATG | 5426 | TGCAGGACCAGAGAATTCGAATA CAGACATTCGNNNGATCGACATG | 5666 |
| TGCAGGACCAGAGAATTCGAATA CAGGAGTCCCNNNGATCGACATG | 5187 | TGCAGGACCAGAGAATTCGAATA CACGGACTGGNNNGATCGACATG | 5427 | TGCAGGACCAGAGAATTCGAATA CAATCTGCGANNNGATCGACATG | 5667 |
| TGCAGGACCAGAGAATTCGAATA CACCACGCAGNNNGATCGACATG | 5188 | TGCAGGACCAGAGAATTCGAATA CACAACGCATNNNGATCGACATG | 5428 | TGCAGGACCAGAGAATTCGAATA CAGGCACCANNNGATCGACATG | 5668 |
| TGCAGGACCAGAGAATTCGAATA CAACTCGCCCNNNGATCGACATG | 5189 | TGCAGGACCAGAGAATTCGAATA CATTTTAATTNNNGATCGACATG | 5429 | TGCAGGACCAGAGAATTCGAATA CAAATGTTTGNNNGATCGACATG | 5669 |
| TGCAGGACCAGAGAATTCGAATA CACTGAAGAGNNNGATCGACATG | 5190 | TGCAGGACCAGAGAATTCGAATA CAAGTGTATTNNNGATCGACATG | 5430 | TGCAGGACCAGAGAATTCGAATA CAACCTGGTANNNGATCGACATG | 5670 |
| TGCAGGACCAGAGAATTCGAATA CAGGAGCACGNNNGATCGACATG | 5191 | TGCAGGACCAGAGAATTCGAATA CAACTTCAGGNNNGATCGACATG | 5431 | TGCAGGACCAGAGAATTCGAATA CAACTGAGAGNNNGATCGACATG | 5671 |
| TGCAGGACCAGAGAATTCGAATA CAGGAGGACCNNNGATCGACATG | 5192 | TGCAGGACCAGAGAATTCGAATA CAAAGCCGCCNNNGATCGACATG | 5432 | TGCAGGACCAGAGAATTCGAATA CAGAATTAAGNNNGATCGACATG | 5672 |
| TGCAGGACCAGAGAATTCGAATA CAGGAACCTTNNNGATCGACATG | 5193 | TGCAGGACCAGAGAATTCGAATA CACCACGGTGNNNGATCGACATG | 5433 | TGCAGGACCAGAGAATTCGAATA CAATTACGGCNNNGATCGACATG | 5673 |
| TGCAGGACCAGAGAATTCGAATA CAGCCCTGTCNNNGATCGACATG | 5194 | TGCAGGACCAGAGAATTCGAATA CAGGCTCTTTNNNGATCGACATG | 5434 | TGCAGGACCAGAGAATTCGAATA CACAGTCTAGNNNGATCGACATG | 5674 |
| TGCAGGACCAGAGAATTCGAATA CAAGTAATCTNNNGATCGACATG | 5195 | TGCAGGACCAGAGAATTCGAATA CACTTAGCCTNNNGATCGACATG | 5435 | TGCAGGACCAGAGAATTCGAATA CAATCCCTTGNNNGATCGACATG | 5675 |
| TGCAGGACCAGAGAATTCGAATA CACGCTCGAGNNNGATCGACATG | 5196 | TGCAGGACCAGAGAATTCGAATA CAATTAGCATNNNGATCGACATG | 5436 | TGCAGGACCAGAGAATTCGAATA CATGTCCACTNNNGATCGACATG | 5676 |
| TGCAGGACCAGAGAATTCGAATA CAGTCATGGTNNNGATCGACATG | 5197 | TGCAGGACCAGAGAATTCGAATA CAGCAGCTTANNNGATCGACATG | 5437 | TGCAGGACCAGAGAATTCGAATA CAGGTACGCCNNNGATCGACATG | 5677 |
| TGCAGGACCAGAGAATTCGAATA CAGATTCCAGNNNGATCGACATG | 5198 | TGCAGGACCAGAGAATTCGAATA CAACATACGCNNNGATCGACATG | 5438 | TGCAGGACCAGAGAATTCGAATA CATGAGCAGANNNGATCGACATG | 5678 |
| TGCAGGACCAGAGAATTCGAATA CACTATTACTNNNGATCGACATG | 5199 | TGCAGGACCAGAGAATTCGAATA CAGTCGAAAGNNNGATCGACATG | 5439 | TGCAGGACCAGAGAATTCGAATA CAGATCCGTANNNGATCGACATG | 5679 |
| TGCAGGACCAGAGAATTCGAATA CAAGGTCTACNNNGATCGACATG | 5200 | TGCAGGACCAGAGAATTCGAATA CATTCTAGTTNNNGATCGACATG | 5440 | TGCAGGACCAGAGAATTCGAATA CATCACTAAANNNGATCGACATG | 5680 |
| TGCAGGACCAGAGAATTCGAATA CACCTGTAGANNNGATCGACATG | 5201 | TGCAGGACCAGAGAATTCGAATA CACACGCTCGNNNGATCGACATG | 5441 | TGCAGGACCAGAGAATTCGAATA CAAATAGATANNNGATCGACATG | 5681 |
| TGCAGGACCAGAGAATTCGAATA CATCCTGTCANNNGATCGACATG | 5202 | TGCAGGACCAGAGAATTCGAATA CACCGAGGTCNNNGATCGACATG | 5442 | TGCAGGACCAGAGAATTCGAATA CATCGCGCTCNNNGATCGACATG | 5682 |
| TGCAGGACCAGAGAATTCGAATA CACCCTGCGTNNNGATCGACATG | 5203 | TGCAGGACCAGAGAATTCGAATA CACATTCAGGNNNGATCGACATG | 5443 | TGCAGGACCAGAGAATTCGAATA CAACCGACCANNNGATCGACATG | 5683 |
| TGCAGGACCAGAGAATTCGAATA CAACAATGANNNGATCGACATG | 5204 | TGCAGGACCAGAGAATTCGAATA CATCCATAGGNNNGATCGACATG | 5444 | TGCAGGACCAGAGAATTCGAATA CACACGGACCNNNGATCGACATG | 5684 |
| TGCAGGACCAGAGAATTCGAATA CAGGTGGAGCNNNGATCGACATG | 5205 | TGCAGGACCAGAGAATTCGAATA CATTACTCATNNNGATCGACATG | 5445 | TGCAGGACCAGAGAATTCGAATA CAATATCCGATNNNGATCGACATG | 5685 |
| TGCAGGACCAGAGAATTCGAATA CAGGATAGACNNNGATCGACATG | 5206 | TGCAGGACCAGAGAATTCGAATA CAATCTGATANNNGATCGACATG | 5446 | TGCAGGACCAGAGAATTCGAATA CATACCACGANNNGATCGACATG | 5686 |
| TGCAGGACCAGAGAATTCGAATA CAGAGTGCCCNNNGATCGACATG | 5207 | TGCAGGACCAGAGAATTCGAATA CAGTCCACTTNNNGATCGACATG | 5447 | TGCAGGACCAGAGAATTCGAATA CAAAGAACGCNNNGATCGACATG | 5687 |
| TGCAGGACCAGAGAATTCGAATA CAAAACGGTGNNNGATCGACATG | 5208 | TGCAGGACCAGAGAATTCGAATA CACAGGAACANNNGATCGACATG | 5448 | TGCAGGACCAGAGAATTCGAATA CAAGTACCTGNNNGATCGACATG | 5688 |
| TGCAGGACCAGAGAATTCGAATA CAAATAGCAANNNGATCGACATG | 5209 | TGCAGGACCAGAGAATTCGAATA CACTAGCTTCNNNGATCGACATG | 5449 | TGCAGGACCAGAGAATTCGAATA CAGTTTTAGANNNGATCGACATG | 5689 |
| TGCAGGACCAGAGAATTCGAATA CATCAATTGANNNGATCGACATG | 5210 | TGCAGGACCAGAGAATTCGAATA CATTTGGCGANNNGATCGACATG | 5450 | TGCAGGACCAGAGAATTCGAATA CAGGATTTTANNNGATCGACATG | 5690 |
| TGCAGGACCAGAGAATTCGAATA CAAGCAATGGNNNGATCGACATG | 5211 | TGCAGGACCAGAGAATTCGAATA CACCCGAAGCNNNGATCGACATG | 5451 | TGCAGGACCAGAGAATTCGAATA CATAGTATACNNNGATCGACATG | 5691 |
| TGCAGGACCAGAGAATTCGAATA CAGTAGTGAGNNNGATCGACATG | 5212 | TGCAGGACCAGAGAATTCGAATA CATCCCAACTNNNGATCGACATG | 5452 | TGCAGGACCAGAGAATTCGAATA CACGTATGGTNNNGATCGACATG | 5692 |
| TGCAGGACCAGAGAATTCGAATA CACACTGCGNNNGATCGACATG | 5213 | TGCAGGACCAGAGAATTCGAATA CATTCACGGANNNGATCGACATG | 5453 | TGCAGGACCAGAGAATTCGAATA CATCCCGGCTNNNGATCGACATG | 5693 |

FIG. 19F

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAACCCCTCCNNNGATCGACATG | 5214 | TGCAGGACCAGAGAATTCGAATA CAATTTTACCNNNGATCGACATG | 5454 | TGCAGGACCAGAGAATTCGAATA CAGCGCTCTCNNNGATCGACATG | 5694 |
| TGCAGGACCAGAGAATTCGAATA CACTAGGTTGNNNGATCGACATG | 5215 | TGCAGGACCAGAGAATTCGAATA CATGGAGTCTNNNGATCGACATG | 5455 | TGCAGGACCAGAGAATTCGAATA CACATTCCCANNNGATCGACATG | 5695 |
| TGCAGGACCAGAGAATTCGAATA CATAAAATAANNNGATCGACATG | 5216 | TGCAGGACCAGAGAATTCGAATA CACGACGACNNNGATCGACATG | 5456 | TGCAGGACCAGAGAATTCGAATA CATCGCCCCANNNGATCGACATG | 5696 |
| TGCAGGACCAGAGAATTCGAATA CAGTCACGTANNNGATCGACATG | 5217 | TGCAGGACCAGAGAATTCGAATA CATCCCATACNNNGATCGACATG | 5457 | TGCAGGACCAGAGAATTCGAATA CATGCATTGGNNNGATCGACATG | 5697 |
| TGCAGGACCAGAGAATTCGAATA CAGGTTCGATNNNGATCGACATG | 5218 | TGCAGGACCAGAGAATTCGAATA CAGCCCTTATNNNGATCGACATG | 5458 | TGCAGGACCAGAGAATTCGAATA CAATCAGATTNNNGATCGACATG | 5698 |
| TGCAGGACCAGAGAATTCGAATA CACAATGGAGNNNGATCGACATG | 5219 | TGCAGGACCAGAGAATTCGAATA CAGTCCCGCTNNNGATCGACATG | 5459 | TGCAGGACCAGAGAATTCGAATA CACTTTTATGNNNGATCGACATG | 5699 |
| TGCAGGACCAGAGAATTCGAATA CACCGAGCGTNNNGATCGACATG | 5220 | TGCAGGACCAGAGAATTCGAATA CACGGCCCTTNNNGATCGACATG | 5460 | TGCAGGACCAGAGAATTCGAATA CAAAAGTCGGNNNGATCGACATG | 5700 |
| TGCAGGACCAGAGAATTCGAATA CACAAACGAGNNNGATCGACATG | 5221 | TGCAGGACCAGAGAATTCGAATA CATCAGCTTCNNNGATCGACATG | 5461 | TGCAGGACCAGAGAATTCGAATA CAACGAGTGANNNGATCGACATG | 5701 |
| TGCAGGACCAGAGAATTCGAATA CAGATATGTTNNNGATCGACATG | 5222 | TGCAGGACCAGAGAATTCGAATA CAGGCTCGGTNNNGATCGACATG | 5462 | TGCAGGACCAGAGAATTCGAATA CAGAAATTAGNNNGATCGACATG | 5702 |
| TGCAGGACCAGAGAATTCGAATA CAGTTCTGTCNNNGATCGACATG | 5223 | TGCAGGACCAGAGAATTCGAATA CAAAGTTCGCNNNGATCGACATG | 5463 | TGCAGGACCAGAGAATTCGAATA CAATTATCTCNNNGATCGACATG | 5703 |
| TGCAGGACCAGAGAATTCGAATA CATCTTTTCTNNNGATCGACATG | 5224 | TGCAGGACCAGAGAATTCGAATA CAAACGCCGNNNGATCGACATG | 5464 | TGCAGGACCAGAGAATTCGAATA CAGCTCGGCANNNGATCGACATG | 5704 |
| TGCAGGACCAGAGAATTCGAATA CAAAAGACATNNNGATCGACATG | 5225 | TGCAGGACCAGAGAATTCGAATA CATTCTACTATCNNNGATCGACATG | 5465 | TGCAGGACCAGAGAATTCGAATA CAGTTAGAGGNNNGATCGACATG | 5705 |
| TGCAGGACCAGAGAATTCGAATA CAACCCATGANNNGATCGACATG | 5226 | TGCAGGACCAGAGAATTCGAATA CATTCAAGATNNNGATCGACATG | 5466 | TGCAGGACCAGAGAATTCGAATA CAACCAGCTANNNGATCGACATG | 5706 |
| TGCAGGACCAGAGAATTCGAATA CATCCTCACANNNGATCGACATG | 5227 | TGCAGGACCAGAGAATTCGAATA CACTCAGTTCNNNGATCGACATG | 5467 | TGCAGGACCAGAGAATTCGAATA CAGGAGTGCGNNNGATCGACATG | 5707 |
| TGCAGGACCAGAGAATTCGAATA CATTGAGGTCNNNGATCGACATG | 5228 | TGCAGGACCAGAGAATTCGAATA CAAAGAATTGNNNGATCGACATG | 5468 | TGCAGGACCAGAGAATTCGAATA CATCGATATANNNGATCGACATG | 5708 |
| TGCAGGACCAGAGAATTCGAATA CAGCGTACTANNNTGCATCAGGT | 5229 | TGCAGGACCAGAGAATTCGAATA CAGACTACCANNNTGCATCAGGT | 5469 | TGCAGGACCAGAGAATTCGAATA CAGCGCTAGCNNNTGCATCAGGT | 5709 |
| TGCAGGACCAGAGAATTCGAATA CAAGGTTAGGNNNTGCATCAGGT | 5230 | TGCAGGACCAGAGAATTCGAATA CACACGCTAANNNTGCATCAGGT | 5470 | TGCAGGACCAGAGAATTCGAATA CACTGATTAANNNTGCATCAGGT | 5710 |
| TGCAGGACCAGAGAATTCGAATA CACTCCACATNNNTGCATCAGGT | 5231 | TGCAGGACCAGAGAATTCGAATA CAAGTCATATNNNTGCATCAGGT | 5471 | TGCAGGACCAGAGAATTCGAATA CACACTTCACNNNTGCATCAGGT | 5711 |
| TGCAGGACCAGAGAATTCGAATA CACGATCTAGNNNTGCATCAGGT | 5232 | TGCAGGACCAGAGAATTCGAATA CATCTAGGACNNNTGCATCAGGT | 5472 | TGCAGGACCAGAGAATTCGAATA CATAGGCGTTNNNTGCATCAGGT | 5712 |
| TGCAGGACCAGAGAATTCGAATA CATCGATAATNNNTGCATCAGGT | 5233 | TGCAGGACCAGAGAATTCGAATA CAAGAACTTTNNNTGCATCAGGT | 5473 | TGCAGGACCAGAGAATTCGAATA CAATATGTCANNNTGCATCAGGT | 5713 |
| TGCAGGACCAGAGAATTCGAATA CACCACGAGCNNNTGCATCAGGT | 5234 | TGCAGGACCAGAGAATTCGAATA CAACCACTGANNNTGCATCAGGT | 5474 | TGCAGGACCAGAGAATTCGAATA CAGTCGATTGNNNTGCATCAGGT | 5714 |
| TGCAGGACCAGAGAATTCGAATA CAGTGGAATGNNNTGCATCAGGT | 5235 | TGCAGGACCAGAGAATTCGAATA CAACACGATCNNNTGCATCAGGT | 5475 | TGCAGGACCAGAGAATTCGAATA CAATAGAGCGNNNTGCATCAGGT | 5715 |
| TGCAGGACCAGAGAATTCGAATA CAAAAAATGCNNNTGCATCAGGT | 5236 | TGCAGGACCAGAGAATTCGAATA CAGTTACCAGNNNTGCATCAGGT | 5476 | TGCAGGACCAGAGAATTCGAATA CAGACTAAGGNNNTGCATCAGGT | 5716 |
| TGCAGGACCAGAGAATTCGAATA CAGACTAGTCNNNTGCATCAGGT | 5237 | TGCAGGACCAGAGAATTCGAATA CACGCTACCCNNNTGCATCAGGT | 5477 | TGCAGGACCAGAGAATTCGAATA CACCTACCTANNNTGCATCAGGT | 5717 |
| TGCAGGACCAGAGAATTCGAATA CACGTAGAAGNNNTGCATCAGGT | 5238 | TGCAGGACCAGAGAATTCGAATA CAAGAGGTACNNNTGCATCAGGT | 5478 | TGCAGGACCAGAGAATTCGAATA CATAGGAGACNNNTGCATCAGGT | 5718 |
| TGCAGGACCAGAGAATTCGAATA CAGTGTGAAGNNNTGCATCAGGT | 5239 | TGCAGGACCAGAGAATTCGAATA CAAATCTCTTNNNTGCATCAGGT | 5479 | TGCAGGACCAGAGAATTCGAATA CACCGTCATTNNNTGCATCAGGT | 5719 |
| TGCAGGACCAGAGAATTCGAATA CAAAGTACTTNNNTGCATCAGGT | 5240 | TGCAGGACCAGAGAATTCGAATA CAATATTTAANNNTGCATCAGGT | 5480 | TGCAGGACCAGAGAATTCGAATA CAGTGTTCAGNNNTGCATCAGGT | 5720 |
| TGCAGGACCAGAGAATTCGAATA CACGAACGTTNNNTGCATCAGGT | 5241 | TGCAGGACCAGAGAATTCGAATA CATATCGAATNNNTGCATCAGGT | 5481 | TGCAGGACCAGAGAATTCGAATA CAAGCGGTTTNNNTGCATCAGGT | 5721 |
| TGCAGGACCAGAGAATTCGAATA CAATTGCTGGNNNTGCATCAGGT | 5242 | TGCAGGACCAGAGAATTCGAATA CAGCTAAATTNNNTGCATCAGGT | 5482 | TGCAGGACCAGAGAATTCGAATA CAAACTCTTTNNNTGCATCAGGT | 5722 |
| TGCAGGACCAGAGAATTCGAATA CATGTGTGTGNNNTGCATCAGGT | 5243 | TGCAGGACCAGAGAATTCGAATA CATTTGACCGNNNTGCATCAGGT | 5483 | TGCAGGACCAGAGAATTCGAATA CATAACGTATNNNTGCATCAGGT | 5723 |
| TGCAGGACCAGAGAATTCGAATA CAACATCTTTNNNTGCATCAGGT | 5244 | TGCAGGACCAGAGAATTCGAATA CAGTTCACAGNNNTGCATCAGGT | 5484 | TGCAGGACCAGAGAATTCGAATA CAAAGGACTGNNNTGCATCAGGT | 5724 |
| TGCAGGACCAGAGAATTCGAATA CACGATGCTANNNTGCATCAGGT | 5245 | TGCAGGACCAGAGAATTCGAATA CAGCGATTCCTNNNTGCATCAGGT | 5485 | TGCAGGACCAGAGAATTCGAATA CAAGGAGACNNNTGCATCAGGT | 5725 |
| TGCAGGACCAGAGAATTCGAATA CATAGTCCAGNNNTGCATCAGGT | 5246 | TGCAGGACCAGAGAATTCGAATA CATTACACCCNNNTGCATCAGGT | 5486 | TGCAGGACCAGAGAATTCGAATA CATCGAACGTNNNTGCATCAGGT | 5726 |

FIG. 19G

| Pool-22 | SEQ ID NO: | Pool-23 | SEQ ID NO: | Pool-24 | SEQ ID NO: |
|---|---|---|---|---|---|
| TGCAGGACCAGAGAATTCGAATACACAGTAATTNNNTGCATCAGGT | 5247 | TGCAGGACCAGAGAATTCGAATACATATTTTATNNNTGCATCAGGT | 5487 | TGCAGGACCAGAGAATTCGAATACACGGACATTNNNTGCATCAGGT | 5727 |
| TGCAGGACCAGAGAATTCGAATACAAAGGTGGTNNNTGCATCAGGT | 5248 | TGCAGGACCAGAGAATTCGAATACATGTCCGCCNNNTGCATCAGGT | 5488 | TGCAGGACCAGAGAATTCGAATACATTCCGCATNNNTGCATCAGGT | 5728 |
| TGCAGGACCAGAGAATTCGAATACACGGTGGTCNNNTGCATCAGGT | 5249 | TGCAGGACCAGAGAATTCGAATACAAAACCCGTNNNTGCATCAGGT | 5489 | TGCAGGACCAGAGAATTCGAATACACGCGGCTANNNTGCATCAGGT | 5729 |
| TGCAGGACCAGAGAATTCGAATACAGTGGTTGTNNNTGCATCAGGT | 5250 | TGCAGGACCAGAGAATTCGAATACAGTACCGATNNNTGCATCAGGT | 5490 | TGCAGGACCAGAGAATTCGAATACAGTTTCTGCNNNTGCATCAGGT | 5730 |
| TGCAGGACCAGAGAATTCGAATACATGTATTCTNNNTGCATCAGGT | 5251 | TGCAGGACCAGAGAATTCGAATACACGCGTTCNNNTGCATCAGGT | 5491 | TGCAGGACCAGAGAATTCGAATACAAGACAGCANNNTGCATCAGGT | 5731 |
| TGCAGGACCAGAGAATTCGAATACATAAGTCGCNNNTGCATCAGGT | 5252 | TGCAGGACCAGAGAATTCGAATACACTCCAATCNNNTGCATCAGGT | 5492 | TGCAGGACCAGAGAATTCGAATACAGACCCTCCNNNTGCATCAGGT | 5732 |
| TGCAGGACCAGAGAATTCGAATACATAGGAGCANNNTGCATCAGGT | 5253 | TGCAGGACCAGAGAATTCGAATACACCGCAGACNNNTGCATCAGGT | 5493 | TGCAGGACCAGAGAATTCGAATACATACTCGCTNNNTGCATCAGGT | 5733 |
| TGCAGGACCAGAGAATTCGAATACACATAAATCNNNTGCATCAGGT | 5254 | TGCAGGACCAGAGAATTCGAATACACGCTTAGANNNTGCATCAGGT | 5494 | TGCAGGACCAGAGAATTCGAATACATTCGTATTNNNTGCATCAGGT | 5734 |
| TGCAGGACCAGAGAATTCGAATACAAGCTGTACNNNTGCATCAGGT | 5255 | TGCAGGACCAGAGAATTCGAATACAGAAAAGCNNNTGCATCAGGT | 5495 | TGCAGGACCAGAGAATTCGAATACATACTTAAGNNNTGCATCAGGT | 5735 |
| TGCAGGACCAGAGAATTCGAATACATTGCGCTNNNTGCATCAGGT | 5256 | TGCAGGACCAGAGAATTCGAATACACTCATCCANNNTGCATCAGGT | 5496 | TGCAGGACCAGAGAATTCGAATACAGACTACGTNNNTGCATCAGGT | 5736 |
| TGCAGGACCAGAGAATTCGAATACAAGCGTGNNNTGCATCAGGT | 5257 | TGCAGGACCAGAGAATTCGAATACAAAGAGTATNNNTGCATCAGGT | 5497 | TGCAGGACCAGAGAATTCGAATACAACGAGTCTNNNTGCATCAGGT | 5737 |
| TGCAGGACCAGAGAATTCGAATACAGTCTAGGTNNNTGCATCAGGT | 5258 | TGCAGGACCAGAGAATTCGAATACAAATTGTCANNNTGCATCAGGT | 5498 | TGCAGGACCAGAGAATTCGAATACAGACCGTTGNNNTGCATCAGGT | 5738 |
| TGCAGGACCAGAGAATTCGAATACATCCGTAAGNNNTGCATCAGGT | 5259 | TGCAGGACCAGAGAATTCGAATACAATAATACCNNNTGCATCAGGT | 5499 | TGCAGGACCAGAGAATTCGAATACAGATGGACANNNTGCATCAGGT | 5739 |
| TGCAGGACCAGAGAATTCGAATACATATCGGCANNNTGCATCAGGT | 5260 | TGCAGGACCAGAGAATTCGAATACAAATTTTGCNNNTGCATCAGGT | 5500 | TGCAGGACCAGAGAATTCGAATACATCGTAGTGNNNTGCATCAGGT | 5740 |
| TGCAGGACCAGAGAATTCGAATACAATCATCGGNNNTGCATCAGGT | 5261 | TGCAGGACCAGAGAATTCGAATACAGCACAGTTNNNTGCATCAGGT | 5501 | TGCAGGACCAGAGAATTCGAATACACCACATCTNNNTGCATCAGGT | 5741 |
| TGCAGGACCAGAGAATTCGAATACAACGTCTGANNNTGCATCAGGT | 5262 | TGCAGGACCAGAGAATTCGAATACATTAAACCANNNTGCATCAGGT | 5502 | TGCAGGACCAGAGAATTCGAATACAGTGCTACANNNTGCATCAGGT | 5742 |
| TGCAGGACCAGAGAATTCGAATACAACGGTACTNNNTGCATCAGGT | 5263 | TGCAGGACCAGAGAATTCGAATACAATGGAGACNNNTGCATCAGGT | 5503 | TGCAGGACCAGAGAATTCGAATACATTCTTCAANNNTGCATCAGGT | 5743 |
| TGCAGGACCAGAGAATTCGAATACATGCAAGGANNNTGCATCAGGT | 5264 | TGCAGGACCAGAGAATTCGAATACAAAAGACGCNNNTGCATCAGGT | 5504 | TGCAGGACCAGAGAATTCGAATACATTACAGTANNNTGCATCAGGT | 5744 |
| TGCAGGACCAGAGAATTCGAATACAAGACTCACNNNTGCATCAGGT | 5265 | TGCAGGACCAGAGAATTCGAATACAATCCGAACNNNTGCATCAGGT | 5505 | TGCAGGACCAGAGAATTCGAATACAAGACGCGGNNNTGCATCAGGT | 5745 |
| TGCAGGACCAGAGAATTCGAATACACAATCAGCNNNTGCATCAGGT | 5266 | TGCAGGACCAGAGAATTCGAATACAGTTAGGAGNNNTGCATCAGGT | 5506 | TGCAGGACCAGAGAATTCGAATACAGGAGCTCCNNNTGCATCAGGT | 5746 |
| TGCAGGACCAGAGAATTCGAATACATGCTGTANNNTGCATCAGGT | 5267 | TGCAGGACCAGAGAATTCGAATACATGGCCCGCNNNTGCATCAGGT | 5507 | TGCAGGACCAGAGAATTCGAATACAATTAACCANNNTGCATCAGGT | 5747 |
| TGCAGGACCAGAGAATTCGAATACAGTTTACCCNNNTGCATCAGGT | 5268 | TGCAGGACCAGAGAATTCGAATACAATGTGCACNNNTGCATCAGGT | 5508 | TGCAGGACCAGAGAATTCGAATACAATCGAGCTNNNTGCATCAGGT | 5748 |
| TGCAGGACCAGAGAATTCGAATACACGTCAGTANNNTGCATCAGGT | 5269 | TGCAGGACCAGAGAATTCGAATACAGTACAACCNNNTGCATCAGGT | 5509 | TGCAGGACCAGAGAATTCGAATACAGGAAACGTNNNTGCATCAGGT | 5749 |
| TGCAGGACCAGAGAATTCGAATACACGACGGAGNNNTGCATCAGGT | 5270 | TGCAGGACCAGAGAATTCGAATACAGTGGCGAGNNNTGCATCAGGT | 5510 | TGCAGGACCAGAGAATTCGAATACATGAAGAGCNNNTGCATCAGGT | 5750 |
| TGCAGGACCAGAGAATTCGAATACAATATGCGCNNNTGCATCAGGT | 5271 | TGCAGGACCAGAGAATTCGAATACAAGCTCTCNNNTGCATCAGGT | 5511 | TGCAGGACCAGAGAATTCGAATACAATCCGGATNNNTGCATCAGGT | 5751 |
| TGCAGGACCAGAGAATTCGAATACAGCTGGCCANNNTGCATCAGGT | 5272 | TGCAGGACCAGAGAATTCGAATACAACCTCTTGNNNTGCATCAGGT | 5512 | TGCAGGACCAGAGAATTCGAATACAGTTGTCTCNNNTGCATCAGGT | 5752 |
| TGCAGGACCAGAGAATTCGAATACACGCGTCTCNNNTGCATCAGGT | 5273 | TGCAGGACCAGAGAATTCGAATACATCAGCGTANNNTGCATCAGGT | 5513 | TGCAGGACCAGAGAATTCGAATACATGGATAGGNNNTGCATCAGGT | 5753 |
| TGCAGGACCAGAGAATTCGAATACAATAAGTGANNNTGCATCAGGT | 5274 | TGCAGGACCAGAGAATTCGAATACATCAGACGTNNNTGCATCAGGT | 5514 | TGCAGGACCAGAGAATTCGAATACAAAACCAGGNNNTGCATCAGGT | 5754 |
| TGCAGGACCAGAGAATTCGAATACAGACAGTCTNNNTGCATCAGGT | 5275 | TGCAGGACCAGAGAATTCGAATACATATAGATCNNNTGCATCAGGT | 5515 | TGCAGGACCAGAGAATTCGAATACACGGCGACTNNNTGCATCAGGT | 5755 |
| TGCAGGACCAGAGAATTCGAATACAGGAGGTANNNTGCATCAGGT | 5276 | TGCAGGACCAGAGAATTCGAATACACCCGCCTNNNTGCATCAGGT | 5516 | TGCAGGACCAGAGAATTCGAATACATTATCGCANNNTGCATCAGGT | 5756 |
| TGCAGGACCAGAGAATTCGAATACACACGAACTNNNTGCATCAGGT | 5277 | TGCAGGACCAGAGAATTCGAATACAGCAGGATANNNTGCATCAGGT | 5517 | TGCAGGACCAGAGAATTCGAATACAAGCCACATNNNTGCATCAGGT | 5757 |
| TGCAGGACCAGAGAATTCGAATACATACACTGGNNNTGCATCAGGT | 5278 | TGCAGGACCAGAGAATTCGAATACAAGAATGCGNNNTGCATCAGGT | 5518 | TGCAGGACCAGAGAATTCGAATACATGCTCATCNNNTGCATCAGGT | 5758 |
| TGCAGGACCAGAGAATTCGAATACAATTTCGTTNNNTGCATCAGGT | 5279 | TGCAGGACCAGAGAATTCGAATACAACAAGTGGNNNTGCATCAGGT | 5519 | TGCAGGACCAGAGAATTCGAATACAGCTGGAGGNNNTGCATCAGGT | 5759 |

FIG. 19H

| Pool-22 | SEQ ID NO: | Pool-23 | SEQ ID NO: | Pool-24 | SEQ ID NO: |
|---|---|---|---|---|---|
| TGCAGGACCAGAGAATTCGAATACATCTGCGCCNNNTGCATCAGGT | 5280 | TGCAGGACCAGAGAATTCGAATACAGTCCGGCANNNTGCATCAGGT | 5520 | TGCAGGACCAGAGAATTCGAATACAAAAGATGTNNNTGCATCAGGT | 5760 |
| TGCAGGACCAGAGAATTCGAATACACGAGCTATNNNTGCATCAGGT | 5281 | TGCAGGACCAGAGAATTCGAATACAGCCCTGAGNNNTGCATCAGGT | 5521 | TGCAGGACCAGAGAATTCGAATACATCAGAAAANNNTGCATCAGGT | 5761 |
| TGCAGGACCAGAGAATTCGAATACAACGCCATANNNTGCATCAGGT | 5282 | TGCAGGACCAGAGAATTCGAATACAAACTATGTNNNTGCATCAGGT | 5522 | TGCAGGACCAGAGAATTCGAATACAGTCCTGAANNNTGCATCAGGT | 5762 |
| TGCAGGACCAGAGAATTCGAATACATCCTCTGANNNTGCATCAGGT | 5283 | TGCAGGACCAGAGAATTCGAATACATCTGATCCNNNTGCATCAGGT | 5523 | TGCAGGACCAGAGAATTCGAATACAGCTAGGCCNNNTGCATCAGGT | 5763 |
| TGCAGGACCAGAGAATTCGAATACAAATTCTAGNNNTGCATCAGGT | 5284 | TGCAGGACCAGAGAATTCGAATACATAATAGAGNNNTGCATCAGGT | 5524 | TGCAGGACCAGAGAATTCGAATACACTCCTGTANNNTGCATCAGGT | 5764 |
| TGCAGGACCAGAGAATTCGAATACACCTCAGCCNNNTGCATCAGGT | 5285 | TGCAGGACCAGAGAATTCGAATACAGGCCGTTGNNNTGCATCAGGT | 5525 | TGCAGGACCAGAGAATTCGAATACATTGATCAANNNTGCATCAGGT | 5765 |
| TGCAGGACCAGAGAATTCGAATACAACCCGGANNNTGCATCAGGT | 5286 | TGCAGGACCAGAGAATTCGAATACACACAAGGNNNTGCATCAGGT | 5526 | TGCAGGACCAGAGAATTCGAATACACTGTTCGTNNNTGCATCAGGT | 5766 |
| TGCAGGACCAGAGAATTCGAATACAGTGATAGGNNNTGCATCAGGT | 5287 | TGCAGGACCAGAGAATTCGAATACACCCTGAAANNNTGCATCAGGT | 5527 | TGCAGGACCAGAGAATTCGAATACATCTTATCANNNTGCATCAGGT | 5767 |
| TGCAGGACCAGAGAATTCGAATACATTGAATTGNNNTGCATCAGGT | 5288 | TGCAGGACCAGAGAATTCGAATACACTGCTGTTNNNTGCATCAGGT | 5528 | TGCAGGACCAGAGAATTCGAATACATACTGGCANNNTGCATCAGGT | 5768 |

FIG. 20A

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAC GCGACGTNNNACGTATGCCA | 5769 | TGCAGGACCAGAGAATTCGAATACAC TCTGCTANNNACGTATGCCA | 6009 | TGCAGGACCAGAGAATTCGAATACAT GTACGCANNNACGTATGCCA | 6249 |
| TGCAGGACCAGAGAATTCGAATACAC CGATCANNNACGTATGCCA | 5770 | TGCAGGACCAGAGAATTCGAATACAT TACATGANNNACGTATGCCA | 6010 | TGCAGGACCAGAGAATTCGAATACAG ATGTGTCNNNACGTATGCCA | 6250 |
| TGCAGGACCAGAGAATTCGAATACAG GCAATCTNNNACGTATGCCA | 5771 | TGCAGGACCAGAGAATTCGAATACAC GAGGATANNNACGTATGCCA | 6011 | TGCAGGACCAGAGAATTCGAATACAC TAGACTGNNNACGTATGCCA | 6251 |
| TGCAGGACCAGAGAATTCGAATACAC TAGGAGANNNACGTATGCCA | 5772 | TGCAGGACCAGAGAATTCGAATACAC GACATGTNNNACGTATGCCA | 6012 | TGCAGGACCAGAGAATTCGAATACAG ATCGTGTNNNACGTATGCCA | 6252 |
| TGCAGGACCAGAGAATTCGAATACAT TGATAACNNNACGTATGCCA | 5773 | TGCAGGACCAGAGAATTCGAATACAC CTTGAAGNNNACGTATGCCA | 6013 | TGCAGGACCAGAGAATTCGAATACAT TATCTCANNNACGTATGCCA | 6253 |
| TGCAGGACCAGAGAATTCGAATACAG AGTACTCNNNACGTATGCCA | 5774 | TGCAGGACCAGAGAATTCGAATACAC AACGATCNNNACGTATGCCA | 6014 | TGCAGGACCAGAGAATTCGAATACAA ACCCTAGNNNACGTATGCCA | 6254 |
| TGCAGGACCAGAGAATTCGAATACAA TGCCGCGNNNACGTATGCCA | 5775 | TGCAGGACCAGAGAATTCGAATACAG ACTAGAGNNNACGTATGCCA | 6015 | TGCAGGACCAGAGAATTCGAATACAT ATCATAGNNNACGTATGCCA | 6255 |
| TGCAGGACCAGAGAATTCGAATACAA AATAGCANNNACGTATGCCA | 5776 | TGCAGGACCAGAGAATTCGAATACAC TGCAGTANNNACGTATGCCA | 6016 | TGCAGGACCAGAGAATTCGAATACAC GTTCGTTNNNACGTATGCCA | 6256 |
| TGCAGGACCAGAGAATTCGAATACAA TCAGACCNNNACGTATGCCA | 5777 | TGCAGGACCAGAGAATTCGAATACAA TGTGACCNNNACGTATGCCA | 6017 | TGCAGGACCAGAGAATTCGAATACAA TACAAGANNNACGTATGCCA | 6257 |
| TGCAGGACCAGAGAATTCGAATACAG GTGCGTCNNNACGTATGCCA | 5778 | TGCAGGACCAGAGAATTCGAATACAA CCGAATTNNNACGTATGCCA | 6018 | TGCAGGACCAGAGAATTCGAATACAG TCCTCATNNNACGTATGCCA | 6258 |
| TGCAGGACCAGAGAATTCGAATACAT CTTTCCCNNNACGTATGCCA | 5779 | TGCAGGACCAGAGAATTCGAATACAA TTGTTTCNNNACGTATGCCA | 6019 | TGCAGGACCAGAGAATTCGAATACAA GTAGCAGNNNACGTATGCCA | 6259 |
| TGCAGGACCAGAGAATTCGAATACAA AATTCCANNNACGTATGCCA | 5780 | TGCAGGACCAGAGAATTCGAATACAC GCCGTGANNNACGTATGCCA | 6020 | TGCAGGACCAGAGAATTCGAATACAG AAAACATNNNACGTATGCCA | 6260 |
| TGCAGGACCAGAGAATTCGAATACAA ATGTGCCNNNACGTATGCCA | 5781 | TGCAGGACCAGAGAATTCGAATACAC ACTCAAGNNNACGTATGCCA | 6021 | TGCAGGACCAGAGAATTCGAATACAT TCGCCTANNNACGTATGCCA | 6261 |
| TGCAGGACCAGAGAATTCGAATACAC ACATGACNNNACGTATGCCA | 5782 | TGCAGGACCAGAGAATTCGAATACAA GCAATCCNNNACGTATGCCA | 6022 | TGCAGGACCAGAGAATTCGAATACAA GAGTTGGNNNACGTATGCCA | 6262 |
| TGCAGGACCAGAGAATTCGAATACAG ACCTGGCNNNACGTATGCCA | 5783 | TGCAGGACCAGAGAATTCGAATACAT CCATTATNNNACGTATGCCA | 6023 | TGCAGGACCAGAGAATTCGAATACAC AATATTGNNNACGTATGCCA | 6263 |
| TGCAGGACCAGAGAATTCGAATACAC CAAAATTNNNACGTATGCCA | 5784 | TGCAGGACCAGAGAATTCGAATACAA ATTGCTANNNACGTATGCCA | 6024 | TGCAGGACCAGAGAATTCGAATACAA AACCTCGNNNACGTATGCCA | 6264 |
| TGCAGGACCAGAGAATTCGAATACAA TTGTCCCNNNACGTATGCCA | 5785 | TGCAGGACCAGAGAATTCGAATACAC GATCCAANNNACGTATGCCA | 6025 | TGCAGGACCAGAGAATTCGAATACAA GTTAATCNNNACGTATGCCA | 6265 |
| TGCAGGACCAGAGAATTCGAATACAC GTCGACGNNNACGTATGCCA | 5786 | TGCAGGACCAGAGAATTCGAATACAC TCGGTGGNNNACGTATGCCA | 6026 | TGCAGGACCAGAGAATTCGAATACAG ACTCTAGNNNACGTATGCCA | 6266 |
| TGCAGGACCAGAGAATTCGAATACAC CCGCTCANNNACGTATGCCA | 5787 | TGCAGGACCAGAGAATTCGAATACAG AGATTAANNNACGTATGCCA | 6027 | TGCAGGACCAGAGAATTCGAATACAA GGAAAAANNNACGTATGCCA | 6267 |
| TGCAGGACCAGAGAATTCGAATACAA TGGACTCNNNACGTATGCCA | 5788 | TGCAGGACCAGAGAATTCGAATACAA TCAGGCTNNNACGTATGCCA | 6028 | TGCAGGACCAGAGAATTCGAATACAT GACTAGCNNNACGTATGCCA | 6268 |
| TGCAGGACCAGAGAATTCGAATACAT TGTAACANNNACGTATGCCA | 5789 | TGCAGGACCAGAGAATTCGAATACAG CGGCCCGNNNACGTATGCCA | 6029 | TGCAGGACCAGAGAATTCGAATACAC ATCGTAGNNNACGTATGCCA | 6269 |
| TGCAGGACCAGAGAATTCGAATACAG TTTACTTNNNACGTATGCCA | 5790 | TGCAGGACCAGAGAATTCGAATACAT TTAAATANNNACGTATGCCA | 6030 | TGCAGGACCAGAGAATTCGAATACAA GGTGTTCNNNACGTATGCCA | 6270 |
| TGCAGGACCAGAGAATTCGAATACAT GGATAAANNNACGTATGCCA | 5791 | TGCAGGACCAGAGAATTCGAATACAC ATGGCGCNNNACGTATGCCA | 6031 | TGCAGGACCAGAGAATTCGAATACAG CCATTAGNNNACGTATGCCA | 6271 |
| TGCAGGACCAGAGAATTCGAATACAA TCCTTTGNNNACGTATGCCA | 5792 | TGCAGGACCAGAGAATTCGAATACAT CCGGTTAGNNNACGTATGCCA | 6032 | TGCAGGACCAGAGAATTCGAATACAC GTTCTGTNNNACGTATGCCA | 6272 |
| TGCAGGACCAGAGAATTCGAATACAC GCATACANNNACGTATGCCA | 5793 | TGCAGGACCAGAGAATTCGAATACAC GGCTGANNNACGTATGCCA | 6033 | TGCAGGACCAGAGAATTCGAATACAT CCGCTGNNNACGTATGCCA | 6273 |
| TGCAGGACCAGAGAATTCGAATACAA CACCGATNNNACGTATGCCA | 5794 | TGCAGGACCAGAGAATTCGAATACAT TCCTGTGNNNACGTATGCCA | 6034 | TGCAGGACCAGAGAATTCGAATACAC CTACACTNNNACGTATGCCA | 6274 |
| TGCAGGACCAGAGAATTCGAATACAA TTGCTCCNNNACGTATGCCA | 5795 | TGCAGGACCAGAGAATTCGAATACAG GCGCCTANNNACGTATGCCA | 6035 | TGCAGGACCAGAGAATTCGAATACAA GAAGATTNNNACGTATGCCA | 6275 |
| TGCAGGACCAGAGAATTCGAATACAA TCTTCTANNNACGTATGCCA | 5796 | TGCAGGACCAGAGAATTCGAATACAC CCGCCGGNNNACGTATGCCA | 6036 | TGCAGGACCAGAGAATTCGAATACAA GTCCTTCNNNACGTATGCCA | 6276 |
| TGCAGGACCAGAGAATTCGAATACAT CGAAATTNNNACGTATGCCA | 5797 | TGCAGGACCAGAGAATTCGAATACAA TTCGGCANNNACGTATGCCA | 6037 | TGCAGGACCAGAGAATTCGAATACAG CATTATANNNACGTATGCCA | 6277 |
| TGCAGGACCAGAGAATTCGAATACAC AAGTCACNNNACGTATGCCA | 5798 | TGCAGGACCAGAGAATTCGAATACAC BAATGANNNACGTATGCCA | 6038 | TGCAGGACCAGAGAATTCGAATACAG TGGCATTNNNACGTATGCCA | 6278 |
| TGCAGGACCAGAGAATTCGAATACAT GACCCGGNNNACGTATGCCA | 5799 | TGCAGGACCAGAGAATTCGAATACAT AGGATGGNNNACGTATGCCA | 6039 | TGCAGGACCAGAGAATTCGAATACAA ACGTCACNNNACGTATGCCA | 6279 |
| TGCAGGACCAGAGAATTCGAATACAA GCTGCCGNNNACGTATGCCA | 5800 | TGCAGGACCAGAGAATTCGAATACAT TGGACGTNNNACGTATGCCA | 6040 | TGCAGGACCAGAGAATTCGAATACAG TTAACTANNNACGTATGCCA | 6280 |

FIG. 20B

| Pool-25 | SEQ ID NO: | Pool-26 | SEQ ID NO: | Pool-27 | SEQ ID NO: |
|---|---|---|---|---|---|
| TGCAGGACCAGAGAATTCGAATACATCACTCGTNNNACGTATGCCA | 5801 | TGCAGGACCAGAGAATTCGAATACATCGTGAGTNNNACGTATGCCA | 6041 | TGCAGGACCAGAGAATTCGAATACATAAAGATGNNNACGTATGCCA | 6281 |
| TGCAGGACCAGAGAATTCGAATACAGTTACCGANNNACGTATGCCA | 5802 | TGCAGGACCAGAGAATTCGAATACAGGAACTTCNNNACGTATGCCA | 6042 | TGCAGGACCAGAGAATTCGAATACAAATTTCCTNNNACGTATGCCA | 6282 |
| TGCAGGACCAGAGAATTCGAATACACTTAGATANNNACGTATGCCA | 5803 | TGCAGGACCAGAGAATTCGAATACAATGTGCCANNNACGTATGCCA | 6043 | TGCAGGACCAGAGAATTCGAATACACGGCAAAANNNACGTATGCCA | 6283 |
| TGCAGGACCAGAGAATTCGAATACAAGGCTAGANNNACGTATGCCA | 5804 | TGCAGGACCAGAGAATTCGAATACACCGGTGCANNNACGTATGCCA | 6044 | TGCAGGACCAGAGAATTCGAATACATCGCACAANNNACGTATGCCA | 6284 |
| TGCAGGACCAGAGAATTCGAATACATCACAGGTNNNACGTATGCCA | 5805 | TGCAGGACCAGAGAATTCGAATACACTATTGCCNNNACGTATGCCA | 6045 | TGCAGGACCAGAGAATTCGAATACAAGGTCGCCNNNACGTATGCCA | 6285 |
| TGCAGGACCAGAGAATTCGAATACATATATTTNNNACGTATGCCA | 5806 | TGCAGGACCAGAGAATTCGAATACATTAAGGCCNNNACGTATGCCA | 6046 | TGCAGGACCAGAGAATTCGAATACAGGATTCGTNNNACGTATGCCA | 6286 |
| TGCAGGACCAGAGAATTCGAATACATTGTGTTTNNNACGTATGCCA | 5807 | TGCAGGACCAGAGAATTCGAATACATGTTAAACNNNACGTATGCCA | 6047 | TGCAGGACCAGAGAATTCGAATACAAGCATCTGNNNACGTATGCCA | 6287 |
| TGCAGGACCAGAGAATTCGAATACAGAAAAAAGNNNACGTATGCCA | 5808 | TGCAGGACCAGAGAATTCGAATACACTTGGTTCNNNACGTATGCCA | 6048 | TGCAGGACCAGAGAATTCGAATACACCCACAAANNNACGTATGCCA | 6288 |
| TGCAGGACCAGAGAATTCGAATACAGGCATGTTNNNACGTATGCCA | 5809 | TGCAGGACCAGAGAATTCGAATACAGGTAATTTNNNACGTATGCCA | 6049 | TGCAGGACCAGAGAATTCGAATACAAGTTATACNNNACGTATGCCA | 6289 |
| TGCAGGACCAGAGAATTCGAATACAGGCTTTTCNNNACGTATGCCA | 5810 | TGCAGGACCAGAGAATTCGAATACAATTATCAGNNNACGTATGCCA | 6050 | TGCAGGACCAGAGAATTCGAATACATCTATCATNNNACGTATGCCA | 6290 |
| TGCAGGACCAGAGAATTCGAATACAACTAATACNNNACGTATGCCA | 5811 | TGCAGGACCAGAGAATTCGAATACATGCGTTCTNNNACGTATGCCA | 6051 | TGCAGGACCAGAGAATTCGAATACACGGCTCTCNNNACGTATGCCA | 6291 |
| TGCAGGACCAGAGAATTCGAATACAGTAGCCCGNNNACGTATGCCA | 5812 | TGCAGGACCAGAGAATTCGAATACATGATCCAGNNNACGTATGCCA | 6052 | TGCAGGACCAGAGAATTCGAATACAGTGATTATNNNACGTATGCCA | 6292 |
| TGCAGGACCAGAGAATTCGAATACATAACGTCNNNACGTATGCCA | 5813 | TGCAGGACCAGAGAATTCGAATACACAGTTCAGNNNACGTATGCCA | 6053 | TGCAGGACCAGAGAATTCGAATACATAGACTCGNNNACGTATGCCA | 6293 |
| TGCAGGACCAGAGAATTCGAATACATTTCAAGANNNACGTATGCCA | 5814 | TGCAGGACCAGAGAATTCGAATACATGCGACATNNNACGTATGCCA | 6054 | TGCAGGACCAGAGAATTCGAATACAAACGTTTANNNACGTATGCCA | 6294 |
| TGCAGGACCAGAGAATTCGAATACACACAAGAGNNNACGTATGCCA | 5815 | TGCAGGACCAGAGAATTCGAATACACGCAGTAGNNNACGTATGCCA | 6055 | TGCAGGACCAGAGAATTCGAATACAAAGTAAGTNNNACGTATGCCA | 6295 |
| TGCAGGACCAGAGAATTCGAATACACCCGTTTANNNACGTATGCCA | 5816 | TGCAGGACCAGAGAATTCGAATACATTAGTGATNNNACGTATGCCA | 6056 | TGCAGGACCAGAGAATTCGAATACAATGTTAACNNNACGTATGCCA | 6296 |
| TGCAGGACCAGAGAATTCGAATACAGTTAAGAANNNACGTATGCCA | 5817 | TGCAGGACCAGAGAATTCGAATACACACATTAANNNACGTATGCCA | 6057 | TGCAGGACCAGAGAATTCGAATACATAATCACANNNACGTATGCCA | 6297 |
| TGCAGGACCAGAGAATTCGAATACAGAACCTACNNNACGTATGCCA | 5818 | TGCAGGACCAGAGAATTCGAATACAAGGTGCCCNNNACGTATGCCA | 6058 | TGCAGGACCAGAGAATTCGAATACACATGCTTCNNNACGTATGCCA | 6298 |
| TGCAGGACCAGAGAATTCGAATACAAGCGACTTNNNACGTATGCCA | 5819 | TGCAGGACCAGAGAATTCGAATACAACCTGGCGNNNACGTATGCCA | 6059 | TGCAGGACCAGAGAATTCGAATACAAGCATTATNNNACGTATGCCA | 6299 |
| TGCAGGACCAGAGAATTCGAATACACGCACTAANNNACGTATGCCA | 5820 | TGCAGGACCAGAGAATTCGAATACACGGCGATCNNNACGTATGCCA | 6060 | TGCAGGACCAGAGAATTCGAATACAAGGCATAGNNNACGTATGCCA | 6300 |
| TGCAGGACCAGAGAATTCGAATACAGGTGTTCANNNACGTATGCCA | 5821 | TGCAGGACCAGAGAATTCGAATACATAGACCTGNNNACGTATGCCA | 6061 | TGCAGGACCAGAGAATTCGAATACACATACGCANNNACGTATGCCA | 6301 |
| TGCAGGACCAGAGAATTCGAATACAGTTTTCAANNNACGTATGCCA | 5822 | TGCAGGACCAGAGAATTCGAATACAAGACTACCNNNACGTATGCCA | 6062 | TGCAGGACCAGAGAATTCGAATACAAGACCCGCNNNACGTATGCCA | 6302 |
| TGCAGGACCAGAGAATTCGAATACAGATTCATANNNACGTATGCCA | 5823 | TGCAGGACCAGAGAATTCGAATACACTTAGACGNNNACGTATGCCA | 6063 | TGCAGGACCAGAGAATTCGAATACATTCCCTAGNNNACGTATGCCA | 6303 |
| TGCAGGACCAGAGAATTCGAATACATTGACGACNNNACGTATGCCA | 5824 | TGCAGGACCAGAGAATTCGAATACACGGCGGCCNNNACGTATGCCA | 6064 | TGCAGGACCAGAGAATTCGAATACAAGTGTGCTNNNACGTATGCCA | 6304 |
| TGCAGGACCAGAGAATTCGAATACACCTTGTACNNNACGTATGCCA | 5825 | TGCAGGACCAGAGAATTCGAATACAGCCGATATNNNACGTATGCCA | 6065 | TGCAGGACCAGAGAATTCGAATACACCTGTACTNNNACGTATGCCA | 6305 |
| TGCAGGACCAGAGAATTCGAATACAGGTGCGANNNACGTATGCCA | 5826 | TGCAGGACCAGAGAATTCGAATACACCCGGCCCNNNACGTATGCCA | 6066 | TGCAGGACCAGAGAATTCGAATACACACACCCCNNNACGTATGCCA | 6306 |
| TGCAGGACCAGAGAATTCGAATACATCATGAATNNNACGTATGCCA | 5827 | TGCAGGACCAGAGAATTCGAATACACCTCGCTGNNNACGTATGCCA | 6067 | TGCAGGACCAGAGAATTCGAATACATTTGGTGNNNACGTATGCCA | 6307 |
| TGCAGGACCAGAGAATTCGAATACAGCGAAAGTNNNACGTATGCCA | 5828 | TGCAGGACCAGAGAATTCGAATACACAGCCATANNNACGTATGCCA | 6068 | TGCAGGACCAGAGAATTCGAATACAGTTAGCCANNNACGTATGCCA | 6308 |
| TGCAGGACCAGAGAATTCGAATACAAAATAATNNNCTAGCGTTAC | 5829 | TGCAGGACCAGAGAATTCGAATACAATGGAGCNNNCTAGCGTTAC | 6069 | TGCAGGACCAGAGAATTCGAATACACGACACTNNNCTAGCGTTAC | 6309 |
| TGCAGGACCAGAGAATTCGAATACATTCGTGTCNNNCTAGCGTTAC | 5830 | TGCAGGACCAGAGAATTCGAATACATCACAGACNNNCTAGCGTTAC | 6070 | TGCAGGACCAGAGAATTCGAATACAGCATGACTNNNCTAGCGTTAC | 6310 |
| TGCAGGACCAGAGAATTCGAATACACGTCTTGNNNCTAGCGTTAC | 5831 | TGCAGGACCAGAGAATTCGAATACATCCGTCCGNNNCTAGCGTTAC | 6071 | TGCAGGACCAGAGAATTCGAATACATAGTTGTANNNCTAGCGTTAC | 6311 |
| TGCAGGACCAGAGAATTCGAATACAGACTGTGTNNNCTAGCGTTAC | 5832 | TGCAGGACCAGAGAATTCGAATACAGAATGGACNNNCTAGCGTTAC | 6072 | TGCAGGACCAGAGAATTCGAATACACCTGTTCANNNCTAGCGTTAC | 6312 |
| TGCAGGACCAGAGAATTCGAATACACCATTGGANNNCTAGCGTTAC | 5833 | TGCAGGACCAGAGAATTCGAATACAGTGCTCAANNNCTAGCGTTAC | 6073 | TGCAGGACCAGAGAATTCGAATACACTGAGTCANNNCTAGCGTTAC | 6313 |

FIG. 20C

| Pool-25 | SEQ ID NO: | Pool-26 | SEQ ID NO: | Pool-27 | SEQ ID NO: |
|---|---|---|---|---|---|
| TGCAGGACCAGAGAATTCGAATACACACAGCGCNNNCTAGCGTTAC | 5834 | TGCAGGACCAGAGAATTCGAATACATGTTCGGANNNCTAGCGTTAC | 6074 | TGCAGGACCAGAGAATTCGAATACATCATCTTANNNCTAGCGTTAC | 6314 |
| TGCAGGACCAGAGAATTCGAATACAACCCGTCNNNCTAGCGTTAC | 5835 | TGCAGGACCAGAGAATTCGAATACACTGCGTGGNNNCTAGCGTTAC | 6075 | TGCAGGACCAGAGAATTCGAATACACACATTTNNNCTAGCGTTAC | 6315 |
| TGCAGGACCAGAGAATTCGAATACATCACCTTGNNNCTAGCGTTAC | 5836 | TGCAGGACCAGAGAATTCGAATACAACCGTCAANNNCTAGCGTTAC | 6076 | TGCAGGACCAGAGAATTCGAATACAGCCACATANNNCTAGCGTTAC | 6316 |
| TGCAGGACCAGAGAATTCGAATACAAGTACCACNNNCTAGCGTTAC | 5837 | TGCAGGACCAGAGAATTCGAATACAGGTAACGANNNCTAGCGTTAC | 6077 | TGCAGGACCAGAGAATTCGAATACATAAACAGANNNCTAGCGTTAC | 6317 |
| TGCAGGACCAGAGAATTCGAATACAACAAATGANNNCTAGCGTTAC | 5838 | TGCAGGACCAGAGAATTCGAATACAATCCGAGTNNNCTAGCGTTAC | 6078 | TGCAGGACCAGAGAATTCGAATACAGGTACCATNNNCTAGCGTTAC | 6318 |
| TGCAGGACCAGAGAATTCGAATACAATTGTTGANNNCTAGCGTTAC | 5839 | TGCAGGACCAGAGAATTCGAATACAACCAACCANNNCTAGCGTTAC | 6079 | TGCAGGACCAGAGAATTCGAATACAAGAAAAGNNNCTAGCGTTAC | 6319 |
| TGCAGGACCAGAGAATTCGAATACAACCGAAACNNNCTAGCGTTAC | 5840 | TGCAGGACCAGAGAATTCGAATACACAGTATATNNNCTAGCGTTAC | 6080 | TGCAGGACCAGAGAATTCGAATACAGCTCTCATNNNCTAGCGTTAC | 6320 |
| TGCAGGACCAGAGAATTCGAATACAGAGAACGTNNNCTAGCGTTAC | 5841 | TGCAGGACCAGAGAATTCGAATACATCCGATAGNNNCTAGCGTTAC | 6081 | TGCAGGACCAGAGAATTCGAATACAAGGCACAANNNCTAGCGTTAC | 6321 |
| TGCAGGACCAGAGAATTCGAATACATACCATGGNNNCTAGCGTTAC | 5842 | TGCAGGACCAGAGAATTCGAATACATTAGTATGNNNCTAGCGTTAC | 6082 | TGCAGGACCAGAGAATTCGAATACAGCGATGAANNNCTAGCGTTAC | 6322 |
| TGCAGGACCAGAGAATTCGAATACACAAAACGNNNCTAGCGTTAC | 5843 | TGCAGGACCAGAGAATTCGAATACAACATTCAANNNCTAGCGTTAC | 6083 | TGCAGGACCAGAGAATTCGAATACATCACTTATNNNCTAGCGTTAC | 6323 |
| TGCAGGACCAGAGAATTCGAATACATAGTGAGGNNNCTAGCGTTAC | 5844 | TGCAGGACCAGAGAATTCGAATACAGTACTGACNNNCTAGCGTTAC | 6084 | TGCAGGACCAGAGAATTCGAATACATAGGCCCGNNNCTAGCGTTAC | 6324 |
| TGCAGGACCAGAGAATTCGAATACACGTGATACNNNCTAGCGTTAC | 5845 | TGCAGGACCAGAGAATTCGAATACACCTCATTGNNNCTAGCGTTAC | 6085 | TGCAGGACCAGAGAATTCGAATACAATTTAAATNNNCTAGCGTTAC | 6325 |
| TGCAGGACCAGAGAATTCGAATACACTGCCCCTNNNCTAGCGTTAC | 5846 | TGCAGGACCAGAGAATTCGAATACAATGGCACTNNNCTAGCGTTAC | 6086 | TGCAGGACCAGAGAATTCGAATACATCTGTTTANNNCTAGCGTTAC | 6326 |
| TGCAGGACCAGAGAATTCGAATACAGGACAGTANNNCTAGCGTTAC | 5847 | TGCAGGACCAGAGAATTCGAATACACCCCACGTNNNCTAGCGTTAC | 6087 | TGCAGGACCAGAGAATTCGAATACAAGTTGAAANNNCTAGCGTTAC | 6327 |
| TGCAGGACCAGAGAATTCGAATACACTAGTATANNNCTAGCGTTAC | 5848 | TGCAGGACCAGAGAATTCGAATACACAAACCTGNNNCTAGCGTTAC | 6088 | TGCAGGACCAGAGAATTCGAATACAATATGACTNNNCTAGCGTTAC | 6328 |
| TGCAGGACCAGAGAATTCGAATACAGAACCTTGNNNCTAGCGTTAC | 5849 | TGCAGGACCAGAGAATTCGAATACACGGCCAGTNNNCTAGCGTTAC | 6089 | TGCAGGACCAGAGAATTCGAATACAGAAGACTGNNNCTAGCGTTAC | 6329 |
| TGCAGGACCAGAGAATTCGAATACACTGTTTATNNNCTAGCGTTAC | 5850 | TGCAGGACCAGAGAATTCGAATACAGACAACCTNNNCTAGCGTTAC | 6090 | TGCAGGACCAGAGAATTCGAATACAGTGCGTGCNNNCTAGCGTTAC | 6330 |
| TGCAGGACCAGAGAATTCGAATACAAATACGATNNNCTAGCGTTAC | 5851 | TGCAGGACCAGAGAATTCGAATACATGGCACATNNNCTAGCGTTAC | 6091 | TGCAGGACCAGAGAATTCGAATACAATGTCCGANNNCTAGCGTTAC | 6331 |
| TGCAGGACCAGAGAATTCGAATACACGTCAAGTNNNCTAGCGTTAC | 5852 | TGCAGGACCAGAGAATTCGAATACACCAAGTACNNNCTAGCGTTAC | 6092 | TGCAGGACCAGAGAATTCGAATACATGTTATAGNNNCTAGCGTTAC | 6332 |
| TGCAGGACCAGAGAATTCGAATACACCTGTTTCNNNCTAGCGTTAC | 5853 | TGCAGGACCAGAGAATTCGAATACACACGACCGNNNCTAGCGTTAC | 6093 | TGCAGGACCAGAGAATTCGAATACATGTCGTAGNNNCTAGCGTTAC | 6333 |
| TGCAGGACCAGAGAATTCGAATACAACCGTGCGNNNCTAGCGTTAC | 5854 | TGCAGGACCAGAGAATTCGAATACACCGTGATANNNCTAGCGTTAC | 6094 | TGCAGGACCAGAGAATTCGAATACAGACGCTTANNNCTAGCGTTAC | 6334 |
| TGCAGGACCAGAGAATTCGAATACAAGCTGCGNNNCTAGCGTTAC | 5855 | TGCAGGACCAGAGAATTCGAATACACATTGCCTNNNCTAGCGTTAC | 6095 | TGCAGGACCAGAGAATTCGAATACAGAATTACTNNNCTAGCGTTAC | 6335 |
| TGCAGGACCAGAGAATTCGAATACATCCTTACGNNNCTAGCGTTAC | 5856 | TGCAGGACCAGAGAATTCGAATACATGTTGTTNNNCTAGCGTTAC | 6096 | TGCAGGACCAGAGAATTCGAATACATCGACCCCNNNCTAGCGTTAC | 6336 |
| TGCAGGACCAGAGAATTCGAATACAAACGAAGCNNNCTAGCGTTAC | 5857 | TGCAGGACCAGAGAATTCGAATACATGTTTTGNNNCTAGCGTTAC | 6097 | TGCAGGACCAGAGAATTCGAATACAGCCTCCACNNNCTAGCGTTAC | 6337 |
| TGCAGGACCAGAGAATTCGAATACAGAAGTTTTNNNCTAGCGTTAC | 5858 | TGCAGGACCAGAGAATTCGAATACAGCTCCTCGNNNCTAGCGTTAC | 6098 | TGCAGGACCAGAGAATTCGAATACACTGTATANNNCTAGCGTTAC | 6338 |
| TGCAGGACCAGAGAATTCGAATACAGCCGTTAANNNCTAGCGTTAC | 5859 | TGCAGGACCAGAGAATTCGAATACACCACCTGCNNNCTAGCGTTAC | 6099 | TGCAGGACCAGAGAATTCGAATACATTCGAGTGNNNCTAGCGTTAC | 6339 |
| TGCAGGACCAGAGAATTCGAATACATGTGCCAANNNCTAGCGTTAC | 5860 | TGCAGGACCAGAGAATTCGAATACAGAGCGGTGNNNCTAGCGTTAC | 6100 | TGCAGGACCAGAGAATTCGAATACATAAGTGCCNNNCTAGCGTTAC | 6340 |
| TGCAGGACCAGAGAATTCGAATACAGCAAAACGNNNCTAGCGTTAC | 5861 | TGCAGGACCAGAGAATTCGAATACAAACAACGGNNNCTAGCGTTAC | 6101 | TGCAGGACCAGAGAATTCGAATACACAGATAAANNNCTAGCGTTAC | 6341 |
| TGCAGGACCAGAGAATTCGAATACACGTAAGAGNNNCTAGCGTTAC | 5862 | TGCAGGACCAGAGAATTCGAATACAATTGCTTTNNNCTAGCGTTAC | 6102 | TGCAGGACCAGAGAATTCGAATACAGAATCACNNNCTAGCGTTAC | 6342 |
| TGCAGGACCAGAGAATTCGAATACATGACGTCANNNCTAGCGTTAC | 5863 | TGCAGGACCAGAGAATTCGAATACACCAGAGAANNNCTAGCGTTAC | 6103 | TGCAGGACCAGAGAATTCGAATACAGAGCTTACNNNCTAGCGTTAC | 6343 |
| TGCAGGACCAGAGAATTCGAATACACTCCCTAANNNCTAGCGTTAC | 5864 | TGCAGGACCAGAGAATTCGAATACAGATACCTGNNNCTAGCGTTAC | 6104 | TGCAGGACCAGAGAATTCGAATACATCATCTCCNNNCTAGCGTTAC | 6344 |
| TGCAGGACCAGAGAATTCGAATACATATTCAGANNNCTAGCGTTAC | 5865 | TGCAGGACCAGAGAATTCGAATACAACTTATTCNNNCTAGCGTTAC | 6105 | TGCAGGACCAGAGAATTCGAATACACCACGTGGNNNCTAGCGTTAC | 6345 |
| TGCAGGACCAGAGAATTCGAATACACTAGCAACNNNCTAGCGTTAC | 5866 | TGCAGGACCAGAGAATTCGAATACAAGTTGTTANNNCTAGCGTTAC | 6106 | TGCAGGACCAGAGAATTCGAATACACTGTATGNNNCTAGCGTTAC | 6346 |

FIG. 20D

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAGAATGCCTNNNCTAGCGTTAC | 5867 | TGCAGGACCAGAGAATTCGAATACAATGACTGCNNNCTAGCGTTAC | 6107 | TGCAGGACCAGAGAATTCGAATACACTCTCCGGNNNCTAGCGTTAC | 6347 |
| TGCAGGACCAGAGAATTCGAATACAGACTTCTCNNNCTAGCGTTAC | 5868 | TGCAGGACCAGAGAATTCGAATACAAGCAAACGNNNCTAGCGTTAC | 6108 | TGCAGGACCAGAGAATTCGAATACACAAGAGTGNNNCTAGCGTTAC | 6348 |
| TGCAGGACCAGAGAATTCGAATACATAATTAGCNNNCTAGCGTTAC | 5869 | TGCAGGACCAGAGAATTCGAATACAAGACTATTNNNCTAGCGTTAC | 6109 | TGCAGGACCAGAGAATTCGAATACATAGCTCTCNNNCTAGCGTTAC | 6349 |
| TGCAGGACCAGAGAATTCGAATACACGTGTGGCNNNCTAGCGTTAC | 5870 | TGCAGGACCAGAGAATTCGAATACACTGAAACCNNNCTAGCGTTAC | 6110 | TGCAGGACCAGAGAATTCGAATACAGTGGCAGGNNNCTAGCGTTAC | 6350 |
| TGCAGGACCAGAGAATTCGAATACAGACTCGATNNNCTAGCGTTAC | 5871 | TGCAGGACCAGAGAATTCGAATACAAGCAAAGGNNNCTAGCGTTAC | 6111 | TGCAGGACCAGAGAATTCGAATACATGCATCGANNNCTAGCGTTAC | 6351 |
| TGCAGGACCAGAGAATTCGAATACACCGATCGCNNNCTAGCGTTAC | 5872 | TGCAGGACCAGAGAATTCGAATACACCCTAGTTNNNCTAGCGTTAC | 6112 | TGCAGGACCAGAGAATTCGAATACAGGGTCGANNNNCTAGCGTTAC | 6352 |
| TGCAGGACCAGAGAATTCGAATACAACTCTACCNNNCTAGCGTTAC | 5873 | TGCAGGACCAGAGAATTCGAATACACAAACCACNNNCTAGCGTTAC | 6113 | TGCAGGACCAGAGAATTCGAATACAAAGCCACTNNNCTAGCGTTAC | 6353 |
| TGCAGGACCAGAGAATTCGAATACAGGAAGGCCNNNCTAGCGTTAC | 5874 | TGCAGGACCAGAGAATTCGAATACATTGTAGTANNNCTAGCGTTAC | 6114 | TGCAGGACCAGAGAATTCGAATACAGATCTTTTNNNCTAGCGTTAC | 6354 |
| TGCAGGACCAGAGAATTCGAATACACATATTAGNNNCTAGCGTTAC | 5875 | TGCAGGACCAGAGAATTCGAATACAGTACAGCTNNNCTAGCGTTAC | 6115 | TGCAGGACCAGAGAATTCGAATACAGGCTCTAANNNCTAGCGTTAC | 6355 |
| TGCAGGACCAGAGAATTCGAATACACGGTGACCNNNCTAGCGTTAC | 5876 | TGCAGGACCAGAGAATTCGAATACAAGTGTACCNNNCTAGCGTTAC | 6116 | TGCAGGACCAGAGAATTCGAATACATCTATGTTNNNCTAGCGTTAC | 6356 |
| TGCAGGACCAGAGAATTCGAATACAGTGCATGTNNNCTAGCGTTAC | 5877 | TGCAGGACCAGAGAATTCGAATACATTTTATGCNNNCTAGCGTTAC | 6117 | TGCAGGACCAGAGAATTCGAATACAACCCGCGTGNNNCTAGCGTTAC | 6357 |
| TGCAGGACCAGAGAATTCGAATACATAAGTGTTNNNCTAGCGTTAC | 5878 | TGCAGGACCAGAGAATTCGAATACAAATCGTGNNNCTAGCGTTAC | 6118 | TGCAGGACCAGAGAATTCGAATACAGTACTCGNNNCTAGCGTTAC | 6358 |
| TGCAGGACCAGAGAATTCGAATACAACCTTATTNNNCTAGCGTTAC | 5879 | TGCAGGACCAGAGAATTCGAATACACGATCTGANNNCTAGCGTTAC | 6119 | TGCAGGACCAGAGAATTCGAATACAGGAGCCCTNNNCTAGCGTTAC | 6359 |
| TGCAGGACCAGAGAATTCGAATACAACTCCACTNNNCTAGCGTTAC | 5880 | TGCAGGACCAGAGAATTCGAATACAGATAGATANNNCTAGCGTTAC | 6120 | TGCAGGACCAGAGAATTCGAATACATATCGAGCNNNCTAGCGTTAC | 6360 |
| TGCAGGACCAGAGAATTCGAATACACCAAATATNNNCTAGCGTTAC | 5881 | TGCAGGACCAGAGAATTCGAATACAGAGTCCTANNNCTAGCGTTAC | 6121 | TGCAGGACCAGAGAATTCGAATACACCGTTGAANNNCTAGCGTTAC | 6361 |
| TGCAGGACCAGAGAATTCGAATACACAAGATGGNNNCTAGCGTTAC | 5882 | TGCAGGACCAGAGAATTCGAATACACATGTGGTNNNCTAGCGTTAC | 6122 | TGCAGGACCAGAGAATTCGAATACACGAAGAACNNNCTAGCGTTAC | 6362 |
| TGCAGGACCAGAGAATTCGAATACACCCAAGGCNNNCTAGCGTTAC | 5883 | TGCAGGACCAGAGAATTCGAATACAGATCGCGCNNNCTAGCGTTAC | 6123 | TGCAGGACCAGAGAATTCGAATACAAGTGATCCNNNCTAGCGTTAC | 6363 |
| TGCAGGACCAGAGAATTCGAATACATAAGCGGANNNCTAGCGTTAC | 5884 | TGCAGGACCAGAGAATTCGAATACAACCACATGNNNCTAGCGTTAC | 6124 | TGCAGGACCAGAGAATTCGAATACAGGTCAACTNNNCTAGCGTTAC | 6364 |
| TGCAGGACCAGAGAATTCGAATACAGAGGCCCTNNNCTAGCGTTAC | 5885 | TGCAGGACCAGAGAATTCGAATACATGGCGATANNNCTAGCGTTAC | 6125 | TGCAGGACCAGAGAATTCGAATACATGACGTGTNNNCTAGCGTTAC | 6365 |
| TGCAGGACCAGAGAATTCGAATACACTTCCTAGNNNCTAGCGTTAC | 5886 | TGCAGGACCAGAGAATTCGAATACACAAAGCCTNNNCTAGCGTTAC | 6126 | TGCAGGACCAGAGAATTCGAATACATTACAACANNNCTAGCGTTAC | 6366 |
| TGCAGGACCAGAGAATTCGAATACACGCAGAAANNNCTAGCGTTAC | 5887 | TGCAGGACCAGAGAATTCGAATACAACTGACGTNNNCTAGCGTTAC | 6127 | TGCAGGACCAGAGAATTCGAATACAAAATGTTCNNNCTAGCGTTAC | 6367 |
| TGCAGGACCAGAGAATTCGAATACATGTGCGTANNNCTAGCGTTAC | 5888 | TGCAGGACCAGAGAATTCGAATACAAAGCTGGTNNNCTAGCGTTAC | 6128 | TGCAGGACCAGAGAATTCGAATACATTATAACGNNNCTAGCGTTAC | 6368 |
| TGCAGGACCAGAGAATTCGAATACACGATGGAANNNGATCGACATG | 5889 | TGCAGGACCAGAGAATTCGAATACAGGATCGAANNNGATCGACATG | 6129 | TGCAGGACCAGAGAATTCGAATACATCCCGATANNNGATCGACATG | 6369 |
| TGCAGGACCAGAGAATTCGAATACACCAATTAANNNGATCGACATG | 5890 | TGCAGGACCAGAGAATTCGAATACATCGCAACANNNGATCGACATG | 6130 | TGCAGGACCAGAGAATTCGAATACAAGCCCTTTNNNGATCGACATG | 6370 |
| TGCAGGACCAGAGAATTCGAATACACATAGGCTNNNGATCGACATG | 5891 | TGCAGGACCAGAGAATTCGAATACACCGACTAANNNGATCGACATG | 6131 | TGCAGGACCAGAGAATTCGAATACAGTACACTGNNNGATCGACATG | 6371 |
| TGCAGGACCAGAGAATTCGAATACAAAAAATTNNNGATCGACATG | 5892 | TGCAGGACCAGAGAATTCGAATACAGACCGTTANNNGATCGACATG | 6132 | TGCAGGACCAGAGAATTCGAATACACGTGTAGTNNNGATCGACATG | 6372 |
| TGCAGGACCAGAGAATTCGAATACAATACACTNNNGATCGACATG | 5893 | TGCAGGACCAGAGAATTCGAATACATGCCCTTNNNGATCGACATG | 6133 | TGCAGGACCAGAGAATTCGAATACAGGAAAGTCNNNGATCGACATG | 6373 |
| TGCAGGACCAGAGAATTCGAATACAATCGAAANNNGATCGACATG | 5894 | TGCAGGACCAGAGAATTCGAATACATCGAAACCNNNGATCGACATG | 6134 | TGCAGGACCAGAGAATTCGAATACATTCTGCGTNNNGATCGACATG | 6374 |
| TGCAGGACCAGAGAATTCGAATACATCTATTACNNNGATCGACATG | 5895 | TGCAGGACCAGAGAATTCGAATACAGACCTTCTNNNGATCGACATG | 6135 | TGCAGGACCAGAGAATTCGAATACATACTCGANNNNGATCGACATG | 6375 |
| TGCAGGACCAGAGAATTCGAATACAACCCGATANNNGATCGACATG | 5896 | TGCAGGACCAGAGAATTCGAATACACTACCCTANNNGATCGACATG | 6136 | TGCAGGACCAGAGAATTCGAATACACGTCCAAANNNGATCGACATG | 6376 |
| TGCAGGACCAGAGAATTCGAATACAAAACGCANNNGATCGACATG | 5897 | TGCAGGACCAGAGAATTCGAATACATGCCTTCNNNGATCGACATG | 6137 | TGCAGGACCAGAGAATTCGAATACATTGAACCGNNNGATCGACATG | 6377 |
| TGCAGGACCAGAGAATTCGAATACAGTGATCGTNNNGATCGACATG | 5898 | TGCAGGACCAGAGAATTCGAATACAGCCGACTATNNNGATCGACATG | 6138 | TGCAGGACCAGAGAATTCGAATACAGGCCGCTANNNGATCGACATG | 6378 |
| TGCAGGACCAGAGAATTCGAATACACGCAGCCANNNGATCGACATG | 5899 | TGCAGGACCAGAGAATTCGAATACAGGCATTCANNNGATCGACATG | 6139 | TGCAGGACCAGAGAATTCGAATACAGATACGTCNNNGATCGACATG | 6379 |

FIG. 20E

| Pool-25 | SEQ ID NO: | Pool-26 | SEQ ID NO: | Pool-27 | SEQ ID NO: |
|---|---|---|---|---|---|
| TGCAGGACCAGAGAATTCGAATACATGACCATGNNNGATCGACATG | 5900 | TGCAGGACCAGAGAATTCGAATACAGCTAGAAGNNNGATCGACATG | 6140 | TGCAGGACCAGAGAATTCGAATACAATTCAACANNNGATCGACATG | 6380 |
| TGCAGGACCAGAGAATTCGAATACAGGTCCACGNNNGATCGACATG | 5901 | TGCAGGACCAGAGAATTCGAATACATTTATAAANNNGATCGACATG | 6141 | TGCAGGACCAGAGAATTCGAATACAGTGTGCATNNNGATCGACATG | 6381 |
| TGCAGGACCAGAGAATTCGAATACAAAGCATAANNNGATCGACATG | 5902 | TGCAGGACCAGAGAATTCGAATACATCCCTACANNNGATCGACATG | 6142 | TGCAGGACCAGAGAATTCGAATACAGCCATAGTNNNGATCGACATG | 6382 |
| TGCAGGACCAGAGAATTCGAATACAGACAGGCGNNNGATCGACATG | 5903 | TGCAGGACCAGAGAATTCGAATACAACGTCTAGNNNGATCGACATG | 6143 | TGCAGGACCAGAGAATTCGAATACACTCATCTGNNNGATCGACATG | 6383 |
| TGCAGGACCAGAGAATTCGAATACAACGTAGANNNGATCGACATG | 5904 | TGCAGGACCAGAGAATTCGAATACAGAGCTTTGNNNGATCGACATG | 6144 | TGCAGGACCAGAGAATTCGAATACAAACCGACTNNNGATCGACATG | 6384 |
| TGCAGGACCAGAGAATTCGAATACATCATTACTNNNGATCGACATG | 5905 | TGCAGGACCAGAGAATTCGAATACAAGAGCGGCNNNGATCGACATG | 6145 | TGCAGGACCAGAGAATTCGAATACAAATCGCCCNNNGATCGACATG | 6385 |
| TGCAGGACCAGAGAATTCGAATACACGAAAATANNNGATCGACATG | 5906 | TGCAGGACCAGAGAATTCGAATACACATATACANNNGATCGACATG | 6146 | TGCAGGACCAGAGAATTCGAATACATAGGATCCNNNGATCGACATG | 6386 |
| TGCAGGACCAGAGAATTCGAATACATGGAAGGTNNNGATCGACATG | 5907 | TGCAGGACCAGAGAATTCGAATACAAAGGCTAGNNNGATCGACATG | 6147 | TGCAGGACCAGAGAATTCGAATACAATGGCGTTNNNGATCGACATG | 6387 |
| TGCAGGACCAGAGAATTCGAATACACTGTTTANNNGATCGACATG | 5908 | TGCAGGACCAGAGAATTCGAATACATATCGACGNNNGATCGACATG | 6148 | TGCAGGACCAGAGAATTCGAATACACTAAATTGNNNGATCGACATG | 6388 |
| TGCAGGACCAGAGAATTCGAATACACGGATTGNNNGATCGACATG | 5909 | TGCAGGACCAGAGAATTCGAATACAAGACGTCTNNNGATCGACATG | 6149 | TGCAGGACCAGAGAATTCGAATACAACTACATANNNGATCGACATG | 6389 |
| TGCAGGACCAGAGAATTCGAATACACGTGGTGCNNNGATCGACATG | 5910 | TGCAGGACCAGAGAATTCGAATACATGTTACCCNNNGATCGACATG | 6150 | TGCAGGACCAGAGAATTCGAATACACATCCTCANNNGATCGACATG | 6390 |
| TGCAGGACCAGAGAATTCGAATACAATGCCTCNNNGATCGACATG | 5911 | TGCAGGACCAGAGAATTCGAATACAGCCTGCAGNNNGATCGACATG | 6151 | TGCAGGACCAGAGAATTCGAATACAGATGTGAGNNNGATCGACATG | 6391 |
| TGCAGGACCAGAGAATTCGAATACACGAGAAGGNNNGATCGACATG | 5912 | TGCAGGACCAGAGAATTCGAATACAGGTAACGTNNNGATCGACATG | 6152 | TGCAGGACCAGAGAATTCGAATACAGGGCCAAANNNGATCGACATG | 6392 |
| TGCAGGACCAGAGAATTCGAATACATCATGGTGNNNGATCGACATG | 5913 | TGCAGGACCAGAGAATTCGAATACAATCTTATCNNNGATCGACATG | 6153 | TGCAGGACCAGAGAATTCGAATACACCAAGCTANNNGATCGACATG | 6393 |
| TGCAGGACCAGAGAATTCGAATACACTGGAGCNNNGATCGACATG | 5914 | TGCAGGACCAGAGAATTCGAATACAACGTTTGGNNNGATCGACATG | 6154 | TGCAGGACCAGAGAATTCGAATACAAGGAGATCNNNGATCGACATG | 6394 |
| TGCAGGACCAGAGAATTCGAATACACTGTTAGGNNNGATCGACATG | 5915 | TGCAGGACCAGAGAATTCGAATACAGATTAAAGNNNGATCGACATG | 6155 | TGCAGGACCAGAGAATTCGAATACACCTCCGACNNNGATCGACATG | 6395 |
| TGCAGGACCAGAGAATTCGAATACACTGGTTCTNNNGATCGACATG | 5916 | TGCAGGACCAGAGAATTCGAATACATTGCCAGANNNGATCGACATG | 6156 | TGCAGGACCAGAGAATTCGAATACACGCTGTGGNNNGATCGACATG | 6396 |
| TGCAGGACCAGAGAATTCGAATACACAAAGTCCNNNGATCGACATG | 5917 | TGCAGGACCAGAGAATTCGAATACACGGCATATNNNGATCGACATG | 6157 | TGCAGGACCAGAGAATTCGAATACATACCGCCCNNNGATCGACATG | 6397 |
| TGCAGGACCAGAGAATTCGAATACACGTAGCCGNNNGATCGACATG | 5918 | TGCAGGACCAGAGAATTCGAATACAGGTCAGCCNNNGATCGACATG | 6158 | TGCAGGACCAGAGAATTCGAATACACGTCGCCTNNNGATCGACATG | 6398 |
| TGCAGGACCAGAGAATTCGAATACAAGCTGAANNNGATCGACATG | 5919 | TGCAGGACCAGAGAATTCGAATACACTACCACTNNNGATCGACATG | 6159 | TGCAGGACCAGAGAATTCGAATACACCTCACCGNNNGATCGACATG | 6399 |
| TGCAGGACCAGAGAATTCGAATACACTAATCTTNNNGATCGACATG | 5920 | TGCAGGACCAGAGAATTCGAATACACGCACGGTNNNGATCGACATG | 6160 | TGCAGGACCAGAGAATTCGAATACAGCCTGGACNNNGATCGACATG | 6400 |
| TGCAGGACCAGAGAATTCGAATACAGACTTAATNNNGATCGACATG | 5921 | TGCAGGACCAGAGAATTCGAATACATGCTTCGTNNNGATCGACATG | 6161 | TGCAGGACCAGAGAATTCGAATACAACTTGGACNNNGATCGACATG | 6401 |
| TGCAGGACCAGAGAATTCGAATACAATCACAATNNNGATCGACATG | 5922 | TGCAGGACCAGAGAATTCGAATACAAGCACTGTNNNGATCGACATG | 6162 | TGCAGGACCAGAGAATTCGAATACATGTTGCCTNNNGATCGACATG | 6402 |
| TGCAGGACCAGAGAATTCGAATACAGAGCCTGCNNNGATCGACATG | 5923 | TGCAGGACCAGAGAATTCGAATACACTTACAAANNNGATCGACATG | 6163 | TGCAGGACCAGAGAATTCGAATACACGGCACGTNNNGATCGACATG | 6403 |
| TGCAGGACCAGAGAATTCGAATACACTCTAGGANNNGATCGACATG | 5924 | TGCAGGACCAGAGAATTCGAATACACGATGGCCNNNGATCGACATG | 6164 | TGCAGGACCAGAGAATTCGAATACAAGGTGTGANNNGATCGACATG | 6404 |
| TGCAGGACCAGAGAATTCGAATACAGGTGAGATNNNGATCGACATG | 5925 | TGCAGGACCAGAGAATTCGAATACACACCGCANNNGATCGACATG | 6165 | TGCAGGACCAGAGAATTCGAATACAAACGACGANNNGATCGACATG | 6405 |
| TGCAGGACCAGAGAATTCGAATACAAGGTTGCTNNNGATCGACATG | 5926 | TGCAGGACCAGAGAATTCGAATACAGCCATAACNNNGATCGACATG | 6166 | TGCAGGACCAGAGAATTCGAATACACATCACTCNNNGATCGACATG | 6406 |
| TGCAGGACCAGAGAATTCGAATACAGAGGTGCGNNNGATCGACATG | 5927 | TGCAGGACCAGAGAATTCGAATACATGAAGTCCNNNGATCGACATG | 6167 | TGCAGGACCAGAGAATTCGAATACATAATGCTANNNGATCGACATG | 6407 |
| TGCAGGACCAGAGAATTCGAATACAACTCAGANNNGATCGACATG | 5928 | TGCAGGACCAGAGAATTCGAATACAGCAAACTNNNGATCGACATG | 6168 | TGCAGGACCAGAGAATTCGAATACACGCCTTGCNNNGATCGACATG | 6408 |
| TGCAGGACCAGAGAATTCGAATACACAATGTATNNNGATCGACATG | 5929 | TGCAGGACCAGAGAATTCGAATACAACGCTTCTNNNGATCGACATG | 6169 | TGCAGGACCAGAGAATTCGAATACATGATCAGCNNNGATCGACATG | 6409 |
| TGCAGGACCAGAGAATTCGAATACAAACCATTANNNGATCGACATG | 5930 | TGCAGGACCAGAGAATTCGAATACATACCGGCGNNNGATCGACATG | 6170 | TGCAGGACCAGAGAATTCGAATACACTTCGGAANNNGATCGACATG | 6410 |
| TGCAGGACCAGAGAATTCGAATACATGGCCCTGNNNGATCGACATG | 5931 | TGCAGGACCAGAGAATTCGAATACATGCTAATANNNGATCGACATG | 6171 | TGCAGGACCAGAGAATTCGAATACACGCAAATCNNNGATCGACATG | 6411 |
| TGCAGGACCAGAGAATTCGAATACACGCCCTGTNNNGATCGACATG | 5932 | TGCAGGACCAGAGAATTCGAATACATAAGGAGCNNNGATCGACATG | 6172 | TGCAGGACCAGAGAATTCGAATACAAGAGAACCNNNGATCGACATG | 6412 |

FIG. 20F

| Pool-25 | SEQ ID NO: | Pool-26 | SEQ ID NO: | Pool-27 | SEQ ID NO: |
|---|---|---|---|---|---|
| TGCAGGACCAGAGAATTCGAATACATAGCCGTANNNGATCGACATG | 5933 | TGCAGGACCAGAGAATTCGAATACATAGTCCGANNNGATCGACATG | 6173 | TGCAGGACCAGAGAATTCGAATACATCGACGATNNNGATCGACATG | 6413 |
| TGCAGGACCAGAGAATTCGAATACAGGATAGTGNNNGATCGACATG | 5934 | TGCAGGACCAGAGAATTCGAATACACTATCCTGNNNGATCGACATG | 6174 | TGCAGGACCAGAGAATTCGAATACACAGCAAGANNNGATCGACATG | 6414 |
| TGCAGGACCAGAGAATTCGAATACATAAGGCAGNNNGATCGACATG | 5935 | TGCAGGACCAGAGAATTCGAATACATTTGGTCCNNNGATCGACATG | 6175 | TGCAGGACCAGAGAATTCGAATACACAAAGTAANNNGATCGACATG | 6415 |
| TGCAGGACCAGAGAATTCGAATACAAGGTCCTANNNGATCGACATG | 5936 | TGCAGGACCAGAGAATTCGAATACAGCCTTTCANNNGATCGACATG | 6176 | TGCAGGACCAGAGAATTCGAATACAGAAATCAANNNGATCGACATG | 6416 |
| TGCAGGACCAGAGAATTCGAATACAAACTGGAGNNNGATCGACATG | 5937 | TGCAGGACCAGAGAATTCGAATACAGTGTTCGNNNGATCGACATG | 6177 | TGCAGGACCAGAGAATTCGAATACACTCCTGATNNNGATCGACATG | 6417 |
| TGCAGGACCAGAGAATTCGAATACATTGTTGTTNNNGATCGACATG | 5938 | TGCAGGACCAGAGAATTCGAATACAACTGTCAGNNNGATCGACATG | 6178 | TGCAGGACCAGAGAATTCGAATACAACTATAGTNNNGATCGACATG | 6418 |
| TGCAGGACCAGAGAATTCGAATACAGCGAAGCGNNNGATCGACATG | 5939 | TGCAGGACCAGAGAATTCGAATACAATCTGACGNNNGATCGACATG | 6179 | TGCAGGACCAGAGAATTCGAATACAGGTAGTTCNNNGATCGACATG | 6419 |
| TGCAGGACCAGAGAATTCGAATACAAGATCCGTNNNGATCGACATG | 5940 | TGCAGGACCAGAGAATTCGAATACATACCTCGTNNNGATCGACATG | 6180 | TGCAGGACCAGAGAATTCGAATACACGGAACTTNNNGATCGACATG | 6420 |
| TGCAGGACCAGAGAATTCGAATACAATACCGTGNNNGATCGACATG | 5941 | TGCAGGACCAGAGAATTCGAATACATGCATACGNNNGATCGACATG | 6181 | TGCAGGACCAGAGAATTCGAATACAGGATCTGTNNNGATCGACATG | 6421 |
| TGCAGGACCAGAGAATTCGAATACAAATCATGTNNNGATCGACATG | 5942 | TGCAGGACCAGAGAATTCGAATACACAGGTAAGNNNGATCGACATG | 6182 | TGCAGGACCAGAGAATTCGAATACAATTCCGCTNNNGATCGACATG | 6422 |
| TGCAGGACCAGAGAATTCGAATACATGTTTTGTNNNGATCGACATG | 5943 | TGCAGGACCAGAGAATTCGAATACAGGACCAAANNNGATCGACATG | 6183 | TGCAGGACCAGAGAATTCGAATACATTTCTACANNNGATCGACATG | 6423 |
| TGCAGGACCAGAGAATTCGAATACAGGATACAGNNNGATCGACATG | 5944 | TGCAGGACCAGAGAATTCGAATACAGGTCGCCANNNGATCGACATG | 6184 | TGCAGGACCAGAGAATTCGAATACATCCCACNNNGATCGACATG | 6424 |
| TGCAGGACCAGAGAATTCGAATACAGTTCGTAGNNNGATCGACATG | 5945 | TGCAGGACCAGAGAATTCGAATACAATGGAAGCNNNGATCGACATG | 6185 | TGCAGGACCAGAGAATTCGAATACACTTACCACNNNGATCGACATG | 6425 |
| TGCAGGACCAGAGAATTCGAATACAGGAGATCANNNGATCGACATG | 5946 | TGCAGGACCAGAGAATTCGAATACACATACGACNNNGATCGACATG | 6186 | TGCAGGACCAGAGAATTCGAATACAACCTTCTGNNNGATCGACATG | 6426 |
| TGCAGGACCAGAGAATTCGAATACACTTTGTTANNNGATCGACATG | 5947 | TGCAGGACCAGAGAATTCGAATACATTCAGCGANNNGATCGACATG | 6187 | TGCAGGACCAGAGAATTCGAATACACGTGGTCGNNNGATCGACATG | 6427 |
| TGCAGGACCAGAGAATTCGAATACAGTGAACCTNNNGATCGACATG | 5948 | TGCAGGACCAGAGAATTCGAATACACTGCGGTGNNNGATCGACATG | 6188 | TGCAGGACCAGAGAATTCGAATACACCAAACTGNNNGATCGACATG | 6428 |
| TGCAGGACCAGAGAATTCGAATACACCTACAGANNNTGCATCAGGT | 5949 | TGCAGGACCAGAGAATTCGAATACACAGTACTGNNNTGCATCAGGT | 6189 | TGCAGGACCAGAGAATTCGAATACACTCACGCCNNNTGCATCAGGT | 6429 |
| TGCAGGACCAGAGAATTCGAATACAGCATCGATNNNTGCATCAGGT | 5950 | TGCAGGACCAGAGAATTCGAATACAGATCGAAGNNNTGCATCAGGT | 6190 | TGCAGGACCAGAGAATTCGAATACAGACGAGCGNNNTGCATCAGGT | 6430 |
| TGCAGGACCAGAGAATTCGAATACATACTGCTCNNNTGCATCAGGT | 5951 | TGCAGGACCAGAGAATTCGAATACATCAAACGCNNNTGCATCAGGT | 6191 | TGCAGGACCAGAGAATTCGAATACAAGAATGCCNNNTGCATCAGGT | 6431 |
| TGCAGGACCAGAGAATTCGAATACAGCTGTTGTNNNTGCATCAGGT | 5952 | TGCAGGACCAGAGAATTCGAATACATTTCAATCNNNTGCATCAGGT | 6192 | TGCAGGACCAGAGAATTCGAATACACCAGTCCNNNTGCATCAGGT | 6432 |
| TGCAGGACCAGAGAATTCGAATACAGAGTGCAANNNTGCATCAGGT | 5953 | TGCAGGACCAGAGAATTCGAATACAGAGATGTNNNTGCATCAGGT | 6193 | TGCAGGACCAGAGAATTCGAATACAAAGTATGNNNTGCATCAGGT | 6433 |
| TGCAGGACCAGAGAATTCGAATACATTGACCAGNNNTGCATCAGGT | 5954 | TGCAGGACCAGAGAATTCGAATACAAGGCTCATNNNTGCATCAGGT | 6194 | TGCAGGACCAGAGAATTCGAATACACGTACGTANNNTGCATCAGGT | 6434 |
| TGCAGGACCAGAGAATTCGAATACAATGGTTATNNNTGCATCAGGT | 5955 | TGCAGGACCAGAGAATTCGAATACATGGCCGCANNNTGCATCAGGT | 6195 | TGCAGGACCAGAGAATTCGAATACACAGCGCCANNNTGCATCAGGT | 6435 |
| TGCAGGACCAGAGAATTCGAATACAGCGCTCAGNNNTGCATCAGGT | 5956 | TGCAGGACCAGAGAATTCGAATACATAACTGCGNNNTGCATCAGGT | 6196 | TGCAGGACCAGAGAATTCGAATACAGCTCTCCGNNNTGCATCAGGT | 6436 |
| TGCAGGACCAGAGAATTCGAATACATGGACCCGNNNTGCATCAGGT | 5957 | TGCAGGACCAGAGAATTCGAATACAATCCTTGCNNNTGCATCAGGT | 6197 | TGCAGGACCAGAGAATTCGAATACAGGCCGTACNNNTGCATCAGGT | 6437 |
| TGCAGGACCAGAGAATTCGAATACATTACCACCNNNTGCATCAGGT | 5958 | TGCAGGACCAGAGAATTCGAATACAACTTAATGNNNTGCATCAGGT | 6198 | TGCAGGACCAGAGAATTCGAATACAGAGAGTGTNNNTGCATCAGGT | 6438 |
| TGCAGGACCAGAGAATTCGAATACAGTATAACTNNNTGCATCAGGT | 5959 | TGCAGGACCAGAGAATTCGAATACACACCTGCCNNNTGCATCAGGT | 6199 | TGCAGGACCAGAGAATTCGAATACAATGGAGTGNNNTGCATCAGGT | 6439 |
| TGCAGGACCAGAGAATTCGAATACAGCCCGTGANNNTGCATCAGGT | 5960 | TGCAGGACCAGAGAATTCGAATACATATGCTTTNNNTGCATCAGGT | 6200 | TGCAGGACCAGAGAATTCGAATACATCGGCCGANNNTGCATCAGGT | 6440 |
| TGCAGGACCAGAGAATTCGAATACATGATGACNNNTGCATCAGGT | 5961 | TGCAGGACCAGAGAATTCGAATACACGGTGCAANNNTGCATCAGGT | 6201 | TGCAGGACCAGAGAATTCGAATACAATCGATTANNNTGCATCAGGT | 6441 |
| TGCAGGACCAGAGAATTCGAATACACATGGCATNNNTGCATCAGGT | 5962 | TGCAGGACCAGAGAATTCGAATACACGGCTAATNNNTGCATCAGGT | 6202 | TGCAGGACCAGAGAATTCGAATACACCCAACAANNNTGCATCAGGT | 6442 |
| TGCAGGACCAGAGAATTCGAATACAATGATATCNNNTGCATCAGGT | 5963 | TGCAGGACCAGAGAATTCGAATACATAGCAAAANNNTGCATCAGGT | 6203 | TGCAGGACCAGAGAATTCGAATACATGTAGATTNNNTGCATCAGGT | 6443 |
| TGCAGGACCAGAGAATTCGAATACATGTAAAGNNNTGCATCAGGT | 5964 | TGCAGGACCAGAGAATTCGAATACAAGCAAGCANNNTGCATCAGGT | 6204 | TGCAGGACCAGAGAATTCGAATACAACCGGAGGNNNTGCATCAGGT | 6444 |
| TGCAGGACCAGAGAATTCGAATACACCTTGCCGNNNTGCATCAGGT | 5965 | TGCAGGACCAGAGAATTCGAATACAATAGTACTNNNTGCATCAGGT | 6205 | TGCAGGACCAGAGAATTCGAATACACACCTGAANNNTGCATCAGGT | 6445 |

FIG. 20G

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAGAGGCACGNNNTGCATCAGGT | 5966 | TGCAGGACCAGAGAATTCGAATACACCCATGTTNNNTGCATCAGGT | 6206 | TGCAGGACCAGAGAATTCGAATACAACATGTGCNNNTGCATCAGGT | 6446 |
| TGCAGGACCAGAGAATTCGAATACACCTGAGCGNNNTGCATCAGGT | 5967 | TGCAGGACCAGAGAATTCGAATACAGAGCAATGNNNTGCATCAGGT | 6207 | TGCAGGACCAGAGAATTCGAATACACAGGATCTNNNTGCATCAGGT | 6447 |
| TGCAGGACCAGAGAATTCGAATACAGGTTGCTANNNTGCATCAGGT | 5968 | TGCAGGACCAGAGAATTCGAATACAAATACCTANNNTGCATCAGGT | 6208 | TGCAGGACCAGAGAATTCGAATACACGTTTGTCNNNTGCATCAGGT | 6448 |
| TGCAGGACCAGAGAATTCGAATACAGTCAAAGGNNNTGCATCAGGT | 5969 | TGCAGGACCAGAGAATTCGAATACAAATATTGCNNNTGCATCAGGT | 6209 | TGCAGGACCAGAGAATTCGAATACAAAATCAAGNNNTGCATCAGGT | 6449 |
| TGCAGGACCAGAGAATTCGAATACAACGTATGCNNNTGCATCAGGT | 5970 | TGCAGGACCAGAGAATTCGAATACAAATCCATANNNTGCATCAGGT | 6210 | TGCAGGACCAGAGAATTCGAATACATCAACATANNNTGCATCAGGT | 6450 |
| TGCAGGACCAGAGAATTCGAATACACGAGCGGANNNTGCATCAGGT | 5971 | TGCAGGACCAGAGAATTCGAATACATCCATTTANNNTGCATCAGGT | 6211 | TGCAGGACCAGAGAATTCGAATACAATGAAGGCNNNTGCATCAGGT | 6451 |
| TGCAGGACCAGAGAATTCGAATACATTTTGCCGNNNTGCATCAGGT | 5972 | TGCAGGACCAGAGAATTCGAATACAGAGGTTCTNNNTGCATCAGGT | 6212 | TGCAGGACCAGAGAATTCGAATACACAAGTGGANNNTGCATCAGGT | 6452 |
| TGCAGGACCAGAGAATTCGAATACAGAGTCTGCNNNTGCATCAGGT | 5973 | TGCAGGACCAGAGAATTCGAATACAGTGATACCNNNTGCATCAGGT | 6213 | TGCAGGACCAGAGAATTCGAATACAAGCAAAATNNNTGCATCAGGT | 6453 |
| TGCAGGACCAGAGAATTCGAATACACTTCCTTCNNNTGCATCAGGT | 5974 | TGCAGGACCAGAGAATTCGAATACAACCTTGCTNNNTGCATCAGGT | 6214 | TGCAGGACCAGAGAATTCGAATACACAGATCCNNNTGCATCAGGT | 6454 |
| TGCAGGACCAGAGAATTCGAATACAATGTGAAANNNTGCATCAGGT | 5975 | TGCAGGACCAGAGAATTCGAATACATATCAAGTNNNTGCATCAGGT | 6215 | TGCAGGACCAGAGAATTCGAATACATACGCCTTNNNTGCATCAGGT | 6455 |
| TGCAGGACCAGAGAATTCGAATACACCCGTGGTNNNTGCATCAGGT | 5976 | TGCAGGACCAGAGAATTCGAATACAACTTAGGCNNNTGCATCAGGT | 6216 | TGCAGGACCAGAGAATTCGAATACAAGCGCTANNNTGCATCAGGT | 6456 |
| TGCAGGACCAGAGAATTCGAATACACAGAGGCGNNNTGCATCAGGT | 5977 | TGCAGGACCAGAGAATTCGAATACAACTGTTCCNNNTGCATCAGGT | 6217 | TGCAGGACCAGAGAATTCGAATACAAGTGATGGNNNTGCATCAGGT | 6457 |
| TGCAGGACCAGAGAATTCGAATACATTTGATCTNNNTGCATCAGGT | 5978 | TGCAGGACCAGAGAATTCGAATACAGGATCCATNNNTGCATCAGGT | 6218 | TGCAGGACCAGAGAATTCGAATACACGGATGAANNNTGCATCAGGT | 6458 |
| TGCAGGACCAGAGAATTCGAATACAGCGTCGACNNNTGCATCAGGT | 5979 | TGCAGGACCAGAGAATTCGAATACACCACTCCGNNNTGCATCAGGT | 6219 | TGCAGGACCAGAGAATTCGAATACAGACATAGGNNNTGCATCAGGT | 6459 |
| TGCAGGACCAGAGAATTCGAATACAGATATAANNNTGCATCAGGT | 5980 | TGCAGGACCAGAGAATTCGAATACACCAAGAGTNNNTGCATCAGGT | 6220 | TGCAGGACCAGAGAATTCGAATACAATTGCGTGNNNTGCATCAGGT | 6460 |
| TGCAGGACCAGAGAATTCGAATACAAATTTTANNNTGCATCAGGT | 5981 | TGCAGGACCAGAGAATTCGAATACAACCGTCTTNNNTGCATCAGGT | 6221 | TGCAGGACCAGAGAATTCGAATACACTACAGTGNNNTGCATCAGGT | 6461 |
| TGCAGGACCAGAGAATTCGAATACAAGCCGTGNNNTGCATCAGGT | 5982 | TGCAGGACCAGAGAATTCGAATACAGGCTTAGTNNNTGCATCAGGT | 6222 | TGCAGGACCAGAGAATTCGAATACACCGTCCACNNNTGCATCAGGT | 6462 |
| TGCAGGACCAGAGAATTCGAATACACAATAAAGNNNTGCATCAGGT | 5983 | TGCAGGACCAGAGAATTCGAATACACCTAAGCANNNTGCATCAGGT | 6223 | TGCAGGACCAGAGAATTCGAATACAAAGCCCATNNNTGCATCAGGT | 6463 |
| TGCAGGACCAGAGAATTCGAATACAGCGACATTNNNTGCATCAGGT | 5984 | TGCAGGACCAGAGAATTCGAATACAGCCCGAAGNNNTGCATCAGGT | 6224 | TGCAGGACCAGAGAATTCGAATACACGAGGCCTNNNTGCATCAGGT | 6464 |
| TGCAGGACCAGAGAATTCGAATACACAGAGAGTNNNTGCATCAGGT | 5985 | TGCAGGACCAGAGAATTCGAATACACATTCTTANNNTGCATCAGGT | 6225 | TGCAGGACCAGAGAATTCGAATACAACCTATCCNNNTGCATCAGGT | 6465 |
| TGCAGGACCAGAGAATTCGAATACACTTCACACNNNTGCATCAGGT | 5986 | TGCAGGACCAGAGAATTCGAATACAACTACGGTNNNTGCATCAGGT | 6226 | TGCAGGACCAGAGAATTCGAATACAAGGGCAGCNNNTGCATCAGGT | 6466 |
| TGCAGGACCAGAGAATTCGAATACATTAAGCTANNNTGCATCAGGT | 5987 | TGCAGGACCAGAGAATTCGAATACACCGGAGCTNNNTGCATCAGGT | 6227 | TGCAGGACCAGAGAATTCGAATACAAGAACTGNNNTGCATCAGGT | 6467 |
| TGCAGGACCAGAGAATTCGAATACAGTGACCGCNNNTGCATCAGGT | 5988 | TGCAGGACCAGAGAATTCGAATACAGTACTTAANNNTGCATCAGGT | 6228 | TGCAGGACCAGAGAATTCGAATACATGGTGTTGNNNTGCATCAGGT | 6468 |
| TGCAGGACCAGAGAATTCGAATACACCGTATGNNNTGCATCAGGT | 5989 | TGCAGGACCAGAGAATTCGAATACATGCCGCTCNNNTGCATCAGGT | 6229 | TGCAGGACCAGAGAATTCGAATACACTAAATCANNNTGCATCAGGT | 6469 |
| TGCAGGACCAGAGAATTCGAATACATAGCATTANNNTGCATCAGGT | 5990 | TGCAGGACCAGAGAATTCGAATACAGCGACTTANNNTGCATCAGGT | 6230 | TGCAGGACCAGAGAATTCGAATACAATTTCCGCNNNTGCATCAGGT | 6470 |
| TGCAGGACCAGAGAATTCGAATACACTAGGCCGNNNTGCATCAGGT | 5991 | TGCAGGACCAGAGAATTCGAATACAATGGCAAGNNNTGCATCAGGT | 6231 | TGCAGGACCAGAGAATTCGAATACACCTCCATANNNTGCATCAGGT | 6471 |
| TGCAGGACCAGAGAATTCGAATACATTAGTAACNNNTGCATCAGGT | 5992 | TGCAGGACCAGAGAATTCGAATACACGGAGGTGNNNTGCATCAGGT | 6232 | TGCAGGACCAGAGAATTCGAATACATTACTACTNNNTGCATCAGGT | 6472 |
| TGCAGGACCAGAGAATTCGAATACATATCACGNNNTGCATCAGGT | 5993 | TGCAGGACCAGAGAATTCGAATACAACATTACNNNTGCATCAGGT | 6233 | TGCAGGACCAGAGAATTCGAATACATCGTTTATNNNTGCATCAGGT | 6473 |
| TGCAGGACCAGAGAATTCGAATACAGATTCTCNNNTGCATCAGGT | 5994 | TGCAGGACCAGAGAATTCGAATACATAGGAAATNNNTGCATCAGGT | 6234 | TGCAGGACCAGAGAATTCGAATACATTTCAATGNNNTGCATCAGGT | 6474 |
| TGCAGGACCAGAGAATTCGAATACAGAGGAAGANNNTGCATCAGGT | 5995 | TGCAGGACCAGAGAATTCGAATACACCTAAGTGNNNTGCATCAGGT | 6235 | TGCAGGACCAGAGAATTCGAATACAAACCACACNNNTGCATCAGGT | 6475 |
| TGCAGGACCAGAGAATTCGAATACATGTCTGCTNNNTGCATCAGGT | 5996 | TGCAGGACCAGAGAATTCGAATACATAGACGCTNNNTGCATCAGGT | 6236 | TGCAGGACCAGAGAATTCGAATACATACCCGCCNNNTGCATCAGGT | 6476 |
| TGCAGGACCAGAGAATTCGAATACAAATACTCANNNTGCATCAGGT | 5997 | TGCAGGACCAGAGAATTCGAATACAGTGAAGCANNNTGCATCAGGT | 6237 | TGCAGGACCAGAGAATTCGAATACACCATGGGCNNNTGCATCAGGT | 6477 |
| TGCAGGACCAGAGAATTCGAATACATAGTTCCCNNNTGCATCAGGT | 5998 | TGCAGGACCAGAGAATTCGAATACAGGACGCAGNNNTGCATCAGGT | 6238 | TGCAGGACCAGAGAATTCGAATACACCTGAGTANNNTGCATCAGGT | 6478 |

FIG. 20H

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAAATTCGTANNNTGCATCAGGT | 5999 | TGCAGGACCAGAGAATTCGAATACATTTTACGTNNNTGCATCAGGT | 6239 | TGCAGGACCAGAGAATTCGAATACAGGATGTCTNNNTGCATCAGGT | 6479 |
| TGCAGGACCAGAGAATTCGAATACAGCTGATTGNNNTGCATCAGGT | 6000 | TGCAGGACCAGAGAATTCGAATACAGATGATTTNNNTGCATCAGGT | 6240 | TGCAGGACCAGAGAATTCGAATACAAAGACCCTNNNTGCATCAGGT | 6480 |
| TGCAGGACCAGAGAATTCGAATACATACCCGAANNNTGCATCAGGT | 6001 | TGCAGGACCAGAGAATTCGAATACAACGGAATGNNNTGCATCAGGT | 6241 | TGCAGGACCAGAGAATTCGAATACAGTACTTGGNNNTGCATCAGGT | 6481 |
| TGCAGGACCAGAGAATTCGAATACAAGGCCATTNNNTGCATCAGGT | 6002 | TGCAGGACCAGAGAATTCGAATACAAATGGCAGNNNTGCATCAGGT | 6242 | TGCAGGACCAGAGAATTCGAATACATCCCTCTTNNNTGCATCAGGT | 6482 |
| TGCAGGACCAGAGAATTCGAATACAGCTCCCCANNNTGCATCAGGT | 6003 | TGCAGGACCAGAGAATTCGAATACACGACTGATNNNTGCATCAGGT | 6243 | TGCAGGACCAGAGAATTCGAATACATACTTACTNNNTGCATCAGGT | 6483 |
| TGCAGGACCAGAGAATTCGAATACATGAACGCTNNNTGCATCAGGT | 6004 | TGCAGGACCAGAGAATTCGAATACAAAAGATACNNNTGCATCAGGT | 6244 | TGCAGGACCAGAGAATTCGAATACAGGTTTTCCNNNTGCATCAGGT | 6484 |
| TGCAGGACCAGAGAATTCGAATACACGAGGCAGNNNTGCATCAGGT | 6005 | TGCAGGACCAGAGAATTCGAATACAACGGCATTNNNTGCATCAGGT | 6245 | TGCAGGACCAGAGAATTCGAATACAGGATCACTNNNTGCATCAGGT | 6485 |
| TGCAGGACCAGAGAATTCGAATACAGGTGCTATNNNTGCATCAGGT | 6006 | TGCAGGACCAGAGAATTCGAATACACACGCTCNNNTGCATCAGGT | 6246 | TGCAGGACCAGAGAATTCGAATACATTGATGGCNNNTGCATCAGGT | 6486 |
| TGCAGGACCAGAGAATTCGAATACAAATTGCCGNNNTGCATCAGGT | 6007 | TGCAGGACCAGAGAATTCGAATACAAACCACTGNNNTGCATCAGGT | 6247 | TGCAGGACCAGAGAATTCGAATACACCACATTCNNNTGCATCAGGT | 6487 |
| TGCAGGACCAGAGAATTCGAATACAGGCCGACTNNNTGCATCAGGT | 6008 | TGCAGGACCAGAGAATTCGAATACAGTCGAGTTNNNTGCATCAGGT | 6248 | TGCAGGACCAGAGAATTCGAATACACAAAAAGTNNNTGCATCAGGT | 6488 |

FIG. 21A

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CACAGTATTANNNACGTATGCCA | 6489 | TGCAGGACCAGAGAATTCGAATA CAGCTGACCGNNNACGTATGCCA | 6729 | TGCAGGACCAGAGAATTCGAATA CATATTCGTTNNNACGTATGCCA | 6969 |
| TGCAGGACCAGAGAATTCGAATA CAGTACTAATNNNACGTATGCCA | 6490 | TGCAGGACCAGAGAATTCGAATA CACCAGCATANNNACGTATGCCA | 6730 | TGCAGGACCAGAGAATTCGAATA CACCATTAAANNNACGTATGCCA | 6970 |
| TGCAGGACCAGAGAATTCGAATA CATTTATGCTNNNACGTATGCCA | 6491 | TGCAGGACCAGAGAATTCGAATA CACGAAGGATNNNACGTATGCCA | 6731 | TGCAGGACCAGAGAATTCGAATA CAGTTGGCGCNNNACGTATGCCA | 6971 |
| TGCAGGACCAGAGAATTCGAATA CAGTCATCCTNNNACGTATGCCA | 6492 | TGCAGGACCAGAGAATTCGAATA CACGACGAGGNNNACGTATGCCA | 6732 | TGCAGGACCAGAGAATTCGAATA CACTGGCGTGNNNACGTATGCCA | 6972 |
| TGCAGGACCAGAGAATTCGAATA CACGAATAAANNNACGTATGCCA | 6493 | TGCAGGACCAGAGAATTCGAATA CATATAACCANNNACGTATGCCA | 6733 | TGCAGGACCAGAGAATTCGAATA CAAATACCCGNNNACGTATGCCA | 6973 |
| TGCAGGACCAGAGAATTCGAATA CAGACGTATCNNNACGTATGCCA | 6494 | TGCAGGACCAGAGAATTCGAATA CAGTGGTTPGNNNACGTATGCCA | 6734 | TGCAGGACCAGAGAATTCGAATA CACACAAACCNNNACGTATGCCA | 6974 |
| TGCAGGACCAGAGAATTCGAATA CAAATTCACANNNACGTATGCCA | 6495 | TGCAGGACCAGAGAATTCGAATA CAGTTGCGATNNNACGTATGCCA | 6735 | TGCAGGACCAGAGAATTCGAATA CAATTAATATNNNACGTATGCCA | 6975 |
| TGCAGGACCAGAGAATTCGAATA CAAATCCGCANNNACGTATGCCA | 6496 | TGCAGGACCAGAGAATTCGAATA CAATACCTCNNNACGTATGCCA | 6736 | TGCAGGACCAGAGAATTCGAATA CAGATTAGCCNNNACGTATGCCA | 6976 |
| TGCAGGACCAGAGAATTCGAATA CAACCTATTNNNACGTATGCCA | 6497 | TGCAGGACCAGAGAATTCGAATA CACTCGAAGTNNNACGTATGCCA | 6737 | TGCAGGACCAGAGAATTCGAATA CAGACAAAATNNNACGTATGCCA | 6977 |
| TGCAGGACCAGAGAATTCGAATA CAGCTTACPCNNNACGTATGCCA | 6498 | TGCAGGACCAGAGAATTCGAATA CACAGGCGTANNNACGTATGCCA | 6738 | TGCAGGACCAGAGAATTCGAATA CAAATATTTANNNACGTATGCCA | 6978 |
| TGCAGGACCAGAGAATTCGAATA CATTGGATGCNNNACGTATGCCA | 6499 | TGCAGGACCAGAGAATTCGAATA CAATAGTCATNNNACGTATGCCA | 6739 | TGCAGGACCAGAGAATTCGAATA CAAAAAGTCANNNACGTATGCCA | 6979 |
| TGCAGGACCAGAGAATTCGAATA CAGCGCGGANNNACGTATGCCA | 6500 | TGCAGGACCAGAGAATTCGAATA CACTCGTCGNNNACGTATGCCA | 6740 | TGCAGGACCAGAGAATTCGAATA CAGTCTATATNNNACGTATGCCA | 6980 |
| TGCAGGACCAGAGAATTCGAATA CAACAAGTTNNNACGTATGCCA | 6501 | TGCAGGACCAGAGAATTCGAATA CAGTGCCGTGNNNACGTATGCCA | 6741 | TGCAGGACCAGAGAATTCGAATA CAAAAAACGTNNNACGTATGCCA | 6981 |
| TGCAGGACCAGAGAATTCGAATA CATATCTCATNNNACGTATGCCA | 6502 | TGCAGGACCAGAGAATTCGAATA CAAGTAAAGTNNNACGTATGCCA | 6742 | TGCAGGACCAGAGAATTCGAATA CATTGCTCTGNNNACGTATGCCA | 6982 |
| TGCAGGACCAGAGAATTCGAATA CAGGTTTGGTNNNACGTATGCCA | 6503 | TGCAGGACCAGAGAATTCGAATA CATATTGCAANNNACGTATGCCA | 6743 | TGCAGGACCAGAGAATTCGAATA CAATGATGAANNNACGTATGCCA | 6983 |
| TGCAGGACCAGAGAATTCGAATA CATAATTCCTNNNACGTATGCCA | 6504 | TGCAGGACCAGAGAATTCGAATA CAACCCAGCGNNNACGTATGCCA | 6744 | TGCAGGACCAGAGAATTCGAATA CATCCCTGTANNNACGTATGCCA | 6984 |
| TGCAGGACCAGAGAATTCGAATA CAACGTCGTANNNACGTATGCCA | 6505 | TGCAGGACCAGAGAATTCGAATA CATGTCAAATNNNACGTATGCCA | 6745 | TGCAGGACCAGAGAATTCGAATA CAACATCCGANNNACGTATGCCA | 6985 |
| TGCAGGACCAGAGAATTCGAATA CAGAAGCTAGNNNACGTATGCCA | 6506 | TGCAGGACCAGAGAATTCGAATA CAGTGAAACGNNNACGTATGCCA | 6746 | TGCAGGACCAGAGAATTCGAATA CATTAGATCANNNACGTATGCCA | 6986 |
| TGCAGGACCAGAGAATTCGAATA CAACGAATCCNNNACGTATGCCA | 6507 | TGCAGGACCAGAGAATTCGAATA CAAGGGATANNNACGTATGCCA | 6747 | TGCAGGACCAGAGAATTCGAATA CACGCCTACCNNNACGTATGCCA | 6987 |
| TGCAGGACCAGAGAATTCGAATA CATCTTAATCNNNACGTATGCCA | 6508 | TGCAGGACCAGAGAATTCGAATA CAACCGAGTTNNNACGTATGCCA | 6748 | TGCAGGACCAGAGAATTCGAATA CACTCTAACCNNNACGTATGCCA | 6988 |
| TGCAGGACCAGAGAATTCGAATA CAGCTTTTCGNNNACGTATGCCA | 6509 | TGCAGGACCAGAGAATTCGAATA CATAAGGATANNNACGTATGCCA | 6749 | TGCAGGACCAGAGAATTCGAATA CACGTCATCTNNNACGTATGCCA | 6989 |
| TGCAGGACCAGAGAATTCGAATA CATGCTGAGTNNNACGTATGCCA | 6510 | TGCAGGACCAGAGAATTCGAATA CATAGTGGANNNACGTATGCCA | 6750 | TGCAGGACCAGAGAATTCGAATA CACACCTATCNNNACGTATGCCA | 6990 |
| TGCAGGACCAGAGAATTCGAATA CACGTTGCAANNNACGTATGCCA | 6511 | TGCAGGACCAGAGAATTCGAATA CATGTGGAAGNNNACGTATGCCA | 6751 | TGCAGGACCAGAGAATTCGAATA CATCGCTATCNNNACGTATGCCA | 6991 |
| TGCAGGACCAGAGAATTCGAATA CACAGTACGTNNNACGTATGCCA | 6512 | TGCAGGACCAGAGAATTCGAATA CACCCACGTCNNNACGTATGCCA | 6752 | TGCAGGACCAGAGAATTCGAATA CAGAAGGCCGNNNACGTATGCCA | 6992 |
| TGCAGGACCAGAGAATTCGAATA CATGGATTTANNNACGTATGCCA | 6513 | TGCAGGACCAGAGAATTCGAATA CAGTAACGGANNNACGTATGCCA | 6753 | TGCAGGACCAGAGAATTCGAATA CAGTTTTCGCNNNACGTATGCCA | 6993 |
| TGCAGGACCAGAGAATTCGAATA CAGTGTAGAGNNNACGTATGCCA | 6514 | TGCAGGACCAGAGAATTCGAATA CATTCTACATNNNACGTATGCCA | 6754 | TGCAGGACCAGAGAATTCGAATA CAAGTGGCCNNNACGTATGCCA | 6994 |
| TGCAGGACCAGAGAATTCGAATA CACTTTAGAANNNACGTATGCCA | 6515 | TGCAGGACCAGAGAATTCGAATA CATCAATGATNNNACGTATGCCA | 6755 | TGCAGGACCAGAGAATTCGAATA CAAGCCTACNNNACGTATGCCA | 6995 |
| TGCAGGACCAGAGAATTCGAATA CAATATAGTCNNNACGTATGCCA | 6516 | TGCAGGACCAGAGAATTCGAATA CATCGCGAATNNNACGTATGCCA | 6756 | TGCAGGACCAGAGAATTCGAATA CAATTCGAGNNNACGTATGCCA | 6996 |
| TGCAGGACCAGAGAATTCGAATA CAGTAGAGCANNNACGTATGCCA | 6517 | TGCAGGACCAGAGAATTCGAATA CATAATGACTNNNACGTATGCCA | 6757 | TGCAGGACCAGAGAATTCGAATA CACAACCGATNNNACGTATGCCA | 6997 |
| TGCAGGACCAGAGAATTCGAATA CATAAATAACNNNACGTATGCCA | 6518 | TGCAGGACCAGAGAATTCGAATA CACAGGTTTGNNNACGTATGCCA | 6758 | TGCAGGACCAGAGAATTCGAATA CAAAGTAGANNNACGTATGCCA | 6998 |
| TGCAGGACCAGAGAATTCGAATA CACAGGACAANNNACGTATGCCA | 6519 | TGCAGGACCAGAGAATTCGAATA CATTCGGCTTNNNACGTATGCCA | 6759 | TGCAGGACCAGAGAATTCGAATA CAATCTGCCTNNNACGTATGCCA | 6999 |
| TGCAGGACCAGAGAATTCGAATA CAAATTANNNACGTATGCCA | 6520 | TGCAGGACCAGAGAATTCGAATA CACCCTTATTNNNACGTATGCCA | 6760 | TGCAGGACCAGAGAATTCGAATA CACTCATTANNNACGTATGCCA | 7000 |
| TGCAGGACCAGAGAATTCGAATA CATGAATCATNNNACGTATGCCA | 6521 | TGCAGGACCAGAGAATTCGAATA CATAGCATGCNNNACGTATGCCA | 6761 | TGCAGGACCAGAGAATTCGAATA CATAAATCACNNNACGTATGCCA | 7001 |

FIG. 21B

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CACTACGTAGNNNACGTATGCCA | 6522 | TGCAGGACCAGAGAATTCGAATA CAAAAACGCGNNNACGTATGCCA | 6762 | TGCAGGACCAGAGAATTCGAATA CACCGAGACCNNNACGTATGCCA | 7002 |
| TGCAGGACCAGAGAATTCGAATA CAGTACATCGNNNACGTATGCCA | 6523 | TGCAGGACCAGAGAATTCGAATA CATAGCTGACNNNACGTATGCCA | 6763 | TGCAGGACCAGAGAATTCGAATA CATCCCCACNNNACGTATGCCA | 7003 |
| TGCAGGACCAGAGAATTCGAATA CACCGCAGTGCNNNACGTATGCCA | 6524 | TGCAGGACCAGAGAATTCGAATA CACTACCCCGNNNACGTATGCCA | 6764 | TGCAGGACCAGAGAATTCGAATA CAACGACTTGNNNACGTATGCCA | 7004 |
| TGCAGGACCAGAGAATTCGAATA CAAACAAAGTNNNACGTATGCCA | 6525 | TGCAGGACCAGAGAATTCGAATA CAAGCTGTCANNNACGTATGCCA | 6765 | TGCAGGACCAGAGAATTCGAATA CAGTTTAGCGNNNACGTATGCCA | 7005 |
| TGCAGGACCAGAGAATTCGAATA CAAAACTTCANNNACGTATGCCA | 6526 | TGCAGGACCAGAGAATTCGAATA CACCCTCAGCNNNACGTATGCCA | 6766 | TGCAGGACCAGAGAATTCGAATA CAGTTTCAAANNNACGTATGCCA | 7006 |
| TGCAGGACCAGAGAATTCGAATA CAAGGAGCCGNNNACGTATGCCA | 6527 | TGCAGGACCAGAGAATTCGAATA CACACGTTCTNNNACGTATGCCA | 6767 | TGCAGGACCAGAGAATTCGAATA CAGAATGCGANNNACGTATGCCA | 7007 |
| TGCAGGACCAGAGAATTCGAATA CACGTGACATNNNACGTATGCCA | 6528 | TGCAGGACCAGAGAATTCGAATA CAACGGAACANNNACGTATGCCA | 6768 | TGCAGGACCAGAGAATTCGAATA CAACCCGTAANNNACGTATGCCA | 7008 |
| TGCAGGACCAGAGAATTCGAATA CAATACATCANNNACGTATGCCA | 6529 | TGCAGGACCAGAGAATTCGAATA CAGATCATTANNNACGTATGCCA | 6769 | TGCAGGACCAGAGAATTCGAATA CAGTCACCAANNNACGTATGCCA | 7009 |
| TGCAGGACCAGAGAATTCGAATA CAAATAACCTNNNACGTATGCCA | 6530 | TGCAGGACCAGAGAATTCGAATA CACTAGAACCNNNACGTATGCCA | 6770 | TGCAGGACCAGAGAATTCGAATA CATTGGACTGNNNACGTATGCCA | 7010 |
| TGCAGGACCAGAGAATTCGAATA CACCAGCTTTNNNACGTATGCCA | 6531 | TGCAGGACCAGAGAATTCGAATA CATTTAGGTANNNACGTATGCCA | 6771 | TGCAGGACCAGAGAATTCGAATA CAAAGCTTGANNNACGTATGCCA | 7011 |
| TGCAGGACCAGAGAATTCGAATA CATCCGTTTGNNNACGTATGCCA | 6532 | TGCAGGACCAGAGAATTCGAATA CATGATATTGNNNACGTATGCCA | 6772 | TGCAGGACCAGAGAATTCGAATA CATTATTTATNNNACGTATGCCA | 7012 |
| TGCAGGACCAGAGAATTCGAATA CACAGTCGGCNNNACGTATGCCA | 6533 | TGCAGGACCAGAGAATTCGAATA CAGCGAAAACNNNACGTATGCCA | 6773 | TGCAGGACCAGAGAATTCGAATA CATACAATGNNNACGTATGCCA | 7013 |
| TGCAGGACCAGAGAATTCGAATA CATGATCGGTNNNACGTATGCCA | 6534 | TGCAGGACCAGAGAATTCGAATA CAACTAACGCNNNACGTATGCCA | 6774 | TGCAGGACCAGAGAATTCGAATA CAAAAGTGGCNNNACGTATGCCA | 7014 |
| TGCAGGACCAGAGAATTCGAATA CAACACACACNNNACGTATGCCA | 6535 | TGCAGGACCAGAGAATTCGAATA CATACTTGCCNNNACGTATGCCA | 6775 | TGCAGGACCAGAGAATTCGAATA CAGCTGCTCNNNACGTATGCCA | 7015 |
| TGCAGGACCAGAGAATTCGAATA CATCACGCAANNNACGTATGCCA | 6536 | TGCAGGACCAGAGAATTCGAATA CACGTGCTAANNNACGTATGCCA | 6776 | TGCAGGACCAGAGAATTCGAATA CAGCTGATACNNNACGTATGCCA | 7016 |
| TGCAGGACCAGAGAATTCGAATA CATCGTACTCNNNACGTATGCCA | 6537 | TGCAGGACCAGAGAATTCGAATA CAAAACAGTANNNACGTATGCCA | 6777 | TGCAGGACCAGAGAATTCGAATA CACTTTGATTNNNACGTATGCCA | 7017 |
| TGCAGGACCAGAGAATTCGAATA CATTCAGACGNNNACGTATGCCA | 6538 | TGCAGGACCAGAGAATTCGAATA CAGCATCATGNNNACGTATGCCA | 6778 | TGCAGGACCAGAGAATTCGAATA CACTTGTGAGNNNACGTATGCCA | 7018 |
| TGCAGGACCAGAGAATTCGAATA CAGCGCACGTNNNACGTATGCCA | 6539 | TGCAGGACCAGAGAATTCGAATA CAACCTGAANNNNACGTATGCCA | 6779 | TGCAGGACCAGAGAATTCGAATA CAACTTCCGTNNNACGTATGCCA | 7019 |
| TGCAGGACCAGAGAATTCGAATA CACCAGACATNNNACGTATGCCA | 6540 | TGCAGGACCAGAGAATTCGAATA CAACGCTACNNNATGCCA | 6780 | TGCAGGACCAGAGAATTCGAATA CACAACGTCNNNACGTATGCCA | 7020 |
| TGCAGGACCAGAGAATTCGAATA CATATTGATGNNNACGTATGCCA | 6541 | TGCAGGACCAGAGAATTCGAATA CACGTCAACANNNACGTATGCCA | 6781 | TGCAGGACCAGAGAATTCGAATA CAGTGCCTCNNNACGTATGCCA | 7021 |
| TGCAGGACCAGAGAATTCGAATA CACGAGATAGNNNACGTATGCCA | 6542 | TGCAGGACCAGAGAATTCGAATA CACCGGCCCNNNACGTATGCCA | 6782 | TGCAGGACCAGAGAATTCGAATA CAGTGGTGAANNNACGTATGCCA | 7022 |
| TGCAGGACCAGAGAATTCGAATA CAATACGAAANNNACGTATGCCA | 6543 | TGCAGGACCAGAGAATTCGAATA CATCCGTGCNNNACGTATGCCA | 6783 | TGCAGGACCAGAGAATTCGAATA CAAGTAAGTANNNACGTATGCCA | 7023 |
| TGCAGGACCAGAGAATTCGAATA CAGATGAGACNNNACGTATGCCA | 6544 | TGCAGGACCAGAGAATTCGAATA CAAAGACTGGNNNACGTATGCCA | 6784 | TGCAGGACCAGAGAATTCGAATA CAATTTATTNNNACGTATGCCA | 7024 |
| TGCAGGACCAGAGAATTCGAATA CATACAATCANNNACGTATGCCA | 6545 | TGCAGGACCAGAGAATTCGAATA CAGCAATGAGNNNACGTATGCCA | 6785 | TGCAGGACCAGAGAATTCGAATA CAGGAATGCANNNACGTATGCCA | 7025 |
| TGCAGGACCAGAGAATTCGAATA CATTTAATAANNNACGTATGCCA | 6546 | TGCAGGACCAGAGAATTCGAATA CAAGGAGCTANNNACGTATGCCA | 6786 | TGCAGGACCAGAGAATTCGAATA CACGTGCTTTNNNACGTATGCCA | 7026 |
| TGCAGGACCAGAGAATTCGAATA CAGCGCGTCANNNACGTATGCCA | 6547 | TGCAGGACCAGAGAATTCGAATA CACCTGAGATNNNACGTATGCCA | 6787 | TGCAGGACCAGAGAATTCGAATA CAGTTAAACTNNNACGTATGCCA | 7027 |
| TGCAGGACCAGAGAATTCGAATA CACGATGATCNNNACGTATGCCA | 6548 | TGCAGGACCAGAGAATTCGAATA CAACGGAGGCNNNACGTATGCCA | 6788 | TGCAGGACCAGAGAATTCGAATA CAATCTTAAGNNNACGTATGCCA | 7028 |
| TGCAGGACCAGAGAATTCGAATA CACCGAAGCCNNNCTAGCGTTAC | 6549 | TGCAGGACCAGAGAATTCGAATA CAGATCGGCNNNCTAGCGTTAC | 6789 | TGCAGGACCAGAGAATTCGAATA CAAACTCAGCNNNCTAGCGTTAC | 7029 |
| TGCAGGACCAGAGAATTCGAATA CACCAAAACANNNCTAGCGTTAC | 6550 | TGCAGGACCAGAGAATTCGAATA CATGCTGCANNNNCTAGCGTTAC | 6790 | TGCAGGACCAGAGAATTCGAATA CAACCAAAGCNNNCTAGCGTTAC | 7030 |
| TGCAGGACCAGAGAATTCGAATA CAGGTCTTCTNNNCTAGCGTTAC | 6551 | TGCAGGACCAGAGAATTCGAATA CATCGGAATCNNNCTAGCGTTAC | 6791 | TGCAGGACCAGAGAATTCGAATA CAGCGTAATCNNNCTAGCGTTAC | 7031 |
| TGCAGGACCAGAGAATTCGAATA CACCTCGGTCNNNCTAGCGTTAC | 6552 | TGCAGGACCAGAGAATTCGAATA CAGACGGCTCNNNCTAGCGTTAC | 6792 | TGCAGGACCAGAGAATTCGAATA CAAGGTGGTANNNCTAGCGTTAC | 7032 |
| TGCAGGACCAGAGAATTCGAATA CACCGGCTCANNNCTAGCGTTAC | 6553 | TGCAGGACCAGAGAATTCGAATA CAAGTTGGANNNNCTAGCGTTAC | 6793 | TGCAGGACCAGAGAATTCGAATA CACTTGAGTGNNNCTAGCGTTAC | 7033 |
| TGCAGGACCAGAGAATTCGAATA CAACCACCTTNNNCTAGCGTTAC | 6554 | TGCAGGACCAGAGAATTCGAATA CAAGTACGTCNNNCTAGCGTTAC | 6794 | TGCAGGACCAGAGAATTCGAATA CACTGCCGTNNNNCTAGCGTTAC | 7034 |

FIG. 21C

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATCTAAGTANNNCTAGCGTTAC | 6555 | TGCAGGACCAGAGAATTCGAATA CACGATTAATNNNCTAGCGTTAC | 6795 | TGCAGGACCAGAGAATTCGAATA CAGGGCTAATNNNCTAGCGTTAC | 7035 |
| TGCAGGACCAGAGAATTCGAATA CAATTATAATNNNCTAGCGTTAC | 6556 | TGCAGGACCAGAGAATTCGAATA CATTACGCCTNNNCTAGCGTTAC | 6796 | TGCAGGACCAGAGAATTCGAATA CAACCCCTGNNNCTAGCGTTAC | 7036 |
| TGCAGGACCAGAGAATTCGAATA CATGGACCGCNNNCTAGCGTTAC | 6557 | TGCAGGACCAGAGAATTCGAATA CAAGGAGTTGNNNCTAGCGTTAC | 6797 | TGCAGGACCAGAGAATTCGAATA CACCCTATCANNNCTAGCGTTAC | 7037 |
| TGCAGGACCAGAGAATTCGAATA CACTTCATTANNNCTAGCGTTAC | 6558 | TGCAGGACCAGAGAATTCGAATA CAGTACACCANNNCTAGCGTTAC | 6798 | TGCAGGACCAGAGAATTCGAATA CATAGAACAANNNCTAGCGTTAC | 7038 |
| TGCAGGACCAGAGAATTCGAATA CAACGCACTANNNCTAGCGTTAC | 6559 | TGCAGGACCAGAGAATTCGAATA CAGGAAAATTNNNCTAGCGTTAC | 6799 | TGCAGGACCAGAGAATTCGAATA CACCGGAGGANNNCTAGCGTTAC | 7039 |
| TGCAGGACCAGAGAATTCGAATA CATCATGGCANNNCTAGCGTTAC | 6560 | TGCAGGACCAGAGAATTCGAATA CACGGTTCTTNNNCTAGCGTTAC | 6800 | TGCAGGACCAGAGAATTCGAATA CAATGAACAANNNCTAGCGTTAC | 7040 |
| TGCAGGACCAGAGAATTCGAATA CAGGCTTAACNNNCTAGCGTTAC | 6561 | TGCAGGACCAGAGAATTCGAATA CAGGTCGACCNNNCTAGCGTTAC | 6801 | TGCAGGACCAGAGAATTCGAATA CATTCGAAGCNNNCTAGCGTTAC | 7041 |
| TGCAGGACCAGAGAATTCGAATA CAATGGTATTNNNCTAGCGTTAC | 6562 | TGCAGGACCAGAGAATTCGAATA CATTCGCTCANNNCTAGCGTTAC | 6802 | TGCAGGACCAGAGAATTCGAATA CAAACAACAANNNCTAGCGTTAC | 7042 |
| TGCAGGACCAGAGAATTCGAATA CAGTATGCTGNNNCTAGCGTTAC | 6563 | TGCAGGACCAGAGAATTCGAATA CACGCAGCGTNNNCTAGCGTTAC | 6803 | TGCAGGACCAGAGAATTCGAATA CATCCTTTGGNNNCTAGCGTTAC | 7043 |
| TGCAGGACCAGAGAATTCGAATA CAATCGTGGTNNNCTAGCGTTAC | 6564 | TGCAGGACCAGAGAATTCGAATA CAGCTGTGCGNNNCTAGCGTTAC | 6804 | TGCAGGACCAGAGAATTCGAATA CAAAACGAATNNNCTAGCGTTAC | 7044 |
| TGCAGGACCAGAGAATTCGAATA CAGCTTAGGTNNNCTAGCGTTAC | 6565 | TGCAGGACCAGAGAATTCGAATA CACACCAGTANNNCTAGCGTTAC | 6805 | TGCAGGACCAGAGAATTCGAATA CATCCAGTGANNNCTAGCGTTAC | 7045 |
| TGCAGGACCAGAGAATTCGAATA CATCTGTATTNNNCTAGCGTTAC | 6566 | TGCAGGACCAGAGAATTCGAATA CAATCATTGANNNCTAGCGTTAC | 6806 | TGCAGGACCAGAGAATTCGAATA CACTTCAAAANNNCTAGCGTTAC | 7046 |
| TGCAGGACCAGAGAATTCGAATA CAGGATAGCANNNCTAGCGTTAC | 6567 | TGCAGGACCAGAGAATTCGAATA CATAATCATGNNNCTAGCGTTAC | 6807 | TGCAGGACCAGAGAATTCGAATA CATATCTAGANNNCTAGCGTTAC | 7047 |
| TGCAGGACCAGAGAATTCGAATA CATTCACTCGNNNCTAGCGTTAC | 6568 | TGCAGGACCAGAGAATTCGAATA CAGTTGACCANNNCTAGCGTTAC | 6808 | TGCAGGACCAGAGAATTCGAATA CAAACGGCTTNNNCTAGCGTTAC | 7048 |
| TGCAGGACCAGAGAATTCGAATA CATTCGGACANNNCTAGCGTTAC | 6569 | TGCAGGACCAGAGAATTCGAATA CAACTCATGGNNNCTAGCGTTAC | 6809 | TGCAGGACCAGAGAATTCGAATA CAACTTTTCANNNCTAGCGTTAC | 7049 |
| TGCAGGACCAGAGAATTCGAATA CACGGTCGGTNNNCTAGCGTTAC | 6570 | TGCAGGACCAGAGAATTCGAATA CACCCAGTTNNNNCTAGCGTTAC | 6810 | TGCAGGACCAGAGAATTCGAATA CAAGTGCTTGNNNCTAGCGTTAC | 7050 |
| TGCAGGACCAGAGAATTCGAATA CAAGATCGCTNNNCTAGCGTTAC | 6571 | TGCAGGACCAGAGAATTCGAATA CATCAAGGAGNNNCTAGCGTTAC | 6811 | TGCAGGACCAGAGAATTCGAATA CAATGGTCANNNNCTAGCGTTAC | 7051 |
| TGCAGGACCAGAGAATTCGAATA CAGCATTCGANNNCTAGCGTTAC | 6572 | TGCAGGACCAGAGAATTCGAATA CAAACGCTTGNNNCTAGCGTTAC | 6812 | TGCAGGACCAGAGAATTCGAATA CAGCCCCTANNNCTAGCGTTAC | 7052 |
| TGCAGGACCAGAGAATTCGAATA CACGCTGATANNNCTAGCGTTAC | 6573 | TGCAGGACCAGAGAATTCGAATA CACTTAATATNNNCTAGCGTTAC | 6813 | TGCAGGACCAGAGAATTCGAATA CAGTTGCTCTNNNCTAGCGTTAC | 7053 |
| TGCAGGACCAGAGAATTCGAATA CACGGTTAACNNNCTAGCGTTAC | 6574 | TGCAGGACCAGAGAATTCGAATA CAAGTGTCCANNNCTAGCGTTAC | 6814 | TGCAGGACCAGAGAATTCGAATA CAGCATATATNNNCTAGCGTTAC | 7054 |
| TGCAGGACCAGAGAATTCGAATA CAAATGTCATNNNCTAGCGTTAC | 6575 | TGCAGGACCAGAGAATTCGAATA CAAGCGACGNNNNCTAGCGTTAC | 6815 | TGCAGGACCAGAGAATTCGAATA CAGGTCTTGANNNCTAGCGTTAC | 7055 |
| TGCAGGACCAGAGAATTCGAATA CAGCAAGACANNNCTAGCGTTAC | 6576 | TGCAGGACCAGAGAATTCGAATA CACTCTCCCNNNNCTAGCGTTAC | 6816 | TGCAGGACCAGAGAATTCGAATA CAACTATTCNNNNCTAGCGTTAC | 7056 |
| TGCAGGACCAGAGAATTCGAATA CACCAGCCTCNNNCTAGCGTTAC | 6577 | TGCAGGACCAGAGAATTCGAATA CAACTCACCTNNNCTAGCGTTAC | 6817 | TGCAGGACCAGAGAATTCGAATA CACTTAAAACNNNCTAGCGTTAC | 7057 |
| TGCAGGACCAGAGAATTCGAATA CACTTGTTGGNNNCTAGCGTTAC | 6578 | TGCAGGACCAGAGAATTCGAATA CAAATTTCGANNNCTAGCGTTAC | 6818 | TGCAGGACCAGAGAATTCGAATA CATCGCAGCGNNNCTAGCGTTAC | 7058 |
| TGCAGGACCAGAGAATTCGAATA CATATCGGTNNNNCTAGCGTTAC | 6579 | TGCAGGACCAGAGAATTCGAATA CAGTAATATNNNNCTAGCGTTAC | 6819 | TGCAGGACCAGAGAATTCGAATA CAGATTCGACNNNCTAGCGTTAC | 7059 |
| TGCAGGACCAGAGAATTCGAATA CACTGGCATANNNCTAGCGTTAC | 6580 | TGCAGGACCAGAGAATTCGAATA CACAAGAAATNNNCTAGCGTTAC | 6820 | TGCAGGACCAGAGAATTCGAATA CATGGCCGTGNNNCTAGCGTTAC | 7060 |
| TGCAGGACCAGAGAATTCGAATA CATGCAGGCNNNNCTAGCGTTAC | 6581 | TGCAGGACCAGAGAATTCGAATA CAATTCCCCANNNCTAGCGTTAC | 6821 | TGCAGGACCAGAGAATTCGAATA CAAAGGCATGNNNCTAGCGTTAC | 7061 |
| TGCAGGACCAGAGAATTCGAATA CATTCCTCCTNNNCTAGCGTTAC | 6582 | TGCAGGACCAGAGAATTCGAATA CACTCTTAGCNNNCTAGCGTTAC | 6822 | TGCAGGACCAGAGAATTCGAATA CAATGATCTANNNCTAGCGTTAC | 7062 |
| TGCAGGACCAGAGAATTCGAATA CATAACGGAGNNNCTAGCGTTAC | 6583 | TGCAGGACCAGAGAATTCGAATA CATACCAGCANNNCTAGCGTTAC | 6823 | TGCAGGACCAGAGAATTCGAATA CATCGGCAATNNNCTAGCGTTAC | 7063 |
| TGCAGGACCAGAGAATTCGAATA CAGAGTGGATNNNCTAGCGTTAC | 6584 | TGCAGGACCAGAGAATTCGAATA CACACGCTNNNNCTAGCGTTAC | 6824 | TGCAGGACCAGAGAATTCGAATA CAATCCGCTTNNNCTAGCGTTAC | 7064 |
| TGCAGGACCAGAGAATTCGAATA CATCGTAAATNNNCTAGCGTTAC | 6585 | TGCAGGACCAGAGAATTCGAATA CAAATCGAGGNNNCTAGCGTTAC | 6825 | TGCAGGACCAGAGAATTCGAATA CAGAGTGGTNNNNCTAGCGTTAC | 7065 |
| TGCAGGACCAGAGAATTCGAATA CACACGACANNNNCTAGCGTTAC | 6586 | TGCAGGACCAGAGAATTCGAATA CACATACAATNNNCTAGCGTTAC | 6826 | TGCAGGACCAGAGAATTCGAATA CAGGAACAGTNNNCTAGCGTTAC | 7066 |
| TGCAGGACCAGAGAATTCGAATA CAGCACCCCTNNNCTAGCGTTAC | 6587 | TGCAGGACCAGAGAATTCGAATA CATTATGTTCNNNCTAGCGTTAC | 6827 | TGCAGGACCAGAGAATTCGAATA CACTAAACATNNNCTAGCGTTAC | 7067 |

FIG. 21D

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CAGATAATTCNNNCTAGCGTTAC | 6588 | TGCAGGACCAGAGAATTCGAATA CAGTCTGTCTNNNCTAGCGTTAC | 6828 | TGCAGGACCAGAGAATTCGAATA CAAAGGAGTCNNNCTAGCGTTAC | 7068 |
| TGCAGGACCAGAGAATTCGAATA CAAACTCAATNNNCTAGCGTTAC | 6589 | TGCAGGACCAGAGAATTCGAATA CAGTCTGAACNNNCTAGCGTTAC | 6829 | TGCAGGACCAGAGAATTCGAATA CATCCATGTCNNNCTAGCGTTAC | 7069 |
| TGCAGGACCAGAGAATTCGAATA CATCAAACTNNNCTAGCGTTAC | 6590 | TGCAGGACCAGAGAATTCGAATA CAAGGTGCGNNNCTAGCGTTAC | 6830 | TGCAGGACCAGAGAATTCGAATA CAGTACGAGANNNCTAGCGTTAC | 7070 |
| TGCAGGACCAGAGAATTCGAATA CAATTATTCCNNNCTAGCGTTAC | 6591 | TGCAGGACCAGAGAATTCGAATA CACAGAAACGNNNCTAGCGTTAC | 6831 | TGCAGGACCAGAGAATTCGAATA CAGGCCAGCTNNNCTAGCGTTAC | 7071 |
| TGCAGGACCAGAGAATTCGAATA CACTTCTTGGNNNCTAGCGTTAC | 6592 | TGCAGGACCAGAGAATTCGAATA CATCTGTTGCNNNCTAGCGTTAC | 6832 | TGCAGGACCAGAGAATTCGAATA CAGTCCGATANNNCTAGCGTTAC | 7072 |
| TGCAGGACCAGAGAATTCGAATA CATAAGTAAGNNNCTAGCGTTAC | 6593 | TGCAGGACCAGAGAATTCGAATA CACGATGGTTNNNCTAGCGTTAC | 6833 | TGCAGGACCAGAGAATTCGAATA CATGTTACAANNNCTAGCGTTAC | 7073 |
| TGCAGGACCAGAGAATTCGAATA CACTAACCCTNNNCTAGCGTTAC | 6594 | TGCAGGACCAGAGAATTCGAATA CAATAATATTNNNCTAGCGTTAC | 6834 | TGCAGGACCAGAGAATTCGAATA CACATTCCACNNNCTAGCGTTAC | 7074 |
| TGCAGGACCAGAGAATTCGAATA CAATAGCGTCNNNCTAGCGTTAC | 6595 | TGCAGGACCAGAGAATTCGAATA CAATCGACGTNNNCTAGCGTTAC | 6835 | TGCAGGACCAGAGAATTCGAATA CATGTTGAATNNNCTAGCGTTAC | 7075 |
| TGCAGGACCAGAGAATTCGAATA CAAAGTAATNNNCTAGCGTTAC | 6596 | TGCAGGACCAGAGAATTCGAATA CAGAGGAAAGNNNCTAGCGTTAC | 6836 | TGCAGGACCAGAGAATTCGAATA CAAGAAACGCNNNCTAGCGTTAC | 7076 |
| TGCAGGACCAGAGAATTCGAATA CATCACGTAGNNNCTAGCGTTAC | 6597 | TGCAGGACCAGAGAATTCGAATA CAATTACACANNNCTAGCGTTAC | 6837 | TGCAGGACCAGAGAATTCGAATA CATCCGACCCNNNCTAGCGTTAC | 7077 |
| TGCAGGACCAGAGAATTCGAATA CAAACCATATNNNCTAGCGTTAC | 6598 | TGCAGGACCAGAGAATTCGAATA CAGGACCTGNNNCTAGCGTTAC | 6838 | TGCAGGACCAGAGAATTCGAATA CACACTAGTGNNNCTAGCGTTAC | 7078 |
| TGCAGGACCAGAGAATTCGAATA CAGAGCAGTANNNCTAGCGTTAC | 6599 | TGCAGGACCAGAGAATTCGAATA CAACCTAGAGNNNCTAGCGTTAC | 6839 | TGCAGGACCAGAGAATTCGAATA CAACCGGCGTNNNCTAGCGTTAC | 7079 |
| TGCAGGACCAGAGAATTCGAATA CAATAAATTNNNCTAGCGTTAC | 6600 | TGCAGGACCAGAGAATTCGAATA CACACGGCGTNNNCTAGCGTTAC | 6840 | TGCAGGACCAGAGAATTCGAATA CACTTGCTACNNNCTAGCGTTAC | 7080 |
| TGCAGGACCAGAGAATTCGAATA CAGAGCTAAGNNNCTAGCGTTAC | 6601 | TGCAGGACCAGAGAATTCGAATA CAATTACGTANNNCTAGCGTTAC | 6841 | TGCAGGACCAGAGAATTCGAATA CATTGCAGTGNNNCTAGCGTTAC | 7081 |
| TGCAGGACCAGAGAATTCGAATA CAGCGGATCCNNNCTAGCGTTAC | 6602 | TGCAGGACCAGAGAATTCGAATA CATATGTTGANNNCTAGCGTTAC | 6842 | TGCAGGACCAGAGAATTCGAATA CAAATGAAGTNNNCTAGCGTTAC | 7082 |
| TGCAGGACCAGAGAATTCGAATA CATTCATAGANNNCTAGCGTTAC | 6603 | TGCAGGACCAGAGAATTCGAATA CACAGACTCANNNCTAGCGTTAC | 6843 | TGCAGGACCAGAGAATTCGAATA CACTCGCCCANNNCTAGCGTTAC | 7083 |
| TGCAGGACCAGAGAATTCGAATA CATTAAGCATNNNCTAGCGTTAC | 6604 | TGCAGGACCAGAGAATTCGAATA CACGGATGCCNNNCTAGCGTTAC | 6844 | TGCAGGACCAGAGAATTCGAATA CAGTGGACCCNNNCTAGCGTTAC | 7084 |
| TGCAGGACCAGAGAATTCGAATA CATCGAGCGCNNNCTAGCGTTAC | 6605 | TGCAGGACCAGAGAATTCGAATA CATACATCTTNNNCTAGCGTTAC | 6845 | TGCAGGACCAGAGAATTCGAATA CAACGACTCANNNCTAGCGTTAC | 7085 |
| TGCAGGACCAGAGAATTCGAATA CATCGCACCCNNNCTAGCGTTAC | 6606 | TGCAGGACCAGAGAATTCGAATA CACTTCGTGTNNNCTAGCGTTAC | 6846 | TGCAGGACCAGAGAATTCGAATA CAACAACTTANNNCTAGCGTTAC | 7086 |
| TGCAGGACCAGAGAATTCGAATA CACTTCGACANNNCTAGCGTTAC | 6607 | TGCAGGACCAGAGAATTCGAATA CAGAACGCGNNNCTAGCGTTAC | 6847 | TGCAGGACCAGAGAATTCGAATA CATCTGGTAGNNNCTAGCGTTAC | 7087 |
| TGCAGGACCAGAGAATTCGAATA CATTCCAGTCNNNCTAGCGTTAC | 6608 | TGCAGGACCAGAGAATTCGAATA CATCGGATTGNNNCTAGCGTTAC | 6848 | TGCAGGACCAGAGAATTCGAATA CACTATGGCANNNCTAGCGTTAC | 7088 |
| TGCAGGACCAGAGAATTCGAATA CAGTTTTACNNNGATCGACATG | 6609 | TGCAGGACCAGAGAATTCGAATA CAAGACAAATNNNGATCGACATG | 6849 | TGCAGGACCAGAGAATTCGAATA CAACCCGCGANNNGATCGACATG | 7089 |
| TGCAGGACCAGAGAATTCGAATA CAAACTTAGTNNNGATCGACATG | 6610 | TGCAGGACCAGAGAATTCGAATA CACGAAGTAGNNNGATCGACATG | 6850 | TGCAGGACCAGAGAATTCGAATA CACGCGGTACNNNGATCGACATG | 7090 |
| TGCAGGACCAGAGAATTCGAATA CACGCGCGCGNNNGATCGACATG | 6611 | TGCAGGACCAGAGAATTCGAATA CAAAGGAGCCNNNGATCGACATG | 6851 | TGCAGGACCAGAGAATTCGAATA CACACATCAGNNNGATCGACATG | 7091 |
| TGCAGGACCAGAGAATTCGAATA CAAACTGTTANNNGATCGACATG | 6612 | TGCAGGACCAGAGAATTCGAATA CATGAGTGGANNNGATCGACATG | 6852 | TGCAGGACCAGAGAATTCGAATA CATAGACACCNNNGATCGACATG | 7092 |
| TGCAGGACCAGAGAATTCGAATA CAGTAAGTTTNNNGATCGACATG | 6613 | TGCAGGACCAGAGAATTCGAATA CACGCTCCCANNNGATCGACATG | 6853 | TGCAGGACCAGAGAATTCGAATA CAATGTAAAGNNNGATCGACATG | 7093 |
| TGCAGGACCAGAGAATTCGAATA CACTTAGCAGNNNGATCGACATG | 6614 | TGCAGGACCAGAGAATTCGAATA CAACACTTCCNNNGATCGACATG | 6854 | TGCAGGACCAGAGAATTCGAATA CAATCCTCTGNNNGATCGACATG | 7094 |
| TGCAGGACCAGAGAATTCGAATA CAACTTTCCGNNNGATCGACATG | 6615 | TGCAGGACCAGAGAATTCGAATA CAGCAGTCATNNNGATCGACATG | 6855 | TGCAGGACCAGAGAATTCGAATA CAGTCGTCCCNNNGATCGACATG | 7095 |
| TGCAGGACCAGAGAATTCGAATA CACTCCTCTTNNNGATCGACATG | 6616 | TGCAGGACCAGAGAATTCGAATA CACCATATGNNNGATCGACATG | 6856 | TGCAGGACCAGAGAATTCGAATA CAACTTGCAGNNNGATCGACATG | 7096 |
| TGCAGGACCAGAGAATTCGAATA CAAGTAATGNNNGATCGACATG | 6617 | TGCAGGACCAGAGAATTCGAATA CAATGCGCGANNNGATCGACATG | 6857 | TGCAGGACCAGAGAATTCGAATA CAGAGCGCTCNNNGATCGACATG | 7097 |
| TGCAGGACCAGAGAATTCGAATA CACAGCCCNNNGATCGACATG | 6618 | TGCAGGACCAGAGAATTCGAATA CAGTTGAACCNNNGATCGACATG | 6858 | TGCAGGACCAGAGAATTCGAATA CATCGCAGGNNNGATCGACATG | 7098 |
| TGCAGGACCAGAGAATTCGAATA CACGTAATTANNNGATCGACATG | 6619 | TGCAGGACCAGAGAATTCGAATA CAAAGGTTGNNNGATCGACATG | 6859 | TGCAGGACCAGAGAATTCGAATA CACGATGCGNNNGATCGACATG | 7099 |
| TGCAGGACCAGAGAATTCGAATA CAGTTCGTTCNNNGATCGACATG | 6620 | TGCAGGACCAGAGAATTCGAATA CAGCACGCTGNNNGATCGACATG | 6860 | TGCAGGACCAGAGAATTCGAATA CAACCCCCACNNNGATCGACATG | 7100 |

FIG. 21E

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATTCCGTCANNNGATCGACATG | 6621 | TGCAGGACCAGAGAATTCGAATA CAGCTCATAGNNNGATCGACATG | 6861 | TGCAGGACCAGAGAATTCGAATA CATCATTTCANNNGATCGACATG | 7101 |
| TGCAGGACCAGAGAATTCGAATA CAACGACGTTNNNGATCGACATG | 6622 | TGCAGGACCAGAGAATTCGAATA CAACAGTCTGNNNGATCGACATG | 6862 | TGCAGGACCAGAGAATTCGAATA CATGCCGGTGNNNGATCGACATG | 7102 |
| TGCAGGACCAGAGAATTCGAATA CAAAGTAGCGNNNGATCGACATG | 6623 | TGCAGTACCAGAGAATTCGAATA CATTTAAGTGNNNGATCGACATG | 6863 | TGCAGGACCAGAGAATTCGAATA CACGCAAGAANNNGATCGACATG | 7103 |
| TGCAGGACCAGAGAATTCGAATA CAAGTGAAGCNNNGATCGACATG | 6624 | TGCAGGACCAGAGAATTCGAATA CAGATTAATCNNNGATCGACATG | 6864 | TGCAGGACCAGAGAATTCGAATA CATAGACCACNNNGATCGACATG | 7104 |
| TGCAGGACCAGAGAATTCGAATA CATTCTCATANNNGATCGACATG | 6625 | TGCAGGACCAGAGAATTCGAATA CAGAGAAAGGNNNGATCGACATG | 6865 | TGCAGGACCAGAGAATTCGAATA CAACCGAAGANNNGATCGACATG | 7105 |
| TGCAGGACCAGAGAATTCGAATA CAAGTAGAGCNNNGATCGACATG | 6626 | TGCAGGACCAGAGAATTCGAATA CAACATTCGGNNNGATCGACATG | 6866 | TGCAGGACCAGAGAATTCGAATA CATCTTGTTANNNGATCGACATG | 7106 |
| TGCAGGACCAGAGAATTCGAATA CATCCCGATTNNNGATCGACATG | 6627 | TGCAGGACCAGAGAATTCGAATA CATTGCGTCTNNNGATCGACATG | 6867 | TGCAGGACCAGAGAATTCGAATA CACAGACTGNNNGATCGACATG | 7107 |
| TGCAGGACCAGAGAATTCGAATA CACAAGGTCTNNNGATCGACATG | 6628 | TGCAGGACCAGAGAATTCGAATA CAGCTCACAANNNGATCGACATG | 6868 | TGCAGGACCAGAGAATTCGAATA CAGATCTGCANNNGATCGACATG | 7108 |
| TGCAGGACCAGAGAATTCGAATA CAGAGTATGNNNGATCGACATG | 6629 | TGCAGGACCAGAGAATTCGAATA CACGTTAACGNNNGATCGACATG | 6869 | TGCAGGACCAGAGAATTCGAATA CATCGAAGGANNNGATCGACATG | 7109 |
| TGCAGGACCAGAGAATTCGAATA CACCGCAGTGNNNGATCGACATG | 6630 | TGCAGGACCAGAGAATTCGAATA CAGTACGTTGNNNGATCGACATG | 6870 | TGCAGGACCAGAGAATTCGAATA CACGGAGCAGNNNGATCGACATG | 7110 |
| TGCAGGACCAGAGAATTCGAATA CAGAAGCTCTNNNGATCGACATG | 6631 | TGCAGGACCAGAGAATTCGAATA CATGCTCAGANNNGATCGACATG | 6871 | TGCAGGACCAGAGAATTCGAATA CACACCGGACNNNGATCGACATG | 7111 |
| TGCAGGACCAGAGAATTCGAATA CAGTGCAAGANNNGATCGACATG | 6632 | TGCAGGACCAGAGAATTCGAATA CATACCAAATNNNGATCGACATG | 6872 | TGCAGGACCAGAGAATTCGAATA CAATAACGTTNNNGATCGACATG | 7112 |
| TGCAGGACCAGAGAATTCGAATA CAAACGGTAGNNNGATCGACATG | 6633 | TGCAGGACCAGAGAATTCGAATA CACCATGATGNNNGATCGACATG | 6873 | TGCAGGACCAGAGAATTCGAATA CATGTCTGGANNNGATCGACATG | 7113 |
| TGCAGGACCAGAGAATTCGAATA CACTTCGACTNNNGATCGACATG | 6634 | TGCAGGACCAGAGAATTCGAATA CATATATGCANNNGATCGACATG | 6874 | TGCAGGACCAGAGAATTCGAATA CATATGGACCNNNGATCGACATG | 7114 |
| TGCAGGACCAGAGAATTCGAATA CACCGACGACNNNGATCGACATG | 6635 | TGCAGGACCAGAGAATTCGAATA CACCGCTTATNNNGATCGACATG | 6875 | TGCAGGACCAGAGAATTCGAATA CACAACTTGGNNNGATCGACATG | 7115 |
| TGCAGGACCAGAGAATTCGAATA CACTACACTCNNNGATCGACATG | 6636 | TGCAGGACCAGAGAATTCGAATA CAGGCGTCACNNNGATCGACATG | 6876 | TGCAGGACCAGAGAATTCGAATA CACAATCGACNNNGATCGACATG | 7116 |
| TGCAGGACCAGAGAATTCGAATA CAAGCTAAGGNNNGATCGACATG | 6637 | TGCAGGACCAGAGAATTCGAATA CAGGCATAAGNNNGATCGACATG | 6877 | TGCAGGACCAGAGAATTCGAATA CAGCAAGGCGNNNGATCGACATG | 7117 |
| TGCAGGACCAGAGAATTCGAATA CAGAGTATCCNNNGATCGACATG | 6638 | TGCAGGACCAGAGAATTCGAATA CAGAATTTGTNNNGATCGACATG | 6878 | TGCAGGACCAGAGAATTCGAATA CAGCCAACGCNNNGATCGACATG | 7118 |
| TGCAGGACCAGAGAATTCGAATA CATCCTACCANNNGATCGACATG | 6639 | TGCAGGACCAGAGAATTCGAATA CATCTTGACCNNNGATCGACATG | 6879 | TGCAGGACCAGAGAATTCGAATA CATCGTTAAANNNGATCGACATG | 7119 |
| TGCAGGACCAGAGAATTCGAATA CATTTTTCTCNNNGATCGACATG | 6640 | TGCAGGACCAGAGAATTCGAATA CAACACCTAGNNNGATCGACATG | 6880 | TGCAGGACCAGAGAATTCGAATA CACTAGCGTANNNGATCGACATG | 7120 |
| TGCAGGACCAGAGAATTCGAATA CACCGATAAGNNNGATCGACATG | 6641 | TGCAGGACCAGAGAATTCGAATA CAATCTCCAANNNGATCGACATG | 6881 | TGCAGGACCAGAGAATTCGAATA CACTGAGTTGNNNGATCGACATG | 7121 |
| TGCAGGACCAGAGAATTCGAATA CACAAATCGCNNNGATCGACATG | 6642 | TGCAGGACCAGAGAATTCGAATA CATTGAGATTNNNGATCGACATG | 6882 | TGCAGGACCAGAGAATTCGAATA CATGCGCGTNNNGATCGACATG | 7122 |
| TGCAGGACCAGAGAATTCGAATA CAGTGTCGGCNNNGATCGACATG | 6643 | TGCAGGACCAGAGAATTCGAATA CATCAACCAGNNNGATCGACATG | 6883 | TGCAGGACCAGAGAATTCGAATA CAGTGACTTGNNNGATCGACATG | 7123 |
| TGCAGGACCAGAGAATTCGAATA CAAAGCTATTNNNGATCGACATG | 6644 | TGCAGGACCAGAGAATTCGAATA CATTTGACGGNNNGATCGACATG | 6884 | TGCAGGACCAGAGAATTCGAATA CACTGCGAATNNNGATCGACATG | 7124 |
| TGCAGGACCAGAGAATTCGAATA CAACCGGACCNNNGATCGACATG | 6645 | TGCAGGACCAGAGAATTCGAATA CAGTTCATTNNNGATCGACATG | 6885 | TGCAGGACCAGAGAATTCGAATA CACATGACACNNNGATCGACATG | 7125 |
| TGCAGGACCAGAGAATTCGAATA CATTAAATGCNNNGATCGACATG | 6646 | TGCAGGACCAGAGAATTCGAATA CAGAGTGGTANNNGATCGACATG | 6886 | TGCAGGACCAGAGAATTCGAATA CAGCGATTTGNNNGATCGACATG | 7126 |
| TGCAGGACCAGAGAATTCGAATA CACTGCAAGTNNNGATCGACATG | 6647 | TGCAGGACCAGAGAATTCGAATA CAAGTTGCTGNNNGATCGACATG | 6887 | TGCAGGACCAGAGAATTCGAATA CAACTAGGAGNNNGATCGACATG | 7127 |
| TGCAGGACCAGAGAATTCGAATA CACCCTTAACNNNGATCGACATG | 6648 | TGCAGGACCAGAGAATTCGAATA CAGATTTACANNNGATCGACATG | 6888 | TGCAGGACCAGAGAATTCGAATA CAGCGCAACANNNGATCGACATG | 7128 |
| TGCAGGACCAGAGAATTCGAATA CAAGTGAGACNNNGATCGACATG | 6649 | TGCAGGACCAGAGAATTCGAATA CACTAACAATNNNGATCGACATG | 6889 | TGCAGGACCAGAGAATTCGAATA CACACAGCCGNNNGATCGACATG | 7129 |
| TGCAGGACCAGAGAATTCGAATA CATATTAGACNNNGATCGACATG | 6650 | TGCAGGACCAGAGAATTCGAATA CAAGCTATCTNNNGATCGACATG | 6890 | TGCAGGACCAGAGAATTCGAATA CAGCCGTTGTNNNGATCGACATG | 7130 |
| TGCAGGACCAGAGAATTCGAATA CAGTTGGCTANNNGATCGACATG | 6651 | TGCAGGACCAGAGAATTCGAATA CACGACCGGCTNNNGATCGACATG | 6891 | TGCAGGACCAGAGAATTCGAATA CAAATATCGTNNNGATCGACATG | 7131 |
| TGCAGGACCAGAGAATTCGAATA CATCGCTAAGNNNGATCGACATG | 6652 | TGCAGGACCAGAGAATTCGAATA CACCGCGTACNNNGATCGACATG | 6892 | TGCAGGACCAGAGAATTCGAATA CACCGAAAGANNNGATCGACATG | 7132 |
| TGCAGGACCAGAGAATTCGAATA CAAGCCCCTCNNNGATCGACATG | 6653 | TGCAGGACCAGAGAATTCGAATA CATTGCAGGTNNNGATCGACATG | 6893 | TGCAGGACCAGAGAATTCGAATA CACAAGGTGNNNGATCGACATG | 7133 |

FIG. 21F

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATTACGAATNNNGATCGACATG | 6654 | TGCAGGACCAGAGAATTCGAATA CATGAGCTGTNNNGATCGACATG | 6894 | TGCAGGACCAGAGAATTCGAATA CAAAATCCATNNNGATCGACATG | 7134 |
| TGCAGGACCAGAGAATTCGAATA CAGGCCACCANNNGATCGACATG | 6655 | TGCAGGACCAGAGAATTCGAATA CAAGTCTCAGNNNGATCGACATG | 6895 | TGCAGGACCAGAGAATTCGAATA CAAACAATCNNNGATCGACATG | 7135 |
| TGCAGGACCAGAGAATTCGAATA CATCCTTATANNNGATCGACATG | 6656 | TGCAGGACCAGAGAATTCGAATA CAATTCCTCTNNNGATCGACATG | 6896 | TGCAGGACCAGAGAATTCGAATA CACATTGGCANNNGATCGACATG | 7136 |
| TGCAGGACCAGAGAATTCGAATA CATCAGTCTCNNNGATCGACATG | 6657 | TGCAGGACCAGAGAATTCGAATA CAGAGAGAGANNNGATCGACATG | 6897 | TGCAGGACCAGAGAATTCGAATA CACTACAACGNNNGATCGACATG | 7137 |
| TGCAGGACCAGAGAATTCGAATA CACGACTTCTNNNGATCGACATG | 6658 | TGCAGGACCAGAGAATTCGAATA CAGCAGAGCGNNNGATCGACATG | 6898 | TGCAGGACCAGAGAATTCGAATA CAATCGAGAGNNNGATCGACATG | 7138 |
| TGCAGGACCAGAGAATTCGAATA CAAGGTAACGNNNGATCGACATG | 6659 | TGCAGGACCAGAGAATTCGAATA CAGGCACTATNNNGATCGACATG | 6899 | TGCAGGACCAGAGAATTCGAATA CACGCGTCCTNNNGATCGACATG | 7139 |
| TGCAGGACCAGAGAATTCGAATA CAAGACACTCNNNGATCGACATG | 6660 | TGCAGGACCAGAGAATTCGAATA CAGACCCTCAANNNGATCGACATG | 6900 | TGCAGGACCAGAGAATTCGAATA CATTACGTTTNNNGATCGACATG | 7140 |
| TGCAGGACCAGAGAATTCGAATA CAGGCTTCGGNNNGATCGACATG | 6661 | TGCAGGACCAGAGAATTCGAATA CAAATAACTCNNNGATCGACATG | 6901 | TGCAGGACCAGAGAATTCGAATA CAGTAGTCGTNNNGATCGACATG | 7141 |
| TGCAGGACCAGAGAATTCGAATA CACAATTCGGNNNGATCGACATG | 6662 | TGCAGGACCAGAGAATTCGAATA CATCATATTCNNNGATCGACATG | 6902 | TGCAGGACCAGAGAATTCGAATA CATGCCTCGCNNNGATCGACATG | 7142 |
| TGCAGGACCAGAGAATTCGAATA CAGGCTCTGGNNNGATCGACATG | 6663 | TGCAGGACCAGAGAATTCGAATA CAGATAGAATNNNGATCGACATG | 6903 | TGCAGGACCAGAGAATTCGAATA CAATACATTGNNNGATCGACATG | 7143 |
| TGCAGGACCAGAGAATTCGAATA CATCTCTGACNNNGATCGACATG | 6664 | TGCAGGACCAGAGAATTCGAATA CACCTGGACGNNNGATCGACATG | 6904 | TGCAGGACCAGAGAATTCGAATA CATATAAAABNNNGATCGACATG | 7144 |
| TGCAGGACCAGAGAATTCGAATA CAGAGTAGGTNNNGATCGACATG | 6665 | TGCAGGACCAGAGAATTCGAATA CATAACAGNNNGATCGACATG | 6905 | TGCAGGACCAGAGAATTCGAATA CATACCTGCTNNNGATCGACATG | 7145 |
| TGCAGGACCAGAGAATTCGAATA CAATTTTTTANNNGATCGACATG | 6666 | TGCAGGACCAGAGAATTCGAATA CAGCAGCCGTNNNGATCGACATG | 6906 | TGCAGGACCAGAGAATTCGAATA CATGAGAACGNNNGATCGACATG | 7146 |
| TGCAGGACCAGAGAATTCGAATA CAATTTCTACNNNGATCGACATG | 6667 | TGCAGGACCAGAGAATTCGAATA CACAGACCGNNNGATCGACATG | 6907 | TGCAGGACCAGAGAATTCGAATA CAGGAACTCANNNGATCGACATG | 7147 |
| TGCAGGACCAGAGAATTCGAATA CAAACGCTGTNNNGATCGACATG | 6668 | TGCAGGACCAGAGAATTCGAATA CATTAAGAAGNNNGATCGACATG | 6908 | TGCAGGACCAGAGAATTCGAATA CAAGAGCGCGNNNGATCGACATG | 7148 |
| TGCAGGACCAGAGAATTCGAATA CAATCGACTGNNNTGCATCAGGT | 6669 | TGCAGGACCAGAGAATTCGAATA CATTCATAAGNNNTGCATCAGGT | 6909 | TGCAGGACCAGAGAATTCGAATA CAACGCCACGNNNTGCATCAGGT | 7149 |
| TGCAGGACCAGAGAATTCGAATA CATAACGATTNNNTGCATCAGGT | 6670 | TGCAGGACCAGAGAATTCGAATA CACCACAGGCNNNTGCATCAGGT | 6910 | TGCAGGACCAGAGAATTCGAATA CATCCCTAANNNNTGCATCAGGT | 7150 |
| TGCAGGACCAGAGAATTCGAATA CAGCCCAGCANNNTGCATCAGGT | 6671 | TGCAGGACCAGAGAATTCGAATA CAGTCAGGCNNNTGCATCAGGT | 6911 | TGCAGGACCAGAGAATTCGAATA CATCGGCATANNNTGCATCAGGT | 7151 |
| TGCAGGACCAGAGAATTCGAATA CAACAAACGGNNNTGCATCAGGT | 6672 | TGCAGGACCAGAGAATTCGAATA CAGTCGGCACNNNTGCATCAGGT | 6912 | TGCAGGACCAGAGAATTCGAATA CACGCCTCCANNNTGCATCAGGT | 7152 |
| TGCAGGACCAGAGAATTCGAATA CAAGAGTGCANNNTGCATCAGGT | 6673 | TGCAGGACCAGAGAATTCGAATA CATAGTCTGGNNNTGCATCAGGT | 6913 | TGCAGGACCAGAGAATTCGAATA CAAGGTGGCNNNTGCATCAGGT | 7153 |
| TGCAGGACCAGAGAATTCGAATA CACGGATCGCNNNTGCATCAGGT | 6674 | TGCAGGACCAGAGAATTCGAATA CACATTATTCNNNTGCATCAGGT | 6914 | TGCAGGACCAGAGAATTCGAATA CAAAGGTTCNNNTGCATCAGGT | 7154 |
| TGCAGGACCAGAGAATTCGAATA CAGGAATCCTNNNTGCATCAGGT | 6675 | TGCAGGACCAGAGAATTCGAATA CAGAAGACCANNNTGCATCAGGT | 6915 | TGCAGGACCAGAGAATTCGAATA CACGGAAGGCNNNTGCATCAGGT | 7155 |
| TGCAGGACCAGAGAATTCGAATA CAACCTAAATNNNTGCATCAGGT | 6676 | TGCAGGACCAGAGAATTCGAATA CAAATTCTCTNNNTGCATCAGGT | 6916 | TGCAGGACCAGAGAATTCGAATA CAAGGCATTCNNNTGCATCAGGT | 7156 |
| TGCAGGACCAGAGAATTCGAATA CACGTATCGANNNTGCATCAGGT | 6677 | TGCAGGACCAGAGAATTCGAATA CAGCCATCGGNNNTGCATCAGGT | 6917 | TGCAGGACCAGAGAATTCGAATA CACACCAGCGNNNTGCATCAGGT | 7157 |
| TGCAGGACCAGAGAATTCGAATA CATCAGATATNNNTGCATCAGGT | 6678 | TGCAGGACCAGAGAATTCGAATA CATATAATTANNNTGCATCAGGT | 6918 | TGCAGGACCAGAGAATTCGAATA CATATGCGTGNNNTGCATCAGGT | 7158 |
| TGCAGGACCAGAGAATTCGAATA CAGCGACCGTNNNTGCATCAGGT | 6679 | TGCAGGACCAGAGAATTCGAATA CAACGAACAGNNNTGCATCAGGT | 6919 | TGCAGGACCAGAGAATTCGAATA CAGCATAGCTNNNTGCATCAGGT | 7159 |
| TGCAGGACCAGAGAATTCGAATA CATCAGACTGNNNTGCATCAGGT | 6680 | TGCAGGACCAGAGAATTCGAATA CAAGGCCCGTNNNTGCATCAGGT | 6920 | TGCAGGACCAGAGAATTCGAATA CATCACTAGGNNNTGCATCAGGT | 7160 |
| TGCAGGACCAGAGAATTCGAATA CAATGCACGTNNNTGCATCAGGT | 6681 | TGCAGGACCAGAGAATTCGAATA CACAAAGAGCNNNTGCATCAGGT | 6921 | TGCAGGACCAGAGAATTCGAATA CAGCCGAGCTNNNTGCATCAGGT | 7161 |
| TGCAGGACCAGAGAATTCGAATA CATCTACTGCNNNTGCATCAGGT | 6682 | TGCAGGACCAGAGAATTCGAATA CATTCAGGACNNNTGCATCAGGT | 6922 | TGCAGGACCAGAGAATTCGAATA CAACTGCCAANNNTGCATCAGGT | 7162 |
| TGCAGGACCAGAGAATTCGAATA CACTCGTTGTNNNTGCATCAGGT | 6683 | TGCAGGACCAGAGAATTCGAATA CAAGCACGCNNNTGCATCAGGT | 6923 | TGCAGGACCAGAGAATTCGAATA CACCGACAATNNNTGCATCAGGT | 7163 |
| TGCAGGACCAGAGAATTCGAATA CACTGTGTAGNNNTGCATCAGGT | 6684 | TGCAGGACCAGAGAATTCGAATA CAGACACATCNNNTGCATCAGGT | 6924 | TGCAGGACCAGAGAATTCGAATA CACAGGCCCANNNTGCATCAGGT | 7164 |
| TGCAGGACCAGAGAATTCGAATA CAGCTTGCTNNNTGCATCAGGT | 6685 | TGCAGGACCAGAGAATTCGAATA CACGATACANNNTGCATCAGGT | 6925 | TGCAGGACCAGAGAATTCGAATA CACABCCCCNNNTGCATCAGGT | 7165 |
| TGCAGGACCAGAGAATTCGAATA CACTTTTCTTNNNTGCATCAGGT | 6686 | TGCAGGACCAGAGAATTCGAATA CAATACGCGTNNNTGCATCAGGT | 6926 | TGCAGGACCAGAGAATTCGAATA CAAAGACGACNNNTGCATCAGGT | 7166 |

FIG. 21G

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATCAACTCCNNNTGCATCAGGT | 6687 | TGCAGGACCAGAGAATTCGAATA CATACACGCANNNTGCATCAGGT | 6927 | TGCAGGACCAGAGAATTCGAATA CATACAAGAANNNTGCATCAGGT | 7167 |
| TGCAGGACCAGAGAATTCGAATA CAATCCAGCANNNTGCATCAGGT | 6688 | TGCAGGACCAGAGAATTCGAATA CACTCTCTCTNNNTGCATCAGGT | 6928 | TGCAGGACCAGAGAATTCGAATA CAATAGGCCTNNNTGCATCAGGT | 7168 |
| TGCAGGACCAGAGAATTCGAATA CAAACCGCTANNNTGCATCAGGT | 6689 | TGCAGGACCAGAGAATTCGAATA CACAATGAGGNNNTGCATCAGGT | 6929 | TGCAGGACCAGAGAATTCGAATA CATTGGATATNNNTGCATCAGGT | 7169 |
| TGCAGGACCAGAGAATTCGAATA CACGCCTGTCNNNTGCATCAGGT | 6690 | TGCAGGACCAGAGAATTCGAATA CACACAGTGTNNNTGCATCAGGT | 6930 | TGCAGGACCAGAGAATTCGAATA CACTATCGCTNNNTGCATCAGGT | 7170 |
| TGCAGGACCAGAGAATTCGAATA CATAAGGCCTNNNTGCATCAGGT | 6691 | TGCAGGACCAGAGAATTCGAATA CAAACATACTNNNTGCATCAGGT | 6931 | TGCAGGACCAGAGAATTCGAATA CACTCTTGACNNNTGCATCAGGT | 7171 |
| TGCAGGACCAGAGAATTCGAATA CATGTCATGGNNNTGCATCAGGT | 6692 | TGCAGGACCAGAGAATTCGAATA CACGGCATCGNNNTGCATCAGGT | 6932 | TGCAGGACCAGAGAATTCGAATA CAAATTAGGANNNTGCATCAGGT | 7172 |
| TGCAGGACCAGAGAATTCGAATA CATAGCAGTCNNNTGCATCAGGT | 6693 | TGCAGGACCAGAGAATTCGAATA CAAGTAGATANNNTGCATCAGGT | 6933 | TGCAGGACCAGAGAATTCGAATA CACGTTGCTTNNNTGCATCAGGT | 7173 |
| TGCAGGACCAGAGAATTCGAATA CAGCGCTGACNNNTGCATCAGGT | 6694 | TGCAGGACCAGAGAATTCGAATA CAGCGATCCGNNNTGCATCAGGT | 6934 | TGCAGGACCAGAGAATTCGAATA CATTTCCCCTNNNTGCATCAGGT | 7174 |
| TGCAGGACCAGAGAATTCGAATA CATATATCCTNNNTGCATCAGGT | 6695 | TGCAGGACCAGAGAATTCGAATA CAATTAAATTNNNTGCATCAGGT | 6935 | TGCAGGACCAGAGAATTCGAATA CAACTACCTCNNNTGCATCAGGT | 7175 |
| TGCAGGACCAGAGAATTCGAATA CACACGAAAGNNNTGCATCAGGT | 6696 | TGCAGGACCAGAGAATTCGAATA CAAGATTCATNNNTGCATCAGGT | 6936 | TGCAGGACCAGAGAATTCGAATA CAACTCTGCTNNNTGCATCAGGT | 7176 |
| TGCAGGACCAGAGAATTCGAATA CAATAAGTCTNNNTGCATCAGGT | 6697 | TGCAGGACCAGAGAATTCGAATA CATCACCTGTNNNTGCATCAGGT | 6937 | TGCAGGACCAGAGAATTCGAATA CACTACCTCANNNTGCATCAGGT | 7177 |
| TGCAGGACCAGAGAATTCGAATA CAGCTGTCCCNNNTGCATCAGGT | 6698 | TGCAGGACCAGAGAATTCGAATA CACAAATACTNNNTGCATCAGGT | 6938 | TGCAGGACCAGAGAATTCGAATA CAACTGCTAGNNNTGCATCAGGT | 7178 |
| TGCAGGACCAGAGAATTCGAATA CAATGACCTGNNNTGCATCAGGT | 6699 | TGCAGGACCAGAGAATTCGAATA CATTTAGCCANNNTGCATCAGGT | 6939 | TGCAGGACCAGAGAATTCGAATA CACGCGCAGTNNNTGCATCAGGT | 7179 |
| TGCAGGACCAGAGAATTCGAATA CAATACCCTNNNTGCATCAGGT | 6700 | TGCAGGACCAGAGAATTCGAATA CATCCTAGTCNNNTGCATCAGGT | 6940 | TGCAGGACCAGAGAATTCGAATA CAGGCTTTCTNNNTGCATCAGGT | 7180 |
| TGCAGGACCAGAGAATTCGAATA CATGAGGTAGNNNTGCATCAGGT | 6701 | TGCAGGACCAGAGAATTCGAATA CATAAAGAGTNNNTGCATCAGGT | 6941 | TGCAGGACCAGAGAATTCGAATA CACTGGACTANNNTGCATCAGGT | 7181 |
| TGCAGGACCAGAGAATTCGAATA CACGAATCTGNNNTGCATCAGGT | 6702 | TGCAGGACCAGAGAATTCGAATA CACATGCACANNNTGCATCAGGT | 6942 | TGCAGGACCAGAGAATTCGAATA CAACATCAGCNNNTGCATCAGGT | 7182 |
| TGCAGGACCAGAGAATTCGAATA CAGCCGACGTNNNTGCATCAGGT | 6703 | TGCAGGACCAGAGAATTCGAATA CATTTCAACTNNNTGCATCAGGT | 6943 | TGCAGGACCAGAGAATTCGAATA CATCAGTTCCNNNTGCATCAGGT | 7183 |
| TGCAGGACCAGAGAATTCGAATA CATTCAAACANNNTGCATCAGGT | 6704 | TGCAGGACCAGAGAATTCGAATA CACTGATGTGNNNTGCATCAGGT | 6944 | TGCAGGACCAGAGAATTCGAATA CATCACGATGNNNTGCATCAGGT | 7184 |
| TGCAGGACCAGAGAATTCGAATA CAAGGCTTACNNNTGCATCAGGT | 6705 | TGCAGGACCAGAGAATTCGAATA CACCCGTTCGNNNTGCATCAGGT | 6945 | TGCAGGACCAGAGAATTCGAATA CAGTATGCACNNNTGCATCAGGT | 7185 |
| TGCAGGACCAGAGAATTCGAATA CAAAAACGGCNNNTGCATCAGGT | 6706 | TGCAGGACCAGAGAATTCGAATA CACATAAGAANNNTGCATCAGGT | 6946 | TGCAGGACCAGAGAATTCGAATA CATCAGGCGCNNNTGCATCAGGT | 7186 |
| TGCAGGACCAGAGAATTCGAATA CAGATAGGACNNNTGCATCAGGT | 6707 | TGCAGGACCAGAGAATTCGAATA CAGATTACGCNNNTGCATCAGGT | 6947 | TGCAGGACCAGAGAATTCGAATA CAGTTTTCCCNNNTGCATCAGGT | 7187 |
| TGCAGGACCAGAGAATTCGAATA CAATGCCGAANNNTGCATCAGGT | 6708 | TGCAGGACCAGAGAATTCGAATA CACTGACGATNNNTGCATCAGGT | 6948 | TGCAGGACCAGAGAATTCGAATA CAGGTCGGAGNNNTGCATCAGGT | 7188 |
| TGCAGGACCAGAGAATTCGAATA CAACCAGAGNNNTGCATCAGGT | 6709 | TGCAGGACCAGAGAATTCGAATA CAACTTTCTANNNTGCATCAGGT | 6949 | TGCAGGACCAGAGAATTCGAATA CAATAGGCGNNNTGCATCAGGT | 7189 |
| TGCAGGACCAGAGAATTCGAATA CACAAACGCTNNNTGCATCAGGT | 6710 | TGCAGGACCAGAGAATTCGAATA CACACATAGCNNNTGCATCAGGT | 6950 | TGCAGGACCAGAGAATTCGAATA CAAGCCGACCNNNTGCATCAGGT | 7190 |
| TGCAGGACCAGAGAATTCGAATA CACGCTTTCANNNTGCATCAGGT | 6711 | TGCAGGACCAGAGAATTCGAATA CATTAGTCAANNNTGCATCAGGT | 6951 | TGCAGGACCAGAGAATTCGAATA CACATGTCAGNNNTGCATCAGGT | 7191 |
| TGCAGGACCAGAGAATTCGAATA CATCCAGGCGNNNTGCATCAGGT | 6712 | TGCAGGACCAGAGAATTCGAATA CATGGTCGCGNNNTGCATCAGGT | 6952 | TGCAGGACCAGAGAATTCGAATA CATTTTAGCTNNNTGCATCAGGT | 7192 |
| TGCAGGACCAGAGAATTCGAATA CATTGAAATCNNNTGCATCAGGT | 6713 | TGCAGGACCAGAGAATTCGAATA CATTCTGACCNNNTGCATCAGGT | 6953 | TGCAGGACCAGAGAATTCGAATA CATCGAGTTGNNNTGCATCAGGT | 7193 |
| TGCAGGACCAGAGAATTCGAATA CACCTGCTGCNNNTGCATCAGGT | 6714 | TGCAGGACCAGAGAATTCGAATA CATAAAACCTNNNTGCATCAGGT | 6954 | TGCAGGACCAGAGAATTCGAATA CAGCCACCTCNNNTGCATCAGGT | 7194 |
| TGCAGGACCAGAGAATTCGAATA CACGAATGAGNNNTGCATCAGGT | 6715 | TGCAGGACCAGAGAATTCGAATA CAACTATAACNNNTGCATCAGGT | 6955 | TGCAGGACCAGAGAATTCGAATA CATGTTGTGGNNNTGCATCAGGT | 7195 |
| TGCAGGACCAGAGAATTCGAATA CATGTGTTAANNNTGCATCAGGT | 6716 | TGCAGGACCAGAGAATTCGAATA CATATGATGTNNNTGCATCAGGT | 6956 | TGCAGGACCAGAGAATTCGAATA CAGTTGTGTGNNNTGCATCAGGT | 7196 |
| TGCAGGACCAGAGAATTCGAATA CATTCAAACNNNTGCATCAGGT | 6717 | TGCAGGACCAGAGAATTCGAATA CATCACCGCNNNTGCATCAGGT | 6957 | TGCAGGACCAGAGAATTCGAATA CACGTGAACTNNNTGCATCAGGT | 7197 |
| TGCAGGACCAGAGAATTCGAATA CACAGCCCAANNNTGCATCAGGT | 6718 | TGCAGGACCAGAGAATTCGAATA CAAGGTTATTNNNTGCATCAGGT | 6958 | TGCAGGACCAGAGAATTCGAATA CAAAGGCTCTNNNTGCATCAGGT | 7198 |
| TGCAGGACCAGAGAATTCGAATA CAGACAGTAGNNNTGCATCAGGT | 6719 | TGCAGGACCAGAGAATTCGAATA CAAGCAGCTTNNNTGCATCAGGT | 6959 | TGCAGGACCAGAGAATTCGAATA CATATTCTTGNNNTGCATCAGGT | 7199 |

FIG. 21H

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CACATTTGTTNNNTGCATCAGGT | 6720 | TGCAGGACCAGAGAATTCGAATA CATCGAGACTNNNTGCATCAGGT | 6960 | TGCAGGACCAGAGAATTCGAATA CACATTACTTNNNTGCATCAGGT | 7200 |
| TGCAGGACCAGAGAATTCGAATA CATAATCCAANNNTGCATCAGGT | 6721 | TGCAGGACCAGAGAATTCGAATA CACACACTTCNNNTGCATCAGGT | 6961 | TGCAGGACCAGAGAATTCGAATA CACCAAGACTNNNTGCATCAGGT | 7201 |
| TGCAGGACCAGAGAATTCGAATA CACGTACAACNNNTGCATCAGGT | 6722 | TGCAGGACCAGAGAATTCGAATA CAAAAAAACCNNNTGCATCAGGT | 6962 | TGCAGGACCAGAGAATTCGAATA CAAGTTCCAGNNNTGCATCAGGT | 7202 |
| TGCAGGACCAGAGAATTCGAATA CAATATTCCANNNTGCATCAGGT | 6723 | TGCAGGACCAGAGAATTCGAATA CATACAGCCANNNTGCATCAGGT | 6963 | TGCAGGACCAGAGAATTCGAATA CAAACCAGTCNNNTGCATCAGGT | 7203 |
| TGCAGGACCAGAGAATTCGAATA CATAATTATANNNTGCATCAGGT | 6724 | TGCAGGACCAGAGAATTCGAATA CAATGAAAACNNNTGCATCAGGT | 6964 | TGCAGGACCAGAGAATTCGAATA CATGGCTCAANNNTGCATCAGGT | 7204 |
| TGCAGGACCAGAGAATTCGAATA CAGATGCAGANNNTGCATCAGGT | 6725 | TGCAGGACCAGAGAATTCGAATA CAGTGATGCTNNNTGCATCAGGT | 6965 | TGCAGGACCAGAGAATTCGAATA CATCTTTATGNNNTGCATCAGGT | 7205 |
| TGCAGGACCAGAGAATTCGAATA CAGGAGCCAGNNNTGCATCAGGT | 6726 | TGCAGGACCAGAGAATTCGAATA CATTAACAGTNNNTGCATCAGGT | 6966 | TGCAGGACCAGAGAATTCGAATA CAGGTGACTTNNNTGCATCAGGT | 7206 |
| TGCAGGACCAGAGAATTCGAATA CAGCGAGTTTNNNTGCATCAGGT | 6727 | TGCAGGACCAGAGAATTCGAATA CACACCGCGNNNNTGCATCAGGT | 6967 | TGCAGGACCAGAGAATTCGAATA CATCCTAACCNNNTGCATCAGGT | 7207 |
| TGCAGGACCAGAGAATTCGAATA CAAAGTGACGNNNTGCATCAGGT | 6728 | TGCAGGACCAGAGAATTCGAATA CATGTGCCCCNNNTGCATCAGGT | 6968 | TGCAGGACCAGAGAATTCGAATA CAGCGTAAAGNNNTGCATCAGGT | 7208 |

FIG. 22A

| Pool-31 | SEQ ID NO: | Pool-32 | SEQ ID NO: |
|---|---|---|---|
| TGCAGGACCAGAGAATTCGAATACATGGTCCAANNNACGTATGCCA | 7209 | TGCAGGACCAGAGAATTCGAATACATTCCAATTNNNACGTATGCCA | 7449 |
| TGCAGGACCAGAGAATTCGAATACAGTACTCAGNNNACGTATGCCA | 7210 | TGCAGGACCAGAGAATTCGAATACATGTACAGCNNNACGTATGCCA | 7450 |
| TGCAGGACCAGAGAATTCGAATACAGAAGCCCCNNNACGTATGCCA | 7211 | TGCAGGACCAGAGAATTCGAATACACAGGAGCGNNNACGTATGCCA | 7451 |
| TGCAGGACCAGAGAATTCGAATACATTAACCGGNNNACGTATGCCA | 7212 | TGCAGGACCAGAGAATTCGAATACAATGCGTTGNNNACGTATGCCA | 7452 |
| TGCAGGACCAGAGAATTCGAATACATAACCTGGNNNACGTATGCCA | 7213 | TGCAGGACCAGAGAATTCGAATACATATATTTCGNNNACGTATGCCA | 7453 |
| TGCAGGACCAGAGAATTCGAATACAGTCGACTANNNACGTATGCCA | 7214 | TGCAGGACCAGAGAATTCGAATACAAAATTCCCCNNNACGTATGCCA | 7454 |
| TGCAGGACCAGAGAATTCGAATACACCAAACGTNNNACGTATGCCA | 7215 | TGCAGGACCAGAGAATTCGAATACATCTGACGANNNACGTATGCCA | 7455 |
| TGCAGGACCAGAGAATTCGAATACAACGTATCGNNNACGTATGCCA | 7216 | TGCAGGACCAGAGAATTCGAATACACCGCGCTTNNNACGTATGCCA | 7456 |
| TGCAGGACCAGAGAATTCGAATACACACGGCCANNNACGTATGCCA | 7217 | TGCAGGACCAGAGAATTCGAATACAAAACACCCNNNACGTATGCCA | 7457 |
| TGCAGGACCAGAGAATTCGAATACAAGGTTTGCNNNACGTATGCCA | 7218 | TGCAGGACCAGAGAATTCGAATACAGGTTGTGNNNACGTATGCCA | 7458 |
| TGCAGGACCAGAGAATTCGAATACACGACGCGTNNNACGTATGCCA | 7219 | TGCAGGACCAGAGAATTCGAATACAACTAACCGNNNACGTATGCCA | 7459 |
| TGCAGGACCAGAGAATTCGAATACACCGACGTGNNNACGTATGCCA | 7220 | TGCAGGACCAGAGAATTCGAATACATCAGGAGANNNACGTATGCCA | 7460 |
| TGCAGGACCAGAGAATTCGAATACACAGTTTTTNNNACGTATGCCA | 7221 | TGCAGGACCAGAGAATTCGAATACAGTCTGCGGNNNACGTATGCCA | 7461 |
| TGCAGGACCAGAGAATTCGAATACATGCCCGGANNNACGTATGCCA | 7222 | TGCAGGACCAGAGAATTCGAATACAACTGGCGCNNNACGTATGCCA | 7462 |
| TGCAGGACCAGAGAATTCGAATACAGCCACTCCNNNACGTATGCCA | 7223 | TGCAGGACCAGAGAATTCGAATACACGACTCTTNNNACGTATGCCA | 7463 |
| TGCAGGACCAGAGAATTCGAATACAGACGAAGTNNNACGTATGCCA | 7224 | TGCAGGACCAGAGAATTCGAATACAGCGAAGGCNNNACGTATGCCA | 7464 |
| TGCAGGACCAGAGAATTCGAATACAGGTTCCTTNNNACGTATGCCA | 7225 | TGCAGGACCAGAGAATTCGAATACAGGCGCCGCNNNACGTATGCCA | 7465 |
| TGCAGGACCAGAGAATTCGAATACACCGGAATTNNNACGTATGCCA | 7226 | TGCAGGACCAGAGAATTCGAATACAGAGCACCCNNNACGTATGCCA | 7466 |
| TGCAGGACCAGAGAATTCGAATACATCGGCAGCNNNACGTATGCCA | 7227 | TGCAGGACCAGAGAATTCGAATACACCCAAAGTNNNACGTATGCCA | 7467 |
| TGCAGGACCAGAGAATTCGAATACAGCTAGAGANNNACGTATGCCA | 7228 | TGCAGGACCAGAGAATTCGAATACACGGAATAGNNNACGTATGCCA | 7468 |
| TGCAGGACCAGAGAATTCGAATACACCACTTACNNNACGTATGCCA | 7229 | TGCAGGACCAGAGAATTCGAATACAAGTAAGATNNNACGTATGCCA | 7469 |
| TGCAGGACCAGAGAATTCGAATACAACCACCGGNNNACGTATGCCA | 7230 | TGCAGGACCAGAGAATTCGAATACATCTCACACNNNACGTATGCCA | 7470 |
| TGCAGGACCAGAGAATTCGAATACAGAAACATANNNACGTATGCCA | 7231 | TGCAGGACCAGAGAATTCGAATACAGGCCCAANNNACGTATGCCA | 7471 |
| TGCAGGACCAGAGAATTCGAATACAGCTGAAAGNNNACGTATGCCA | 7232 | TGCAGGACCAGAGAATTCGAATACAGGATTTGCNNNACGTATGCCA | 7472 |
| TGCAGGACCAGAGAATTCGAATACATAAGAAGTNNNACGTATGCCA | 7233 | TGCAGGACCAGAGAATTCGAATACAAATGACAANNNACGTATGCCA | 7473 |
| TGCAGGACCAGAGAATTCGAATACACGTGACTANNNACGTATGCCA | 7234 | TGCAGGACCAGAGAATTCGAATACATAAAAAATNNNACGTATGCCA | 7474 |
| TGCAGGACCAGAGAATTCGAATACATTAAGATCNNNACGTATGCCA | 7235 | TGCAGGACCAGAGAATTCGAATACATAATGGCNNNACGTATGCCA | 7475 |
| TGCAGGACCAGAGAATTCGAATACATGGATCACNNNACGTATGCCA | 7236 | TGCAGGACCAGAGAATTCGAATACAGTTGCTTCNNNACGTATGCCA | 7476 |
| TGCAGGACCAGAGAATTCGAATACACCGAGCTGNNNACGTATGCCA | 7237 | TGCAGGACCAGAGAATTCGAATACACGTTTCACNNNACGTATGCCA | 7477 |
| TGCAGGACCAGAGAATTCGAATACACTCATAAANNNACGTATGCCA | 7238 | TGCAGGACCAGAGAATTCGAATACAGAACAAATNNNACGTATGCCA | 7478 |
| TGCAGGACCAGAGAATTCGAATACACTCTACTGNNNACGTATGCCA | 7239 | TGCAGGACCAGAGAATTCGAATACAATAGAAGTNNNACGTATGCCA | 7479 |
| TGCAGGACCAGAGAATTCGAATACAAGGTGAGTNNNACGTATGCCA | 7240 | TGCAGGACCAGAGAATTCGAATACAGTAAGGCANNNACGTATGCCA | 7480 |
| TGCAGGACCAGAGAATTCGAATACAGAACACTCNNNACGTATGCCA | 7241 | TGCAGGACCAGAGAATTCGAATACAGAGATGCANNNACGTATGCCA | 7481 |

FIG. 22B

| Pool-31 | SEQ ID NO: | Pool-32 | SEQ ID NO: |
|---|---|---|---|
| TGCAGGACCAGAGAATTCGAATACAGGCAGAGCNNNACGTATGCCA | 7242 | TGCAGGACCAGAGAATTCGAATACACACCATCTNNNACGTATGCCA | 7482 |
| TGCAGGACCAGAGAATTCGAATACATTTCCAGCNNNACGTATGCCA | 7243 | TGCAGGACCAGAGAATTCGAATACAGATACACCNNNACGTATGCCA | 7483 |
| TGCAGGACCAGAGAATTCGAATACACCCATCATNNNACGTATGCCA | 7244 | TGCAGGACCAGAGAATTCGAATACAGATACTGCNNNACGTATGCCA | 7484 |
| TGCAGGACCAGAGAATTCGAATACAATCAGCGTNNNACGTATGCCA | 7245 | TGCAGGACCAGAGAATTCGAATACACGTAACTGNNNACGTATGCCA | 7485 |
| TGCAGGACCAGAGAATTCGAATACATGAAAAACNNNACGTATGCCA | 7246 | TGCAGGACCAGAGAATTCGAATACATCCTCTTCNNNACGTATGCCA | 7486 |
| TGCAGGACCAGAGAATTCGAATACAATGCGGAANNNACGTATGCCA | 7247 | TGCAGGACCAGAGAATTCGAATACATCGCGTCGNNNACGTATGCCA | 7487 |
| TGCAGGACCAGAGAATTCGAATACACGGATTCANNNACGTATGCCA | 7248 | TGCAGGACCAGAGAATTCGAATACAACAGGAACNNNACGTATGCCA | 7488 |
| TGCAGGACCAGAGAATTCGAATACAGTCATACGNNNACGTATGCCA | 7249 | TGCAGGACCAGAGAATTCGAATACAAAAATTTNNNACGTATGCCA | 7489 |
| TGCAGGACCAGAGAATTCGAATACAACCTGCTTNNNACGTATGCCA | 7250 | TGCAGGACCAGAGAATTCGAATACAAAGTCACCNNNACGTATGCCA | 7490 |
| TGCAGGACCAGAGAATTCGAATACAGTTGTGCANNNACGTATGCCA | 7251 | TGCAGGACCAGAGAATTCGAATACATCTACGAGNNNACGTATGCCA | 7491 |
| TGCAGGACCAGAGAATTCGAATACAGAAATCGGNNNACGTATGCCA | 7252 | TGCAGGACCAGAGAATTCGAATACAGATCTTCCNNNACGTATGCCA | 7492 |
| TGCAGGACCAGAGAATTCGAATACAAAGTTAGANNNACGTATGCCA | 7253 | TGCAGGACCAGAGAATTCGAATACAGGACACCNNNACGTATGCCA | 7493 |
| TGCAGGACCAGAGAATTCGAATACATGTAACGCNNNACGTATGCCA | 7254 | TGCAGGACCAGAGAATTCGAATACAATAGGTGGNNNACGTATGCCA | 7494 |
| TGCAGGACCAGAGAATTCGAATACAGTTTTGAANNNACGTATGCCA | 7255 | TGCAGGACCAGAGAATTCGAATACACCATCGCCNNNACGTATGCCA | 7495 |
| TGCAGGACCAGAGAATTCGAATACACAAACTGCNNNACGTATGCCA | 7256 | TGCAGGACCAGAGAATTCGAATACATGATCTCCNNNACGTATGCCA | 7496 |
| TGCAGGACCAGAGAATTCGAATACAGCCTGAGCNNNACGTATGCCA | 7257 | TGCAGGACCAGAGAATTCGAATACACGCGAATTNNNACGTATGCCA | 7497 |
| TGCAGGACCAGAGAATTCGAATACATCTTCCAGNNNACGTATGCCA | 7258 | TGCAGGACCAGAGAATTCGAATACATATATAATNNNACGTATGCCA | 7498 |
| TGCAGGACCAGAGAATTCGAATACATACCCTACNNNACGTATGCCA | 7259 | TGCAGGACCAGAGAATTCGAATACATATCGCCTNNNACGTATGCCA | 7499 |
| TGCAGGACCAGAGAATTCGAATACATCATAGATNNNACGTATGCCA | 7260 | TGCAGGACCAGAGAATTCGAATACATTACGAGCNNNACGTATGCCA | 7500 |
| TGCAGGACCAGAGAATTCGAATACAGTATAGAANNNACGTATGCCA | 7261 | TGCAGGACCAGAGAATTCGAATACAGGTTTCTCNNNACGTATGCCA | 7501 |
| TGCAGGACCAGAGAATTCGAATACACCCTAAAGNNNACGTATGCCA | 7262 | TGCAGGACCAGAGAATTCGAATACACTTGCAGANNNACGTATGCCA | 7502 |
| TGCAGGACCAGAGAATTCGAATACAGCGGTTTANNNACGTATGCCA | 7263 | TGCAGGACCAGAGAATTCGAATACAGACATTTANNNACGTATGCCA | 7503 |
| TGCAGGACCAGAGAATTCGAATACATAGCTCAGNNNACGTATGCCA | 7264 | TGCAGGACCAGAGAATTCGAATACAACACGAGANNNACGTATGCCA | 7504 |
| TGCAGGACCAGAGAATTCGAATACACCGTCCCANNNACGTATGCCA | 7265 | TGCAGGACCAGAGAATTCGAATACATTGCCCGCNNNACGTATGCCA | 7505 |
| TGCAGGACCAGAGAATTCGAATACAAGTGCGAANNNACGTATGCCA | 7266 | TGCAGGACCAGAGAATTCGAATACACAGTCCTTNNNACGTATGCCA | 7506 |
| TGCAGGACCAGAGAATTCGAATACATGAGCTTGNNNACGTATGCCA | 7267 | TGCAGGACCAGAGAATTCGAATACAGCATTTGGNNNACGTATGCCA | 7507 |
| TGCAGGACCAGAGAATTCGAATACATATCGTGGNNNACGTATGCCA | 7268 | TGCAGGACCAGAGAATTCGAATACAGGATATCCNNNACGTATGCCA | 7508 |
| TGCAGGACCAGAGAATTCGAATACATCAGACACNNNCTAGCGTTAC | 7269 | TGCAGGACCAGAGAATTCGAATACACCAGGAGGNNNCTAGCGTTAC | 7509 |
| TGCAGGACCAGAGAATTCGAATACATACCCTTGNNNCTAGCGTTAC | 7270 | TGCAGGACCAGAGAATTCGAATACATCGCCTTANNNCTAGCGTTAC | 7510 |
| TGCAGGACCAGAGAATTCGAATACACATCGAGTNNNCTAGCGTTAC | 7271 | TGCAGGACCAGAGAATTCGAATACATTACCCGTNNNCTAGCGTTAC | 7511 |
| TGCAGGACCAGAGAATTCGAATACATGAATCTANNNCTAGCGTTAC | 7272 | TGCAGGACCAGAGAATTCGAATACAATCACCTCNNNCTAGCGTTAC | 7512 |
| TGCAGGACCAGAGAATTCGAATACAAGTGGAGTNNNCTAGCGTTAC | 7273 | TGCAGGACCAGAGAATTCGAATACACCAATTCCNNNCTAGCGTTAC | 7513 |
| TGCAGGACCAGAGAATTCGAATACACTGAAGGANNNCTAGCGTTAC | 7274 | TGCAGGACCAGAGAATTCGAATACATGCGTGATNNNCTAGCGTTAC | 7514 |

FIG. 22C

| Pool-31 | SEQ ID NO: | Pool-32 | SEQ ID NO: |
|---|---|---|---|
| TGCAGGACCAGAGAATTCGAATACAAATCAGTTNNNCTAGCGTTAC | 7275 | TGCAGGACCAGAGAATTCGAATACACTCGGCCTNNNCTAGCGTTAC | 7515 |
| TGCAGGACCAGAGAATTCGAATACACGCAGGCTNNNCTAGCGTTAC | 7276 | TGCAGGACCAGAGAATTCGAATACAACGAATTANNNCTAGCGTTAC | 7516 |
| TGCAGGACCAGAGAATTCGAATACACGGTGCACNNNCTAGCGTTAC | 7277 | TGCAGGACCAGAGAATTCGAATACACCCTACATNNNCTAGCGTTAC | 7517 |
| TGCAGGACCAGAGAATTCGAATACACGTATCAGNNNCTAGCGTTAC | 7278 | TGCAGGACCAGAGAATTCGAATACACGGTTTAGNNNCTAGCGTTAC | 7518 |
| TGCAGGACCAGAGAATTCGAATACATAACGCTGNNNCTAGCGTTAC | 7279 | TGCAGGACCAGAGAATTCGAATACATCGTATAANNNCTAGCGTTAC | 7519 |
| TGCAGGACCAGAGAATTCGAATACAACCGTACANNNCTAGCGTTAC | 7280 | TGCAGGACCAGAGAATTCGAATACATAAGCAAANNNCTAGCGTTAC | 7520 |
| TGCAGGACCAGAGAATTCGAATACAGCTTAGTGNNNCTAGCGTTAC | 7281 | TGCAGGACCAGAGAATTCGAATACACGGTCTGGNNNCTAGCGTTAC | 7521 |
| TGCAGGACCAGAGAATTCGAATACACGAACGCCNNNCTAGCGTTAC | 7282 | TGCAGGACCAGAGAATTCGAATACACCACAGTANNNCTAGCGTTAC | 7522 |
| TGCAGGACCAGAGAATTCGAATACAGTATCGTGNNNCTAGCGTTAC | 7283 | TGCAGGACCAGAGAATTCGAATACAACCACTAGNNNCTAGCGTTAC | 7523 |
| TGCAGGACCAGAGAATTCGAATACATACAAATCNNNCTAGCGTTAC | 7284 | TGCAGGACCAGAGAATTCGAATACACGCAAACTNNNCTAGCGTTAC | 7524 |
| TGCAGGACCAGAGAATTCGAATACACGTCCTTANNNCTAGCGTTAC | 7285 | TGCAGGACCAGAGAATTCGAATACACTTCAACCNNNCTAGCGTTAC | 7525 |
| TGCAGGACCAGAGAATTCGAATACAAGACCACTNNNCTAGCGTTAC | 7286 | TGCAGGACCAGAGAATTCGAATACAGAGAGGCCNNNCTAGCGTTAC | 7526 |
| TGCAGGACCAGAGAATTCGAATACAACAAGGTGNNNCTAGCGTTAC | 7287 | TGCAGGACCAGAGAATTCGAATACAATATTGGTNNNCTAGCGTTAC | 7527 |
| TGCAGGACCAGAGAATTCGAATACAATACTTGANNNCTAGCGTTAC | 7288 | TGCAGGACCAGAGAATTCGAATACACTATATGANNNCTAGCGTTAC | 7528 |
| TGCAGGACCAGAGAATTCGAATACACTTCCGATNNNCTAGCGTTAC | 7289 | TGCAGGACCAGAGAATTCGAATACAATCTTGTTNNNCTAGCGTTAC | 7529 |
| TGCAGGACCAGAGAATTCGAATACACGTCTTGTNNNCTAGCGTTAC | 7290 | TGCAGGACCAGAGAATTCGAATACATAAAGGCGNNNCTAGCGTTAC | 7530 |
| TGCAGGACCAGAGAATTCGAATACAAAGTGGTGNNNCTAGCGTTAC | 7291 | TGCAGGACCAGAGAATTCGAATACACCATTTGCNNNCTAGCGTTAC | 7531 |
| TGCAGGACCAGAGAATTCGAATACATCGGTGGCNNNCTAGCGTTAC | 7292 | TGCAGGACCAGAGAATTCGAATACATACCCCTANNNCTAGCGTTAC | 7532 |
| TGCAGGACCAGAGAATTCGAATACAAAAATCAGNNNCTAGCGTTAC | 7293 | TGCAGGACCAGAGAATTCGAATACAAGAACCGANNNCTAGCGTTAC | 7533 |
| TGCAGGACCAGAGAATTCGAATACATCCCGCGTNNNCTAGCGTTAC | 7294 | TGCAGGACCAGAGAATTCGAATACAACGATAGGNNNCTAGCGTTAC | 7534 |
| TGCAGGACCAGAGAATTCGAATACAGGCACGCTNNNCTAGCGTTAC | 7295 | TGCAGGACCAGAGAATTCGAATACAGGCGCCATNNNCTAGCGTTAC | 7535 |
| TGCAGGACCAGAGAATTCGAATACAGCTGTCTTNNNCTAGCGTTAC | 7296 | TGCAGGACCAGAGAATTCGAATACAAAAATCTCNNNCTAGCGTTAC | 7536 |
| TGCAGGACCAGAGAATTCGAATACAAGCATAAANNNCTAGCGTTAC | 7297 | TGCAGGACCAGAGAATTCGAATACAGACTAGCTNNNCTAGCGTTAC | 7537 |
| TGCAGGACCAGAGAATTCGAATACATGCGAATCNNNCTAGCGTTAC | 7298 | TGCAGGACCAGAGAATTCGAATACACGTGAGTTNNNCTAGCGTTAC | 7538 |
| TGCAGGACCAGAGAATTCGAATACACGTTTCGTNNNCTAGCGTTAC | 7299 | TGCAGGACCAGAGAATTCGAATACACCCGCTGTNNNCTAGCGTTAC | 7539 |
| TGCAGGACCAGAGAATTCGAATACAGCACTCTTNNNCTAGCGTTAC | 7300 | TGCAGGACCAGAGAATTCGAATACAAAAACTTCNNNCTAGCGTTAC | 7540 |
| TGCAGGACCAGAGAATTCGAATACACTCGCTGCNNNCTAGCGTTAC | 7301 | TGCAGGACCAGAGAATTCGAATACAAGTAACGGNNNCTAGCGTTAC | 7541 |
| TGCAGGACCAGAGAATTCGAATACACATACAGCNNNCTAGCGTTAC | 7302 | TGCAGGACCAGAGAATTCGAATACAATCAACATNNNCTAGCGTTAC | 7542 |
| TGCAGGACCAGAGAATTCGAATACAGAGCAAACNNNCTAGCGTTAC | 7303 | TGCAGGACCAGAGAATTCGAATACACTTTTGATNNNCTAGCGTTAC | 7543 |
| TGCAGGACCAGAGAATTCGAATACAGCTTCCATNNNCTAGCGTTAC | 7304 | TGCAGGACCAGAGAATTCGAATACAGTGTACCANNNCTAGCGTTAC | 7544 |
| TGCAGGACCAGAGAATTCGAATACACCTAATTTNNNCTAGCGTTAC | 7305 | TGCAGGACCAGAGAATTCGAATACATGCACACANNNCTAGCGTTAC | 7545 |
| TGCAGGACCAGAGAATTCGAATACAAGCCCGACNNNCTAGCGTTAC | 7306 | TGCAGGACCAGAGAATTCGAATACATATACTTCNNNCTAGCGTTAC | 7546 |
| TGCAGGACCAGAGAATTCGAATACATGGTGAAGNNNCTAGCGTTAC | 7307 | TGCAGGACCAGAGAATTCGAATACAGAAACTAANNNCTAGCGTTAC | 7547 |

FIG. 22D

| Pool-31 | SEQ ID NO: | Pool-32 | SEQ ID NO: |
|---|---|---|---|
| TGCAGGACCAGAGAATTCGAATACAATCGCTGANNNCTAGCGTTAC | 7308 | TGCAGGACCAGAGAATTCGAATACAATCTCGAGNNNCTAGCGTTAC | 7548 |
| TGCAGGACCAGAGAATTCGAATACATTACTGCCNNNCTAGCGTTAC | 7309 | TGCAGGACCAGAGAATTCGAATACAATGTCTGGNNNCTAGCGTTAC | 7549 |
| TGCAGGACCAGAGAATTCGAATACAGGAGGCCANNNCTAGCGTTAC | 7310 | TGCAGGACCAGAGAATTCGAATACAAGACATGGNNNCTAGCGTTAC | 7550 |
| TGCAGGACCAGAGAATTCGAATACATACCTGTCNNNCTAGCGTTAC | 7311 | TGCAGGACCAGAGAATTCGAATACACGGCAATTNNNCTAGCGTTAC | 7551 |
| TGCAGGACCAGAGAATTCGAATACAATATGCTANNNCTAGCGTTAC | 7312 | TGCAGGACCAGAGAATTCGAATACATAATGTTGNNNCTAGCGTTAC | 7552 |
| TGCAGGACCAGAGAATTCGAATACAGATCACCANNNCTAGCGTTAC | 7313 | TGCAGGACCAGAGAATTCGAATACAGCGAGGACNNNCTAGCGTTAC | 7553 |
| TGCAGGACCAGAGAATTCGAATACAGCGGAACGNNNCTAGCGTTAC | 7314 | TGCAGGACCAGAGAATTCGAATACACGAACATCNNNCTAGCGTTAC | 7554 |
| TGCAGGACCAGAGAATTCGAATACAAATCCTTTNNNCTAGCGTTAC | 7315 | TGCAGGACCAGAGAATTCGAATACAGCATGTACNNNCTAGCGTTAC | 7555 |
| TGCAGGACCAGAGAATTCGAATACATACTATAGNNNCTAGCGTTAC | 7316 | TGCAGGACCAGAGAATTCGAATACAGCAACTGTNNNCTAGCGTTAC | 7556 |
| TGCAGGACCAGAGAATTCGAATACAGTCTGTAGNNNCTAGCGTTAC | 7317 | TGCAGGACCAGAGAATTCGAATACAGTACTCTCNNNCTAGCGTTAC | 7557 |
| TGCAGGACCAGAGAATTCGAATACAGACTATCGNNNCTAGCGTTAC | 7318 | TGCAGGACCAGAGAATTCGAATACAGGCTAAAGNNNCTAGCGTTAC | 7558 |
| TGCAGGACCAGAGAATTCGAATACAAGGATTAANNNCTAGCGTTAC | 7319 | TGCAGGACCAGAGAATTCGAATACACCCTTTGANNNCTAGCGTTAC | 7559 |
| TGCAGGACCAGAGAATTCGAATACATTACATCTNNNCTAGCGTTAC | 7320 | TGCAGGACCAGAGAATTCGAATACACGGAGGAGNNNCTAGCGTTAC | 7560 |
| TGCAGGACCAGAGAATTCGAATACATTTGGCAGNNNCTAGCGTTAC | 7321 | TGCAGGACCAGAGAATTCGAATACAGTAAGAATNNNCTAGCGTTAC | 7561 |
| TGCAGGACCAGAGAATTCGAATACACAGTATGCNNNCTAGCGTTAC | 7322 | TGCAGGACCAGAGAATTCGAATACATGATTACANNNCTAGCGTTAC | 7562 |
| TGCAGGACCAGAGAATTCGAATACATTCGATCCNNNCTAGCGTTAC | 7323 | TGCAGGACCAGAGAATTCGAATACACAAAAATGNNNCTAGCGTTAC | 7563 |
| TGCAGGACCAGAGAATTCGAATACAAATCCCCTNNNCTAGCGTTAC | 7324 | TGCAGGACCAGAGAATTCGAATACACCGTGGTGNNNCTAGCGTTAC | 7564 |
| TGCAGGACCAGAGAATTCGAATACACTCTCCCCNNNCTAGCGTTAC | 7325 | TGCAGGACCAGAGAATTCGAATACAAACGTTATNNNCTAGCGTTAC | 7565 |
| TGCAGGACCAGAGAATTCGAATACACAATTAACNNNCTAGCGTTAC | 7326 | TGCAGGACCAGAGAATTCGAATACAGCTTGCAANNNCTAGCGTTAC | 7566 |
| TGCAGGACCAGAGAATTCGAATACAATTTTGCTNNNCTAGCGTTAC | 7327 | TGCAGGACCAGAGAATTCGAATACATTAGTCGGNNNCTAGCGTTAC | 7567 |
| TGCAGGACCAGAGAATTCGAATACAATAAATCCNNNCTAGCGTTAC | 7328 | TGCAGGACCAGAGAATTCGAATACAACGGCCGTNNNCTAGCGTTAC | 7568 |
| TGCAGGACCAGAGAATTCGAATACATACTCGTCNNNGATCGACATG | 7329 | TGCAGGACCAGAGAATTCGAATACAGCGTGAAANNNGATCGACATG | 7569 |
| TGCAGGACCAGAGAATTCGAATACAATGCGAAGNNNGATCGACATG | 7330 | TGCAGGACCAGAGAATTCGAATACATGCCTGCCNNNGATCGACATG | 7570 |
| TGCAGGACCAGAGAATTCGAATACATGCCAGCNNNGATCGACATG | 7331 | TGCAGGACCAGAGAATTCGAATACATCGACGCGNNNGATCGACATG | 7571 |
| TGCAGGACCAGAGAATTCGAATACATGGTAAAANNNGATCGACATG | 7332 | TGCAGGACCAGAGAATTCGAATACATCATCCTGNNNGATCGACATG | 7572 |
| TGCAGGACCAGAGAATTCGAATACACACTCCATNNNGATCGACATG | 7333 | TGCAGGACCAGAGAATTCGAATACAGTCAGTCANNNGATCGACATG | 7573 |
| TGCAGGACCAGAGAATTCGAATACACCTATGCANNNGATCGACATG | 7334 | TGCAGGACCAGAGAATTCGAATACACCGGTGACNNNGATCGACATG | 7574 |
| TGCAGGACCAGAGAATTCGAATACAATGCTCCTNNNGATCGACATG | 7335 | TGCAGGACCAGAGAATTCGAATACATATCGCGANNNGATCGACATG | 7575 |
| TGCAGGACCAGAGAATTCGAATACAGATTGAAANNNGATCGACATG | 7336 | TGCAGGACCAGAGAATTCGAATACAGACGCGTCNNNGATCGACATG | 7576 |
| TGCAGGACCAGAGAATTCGAATACAACACCCAANNNGATCGACATG | 7337 | TGCAGGACCAGAGAATTCGAATACAGAACAGACNNNGATCGACATG | 7577 |
| TGCAGGACCAGAGAATTCGAATACACCGGCATGNNNGATCGACATG | 7338 | TGCAGGACCAGAGAATTCGAATACAGTGTGTNNNGATCGACATG | 7578 |
| TGCAGGACCAGAGAATTCGAATACATCCGATTCNNNGATCGACATG | 7339 | TGCAGGACCAGAGAATTCGAATACAGATTGCGNNNGATCGACATG | 7579 |
| TGCAGGACCAGAGAATTCGAATACAGAATCCTGNNNGATCGACATG | 7340 | TGCAGGACCAGAGAATTCGAATACAGTAGATTTNNNGATCGACATG | 7580 |

FIG. 22E

| Pool-31 | SEQ ID NO: | Pool-32 | SEQ ID NO: |
|---|---|---|---|
| TGCAGGACCAGAGAATTCGAATACATTTCGTCGNNNGATCGACATG | 7341 | TGCAGGACCAGAGAATTCGAATACAGCTTGAGTNNNGATCGACATG | 7581 |
| TGCAGGACCAGAGAATTCGAATACACTTCACTGNNNGATCGACATG | 7342 | TGCAGGACCAGAGAATTCGAATACACGCAACGCNNNGATCGACATG | 7582 |
| TGCAGGACCAGAGAATTCGAATACACCCTATTGNNNGATCGACATG | 7343 | TGCAGGACCAGAGAATTCGAATACACCTAATGGNNNGATCGACATG | 7583 |
| TGCAGGACCAGAGAATTCGAATACAAGTAGTAANNNGATCGACATG | 7344 | TGCAGGACCAGAGAATTCGAATACAGACAGGATNNNGATCGACATG | 7584 |
| TGCAGGACCAGAGAATTCGAATACACACCGTAANNNGATCGACATG | 7345 | TGCAGGACCAGAGAATTCGAATACACTTCCCTTNNNGATCGACATG | 7585 |
| TGCAGGACCAGAGAATTCGAATACATGTTTCCGNNNGATCGACATG | 7346 | TGCAGGACCAGAGAATTCGAATACATAAGAGATNNNGATCGACATG | 7586 |
| TGCAGGACCAGAGAATTCGAATACAGCTGGACCNNNGATCGACATG | 7347 | TGCAGGACCAGAGAATTCGAATACAACCGAATCNNNGATCGACATG | 7587 |
| TGCAGGACCAGAGAATTCGAATACAGTAATTGTNNNGATCGACATG | 7348 | TGCAGGACCAGAGAATTCGAATACAGCCAACATNNNGATCGACATG | 7588 |
| TGCAGGACCAGAGAATTCGAATACAAGCTTATANNNGATCGACATG | 7349 | TGCAGGACCAGAGAATTCGAATACATGGCTAACNNNGATCGACATG | 7589 |
| TGCAGGACCAGAGAATTCGAATACAGCTACCAANNNGATCGACATG | 7350 | TGCAGGACCAGAGAATTCGAATACATCGTTCGTNNNGATCGACATG | 7590 |
| TGCAGGACCAGAGAATTCGAATACAGATAATGANNNGATCGACATG | 7351 | TGCAGGACCAGAGAATTCGAATACACAGTTGCANNNGATCGACATG | 7591 |
| TGCAGGACCAGAGAATTCGAATACAAAATCATCNNNGATCGACATG | 7352 | TGCAGGACCAGAGAATTCGAATACAACTAGCTGNNNGATCGACATG | 7592 |
| TGCAGGACCAGAGAATTCGAATACAAATAGCCCNNNGATCGACATG | 7353 | TGCAGGACCAGAGAATTCGAATACAAAACTAAGNNNGATCGACATG | 7593 |
| TGCAGGACCAGAGAATTCGAATACATGCTGCTTNNNGATCGACATG | 7354 | TGCAGGACCAGAGAATTCGAATACAGTTCGAGNNNGATCGACATG | 7594 |
| TGCAGGACCAGAGAATTCGAATACATTACGCAGNNNGATCGACATG | 7355 | TGCAGGACCAGAGAATTCGAATACACTCATAGGNNNGATCGACATG | 7595 |
| TGCAGGACCAGAGAATTCGAATACACCCAGCCTNNNGATCGACATG | 7356 | TGCAGGACCAGAGAATTCGAATACAGCAGTATCNNNGATCGACATG | 7596 |
| TGCAGGACCAGAGAATTCGAATACACCATTTATNNNGATCGACATG | 7357 | TGCAGGACCAGAGAATTCGAATACATATAGTCANNNGATCGACATG | 7597 |
| TGCAGGACCAGAGAATTCGAATACAGTGCAATCNNNGATCGACATG | 7358 | TGCAGGACCAGAGAATTCGAATACAGGTGTAAGNNNGATCGACATG | 7598 |
| TGCAGGACCAGAGAATTCGAATACACATCAGGTNNNGATCGACATG | 7359 | TGCAGGACCAGAGAATTCGAATACAAGTGAAATNNNGATCGACATG | 7599 |
| TGCAGGACCAGAGAATTCGAATACAGGCCCACANNNGATCGACATG | 7360 | TGCAGGACCAGAGAATTCGAATACAGGTCGTTANNNGATCGACATG | 7600 |
| TGCAGGACCAGAGAATTCGAATACAAAGCACGANNNGATCGACATG | 7361 | TGCAGGACCAGAGAATTCGAATACATCGCGCCTNNNGATCGACATG | 7601 |
| TGCAGGACCAGAGAATTCGAATACACACAGGAANNNGATCGACATG | 7362 | TGCAGGACCAGAGAATTCGAATACAAAGAAACTNNNGATCGACATG | 7602 |
| TGCAGGACCAGAGAATTCGAATACAGCAGCCTGNNNGATCGACATG | 7363 | TGCAGGACCAGAGAATTCGAATACATCCTTTCCNNNGATCGACATG | 7603 |
| TGCAGGACCAGAGAATTCGAATACAGGCTGCGTNNNGATCGACATG | 7364 | TGCAGGACCAGAGAATTCGAATACATGGCGTCGNNNGATCGACATG | 7604 |
| TGCAGGACCAGAGAATTCGAATACACTCTAGCTNNNGATCGACATG | 7365 | TGCAGGACCAGAGAATTCGAATACAGGCTGTCGNNNGATCGACATG | 7605 |
| TGCAGGACCAGAGAATTCGAATACAGAAGGCTANNNGATCGACATG | 7366 | TGCAGGACCAGAGAATTCGAATACATGTCCATCNNNGATCGACATG | 7606 |
| TGCAGGACCAGAGAATTCGAATACATATCTGAANNNGATCGACATG | 7367 | TGCAGGACCAGAGAATTCGAATACAGTGGAAGNNNGATCGACATG | 7607 |
| TGCAGGACCAGAGAATTCGAATACATACTATTCNNNGATCGACATG | 7368 | TGCAGGACCAGAGAATTCGAATACAGTGGACGGNNNGATCGACATG | 7608 |
| TGCAGGACCAGAGAATTCGAATACACATGACCANNNGATCGACATG | 7369 | TGCAGGACCAGAGAATTCGAATACATCCTGGCCNNNGATCGACATG | 7609 |
| TGCAGGACCAGAGAATTCGAATACAATTCAGGCNNNGATCGACATG | 7370 | TGCAGGACCAGAGAATTCGAATACAATAGGCGANNNGATCGACATG | 7610 |
| TGCAGGACCAGAGAATTCGAATACAAACCAACCNNNGATCGACATG | 7371 | TGCAGGACCAGAGAATTCGAATACAATCCGTGANNNGATCGACATG | 7611 |
| TGCAGGACCAGAGAATTCGAATACATTACTGTTNNNGATCGACATG | 7372 | TGCAGGACCAGAGAATTCGAATACAGTAGCTGTNNNGATCGACATG | 7612 |
| TGCAGGACCAGAGAATTCGAATACAGGTTCCCCNNNGATCGACATG | 7373 | TGCAGGACCAGAGAATTCGAATACAGAAGACGTNNNGATCGACATG | 7613 |

FIG. 22F

| Pool-31 | SEQ ID NO: | Pool-32 | SEQ ID NO: |
|---|---|---|---|
| TGCAGGACCAGAGAATTCGAATACAATAAACCTNNNGATCGACATG | 7374 | TGCAGGACCAGAGAATTCGAATACATCCGTACTNNNGATCGACATG | 7614 |
| TGCAGGACCAGAGAATTCGAATACATTTCGTGCNNNGATCGACATG | 7375 | TGCAGGACCAGAGAATTCGAATACATGAGGCAANNNGATCGACATG | 7615 |
| TGCAGGACCAGAGAATTCGAATACAGTGACCATNNNGATCGACATG | 7376 | TGCAGGACCAGAGAATTCGAATACATGAGTTATNNNGATCGACATG | 7616 |
| TGCAGGACCAGAGAATTCGAATACACCCTATACNNNGATCGACATG | 7377 | TGCAGGACCAGAGAATTCGAATACAATTGGTGCNNNGATCGACATG | 7617 |
| TGCAGGACCAGAGAATTCGAATACACCCCATATNNNGATCGACATG | 7378 | TGCAGGACCAGAGAATTCGAATACAGGCGTTGCNNNGATCGACATG | 7618 |
| TGCAGGACCAGAGAATTCGAATACAGATAGGTGNNNGATCGACATG | 7379 | TGCAGGACCAGAGAATTCGAATACAGCATCTCTNNNGATCGACATG | 7619 |
| TGCAGGACCAGAGAATTCGAATACAAAATAACGNNNGATCGACATG | 7380 | TGCAGGACCAGAGAATTCGAATACAACTCTCCANNNGATCGACATG | 7620 |
| TGCAGGACCAGAGAATTCGAATACAATAATCGTNNNGATCGACATG | 7381 | TGCAGGACCAGAGAATTCGAATACAATAAGTAGNNNGATCGACATG | 7621 |
| TGCAGGACCAGAGAATTCGAATACAGTGGACTTNNNGATCGACATG | 7382 | TGCAGGACCAGAGAATTCGAATACAGATTGCCANNNGATCGACATG | 7622 |
| TGCAGGACCAGAGAATTCGAATACAGTTACTGGNNNGATCGACATG | 7383 | TGCAGGACCAGAGAATTCGAATACAGTTCCAGANNNGATCGACATG | 7623 |
| TGCAGGACCAGAGAATTCGAATACATCCTAGGANNNGATCGACATG | 7384 | TGCAGGACCAGAGAATTCGAATACAAACCGTACNNNGATCGACATG | 7624 |
| TGCAGGACCAGAGAATTCGAATACAAAACTTACNNNGATCGACATG | 7385 | TGCAGGACCAGAGAATTCGAATACACGCGTTGGNNNGATCGACATG | 7625 |
| TGCAGGACCAGAGAATTCGAATACAAAGTGCTCNNNGATCGACATG | 7386 | TGCAGGACCAGAGAATTCGAATACAAATTCCAANNNGATCGACATG | 7626 |
| TGCAGGACCAGAGAATTCGAATACAGTATTTTCNNNGATCGACATG | 7387 | TGCAGGACCAGAGAATTCGAATACATGACAGTNNNGATCGACATG | 7627 |
| TGCAGGACCAGAGAATTCGAATACAGAAAGCTGNNNGATCGACATG | 7388 | TGCAGGACCAGAGAATTCGAATACAATGGATTTNNNGATCGACATG | 7628 |
| TGCAGGACCAGAGAATTCGAATACAATCACGACNNNTGCATCAGGT | 7389 | TGCAGGACCAGAGAATTCGAATACAAAGTCCACNNNTGCATCAGGT | 7629 |
| TGCAGGACCAGAGAATTCGAATACAAGGACCTTNNNTGCATCAGGT | 7390 | TGCAGGACCAGAGAATTCGAATACAGTGGCGCTNNNTGCATCAGGT | 7630 |
| TGCAGGACCAGAGAATTCGAATACAGAATGTAANNNTGCATCAGGT | 7391 | TGCAGGACCAGAGAATTCGAATACATCTGGATGNNNTGCATCAGGT | 7631 |
| TGCAGGACCAGAGAATTCGAATACAAAACTGCCNNNTGCATCAGGT | 7392 | TGCAGGACCAGAGAATTCGAATACACCGATGCGNNNTGCATCAGGT | 7632 |
| TGCAGGACCAGAGAATTCGAATACAATACAATCNNNTGCATCAGGT | 7393 | TGCAGGACCAGAGAATTCGAATACAAGTGCTCANNNTGCATCAGGT | 7633 |
| TGCAGGACCAGAGAATTCGAATACAGAGCAGCGNNNTGCATCAGGT | 7394 | TGCAGGACCAGAGAATTCGAATACACAATAGTTNNNTGCATCAGGT | 7634 |
| TGCAGGACCAGAGAATTCGAATACATCGTGTTCNNNTGCATCAGGT | 7395 | TGCAGGACCAGAGAATTCGAATACATACAGGCTNNNTGCATCAGGT | 7635 |
| TGCAGGACCAGAGAATTCGAATACACTGAGCCGNNNTGCATCAGGT | 7396 | TGCAGGACCAGAGAATTCGAATACATATACCTTNNNTGCATCAGGT | 7636 |
| TGCAGGACCAGAGAATTCGAATACACAAGCAGANNNTGCATCAGGT | 7397 | TGCAGGACCAGAGAATTCGAATACAGGAGTAACNNNTGCATCAGGT | 7637 |
| TGCAGGACCAGAGAATTCGAATACAGTCTTACCNNNTGCATCAGGT | 7398 | TGCAGGACCAGAGAATTCGAATACAGCTATGACNNNTGCATCAGGT | 7638 |
| TGCAGGACCAGAGAATTCGAATACACGTCTCCGNNNTGCATCAGGT | 7399 | TGCAGGACCAGAGAATTCGAATACAGTTACACGNNNTGCATCAGGT | 7639 |
| TGCAGGACCAGAGAATTCGAATACAGGCGTTCGNNNTGCATCAGGT | 7400 | TGCAGGACCAGAGAATTCGAATACAGAAGGAAGNNNTGCATCAGGT | 7640 |
| TGCAGGACCAGAGAATTCGAATACACCGCACCTNNNTGCATCAGGT | 7401 | TGCAGGACCAGAGAATTCGAATACAATGACTTANNNTGCATCAGGT | 7641 |
| TGCAGGACCAGAGAATTCGAATACAAGTGGTTCNNNTGCATCAGGT | 7402 | TGCAGGACCAGAGAATTCGAATACATCTCTAATNNNTGCATCAGGT | 7642 |
| TGCAGGACCAGAGAATTCGAATACAGTTGCGTANNNTGCATCAGGT | 7403 | TGCAGGACCAGAGAATTCGAATACAGGAATAATNNNTGCATCAGGT | 7643 |
| TGCAGGACCAGAGAATTCGAATACACCAAATGCNNNTGCATCAGGT | 7404 | TGCAGGACCAGAGAATTCGAATACAATTATACGNNNTGCATCAGGT | 7644 |
| TGCAGGACCAGAGAATTCGAATACAGCTTTGTCNNNTGCATCAGGT | 7405 | TGCAGGACCAGAGAATTCGAATACACAAAGGACNNNTGCATCAGGT | 7645 |
| TGCAGGACCAGAGAATTCGAATACACTTCAATTNNNTGCATCAGGT | 7406 | TGCAGGACCAGAGAATTCGAATACAATAGAATGNNNTGCATCAGGT | 7646 |

FIG. 22G

| Pool-31 | SEQ ID NO: | Pool-32 | SEQ ID NO: |
|---|---|---|---|
| TGCAGGACCAGAGAATTCGAATACAGAATCTGCNNNTGCATCAGGT | 7407 | TGCAGGACCAGAGAATTCGAATACAGGTCTGCGNNNTGCATCAGGT | 7647 |
| TGCAGGACCAGAGAATTCGAATACACCAGGACCNNNTGCATCAGGT | 7408 | TGCAGGACCAGAGAATTCGAATACACATTTTCANNNTGCATCAGGT | 7648 |
| TGCAGGACCAGAGAATTCGAATACAAGAGCATGNNNTGCATCAGGT | 7409 | TGCAGGACCAGAGAATTCGAATACAGCAGAGGCNNNTGCATCAGGT | 7649 |
| TGCAGGACCAGAGAATTCGAATACAACGGCCACNNNTGCATCAGGT | 7410 | TGCAGGACCAGAGAATTCGAATACAGCGGTAGGNNNTGCATCAGGT | 7650 |
| TGCAGGACCAGAGAATTCGAATACACCTAAACGNNNTGCATCAGGT | 7411 | TGCAGGACCAGAGAATTCGAATACAGGAGTCGGNNNTGCATCAGGT | 7651 |
| TGCAGGACCAGAGAATTCGAATACAGGTAACTCNNNTGCATCAGGT | 7412 | TGCAGGACCAGAGAATTCGAATACAACCATTCCNNNTGCATCAGGT | 7652 |
| TGCAGGACCAGAGAATTCGAATACATGGCTGATNNNTGCATCAGGT | 7413 | TGCAGGACCAGAGAATTCGAATACATCAAATGTNNNTGCATCAGGT | 7653 |
| TGCAGGACCAGAGAATTCGAATACAGCCGTAGCNNNTGCATCAGGT | 7414 | TGCAGGACCAGAGAATTCGAATACACAGTTCGANNNTGCATCAGGT | 7654 |
| TGCAGGACCAGAGAATTCGAATACATATCATTCNNNTGCATCAGGT | 7415 | TGCAGGACCAGAGAATTCGAATACAGATCTAATNNNTGCATCAGGT | 7655 |
| TGCAGGACCAGAGAATTCGAATACAGAGCAGTANNNTGCATCAGGT | 7416 | TGCAGGACCAGAGAATTCGAATACATTTCAGTNNNTGCATCAGGT | 7656 |
| TGCAGGACCAGAGAATTCGAATACAGCGTAAGANNNTGCATCAGGT | 7417 | TGCAGGACCAGAGAATTCGAATACAGACAATTTNNNTGCATCAGGT | 7657 |
| TGCAGGACCAGAGAATTCGAATACATCGCAAACNNNTGCATCAGGT | 7418 | TGCAGGACCAGAGAATTCGAATACAGCCGTAATNNNTGCATCAGGT | 7658 |
| TGCAGGACCAGAGAATTCGAATACAGAAGCTTCNNNTGCATCAGGT | 7419 | TGCAGGACCAGAGAATTCGAATACAAATACAAGNNNTGCATCAGGT | 7659 |
| TGCAGGACCAGAGAATTCGAATACATATTACCTNNNTGCATCAGGT | 7420 | TGCAGGACCAGAGAATTCGAATACAGTCCGCGANNNTGCATCAGGT | 7660 |
| TGCAGGACCAGAGAATTCGAATACATGCATGTGNNNTGCATCAGGT | 7421 | TGCAGGACCAGAGAATTCGAATACACCATCATCNNNTGCATCAGGT | 7661 |
| TGCAGGACCAGAGAATTCGAATACAGCTTTGAGNNNTGCATCAGGT | 7422 | TGCAGGACCAGAGAATTCGAATACACCTGTCATNNNTGCATCAGGT | 7662 |
| TGCAGGACCAGAGAATTCGAATACATCCTATTANNNTGCATCAGGT | 7423 | TGCAGGACCAGAGAATTCGAATACAGCTTCCTANNNTGCATCAGGT | 7663 |
| TGCAGGACCAGAGAATTCGAATACACGTCAGGCNNNTGCATCAGGT | 7424 | TGCAGGACCAGAGAATTCGAATACAACCCAACANNNTGCATCAGGT | 7664 |
| TGCAGGACCAGAGAATTCGAATACACCGCGATGNNNTGCATCAGGT | 7425 | TGCAGGACCAGAGAATTCGAATACAAAACGCGANNNTGCATCAGGT | 7665 |
| TGCAGGACCAGAGAATTCGAATACAGGTTGTCANNNTGCATCAGGT | 7426 | TGCAGGACCAGAGAATTCGAATACATCTGCATCNNNTGCATCAGGT | 7666 |
| TGCAGGACCAGAGAATTCGAATACAGCAGCAAANNNTGCATCAGGT | 7427 | TGCAGGACCAGAGAATTCGAATACAATTCCAAANNNTGCATCAGGT | 7667 |
| TGCAGGACCAGAGAATTCGAATACAGCGTAACTNNNTGCATCAGGT | 7428 | TGCAGGACCAGAGAATTCGAATACACACCAAGTNNNTGCATCAGGT | 7668 |
| TGCAGGACCAGAGAATTCGAATACAGAGAGTCANNNTGCATCAGGT | 7429 | TGCAGGACCAGAGAATTCGAATACAGCACAACTNNNTGCATCAGGT | 7669 |
| TGCAGGACCAGAGAATTCGAATACACTATGCCTNNNTGCATCAGGT | 7430 | TGCAGGACCAGAGAATTCGAATACAAGGTGGATNNNTGCATCAGGT | 7670 |
| TGCAGGACCAGAGAATTCGAATACAAACCGAAGNNNTGCATCAGGT | 7431 | TGCAGGACCAGAGAATTCGAATACATGCTAGCANNNTGCATCAGGT | 7671 |
| TGCAGGACCAGAGAATTCGAATACACGGCCCGGNNNTGCATCAGGT | 7432 | TGCAGGACCAGAGAATTCGAATACATTGTGAGCNNNTGCATCAGGT | 7672 |
| TGCAGGACCAGAGAATTCGAATACAAAGCGCCCNNNTGCATCAGGT | 7433 | TGCAGGACCAGAGAATTCGAATACAAGTTTCGGNNNTGCATCAGGT | 7673 |
| TGCAGGACCAGAGAATTCGAATACAATAAGGATNNNTGCATCAGGT | 7434 | TGCAGGACCAGAGAATTCGAATACAGCTAGTACNNNTGCATCAGGT | 7674 |
| TGCAGGACCAGAGAATTCGAATACAAGCTGAGANNNTGCATCAGGT | 7435 | TGCAGGACCAGAGAATTCGAATACATAGGTGCTNNNTGCATCAGGT | 7675 |
| TGCAGGACCAGAGAATTCGAATACACTCTGACTNNNTGCATCAGGT | 7436 | TGCAGGACCAGAGAATTCGAATACACATTACGGNNNTGCATCAGGT | 7676 |
| TGCAGGACCAGAGAATTCGAATACATCGCAGGCNNNTGCATCAGGT | 7437 | TGCAGGACCAGAGAATTCGAATACATGCAATTANNNTGCATCAGGT | 7677 |
| TGCAGGACCAGAGAATTCGAATACAATATTAGCNNNTGCATCAGGT | 7438 | TGCAGGACCAGAGAATTCGAATACATGGCCCTNNNTGCATCAGGT | 7678 |
| TGCAGGACCAGAGAATTCGAATACAACCGTATGNNNTGCATCAGGT | 7439 | TGCAGGACCAGAGAATTCGAATACAGCTGCAGCNNNTGCATCAGGT | 7679 |

FIG. 22H

| Pool-31 | SEQ ID NO: | Pool-32 | SEQ ID NO: |
|---|---|---|---|
| TGCAGGACCAGAGAATTCGAATAC AGGTCGGTCNNNTGCATCAGGT | 7440 | TGCAGGACCAGAGAATTCGAATA CATTTGCCCANNNTGCATCAGGT | 7680 |
| TGCAGGACCAGAGAATTCGAATAC AATATCGTANNNTGCATCAGGT | 7441 | TGCAGGACCAGAGAATTCGAATA CAGACCATTGNNNTGCATCAGGT | 7681 |
| TGCAGGACCAGAGAATTCGAATAC AACCTCTCANNNTGCATCAGGT | 7442 | TGCAGGACCAGAGAATTCGAATA CACCGCGTAGNNNTGCATCAGGT | 7682 |
| TGCAGGACCAGAGAATTCGAATAC AGTCGGTGCNNNTGCATCAGGT | 7443 | TGCAGGACCAGAGAATTCGAATA CATTAGCTGGNNNTGCATCAGGT | 7683 |
| TGCAGGACCAGAGAATTCGAATAC ATTCGCCCGNNNTGCATCAGGT | 7444 | TGCAGGACCAGAGAATTCGAATA CATCTGATTTNNNTGCATCAGGT | 7684 |
| TGCAGGACCAGAGAATTCGAATAC ACAGGCTGCNNNTGCATCAGGT | 7445 | TGCAGGACCAGAGAATTCGAATA CATCATAGGCNNNTGCATCAGGT | 7685 |
| TGCAGGACCAGAGAATTCGAATAC ATCGCTTACNNNTGCATCAGGT | 7446 | TGCAGGACCAGAGAATTCGAATA CATGGAGGTANNNTGCATCAGGT | 7686 |
| TGCAGGACCAGAGAATTCGAATAC ACGGATTGTNNNTGCATCAGGT | 7447 | TGCAGGACCAGAGAATTCGAATA CAGTCTCTACNNNTGCATCAGGT | 7687 |
| TGCAGGACCAGAGAATTCGAATAC ACAAGCTGTNNNTGCATCAGGT | 7448 | TGCAGGACCAGAGAATTCGAATA CAGCCTGGTGNNNTGCATCAGGT | 7688 |

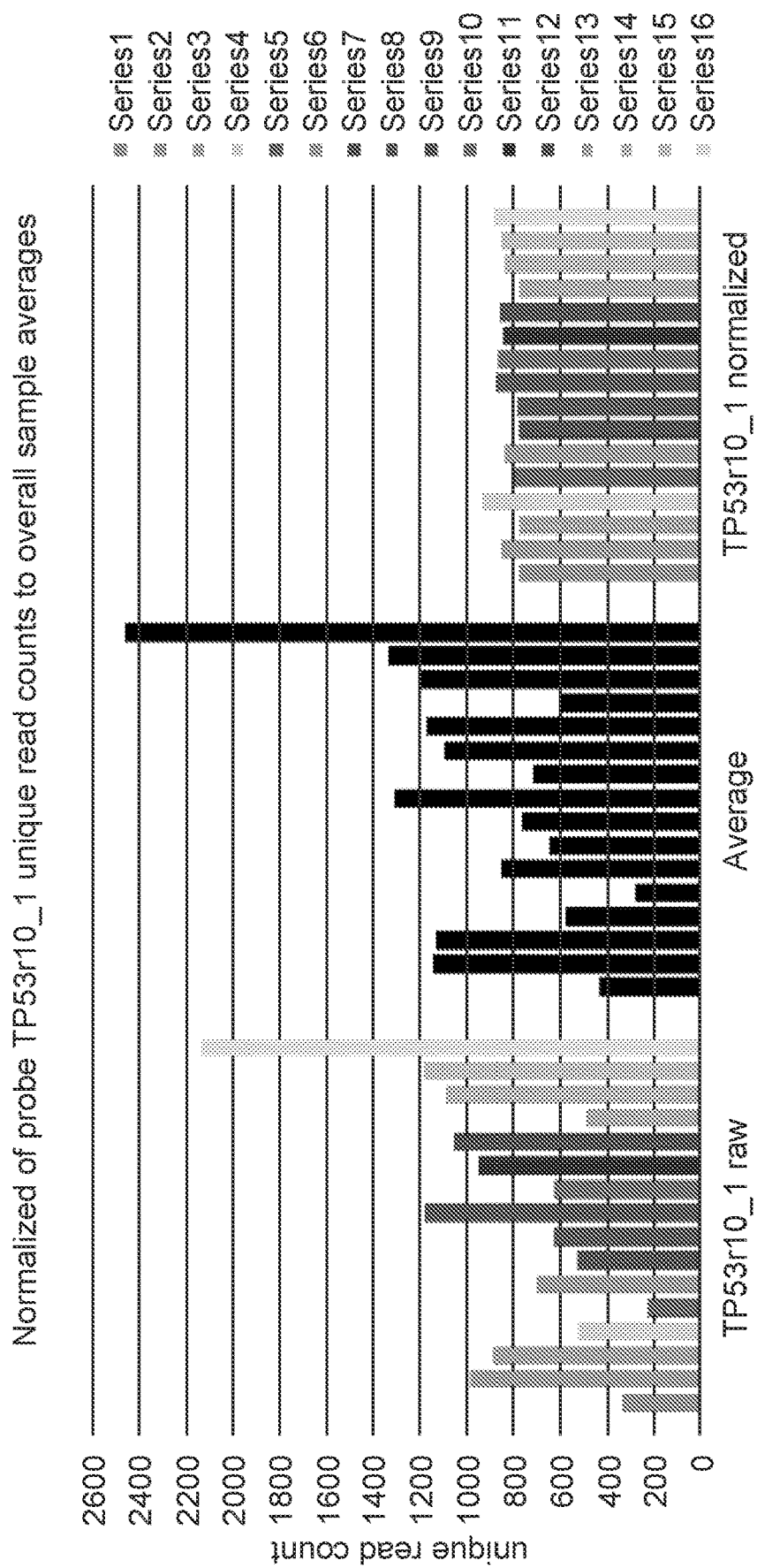

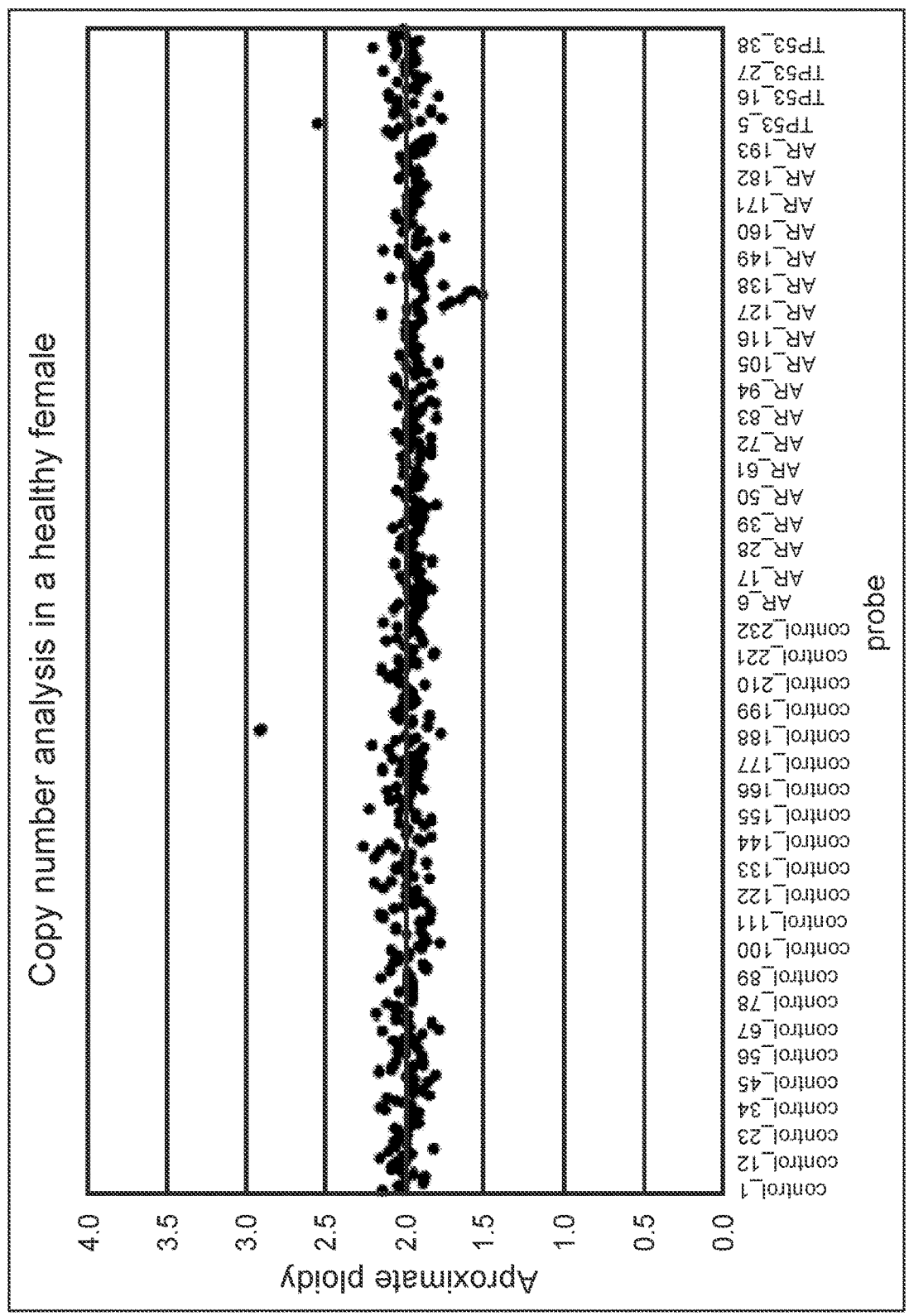

METHODS FOR THE DETECTION OF GENOMIC COPY CHANGES IN DNA SAMPLES

REFERENCE TO RELATED APPLICATIONS

This application claims priority to U.S. Provisional Patent Application No. 62/379,593, filed Aug. 25, 2016, and U.S. Provisional Patent Application No. 62/481,538, filed Apr. 4, 2017, each of which are incorporated herein by reference in their entireties.

STATEMENT REGARDING SEQUENCE LISTING

The sequence listing associated with this application is provided in text format in lieu of a paper copy, and is hereby incorporated by reference into the specification. The name of the text file containing the sequence listing is CLFK_005_02US_SeqList_ST25. The text file is 2,238 KB, was created on Aug. 24, 2017, and is being submitted electronically via EFS-Web.

TECHNICAL FIELD

The invention relates generally to compositions and methods for the quantitative genetic analysis of biological samples, e.g., direct tissue biopsies or peripheral blood. In particular, the present invention relates to methods for detection of target-specific copy number change, as well as genetic characterization and analysis, of biological samples.

BACKGROUND

It is becoming increasing clear that most, if not all, of the most common human cancers are diseases of the human genome. It is thought that somatic mutations accumulate during an individual's lifetime, some of which increase the probability that the cell in which they are harbored can develop into a tumor. With just the wrong combination of accumulated mutational events, a precancerous growth loses constraints that keep uncontrolled proliferation in check and the resulting cell mass becomes a cancer. The constellations of mutations that are necessary and sufficient to cause cancer are often collectively referred to as "driver mutations." One of the themes that have emerged from recent and intensive molecular analysis is that cancer, once thought of as a single, tissue-specific disease, is in fact a group of related diseases, each with a unique molecular pathology. The human genome project laid the groundwork for genome-wide analysis of cancers.

Changes in gene copy number are a fundamental driver of biological diversity. In the context of evolution, duplication of genes and divergence of function is a well-recognized driver of species diversity. In the context of human disease, gene loss and gene amplification within somatic cells are hallmarks of diseased tissues such as cancer. Certain therapeutic agents act specifically on cells with these genomic gain and/or loss mutations, however, the identification of these copy number variations is difficult because often such mutations are only present within the DNA of diseased or cancerous cells and are not found in other cells of the body. While the diseased tissue or cells is the major source of the mutated DNA, acquiring DNA through a biopsy is invasive, risky and often not possible. The observation that dying tumor or cancer cells release small pieces of their DNA into the bloodstream, termed cell free DNA or circulating DNA has allowed for the development of genetic tests that can be performed with less invasive techniques, such as a blood sample. However, only small amounts of DNA can be obtained from isolating cell free DNA from a sample, and only a portion of the total DNA will carry the mutation associated with the disease. For example, in the context of cancer genomics, diagnostically significant tumor mutations are often only found at minor allele frequencies that are significantly less than 50%. This is in contrast to conventional SNP genotyping where allele frequencies are generally ~100%, 50% or 0%.

Thus there is a need for genomic techniques capable of detecting genetic copy number changes in specific target loci.

BRIEF SUMMARY

Methods of detecting rare mutations in cfDNA have been previously described in International PCT Publication No. WO 2016/028316. However, these techniques still lack the requisite sensitivity to detect the rarest copy number losses at very minor allele frequencies. Provided herein are compositions and methods for detection of target-specific copy number change that are applicable to several sample types, including direct tissue biopsies, peripheral blood, and in particular cfDNA, The compositions and methods described herein are sensitive enough to detect changes in copy number that are present only a tiny fraction of the total DNA.

The present invention includes, inter alia, compositions and methods that are useful for the detection of a mutational change, SNP, translocation, inversion, deletion, change in copy number, or other genetic variation within a sample of cellular genomic DNA (e.g., from a tissue biopsy sample) or cfDNA (e.g., from a blood sample). In particular, the compositions and methods of the present invention provide an extremely high level of resolution that is particularly useful in detecting copy number variations in a small fraction of the total cfDNA from a biological sample (e.g., blood).

Particular embodiments are drawn to a method for performing a genetic analysis on a DNA target region from a test sample comprising: (a) generating a genomic DNA library comprising a plurality of DNA library fragments, wherein each of the DNA library fragments comprises a genomic DNA fragment from the test sample and an adaptor; (b) contacting the genomic DNA library with a plurality of capture probes that specifically bind to a DNA target region, thereby forming complexes between the capture probes and DNA library fragments comprising the DNA target region; and (c) performing a quantitative genetic analysis of the genomic DNA fragments comprising the DNA target region; wherein the adaptor is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes an identity of the unique library DNA fragment and encodes an identity of the test sample; wherein the anchor region comprises a polynucleotide sequence that encodes the identity of the test sample and wherein the anchor region is capable of attaching to the genomic DNA fragment; and wherein the genetic analysis is performed to detect a genetic change indicative of a disease state.

In some embodiments, the genetic change indicative of a disease state is selected from a single nucleotide variant (SNV), an insertion less than 40 nucleotides in length, a deletion of a DNA region less than 40 nucleotides in length, and/or a change in copy number. In particular embodiments, the genetic change indicative of a disease state is a change in copy number. In some embodiments, the test sample is a tissue biopsy. In various embodiments, the tissue biopsy is taken from a tumor or a tissue suspected of being a tumor. In certain embodiments, the genomic DNA is cell free DNA (cfDNA) or cellular DNA. In particular embodiments, the genomic DNA is cfDNA is isolated from the test sample; and wherein the test sample is a biological sample selected from the group consisting of: amniotic fluid, blood, plasma, serum, semen, lymphatic fluid, cerebral spinal fluid, ocular fluid, urine, saliva, stool, mucous, and sweat.

In certain embodiments, the genomic DNA fragments are obtained the steps comprising; (i) isolating cellular DNA from the test sample; and (ii) fragmenting the cellular DNA to obtain the genomic DNA fragments. In particular embodiments, step (ii) is performed by contacting the cellular DNA with at least one digestion enzyme. In some embodiments, step (ii) is performed by applying mechanical stress to the cellular DNA. In certain embodiments, the mechanical stress is applied by sonicating the cellular DNA.

In particular embodiments, the sample tag further comprises a unique molecule identifier (UMI) that facilitates the identification of the unique genomic DNA fragment.

In some embodiments, the amplification region is between 10 and 50 nucleotides in length. In particular embodiments, the amplification region is between 20 and 30 nucleotides in length. In certain embodiments, the amplification region is 25 nucleotides in length.

In some embodiments, the sample tag is between 5 and 50 nucleotides in length. In particular embodiments, the sample tag is between 5 and 15 nucleotides in length. In certain embodiments, the sample tag is 8 nucleotides in length. In some embodiments, the UMI multiplier is adjacent to or contained within the sample tag region.

In certain embodiments, the UMI multiplier is between 1 and 5 nucleotides in length. In particular embodiments, the UMI multiplier is 3 nucleotides in length, and comprises one of 64 possible nucleotide sequences.

In some embodiments, the anchor region is between 1 and 50 nucleotides in length. In particular embodiments, the anchor region is between 5 and 25 nucleotides in length. In certain embodiments, the anchor region is 10 nucleotides in length.

Particular embodiments of the present invention are drawn to methods where the step of (a) generating a genomic DNA library comprising a plurality of DNA library fragments, comprises attaching the genomic DNA fragments to a plurality of adaptors. In certain embodiments, the genomic DNA fragments are end repaired prior to attaching the genomic DNA fragments with a plurality of adaptors. In particular embodiments, the amplification regions of each adaptor of the plurality of adaptors comprises an identical nucleotide sequence.

In certain embodiments, the sample tag region of each adaptor of the plurality of adaptors comprise one of between 2 and 1,000 nucleotide sequences. In particular embodiments, the sample tag region of each adaptor of the plurality of adaptors comprise one of between 50 and 500 nucleotide sequences. In various embodiments, the sample tag region of each adaptor of the plurality of adaptors comprises one of between 100 and 400 nucleotide sequences. In some embodiments, the sample tag region of each adaptor of the plurality of adaptors comprises one of between 200 and 300 nucleotide sequences. In certain embodiments, the sample tag region of each adaptor of the plurality of adaptors is 8 nucleotides in length. In some embodiments, each sequence of the nucleotide sequences are discrete from any other sequence of the 240 nucleotide sequences by Hamming distance of at least two.

In particular embodiments, each of the plurality of adaptors comprises a UMI multiplier that is adjacent to or contained within the sample tag region. In some embodiments, each of the plurality of adaptors comprises a UMI multiplier that is adjacent to the sample tag region. In certain embodiments, the UMI multiplier of each adaptor of the plurality of adaptors is between 1 and 5 nucleotides in length. In some embodiments, the UMI multiplier of each adaptor of the plurality of adaptors is three nucleotides in length.

In particular embodiments, the anchor tag region of each adaptor of the plurality of adaptors comprises one of four nucleotide sequences, and each sample region of a given sequence is paired to only one of the four anchor regions of a given sequence.

In some embodiments, the amplification regions of each adaptor of the plurality of adaptors comprises an identical nucleotide sequence; the sample tag region of each adaptor of the plurality of adaptors is 8 nucleotides in length; the nucleotide sequence of each sample tag is discrete from any other nucleotide sequence of the sample tags of the plurality of adaptors by Hamming distance of at least two; each of the plurality of adaptors comprises a UMI multiplier that is adjacent to or contained within the sample tag region; the UMI multiplier of each adaptor of the plurality of adaptors is three nucleotides in length; and the UMI multiplier of each of the possible nucleotide sequences is paired to each sample tag region of the plurality of adaptors; the anchor tag region of each adaptor of the plurality of adaptors comprises one of four nucleotide sequences: and each sample region of a given sequence is paired to only one of the four anchor regions of a given sequence.

Particular embodiments of the present invention are drawn to a method where the step of attaching the genomic DNA fragments with a plurality of adaptors comprises: (i) attaching an oligonucleotide comprising least a portion of an anchor region to each genomic DNA fragment, wherein the oligonucleotide comprising least a portion of an anchor region is a DNA duplex comprising a 5' phosphorylated attachment strand duplexed with a partner strand, wherein the partner strand is blocked from attachment by chemical modification at its 3' end, and wherein the attachment strand is attached to the genomic DNA fragment; (ii) contacting the genomic DNA fragments attached to the oligonucleotides comprising at least a portion of the anchor region with DNA oligonucleotides encoding full length adaptor sequences for each adaptor nucleotide sequence of the plurality of adaptors; and (iii) contacting the genomic DNA fragments and the DNA oligonucleotides encoding the full length adaptor sequence with T4 polynucleotide kinase, Taq DNA ligase and full-length Bst polymerase under conditions suitable for DNA ligation; thereby attaching the plurality of adaptors to the genomic DNA fragments. In some embodiments, the genomic DNA fragments are cfDNA. In certain embodiments, the DNA target region is analyzed for a change in copy number.

In particular embodiments, step (c) performing a quantitative genetic analysis of the genomic DNA fragments comprising the DNA target region comprises purification of the complexes formed between the capture probes and DNA library fragments comprising the DNA target region. In certain embodiments, step (c) comprises purification of the complexes formed between the capture probes and DNA library fragments comprising the DNA target region, preforming primer extension and/or amplification of the DNA library fragments comprising the region of interest from the genomic DNA library. In some embodiments, step (c) comprises purification of the complexes formed between the capture probes and DNA library fragments comprising the DNA target region, preforming primer extension and amplification of the DNA library fragments comprising the region of interest from the genomic DNA library. In certain embodiments, step (c) comprises DNA sequencing of the DNA library fragments comprising the DNA target region to generate a plurality of sequencing reads.

In some embodiments, the present invention is drawn to a method wherein the genomic analysis comprises determining a change of copy number in a DNA region of interest, and wherein step (c), performing a quantitative genetic analysis of the genomic DNA fragments comprising the DNA target region, comprises determining a copy number of the region of interest present in the genomic DNA library derived from the test sample, and comparing it to a copy number of the region of interest present in the genomic DNA library derived from a reference sample, wherein the reference sample comprises a known copy number of the DNA target region.

In some embodiments, determining the copy number in the region of interest comprises DNA sequencing of the DNA library fragments comprising the DNA target region to generate a plurality of sequencing reads, wherein each sequencing read comprises a unique molecular identification element (UMIE). In some embodiments, the UMIE comprises sequencing information from the adaptor and at least a portion of the genomic DNA sequence. In some embodiments, sequencing reads comprising identical UMIEs are identified as a unique genomic sequence (UGS).

In some embodiments, methods of determining the copy number further comprise determining a raw genomic depth (RGD) for each of the capture probes contacted with the genomic DNA library. In some embodiments, determining the RGD comprises determining the average number of UGSs associated with each capture probe sequence within a group of sample replicates. In some embodiments, capture probes associated with a highly variable number of UGSs are identified as noisy probes and are removed from further calculations. In some embodiments, determining the RGD further comprises calculating an RGD for a sample, comprising calculating a numerical average of all RGDs for all capture probes in the sample. In some embodiments, the RGD values for noisy probes are not included in calculating an RGD for a sample.

In some embodiments, the RGDs for the capture probes are normalized across all samples in an experimental group by converting the RGD for each capture probe into a probe-specific, normalized read count comprising (i) multiplying each capture probe RGD in a sample by a normalization constant, wherein the normalization constant comprises any real number; and (ii) dividing the product of (i) by the RGD calculated for the corresponding sample; or (iii) dividing the product of (i) by an average RGD calculated from a subset of probes. In some embodiments, the subset of probes is a set of control probes.

In some embodiments, the probe-specific, normalized read counts are converted in to a copy number value comprising (i) multiplying the probe-specific, normalized read counts of probes directed to autosomal and/or X-linked regions by 2 in samples derived from females; (ii) multiplying the probe-specific, normalized read counts of probes directed to Y-linked and/or X-linked regions by 1 in samples derived from males; (iii) averaging the products of (i) and/or (ii) across all samples in an experiment; and (iv) dividing the product of (i) and/or (ii) by the average of (iii). In some embodiments, the approximate copy number values for all probes that target a specific gene are averaged.

In some embodiments, the present invention is drawn to a method for highly sensitive detection of copy number gain and copy number loss comprising (i) determining an RGD for a capture probe; (ii) normalizing the RGD for the capture probe across all samples in an experimental group by converting the RGD for the capture probe into a probe-specific, normalized read count; (iii) calculating an approximate copy number value for each probe-specific, normalized read count; and (iv) averaging the approximate copy number values for all probes that target a specific gene.

In some embodiments, the present invention is drawn to a method for measuring chromosome stability comprising (i) designing and validating a set of one or more chromosomal stability probes, wherein the chromosomal stability probes are uniformly distributed across human chromosomes; (ii) performing targeted sequencing on patient samples using the one or more chromosomal stability probes; (iii) determining an approximate copy number value for each chromosomal probe; (iv) determining a genomic phenotype of a patient sample, wherein fluctuations in the copy number values for one or more chromosomal probes in the patient sample indicate genomic instability.

In some embodiments, the present invention is drawn to a method of treating a cancer in a subject in need thereof, wherein the subject has been identified as having a destabilized genome according to the method claim 62, wherein the method of treating the cancer comprises administering a pharmaceutically effective amount of a PARP inhibitor.

In some embodiments, the present invention is drawn to a method wherein the genomic analysis comprises determining a change of copy number in a DNA region of interest, and wherein step (c), performing a quantitative genetic analysis of the genomic DNA fragments comprising the DNA target region, comprises determining a copy number of the region of interest present in the genomic DNA library derived from the test sample, and comparing it to a copy number of the region of interest present in the genomic DNA library derived from a reference sample, wherein the reference sample comprises a known copy number of the DNA target region. In some embodiments, the region of interest is a gene or a portion of the gene. In particular embodiments, the gene is associated with a disease. In certain embodiments, the disease is a cancer. In various embodiments, the gene is BRCA2, ATM, BRCA1, BRIP1, CHEK2, FANCA, HDAC2, and/or PALB2.

Particular embodiments are drawn to a genomic DNA library comprising a plurality of DNA library fragments, wherein each of the DNA library fragments comprises an adaptor and a genomic DNA fragment; wherein the adaptor is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes an identity of the unique library DNA fragment and encodes an identity of the test sample; and wherein the anchor region comprises a polynucleotide sequence that encodes the identity of the test sample, and wherein the anchor region is capable of attaching to the genomic DNA fragment. In some embodiments, the sample tag further comprises a unique molecule identifier (UMI), wherein the UMI facilitates the identification of the unique genomic DNA fragment. In particular embodiments, the amplification region is between 10 and 50 nucleotides in length. In particular embodiments, the amplification region is 25 nucleotides in length. In particular embodiments, the sample tag is between 5 and 50 nucleotides in length. In certain embodiments, the sample tag is 8 nucleotides in length. In some embodiments, the UMI multiplier is adjacent to or contained within the sample tag region. In particular embodiments, the UMI multiplier is between 1 and 5 nucleotides in length. In certain embodiments, the anchor region is between 1 and 50 nucleotides in length. In some embodiments, the anchor region is 10 nucleotides in length. In particular embodiments, the amplification regions of each adaptor of the plurality of adaptors comprises an identical nucleotide sequence. In some embodiments, each nucleotide sequence of the sample tags are discrete from any other sequence of the nucleotide sequences of the sample by Hamming distance of at least two. In certain embodiments, each of the plurality of adaptors comprises a UMI multiplier that is adjacent to or contained within the sample tag region. In particular embodiments, each of the plurality of adaptors comprises a UMI multiplier that is adjacent to the sample tag region. In some embodiments, the anchor tag region of each adaptor of the plurality of adaptors comprises one of four nucleotide sequences, and wherein each sample region of a given sequence is paired to only one of the four anchor regions of a given sequence. In some embodiments, the genomic DNA fragment is cfDNA.

In certain embodiments, the amplification regions of each adaptor of the plurality of adaptors comprises an identical nucleotide sequence; the sample tag region of each adaptor of the plurality of adaptors is 8 nucleotides in length, the sample tag region of each adaptor of the plurality of adaptors comprises a nucleotide sequence that is discrete from any other nucleotide sequence of the sample tags of the plurality of adaptors by Hamming distance of at least two, the each of the plurality of adaptors comprises a UMI multiplier that is adjacent to or contained within the sample tag region, the UMI multiplier of each adaptor of the plurality of adaptors is three nucleotides in length, and the UMI multiplier of each of the possible nucleotide sequences is paired to each of the sample tag regions of the plurality of adaptors, the anchor tag region of each adaptor of the plurality of adaptors comprises one of four nucleotide sequences, and each sample region of a given sequence is paired to only one of the four anchor regions of a given sequence. In some embodiments, the genomic DNA fragment is cfDNA.

Certain embodiments are drawn to a plurality of genomic DNA libraries, comprising more than one genomic library described herein. In some embodiments, the nucleic acid sequences of the sample tag regions of a genomic DNA library belonging to the plurality of genomic DNA libraries are different from the nucleic acid sequences of the sample tag regions of other genomic DNA libraries belonging to the plurality of genomic DNA libraries. In particular embodiments, the nucleic acid sequences of the amplification regions of a genomic DNA library belonging to the plurality of genomic DNA libraries are identical to the nucleic acid sequences of the amplification regions of other genomic DNA libraries belonging to the plurality of genomic DNA libraries.

Certain embodiments are drawn to a method for genetic analysis of a DNA target region of cell free DNA (cfDNA) comprising: (a) generating a DNA library as described herein; (b) contacting the cfDNA library with a plurality of capture probes that specifically bind to a DNA target region, thereby forming complexes between the capture probes and DNA library fragments comprising the DNA target region; and (c) performing a quantitative genetic analysis of the cfDNA fragments comprising the DNA target region; thereby performing genetic analysis of the DNA target region.

Certain embodiments are directed to a method of predicting, diagnosing, or monitoring a genetic disease in a subject comprising: (a) obtaining a test sample from the subject; (b) isolating genomic DNA from the test sample; (c) generating a DNA library comprising a plurality of DNA library fragments, wherein each of the DNA library fragments comprises a genomic DNA fragment from the test sample and an adaptor; (d) contacting the cfDNA library with a plurality of capture probes that specifically bind to a DNA target region, thereby forming complexes between the capture probes and DNA library fragments comprising the DNA target region; and (e) performing a quantitative genetic analysis of one or more target genetic loci associated with the genetic disease in the cfDNA clone library, wherein the identification or detection of one or more genetic lesions in the one or more target genetic loci is prognostic for, diagnostic of, or monitors the progression of the genetic disease. In particular embodiments, the quantitative genetic analysis comprises DNA sequencing to generate a plurality of sequencing reads.

Particular embodiments are drawn to a set of adaptors that encode an identify of a unique genomic DNA fragment and an identity of a test sample, for use in generating a genomic DNA library, wherein each adaptor in said set of adapters is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes the identity of the unique library DNA fragment and encodes the identity of the test sample; and wherein the anchor region comprises a polynucleotide sequence that encodes the identity of the test sample, and wherein the anchor region is capable of attaching to the genomic DNA fragment. In some embodiments, the sample tag further comprises a unique molecule identifier (UMI), wherein the UMI facilitates the identification of the unique genomic DNA fragment. In various embodiments, the amplification region is between 10 and 50 nucleotides in length. In certain embodiments, the amplification region is 25 nucleotides in length. In particular embodiments, the sample tag is between 5 and 50 nucleotides in length. In some embodiments, the sample tag is 8 nucleotides in length. In particular embodiments, the UMI multiplier is adjacent to or contained within the sample tag region. In some embodiments, the UMI multiplier is between 1 and 5 nucleotides in length. In particular embodiments, the anchor region is between 1 and 50 nucleotides in length. In some embodiments, the anchor region is 10 nucleotides in length. In certain embodiments, the amplification regions of each adaptor of the plurality of adaptors comprises an identical nucleotide sequence.

In some embodiments, each nucleotide sequence of the sample tags is discrete from any other nucleotide sequence of the sample tags of the set of adaptors by Hamming distance of at least two. In various embodiments, each of the plurality of adaptors comprises a UMI multiplier that is adjacent to or contained within the sample tag region. In particular embodiments, each of the plurality of adaptors comprises a UMI multiplier that is adjacent to the sample tag region.

In some embodiments, the anchor tag region of each adaptor of the plurality of adaptors comprises one of four nucleotide sequences, and wherein each sample region of a given sequence is paired to only one of the four anchor regions of a given sequence. The set of adaptors claim 75, wherein the amplification regions of each adaptor of the plurality of adaptors comprises an identical nucleotide sequence; wherein the sample tag region of each adaptor is 8 nucleotides in length, wherein each nucleotide sequence of the sample tags is discrete from any other nucleotide sequence of the sample tags of the set of adaptors by Hamming distance of at least two, wherein each of the plurality of adaptors comprises a UMI multiplier that is adjacent to or contained within the sample tag region, wherein the UMI multiplier of each adaptor of the plurality of adaptors is three nucleotides in length, wherein the UMI multiplier comprises one of 64 possible nucleotide sequences, and wherein the UMI multiplier of each of the 64 possible nucleotide sequences is paired to each of the sample tag region of the plurality of adaptors, wherein the anchor tag region of each adaptor of the plurality of adaptors comprises one of four nucleotide sequences, and wherein each sample region of a given sequence is paired to only one of the four anchor regions of a given sequence.

BRIEF DESCRIPTION OF THE SEVERAL VIEWS OF THE DRAWINGS

FIG. 4A shows the first generation adaptor design. FIG. 4B shows that in the first generation adaptors, there were a collection of 249 possible sequence tags, each 5 nucleotides (nt) in length that attached to a single anchor sequence. FIG. 4C shows a diagram of a second generation adaptor. FIG. 4D shows an illustrative set of adaptors that are applied to a single sample that consists of four sets of 8 mer tag sequences with each set having 60 members. Each set of 60 tags is specific to one of four anchor sequences. FIG. 4E shows an illustrative DNA sequence of a 47 nt adaptor.

FIG. 6A shows the step where the 10 nt anchor sequence is attached to the 3' ends of genomic fragments. FIG. 6B shows the step where the full length genomic adaptors are annealed to the initial anchor sequence.

FIG. 8A-FIG. 8C shows conventional box-and-whiskers plots of measured gene copies across eight samples as determined by CNL analysis.

FIG. 11A shows conversion of cfDNA to a genomic library by the addition of adaptor sequences that provide universal, single-primer PCR amplification sequences, sample multiplexing tags, and unique molecular identifiers to every genomic clone. FIG. 11B shows denatured amplified genomic hybridized with target specific capture probes and primer extension. FIG. 11C shows a schematic of asymmetric paired-end sequencing. FIG. 11D shows mapping statistics for 377,711,020 Illumina NextSeq reads from a typical targeted capture sequence run. 98.5% of reads map to their intended targets. Following de-duplication, 20.40% of reads (77,053,048) are derived from unique genomic clones.

FIG. 12A-FIG. 12H shows sequences of adaptor oligonucleotides from Pools 1-3.

FIG. 13A-FIG. 13H shows sequences of adaptor oligonucleotides from Pools 4-6.

FIG. 14A-FIG. 14I shows sequences of adaptor oligonucleotides from Pools 7-9.

FIG. 15A-FIG. 15H shows sequences of adaptor oligonucleotides from Pools 10-12.

FIG. 16A-FIG. 16H shows sequences of adaptor oligonucleotides from Pools 13-15.

FIG. 17A-FIG. 17H shows sequences of adaptor oligonucleotides from Pools 16-18.

FIG. 18A-FIG. 18H shows sequences of adaptor oligonucleotides from Pools 19-21.

FIG. 19A-FIG. 19H shows sequences of adaptor oligonucleotides from Pools 22-24.

FIG. 20A-FIG. 20H shows sequences of adaptor oligonucleotides from Pools 25-27.

FIG. 21A-FIG. 21H shows sequences of adaptor oligonucleotides from Pools 28-30.

FIG. 22A-FIG. 22H shows sequences of adaptor oligonucleotides from Pools 31-32.

FIG. 23A illustrates BedFile display of capture probes. FIG. 23B illustrates coverage depth at each base position on a scale of 0 to 8000 unique reads. FIG. 23C illustrates a UCSC gene model display of known TP53 splice variants. The thicker rectangular regions represent the amino acid coding regions for the TP53-encoded protein.

FIG. 24A-FIG. 24C illustrate raw and normalized unique read density for a single probe, TP53r10_1, across 16 samples. FIG. 24A illustrates the number of raw unique reads capture by probe TP53r10_1 for 16 independent sample after removal of redundant reads by "de-duplication." FIG. 24B shows global average of unique reads across 2596 capture probes for all 16 samples. FIG. 24C shows normalized unique read depth across 16 samples (Calculated as: [sample n unique reads from probe TP53r10_1× constant÷global average unique reads/probe from sample n]).

FIG. 27A-FIG. 27C illustrate copy number analysis of cfDNA from a healthy female and male donor and from an advanced stage prostate cancer patient. FIG. 27A shows analysis of a cfDNA from a healthy female donor. The x-axis is a series of control probes that target regions from all 22 autosomal chromosomes, a series of probes that target the X-linked AR gene, and a series of probes that target the coding regions of the TP53 gene. The Y-axis shows the calculated ploidy for each probe. This approximation is calculated for each probe by normalizing the observed unique read counts to a series of control samples whose ploidy is known ([unique read count for probe_Y of sample_Z]×2÷[average unique read count for probe_Y for multiple control samples]). FIG. 27B illustrates that the X-linked AR gene exhibits a haploid copy number in healthy males. FIG. 27C illustrates copy number analysis of cfDNA from an advanced prostate cancer patient and shows evidence of very significant aneuploidy across the control probes, amplification of the AR gene, and loss of the TP53 gene.

DETAILED DESCRIPTION

A. Overview

Figure 1:
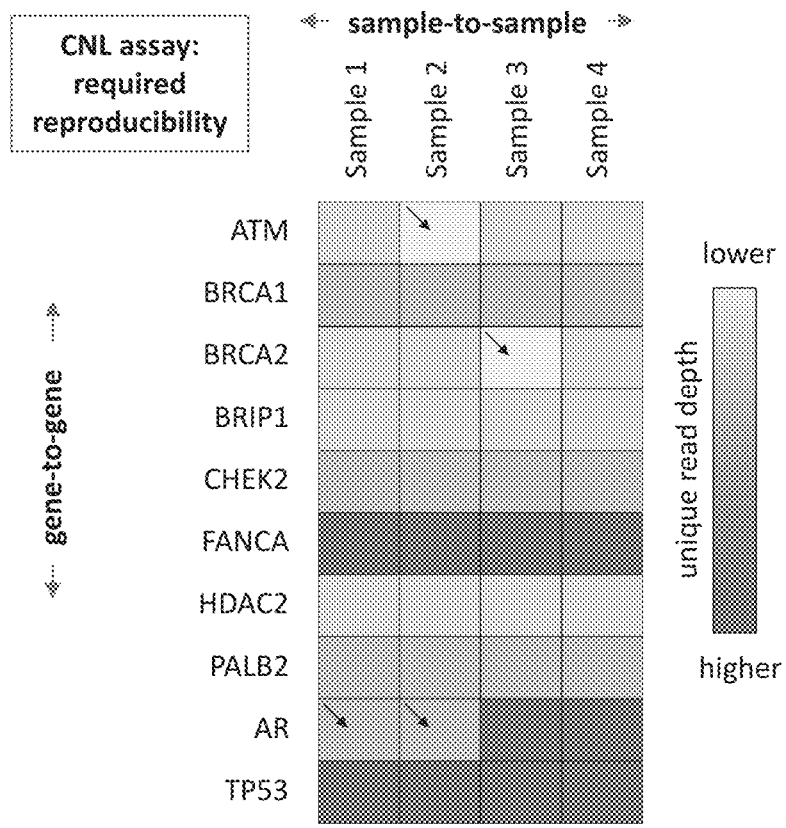
FIG. 1 shows the framework of the copy number loss (CNL) assay. Each gene (rows) exhibits a characteristic unique read value that is represented here by a shade. Each sample (columns) is interrogated across the same panel of genes.

The present invention includes, inter alia, compositions and methods that are useful for the detection of a mutational change, SNP, translocation, inversion, deletion, change in copy number or other genetic variation within a sample of cellular genomic DNA (e.g. from a tissue biopsy sample) or cfDNA (e.g. from a blood sample). The compositions and methods of the current invention are particularly useful in detecting incredibly hard to detect copy number variations in cfDNA from a biological sample (e.g. blood) with exquisite resolution. In particular, some embodiments of the present invention are drawn to a method for the detecting copy number of a DNA target region from a test sample by generating a genomic DNA library made up of genomic DNA fragments attached to an adaptor, capturing DNA target regions with a plurality of capture probes, isolating the DNA library fragments comprising the DNA target region, and performing a quantitative genetic analysis of the DNA target region to thereby determining the copy number of the DNA target region. The adaptors described herein allow for the identification of the individual DNA fragment that is being sequenced, as well as the identity of the sample or source of the genomic DNA.

The present invention contemplates, in part, compositions and methods for detection of target-specific copy number changes that are applicable to several sample types, including but not limited to direct tissue biopsies and peripheral blood. In the context of cancer genomics, and in particular cell free DNA (cfDNA) assays for the analysis of solid tumors, the amount of tumor DNA is often a very small fraction of the overall DNA. Further, copy number loss is difficult to detect in genomic DNA assays, and in particular, genomic DNA assays where copy number change may only be present in a portion of the total genomic DNA from a sample, e.g., cfDNA assays. For example, most of the cell-free DNA extracted from a cancer patient will be derived from normal sources and have a diploid copy number (except for X-linked genes in male subjects). In a cancer patient, the fraction of DNA derived from tumors often has a low minor allele frequency, such as for example, a patient in which 2% of the circulating DNA extracted from plasma is derived from the tumor. The loss of one copy of a tumor suppressor gene (for example, BRCA1 in breast cancer) means that the minor allele frequency for the absence of detectable genomic fragments is 1%. In this scenario, a copy number loss assay engineered must be able to discriminate between 100 copies (normal) and 99 copies (heterozygous gene loss). Thus, particular embodiments contemplate that the methods and compositions of the present invention allow for the detection of copy number change with sufficient resolution to detect changes in copy number at minor allele frequencies even in the context of cfDNA.

To achieve this level of discrimination, the present invention provides novel sample adaptor designs. The adaptors of the present invention are designed to include features that are critical for successful copy number loss assay performance including (i) even performance across adaptors; (ii) a high number of unique molecule identifiers (UMIs); (iii) high efficiency attachment; and (iv) accommodation of sample multiplexing. For example, the adaptors of the present invention provide the following:

Even performance across adaptors: Bioinformatics analysis often looks at intra-sample probe performance and inter-sample probe performance. Thus, it is contemplated that any performance fluctuation between adaptor pools across samples will negatively impact the ability to detect the subtle variations required by CNL analysis. In the present invention, this evenness of performance is achieved by having multiple anchor tags that are all represented in each sample tag pool, with the fixed sample tag regions (which serve to identify both the sample and the genomic fragments) being randomly selected for each pool, and a UMI multiplier that increases the unique sample tag sequences for identifying the genomic fragments.

High number of Unique Molecule Identifiers (UMIs): While adaptors must be functionally equivalent from a molecular biology perspective, they must possess a very large number of unique sequence tags (≥10,000) that augment the identification of unique genomic fragments. In this context, by "augment," it is meant that each genomic clone fragment has a particular pair of fragmentation sites corresponding to the position in the genomic sequence where the double-strand DNA was cleaved. This cleavage site is used to differentiate unique genomic clones since each clone is likely to possess a different cleavage site. However, in libraries that possess thousands of independent clones, uniquely derived fragments will often possess the exact same cleavage sites. Genomic clones (i.e. fragments) sharing the same cleavage site can be classified as either unique or as redundant with respect to other clone sequences derived from the same sample. By attaching adaptors that introduce a high diversity of sequence tags, different genomic clones sharing the same cleavage site are more likely to be identified as unique. In this system, the UMI is created by a combination of the sample tag region with the UMI multiplier. The combination of the UMI and the cleavage site create a unique molecular identifier element (UMIE), which facilitates the classification of sequence reads as redundant reads or unique reads. Particular embodiments contemplate that the UMI multiplier could comprise longer or shorter sequences to increase or lower the overall UMI complexity.

High efficiency attachment: Adaptors must attach to genomic fragments with high efficiency. In most oncology applications, the quantities of available cellular DNA or cfDNA are limited and therefore conversion of these genomic fragments to genomic library clones must be highly efficient. In order to achieve this, in some aspects of the present invention, the adaptor systems described herein convert about 25% to about 50% or greater of the genomic input fragments are converted into genomic library clones.

Accommodation of sample multiplexing: In general, there must be pools of different sets of adaptors where each unique adaptor of the set is attached to a different sample. At the same time, each member of the set of adaptors must possess essentially identical behavior (from a sequence counting perspective) to all other members in a set. In order to achieve this, in some embodiments, the sample tag regions have a Hamming distance of 2 between any other possible sample tag combinations reducing the chance for a read to be spuriously assigned to the wrong sample. In some embodiments, each set of adaptors is split into pools that are paired with specific anchor regions, allowing for further reduction in the possibility of an error in sample de-multiplexing. For example, in an 8 mer tag with Hamming distance of 2, the total number of possible sequences is 16,384.

In a particular embodiment, pre-specified pools of adaptor oligonucleotides are provided. Such pre-specified pools are used to represent a single sample. That is, each adapter sequence in each pool of X adapter oligonucleotides (16,384 in the example given above) is distinct from each adapter sequence in every other pool used to identify other samples. One of skill in the art will recognize the number of distinct pre-specified pools that are possible for the adapter oligonucleotides will depend on the length of the sample tag and/or the UMI multiplier.

Thus, in certain embodiments the adaptors comprise a sequence, i.e., the sample tag and adjacent and/or encompassed UMI multiplier that represents or identifies both the sample and uniquely identifies the genetic fragment. This is in stark contrast to the current systems that are used in the art that use a randomly generated tag to identify the sequence and a separate barcode or sequencer indexing to allow for multiplexing.

Figure 3:
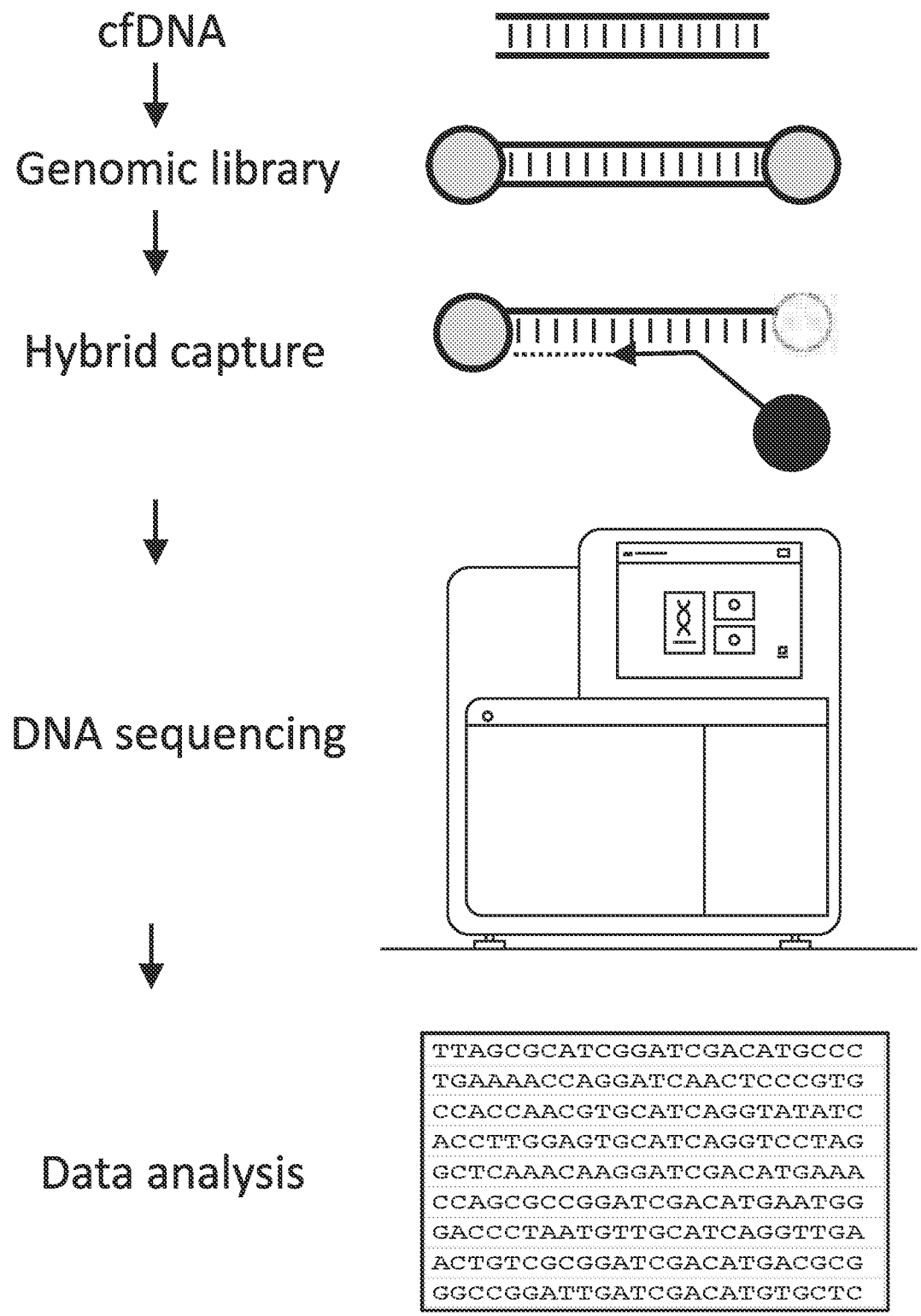
FIG. 3 shows a diagram illustrating steps of an illustrative CNL assay performed on cell free DNA (cfDNA).

An illustrative embodiment for detecting target-specific copy number changes within DNA obtained from a sample is shown in FIG. 3. While FIG. 3 generates a DNA library from cfDNA, this illustrative procedure could be used with DNA from other sources, e.g., fragmented cellular DNA. As shown in FIG. 3, cfDNA is collected (top panel). Next, a genomic library is generated from cfDNA by conjugating genomic library adaptors (gray circles) of the present invention to the genomic DNA. Genomic DNA fragments are captured with capture probes (black circles) that recognize the genomic region of interested. The genomic DNA of interest is sequenced, and data analysis is performed for copy loss analysis and/or characterization of the genomic DNA of interest.

The practice of particular embodiments of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*. Greene Pub. Associates and Wiley-Interscience; Glover, *DNA Cloning: A Practical Approach*, vol. I & II (IRL Press. Oxford, 1985); Anand, *Techniques for the Analysis of Complex Genomes*, (Academic Press, New York, 1992); *Transcription and Translation* (B. Hames & S. Higgins. Eds., 1984); Perbal. *A Practical Guide to Molecular Cloning* (1984); and Harlow and Lane, Antibodies. (Cold Spring Harbor Laboratory Press. Cold Spring Harbor, N.Y., 1998).

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers to a range of quantity, level, value, number, frequency, percentage, dimension, size, amount, weight or length±15%, ±10%, ±9%, ±8%, ±7%, ±6%, ±5%, ±4%, ±3%, +2%, or ±1% about a reference quantity, level, value, number, frequency, percentage, dimension, size, amount, weight or length.

Throughout this specification, unless the context requires otherwise, the words "comprise", "comprises," and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

As used herein, the term "DNA" refers to deoxyribonucleic acid. In various embodiments, the term DNA refers to genomic DNA, recombinant DNA, synthetic DNA, or cDNA. In one embodiment, DNA refers to genomic DNA or cDNA. In particular embodiments, the DNA comprises a "target region." DNA libraries contemplated herein include genomic DNA libraries and cDNA libraries constructed from RNA, e.g., an RNA expression library. In various embodiments, the DNA libraries comprise one or more additional DNA sequences and/or tags.

The terms "target genetic locus" and "DNA target region" are used interchangeably herein and refer to a region of interest within a DNA sequence. In various embodiments, targeted genetic analyses are performed on the target genetic locus. In particular embodiments, the DNA target region is a region of a gene that is associated with a particular genetic state, genetic condition, genetic diseases; fetal testing; genetic mosaicism, paternity testing; predicting response to drug treatment; diagnosing or monitoring a medical condition; microbiome profiling; pathogen screening; or organ transplant monitoring. In further embodiments, the DNA target region is a DNA sequence that is associated with a particular human chromosome, such as a particular autosomal or X-linked chromosome, or region thereof (e.g., a unique chromosome region).

As used herein, the terms "circulating DNA," "circulating cell-free DNA," and "cell-free DNA" are often used interchangeably and refer to DNA that is extracellular DNA, DNA that has been extruded from cells, or DNA that has been released from necrotic or apoptotic cells. This term is often used in contrast to "cellular genomic DNA" or "cellular DNA," which are used interchangeably herein and refer to genomic DNA that is contained within the cell (i.e. the nuclease) and is only accessible to molecular biological techniques such as those described herein, by lysing or otherwise disrupting the integrity of the cell.

A "subject," "individual," or "patient" as used herein, includes any animal that exhibits a symptom of a condition that can be detected or identified with compositions contemplated herein. Suitable subjects include laboratory animals (such as mouse, rat, rabbit, or guinea pig), farm animals (such as horses, cows, sheep, pigs), and domestic animals or pets (such as a cat or dog). In particular embodiments, the subject is a mammal. In certain embodiments, the subject is a non-human primate and, in preferred embodiments, the subject is a human.

As used herein, the term "paired" when used with respect to two different polynucleotide sequences or regions of DNA comprising different polynucleotide sequences, means that the two different polynucleotide sequences or regions of DNA comprising different polynucleotide sequences are present on the same polynucleotide. For example, if a particular sample tag region of DNA is said to be paired to particular amplification region of DNA, it is meant that the sample tag region and the amplification tag are present on the same DNA polynucleotide molecule.

C. Methods of Copy Number Analysis

In various embodiments, a method for copy number analysis of a DNA target region DNA is provided. In certain embodiments, copy number analysis is performed by generating a genomic DNA library of DNA library fragments that each contain genomic DNA fragment and an adaptor, isolating the DNA library fragments containing the DNA target regions, and performing a quantitative genetic analysis of the DNA target region. By "quantitative genetic analysis" it is meant an analysis performed by any molecular biological technique that is able to quantify changes in a DNA (e.g., a gene, genetic locus, target region of interest, etc.) including but not limited to DNA mutations, SNPs, translocations, deletions, and copy number variations (CNVs). In certain embodiments, the quantitative genetic analysis is performed by sequencing, for example, next generation sequencing.

Next-generation DNA sequencing (NGS) is ideally suited for two diagnostic applications. The first is the determination of DNA sequence on a vast scale. In the present context, this capability enables the search for rare, actionable variants that guide effective treatment decisions. The second is counting gene copy number. The output of millions of independent sequences can enable precise measurement of gene copy number on a genome-wide scale. The emergence of non-invasive prenatal testing for fetal trisomy from maternal blood samples is a testament to this capability. RNAseq, that is, the technology of gene expression profiling using NGS is another example, albeit the input is RNA (cDNA) rather than genomic DNA. Comparisons of current capture methods are described Samorodnitsky et al. J Mol Diagn. 2015 January; 17(1):64-75.

The present invention extends NGS counting capability into the realm of targeted hybrid capture methods. The methods described here are effective for the detection of copy number variation at least in part because they possess the following four qualities:

(a) The present methods differentiate between unique clones and redundant clones. NGS sequencing of amplified genomic DNA library fragments results in a plurality of individual NGS reads, each comprising adaptor-encoded sequence information linked to a specific human genomic sequence. These elements define the identity of every clone. Because captured genomic regions are amplified by PCR, it is not uncommon for the same clone to be encountered several times in a subsequent NGS analysis. Groups of reads that are derived from a single cloning and capture process are termed "redundant reads." Two or more redundant reads are identified as redundant reads based on the sequencing information provided by the unique molecular identification elements (UMIE). The UMIE refers to the combination of the sequence information from the adaptor tags and the start of the genomic DNA sequence. Two or more reads comprising identical UMIEs are identified as redundant reads. Redundant reads are grouped together and a single, representative consensus sequence is assembled from families of redundant reads. This consensus sequence is designated as a "unique read" or a "unique genomic sequence" (UGS). Each unique read represents a separate clone from the original DNA specimen. The process of identifying and grouping redundant clone families and of generating a single unique read representative of this family is defined as "deduplication." The adaptors used to create genomic libraries possess a very deep repertoire of unique sample tag information (15,360 codes per adaptor). When applied in conjunction with the exact mapping coordinates of each captured genomic clone (which can span >100 different positions relative to a capture probe), each unique clone that is generated in a genomic library and subsequently retrieved by a target-specific capture probe has an extremely high likelihood of being differentiable from all other unique clones that encompass the same capture environment. The ability to differentiate between unique clones and redundant clones is central to the methods described herein.

(b) The adaptors used to create genomic libraries permit sample multiplexing without creating adaptor-to-adaptor variability in copy number counts. A central foundation of copy number determination is the simultaneous analysis of a set of samples that have all been processed within a single sequencing run. This allows positive and negative controls to be included along with clinical samples. A major issue with previous adaptor design iterations induced subtle shifts in gene copy counts among identical control samples, in effect setting a signal-to-noise uncertainty threshold that was too high to be clinically useful in blood-based, solid tumor genotyping assays. The present invention overcomes this issue and substantially lowers the signal-to-noise threshold such that single copy gene loss is detectable at ≤2% minor allele frequency. This improved signal recognition enables the methods of the present invention to have significant clinical utility in circulating tumor DNA assays.

(c) The proprietary targeted hybrid capture method used herein must produce highly uniform "on-target" read coverage across all targets. Methods that rely on counting of unique genomic fragments to estimate copy number, such as the ones described herein, must achieve near-saturation in terms of encountering all possible unique fragments. Near-saturation is only achieved by oversampling, that is to say, gathering more sequencing reads than the number of unique reads that will ultimately be encountered. To be practical, scalable, and economical, the unique reads in a targeted hybrid capture library must exhibit sufficient uniformity such that <10-fold oversampling of on-target reads, and preferably <4-fold oversampling of on-target reads will capture >90% of unique on-target reads at all target loci.

(d) The targeted hybrid capture method (See U.S. Patent Publication No. 2014-0274731) must have high on-target capture rates. To be practical, scalable and economical, in other words to be a distinguishing feature of the present disclosure relative to other art in the field, the method must achieve >90%, preferably >95% on-target reads. With on-target mapping rates exceeding 95%, the requirement for 4 to 10-fold oversampling of on-target reads and the requirement for overall oversampling are one in the same.

In some embodiments, the number of copies of the DNA target region present in the sample is determined by the quantitative genetic analysis. In some embodiments, the copy number of the DNA target region is determined by comparing the amount of copies of DNA target regions present in the sample and comparing it to amounts of DNA target regions present in one or more samples with known copy number.

Particular embodiments contemplate that the compositions and methods described herein are particularly useful for detecting changes in copy number in a sample of genomic DNA, where only a portion of the total genomic DNA in the sample has a change in copy number. For example, a significant tumor mutation may be present in a sample, e.g. a sample of cell free DNA, that is present in a minor allele frequency that is significantly less than 50% (e.g., in the range of 0.1% to >20%), in contrast to conventional SNP genotyping where allele frequencies are generally ~100%, 50% or 0%. One of skill of the art will recognize that the compositions and methods of the current invention are also useful in detecting other types of mutation including single nucleotide variants (SNVs), short (e.g., less than 40 base pairs (bp)) insertions, and deletions (indels), and genomic rearrangements including oncogenic gene fusions.

In certain embodiments, the compositions and/or methods of the present invention described herein are useful for, capable of, suited for, and/or able to detect, identify, observe, and/or reveal a change in copy number of one or more DNA target regions present in less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.5%, less than about 0.2%, or less than about 0.1% of the total genomic DNA from the sample. In some embodiments, the methods of the present invention are useful for, capable of, suited for, and/or able to detect, identify, observe, and/or reveal a change in copy number of one or more DNA target regions present in between about 0.01% to about 100%, about 0.01% to about 50%, and or about 0.1% to about 20% of the total genomic DNA from the sample.

Particular embodiments are represented by the conceptual framework that is illustrated in FIG. 1. In FIG. 1, each gene is represented by a row and each patient sample is represented as a column. Within any given genomic DNA sample, the number of fragments counted for each individual gene will have some variability, and that for any given DNA region of interest, e.g. a gene, perturbations in copy number are detected as significant fragment count deviations relative to the normalized counts to the DNA target region in other samples. Such an assay requires the gene-by-gene fragment counting profile within a sample to be reproducible, and also requires the sample-by-sample counting profiles to be highly comparable. Both assay requirements demand excellent signal-to-noise counting discrimination.

Figure 2:
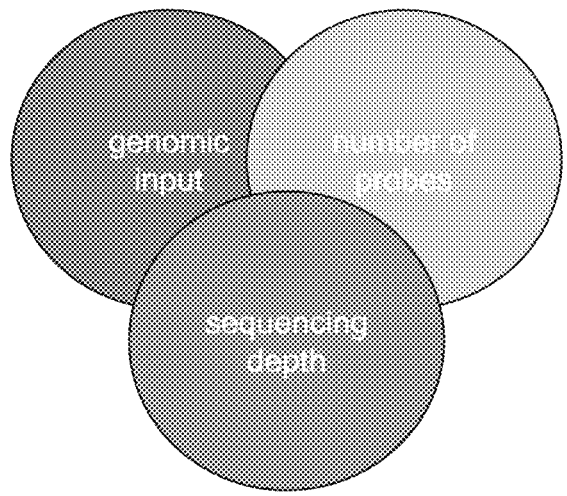
FIG. 2 shows a diagram illustrating the drivers of the CNL assay signal.

Some embodiments contemplate that the assay elements that contribute to increasing the signal to noise ratio are the genomic input, the number of probes, and the sequencing depth, as illustrated in FIG. 2.

In particular embodiments, a method for genetic analysis of cfDNA comprises: generating and amplifying a cfDNA library, determining the number of genome equivalents in the cfDNA library; and performing a quantitative genetic analysis of one or more genomic target loci.

Particular embodiments contemplate that the any of the methods and compositions described herein are effective for use to efficiently analyze, detect, diagnose, and/or monitor genetic states, genetic conditions, genetic diseases, genetic mosaicism, fetal diagnostics, paternity testing, microbiome profiling, pathogen screening, and organ transplant monitoring using genomic DNA, e.g., cellular or cfDNA, where all or where only a portion of the total genomic DNA in the sample has a feature of interest, e.g. a genetic lesion, mutation, single nucleotide variant (SNV). In some embodiments, a feature of interest is a genetic feature associated with a disease or condition. For example, a significant tumor mutation may be present in a sample, e.g. a sample of cfDNA, that is present in a minor allele frequency that is significantly less than 50% (e.g. in the range of 0.1% to >20%), in contrast to conventional SNP genotyping where allele frequencies are generally ~100%, 50% or 0%.

In certain embodiments, the compositions and/or methods of the present invention described herein are useful for, capable of, suited for, and/or able to detect, identify, observe, and/or reveal a genetic lesion of one or more DNA target regions present in less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.5%, less than about 0.2%, or less than about 0.1% of the total genomic DNA from the sample. In some embodiments, the methods of the present invention are useful for, capable of, suited for, and/or able to detect, identify, observe, and/or reveal a genetic lesion of one or more DNA target regions present in between about 0.01% to about 100%, about 0.01% to about 50%, and or about 0.1% to about 20% of the total genomic DNA from the sample.

1. Generating a DNA Library

In particular embodiments, methods of genetic analysis contemplated herein comprise generating a DNA library comprising treating cfDNA or fragmented cellular genomic DNA with one or more end-repair enzymes to generate end-repaired DNA and attaching one or more adaptors to each end of the end-repaired DNA to generate the DNA library. Genomic DNA In particular embodiments, the methods and compositions contemplated herein are designed to efficiently analyze, detect, diagnose, and/or monitor change in copy number using genomic DNA as an analyte. In certain embodiments, copy number analysis is performed by generating a genomic DNA library from genomic DNA obtained from a test sample, e.g., a biological sample such as a tissue biopsy. In certain embodiments, the genomic DNA is circulating or cell free DNA. In some embodiments, the genomic DNA is cellular genomic DNA.

In certain embodiments, genomic DNA is obtained from a tissue sample or biopsy taken from a tissue, including but not limited to, bone marrow, esophagus, stomach, duodenum, rectum, colon, ileum, pancreases, lung, liver, prostate, brain, nerves, meningeal tissue, renal tissue, endometrial tissue, cervical tissue, breast, lymph node, muscle, and skin. In certain embodiments, the tissue sample is a biopsy of a tumor or a suspected tumor. In particular embodiments, the tumor is cancerous or suspected of being cancerous. In particular embodiments, the tissue sample comprises cancer cells or cells suspected of being cancerous.

Methods for purifying genomic DNA from cells or from a biologic tissue comprised of cells are well known in the art, and the skilled artisan will recognize optimal procedures or commercial kits depending on the tissue and the conditions in which the tissue is obtained. Some embodiments contemplate that purifying cellular DNA from a tissue will require cell disruption or cell lysis to expose the cellular DNA within, for example by chemical and physical methods such as blending, grinding or sonicating the tissue sample; removing membrane lipids by adding a detergent or surfactants which also serves in cell lysis, optionally removing proteins, for example by adding a protease; removing RNA, for example by adding an RNase; and DNA purification, for example from detergents, proteins, salts and reagents used during cell lysis step. DNA purification may be performed by precipitation, for example with ethanol or isopropanol; by phenol-chloroform extraction.

In particular embodiments, cellular DNA obtained from tissues and/or cells are fragmented prior to and or during obtaining, generating, making, forming, and/or producing a genomic DNA library as described herein. One of skill in the art will understand that there are several suitable techniques for DNA fragmentation, and is able to recognize and identify suitable techniques for fragmenting cellular DNA for the purposes of generating a genomic DNA library for DNA sequencing, including but not limited to next-generation sequencing. Certain embodiments contemplate that cellular DNA can be fragmented into fragments of appropriate and/or sufficient length for generating a library by methods including but not limited to physical fragmentation, enzymatic fragmentation, and chemical shearing.

Physical fragmentation can include, but is not limited to, acoustic shearing, sonication, and hydrodynamic shear. In some embodiments, cellular DNA is fragmented by physical fragmentation. In particular embodiments, cellular DNA is fragmented by acoustic shearing or sonication. Particular embodiments contemplate that acoustic shearing and sonication are common physical methods used to shear cellular DNA. The Covaris® instrument (Woburn, Mass.) is an acoustic device for breaking DNA into 100-5 kb bp. Covaris also manufactures tubes (gTubes) which will process samples in the 6-20 kb for Mate-Pair libraries. The Bioruptor® (Denville, N.J.) is a sonication device utilized for shearing chromatin, DNA and disrupting tissues. Small volumes of DNA can be sheared to 150-1 kb in length. Hydroshear from Digilab (Marlborough, Mass.) utilizes hydrodynamic forces to shear DNA. Nebulizers (Life Tech, Grand Island, N.Y.) can also be used to atomize liquid using compressed air, shearing DNA into 100-3 kb fragments in seconds. Nebulization is low cost, but the process can cause a loss of about 30% of the cellular DNA from the original sample. In certain embodiments, cellular DNA is fragmented by sonication.

Enzymatic fragmentation can include, but is not limited to, treatment with a restriction endonuclease, e.g. DNase I, or treatment with a nonspecific nuclease. In some embodiments, cellular DNA is fragmented by enzymatic fragmentation. In particular embodiments, the cellular DNA is fragmented by treatment with a restriction endonuclease. In some embodiments, the cellular DNA is fragmented by treatment with a nonspecific nuclease. In certain embodiments, the cellular DNA is fragmented by treatment with a transposase. Certain embodiments contemplate that enzymatic methods to shear cellular DNA into small pieces include DNAse I, a combination of maltose binding protein (MBP)-T7 Endo I and a non-specific nuclease *Vibrio vulnificus* (Vvn) New England Biolabs's (Ipswich, Mass.) Fragmentase and Nextera tagmentation technology (Illumina, San Diego. Calif.). The combination of non-specific nuclease and T7 Endo synergistically work to produce non-specific nicks and counter nicks, generating fragments that disassociate 8 nucleotides or less from the nick site. Tagmentation uses a transposase to simultaneously fragment and insert adapters onto double stranded DNA.

Chemical fragmentation can include treatment with heat and divalent metal cation. In some embodiments, genomic DNA is fragmented by chemical fragmentation. Particular embodiments contemplate that chemical shear is more commonly used for the breakup of long RNA fragments as opposed to genomic DNA. Chemical fragmentation is typically performed through the heat digestion of DNA with a divalent metal cation (magnesium or zinc). The length of DNA fragments can be adjusted by increasing or decreasing the time of incubation.

In particular embodiments, the methods and compositions contemplated herein are designed to efficiently analyze, detect, diagnose, and/or monitor change in copy number using cell-free DNA (cfDNA) as an analyte. The size distribution of cfDNA ranges from about 150 bp to about 180 bp fragments. Fragmentation of cfDNA may be the result of endonucleolytic and/or exonucleolytic activity and presents a formidable challenge to the accurate, reliable, and robust analysis of cfDNA. Another challenge for analyzing cfDNA is its short half-life in the blood stream, on the order of about 15 minutes. Without wishing to be bound to any particular theory, the present invention contemplates, in part, that analysis of cfDNA is like a "liquid biopsy" and is a real-time snapshot of current biological processes.

Moreover, because cfDNA is not found within cells and may be obtained from a number of suitable sources including, but not limited to, biological fluids and stool samples, it is not subject to the existing limitations that plague next generation sequencing analysis, such as direct access to the tissues being analyzed.

Illustrative examples of biological fluids that are suitable sources from which to isolate cfDNA in particular embodiments include, but are not limited to amniotic fluid, blood, plasma, serum, semen, lymphatic fluid, cerebral spinal fluid, ocular fluid, urine, saliva, mucous, and sweat. In particular embodiments, the biological fluid is blood or blood plasma.

In certain embodiments, commercially available kits and other methods known to the skilled artisan can used to isolate cfDNA directly from the biological fluids of a subject or from a previously obtained and optionally stabilized biological sample. e.g., by freezing and/or addition of enzyme chelating agents including, but not limited to EDTA, EGTA, or other chelating agents specific for divalent cations.

(a) Generating End-Repaired cfDNA

In particular embodiments, generating a genomic DNA library comprises the end-repair of isolated cfDNA or fragmented cellular DNA. The fragmented cfDNA or cellular DNA is processed by end-repair enzymes to generate end-repaired cfDNA with blunt ends, 5'-overhangs, or 3'-overhangs. In some embodiments, the end-repair enzymes can yield for example. In some embodiments, the end-repaired cfDNA or cellular DNA contains blunt ends. In some embodiments, the end-repaired cellular DNA or cfDNA is processed to contain blunt ends. In some embodiments, the blunt ends of the end-repaired cfDNA or cellular DNA are further modified to contain a single base pair overhang. In some embodiments, end-repaired cfDNA or cellular DNA containing blunt ends can be further processed to contain adenine (A)/thymine (T) overhang. In some embodiments, end-repaired cfDNA or cellular DNA containing blunt ends can be further processed to contain adenine (A)/thymine (T) overhang as the single base pair overhang. In some embodiments, the end-repaired cfDNA or cellular DNA has non-templated 3' overhangs. In some embodiments, the end-repaired cfDNA or cellular DNA is processed to contain 3' overhangs. In some embodiments, the end-repaired cfDNA or cellular DNA is processed with terminal transferase (TdT) to contain 3' overhangs. In some embodiments, a G-tail can be added by TdT. In some embodiments, the end-repaired cfDNA or cellular DNA is processed to contain overhang ends using partial digestion with any known restriction enzymes (e.g., with the enzyme Sau3A, and the like.

(b) Attaching Adaptor Molecules to End-Repaired cfDNA

In particular embodiments, generating a cfDNA library comprises attaching one or more adaptors to each end of the end-repaired cfDNA. The present invention contemplates, in part, an adaptor module designed to accommodate large numbers of genome equivalents in cfDNA libraries. Adaptor modules are configured to measure the number of genome equivalents present in cfDNA libraries, and, by extension, the sensitivity of sequencing assays used to identify sequence mutations.

As used herein, the terms "adaptor" and "adaptor module" are used for interchangeably, and refer to a polynucleotide comprising that comprises at least three elements: an amplification region, a sample tag region, and an anchor region. In particular embodiments, the adaptor comprises an amplification region, a sample tag region, and an anchor region. In some embodiments, the adaptor also comprises a unique molecule identifier (UMI). In particular embodiments, the adaptor comprises one or amplification regions, one or more sample tag regions, one or more UMIs, and/or one or more anchor regions. In some embodiments, the adaptor comprises, in order from 5' to 3', an amplification region, a sample tag region, a UMI, and an anchor region. In particular embodiments, the adaptor comprises, in order from 5' to 3', an amplification region, a sample tag region, a UMI, and an anchor region. In certain embodiments, the UMI is contained within the sample tag region, and the adaptor comprises, in order from 5' to 3', an amplification region, an integrated sample tag/UMI region, and an anchor region.

As used herein, the term "amplification region" refers to an element of the adaptor molecule that comprises a polynucleotide sequence capable of serving as a primer recognition site for PCR amplification. In particular embodiments, an adaptor comprises an amplification region that comprises one or more primer recognition sequences for single-primer amplification of a genomic DNA library. In some embodiments, the amplification region comprises one, two, three, four, five, six, seven, eight, nine, ten, or more primer recognition sequences for single-primer amplification of a genomic DNA library.

In some embodiments, the amplification region is about is between 5 and 50 nucleotides, between 10 and 45 nucleotides, between 15 and 40 nucleotides, or between 20 and 30 nucleotides in length. In some embodiments, the amplification region is 10 nucleotides, 11 nucleotides, 12 nucleotides, 13 nucleotides, 14 nucleotides, 15 nucleotides, 16 nucleotides, 17 nucleotides, about 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, or 40 nucleotides or more. In particular embodiments, the amplification region is 25 nucleotides in length.

As used herein, the term "sample tag" or sample tag region" are used interchangeably and refer to an element of the adaptor that comprises a polynucleotide sequence that uniquely identifies the particular DNA fragment as well as the sample from which it was derived.

In certain embodiments, the sample tag region is about is between 3 and 50 nucleotides, between 3 and 25 nucleotides, or between 5 and 15 nucleotides in length. In some embodiments, the sample tag region is 3 nucleotides, 4 nucleotides, 5 nucleotides, 6 nucleotides, 7 nucleotides, 8 nucleotides, 9 nucleotides, 10 nucleotides, about 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides or more in length.

In certain embodiments, the adaptor comprises a UMI multiplier, wherein the UMI multiplier is at least 1, at least 2, at least 3, at least 4, at least 5, at least 6, at least 7, at least 8, at least 9, or at least 10 nucleotides in length.

In certain embodiments, each nucleotide position of the UMI multiplier can comprise any of adenine, guanine, cytosine, or thymine. Thus, in some embodiments, a UMI multiplier comprising n number of nucleotides can comprise any of $n^4$ possible nucleotide sequences. In some embodiments, the UMI multiplier is one nucleotide in length and comprises one of four possible sequences. In some embodiments, the UMI multiplier is two nucleotides in length and comprises one of sixteen possible sequences. In some embodiments, the UMI multiplier is three nucleotides in length and comprises one of 64 possible sequences. In some embodiments, the UMI multiplier is four nucleotides in length and comprises one of 256 possible sequences. In some embodiments, the UMI multiplier is five nucleotides in length and comprises one of 1,024 possible sequences. In some embodiments, the UMI multiplier is six nucleotides in length and comprises one of 4,096 possible sequences. In some embodiments, the UMI multiplier is seven nucleotides in length and comprises one of 16,384 possible sequences. In some embodiments, the UMI multiplier is eight nucleotides in length and comprises one of 65,5336 possible sequences. In some embodiments, the UMI multiplier is nine nucleotides in length and comprises one of 262,144 possible sequences. In some embodiments, the UMI multiplier is ten or more nucleotides in length and comprises one of 1,048, 576 or more possible sequences.

Figure 5A:
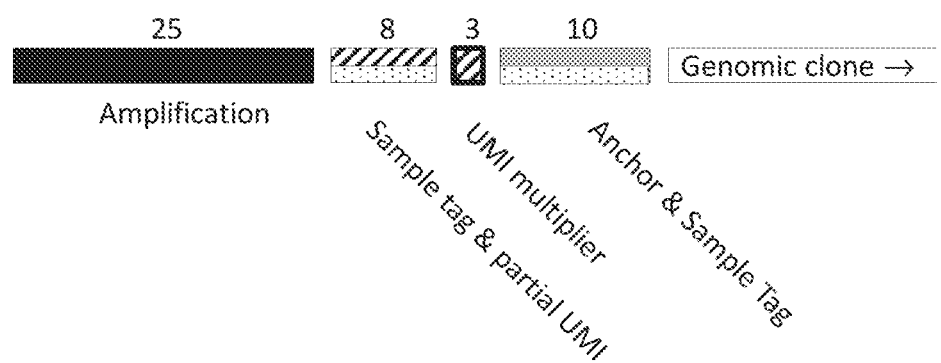
FIG. 5A-FIG. 5B shows a diagram illustrating that shifting the position of the UMI multiplier within the sample tag can increase the number of unique sample tags.
Figure 5B:
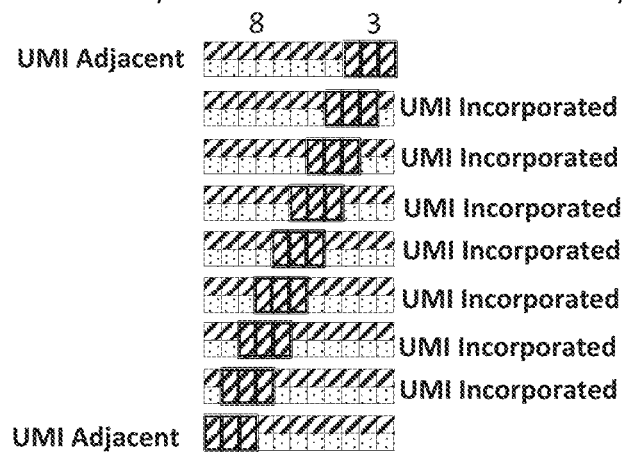

In particular embodiments, the adaptor comprises a UMI multiplier, wherein the UMI multiplier is adjacent to or contained within the sample tag region (FIG. 5A). Illustrative examples of UMI multipliers adjacent or contained within the sample tag are shown in FIG. 5B. In FIG. 5B, an 8-mer sample tag region is shown with an adjacent UMI multiplier (top and bottom rows) or a UMI multiplier incorporated within the sample tag (middle 7 rows). In some embodiments, that adaptor comprises a sample tag that is eight nucleotides in length and a UMI multiplier that is three nucleotides in length and comprises one of 64 possible sequences, and wherein the UMI multiplier is adjacent to or contained within the sample tag region. In some embodiments, identical processes attach full length adaptor to the other end of the genomic fragments.

In particular embodiments, an adaptor module comprises one or more anchor sequences. As used herein, an "anchor region" and "anchor sequence" are used interchangeably and refer to a nucleotide sequence that hybridizes to a partner oligonucleotide. In some embodiments, the anchor region comprises the following three properties: (1) each anchor sequence is part of a family of two or more anchor sequences that collectively represent each of the four possible DNA bases at each site within extension; this feature, balanced base representation, is useful to calibrate proper base calling in sequencing reads in particular embodiments; (2) each anchor sequence is composed of only two of four possible bases, and these are specifically chosen to be either and equal number of A+C or an equal number of G+T; an anchor sequence formed from only two bases reduces the possibility that the anchor sequence will participate in secondary structure formation that would preclude proper adaptor function; and (3) because each anchor sequence is composed of equal numbers of A+C or G+T, each anchor sequence shares roughly the same melting temperature and duplex stability as every other anchor sequence in a set of four.

In some embodiments, the anchor sequences is between 1 and 50 nucleotides in length. In some embodiments, the anchor sequences is between 4 and 40 nucleotides in length. In certain embodiments, the anchor region is between 5 and 25 nucleotides in length. In particular embodiments, the anchor region is at least 4 nucleotides, at least six nucleotides, at least 8 nucleotides, at least 10 nucleotides, at least 12 nucleotides, at least 14 nucleotides, or at least 16 nucleotides in length. In particular embodiments, the anchor region is 10 nucleotides in length.

In particular embodiments, an attachment step comprises attaching/ligating an adaptor module to the end-repaired cfDNA or cellular DNA to generate a "tagged" genomic DNA library. In some embodiments, a single adaptor module is employed. In some embodiments, two, three, four or five adaptor modules are employed. In some embodiments, an adaptor module of identical sequence is attached to each end of the fragmented end-repaired DNA.

In some embodiments, a plurality of adaptor species is attached to an end-repaired cellular or cell free genomic DNA fragments. Each of the plurality of adaptors may comprise one or more amplification regions for the amplification of the cfDNA or cellular DNA library, one or more sample tag regions for the identification of the cfDNA or cellular genomic DNA fragment and identification of the individual sample; and one or more sequences for DNA sequencing.

In some embodiments, a plurality of adaptor species is attached to an end-repaired cellular or cell free genomic DNA fragments of a sample, and the plurality of adaptors all comprise amplification regions of an identical nucleotide sequence.

In certain embodiments, the genomic DNA from a sample is attached with a plurality of adaptors that comprise sample tag sequences that all are different from other sequences of sample tag regions in adaptors that are attached to genomic DNA fragments from other samples.

In particular embodiments, a plurality of adaptor species is attached to an end-repaired cellular or cell free genomic DNA fragments from a sample, and the plurality of adaptors all comprise one or more sample tag regions comprising one of between 2 and 10,000 nucleotide sequences, one of between 5 and 5,000 nucleotide sequences, one of between 25 and 1,000 nucleotide sequences, one of between 50 and 500 nucleotide sequences one of between 100 and 400 nucleotide sequences, or one of between 200 and 300 nucleotide sequences. In some embodiments, the sample tag region of each adaptor is 8 nucleotides in length, and each sample tag region of the plurality of adaptors comprises one of 240 nucleotide sequences.

In certain embodiments, a plurality of adaptor species is attached to an end-repaired cellular or cell free genomic DNA fragments from a sample, and the sample tag regions of the plurality of adaptors comprises nucleotide sequences that are different from each other by a Hamming distance of 1, 2, 3, 4 or greater than 4. In particular embodiments, the Hamming distance is 2.

In particular embodiments, the sample tag regions of the plurality of adaptors that are attached to genomic DNA fragments of a sample are 8 nucleotides in length, and comprise one of 240 nucleotide sequences that are different from each other by a Hamming distance of 2.

In certain embodiments, the sample tag region serves to identify individual genomic DNA fragments and to identify the individual sample, i.e., the genomic library source. For example, when the sample tags of a plurality of adaptors attached to a sample have one of 240 possible sequences, each sample is identified as having one of 240 possible tags, and each sample receives a set of 240 tags that are discrete from any other sample by Hamming distance of two (meaning two base changes are required to change one tag into another). These same tags are used to enumerate clone diversity and thus they also serve as sequence tags, i.e., to identify genomic DNA fragments. To further augment the diversity of possible sequence tags, UMI multipliers may be added. For example, a UMI multiplier can be added to the adaptor region comprising 3 nucleotides consisting of the 64 possible combinations of 3 bases. In addition, the plurality of adaptors can comprise more than one anchor sequence. For example, a plurality of adaptors may contain 4 different anchor sequences are used simultaneously. These anchor sequences may also be used during sample de-multiplexing to lower errors.

Figure 4A:
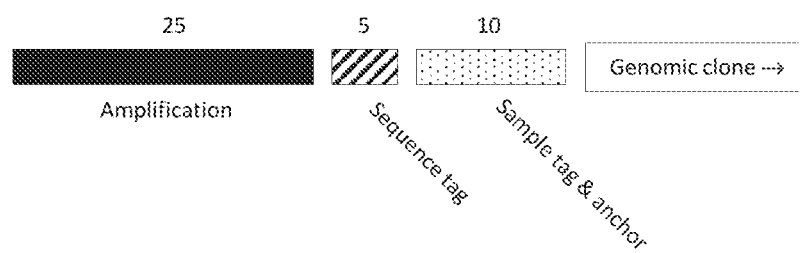
FIG. 4A-FIG. 4E shows diagrams of an illustrative first generation adaptor (FIG. 4A and FIG. 4B) and an adaptor of the present invention (FIG. 4C-FIG. 4E).
Figure 4B:
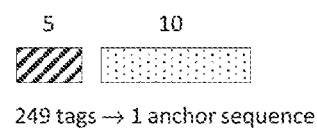
Figure 4C:
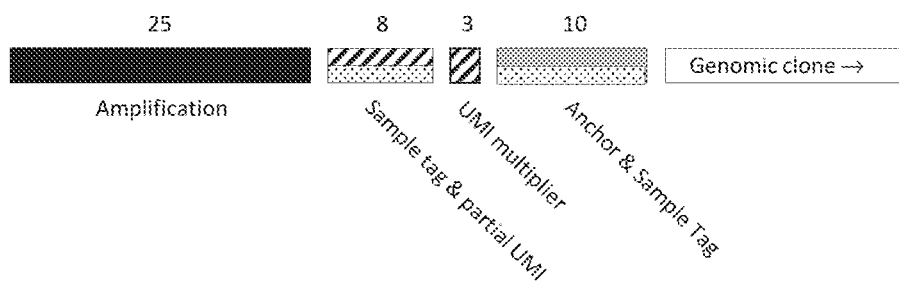
Figure 4D:
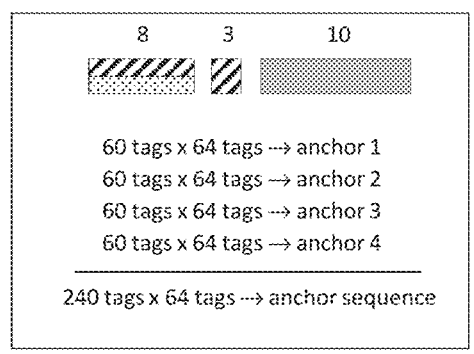
Figure 4E:

FIG. 4 shows an illustrative comparison between a first generation adaptor (FIGS. 4A and 4B) and an adaptor of the present invention (FIG. 4C-FIG. 4E). FIG. 4A and FIG. 4B show an example of first generation adaptor that is 40 nt in length and consisted of a discrete PCR amplification sequence, sequence tag, and sample tag. Here, the sample is identified by a fixed sequence (sequence tag) that is present on all adaptors that are used to generate a DNA library from the sample. Individual genomic fragments are identified by a separate and distinct sequences (sequence tag). FIG. 4C-FIG. 4E show an illustrative example of an adaptor from the present invention. The illustrative adaptor shown is 47 nucleotides in length, and the sequence tag is combined with the sample tag. There is an additional 3 nt sequence, the UMI multiplier, consisting of the 64 possible combinations of 3 bases. The 10 nt anchor sequence is one of four different distinct sequences.

Thus, in the illustrative example (See FIG. 4C-FIG. 4E), a set of adaptors that are used in connection with a single sample comprise 240 sample tag sequences that can be split into four sets of sample tag sequences with each set comprising 60 tags (one for each nucleotide. A, C, T and G). Thus, each set of 60 tags is specific to one of four anchor sequences. In total, a pool of 240 possible sample tag configurations are possible per sample. Specifically, in this scenario, the 240 sample tag sequences are divided into four sets of 60 sequences, with each set directed to a specific anchor region. Therefore, the sample ID involves not only the sequence information from the eight nucleotide sample tag, but also the associated anchor sequence information. In addition, the position of sequences within the read is fixed, and therefore the sample tags and anchor sequences must have a fixed position within a sequencing read in order to pass inclusion filters for downstream consideration. Further, the inclusion of the UMI multiplier increases the sequence tag diversity from 240 to 240×64=15,360 possible sequence tags.

Attachment of one or more adaptors contemplated herein may be carried out by methods known to those of ordinary skill in the art. In particular embodiments, one or more adaptors contemplated herein are attached to end-repaired cfDNA that comprises blunt ends. In certain embodiments, one or more adaptors contemplated herein are attached to end-repaired cfDNA that comprises complementary ends appropriate for the attachment method employed. In certain embodiments, one or more adaptors contemplated herein are attached to end-repaired cfDNA that comprises a 3' overhang.

In some embodiments, attaching the genomic DNA fragments to a plurality of adaptors includes the steps of attaching the end repaired cfDNA or cellular DNA fragments to an oligonucleotide containing at least a portion of an anchor region. In some embodiments, the oligonucleotide contains the whole anchor region. In particular embodiments, the oligonucleotide is a DNA duplex comprising a 5' phosphorylated attachment strand duplexed with a partner strand, wherein the partner strand is blocked from attachment by chemical modification at its 3' end, and wherein the attachment strand is attached to the genomic DNA fragment. In certain embodiments, the DNA fragments attached with at least a portion of the anchor region are then annealed with DNA oligonucleotides encoding the full length adaptor sequences. In particular embodiments, one or more polynucleotide kinases, one or more DNA ligases, and/or one or more DNA polymerases are added to the genomic DNA fragments and the DNA oligonucleotides encoding the full length adaptor sequence. In some embodiments, the polynucleotide kinase is T4 polynucleotide kinase. In some embodiments, the DNA ligase is Taq DNA ligase. In certain embodiments, the DNA polymerase is Taq polymerase. In particular embodiments, the DNA polymerase is full length Bst polymerase.

Figure 6A:
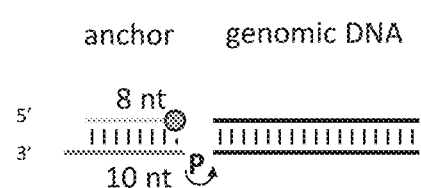
FIG. 6A and FIG. 6B shows a diagram illustrating the process of constructing genomic libraries for a CNL assay.
Figure 6B:
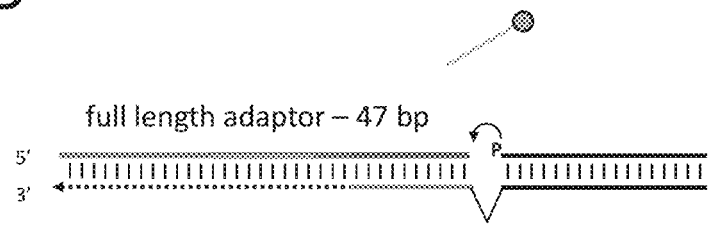

FIG. 6 shows an illustrative method for attaching a plurality of adaptors to the 3' end of repaired DNA fragments. In the first step, the anchor sequence is attached to the 3' ends of genomic fragments. In this step, the anchor portion is a DNA duplex in which the ten nucleotide 5' phosphorylated "attachment strand" is duplexed with an eight nucleotide "partner strand" that is blocked from attachment by chemical modification at its 3' end. The anchor duplex is blunt-ended on the phosphorylated/blocked end and can therefore attach to blunt-ended genomic fragments. In the next step, pools of oligonucleotides encoding the full adaptor sequences are annealed to the initial anchor sequence. The combined action of T4 polynucleotide kinase, Taq DNA ligase, and full-length Bst polymerase attach this oligonucleotide via ligation as illustrated for the top strand and extend the initial anchor sequence by DNA polymerization on the bottom strand to complete the full-length adaptor sequence. Identical processes may be used to attach full length adaptors to the 5' end of the genomic fragments.

2. DNA Library Amplification

In particular embodiments, methods of genetic analysis contemplated herein comprise amplification of a genomic DNA library, e.g. a cellular DNA library or a cfDNA library, to generate a DNA clone library or a library of DNA clones, e.g., a cfDNA clone library or a library of cfDNA clones, or a cellular DNA clone library or a library of cellular DNA clones. Each molecule of the DNA library comprises an adaptor attached to each end of an end-repaired DNA fragments, and each adaptor comprises one or more amplification regions. In some embodiments, different adaptors are attached to different ends of the end-repaired cfDNA. In particular embodiments, different adaptors are attached to different ends of the end-repaired cellular DNA.

In some embodiments, the same adaptor is attached to both ends of the DNA fragment. Attachment of the same adaptor to both ends of end-repaired DNA allows for PCR amplification with a single primer sequence. In particular embodiments, a portion of the adaptor attached-cfDNA library will be amplified using standard PCR techniques with a single primer sequence driving amplification. In one embodiment, the single primer sequence is about 25 nucleotides, optionally with a projected Tm of ≥55° C. under standard ionic strength conditions.

In particular embodiments, picograms of the initial genomic DNA library, e.g. a cellular DNA library or cfDNA library, are amplified into micrograms of DNA clones, implying a 10,000-fold amplification. The amount of amplified product can be measured using methods known in the art. e.g., quantification on a Qubit 2.0 or Nanodrop instrument.

3. Determining the Number of Genome Equivalents

In various embodiments, a method for genetic analysis of genomic DNA comprises determining the number of genome equivalents in the DNA clone library. As used herein, the term "genome equivalent" refers to the number of genome copies in each library. An important challenge met by the compositions and methods contemplated herein is achieving sufficient assay sensitivity to detect and analysis rare genetic mutations or differences in genetic sequence. To determine assay sensitivity value on a sample-by-sample basis, the numbers of different and distinct sequences that are present in each sample are measured by measuring the number of genome equivalents that are present in a sequencing library. To establish sensitivity, the number of genome equivalents must be measured for each sample library.

The number of genome equivalents can be determined by qPCR assay or by using bioinformatics-based counting after sequencing is performed. In the process flow of clinical samples, qPCR measurement of genome equivalents is used as a QC step for DNA libraries, e.g., cfDNA libraries or genomic DNA libraries. It establishes an expectation for assay sensitivity prior to sequence analysis and allows a sample to be excluded from analysis if its corresponding DNA clone library lacks the required depth of genome equivalents. Ultimately, the bioinformatics-based counting of genome equivalents is also used to identify the genome equivalents—and hence the assay sensitivity and false negative estimates—for each given DNA clone library.

The empirical qPCR assay and statistical counting assays should be well correlated. In cases where sequencing fails to reveal the sequence depth in a DNA clone library, reprocessing of the DNA clone library and/or additional sequencing may be required.

In one embodiment, the genome equivalents in a cellular DNA or cfDNA clone library are determined using a quantitative PCR (qPCR) assay. In a particular embodiment, a standard library of known concentration is used to construct a standard curve and the measurements from the qPCR assay are fit to the resulting standard curve and a value for genome equivalents is derived from the fit. The present inventors have discovered that a qPCR "repeat-based" assay comprising one primer that specifically hybridizes to a common sequence in the genome, e.g. a repeat sequence, and another primer that binds to the primer binding site in the adaptor, measured an 8-fold increase in genome equivalents compared to methods using just the adaptor specific primer (present on both ends of the cfDNA clone). The number of genome equivalents measured by the repeat-based assays provides a more consistent library-to-library performance and a better alignment between qPCR estimates of genome equivalents and bioinformatically counted tag equivalents in sequencing runs.

Illustrative examples of repeats suitable for use in the repeat-based genome equivalent assays contemplated herein include, but are not limited to: short interspersed nuclear elements (SINEs), e.g., Alu repeats; long interspersed nuclear elements (LINEs), e.g., LINE1, LINE2, LINE3; microsatellite repeat elements, e.g., short tandem repeats (STRs), simple sequence repeats (SSRs); and mammalian-wide interspersed repeats (MIRs).

In one embodiment, the repeat is an Alu repeat.

4. Quantitative Genetic Analysis

In various embodiments, a method for genetic analysis of genomic DNA, e.g., genomic cellular or cfDNA, comprises quantitative genetic analysis of one or more target genetic loci of the DNA library clones. Quantitative genetic analysis comprises one or more of, or all of, the following steps: capturing DNA clones comprising a target genetic locus; amplification of the captured targeted genetic locus; sequencing of the amplified captured targeted genetic locus; and bioinformatic analysis of the resulting sequence reads. As used herein, the terms "DNA library clone" refer to a DNA library fragment wherein the combination of the adaptor and the genomic DNA fragment result in a unique DNA sequence (e.g., a DNA sequence that can be distinguished from that of another DNA library clone).

(a) Capture of Target Genetic Locus

The present invention contemplates, in part, a capture probe module designed to retain the efficiency and reliability of larger probes but that minimizes uninformative sequence generation in a genomic DNA library that comprises smaller DNA fragments, e.g., a cfDNA clone library. A "capture probe" or "capture probe module" as used herein, are used interchangeably and refer to a polynucleotide that comprises a capture probe sequence and a tail sequence. In particular embodiments, the capture probe module sequence or a portion thereof serves as a primer binding site for one or more sequencing primers.

In particular embodiments, a capture probe module comprises a capture probe. As used herein a "capture probe" refers to a region capable of hybridizing to a specific DNA target region. In some embodiments, the capture probes are used with genomic DNA library constructed from cellular DNA. In particular embodiments, the capture probes are used with genomic DNA library constructed from cfDNA. Because the average size of cfDNA is about 150 to about 170 bp and is highly fragmented, certain embodiments are directed compositions and methods contemplated herein comprise the use of high density and relatively short capture probes to interrogate DNA target regions of interest. In some embodiments, the capture probes are capable of hybridizing to DNA target regions that are distributed across all chromosomal segments at a uniform density. A set of such capture probes is referred to herein as "chromosomal stability probes." Chromosomal stability probes are used to interrogate copy number variations on a genome-wide scale in order to provide a genome-wise measurement of chromosomal copy number (e.g., chromosomal ploidy).

One particular concern with using high density capture probes is that generally capture probes are designed using specific "sequence rules." For example, regions of redundant sequence or that exhibit extreme base composition biases are generally excluded in designing capture probes. However, the present inventors have discovered that the lack of flexibility in capture probe design rules does not substantially impact probe performance. In contrast, capture probes chosen strictly by positional constraint provided on-target sequence information; exhibit very little off-target and unmappable read capture; and yield uniform, useful, on-target reads with only few exceptions. Moreover, the high redundancy at close probe spacing more than compensates for occasional poor-performing capture probes.

In particular embodiments, a target region is targeted by a plurality of capture probes, wherein any two or more capture probes are designed to bind to the target region within 10 nucleotides of each other, within 15 nucleotides of each other, within 20 nucleotides of each other, within 25 nucleotides of each other, within 30 nucleotides of each other, within 35 nucleotides of each other, within 40 nucleotides of each other, within 45 nucleotides of each other, or within 50 nucleotides or more of each other, as well as all intervening nucleotide lengths.

In one embodiment, the capture probe is about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, or about 45 nucleotides.

In one embodiment, the capture probe is about 100 nucleotides, about 200 nucleotides, about 300 nucleotides, about 400 nucleotides, or about 100 nucleotides. In another embodiment, the capture probe is from about 100 nucleotides to about 500 nucleotides, about 200 nucleotides to about 500 nucleotides, about 300 nucleotides to about 500 nucleotides, or about 400 nucleotides to about 500 nucleotides, or any intervening range thereof.

In a particular embodiment, the capture probe is 60 nucleotides. In another embodiment, the capture probe is substantially smaller than 60 nucleotides but hybridizes comparably, as well as, or better than a 60 nucleotide capture probe targeting the same DNA target region. In a certain embodiment, the capture probe is 40 nucleotides.

In certain embodiments, a capture probe module comprises a tail sequence. As used herein, the term "tail sequence" refers to a polynucleotide at the 5' end of the capture probe module, which in particular embodiments can serve as a primer binding site. In particular embodiments, a sequencing primer binds to the primer binding site in the tail region.

In particular embodiments, the tail sequence is about 5 to about 100 nucleotides, about 10 to about 100 nucleotides, about 5 to about 75 nucleotides, about 5 to about 50 nucleotides, about 5 to about 25 nucleotides, or about 5 to about 20 nucleotides. In certain embodiments, the third region is from about 10 to about 50 nucleotides, about 15 to about 40 nucleotides, about 20 to about 30 nucleotides or about 20 nucleotides, or any intervening number of nucleotides.

In particular embodiments, the tail sequence is about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides.

In various embodiments, the capture probe module comprises a specific member of a binding pair to enable isolation and/or purification of one or more captured fragments of a tagged and or amplified genomic DNA library (e.g., a cellular or cfDNA library) that hybridizes to the capture probe. In particular embodiments, the capture probe module is conjugate to biotin or another suitable hapten, e.g., dinitrophenol, digoxigenin.

In various embodiments, the capture probe module is hybridized to a tagged and optionally amplified DNA library to form a complex. In some embodiments, the multifunctional capture probe module substantially hybridizes to a specific genomic target region in the DNA library.

Hybridization or hybridizing conditions can include any reaction conditions where two nucleotide sequences form a stable complex; for example, the tagged DNA library and capture probe module forming a stable tagged DNA library-capture probe module complex. Such reaction conditions are well known in the art and those of skill in the art will appreciated that such conditions can be modified as appropriate, e.g., decreased annealing temperatures with shorter length capture probes, and within the scope of the present invention. Substantial hybridization can occur when the second region of the capture probe complex exhibits 100%, 99%, 98%, 97%, 96%, 95%, 94%, 93%, 92% 91%, 90%, 89%, 88%, 85%, 80%, 75%, or 70% sequence identity, homology or complementarity to a region of the tagged DNA library.

In particular embodiments, the capture probe is about 40 nucleotides and has an optimal annealing temperature of about 44° C. to about 47° C.

In certain embodiments, the methods contemplated herein comprise isolating a tagged cfDNA library-capture probe module complex. In particular embodiments, methods for isolating DNA complexes are well known to those skilled in the art and any methods deemed appropriate by one of skill in the art can be employed with the methods of the present invention (Ausubel et al., *Current Protocols in Molecular Biology*, 2007-2012). In particular embodiments, the complexes are isolated using biotin-streptavidin isolation techniques.

In particular embodiments, removal of the single stranded 3'-ends from the isolated tagged DNA library fragments-capture probe module complex is contemplated. In certain embodiments, the methods comprise 3'-5' exonuclease enzymatic processing of the isolated tagged DNA library-multifunctional capture probe module complex to remove the single stranded 3' ends.

In certain other embodiments, the methods comprise performing 5'-3' DNA polymerase extension of multifunctional capture probe utilizing the isolated tagged DNA library fragments as template.

In certain other embodiments, the methods comprise creating a hybrid capture probe-isolated tagged DNA target molecule, e.g., a tagged cfDNA target molecule or a tagged cellular DNA target molecule, through the concerted action of a 5' FLAP endonuclease, DNA polymerization and nick closure by a DNA ligase.

A variety of enzymes can be employed for the 3'-5' exonuclease enzymatic processing of the isolated tagged DNA library-multifunctional capture probe module complex. Illustrative examples of suitable enzymes, which exhibit 3'-5' exonuclease enzymatic activity, that can be employed in particular embodiments include, but are not limited to: T4 or Exonucleases I, III, V (See also, Shevelev I V, Hübscher U., *Nat Rev Mol Cell Biol.* 3(5):364-76 (2002)). In particular embodiments, the enzyme comprising 3'-5' exonuclease activity is T4 polymerase. In particular embodiments, an enzyme which exhibits 3'-5' exonuclease enzymatic activity and is capable of primer template extension can be employed, including for example T4 or Exonucleases I, III, V. Id.

In some embodiments, the methods contemplated herein comprise performing sequencing and/or PCR on the 3'-5' exonuclease enzymatically processed complex discussed supra and elsewhere herein. In particular embodiments, a tail portion of a capture probe molecule is copied in order to generate a hybrid nucleic acid molecule. In one embodiment, the hybrid nucleic acid molecule generated comprises the target region capable of hybridizing to the capture probe module and the complement of the capture probe module tail sequence.

In a particular embodiment, genetic analysis comprises a) hybridizing one or more capture probe modules to one or more target genetic loci in a plurality of genomic DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genomic locus capable of hybridizing to the capture probe and the complement of the capture probe module tail sequence; and e) performing quantitative genetic analysis on the amplified hybrid nucleic acid molecules from d).

In a particular embodiment, methods for determining copy number of a specific target genetic locus are contemplated comprising: a) hybridizing one or more capture probe modules to one or more target genetic loci in a plurality of DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genetic locus capable of hybridizing to the capture probe and the complement of the capture probe module tail sequence; e) performing PCR amplification of the amplified hybrid nucleic acid molecules in d); and f) quantitating the PCR reaction in e), wherein the quantitation allows for a determination of copy number of the specific target region.

In one embodiment, the enzymatic processing of step c) comprises performing 3'-5' exonuclease enzymatic processing on the one or more capture probe module-DNA library clone complexes from b) using an enzyme with 3'-5' exonuclease activity to remove the single stranded 3' ends; creating one or more hybrid capture probe module-cfDNA library clone molecules through the concerted action of a 5' FLAP endonuclease, DNA polymerization and nick closure by a DNA ligase; or performing 5'-3' DNA polymerase extension of the capture probe using the isolated DNA clone in the complex as a template.

In one embodiment, the enzymatic processing of step c) comprises performing 5'-3' DNA polymerase extension of the capture probe using the isolated DNA clone in the complex as a template.

In particular embodiments, PCR can be performed using any standard PCR reaction conditions well known to those of skill in the art. In certain embodiments, the PCR reaction in e) employs two PCR primers. In one embodiment, the PCR reaction in e) employs a first PCR primer that hybridizes to a repeat within the target genetic locus. In a particular embodiment, the PCR reaction in e) employs a second PCR primer that hybridizes to the hybrid nucleic acid molecules at the target genetic locus/tail junction. In certain embodiments, the PCR reaction in e) employs a first PCR primer that hybridizes to the target genetic locus and a second PCR primer hybridizes to the amplified hybrid nucleic acid molecules at the target genetic locus/tail junction. In particular embodiments, the second primer hybridizes to the target genetic locus/tail junction such that at least one or more nucleotides of the primer hybridize to the target genetic locus and at least one or more nucleotides of the primer hybridize to the tail sequence.

In certain embodiments, the amplified hybrid nucleic acid molecules obtained from step e) are sequenced and the sequences aligned horizontally, i.e., aligned to one another but not aligned to a reference sequence. In particular embodiments, steps a) through e) are repeated one or more times with one or more capture probe modules. The capture probe modules can be the same or different and designed to target either cfDNA strand of a target genetic locus. In some embodiments, when the capture probes are different, they hybridize at overlapping or adjacent target sequences within a target genetic locus in the tagged cfDNA clone library. In one embodiment, a high density capture probe strategy is used wherein a plurality of capture probes hybridize to a target genetic locus, and wherein each of the plurality of capture probes hybridizes to the target genetic locus within about 5, 10, 15, 20, 25, 30, 35, 40, 45, 50, 100, 200 bp or more of any other capture probe that hybridizes to the target genetic locus in a tagged DNA clone library, including all intervening distances.

In some embodiments, the method can be performed using two capture probe modules per target genetic locus, wherein one hybridizes to the "Watson" strand (non-coding or template strand) upstream of the target region and one hybridizes to the "Crick" strand (coding or non-template strand) downstream of the target region.

In particular embodiments, the methods contemplated herein can further be performed multiple times with any number of capture probe modules, for example 2, 3, 4, 5, 6, 7, 8, 9, or 10 or more capture probe modules per target genetic locus any number of which hybridize to the Watson or Crick strand in any combination. In some embodiments, the sequences obtained can be aligned to one another in order to identify any of a number of differences.

In certain embodiments, a plurality of target genetic loci are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more capture probe modules.

(b) Sequencing

In particular embodiments, the quantitative genetic analysis comprises sequencing a plurality of hybrid nucleic acid molecules, as discussed elsewhere herein, supra, to generate sufficient sequencing depths to obtain a plurality of unique sequencing reads. The terms "unique reads" or "unique genomic sequences" (UGS) are used interchangeably herein and are identified by grouping individual redundant reads together into a "family." Redundant reads are sequence reads that share an identical UMIE (e.g., share the same read code and the same DNA sequence start position within genomic sequence) and are derived from a single attachment event and are therefore amplification-derived "siblings" of one another. A single consensus representative of a family of redundant reads is carried forward as a unique read or UGS. Each unique read or UGS is considered a unique attachment event. The sum of unique reads corresponding to a particular capture probe is referred to as the "raw genomic depth" (RGD) for that particular capture probe. Each capture probe yields a set of unique reads that are computationally distilled from total reads by grouping into families. The unique reads for a given sample (e.g., raw genomic depth for a sample) are then computed as the average of all the unique reads observed on a probe-by-probe basis. Unique reads are important because each unique read must be derived from a unique genomic DNA clone. Each unique read represents the input and analysis of a haploid equivalent of genomic DNA. The sum of unique reads is the sum of haploid genomes analyzed. The number of genomes analyzed, in turn, defines the sensitivity of the sequencing assay. By way of a non-limiting example, if the average unique read count is 100 genome equivalents, then that particular assay has a sensitivity of being able to detect one mutant read in 100, or 1%. Any observation less than this is not defensible.

Cases where there is an obvious copy number change (e.g., instances of noisy probes) are excluded from the data set used to compute the sample average. Herein, a "noisy probe" refers to a probe that captures a highly variable number of unique reads among a large set identical samples (e.g., a highly variable number of unique reads among 12-16 sample replicates). In some embodiments, the number of unique reads associated with a noisy probe is increased compared to the average number of unique reads for the sample by 50% or more. In some embodiments, the number of unique reads associated with a noisy probe is decreased compared to the average number of unique reads for the sample by 50% or more. In some embodiments, about 2% to about 4% of probes used in a particular analysis are identified as noisy probes and are excluded from calculations to determine the average number of unique reads for a given sample.

In some embodiments, sequencing reads are identified as either "on-target reads" or "off-target reads." On-target reads possess a genomic DNA sequence that maps within the vicinity of a capture probe used to create the genomic library. In some embodiments, where each genomic sequence is physically linked to a specific capture probe and where the sequence of the genomic segment and capture probe are both determined as a unified piece of information, an on-target read is defined as any genomic sequence whose starting coordinate maps within 400 bp, and more generally within 200 bp of the 3' end of the corresponding capture probe. Off-target reads are defined as having genomic sequence that aligns to the reference genome at a location ≥500 base pairs (and more often mapping to entirely different chromosomes) relative to the capture probe.

In particular embodiments, the quantitative genetic analysis comprises multiplex sequencing of hybrid nucleic acid molecules derived from a plurality of samples.

In various embodiments, the quantitative genetic analysis comprises obtaining one or more or a plurality of tagged DNA library clones, each clone comprising a first DNA sequence and a second DNA sequence, wherein the first DNA sequence comprises a sequence in a targeted genetic locus and the second DNA sequence comprises a capture probe sequence; performing a paired end sequencing reaction on the one or more clones and obtaining one or more sequencing reads or performing a sequencing reaction on the one or more clones in which a single long sequencing read of greater than about 100, 200, 300, 400, 500 or more nucleotides is obtained, wherein the read is sufficient to identify both the first DNA sequence and the second DNA sequence; and ordering or clustering the sequencing reads of the one or more clones according to the probe sequences of the sequencing reads.

(c) Bioinformatics Analysis

In various embodiments, the quantitative genetic analysis further comprises bioinformatic analysis of the sequencing reads. Bioinformatic analysis excludes any purely mental analysis performed in the absence of a composition or method for sequencing. In certain embodiments, bioinformatics analysis includes, but is not limited to: sequence alignments; genome equivalents analysis; single nucleotide variant (SNV) analysis; gene copy number variation (CNV) analysis; measurement of chromosomal copy number; and detection of genetic lesions. In particular embodiments, bioinformatics analysis is useful to quantify the number of genome equivalents analyzed in the cfDNA clone library; to detect the genetic state of a target genetic locus; to detect genetic lesions in a target genetic locus; and to measure copy number fluctuations within a target genetic locus.

Sequence alignments may be performed between the sequence reads and one or more human reference DNA sequences. In particular embodiments, sequencing alignments can be used to detect genetic lesions in a target genetic locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease.

Also contemplated herein, are methods for sequence alignment analysis that can be performed without the need for alignment to a reference sequence, referred to herein as horizontal sequence analysis. Such analysis can be performed on any sequences generated by the methods contemplated herein or any other methods. In particular embodiments, the sequence analysis comprises performing sequence alignments on the reads obtained by the methods contemplated herein.

In one embodiment, the genome equivalents in a cfDNA clone library are determined using bioinformatics-based counting after sequencing is performed. Each sequencing read is associated with a particular capture probe, and the collection of reads assigned to each capture probe is parsed into groups. Within a group, sets of individual reads share the same read code and the same DNA sequence start position within genomic sequence. These individual reads are grouped into a "family" and a single consensus representative of this family is carried forward as a "unique read."

All of the individual reads that constituted a family are derived from a single attachment event and thus, they are amplification-derived "siblings" of one another. Each unique read is considered a unique attachment event and the sum of unique reads is considered equivalent to the number of genome equivalents analyzed.

As the number of unique clones approaches the total number of possible sequence combinations, probability dictates that the same code and start site combinations will be created by independent events and that these independent events will be inappropriately grouped within single families. The net result will be an underestimate of genome equivalents analyzed, and rare mutant reads may be discarded as sequencing errors because they overlap with wild-type reads bearing the same identifiers.

In particular embodiments, to provide an accurate analysis for cfDNA clone libraries, the number of genome equivalents analyzed is about 1/10, about 1/12, about 1/14, about 1/16, about 1/18, about 1/20, about 1/25 or less the number of possible unique clones. It should be understood that the procedure outlined above is merely illustrative and not limiting.

In some embodiments, the number of genome equivalents to be analyzed may need to be increased. To expand the depth of genome equivalents, at least two solutions are contemplated. The first solution is to use more than one adaptor set per sample. By combining adaptors, it is possible to multiplicatively expand the total number of possible clones and therefore, expand the comfortable limits of genomic input. The second solution is to expand the read code by 1, 2, 3, 4, or 5, or more bases. The number of possible read codes that differ by at least 2 bases from every other read code scales as $4^{(n-1)}$ where n is the number of bases within a read code. Thus, in a non-limiting example, if a read code is 5 nucleotides and $4^{(5-1)}=256$; therefore, the inclusion of additional bases expands the available repertoire by a factor of four for each additional base.

In one embodiment, quantitative genetic analysis comprises bioinformatic analysis of sequencing reads to identify rare single nucleotide variants (SNV).

Next-generation sequencing has an inherent error rate of roughly 0.02-0.02%, meaning that anywhere from 1/200 to 1/500 base calls are incorrect. To detect variants and other mutations that occur at frequencies lower than this, for example at frequencies of 1 per 1000 sequences, it is necessary to invoke molecular annotation strategies. By way of a non-limiting example, analysis of 5000 unique molecules using targeted sequence capture technology would generate—at sufficient sequencing depths of >50,000 reads—a collection of 5000 unique reads, with each unique read belonging to a "family" of reads that all possess the same read code. A SNV that occurs within a family is a candidate for being a rare variant. When this same variant is observed in more than one family, it becomes a very strong candidate for being a rare variant that exists within the starting sample. In contrast, variants that occur sporadically within families are likely to be sequencing errors and variants that occur within one and only one family are either rare or the result of a base alteration that occurred ex vivo (e.g., oxidation of a DNA base or PCR-introduced errors).

In one embodiment, the methods of detecting SNVs comprise introducing 10-fold more genomic input (genomes or genome equivalents) as the desired target sensitivity of the assay. In one non-limiting example, if the desired sensitivity is 2% (2 in 100), then the experimental target is an input of 2000 genomes.

In particular embodiments, bioinformatics analysis of sequencing data is used to detect or identify SNV associated with a genetic state, condition or disease, genetic mosaicism, fetal testing, paternity testing, predicting response to drug treatment, diagnosing or monitoring a medical condition, microbiome profiling, pathogen screening, and monitoring organ transplants.

In various embodiments, a method for copy number determination analysis is provided comprising obtaining one or more or a plurality of clones, each clone comprising a first DNA sequence and a second DNA sequence, wherein the first DNA sequence comprises a sequence in a targeted genetic locus and the second DNA sequence comprises a capture probe sequence. In related embodiments, a paired end sequencing reaction on the one or more clones is performed and one or more sequencing reads are obtained. In another embodiment, a sequencing reaction on the one or more clones is performed in which a single long sequencing read of greater than about 100 nucleotides is obtained, wherein the read is sufficient to identify both the first DNA sequence and the second DNA sequence. The sequencing reads of the one or more clones can be ordered or clustered according to the probe sequence of the sequencing reads.

Copy number analyses include, but are not limited to, analyses that examine the number of copies of a particular gene or mutation that occurs in a given genomic DNA sample and can further include quantitative determination of the number of copies of a given gene or sequence differences in a given sample. In particular embodiments, copy number analysis is used to detect or identify gene amplification associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

In some embodiments, copy number analysis is used to measure chromosomal instability. In such embodiments, sets of capture probes that comprise chromosomal stability probes are used to determine copy number variations at a uniform density across all sets of chromosomes. Copy number analyses are performed for each chromosomal stability probe and the chromosomal stability probes are then ordered according to their chromosomal target. This allows for visualization of copy number losses or gains across the genome and can serve as a measure of chromosomal stability.

In particular embodiments, bioinformatics analysis of sequencing data is used to detect or identify one or more sequences or genetic lesions in a target locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease. In one embodiment, genetic lesions are associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

D. Clinical Applications of Quantitative CNL Assays

In various embodiments, the present invention contemplates a method of detecting, identifying, predicting, diagnosing, or monitoring a condition or disease in a subject by detecting a mutational change, SNP, translocation, inversion, deletion, change in copy number or other genetic variation in a region of interest.

E. Clinical Applications of Quantitative Genetic Analysis

In various embodiments, the present invention contemplates a method of detecting, identifying, predicting, diagnosing, or monitoring a condition or disease in a subject.

In particular embodiments, a method of detecting, identifying, predicting, diagnosing, or monitoring a genetic state, condition or disease in a subject comprises performing a quantitative genetic analysis of one or more target genetic loci in a DNA clone library to detect or identify a change in the sequence at the one or more target genetic loci. In some embodiments, the change is a change in copy number.

In one embodiment, a method of detecting, identifying, predicting, diagnosing, or monitoring a genetic state, condition or disease comprises isolating or obtaining cellular DNA or cfDNA from a biological sample of a subject; treating the cellular DNA or cfDNA with one or more end-repair enzymes to generate end-repaired DNA; attaching one or more adaptors to each end of the end-repaired DNA to generate a genomic DNA library; amplifying the DNA library to generate a DNA clone library; determining the number of genome equivalents in the DNA clone library; and performing a quantitative genetic analysis of one or more target genetic loci in a DNA clone library to detect or identify a change in the sequence, e.g., an SNP, a translocation, an inversion, a deletion, or a change in copy number at of the one or more target genetic loci.

In particular embodiments, a method of detecting, identifying, predicting, diagnosing, or monitoring a genetic state, or genetic condition or disease selected from the group consisting of: genetic diseases; genetic mosaicism; fetal testing; paternity testing; paternity testing; predicting response to drug treatment; diagnosing or monitoring a medical condition; microbiome profiling; pathogen screening; and organ transplant monitoring comprising isolating or obtaining genomic DNA from a biological sample of a subject; treating the DNA with one or more end-repair enzymes to generate end-repaired DNA; attaching one or more adaptors to each end of the end-repaired DNA to generate a genomic DNA library; amplifying the genomic DNA library to generate a DNA clone library; determining the number of genome equivalents in the DNA clone library; and performing a quantitative genetic analysis of one or more target genetic loci in a DNA clone library to detect or identify a nucleotide transition or transversion, a nucleotide insertion or deletion, a genomic rearrangement, a change in copy number, or a gene fusion in the sequence at the one or more target genetic loci.

Illustrative examples of genetic diseases that can be detected, identified, predicted, diagnosed, or monitored with the compositions and methods contemplated herein include, but are not limited to cancer, Alzheimer's disease (APOE1), Charcot-Marie-Tooth disease, Leber hereditary optic neuropathy (LHON), Angelman syndrome (UBE3A, ubiquitin-protein ligase E3A), Prader-Willi syndrome (region in chromosome 15), β-Thalassaemia (HBB, β-Globin), Gaucher disease (type I) (GBA, Glucocerebrosidase), Cystic fibrosis (CFTR Epithelial chloride channel), Sickle cell disease (HBB, β-Globin), Tay-Sachs disease (HEXA, Hexosaminidase A), Phenylketonuria (PAH, Phenylalanine hydrolyase), Familial hypercholesterolaemia (LDLR, Low density lipoprotein receptor), Adult polycystic kidney disease (PKD1, Polycystin), Huntington disease (HDD, Huntingtin), Neurofibromatosis type I (NF1, NF1 tumour suppressor gene), Myotonic dystrophy (DM, Myotonin), Tuberous sclerosis (TSC1, Tuberin), Achondroplasia (FGFR3, Fibroblast growth factor receptor), Fragile X syndrome (FMR1, RNA-binding protein), Duchenne muscular dystrophy (DMD, Dystrophin), Haemophilia A (F8C, Blood coagulation factor VIII), Lesch-Nyhan syndrome (HPRT1, Hypoxanthine guanine ribosyltransferase 1), and Adrenoleukodystrophy (ABCD1).

Illustrative examples of cancers that can be detected, identified, predicted, diagnosed, or monitored with the compositions and methods contemplated herein include, but are not limited to: B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the genetic lesion is a lesion annotated in the Cosmic database (the lesions and sequence data are available online and can be downloaded from the Cancer Gene Census section of the Cosmic website) or a lesion annotated in the Cancer Genome Atlas (the lesions and sequence data are available online and can be downloaded from The Cancer Genome Atlas website).

Illustrative examples of genes that harbor one or more genetic lesions associated with cancer that can be detected, identified, predicted, diagnosed, or monitored with the compositions and methods contemplated herein include, but are not limited to ABCB1, ABCC2, ABCC4, ABCG2, ABL1, ABL2, AKT1, AKT2, AKT3, ALDH4A1, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, EPHX1, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, M1TF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1. SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TNFRSF14, TOP1, TP53, TPMT, TSC1, TSC2, TYMS, UGT1A1, UMPS, USP9X, VHL, and WT1.

In particular embodiments, the genetic lesion comprises a nucleotide transition or transversion, a nucleotide insertion or deletion, a genomic rearrangement, a change in copy number, or a gene fusion.

In one embodiment, the genetic lesion is a gene fusion that fuses the 3' coding region of the ALK gene to another gene.

In one embodiment, the genetic lesion is a gene fusion that fuses the 3' coding region of the ALK gene to the EML4 gene.

Illustrative examples of conditions suitable for fetal testing that can be detected, identified, predicted, diagnosed, or monitored with the compositions and methods contemplated herein include but are not limited to: Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomv 16, Turner Syndrome (XO), Robertsonian translocation, DiGeorge Syndrome and Wolf-Hirschhom Syndrome.

Illustrative examples of alleles suitable for paternity testing that can be detected, identified, predicted, diagnosed, or monitored with the compositions and methods contemplated herein include but are not limited to 16 or more of: D20S1082, D6S474, D12ATA63, D22S1045, D10S1248, D1S1677, D11S4463, D4S2364, D9S1122, D2S1776, D10S1425, D3S3053, D5S2500, D1S1627, D3S4529, D2S441, D17S974, D6S1017, D4S2408, D9S2157, Amelogenin, D17S1301, D1GATA113, D18S853, D20S482, and D14S1434.

Illustrative examples of genes suitable for predicting the response to drug treatment that can be detected, identified, predicted, diagnosed, or monitored with the compositions and methods contemplated herein include, but are not limited to, one or more of the following genes: ABCB1 (ATP-binding cassette, sub-family B (MDR/TAP), member 1), ACE (angiotensin I converting enzyme), ADH1A (alcohol dehydrogenase 1A (class I), alpha polypeptide), ADH1B (alcohol dehydrogenase IB (class I), beta polypeptide), ADH1C (alcohol dehydrogenase 1C (class I), gamma polypeptide), ADRB1 (adrenergic, beta-1-, receptor), ADRB2 (adrenergic, beta-2-, receptor, surface), AHR (aryl hydrocarbon receptor), ALDH1A1 (aldehyde dehydrogenase 1 family, member A1), ALOX5 (arachidonate 5-lipoxygenase), BRCA1 (breast cancer 1, early onset), COMT (catechol-O-methyltransferase), CYP2A6 (cytochrome P450, family 2, subfamily A, polypeptide 6), CYP2B6 (cytochrome P450, family 2, subfamily B, polypeptide 6), CYP2C9 (cytochrome P450, family 2, subfamily C, polypeptide 9), CYP2C19 (cytochrome P450, family 2, subfamily C, polypeptide 19), CYP2D6 (cytochrome P450, family 2, subfamily D, polypeptide 6), CYP2J2 (cytochrome P450, family 2, subfamily J, polypeptide 2), CYP3A4 (cytochrome P450, family 3, subfamily A, polypeptide 4), CYP3A5 (cytochrome P450, family 3, subfamily A, polypeptide 5), DPYD (dihydropyrimidine dehydrogenase), DRD2 (dopamine receptor D2), F5 (coagulation factor V), GSTP1 (glutathione S-transferase pi), HMGCR (3-hydroxy-3-methylglutaryl-Coenzyme A reductase), KCNH2 (potassium voltage-gated channel, subfamily H (eag-related), member 2), KCNJ11 (potassium inwardly-rectifying channel, subfamily J, member 11), MTHFR (5,10-methylenetetrahydrofolate reductase (NADPH)), NQO1 (NAD(P)H dehydrogenase, quinone 1), P2RY1 (purinergic receptor P2Y, G-protein coupled, 1), P2RY12 (purinergic receptor P2Y, G-protein coupled, 12), PTGIS (prostaglandin I2 (prostacyclin) synthase), SCN5A (sodium channel, voltage-gated, type V, alpha (long QT syndrome 3)), SLC19A1 (solute carrier family 19 (folate transporter), member 1), SLCO1B1 (solute carrier organic anion transporter family, member 1B1), SULT1A1 (sulfotransferase family, cytosolic, 1A, phenol-preferring, member 1), TPMT (thiopurine S-methyltransferase), TYMS (thymidylate synthetase), UGT1A1 (UDP glucuronosyltransferase 1 family, polypeptide A1), VDR (vitamin D (1,25-dihydroxyvitamin D3) receptor), VKORC1 (vitamin K epoxide reductase complex, subunit 1).

Illustrative examples of medical conditions that can be detected, identified, predicted, diagnosed, or monitored with the compositions and methods contemplated herein include, but are not limited to: stroke, transient ischemic attack, traumatic brain injury, heart disease, heart attack, angina, atherosclerosis, and high blood pressure.

Illustrative examples of pathogens that can be screened for with the compositions and methods contemplated herein include, but are not limited to: bacteria fungi, and viruses.

Illustrative examples of bacterial species that can be screened for with the compositions and methods contemplated herein include, but are not limited to: a *Mycobacterium* spp., a *Pneumococcus* spp., an *Escherichia* spp., a *Campylobacter* spp., a *Corynebacterium* spp., a *Clostridium* spp., a *Streptococcus* spp., a *Staphylococcus* spp., a *Pseudomonas* spp., a *Shigella* spp., a *Treponema* spp., or a *Salmonella* spp.

Illustrative examples of fungal species that can be screened for with the compositions and methods contemplated herein include, but are not limited to: an *Aspergillis* spp., a *Blastomyces* spp., a *Candida* spp., a *Coccicioides* spp., a *Cryptococcus* spp., dermatophytes, a *Tinea* spp., a *Trichophyton* spp., a *Microsporum* spp., a *Fusarium* spp., a *Histoplasma* spp., a *Mucoromycotina* spp., a *Pneumocystis* spp., a *Sporothrix* spp., an *Exserophilum* spp., or a *Cladosporium* spp.

Illustrative examples of viruses that can be screened for with the compositions and methods contemplated herein include, but are not limited to: Influenza A such as H1N1, H1N2, H3N2 and H5N1 (bird flu), Influenza B, Influenza C virus, Hepatitis A virus. Hepatitis B virus, Hepatitis C virus. Hepatitis D virus, Hepatitis E virus. Rotavirus, any virus of the Norwalk virus group, enteric adenoviruses, parvovirus, Dengue fever virus. Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV), HIV (human immunodeficiency virus; including HIV type 1, and HIV type 2), visna-maedi virus (VMV) virus, the caprine arthritis-encephalitis virus (CAEV), equine infectious anemia virus (EIAV), feline immunodeficiency virus (FIV), bovine immune deficiency virus (BIV), and simian immunodeficiency virus (SIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephaliltus causing virus.

Illustrative examples of genes suitable for monitoring an organ transplant in a transplant recipient that can be detected, identified, predicted, diagnosed, or monitored with the compositions and methods contemplated herein include, but are not limited to, one or more of the following genes: HLA-A, HLA-B, HLA-C, HLA-DR, HLA-DP, and HLA-DQ.

In particular embodiments, a bioinformatic analysis is used to quantify the number of genome equivalents analyzed in the cfDNA clone library; detect genetic variants in a target genetic locus; detect mutations within a target genetic locus; detect genetic fusions within a target genetic locus; or measure copy number fluctuations within a target genetic locus.

F. Companion Diagnostics

In various embodiments, a companion diagnostic for a genetic disease is provided, comprising: isolating or obtaining genomic DNA from a biological sample of a subject; treating the DNA with one or more end-repair enzymes to generate end-repaired DNA; attaching one or more adaptors to each end of the end-repaired DNA to generate a DNA library; amplifying the DNA library to generate a DNA clone library; determining the number of genome equivalents in the DNA clone library; and performing a quantitative genetic analysis of one or more biomarkers associated with the genetic disease in the DNA clone library, wherein detection of, or failure to detect, at least one of the one or more biomarkers indicates whether the subject should be treated for the genetic disease. In some embodiments, the DNA is cfDNA. In particular embodiments, the DNA is cellular DNA.

As used herein, the term "companion diagnostic" refers to a diagnostic test that is linked to a particular anti-cancer therapy. In a particular embodiment, the diagnostic methods comprise detection of genetic lesion in a biomarker associated with in a biological sample, thereby allowing for prompt identification of patients should or should not be treated with the anti-cancer therapy.

Anti-cancer therapy includes, but is not limited to surgery, radiation, chemotherapeutics, anti-cancer drugs, and immunomodulators.

Illustrative examples of anti-cancer drugs include, but are not limited to: alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin and its pegylated formulations, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Illustrative examples of immunomodulators include, but are not limited to: cyclosporine, tacrolimus, tresperimus, pimecrolimus, sirolimus, verolimus, laflunimus, laquinimod and imiquimod, as well as analogs, derivatives, salts, ions and complexes thereof.

In some embodiments, an anti-cancer drug may include a poly-ADP ribose polymerase (PARP) inhibitor. Illustrative examples of PARP inhibitors include, but are not limited to, olaparib (AZD-2281), rucaparib (AG014699 or PF-01367338, niraparib (MK-4827), talazoparib (BMN-673) veliparib (ABT-888), CEP 9722, E7016, BGB-290, 3-aminobenzamide.

All publications, patent applications, and issued patents cited in this specification are herein incorporated by reference as if each individual publication, patent application, or issued patent were specifically and individually indicated to be incorporated by reference. In particular, the entire contents of International PCT Publication No. WO 2016/028316 are specifically incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Copy Number Analysis of Samples Containing Blends of Fragmented Genomic DNA Meticulous blends of fragmented genomic DNA were generated that contained DNA derived from ΔATM or ΔBRCA2 immortalized human samples spiked into a fragmented wild-type human gDNA sample. The advantage of this sample type is that the composition can be carefully controlled and sample availability is essentially unlimited.

Figure 7:
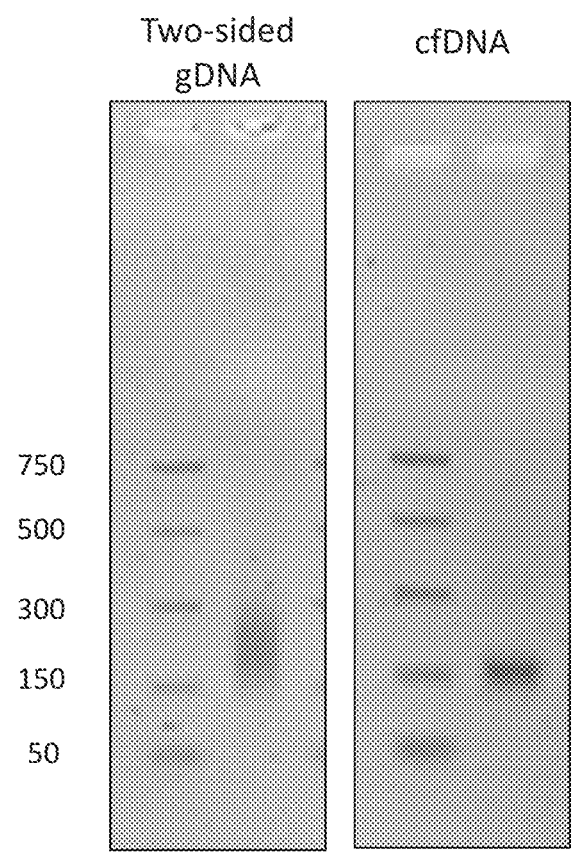
FIG. 7 shows DNA inputs into CNL libraries. Agarose gel images are shown with the sizes of markers (bp) indicated at left.

Wild-type, human female genomic DNA was purified from whole blood samples donated by a healthy volunteer. Genomic DNA isolated from an immortalized cell harboring a heterozygous deletion covering the entire ATM gene (NA09596, ΔATM) and a separate sample bearing a heterozygous deletion of BRCA2 (NA02718, ΔBRCA2) were obtained from the Coriell repository. Importantly, these samples appeared to have an otherwise normal ploidy across the remainder of the genomes. The ΔATM sample was derived from a male donor and was therefore also hemizygous in copy number for the X-linked AR gene. Cell free DNA (cfDNA) was obtained from healthy donor plasma samples of female or male origin. For library construction, genomic DNA was sonicated on a setting of 200 bp with a Covaris instrument, then further size selected using a "two-sided" DNA bead purification. Library input DNA samples are shown in FIG. 7.

Appropriate combinations of fragmented and cfDNA samples were blended to defined percentages, end-repaired, and converted to genomic libraries. Approximately 500 ng of each library was combined in sets of eight samples and hybridized to the copy number loss (CNL) prostate probe pool that contained 2304 DNA probes. Following sample processing, each set of eight samples was sequenced on an Illumina NextSeq NGS instrument to a depth of ~480 million pass-filter reads; this corresponds to 60 million reads/sample. Roughly 95% of reads possessed legitimate sample ID tags and aligned to the human reference genome and of these, ~98% mapped to the intended target loci. The overall sequencing depth, measured as the number of reads per input genome per probe (calculated as on-target reads (60 million) divided by average genome depth (2500) and divided by probe count (2400)) was approximately 10 reads per genome per probe. A graphic representation of the copy number loss analysis is shown in FIG. 1. Copy number perturbations are highlighted by arrows. (Sample 1, 5% male DNA into female DNA; sample 2, 5% ΔATM DNA (male) into female DNA; sample 3, 5% ΔBRCA2 DNA (female) into female DNA; sample 4, pure female DNA).

The CNL caller identifies redundant reads and condenses these into a single consensus reads that are then quantified at each probe location. This information was further condensed into gene-by-gene copy number averages. Finally, a statistical significance was assigned to deviations detected in each CNL measurement; this is shown graphically as the $\log_{10}$P-value of statistical significance.

Figures 9A, 9B:
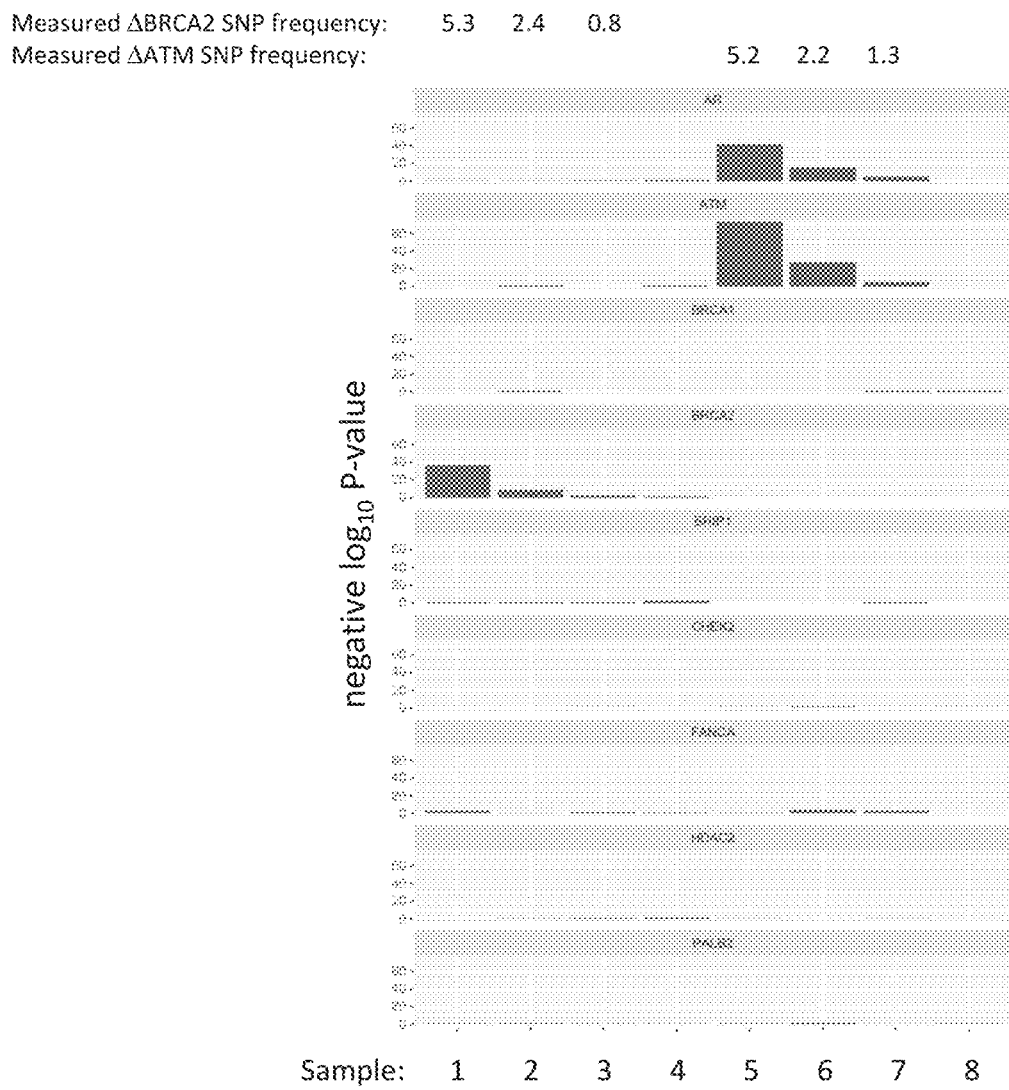
FIG. 9A-FIG. 9B shows $Log_{10}$ P-value plots that quantify significant deviation-from-normal in CNL measurements for fragmented genomic samples. The SNP percentages at the top show the minor allele frequencies of rare, heterozygous SNPs that are present in the ΔATM and ΔBRCA2 samples.
Figures 10A, 10B:
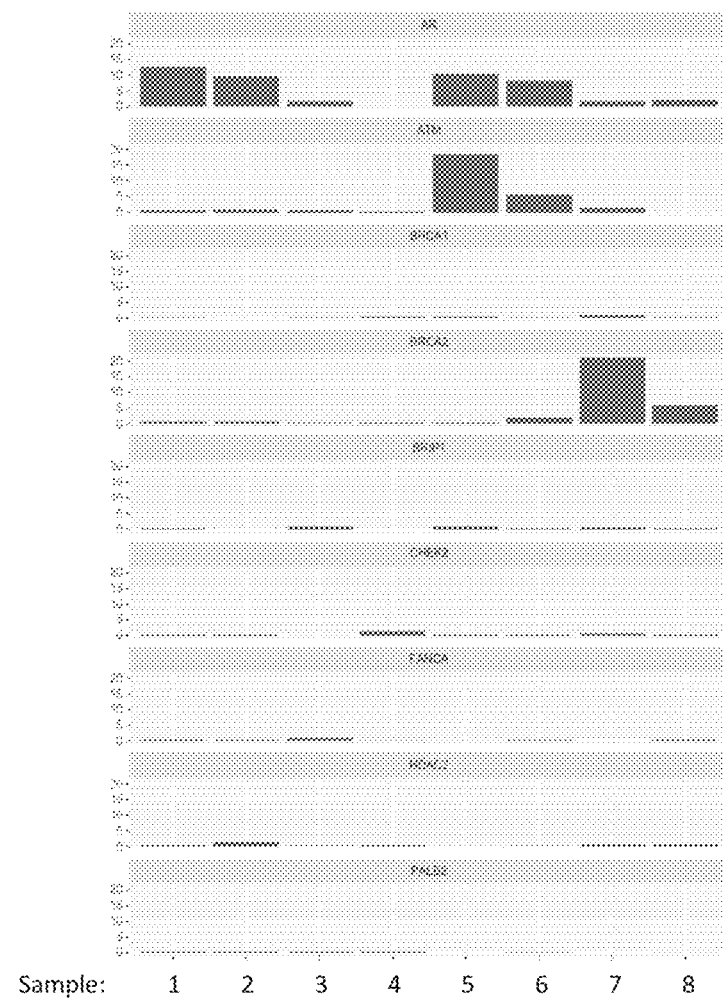
FIG. 10A-FIG. 10B shows $Log_{10}$ P-value plots that quantify significant deviation-from-normal in CNL measurements for cfDNA samples spiked with fragmented genomic DNA. The SNP percentages at the top show the minor allele frequencies of rare, heterozygous SNPs that are present in the ΔATM and ΔBRCA2 samples.

FIG. 8 shows box-and-whisker plots of copy number determinations for the AR (FIG. 8B) and ATM (FIG. 8C) genes in fragmented and blended genomic libraries. Because the ΔATM sample is male, the AR gene (X-linked, hemizygous) and the ATM gene both exhibited CNL behavior. As anticipated, the magnitude of measured copy variation was modest. The statistical analysis shown in FIG. 9B demonstrates that the observed copy fluctuation was statistically significant. Moreover, very little significant fluctuation was observed in the remaining genes that were predicted to exhibit uniform copy characteristics. These values correlated well with frequencies predicted for the various genomic blends. FIG. 10 shows that statistically significant copy fluctuation was also readily observed in samples that were primarily cfDNA with minor spike-ins of either cfDNA from the opposite sex or minor additions of fragmented gDNA. These values correlated well with frequencies predicted for the various genomic blends. The results seen with both fragmented gDNA and with cfDNA were comparable, thereby demonstrating the integrity of the assay and suggesting that the integrity will translate to clinical samples.

These data demonstrate the ability of the assay system to detect subtle changes in gene copy number down to minor allele frequencies of 2%. While the focus of demonstrated examples presented is on copy number loss, the technology is equally well suited to the detection of copy number gains, including increases in gene copy that occur through chromosomal arm duplications and focal amplifications. This assay further retains the ability to detect other types of genomic variants, including SNVs, indels and gene fusions (chromosomal rearrangements). Importantly, these data demonstrate that the method can be applied to genomic DNA derived from plasma, but also to genomic DNA derived from other sources such as tissue and other bodily sources.

Example 2: Copy Number Analysis of cfDNA from Healthy Donors and a Cancer Patient The following example illustrate the manner in which the molecular features added during genomic library construction and post-hybridization processing are used to generate copy number analysis. DNA was extracted from the plasma of sixteen healthy donors and one castration-resistant prostate cancer patient using the Qiagen Circulating Nucleic Acids Extraction kit (Qiagen, Hilden, Germany). The yield of double-strand DNA was quantified using a Qubit fluorometer (Thermo Fisher, Waltham, Mass.) and the corresponding hsDNA quantitation kit. Size analysis was performed using gel electrophoresis on 2% agarose gels with PCR markers as size standards (New England Biolabs, Ipswich, Mass.). Approximately 40-100) ng of cfDNA, depending on the yield of cfDNA from the sample, was used for library construction.

Figure 11A:
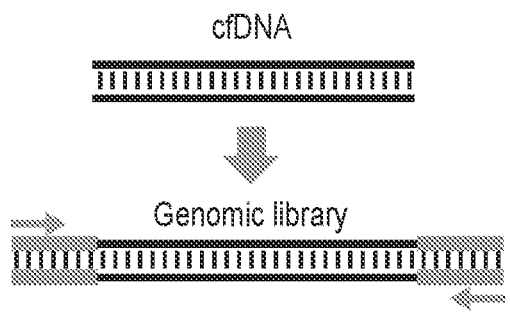
FIG. 11A-FIG. 11D illustrate the targeted hybrid capture platform.
Figure 11B:
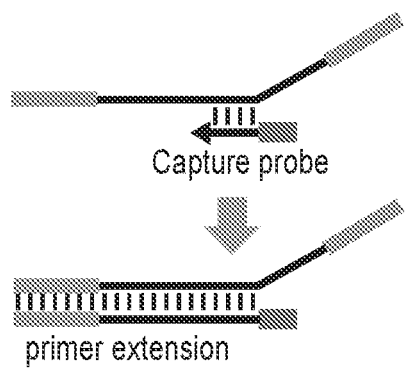
Figure 11C:
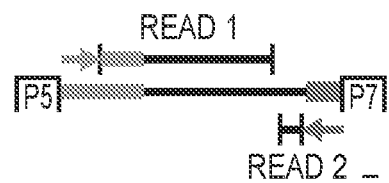

The basic features of library construction are illustrated in FIG. 11A-11C. The cfDNA was first dephosphorylated and then repaired to blunt ends in a two-step process. Short, 10 nt anchor sequences consisting of a phosphorylated ligation strand and an inert partner strand were then ligated to the cfDNA. The eight oligonucleotides used to create the set of four anchor sequences are shown in Table 1.

Figure 11D:
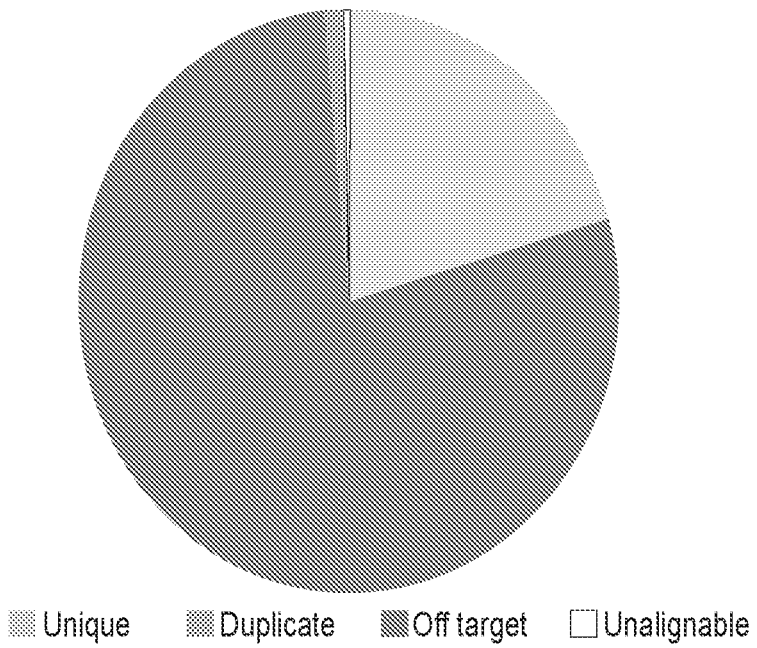

The adaptor structures were completed by the addition of full-length adaptor sequences that annealed to the anchor sequence. Thirty-two sets of adaptor sequences, each composed of 240 members, are shown in FIG. 12-FIG. 22. These adaptors were attached to the cfDNA and extended through the concerted actions of polynucleotide kinase, DNA polymerase and DNA ligase to generate genomic libraries. As a pre-sequencing quality control step, the resulting genomic libraries were quantified by qPCR for depth of coverage. The genomic libraries were then amplified and hybridized to probe sets targeting specific genes (FIG. 11B). Following hybridization, primer extension of the probe was used to copy the captured genomic sequences and the information encoded in the attached adaptor (FIG. 11C). An example of post sequencing analysis using standard next-generation analysis software is shown in FIG. 11D. This analysis was performed on a sequencing run that contained 32 samples (28 cancer patient samples and 4 wild-type controls) and it displays the overall distribution of sequencing reads.

Figures 23A, 23B, 23C:
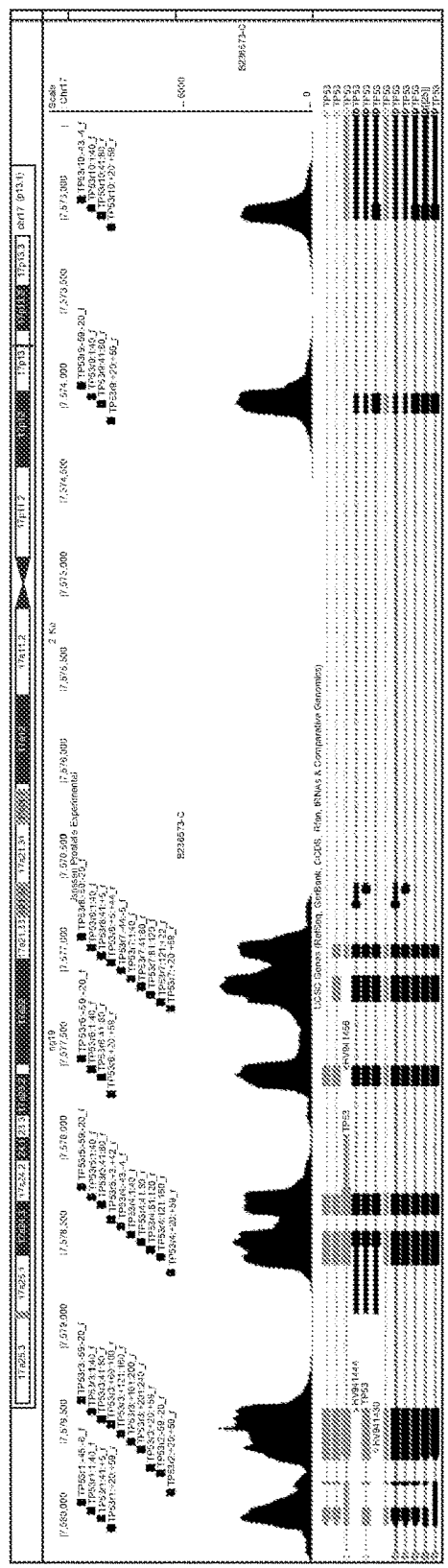
FIG. 23A-FIG. 23C shows targeted sequencing of the TP53 gene.

A central feature of the targeted hybrid capture platform described herein is that it provides multiple types of genomic information. One essential function of capture probes is to provide mutation detection across target regions at a high depth of coverage. This function is governed by the sequence context, density, and placement of the capture probes and is illustrated in FIG. 23 with the TP53 gene (TP53 probe sequences are shown in Table 2 below). Of equal significance, the targeted hybrid capture platform assay generated a readout of equal depth of coverage in regions where no significant mutations were detected. These data are critical to physicians and patients as they add statistical significance in cases where no deleterious mutations were detected.

TABLE 2

TP53 Probes

| Name | Sequence | SEQ ID NO: |
|---|---|---|
| TP53_1 | GGCACAGACCCTCTCACTCATGTGATGTCATCT CTCCTCC | 7689 |
| TP53_2 | ATGGGGGTGGGAGGCTGTCAGTGGGGAACAAGA AGTGGAG | 7690 |

TABLE 1

Ligation anchor oligonucleotides

| Oligo ID | Nucleic Acid Sequence | SEQ ID NO: |
|---|---|---|
| Partner strand oLigation strand oligoo_16-1 | GTATGCC[3-dA-Q]* | 1 |
| Partner strand oLigation strand oligoo_16-2 | AGCGTTA[3-dC-Q]* | 2 |
| Partner strand oLigation strand oligoo_16-3 | TCGACAT[3-dA-Q]* | 3 |
| Partner strand oLigation strand oligoo_16-4 | CATCAGG[3-dA-Q]* | 4 |
| Ligation strand oligo_16-1 | /5Phos/TGG CAT ACG T** | 5 |
| Ligation strand oligo_16-2 | /5Phos/GTA ACG CTA G** | 6 |
| Ligation strand oligo_16-3 | /5Phos/CAT GTC GAT C** | 7 |
| Ligation strand oligo_16-4 | /5Phos/ACC TGA TGC A** | 8 |

*[3-d(A, C, G, or T)-Q] denotes a modified base in which the hydroxyl group resides on the 2' position of the ribose ring
**/5Phos/ denotes the chemical addition of a 5' phosphate group to the 5' base position TABLE 2-continued TP53 Probes

| Name | Sequence | SEQ ID NO: |
|---|---|---|
| TP53_3 | GTCAGTCTGAGTCAGGCCCTTCTGTCTTGAACA TGAGTTT | 7691 |
| TP53_4 | CCTGAAGTCCAAAAAGGGTCAGTCTACCTCCCG CCATAAA | 7692 |

TABLE 2-continued

TP53 Probes

| Name | Sequence | SEQ ID NO: |
|---|---|---|
| TP53_5 | TCATGCTGGATCCCCACTTTTCCTCTTGCAGCAGCCAGAC | 7693 |
| TP53_6 | GTTGGGGTGGGGGTGGTGGGCCTGCCCTTCCAATGGATCC | 7694 |
| TP53_7 | CAGTTTCCATAGGTCTGAAAATGTTTCCTGACTCAGAGGG | 7695 |
| TP53_8 | CTGCCATGGAGGAGCCGCAGTCAGATCCTAGCGTCGAGCC | 7696 |
| TP53_9 | GCAGAGACCTGTGGGAAGCGAAAATTCCATGGGACTGACT | 7697 |
| TP53_10 | CTGGGGGGCTGGGGGGCTGAGGACCTGGTCCTCTGACTGC | 7698 |
| TP53_11 | GCAGGGGGATACGGCCAGGCATTGAAGTCTCATGGAAGCC | 7699 |
| TP53_12 | GTGGCCCCTGCACCAGCAGCTCCTACACCGGCGGCCCCTG | 7700 |
| TP53_13 | GGGGGGAGCAGCCTCTGGCATTCTGGGAGCTTCATCTGGA | 7701 |
| TP53_14 | CCGTGCAAGTCACAGACTTGGCTGTCCCAGAATGCAAGAA | 7702 |
| TP53_15 | CCCCGGACGATATTGAACAATGGTTCACTGAAGACCCAGG | 7703 |
| TP53_16 | CCAGAAAACCTACCAGGGCAGCTACGGTTTCCGTCTGGGC | 7704 |
| TP53_17 | TAGGTTTTCTGGGAAGGGACAGAAGATGACAGGGGCCAGG | 7705 |
| TP53_18 | TGCTTTATCTGTTCACTTGTGCCCTGACTTTCAACTCTGT | 7706 |
| TP53_19 | CCTGGGCAACCAGCCCTGTCGTCTCTCCAGCCCCAGCTGC | 7707 |
| TP53_20 | TTTGCCAACTGGCCAAGACCTGCCCTGTGCAGCTGTGGGT | 7708 |
| TP53_21 | CCATCGCTATCTGAGCAGCGCTCATGGTGGGGCAGCGCC | 7709 |
| TP53_22 | GCCATCTACAAGCAGTCACAGCACATGACGGAGGTTGTGA | 7710 |
| TP53_23 | CATGGCGCGGACGCGGGTGCCGGGCGGGGTGTGGAATCA | 7711 |
| TP53_24 | CCAGGGTCCCCAGGCCTCTGATTCCTCACTGATTGCTCTT | 7712 |
| TP53_25 | GAGGGCCACTGACAACCACCCTTAACCCCTCCTCCCAGAG | 7713 |
| TP53_26 | CCTCAGGCGGCTCATAGGGCACCACCACACTATGTCGAAA | 7714 |
| TP53_27 | AGGAAATTTGCGTGTGGAGTATTTGGATGACAGAAACACT | 7715 |
| TP53_28 | CTTGCCACAGGTCTCCCCAAGGCGCACTGGCCTCATCTTG | 7716 |
| TP53_29 | GAGGCAAGCAGAGGCTGGGGCACAGCAGGCCAGTGTGCAG | 7717 |
| TP53_30 | CCTGGAGTCTTCCAGTGTGATGATGGTGAGGATGGGCCTC | 7718 |
| TP53_31 | ACTACATGTGTAACAGTTCCTGCATGGGCGGCATGAACCG | 7719 |
| TP53_32 | GGACAGGTAGGACCTGATTTCCTTACTGCCTCTTGCTTCT | 7720 |
| TP53_33 | CTGCACCCTTGGTCTCCTCCACCGCTTCTTGTCCTGCTTG | 7721 |
| TP53_34 | TCTCTTTTCCTATCCTGAGTAGTGGTAATCTACTGGGACG | 7722 |
| TP53_35 | CCTCGCTTAGTGCTCCCTGGGGGCAGCTCGTGGTGAGGCT | 7723 |
| TP53_36 | GACCGGCGCACAGAGGAAGAGAATCTCCGCAAGAAAGGGG | 7724 |
| TP53_37 | TCTCCCAGGACAGGCACAAACACGCACCTCAAAGCTGTTC | 7725 |
| TP53_38 | TGCCTCAGATTCACTTTTATCACCTTTCCTTGCCTCTTTC | 7726 |
| TP53_39 | GGCATTTTGAGTGTTAGACTGGAAACTTTCCACTTGATAA | 7727 |
| TP53_40 | CCTGAAGGGTGAAATATTCTCCATCCAGTGGTTTCTTCTT | 7728 |
| TP53_41 | CCTAGCACTGCCCAACAACACCAGCTCCTCTCCCCAGCCA | 7729 |
| TP53_42 | CATCTTTTAACTCAGGTACTGTGTATATACTTACTTCTCC | 7730 |
| TP53_43 | ATGGCTTTCCAACCTAGGAAGGCAGGGGAGTAGGGCCAGG | 7731 |
| TP53_44 | CCTGGAGTGAGCCCTGCTCCCCCCTGGCTCCTTCCCAGCC | 7732 |
| TP53_45 | TCCGAGAGCTGAATGAGGCCTTGGAACTCAAGGATGCCCA | 7733 |

The linkage of the capture probe with captured genomic sequence (FIG. 11C) also facilitated measurement of genomic depth at each probe location. The number of unique reads associated with every capture probe used in the experiment was measured (FIG. 24). The data shown in FIG. 24 was derived from a sequencing run in which 16 healthy donor cfDNA samples were analyzed. The depth of unique reads encountered in each sample at one probe location in the TP53 gene were calculated (Raw unique read counts shown in FIG. 24A). Each sample comprised a unique library depth, as reflected in the broad sample-to-sample distribution of unique reads. The global average of unique read depth across all 2596 capture probes in the experiment was also calculated (FIG. 24B). Significantly, normalization of the observed read depth at the single probe site displayed in FIG. 24C by the global unique read depth measured for all probes revealed a uniform density of normalized unique reads. These data indicate that the capture performance of a particular probe chosen for analysis was uniform from sample-to-sample and proportional to the genomic depth of each individual library.

Figure 25:
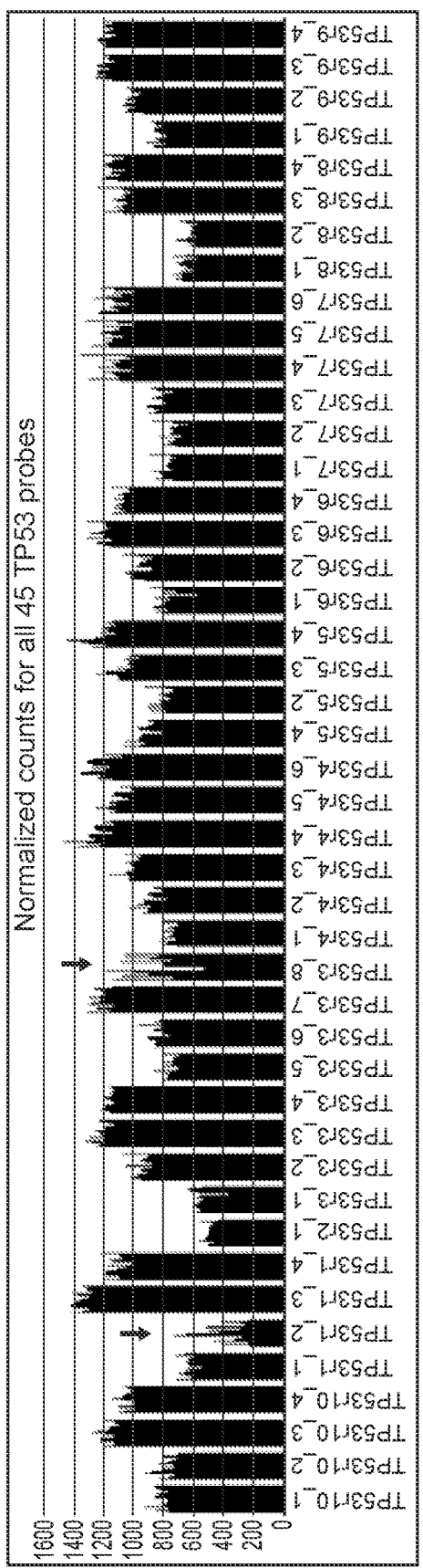
FIG. 25 shows general consistency of the normalized unique read counts for all 16 samples within any given TP53 probe despite significant average depth variation between probes. The normalized unique read counts for all 16 samples are shown as "pillars" of tightly spaced bar graphs; the results for all 45 probes that target TP53 are shown. Two probes that exhibit "noisy" counting behavior are highlighted with arrows. Counts from such probes often appear as outliers in subsequent copy number analysis.

This same normalization function was applied to the 45 TP53-specific probes shown in FIG. 23 (normalization data shown in FIG. 25). Whereas FIG. 23 shows the aggregate contribution of all probes to the sequencing depth of TP53 coding regions, FIG. 25 shows the normalized depth retrieved by each individual probe. The normalized depth retrieved by each individual probe was generally consistent from sample-to-sample for any given probe but somewhat variable when one probe was compared to another. Several factors governed the differences in the post-normalization capture depths observed between probes, the most significant being the placement of probes relative to one another and the proximity of probes to genomic repeat regions. Not all probes exhibited uniform capture behavior; two probes whose capture performance were not consistent are highlighted by arrows in FIG. 25. However, these data indicate that such probes are rare and easily identified. As such, and they can be excluded from downstream copy number analysis.

Figure 26:
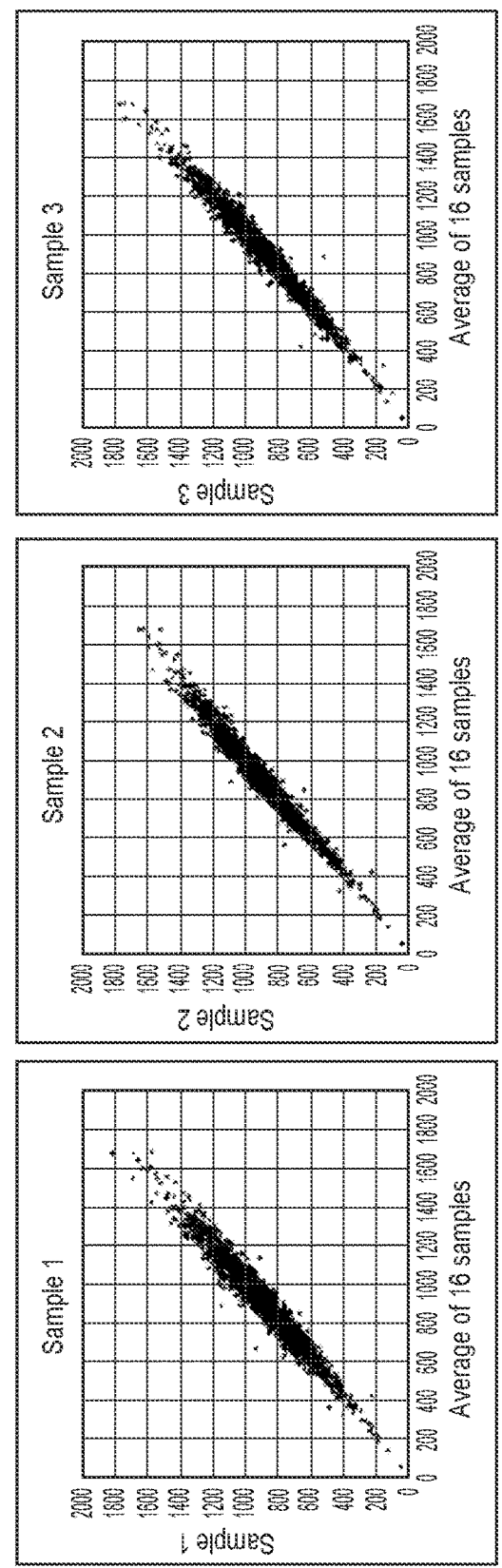
FIG. 26 illustrates sample-to-sample consistency of normalized probe-by-probe unique read counts across a broad panel of 2596 probes. The scatter plots from three representative samples are shown. Each dot represents a different probe. The x-axis is the normalized average unique read depth per probe across 16 samples. The y-axis is the normalized unique read depth per probe for three different individual samples. The consistent probe-by-probe unique read counts support quantitative analysis of chromosomal copy variation.

The uniform capture performance exhibited by the 45 TP53 targeting probes in FIG. 25 is a general feature of the targeted hybrid capture platform described herein. In FIG. 26, the average capture depth for each probe in a panel of 2596 capture probes was calculated for all 16 normal cfDNA libraries that were profiled in this experiment. The average was then compared individually with three representative samples using scatter plot analysis. Each dot represents a different probe and its position on the graph is a comparison of the average on the x-axis and the individual sample on the y-axis. The tight diagonal distribution of the majority of probes reflected the highly-correlated unique read capture performance of most probes ($R^2$ correlation ≥0.95 for all three graphs). Importantly, the consistency of probe-by-probe sequencing depth supports the use of the targeted hybrid capture platform in copy number measurement.

Figure 27B:
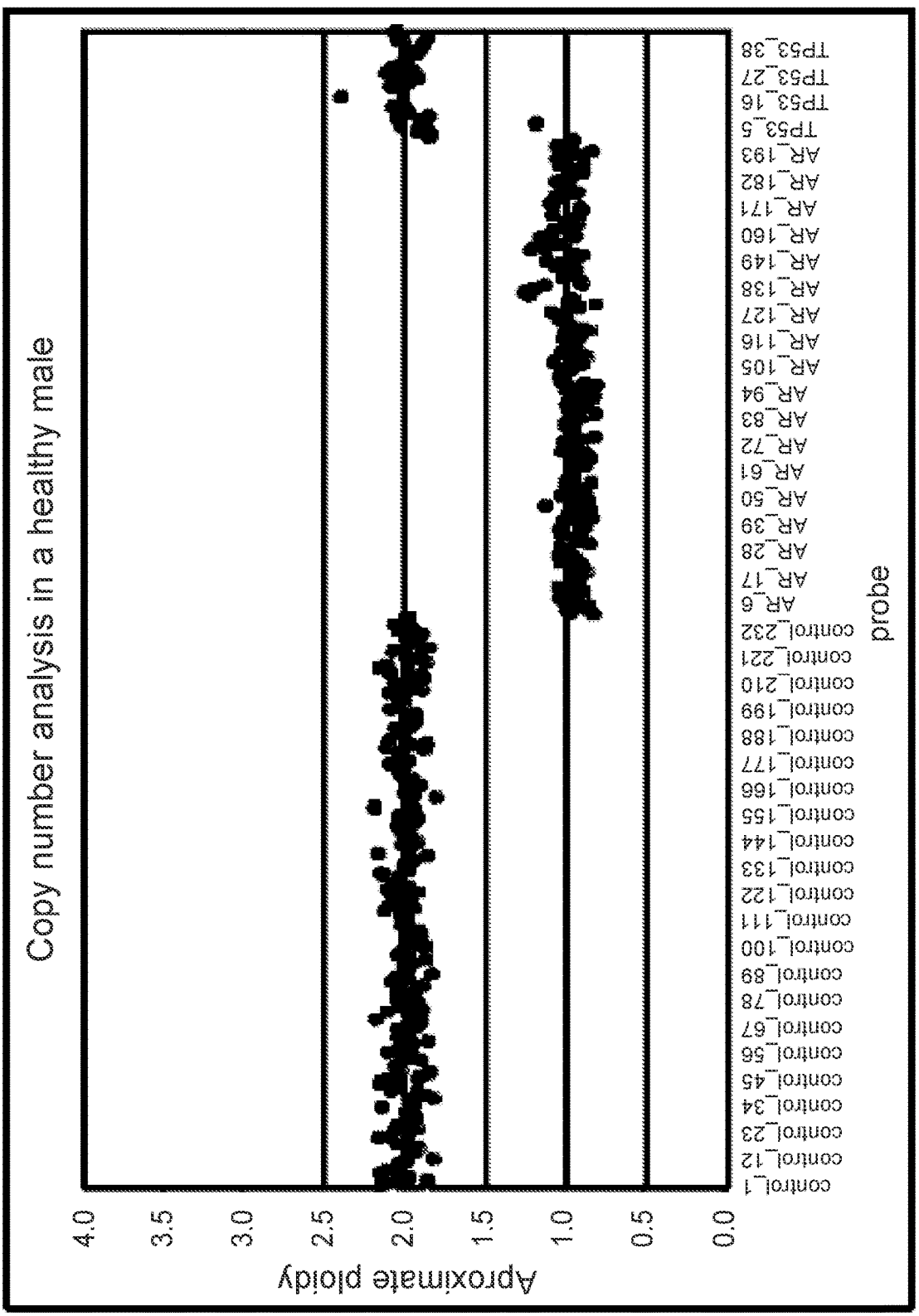

With respect to copy number, the most straightforward treatment of probe data is to further normalize the adjusted genomic depth values that occur in autosomal chromosomes to a diploid-averaged value of "2". The same is true for probe values that occur in females for X-linked loci. For X-linked and Y-linked regions in normal males, averaged copy values are appropriately set to "1". This numerical transformation was applied to a set of chromosomal control probes (239 probes that target select loci on all 22 autosomal chromosomes, Table 3), a set of 199 probes that target the X-linked AR gene, and the 45 TP53-specific probes considered in detail above (FIGS. 27A and 27B). Each dot represents the value for an individual probe. With the exception of infrequent "noisy" probes, the vast majority of individual probe counts in regions anticipated to be diploid possessed values that were approximately "2". Probes for the AR gene in a healthy male fluctuated with an average value close to the anticipated "1."

TABLE 3

Chromosomal Control Probes

| Name | Sequence | SEQ ID NO: |
|---|---|---|
| Chr_1_1 | GTGTCTCGGCAACCACTCTTCACCAATATCACAGTGGACA | 7734 |
| Chr_1_2 | ATCCAAGGGGAGGAGATCAGTGCCCCTATTTGTATCGCAC | 7735 |
| Chr_1_3 | ACTTACTGAAGCAAGAACCTCATCAAGCTGCCTCCCACCA | 7736 |
| Chr_1_4 | AGTTTGTGATCCTCCTGTGGGCAACCTCAGCAGTCTGGTT | 7737 |
| Chr_1_5 | GGAGAGCGGAGCTGCTCAGAGCTTGGCCAGGTTCTAAGTG | 7738 |
| Chr_1_6 | GACTGTGGCAATGAGGCAGCTAAGTGGTTCACCAACTTCT | 7739 |
| Chr_1_7 | GGTGTATTTTGACAACGGTGGACCCAGACACTGGAGTCAT | 7740 |
| Chr_1_8 | GTTGGTCTATTCTTGCGGTTGTAAAAGTGGCCCAGAGTGA | 7741 |
| Chr_1_9 | GTGAGCCTTCTCTCACCATTCTGTCCAAAATAGCAGCCCT | 7742 |
| Chr_1_10 | CAGCCTAGATATGATTCCTCACTACCCTGTTCCATGGTTC | 7743 |
| Chr_1_11 | AAAGAATGTGTTGGCTCATGATCAGACTTGAGCACTTGGG | 7744 |
| Chr_1_12 | CCTAGGCTGTTGCTGCTGGACCTGTTTGTGCTTCATCACA | 7745 |
| Chr_2_1 | CAGTTGACCCTTCAGCCACAGGGGTTTGAACTTTGAAGGA | 7746 |
| Chr_2_2 | AGGACCTGAGTATGCACGTTTTGGTATACTGGGTAGGGGT | 7747 |
| Chr_2_3 | TATCAGCTGGGATGGTCCGGTCAGCAGCATTACCCTGTTT | 7748 |
| Chr_2_4 | TGCCTGCTCAGCCCAGATTTCAGTCATGCTGGCCATAAAC | 7749 |
| Chr_2_5 | CTGGGGGGTGAGGTTTGAGGTTTGAGTGTGGGATGTGAGG | 7750 |
| Chr_2_6 | CCAGCTTTTTCAGAAGCTGGGAAAGTAATAACCCGTGTTG | 7751 |
| Chr_2_7 | CCCAGCGCCCGTGGCTTTGGCTCCTCAGTCCCATTTAAAT | 7752 |
| Chr_2_8 | TATACCACCAAGTCTACCTACTGCCTGCACATGCTATGGC | 7753 |
| Chr_2_9 | GGTCAATCCGGCACTACTGGTTGTCCAAAGGGAGGTTACT | 7754 |

TABLE 3-continued

Chromosomal Control Probes

| Name | Sequence | SEQ ID NO: |
|---|---|---|
| Chr_2_10 | AATCAAACATCAGGACCGCCCACAGCACAGGTCAATGAAC | 7755 |
| Chr_2_11 | GTGTCTCCTGGAGGTGCATGGGTGGTTTTGAACTTCATTG | 7756 |
| Chr_2_12 | GACCCATGTAAGGGGTTGGGTTATGTTCTCCTTTTGCCCA | 7757 |
| Chr_2_13 | TCACTGACATGCGAAGCTGGGAACGAGAAAATGCACATCC | 7758 |
| Chr_2_14 | TCCTACAGTGCTTAGGGATGAATCTGGCAAAGAAGGATGC | 7759 |
| Chr_2_15 | GAAAGCAGTCCTTACCACAAGAAGACCCCGATGTGGTGGT | 7760 |
| Chr_2_16 | ATTGCTCACTGGCTGGCTTGCATTTGGTATGCGATTGGGA | 7761 |
| Chr_2_17 | GTCCCTGGGACCATCTGTGCATTGTTCTTGTAACTGGAAA | 7762 |
| Chr_2_18 | GACCGAATGGCGAACGCAGTGAATAGATCAGGAGGGAAAA | 7763 |
| Chr_3_1 | GAAGGAATGGAGTGGAACAGATAGGGGTGAGGGAATAACG | 7764 |
| Chr_3_2 | CCACTGCCATCCTCAGAGGGAGATTCACAAGTCTCACAAT | 7765 |
| Chr_3_3 | ATCCAGGCTTCATGTTCAAATGCAATGGCCCTTGCCCCAT | 7766 |
| Chr_3_4 | AAATTTCCCCTGGCTCCCTACTGCTTTGCAGGCCAAGTAA | 7767 |
| Chr_3_5 | ACCTTAAAGACGGGCCCACATCTCTTTGGATGGGATTAGG | 7768 |
| Chr_3_6 | GGGCTTCGGTTTTGGCGAAGGTGCTCACAATCTTGATATC | 7769 |
| Chr_3_7 | TGAGCTGTCCTTCATGCCTGCATTTCCCATGTCTGTCTTC | 7770 |
| Chr_3_8 | ATCTTTATCCAGGGCTACCAGTGGTGGGTCCAAAATGACT | 7771 |
| Chr_3_9 | TACAGGTGAAGGATGTCAACGAGTTTGCTCCCACCTTCAA | 7772 |
| Chr_3_10 | GCTGTTGTGACGGAGGGCAAGATCTATGACAGCATTCTGC | 7773 |
| Chr_3_11 | AATGAAGGGGATTCAAGCCTTGCCACCGACTTACAGGAAG | 7774 |
| Chr_3_12 | TGTGAGCGTACTTTCTCCCCCAGGTTGAAGAGGAATGAGT | 7775 |
| Chr_4_1 | ATTCCAAGTCCAGGTCCCAAATCTATCAGTACCGGCTGGC | 7776 |
| Chr_4_2 | GACACAGAGTGCATGAAGACCGTTCAAATATGTCAGGGAC | 7777 |
| Chr_4_3 | CATGAGTCCTTCTATGACTCCCTCTCAGACATGCAGGAAG | 7778 |
| Chr_4_4 | TTTTTAGGAGACAGGTACCCACTGTCTGGTGACGAGGACT | 7779 |
| Chr_4_5 | CCTTCTGTTGAGTCGCTAGGAGATGCCTCAGTTCAACAAT | 7780 |
| Chr_4_6 | GACAGAAACTTCATACCCAAGAGCTGCTTTCTCAGCTGGA | 7781 |
| Chr_4_7 | CAGGCAACTTTGGCAAGACCAAGTCAGCCTTCTCATCTCT | 7782 |
| Chr_4_8 | CCCTTGCTACCATCACTGTTGTCATCTGTGCTTGCATTCC | 7783 |
| Chr_5_1 | AGGTCTCACTCCAACTGCCCCTGTATTAGAGCTAGGCTGC | 7784 |
| Chr_5_2 | GAAACCATGCGGGATTCATCTTTGTCAGAGTGGAGCGGCA | 7785 |
| Chr_5_3 | TATGAAATTAGGCGGTGGTTGGACGTGACTGTGTGTTGAC | 7786 |
| Chr_5_4 | TGAAACTTGCATGACATACTGCGGCTGCCCATTCACTAGG | 7787 |
| Chr_5_5 | TGCTTCTTGTTTATAACTCCCCTGGCCACCATCTCGGGCT | 7788 |
| Chr_5_6 | ATTCCCTCTCATTTGTGGTTGGTGGCTGGATATCTGTTCC | 7789 |
| Chr_5_7 | AGCATCAGCATTTCCCTGTGGACTTACCTCTCTCAGTAGT | 7790 |
| Chr_5_8 | AAAATTTAAAGGTCGGCGGTAAGGCTGAAAGCCAACAGGC | 7791 |
| Chr_5_9 | GAGTGTGTCGGTCAGAAGGAACACCTGAGAAACCGCTTTA | 7792 |

TABLE 3-continued

Chromosomal Control Probes

| Name | Sequence | SEQ ID NO: |
|---|---|---|
| Chr_5_10 | CATAGCAAATACCTGTCGCTGAGCCAGGAGTAAAGTCTGG | 7793 |
| Chr_5_11 | AAGAGGCTCTGAGCTCTTGATAGAGGTTACATGGGGAGCA | 7794 |
| Chr_5_12 | GGAGACAACTTAGGAGGTTATCTAGACCATTCCCGCCTTC | 7795 |
| Chr_5_13 | GTGTTTCCTCCCAGCATGCACTTTGTGGCTGCCTTTCTTT | 7796 |
| Chr_5_14 | TGGCTTGTGTAGCGTGTTTCATTTTGGAACCTTGGAGCCG | 7797 |
| Chr_5_15 | GACACCTCTGGTGCAGTTTTGAGGCTGGCCGGGAAGGGAT | 7798 |
| Chr_5_16 | GTTTCAGATCTTGCAATGGGAGGGATCGACTCGGCCCTTT | 7799 |
| Chr_5_17 | TGCCTAAATCAGAAATGGGCTACTTCCCTTGGCCACATCC | 7800 |
| Chr_5_18 | CAATCTACCACCTCAAGGTTCACGCGTGGATTCTACACCT | 7801 |
| Chr_6_1 | GAGTTTTTCTTTCAGGTAGTCTGAGATGGCCCGCACCAAG | 7802 |
| Chr_6_2 | TACTATAAAGAAGGCACCTCTAGGCTTGGCAAGCACACGT | 7803 |
| Chr_6_3 | GGCAGATTCGATGGGACTTTAGACACTTGCTTTGCTCCCT | 7804 |
| Chr_6_4 | CAAATGTCCCCATGCAAACATGTCCCGCACTGTGTGGTAA | 7805 |
| Chr_6_5 | ACATGTGTAATCTTCTTCTCCTAGGGCGGCAGAACTCATG | 7806 |
| Chr_6_6 | CCCGAGGAAAGCTCCTCTTTGCTGACTGTAATGTACTGCA | 7807 |
| Chr_6_7 | GAGGACAGCATTCGCATATCAGGTCGAAATTTCTCCGCGA | 7808 |
| Chr_6_8 | GTCCAGCTTTCATCCTTGATCCTGCTACTCTAGGCTCTCC | 7809 |
| Chr_6_9 | ACTGATGGTGTTCACTTGCACCATCAGGTCTGATGGAGGA | 7810 |
| Chr_6_10 | AATTGGTTCACAAAGCGTCGGGTGATCCAGTAACAGTCGA | 7811 |
| Chr_6_11 | CAGAACTCTGCTCTAACGCCAAGCCTTCAATATGTCTTCG | 7812 |
| Chr_7_1 | CAATTCTTACCATCCACAAAATGGATCCAGACAACTGTTC | 7813 |
| Chr_7_2 | ACTACACCTCAGATATATTTCTTCATGAAGACCTCACAGT | 7814 |
| Chr_7_3 | TGCTATAGACGCACAAACGACCGCGAGCCACAAATCAAGC | 7815 |
| Chr_7_4 | CCATGACTTATGTGCAGCTTGCGCATCCAGGGGTAGATCT | 7816 |
| Chr_7_5 | AGGAGTTGGTGGCTAAACCGCTGACTTTTCTATTGCAGAC | 7817 |
| Chr_7_6 | GAAATATAACAGGACCAGAAGTGGCTCGCAGGAGACTCAT | 7818 |
| Chr_7_7 | TAGCCAGACAGAAGGCGGACACTGATGATACCTCAAGACT | 7819 |
| Chr_7_8 | GTTTGCCACCAGCGAAGAGAGCCATCCTGGTAGAATTGGA | 7820 |
| Chr_7_9 | GGAGATATGCACTTGCCCTTTGGTAATCCTGCTCCTTCTG | 7821 |
| Chr_7_10 | AAAACTAACCAGTAAGTACAGGGAGGGACCGAGAGGCATC | 7822 |
| Chr_7_11 | AAGAACACCAGTCCATAAAGACGCATGTCCGGTGATGCCT | 7823 |
| Chr_7_12 | AATCTGTTTAGACTGAGCAACTGTGCCAGCAGAGGGACCT | 7824 |
| Chr_8_1 | AAGATGGCGAAGGTCTCAGAGCTTTACGATGTCACTTGGG | 7825 |
| Chr_8_2 | CCATGCCTGCCAGCTGATAAGATTTGGTTACCTTTCCATG | 7826 |
| Chr_8_3 | GCTGCAAGAAAGCGTAAGATTGCCATTCGAAAAGCCCAGG | 7827 |
| Chr_8_4 | ATGCAGGAGTACAATGTGGGCATGTCCACCCTCTACGACA | 7828 |
| Chr_8_5 | AGAACGGCTTTGCTGTCTTCCGGCAAACCTATGGTTCTGA | 7829 |
| Chr_8_6 | TGGCTTTGGCGCTTTAAGGCCAGACACGGCATTAAAAAGC | 7830 |

TABLE 3-continued

Chromosomal Control Probes

| Name | Sequence | SEQ ID NO: |
|---|---|---|
| Chr_8_7 | GCAGGCAGAGAAAGATGGCTTTAGAAACCTCTTCCCCACC | 7831 |
| Chr_8_8 | TCAGCTGTGGCCATTGGTGGATCTCATCCTTAGTACTAGT | 7832 |
| Chr_8_9 | CCATGGTTCTGTGAGACTGGTAGAAAGCACAGACCCCTTA | 7833 |
| Chr_9_1 | AATGTGCTTATCACTCGTGATGGGGTCCTGAAGCTGGCAG | 7834 |
| Chr_9_2 | AGGGTCTCATTTTAAGACAGCTTGATTTGAGGGTGAGGGG | 7835 |
| Chr_9_3 | CAGTTGCAAACCATACTTCCTTCAGCCCAGTCCTGTCTAT | 7836 |
| Chr_9_4 | GTCTAAGGGCATCTTACCTCCAAGAACTGCTTGAGGCGTA | 7837 |
| Chr_9_5 | TACCTAGGGAATGACCACTAAGCACCATCTCCGTCACTCT | 7838 |
| Chr_9_6 | GGAAGAGAGGAGGGTCATCCAGTCAGTTTTGCAGGAATCT | 7839 |
| Chr_9_7 | TGCTGCAGTGTCGGAAGAAACCTACCTGCGTTTCTTAGAA | 7840 |
| Chr_9_8 | CATCATACCTATGGCATAGCCATCAGGGCACTGCAGTTTG | 7841 |
| Chr_9_9 | TATATCTCACGTGACCGAGGATGGGTCGTGGGCATTCACA | 7842 |
| Chr_9_10 | GAAATGGCCATCTATAGGTGGGAACCACTCCAGTGTCACA | 7843 |
| Chr_10_1 | GGAAACCTTTCAGTCTCTACTAGAAGCGCGGAGAGAACTC | 7844 |
| Chr_10_2 | TCTGGCCGGCATTCATTTAAGGCCTAAGGATGAAGGCGGT | 7845 |
| Chr_10_3 | AGATACCCTATCGTTCCTTATCTCAGCGAAACAACTCCCC | 7846 |
| Chr_10_4 | CGCAACTCCTCCAGATCGCAGTGGTGCTTCTTCACTTTCA | 7847 |
| Chr_10_5 | TGATTCCATGGTTGCCCGTATACTCCATAAGGCGGTACTT | 7848 |
| Chr_10_6 | ATACCATATCCGGCTTGGTTAGGAGGAGGTATTACAGGGG | 7849 |
| Chr_10_7 | GTACCTGTTAACCCAGACGCAATTCTCCACAGGTACACAG | 7850 |
| Chr_11_1 | ATGTGACACTTGCATCCAGGGAGGTCACCATCTGTGTATG | 7851 |
| Chr_11_2 | CTAGGTCCTGAAGAGGTGGCAAGGAACCAGGACAGAACAT | 7852 |
| Chr_11_3 | TCTGTCATTGGTGACGCCATCTAGACTCTTGGCTTTGGGA | 7853 |
| Chr_11_4 | AAGGTATAGAGCTGGGCGGCTTTCCTCGTTATAGGTGGAG | 7854 |
| Chr_11_5 | CTCCTACGTAGCCGGGTAGAAACTTATGGCAGAAGTCAGG | 7855 |
| Chr_11_6 | TGGATTCCCAGGGTTAATTGTGACCCATTGCAGGAAGGTG | 7856 |
| Chr_11_7 | AATGCTGTCCTACTATGGTCTGTACCTGTCCCAGAGGTGG | 7857 |
| Chr_11_8 | GTGCACCTGGAGAGCATACAGGGCACTGACTTGTAGATCA | 7858 |
| Chr_11_9 | TTCCATCTCGCATAACCTGCCCCTAAACTCTTCTCGGTTC | 7859 |
| Chr_11_10 | ATGAAGGCCTGCTTTGAGTTATCAGATAGGAAGGGGCCAG | 7860 |
| Chr_11_11 | AGGTCATGTCCCGCTTTTGGCTGAACCTAGTTTTGCCCAA | 7861 |
| Chr_12_1 | CTGCATTCTCCATGAGTAGAGTACGAGCCTCATGTTGGTA | 7862 |
| Chr_12_2 | AAGGCTGTCTTCACCAACTGGGTAGGTGTGGATCAAGACC | 7863 |
| Chr_12_3 | CTGACTTTGGTGTTGGGGAGTCGGTGGTCCTTCTTCCATT | 7864 |
| Chr_12_4 | ACTGCAGAGGACCAGACTGGGAAAACAACGATATGGCAGG | 7865 |
| Chr_12_5 | CCTGGCTTAGAAGTCTGGCCGGTCCTTCTTCAGCTTCTTA | 7866 |
| Chr_12_6 | AATCTCAGAAAGAGTTCCTGGGACCATGGCAAATGGTGGC | 7867 |
| Chr_12_7 | ACATTATATCCGGTCCAGGAATATCTGGCTCAGGCTGGGT | 7868 |

TABLE 3-continued

Chromosomal Control Probes

| Name | Sequence | SEQ ID NO: |
|---|---|---|
| Chr_12_8 | AAGCACAGGAAATGTGCCTCACACGACTTCACATGCCCTT | 7869 |
| Chr_12_9 | GGGGGCTTTGCGGGAAGAGGGGACTAAACAACCCTTCTGT | 7870 |
| Chr_12_10 | AAAAGAAATGCGATCAGCGCAACCCATCCGGTGTGGCGCT | 7871 |
| Chr_12_11 | GGCAGTGGTACCATGACATACTTAGCAGAGATGGACTACA | 7872 |
| Chr_13_1 | ATTTCCCATGCGAGAGGTAGCTTGCCCAGGCTGTTGGATA | 7873 |
| Chr_13_2 | TTCCATGCCGAGTCCTGATGGAAACTAGCACTGAAAGACC | 7874 |
| Chr_13_3 | TCACGGGAGCTTCCTTCACTGAGTTCTGCGAATCTGAAGC | 7875 |
| Chr_13_4 | TTTCCAGAGATGAAGCACTACCCAGTCTTACCCAAGTTCG | 7876 |
| Chr_13_5 | CCACCGAGAACAGTGATGAAGGACTTAAAGTGAGAGATGG | 7877 |
| Chr_13_6 | GTTCACTCGTCGGTTTTTCACCAACCACAGACTAGCCTCA | 7878 |
| Chr_13_7 | ACGCAGCTGTGTTGAGTGCACAGGAAGCTCTTAGGGTTAA | 7879 |
| Chr_13_8 | TCTCAGTGAACAGAGGGCTCACTGAGAGGACTTTGAATAC | 7880 |
| Chr_13_9 | ATGGCACAGGCCACATACTGGAATGAATGACGGGCTTCAT | 7881 |
| Chr_13_10 | TGCTGCTTGATGGTGGCATCACTGTCCCCTCATTCCATGA | 7882 |
| Chr_14_1 | GGACACATGTGGACAGTGTGAAACCTCAGAACACTAACCC | 7883 |
| Chr_14_2 | AAGTTCTTATCCTTAGGGACCCAGCGGAGACCTTGGTTCT | 7884 |
| Chr_14_3 | CGACGATGCCTGGGAATAGGATCCATGGGATTGATGAGAA | 7885 |
| Chr_14_4 | GGGAGCCATGAAGATTTCTCCCAGCTCCTGAGGAACTTTG | 7886 |
| Chr_14_5 | TCTGGTCCTCAAGTCCTCAGCTGTAGAAGTTCTCATTGCG | 7887 |
| Chr_14_6 | TGCCAACCCTGGAAACTGGCTTGTGTGTCCACAACAGAAA | 7888 |
| Chr_15_1 | TAGGTGACAGCACTGTCCTTTCCCTGCCATTTGCAGGGAA | 7889 |
| Chr_15_2 | TTCTTCTAGATGGCAGACATTGTTGAGGCCTCCCGTACCT | 7890 |
| Chr_15_3 | AGAGAGCTGCGAGACAAGACTTGGAGTGCGACAAGATTTC | 7891 |
| Chr_15_4 | TTCAATCAGGTACTCCGAGTTCCCTTGGAGGCCAAAAGGA | 7892 |
| Chr_15_5 | AGGAATATGGGGTCCATCTGAGACTCGCAAGTGATGATAC | 7893 |
| Chr_15_6 | GATCTCCAGGACCAGCTCTCAGAAATGCACGATGAACTGG | 7894 |
| Chr_15_7 | ACAGTGTGATGGAGCAGCAGTCCAAGTTCATCCTCCAAGA | 7895 |
| Chr_15_8 | AAGATGACAGGATCCAGGAAACAAGACGCATGGGCCAGAA | 7896 |
| Chr_15_9 | AAAGAGTGGGTCTGTTAATAATCAGGCCGAGACCACCAGC | 7897 |
| Chr_15_10 | CACCCTTGTTCGTGGCCCTTGCTTGGTAAACTGGTATCCA | 7898 |
| Chr_15_11 | CCCAAGTATGGGTGAGGATGCTAGAAATGCCCACATAATG | 7899 |
| Chr_15_12 | AAGACTGTCATTGGTAGGTCATGATCCTTGGCAGCATGAC | 7900 |
| Chr_16_1 | GTGGGGACGGTCATTATCAGCTTTCTGGACACACAGACAG | 7901 |
| Chr_16_2 | TGAGAGGCCAAAGAATATCAGTTGACTCTGGATCAGGGGC | 7902 |
| Chr_16_3 | GAGGCTTTTTAGGGCAGCGAGAAAACGGGAACTTCATTCC | 7903 |
| Chr_16_4 | AGGACTTCTCTGGACCTGTGCCTCAACTACTCACCTGGAT | 7904 |
| Chr_16_5 | TGGCCACAAATGTTGCCTCCAGCTGCTCAATGTTCTCCAA | 7905 |
| Chr_16_6 | CTGGCATTGGTGAGTAATAGGAGCCAGACGGGTCTGTGTT | 7906 |

TABLE 3-continued

Chromosomal Control Probes

| Name | Sequence | SEQ ID NO: |
|---|---|---|
| Chr_16_7 | ATACTTACCTGCACGAGAATGAGTTTGGAGCGCAAGGGGG | 7907 |
| Chr_16_8 | TTCCCCCAGAGACTCTGTCCACTATGGACATTAAAATGTG | 7908 |
| Chr_16_9 | GTGCTACCCTCCTCCCTTCAGGTTATGTGGTCCAGGCTTT | 7909 |
| Chr_16_10 | TAAGTGGAACAACATTCCCTTCATTATAGCCCTTCGTGGG | 7910 |
| Chr_16_11 | GCAACGTCAACAACTACTACGTGCACAAGCGCCTCTACTG | 7911 |
| Chr_17_1 | GCGGATGTCGTTATGGGACAGGTACAAGTAGATAAGTTGC | 7912 |
| Chr_17_2 | GTGGTCACCATCTCTTCAAACCATTTGGACTGGGCCTGGT | 7913 |
| Chr_17_3 | AAGCCAAGGAGTTCTGAGAGAGCTTAGCTAAGTTCTTCGC | 7914 |
| Chr_17_4 | TTTTTTAGTACCCCAGTGTGTAAGACCAACTGAGGGTGGC | 7915 |
| Chr_17_5 | GTTGTCATTGGGGCTATAGACATAAGCACCTTCCGGAATC | 7916 |
| Chr_17_6 | CTGAGTGTGCGAGGGGAAGATATTGGTGAAGACCTGTTCT | 7917 |
| Chr_17_7 | GTCAGACCCTGTCCTCGTCTCCTTTACCTTGTCTCGATTT | 7918 |
| Chr_17_8 | TAAACTATGCTCGCCACCACTCAGCACTCACCTCTTGGGC | 7919 |
| Chr_17_9 | GGCAACTTCCTGAGACAGATCGGTAAAAACAACCCCTTCT | 7920 |
| Chr_17_10 | TCAACTGTATTTCATCAGAGAGATGTGGCTTTCCCAGACA | 7921 |
| Chr_17_11 | GTTTCCCTCATGTTCCCCCAGGTTCTGTCAGGTGAAGCTG | 7922 |
| Chr_18_1 | TTAACCCATCTCTACCCGTCCTGTGTCAAGAACGGAGGCT | 7923 |
| Chr_18_2 | CTGCCCAAAATAGAAACCGAGGTTCTCCGTGACCTACATC | 7924 |
| Chr_18_3 | TTCCTTTGCAGTAACAGCGGGAACATGAAGCCGCCACTCT | 7925 |
| Chr_18_4 | TGGTTTGCCAGTTCAGACACCCAGCCAAATTGCCCTCTCA | 7926 |
| Chr_18_5 | TAGTGCAGCTGGCTTTGAGCCTGTTCCCGAATGTTCAGAT | 7927 |
| Chr_18_6 | AGGGTAATAGCACCAAGCTCTAGTCTACCCACCTCTCTGA | 7928 |
| Chr_18_7 | CCGCATCTCTGGAGTAGGAATTGATCAGCCACCATATGGG | 7929 |
| Chr_18_8 | CTATGAGCATACTGGGGAGGGAAACCTCTAAGCGGAACTT | 7930 |
| Chr_18_9 | AAAAACCTGCAGGAAGGAGACCTGAATGCAACTGTGGGTC | 7931 |
| Chr_18_10 | CAGGTGCTCCAAACCTTCCAGTCTATGTTGTAGATTGCAG | 7932 |
| Chr_18_11 | GCCATACTAACCTACTTCTCCTTGAAGCTCTTGGCCCATC | 7933 |
| Chr_19_1 | ACTGTGAGATAGCCCTCATCATCTTCAACAGCGCCAACCG | 7934 |
| Chr_19_2 | AGATACACGGTCACAGACGCCATGTGTTGTGGCTTCTGCA | 7935 |
| Chr_19_3 | CACATCCTCTCACCTTTTCCGAAGGTTGCAGCTCCTTCTC | 7936 |
| Chr_19_4 | TCTGTCTCACCGGTCCCTTCATTCCTAGGCAACTGTAGAT | 7937 |
| Chr_19_5 | ATATCATGGTCTGTATCCCCCAGGTACCTTGACACAGGCC | 7938 |
| Chr_19_6 | CTCTCCGCCTTTCTTTAGACCTGAGCATGCAGAATTCCGA | 7939 |
| Chr_19_7 | AAGGCATTTAAATGGGACAGCGTCCCATGCGTGACTTCTC | 7940 |
| Chr_19_8 | TCTTTCTAACAGACGAACAGCCTACACCTACAACCCCGAG | 7941 |
| Chr_19_9 | GTCCCAGCCCAAAAGCATCTTGGGTAAGGATTTGGGATCA | 7942 |
| Chr_19_10 | GTTGTTCTGGGCCAGTGTTAGTTGCTCACATGTCCTGTCT | 7943 |
| Chr_19_11 | AACATGCCTCTTAGTCCTGGGCCATACCTTAGCCTTGTGC | 7944 |

TABLE 3-continued

Chromosomal Control Probes

| Name | Sequence | SEQ ID NO: |
|---|---|---|
| Chr_20_1 | TAACCTCCAAAAGAGGTACCCATTGGCGCTCAACCGAATT | 7945 |
| Chr_20_2 | CTATATCTCCGACTATGCCTTCTTGGGCACTGCACTGCTG | 7946 |
| Chr_20_3 | TCTAGATGGAAGCTGTATCCAAGGATGCTCCGGAATGTTG | 7947 |
| Chr_20_4 | ATCTTCTCTGCCTGCCGCACTAGCTTCTTGGTGACTTCTC | 7948 |
| Chr_20_5 | ATCGAGTTGTCGAGCCCCATGATTCGACACCAAGATCCCA | 7949 |
| Chr_20_6 | AGGTGCTTGTTTTACTCTCTCCAGGTGATGATGCCAGGGA | 7950 |
| Chr_20_7 | GTGCACTGTCAGATCTTGGAAACGGCCAAAGGATTTTTCC | 7951 |
| Chr_20_8 | CATTTTGCAGGAGGCTGCTAATTAAGGCTGAGGGCCATCA | 7952 |
| Chr_20_9 | TCAATGGTAGACTGGAGTACCTTGCCAGGGCAGAGAAAAA | 7953 |
| Chr_20_10 | CTCCTCCAGGAGCTGGCAGCATCAAGACCCCACTTCGCTT | 7954 |
| Chr_21_1 | AAATAATAGCAGGCGTTGAGATGTCCCTTCCCCAGCACTC | 7955 |
| Chr_21_2 | AAGTCTGACAGCATCTGCTTGAACTGAGGCACAGTGATGG | 7956 |
| Chr_21_3 | ATTCGTGATGGCGCTCATTTCCATAAAGGACGACAGGTCA | 7957 |
| Chr_21_4 | GAAGAGTGAATTCCCGCTTCTGCGCCAACATTCTGTTTCC | 7958 |
| Chr_21_5 | ACAGGTGAAGTCTTTGCGTGCCTCCCTGTTGGACTCAAAT | 7959 |
| Chr_21_6 | TAATGATATTCTGGCACAAGGAGCAGAGCCCCTCTTCTTC | 7960 |
| Chr_21_7 | AGACCCAGCCTACCTGCATGATCTCTTGTACAGCTTTGCA | 7961 |
| Chr_21_8 | TCATGGAACATGGGCCTTGCAAAGGGGTCAAGATCACAAC | 7962 |
| Chr_21_9 | GTCAAAAAGGTCCAATCAGCTAGAGACTAGGCCAGACCCA | 7963 |
| Chr_22_1 | TGTGACCACCCTAAAGGGAGGGCAGAAGCCGAGTCACCCT | 7964 |
| Chr_22_2 | ACGCCTCCACCTGCTGCTAGGACTCCCCTCCCAAACAAAG | 7965 |
| Chr_22_3 | CACAGTCTAGACCCTGATGGGCGATCTCAGTAGTGCTGTT | 7966 |
| Chr_22_4 | CCTATCAACGTGCAAGTGGGATTTGTCTCCACTGGCTTTC | 7967 |
| Chr_22_5 | GAAAATCATTCCCCATTCTGCAGGATCCGTTCCCCTGGCA | 7968 |
| Chr_22_6 | AGTGGGACATACCAACTTGATGAGGCAGTTGTGCGAGTTC | 7969 |
| Chr_22_7 | GTAAACAGCTGTCTTCTTACCCTACAGATCATTGGGCAGG | 7970 |
| Chr_22_8 | CAGAAGGATACTAGAATGGAATGTCCTGCGTGACGAAAGC | 7971 |
| Chr_22_9 | AGTTCACATCTGATTCTCCTATGGCTGCTAGGCTCCAGGA | 7972 |

Figure 27C:
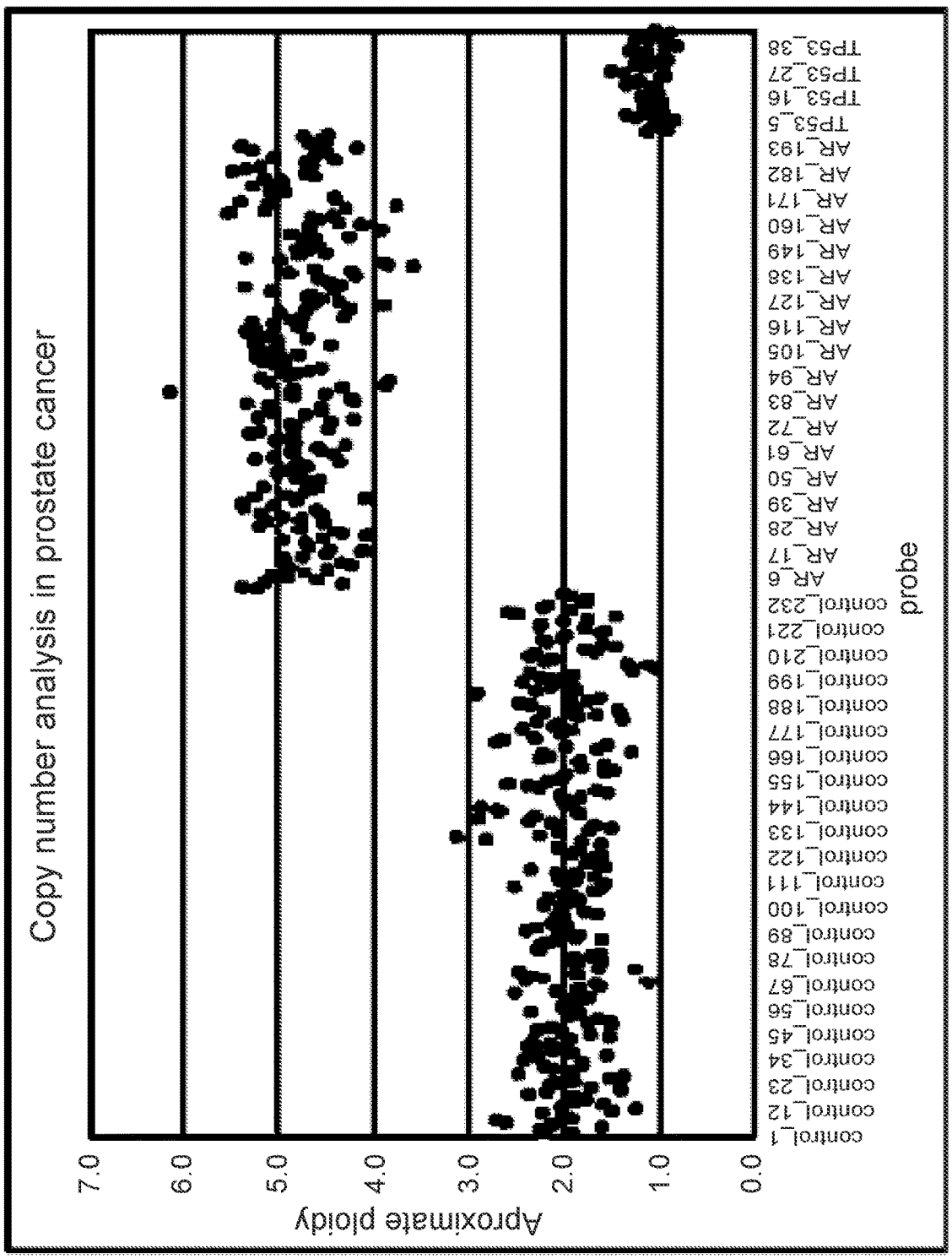

Significantly, when the same analysis was applied to cfDNA collected from the blood plasma fraction of a castration-resistant prostate cancer patient using healthy samples as normalization controls, three prominent features emerged (FIG. 27C). First, all of the control probes exhibited noisy counting behavior. Second, the counts across all AR probes were significantly elevated from a normal value of "1" to an amplified value of approximately "5". Amplification of the AR gene is consistently observed in advanced prostate cancer patients. Third, the TP53 probe counts, while more tightly clustered, possessed an average value far closer to "1" than the expected value of "2." This likely reflected inactivation of one or both alleles of TP53 by copy number loss in the fraction of circulating DNA derived from tumor tissue.

These data indicated that the methods of the present invention comprise three important karyotyping aspects. Namely, the methods described herein detect generalized chromosomal aneuploidy, copy increases of specific, targeted genes, and copy losses in the same specific, targeted genes. These result further indicate that the methods and platforms described herein can guide the use of precision therapies, as all three of these genomic abnormalities occur frequently in cancer.

Figure 28:
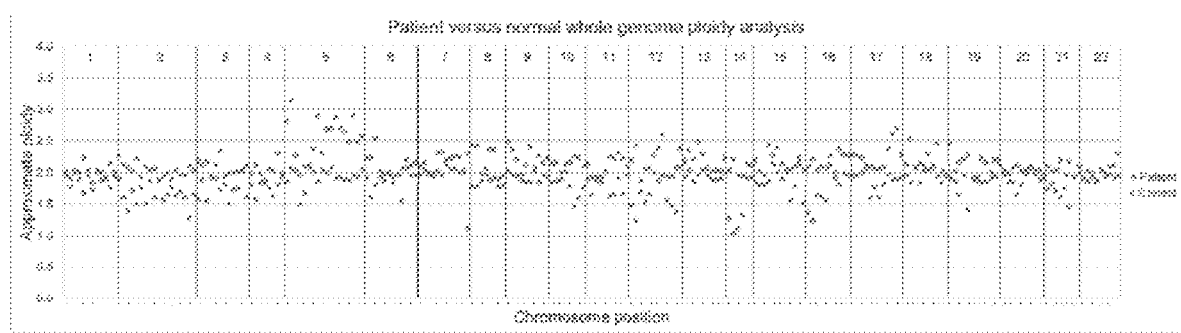
FIG. 28 shows whole genome aneuploidy analysis of a prostate patient cfDNA library relative to a control sample. The approximate ploidy for each of 239 control probes is shown sorted by chromosome. Patient chromosome 2 probes show consistent copy loss and the majority of chromosome 5 probes show copy gain. Significant deviation of approximate ploidy are seen for many, but not all, of the patient control probes.

Generalized chromosomal aneuploidy for castration-resistant prostate cancer patient samples (blue dots) relative to a healthy control (brown dots) was measured (FIG. 28). In this analysis, the approximate ploidy for all 239 control probes used in the experiment were ordered according to their chromosomal targets. For some chromosomes (e.g., chromosome 1 and chromosome 22) a similar ploidy value of "2" was observed between patient and control samples. In other cases, deviation between the two samples was observed. The degree of information regarding overall genomic ploidy provided by these experiments was constrained by the number and density of control probes used. However, these data indicate that a denser probe panel covering all chromosomal segments at uniform density can be used—in conjunction with the additional unique features of the present invention. Such analyses will provide a higher resolution, genome-wide measurement of chromosomal copy number.

These data further highlight the capabilities of the present invention as a guide for precision therapy. For example, tumors that possess genomic deficiencies in homologous recombination repair often exhibit highly destabilized chromosomal ploidies, and patients with such tumors are good candidates for inhibitors of the PARP enzyme complex (See Popova et al., Genome Biol. 2009; 10(11):R128). Unlike most sequencing assays that seek to genotype a tumor, the assays described herein use sequencing to detect destabilized chromosomal ploidy as a tumor phenotype, even if the causal mutations driving this phenotype remain hidden from targeted analysis.

Figure 29:
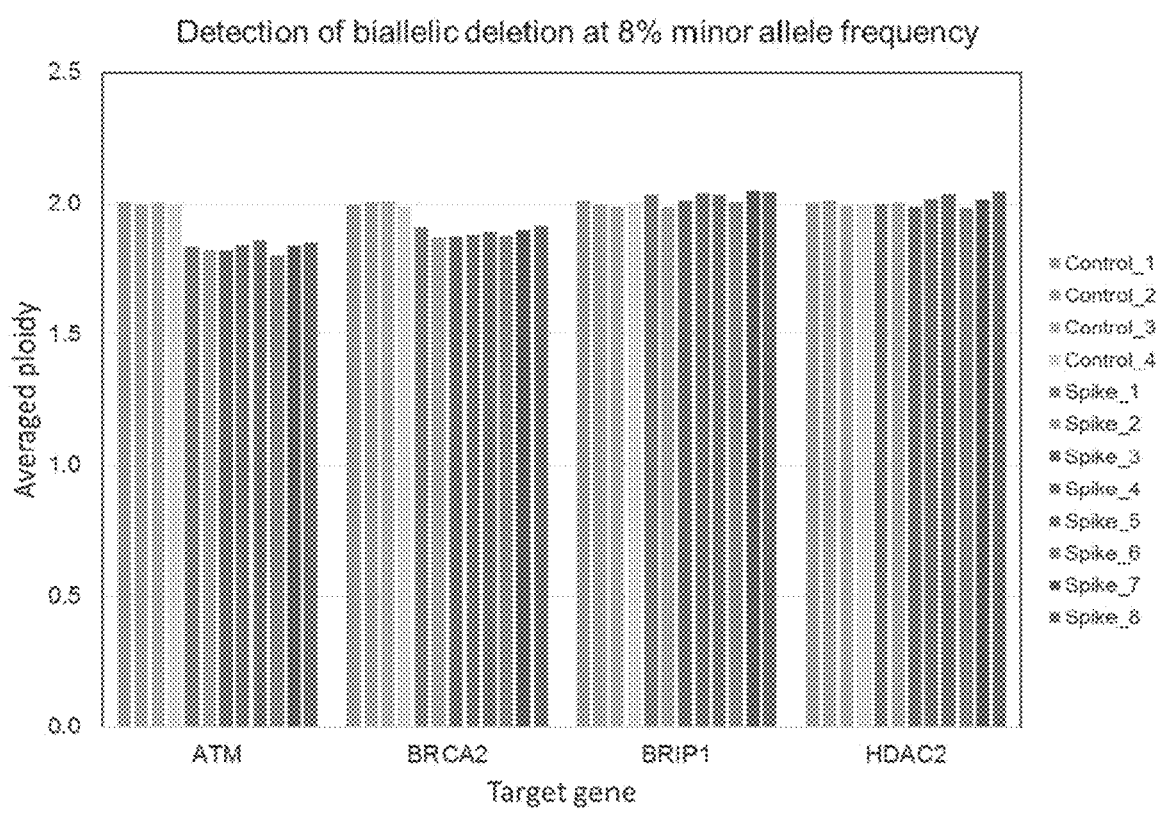
FIG. 29 shows analytical validation of copy number loss detection. Genomic DNA from immortalized line NA02718 (monoallelic ΔATM) and from NA09596 (monoallelic ΔBRCA2) were spiked into the "gold standard" genomic DNA from NA12878 at 16%, resulting in the equivalent of an 8% biallelic deletion minor allele frequency. Following targeted sequencing and CNV analysis, the probe-by-probe ploidies were averaged for the two target genes. Two unperturbed control genes, BRIP1 and HDAC2, are shown for comparison.

The ability to detect gene loss in DNA shed from solid tumors is especially significant. Mutation and deletion of tumor suppressor genes is a frequent event in cancer genomes; moreover, individuals with germline loss of tumor suppressor genes are uniquely vulnerable to developing cancer later in life. The diagnostic value of a liquid biopsy copy number loss (CNL) assay is directly proportional to its sensitivity. To determine the lower limit of detection for the invention described here, the immortalized lines described in Example 1 were systematically diluted into the "genome-in-a-bottle" reference cell line, NA12878. One line had a single copy deletion (monoallelic loss) of ATM, the other a single copy deletion of BRCA2. The experiment included four control samples of pure NA12878 and eight spike-in samples containing 16% of each monoallelic deletion line (FIG. 29). For reporting purposes, this corresponds to an 8% minor allele frequency of biallelic loss. Averaged values for all probes targeting specific genes and two additional, undeleted control genes are shown in FIG. 29. Copy loss of ATM and BRCA2 was confined to spike-in samples only. Additional computational treatment of the data revealed confident copy loss calling of biallelic deletions down to 2% minor allele frequencies. This sensitivity indicated that the present invention required no specialized considerations in order to routinely include copy loss calls in standard blood-based genotyping assays.

These data demonstrate the use of probe-specific genomic capture data for the analysis of copy number, including both copy number gain and copy number loss of target genomic loci. Additionally, the invention described herein has been shown to possess the sensitive ability to detect single nucleotide variants, insertions and deletions ranging from single nucleotides to many thousands of base pairs, and gene fusions resulting from chromosomal rearrangement by aberrant mutational processes (See PCT Publication No. WO 2016/028316; and U.S. Patent Publication No. 2014-0274731). All of these mutational processes can contribute to the transformation of normal tissue to neoplastic cancers, and as precision therapies continue to emerge, accurate diagnosis of these diseased genomic signatures will become an increasingly indispensable feature of precision medicine.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11319594B2). An electronic copy of the "Sequence Listing" will also be available from the USPTO upon request and payment of the fee set forth in 37 CFR 1.19(b)(3).

The invention claimed is:

1. A method for performing a genetic analysis on a DNA target region from a test sample comprising a plurality of genomic DNA fragments, the method comprising: (a) generating a genomic DNA library by contacting the test sample with a set of adaptors, wherein each adaptor of the set of adaptors comprises a sample tag region selected from a pool of unique sample tag regions, wherein the pool is selected from a plurality of pools, and wherein the selected pool is unique to the test sample;
   wherein the genomic DNA library comprises a plurality of library DNA fragments and at least two unique sample tag regions;
   wherein each of the library DNA fragments comprises a genomic DNA fragment from the test sample attached to an adaptor;
   (b) contacting the genomic DNA library with a plurality of capture probes that specifically bind to the DNA target region, thereby forming complexes between the capture probes and library DNA fragments comprising the DNA target region; and
   (c) performing a quantitative genetic analysis of the genomic DNA fragments comprising the DNA target region;
   wherein the adaptor is a DNA polynucleotide that comprises: (i) an amplification region, (ii) a sample tag region, and (iii) an anchor region;
   wherein the amplification region comprises a polynucleotide sequence capable of serving as a primer recognition site for PCR amplification;
   wherein the sample tag region identifies the test sample; and
   wherein the anchor region comprises a polynucleotide sequence that is capable of attaching to the genomic DNA fragment.

2. The method of claim 1, wherein the method identifies a genetic change indicative of a disease state selected from a single nucleotide variant (SNV), an insertion less than 40 nucleotides in length, a deletion of a DNA region less than 40 nucleotides in length, and/or a change in copy number.

3. The method of claim 2, wherein the genetic change indicative of a disease state is a change in copy number.

4. The method of claim 1, wherein the test sample is a tissue biopsy.

5. The method of claim 4, wherein the tissue biopsy is taken from a tumor or a tissue suspected of being a tumor.

6. The method of claim 1, wherein the genomic DNA fragments are cell free DNA (cfDNA) or cellular DNA.

7. The method of claim 6, wherein the genomic DNA fragments are isolated from the test sample; and wherein the test sample is a biological sample selected from the group consisting of: amniotic fluid, blood, plasma, serum, semen, lymphatic fluid, cerebral spinal fluid, ocular fluid, urine, saliva, stool, mucous, and sweat.

8. The method of claim 1, wherein the genomic DNA fragments are obtained by the steps comprising;
   (i) isolating cellular DNA from the test sample;
   (ii) fragmenting the cellular DNA to obtain the genomic DNA fragments.

9. The method of claim 8, wherein step (ii) is performed by contacting the cellular DNA with at least one digestion enzyme.

10. The method of claim 8, wherein step (ii) is performed by applying mechanical stress to the cellular DNA.

11. The method of claim 10, where the mechanical stress is applied by sonicating the cellular DNA.

12. The method of claim 1, wherein the amplification region is between 10 and 50 nucleotides in length.

13. The method of claim 1, wherein the amplification region is between 20 and 30 nucleotides in length.

14. The method of claim 1, wherein the amplification region is 25 nucleotides in length.

15. The method of claim 1, wherein the sample tag region is between 5 and 50 nucleotides in length.

16. The method of claim 15, wherein the sample tag region is between 5 and 15 nucleotides in length.

17. The method of claim 15, wherein the sample tag region is 8 nucleotides in length.

18. The method of claim 1, wherein the adaptor further comprises a unique molecule identifier multiplier (UMI multiplier) that is adjacent to or contained within the sample tag region.

19. The method of claim 18, wherein the UMI multiplier is between 1 and 5 nucleotides in length.

20. The method of claim 18, wherein the UMI multiplier is 3 nucleotides in length, and comprises one of 64 possible nucleotide sequences.

21. The method of claim 1, wherein the anchor region is between 1 and 50 nucleotides in length.

22. The method of claim 21, wherein the anchor region is between 5 and 25 nucleotides in length.

23. The method of claim 21, wherein the anchor region is 10 nucleotides in length.

24. The method of claim 1, wherein step (a) comprises attaching a first adaptor to one end of a genomic DNA fragment of the test sample and attaching a second adaptor to the other end of the genomic DNA fragment.

25. The method of claim 24, wherein the genomic DNA fragment is end repaired prior to attaching the first and second adaptors.

26. The method of claim 1, wherein the amplification region of each adaptor of the set of adaptors is identical to the amplification region of every other adaptor of the set of adaptors.

27. The method of claim 1, wherein the pool of sample tag regions comprises between 2 and 1,000 unique sample tag region sequences.

28. The method of claim 27, wherein the pool of sample tag regions comprises between 50 and 500 unique sample tag region sequences.

29. The method of claim 27, wherein the pool of sample tag regions comprises between 100 and 400 unique sample tag region sequences.

30. The method of claim 27, wherein the pool of sample tag regions comprises between 200 and 300 unique sample tag region sequences.

31. The method of claim 27, wherein each sample tag region of the pool of sample tag regions is 8 nucleotides in length.

32. The method of claim 27, wherein the pool of sample tag regions comprises 240 unique sample tag region sequences.

33. The method of claim 27, wherein each unique sample tag region sequence is discrete from any other unique sample tag region sequence by Hamming distance of at least two.

34. The method of claim 1, wherein the sample tag region identifies the genomic DNA fragment attached thereto.

35. The method of claim 34, wherein the adaptor further comprises a UMI multiplier which increases the number of unique sequences for identifying the genomic fragments.

36. The method of claim 1, wherein the anchor region of each adaptor of the set of adaptors comprises one of four sequences, and wherein each sample tag region of a given sequence is paired to only one of the four anchor regions of a given sequence.

37. The method of claim 1, wherein the amplification region of each adaptor of the set of adaptors comprises an identical nucleotide sequence;
   wherein each sample tag region of the pool of sample tag regions is 8 nucleotides in length, wherein each unique sample tag region sequence is discrete from any other unique sample tag region sequence by Hamming distance of at least two,
   wherein each adaptor of the set of adaptors comprises a UMI multiplier that is adjacent to or contained within the sample tag region, wherein the UMI multiplier of each adaptor of the set of adaptors is three nucleotides in length, and wherein the UMI multiplier of a given sequence is paired to one sample tag region of a given sequence,
   wherein the anchor region of each adaptor of the set of adaptors comprises one of four nucleotide sequences, and wherein each sample tag region of a given sequence is paired to only one of the four anchor regions of a given sequence.

38. The method of claim 24, wherein the step of attaching each of the first and second adaptors to the genomic DNA fragment comprises:
   (i) attaching an oligonucleotide comprising at least a portion of an anchor region to the genomic DNA fragment, wherein the oligonucleotide is part of a DNA duplex comprising a 5' phosphorylated attachment strand duplexed with a partner strand, wherein the partner strand is blocked from attachment to the genomic DNA fragment by chemical modification at its 3' end, and wherein the attachment strand is attached to the genomic DNA fragment; and
   (ii) contacting the genomic DNA fragment attached to the attachment strand with a DNA oligonucleotide encoding a full-length adaptor sequence, a T4 polynucleotide kinase, a Taq DNA ligase, and a full-length Bst polymerase under conditions suitable for DNA ligation;

thereby attaching each of the first and second adaptors to the genomic DNA fragment.

39. The method of claim 1, wherein the DNA target region is analyzed for a change in copy number.

40. The method of claim 1, wherein step (c) comprises purification of the complexes formed between the capture probes and DNA library fragments comprising the DNA target region.

41. The method of claim 1, wherein step (c) comprises purification of the complexes formed between the capture probes and DNA library fragments comprising the DNA target region and performing primer extension and/or amplification of the DNA library fragments comprising the DNA target region.

42. The method of claim 1, wherein step (c) comprises purification of the complexes formed between the capture probes and DNA library fragments comprising the DNA target region and performing primer extension and amplification of the DNA library fragments comprising the DNA target region.

43. The method of claim 1, wherein step (c) comprises DNA sequencing of the DNA library fragments comprising the DNA target region to generate a plurality of sequencing reads.

44. The method of claim 1, wherein the genomic analysis comprises determining a change of a copy number in a DNA region of interest, and wherein step (c) comprises:
   (i) determining a copy number of the region of interest present in the genomic DNA library derived from the test sample, and
   (ii) comparing the copy number determined in step (i) to a copy number of the region of interest present in a genomic DNA library derived from a reference sample, wherein the reference sample comprises a known copy number of the DNA target region.

45. The method of claim 44, wherein determining the copy number in the region of interest comprises DNA sequencing of the DNA library fragments comprising the DNA target region to generate a plurality of sequencing reads, wherein each sequencing read comprises a unique molecular identification element (UMIE).

46. The method of claim 45, wherein the UMIE comprises sequencing information from the adaptor and at least a portion of the genomic DNA fragment sequence.

47. The method of claim 46, wherein sequencing reads comprising identical UMIEs are identified as a unique genomic sequence (UGS).

48. The method of claim 44, further comprising determining a raw genomic depth (RGD) for each of the capture probes contacted with the genomic DNA library.

49. The method of claim 48, wherein determining the RGD comprises determining the average number of UGSs associated with each capture probe sequence within a group of sample replicates.

50. The method of claim 49, wherein capture probes associated with a highly variable number of UGSs are identified as noisy probes and are removed from further calculations.

51. The method of claim 49, further comprising calculating an RGD for a sample, comprising calculating a numerical average of all RGDs for all capture probes in the sample.

52. The method of claim 49, wherein the RGD values for noisy probes are not included in calculating an RGD for a sample.

53. The method of claim 48, wherein the RGDs for the capture probes are normalized across all samples in an experimental group by converting the RGD for each capture probe into a probe-specific, normalized read count comprising:
   (i) multiplying each capture probe RGD in a sample by a normalization constant, wherein the normalization constant comprises any real number; and
   (ii) dividing the product of (i) by the RGD calculated for the corresponding sample; or
   (iii) dividing the product of (i) by an average RGD calculated from a subset of probes.

54. The method of claim 53, wherein the subset of probes is a set of control probes.

55. The method of claim 54, wherein the probe-specific, normalized read counts are converted to a copy number value comprising:
   (i) multiplying the probe-specific, normalized read counts of probes directed to autosomal and/or X-linked regions by 2 in samples derived from females;
   (ii) multiplying the probe-specific, normalized read counts of probes directed to Y-linked and/or X-linked regions by 1 in samples derived from males;
   (iii) averaging the products of (i) and/or (ii) across all samples in an experiment; and
   (iv) dividing the product of (i) and/or (ii) by the average of (iii).

56. The method of claim 55, wherein the approximate copy number values for all probes that target a specific gene are averaged.

* * * * *